US007485308B2

(12) United States Patent
Meyers et al.

(10) Patent No.: US 7,485,308 B2

(45) Date of Patent: Feb. 3, 2009

(54) 26199, 33530, 33949, 47148, 50226, 58764, 62113, 32144, 32235, 23565, 13305, 14911, 86216, 25206, AND 8843 MOLECULES AND USES THEREFOR

(75) Inventors: Rachel E. Meyers, Newton, MA (US); Kyle J. MacBeth, Boston, MA (US); Rory A. J. Curtis, Ashland, MA (US); Laura A. Rudolph-Owen, Medford, MA (US); Nadine S. Weich, Brookline, MA (US); Peter J. Olandt, Buffalo, NY (US); Fong-Ying Tsai, Newton, MA (US); Rosana Kapeller-Libermann, Chestnut Hill, MA (US); Joseph M. Carroll, Cambridge, MA (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 11/493,347

(22) Filed: Jul. 26, 2006

(65) Prior Publication Data

US 2007/0065848 A1 Mar. 22, 2007

Related U.S. Application Data

(63) Continuation of application No. 10/410,764, filed on Apr. 10, 2003, now abandoned, which is a continuation-in-part of application No. 09/924,358, filed on Aug. 6, 2001, now abandoned, said application No. 10/410,764 is a continuation-in-part of application No. 10/350,553, filed on Jan. 24, 2003, now abandoned, and a continuation-in-part of application No. 10/281,094, filed on Oct. 25, 2002, now abandoned, and a continuation-in-part of application No. 10/226,410, filed on Aug. 23, 2002, now abandoned, and a continuation-in-part of application No. 10/076,535, filed on Feb. 15, 2002, now abandoned, and a continuation-in-part of application No. 09/997,816, filed on Nov. 29, 2001, now abandoned, and a continuation-in-part of application No. 09/966,614, filed on Sep. 27, 2001, now abandoned, and a continuation-in-part of application No. 09/860,352, filed on May 17, 2001, now abandoned, and a continuation-in-part of application No. 09/686,673, filed on Oct. 11, 2000, now abandoned, and a continuation-in-part of application No. 09/593,927, filed on Jun. 15, 2000, now abandoned.

(60) Provisional application No. 60/229,300, filed on Sep. 1, 2000, provisional application No. 60/351,572, filed on Jan. 24, 2002, provisional application No. 60/238,054, filed on Oct. 5, 2000, provisional application No. 60/347,815, filed on Oct. 29, 2001, provisional application No. 60/269,440, filed on Feb. 16, 2001, provisional application No. 60/205,301, filed on May 19, 2000, provisional application No. 60/199,391, filed on Apr. 25, 2000, provisional application No. 60/314,884, filed on Aug. 24, 2001, provisional application No. 60/250,186, filed on Nov. 30, 2000.

(51) Int. Cl.
*A61K 39/00* (2006.01)
*C12P 21/06* (2006.01)

(52) U.S. Cl. .................................. 424/192.1; 435/69.1

(58) Field of Classification Search ................ 435/69.1; 424/192.1
See application file for complete search history.

(56) References Cited

FOREIGN PATENT DOCUMENTS

| | | | |
|---|---|---|---|
| EP | 1074617 | A2 | 2/2001 |
| WO | WO 01/54472 | A2 | 8/2001 |
| WO | WO 02/20801 | A2 | 3/2002 |

OTHER PUBLICATIONS

Strausberg, Robert, "oa77e04.s1 NCI_CGAP_GCB1 *Homo sapiens* cDNA Clone Image: 1318302 3', mRNA Sequence," Feb. 16, 1998, (sequence), EMBL Database [online], Hinxton, Cambridge, U.K., European Bioinformatics Institute, [retrieved on Sep. 10, 2002]. Retrieved from the Internet: URL: http://www.ebi.ac.uk/embl/>. EMBL Accession No. AA810935.

Hedge, P., et al., "EST379978 MAGE Resequences, MAGJ *Homo sapiens* cDNA, mRNA Sequence," Jun. 8, 2000, (sequence), EMBL Database [online], Hinxton, Cambridge, U.K., European Bioinformatics Institute, [retrieved on Sep. 10, 2002]. Retrieved from the Internet: URL: http://www.ebi.ac.uk/embl/>. EMBL Accession No. AW967903.

Ota, T., et al., "Human Protein Sequence SEQ ID No. 15961," Jun. 26, 2001, (sequence), EMBL Database [online], Hinxton, Cambridge, U.K., European Bioinformatics Institute, [retrieved on Sep. 9, 2002]. Retrieved from the Internet: URL: http://www.ebi.ac.uk/embl/>. EMBL Accession No. AAB94815.

(Continued)

*Primary Examiner*—Tekchand Saidha

(57) ABSTRACT

The invention provides isolated nucleic acids molecules, designated 26199, 33530, 33949, 47148, 50226, 58764, 62113, 32144, 32235, 23565, 13305, 14911, 86216, 25206 and 8843 nucleic acid molecules. The invention also provides antisense nucleic acid molecules, recombinant expression vectors containing 26199, 33530, 33949, 47148, 50226, 58764, 62113, 32144, 32235, 23565, 13305, 14911, 86216, 25206 and 8843 nucleic acid molecules, host cells into which the expression vectors have been introduced, and nonhuman transgenic animals in which a 26199, 33530, 33949, 47148, 50226, 58764, 62113, 32144, 32235, 23565, 13305, 14911, 86216, 25206 or 8843 gene has been introduced or disrupted. The invention still further provides isolated 26199, 33530, 33949, 47148, 50226, 58764, 62113, 32144, 32235, 23565, 13305, 14911, 86216, 25206 or 8843 proteins, fusion proteins, antigenic peptides and anti-26199, 33530, 33949, 47148, 50226, 58764, 62113, 32144, 32235, 23565, 13305, 14911, 86216, 25206 or 8843 antibodies. Diagnostic and therapeutic methods utilizing compositions of the invention are also provided.

10 Claims, No Drawings

OTHER PUBLICATIONS

Ota, T., et al., "Human cDNA Sequence SEQ ID No. 15960," Jun. 26, 2001, (sequence), EMBL Database [online], Hinxton, Cambridge, U.K., European Bioinformatics Institute, [retrieved on Sep. 10, 2002]. Retrieved from the Internet: URL: http://www.ebi.ac.uk/embl/>. EMBL Accession No. AAH16756.

Rosen, C.A., et al., "Human Immune/Haematopoietic Antigen Genomic Sequence SEQ ID No. 40543," Nov. 7, 2001, (sequence), EMBL Database [online], Hinxton, Cambridge, U.K., European Bioinformatics Institute, [retrieved on Sep. 10, 2002]. Retrieved from the Internet: URL: http://www.ebi.ac.uk/embl/>. EMBL Accession No. AAK85731.

Heilig, R., et al., "Human Chromosome 14 DNA Sequence BAC R-873E2 of Library RPCI-11 From Chromosome 14 of *Homo sapiens* (Human)," Aug. 6, 1999, (sequence), EMBL Database [online], Hinxton, Cambridge, U.K., European Bioinformatics Institute. Retrieved from the Internet: URL: http://www.ebi.ac.uk/embl/>. EMBL Accession No. AL109758.

SEQUENCE LISTING

<160> NUMBER OF SEQ ID NOS: 136

<210> SEQ ID NO 1
<211> LENGTH: 1828
<212> TYPE: DNA
<213> ORGANISM: Homo sapiens
<220> FEATURE:
<221> NAME/KEY: CDS
<222> LOCATION: (56)...(745)

<400> SEQUENCE: 1

```
gcggtgcgcg ttgatgtgac gtccctgcgc gcgccgcttt ctgttgccgg gcgca atg      58
                                                             Met
                                                              1

gcg gat acg ctg gag tcc tcg ctg gag gac cca ctg cgg agc ttt gtg      106
Ala Asp Thr Leu Glu Ser Ser Leu Glu Asp Pro Leu Arg Ser Phe Val
            5                  10                  15

cga gtt ttg gag aag cgg gat ggt aca gtg cta cga cta cag cag tat      154
Arg Val Leu Glu Lys Arg Asp Gly Thr Val Leu Arg Leu Gln Gln Tyr
        20                  25                  30

agc tcc ggt ggc gtg ggt tgc gtt gtg tgg gac gct gcc att gtc ctt      202
Ser Ser Gly Gly Val Gly Cys Val Val Trp Asp Ala Ala Ile Val Leu
    35                  40                  45

tct aaa tac ctg gaa acg ccc gag ttt tct ggc gac ggg gcc cac gcg      250
Ser Lys Tyr Leu Glu Thr Pro Glu Phe Ser Gly Asp Gly Ala His Ala
 50                  55                  60                  65

ctg agc cgg cgg tcg gtg ctg gag ctg ggt tcg ggc acc ggg gcc gtg      298
Leu Ser Arg Arg Ser Val Leu Glu Leu Gly Ser Gly Thr Gly Ala Val
                70                  75                  80

ggg ctc atg gct gct acc ctc ggg gct gat gtt gta gtc acc gat ctt      346
Gly Leu Met Ala Ala Thr Leu Gly Ala Asp Val Val Val Thr Asp Leu
            85                  90                  95

gag gaa ttg caa gac ttg ctg aag atg aat att aat atg aac aag cat      394
Glu Glu Leu Gln Asp Leu Leu Lys Met Asn Ile Asn Met Asn Lys His
        100                 105                 110

ctt gtc act ggt tct gtt caa gcc aag gta ctg aaa tgg ggg gaa gaa      442
Leu Val Thr Gly Ser Val Gln Ala Lys Val Leu Lys Trp Gly Glu Glu
    115                 120                 125

ata gaa ggc ttt cct tct cca ccc gac ttc ata ctg atg gcc gac tgc      490
Ile Glu Gly Phe Pro Ser Pro Pro Asp Phe Ile Leu Met Ala Asp Cys
130                 135                 140                 145

ata tac tat gaa gag tct ttg gag cca ttg ctg aaa act cta aaa gat      538
Ile Tyr Tyr Glu Glu Ser Leu Glu Pro Leu Leu Lys Thr Leu Lys Asp
                150                 155                 160

atc agc gga ttt gaa act tgt att ata tgt tgt tat gaa caa cga aca      586
Ile Ser Gly Phe Glu Thr Cys Ile Ile Cys Cys Tyr Glu Gln Arg Thr
            165                 170                 175

atg ggg aaa aat cca gaa att gag aaa aaa tat ttt gag ctc ctt cag      634
Met Gly Lys Asn Pro Glu Ile Glu Lys Lys Tyr Phe Glu Leu Leu Gln
        180                 185                 190

cta gat ttt gac ttt gaa aaa att cct ttg gaa aaa cat gat gaa gag      682
Leu Asp Phe Asp Phe Glu Lys Ile Pro Leu Glu Lys His Asp Glu Glu
    195                 200                 205

tat cga agt gaa gat att cat att ata tac atc aga aag aaa aaa tcg      730
Tyr Arg Ser Glu Asp Ile His Ile Ile Tyr Ile Arg Lys Lys Lys Ser
210                 215                 220                 225

aaa ttt cca tcg tga agcctttaat catcttaccc aaggctctaa caacctgggt      785
Lys Phe Pro Ser  *
```

-continued

```
aaactaaaga tgtgaataga gcatgtgaat acagcatggg aagattgtgt tcacagattt    845

tttttccgg cacgtcctta gagatccgat gtatagatga tgaccaccag gggctgtctg    905

caatacgaaa aattcctgct tgcctgcctg cctgccaatg gccctgaatc cagcttaggt    965

tacttagttc agcatcaagt tcttcttaaa tgttgggaat cagttattca aataaaaatt   1025

ggtattgagg cgaggctgaa atctgccaaa aacagccaac atgatttgac tggacctttt   1085

acaggaagct agagataaat ttctgaagag aactatctgc tattatataa taatgtttta   1145

aattcaaact agtaaatttt agtttgtctt cagagtttaa aaggttttca ttttgtacat   1205

aattatacaa tatttatcat ttgtattttc cacttcattt cttttaaaat atctttaata   1265

ctgaaatgtt cttttaattt taaaaagaac tgagatattg tcttgtatac ttatattggc   1325

caaagttttc ttttcctcca ccatacatat ctatgtgatt taatcagtaa attgtactgt   1385

aatgagttgc taagaagaca aatcagaaga ttggaggaac aaaagatatc tttacagatt   1445

tttcatttga gcatggagtg agaatagaaa gaccagtttc aggcttatgc acttacgtgg   1505

ctcatgcact ttatgtatat gttccaggaa aatctggctt aaaaatactg gtattgttta   1565

catgaagcag tgaaaggttt ttgaataact acaaatgtag ttctatatgt atataccaaa   1625

tgaatttctg ttctgtgtct ctctgtttta tgttatgaag ccattcgctc atatacaata   1685

atctgtcaag gactttaatc atacttgttc caaagagtag taaccggatg gaattctggt   1745

atttacaggc attggtgcta gatggtacat tttatgtgtt aaaataaaca ttgtttttga   1805

gaaaaaaaaa aaaaaaaars gaa                                            1828


<210> SEQ ID NO 2
<211> LENGTH: 229
<212> TYPE: PRT
<213> ORGANISM: Homo sapiens

<400> SEQUENCE: 2

Met Ala Asp Thr Leu Glu Ser Ser Leu Glu Asp Pro Leu Arg Ser Phe
1               5                   10                  15

Val Arg Val Leu Glu Lys Arg Asp Gly Thr Val Leu Arg Leu Gln Gln
            20                  25                  30

Tyr Ser Ser Gly Gly Val Gly Cys Val Val Trp Asp Ala Ala Ile Val
        35                  40                  45

Leu Ser Lys Tyr Leu Glu Thr Pro Glu Phe Ser Gly Asp Gly Ala His
    50                  55                  60

Ala Leu Ser Arg Arg Ser Val Leu Glu Leu Gly Ser Gly Thr Gly Ala
65                  70                  75                  80

Val Gly Leu Met Ala Ala Thr Leu Gly Ala Asp Val Val Val Thr Asp
                85                  90                  95

Leu Glu Glu Leu Gln Asp Leu Leu Lys Met Asn Ile Asn Met Asn Lys
            100                 105                 110

His Leu Val Thr Gly Ser Val Gln Ala Lys Val Leu Lys Trp Gly Glu
        115                 120                 125

Glu Ile Glu Gly Phe Pro Ser Pro Pro Asp Phe Ile Leu Met Ala Asp
    130                 135                 140

Cys Ile Tyr Tyr Glu Glu Ser Leu Glu Pro Leu Leu Lys Thr Leu Lys
145                 150                 155                 160

Asp Ile Ser Gly Phe Glu Thr Cys Ile Ile Cys Cys Tyr Glu Gln Arg
                165                 170                 175

Thr Met Gly Lys Asn Pro Glu Ile Glu Lys Lys Tyr Phe Glu Leu Leu
            180                 185                 190
```

-continued

```
Gln Leu Asp Phe Asp Phe Glu Lys Ile Pro Leu Glu Lys His Asp Glu
        195                 200                 205

Glu Tyr Arg Ser Glu Asp Ile His Ile Ile Tyr Ile Arg Lys Lys Lys
    210                 215                 220

Ser Lys Phe Pro Ser
225
```

<210> SEQ ID NO 3
<211> LENGTH: 690
<212> TYPE: DNA
<213> ORGANISM: Homo sapiens
<220> FEATURE:
<221> NAME/KEY: CDS
<222> LOCATION: (1)...(690)

<400> SEQUENCE: 3

```
atg gcg gat acg ctg gag tcc tcg ctg gag gac cca ctg cgg agc ttt       48
Met Ala Asp Thr Leu Glu Ser Ser Leu Glu Asp Pro Leu Arg Ser Phe
 1               5                  10                  15

gtg cga gtt ttg gag aag cgg gat ggt aca gtg cta cga cta cag cag       96
Val Arg Val Leu Glu Lys Arg Asp Gly Thr Val Leu Arg Leu Gln Gln
            20                  25                  30

tat agc tcc ggt ggc gtg ggt tgc gtt gtg tgg gac gct gcc att gtc      144
Tyr Ser Ser Gly Gly Val Gly Cys Val Val Trp Asp Ala Ala Ile Val
        35                  40                  45

ctt tct aaa tac ctg gaa acg ccc gag ttt tct ggc gac ggg gcc cac      192
Leu Ser Lys Tyr Leu Glu Thr Pro Glu Phe Ser Gly Asp Gly Ala His
    50                  55                  60

gcg ctg agc cgg cgg tcg gtg ctg gag ctg ggt tcg ggc acc ggg gcc      240
Ala Leu Ser Arg Arg Ser Val Leu Glu Leu Gly Ser Gly Thr Gly Ala
 65                 70                  75                  80

gtg ggg ctc atg gct gct acc ctc ggg gct gat gtt gta gtc acc gat      288
Val Gly Leu Met Ala Ala Thr Leu Gly Ala Asp Val Val Val Thr Asp
                85                  90                  95

ctt gag gaa ttg caa gac ttg ctg aag atg aat att aat atg aac aag      336
Leu Glu Glu Leu Gln Asp Leu Leu Lys Met Asn Ile Asn Met Asn Lys
            100                 105                 110

cat ctt gtc act ggt tct gtt caa gcc aag gta ctg aaa tgg ggg gaa      384
His Leu Val Thr Gly Ser Val Gln Ala Lys Val Leu Lys Trp Gly Glu
        115                 120                 125

gaa ata gaa ggc ttt cct tct cca ccc gac ttc ata ctg atg gcc gac      432
Glu Ile Glu Gly Phe Pro Ser Pro Pro Asp Phe Ile Leu Met Ala Asp
    130                 135                 140

tgc ata tac tat gaa gag tct ttg gag cca ttg ctg aaa act cta aaa      480
Cys Ile Tyr Tyr Glu Glu Ser Leu Glu Pro Leu Leu Lys Thr Leu Lys
145                 150                 155                 160

gat atc agc gga ttt gaa act tgt att ata tgt tgt tat gaa caa cga      528
Asp Ile Ser Gly Phe Glu Thr Cys Ile Ile Cys Cys Tyr Glu Gln Arg
                165                 170                 175

aca atg ggg aaa aat cca gaa att gag aaa aaa tat ttt gag ctc ctt      576
Thr Met Gly Lys Asn Pro Glu Ile Glu Lys Lys Tyr Phe Glu Leu Leu
            180                 185                 190

cag cta gat ttt gac ttt gaa aaa att cct ttg gaa aaa cat gat gaa      624
Gln Leu Asp Phe Asp Phe Glu Lys Ile Pro Leu Glu Lys His Asp Glu
        195                 200                 205

gag tat cga agt gaa gat att cat att ata tac atc aga aag aaa aaa      672
Glu Tyr Arg Ser Glu Asp Ile His Ile Ile Tyr Ile Arg Lys Lys Lys
    210                 215                 220

tcg aaa ttt cca tcg tga                                              690
Ser Lys Phe Pro Ser  *
225
```

-continued

```
<210> SEQ ID NO 4
<211> LENGTH: 1408
<212> TYPE: DNA
<213> ORGANISM: Homo sapiens
<220> FEATURE:
<221> NAME/KEY: CDS
<222> LOCATION: (36)...(1286)

<400> SEQUENCE: 4

ccagtgtggt ggaattcagt tgcggctcca gggcc atg gcg gag gag cag gcc        53
                                       Met Ala Glu Glu Gln Ala
                                        1               5

cgg gaa cgg gac tcg gtt ccc aag ccg tcg gtg ctg ttc ctc cac cca      101
Arg Glu Arg Asp Ser Val Pro Lys Pro Ser Val Leu Phe Leu His Pro
             10                  15                  20

gac ctg ggc gtg ggc ggc gct gag cgg ctg gtg ttg gac gcg gcg ctg      149
Asp Leu Gly Val Gly Gly Ala Glu Arg Leu Val Leu Asp Ala Ala Leu
         25                  30                  35

gcg ctg cag gcg cgc ggg tgt agc gtg aag atc tgg aca gcg cac tac      197
Ala Leu Gln Ala Arg Gly Cys Ser Val Lys Ile Trp Thr Ala His Tyr
     40                  45                  50

gac ccg ggc cac tgt ttc gcc gag agc cgc gag cta ccg gtg cgc tgt      245
Asp Pro Gly His Cys Phe Ala Glu Ser Arg Glu Leu Pro Val Arg Cys
 55                  60                  65                  70

gcc ggg gac tgg ctg ccg cga ggc ctg ggc tgg ggc ggc cgc ggc gcc      293
Ala Gly Asp Trp Leu Pro Arg Gly Leu Gly Trp Gly Gly Arg Gly Ala
                 75                  80                  85

gcc gtc tgc gcc tac gtg cgc atg gtt ttc ctg gcg ctc tac gtg ctg      341
Ala Val Cys Ala Tyr Val Arg Met Val Phe Leu Ala Leu Tyr Val Leu
             90                  95                 100

ttc ctc gcc gac gag gag ttc gac gtg gta gtg tgc gac cag gtg tct      389
Phe Leu Ala Asp Glu Glu Phe Asp Val Val Val Cys Asp Gln Val Ser
        105                 110                 115

gcc tgt atc cca gtg ttc agg ctg gct aga cgg cgg aag aag atc cta      437
Ala Cys Ile Pro Val Phe Arg Leu Ala Arg Arg Arg Lys Lys Ile Leu
    120                 125                 130

ttt tac tgt cac ttc cca gat ctg ctt ctc acc aag aga gat tct ttt      485
Phe Tyr Cys His Phe Pro Asp Leu Leu Leu Thr Lys Arg Asp Ser Phe
135                 140                 145                 150

ctt aaa cga cta tac agg gcc cca att gac tgg ata gag gaa tac acc      533
Leu Lys Arg Leu Tyr Arg Ala Pro Ile Asp Trp Ile Glu Glu Tyr Thr
                155                 160                 165

aca ggc atg gca gac tgc atc tta gtc aac agc cag ttc aca gct gct      581
Thr Gly Met Ala Asp Cys Ile Leu Val Asn Ser Gln Phe Thr Ala Ala
            170                 175                 180

gtt ttt aag gaa aca ttc aag tcc ctg tct cac ata gac cct gat gtc      629
Val Phe Lys Glu Thr Phe Lys Ser Leu Ser His Ile Asp Pro Asp Val
        185                 190                 195

ctc tat cca tct cta aat gtc acc agc ttt gac tca gtt gtt cct gaa      677
Leu Tyr Pro Ser Leu Asn Val Thr Ser Phe Asp Ser Val Val Pro Glu
    200                 205                 210

aag ctg gat gac cta gtc ccc aag ggg aaa aaa ttc ctg ctg ctc tcc      725
Lys Leu Asp Asp Leu Val Pro Lys Gly Lys Lys Phe Leu Leu Leu Ser
215                 220                 225                 230

atc aac aga tac gaa agg aag aaa aat ctg act ttg gca ctg gaa gcc      773
Ile Asn Arg Tyr Glu Arg Lys Lys Asn Leu Thr Leu Ala Leu Glu Ala
                235                 240                 245

cta gta cag ctg cgt gga aga ttg aca tcc caa gat tgg gag agg gtt      821
Leu Val Gln Leu Arg Gly Arg Leu Thr Ser Gln Asp Trp Glu Arg Val
            250                 255                 260
```

-continued

```
cat ctg atc gtg gca ggt ggt tat gac gag aga gtc ctg gag aat gtg      869
His Leu Ile Val Ala Gly Gly Tyr Asp Glu Arg Val Leu Glu Asn Val
        265                 270                 275

gaa cat tat cag gaa ttg aag aaa atg gtc caa cag tcc gac ctt ggc      917
Glu His Tyr Gln Glu Leu Lys Lys Met Val Gln Gln Ser Asp Leu Gly
    280                 285                 290

cag tat gtg acc ttc ttg agg tct ttc tca gac aaa cag aaa atc tcc      965
Gln Tyr Val Thr Phe Leu Arg Ser Phe Ser Asp Lys Gln Lys Ile Ser
295                 300                 305                 310

ctc ctc cac agc tgc acg tgt gtg ctt tac aca cca agc aat gag cac     1013
Leu Leu His Ser Cys Thr Cys Val Leu Tyr Thr Pro Ser Asn Glu His
                315                 320                 325

ttt ggc att gtc cct ctg gaa gcc atg tac atg cag tgc cca gtc att     1061
Phe Gly Ile Val Pro Leu Glu Ala Met Tyr Met Gln Cys Pro Val Ile
            330                 335                 340

gct gtt aat tcg ggt gga ccc ttg gag tcc att gac cac agt gtc aca     1109
Ala Val Asn Ser Gly Gly Pro Leu Glu Ser Ile Asp His Ser Val Thr
        345                 350                 355

ggg ttt ctg tgt gag cct gac ccg gtg cac ttc tca gaa gca ata gaa     1157
Gly Phe Leu Cys Glu Pro Asp Pro Val His Phe Ser Glu Ala Ile Glu
    360                 365                 370

aag ttc atc cgt gaa cct tcc tta aaa gcc acc atg ggc ctg gct gga     1205
Lys Phe Ile Arg Glu Pro Ser Leu Lys Ala Thr Met Gly Leu Ala Gly
375                 380                 385                 390

aga gcc aga gtg aag gaa aaa ttt tcc cct gaa gca ttt aca gaa cag     1253
Arg Ala Arg Val Lys Glu Lys Phe Ser Pro Glu Ala Phe Thr Glu Gln
                395                 400                 405

ctc tac cga tat gtt acc aaa ctg ctg gta taa ctcgagtcta gagggcccgt   1306
Leu Tyr Arg Tyr Val Thr Lys Leu Leu Val  *
            410                 415

ttaaacccgc tgatcagcct cgactgtgcc ttctagttgc cagccatctg ttgtttgccc   1366

ctcccccgtg ccttgccttg accctggaag gtgccacgcc ca                      1408


<210> SEQ ID NO 5
<211> LENGTH: 416
<212> TYPE: PRT
<213> ORGANISM: Homo sapiens

<400> SEQUENCE: 5

Met Ala Glu Glu Gln Ala Arg Glu Arg Asp Ser Val Pro Lys Pro Ser
 1               5                  10                  15

Val Leu Phe Leu His Pro Asp Leu Gly Val Gly Gly Ala Glu Arg Leu
            20                  25                  30

Val Leu Asp Ala Ala Leu Ala Leu Gln Ala Arg Gly Cys Ser Val Lys
        35                  40                  45

Ile Trp Thr Ala His Tyr Asp Pro Gly His Cys Phe Ala Glu Ser Arg
    50                  55                  60

Glu Leu Pro Val Arg Cys Ala Gly Asp Trp Leu Pro Arg Gly Leu Gly
65                  70                  75                  80

Trp Gly Gly Arg Gly Ala Ala Val Cys Ala Tyr Val Arg Met Val Phe
                85                  90                  95

Leu Ala Leu Tyr Val Leu Phe Leu Ala Asp Glu Glu Phe Asp Val Val
            100                 105                 110

Val Cys Asp Gln Val Ser Ala Cys Ile Pro Val Phe Arg Leu Ala Arg
        115                 120                 125

Arg Arg Lys Lys Ile Leu Phe Tyr Cys His Phe Pro Asp Leu Leu Leu
    130                 135                 140
```

-continued

```
Thr Lys Arg Asp Ser Phe Leu Lys Arg Leu Tyr Arg Ala Pro Ile Asp
145                 150                 155                 160

Trp Ile Glu Glu Tyr Thr Thr Gly Met Ala Asp Cys Ile Leu Val Asn
                165                 170                 175

Ser Gln Phe Thr Ala Ala Val Phe Lys Glu Thr Phe Lys Ser Leu Ser
            180                 185                 190

His Ile Asp Pro Asp Val Leu Tyr Pro Ser Leu Asn Val Thr Ser Phe
        195                 200                 205

Asp Ser Val Val Pro Glu Lys Leu Asp Asp Leu Val Pro Lys Gly Lys
    210                 215                 220

Lys Phe Leu Leu Leu Ser Ile Asn Arg Tyr Glu Arg Lys Lys Asn Leu
225                 230                 235                 240

Thr Leu Ala Leu Glu Ala Leu Val Gln Leu Arg Gly Arg Leu Thr Ser
                245                 250                 255

Gln Asp Trp Glu Arg Val His Leu Ile Val Ala Gly Gly Tyr Asp Glu
            260                 265                 270

Arg Val Leu Glu Asn Val Glu His Tyr Gln Glu Leu Lys Lys Met Val
        275                 280                 285

Gln Gln Ser Asp Leu Gly Gln Tyr Val Thr Phe Leu Arg Ser Phe Ser
    290                 295                 300

Asp Lys Gln Lys Ile Ser Leu Leu His Ser Cys Thr Cys Val Leu Tyr
305                 310                 315                 320

Thr Pro Ser Asn Glu His Phe Gly Ile Val Pro Leu Glu Ala Met Tyr
                325                 330                 335

Met Gln Cys Pro Val Ile Ala Val Asn Ser Gly Gly Pro Leu Glu Ser
            340                 345                 350

Ile Asp His Ser Val Thr Gly Phe Leu Cys Glu Pro Asp Pro Val His
        355                 360                 365

Phe Ser Glu Ala Ile Glu Lys Phe Ile Arg Glu Pro Ser Leu Lys Ala
    370                 375                 380

Thr Met Gly Leu Ala Gly Arg Ala Arg Val Lys Glu Lys Phe Ser Pro
385                 390                 395                 400

Glu Ala Phe Thr Glu Gln Leu Tyr Arg Tyr Val Thr Lys Leu Leu Val
                405                 410                 415


<210> SEQ ID NO 6
<211> LENGTH: 1251
<212> TYPE: DNA
<213> ORGANISM: Homo sapiens
<220> FEATURE:
<221> NAME/KEY: CDS
<222> LOCATION: (1)...(1251)

<400> SEQUENCE: 6

atg gcg gag gag cag gcc cgg gaa cgg gac tcg gtt ccc aag ccg tcg       48
Met Ala Glu Glu Gln Ala Arg Glu Arg Asp Ser Val Pro Lys Pro Ser
 1               5                  10                  15

gtg ctg ttc ctc cac cca gac ctg ggc gtg ggc ggc gct gag cgg ctg       96
Val Leu Phe Leu His Pro Asp Leu Gly Val Gly Gly Ala Glu Arg Leu
             20                  25                  30

gtg ttg gac gcg gcg ctg gcg ctg cag gcg cgc ggg tgt agc gtg aag      144
Val Leu Asp Ala Ala Leu Ala Leu Gln Ala Arg Gly Cys Ser Val Lys
         35                  40                  45

atc tgg aca gcg cac tac gac ccg ggc cac tgt ttc gcc gag agc cgc      192
Ile Trp Thr Ala His Tyr Asp Pro Gly His Cys Phe Ala Glu Ser Arg
     50                  55                  60
```

-continued

```
gag cta ccg gtg cgc tgt gcc ggg gac tgg ctg ccg cga ggc ctg ggc       240
Glu Leu Pro Val Arg Cys Ala Gly Asp Trp Leu Pro Arg Gly Leu Gly
 65                  70                  75                  80

tgg ggc ggc cgc ggc gcc gcc gtc tgc gcc tac gtg cgc atg gtt ttc       288
Trp Gly Gly Arg Gly Ala Ala Val Cys Ala Tyr Val Arg Met Val Phe
                 85                  90                  95

ctg gcg ctc tac gtg ctg ttc ctc gcc gac gag gag ttc gac gtg gta       336
Leu Ala Leu Tyr Val Leu Phe Leu Ala Asp Glu Glu Phe Asp Val Val
            100                 105                 110

gtg tgc gac cag gtg tct gcc tgt atc cca gtg ttc agg ctg gct aga       384
Val Cys Asp Gln Val Ser Ala Cys Ile Pro Val Phe Arg Leu Ala Arg
        115                 120                 125

cgg cgg aag aag atc cta ttt tac tgt cac ttc cca gat ctg ctt ctc       432
Arg Arg Lys Lys Ile Leu Phe Tyr Cys His Phe Pro Asp Leu Leu Leu
    130                 135                 140

acc aag aga gat tct ttt ctt aaa cga cta tac agg gcc cca att gac       480
Thr Lys Arg Asp Ser Phe Leu Lys Arg Leu Tyr Arg Ala Pro Ile Asp
145                 150                 155                 160

tgg ata gag gaa tac acc aca ggc atg gca gac tgc atc tta gtc aac       528
Trp Ile Glu Glu Tyr Thr Thr Gly Met Ala Asp Cys Ile Leu Val Asn
                165                 170                 175

agc cag ttc aca gct gct gtt ttt aag gaa aca ttc aag tcc ctg tct       576
Ser Gln Phe Thr Ala Ala Val Phe Lys Glu Thr Phe Lys Ser Leu Ser
            180                 185                 190

cac ata gac cct gat gtc ctc tat cca tct cta aat gtc acc agc ttt       624
His Ile Asp Pro Asp Val Leu Tyr Pro Ser Leu Asn Val Thr Ser Phe
        195                 200                 205

gac tca gtt gtt cct gaa aag ctg gat gac cta gtc ccc aag ggg aaa       672
Asp Ser Val Val Pro Glu Lys Leu Asp Asp Leu Val Pro Lys Gly Lys
    210                 215                 220

aaa ttc ctg ctg ctc tcc atc aac aga tac gaa agg aag aaa aat ctg       720
Lys Phe Leu Leu Leu Ser Ile Asn Arg Tyr Glu Arg Lys Lys Asn Leu
225                 230                 235                 240

act ttg gca ctg gaa gcc cta gta cag ctg cgt gga aga ttg aca tcc       768
Thr Leu Ala Leu Glu Ala Leu Val Gln Leu Arg Gly Arg Leu Thr Ser
                245                 250                 255

caa gat tgg gag agg gtt cat ctg atc gtg gca ggt ggt tat gac gag       816
Gln Asp Trp Glu Arg Val His Leu Ile Val Ala Gly Gly Tyr Asp Glu
            260                 265                 270

aga gtc ctg gag aat gtg gaa cat tat cag gaa ttg aag aaa atg gtc       864
Arg Val Leu Glu Asn Val Glu His Tyr Gln Glu Leu Lys Lys Met Val
        275                 280                 285

caa cag tcc gac ctt ggc cag tat gtg acc ttc ttg agg tct ttc tca       912
Gln Gln Ser Asp Leu Gly Gln Tyr Val Thr Phe Leu Arg Ser Phe Ser
    290                 295                 300

gac aaa cag aaa atc tcc ctc ctc cac agc tgc acg tgt gtg ctt tac       960
Asp Lys Gln Lys Ile Ser Leu Leu His Ser Cys Thr Cys Val Leu Tyr
305                 310                 315                 320

aca cca agc aat gag cac ttt ggc att gtc cct ctg gaa gcc atg tac      1008
Thr Pro Ser Asn Glu His Phe Gly Ile Val Pro Leu Glu Ala Met Tyr
                325                 330                 335

atg cag tgc cca gtc att gct gtt aat tcg ggt gga ccc ttg gag tcc      1056
Met Gln Cys Pro Val Ile Ala Val Asn Ser Gly Gly Pro Leu Glu Ser
            340                 345                 350

att gac cac agt gtc aca ggg ttt ctg tgt gag cct gac ccg gtg cac      1104
Ile Asp His Ser Val Thr Gly Phe Leu Cys Glu Pro Asp Pro Val His
        355                 360                 365

ttc tca gaa gca ata gaa aag ttc atc cgt gaa cct tcc tta aaa gcc      1152
Phe Ser Glu Ala Ile Glu Lys Phe Ile Arg Glu Pro Ser Leu Lys Ala
    370                 375                 380
```

-continued

```
acc atg ggc ctg gct gga aga gcc aga gtg aag gaa aaa ttt tcc cct     1200
Thr Met Gly Leu Ala Gly Arg Ala Arg Val Lys Glu Lys Phe Ser Pro
385                 390                 395                 400

gaa gca ttt aca gaa cag ctc tac cga tat gtt acc aaa ctg ctg gta     1248
Glu Ala Phe Thr Glu Gln Leu Tyr Arg Tyr Val Thr Lys Leu Leu Val
                405                 410                 415

taa                                                                 1251
 *


<210> SEQ ID NO 7
<211> LENGTH: 2327
<212> TYPE: DNA
<213> ORGANISM: Homo sapiens
<220> FEATURE:
<221> NAME/KEY: CDS
<222> LOCATION: (148)...(1974)

<400> SEQUENCE: 7

ggcagttcag cccgcgccgc tcctgcgggt cggactgggg ctgtggcggg agagaagatg     60

ccgcagcccg agtcccagaa ggcggcgatc ctgggctgcg ggcaaggcgg aaattgacaa    120

tggcccttca gctatgctag gtctata atg gga agt gtc aca gtt cgg tat ttc    174
                              Met Gly Ser Val Thr Val Arg Tyr Phe
                               1               5

tgt tat ggg tgc ctt ttt aca tct gcg acc tgg aca gtt ttg ctt ttt      222
Cys Tyr Gly Cys Leu Phe Thr Ser Ala Thr Trp Thr Val Leu Leu Phe
 10                  15                  20                  25

gtt tat ttc aac ttc agt gaa gtg act cag cca ctt aag aat gtg ccc      270
Val Tyr Phe Asn Phe Ser Glu Val Thr Gln Pro Leu Lys Asn Val Pro
                 30                  35                  40

gtc aag ggg tct ggg ccc cac gga cca tct cca aaa aaa ttc tat ccc      318
Val Lys Gly Ser Gly Pro His Gly Pro Ser Pro Lys Lys Phe Tyr Pro
             45                  50                  55

cgt ttc act cga ggc cca agt cga gtg ctc gag cca cag ttc aaa gca      366
Arg Phe Thr Arg Gly Pro Ser Arg Val Leu Glu Pro Gln Phe Lys Ala
         60                  65                  70

aac aaa att gac gat gtg ata gac agt cgt gtt gaa gat cca gaa gaa      414
Asn Lys Ile Asp Asp Val Ile Asp Ser Arg Val Glu Asp Pro Glu Glu
     75                  80                  85

ggc cac ttg aaa ttc tct tct gaa tta ggt atg att ttt aat gaa cgc      462
Gly His Leu Lys Phe Ser Ser Glu Leu Gly Met Ile Phe Asn Glu Arg
 90                  95                 100                 105

gat caa gag ttg aga gac ttg ggc tat cag aaa cat gct ttt aat atg      510
Asp Gln Glu Leu Arg Asp Leu Gly Tyr Gln Lys His Ala Phe Asn Met
                110                 115                 120

ctt atc agt gac cgc ttg ggc tac cac aga gat gtg cca gac aca agg      558
Leu Ile Ser Asp Arg Leu Gly Tyr His Arg Asp Val Pro Asp Thr Arg
            125                 130                 135

aat gca gca tgt aaa gaa aag ttc tac cca cct gac ctg cca gct gct      606
Asn Ala Ala Cys Lys Glu Lys Phe Tyr Pro Pro Asp Leu Pro Ala Ala
        140                 145                 150

agt gtt gtt atc tgt ttc tat aat gaa gcg ttt tct gcc ttg ctt cgg      654
Ser Val Val Ile Cys Phe Tyr Asn Glu Ala Phe Ser Ala Leu Leu Arg
    155                 160                 165

aca gtg cac agt gtc ata gac cgc acg cca gca cac ctg ctt cat gag      702
Thr Val His Ser Val Ile Asp Arg Thr Pro Ala His Leu Leu His Glu
170                 175                 180                 185

atc atc ctt gtg gat gat gat agt gac ttt gat gat ttg aaa gga gaa      750
Ile Ile Leu Val Asp Asp Asp Ser Asp Phe Asp Asp Leu Lys Gly Glu
                190                 195                 200
```

-continued

```
cta gat gaa tat gtc caa aaa tac ctc cct gga aaa att aaa gtc ata      798
Leu Asp Glu Tyr Val Gln Lys Tyr Leu Pro Gly Lys Ile Lys Val Ile
            205                 210                 215

aga aat aca aag cgt gag ggg ttg att cga ggg aga atg att ggc gcg      846
Arg Asn Thr Lys Arg Glu Gly Leu Ile Arg Gly Arg Met Ile Gly Ala
        220                 225                 230

gcc cac gcg aca gga gaa gtc ctt gtg ttc ctg gac agc cac tgt gaa      894
Ala His Ala Thr Gly Glu Val Leu Val Phe Leu Asp Ser His Cys Glu
    235                 240                 245

gtg aat gtg atg tgg ctg cag ccc ttg ctg gcc gcc atc cgt gag gac      942
Val Asn Val Met Trp Leu Gln Pro Leu Leu Ala Ala Ile Arg Glu Asp
250                 255                 260                 265

cgg cac acc gtg gtg tgc cca gtg att gac atc atc agc gcc gac acg      990
Arg His Thr Val Val Cys Pro Val Ile Asp Ile Ile Ser Ala Asp Thr
                270                 275                 280

ctg gcc tac agc tcg tcc cct gtc gtc cgc gga ggg ttc aac tgg gga     1038
Leu Ala Tyr Ser Ser Ser Pro Val Val Arg Gly Gly Phe Asn Trp Gly
            285                 290                 295

ctg cac ttc aaa tgg gat ctt gtc ccc ctt tct gag cta gga cga gcg     1086
Leu His Phe Lys Trp Asp Leu Val Pro Leu Ser Glu Leu Gly Arg Ala
        300                 305                 310

gag gga gcc act gca cca ata aag tca cca aca atg gct gga ggt ttg     1134
Glu Gly Ala Thr Ala Pro Ile Lys Ser Pro Thr Met Ala Gly Gly Leu
    315                 320                 325

ttt gcc atg aac aga cag tat ttc cat gaa ctt gga cag tat gat agt     1182
Phe Ala Met Asn Arg Gln Tyr Phe His Glu Leu Gly Gln Tyr Asp Ser
330                 335                 340                 345

ggc atg gat atc tgg gga gga gaa aat ttg gaa ata tca ttt cgg atc     1230
Gly Met Asp Ile Trp Gly Gly Glu Asn Leu Glu Ile Ser Phe Arg Ile
                350                 355                 360

tgg atg tgt ggc ggt aag ctc ttc atc atc cct tgc tct aga gta gga     1278
Trp Met Cys Gly Gly Lys Leu Phe Ile Ile Pro Cys Ser Arg Val Gly
            365                 370                 375

cac att ttc cga aaa agg cga cca tat gga tct ccc gaa ggc cag gac     1326
His Ile Phe Arg Lys Arg Arg Pro Tyr Gly Ser Pro Glu Gly Gln Asp
        380                 385                 390

acc atg aca cac aac tct ttg cgg ctg gca cat gtc tgg ttg gat gaa     1374
Thr Met Thr His Asn Ser Leu Arg Leu Ala His Val Trp Leu Asp Glu
    395                 400                 405

tac aag gag cag tat ttt tcc tta aga cct gac ctg aag acg aaa agc     1422
Tyr Lys Glu Gln Tyr Phe Ser Leu Arg Pro Asp Leu Lys Thr Lys Ser
410                 415                 420                 425

tat ggc aat atc agt gag cgt gtg gaa ctg aga aag aag ttg ggc tgt     1470
Tyr Gly Asn Ile Ser Glu Arg Val Glu Leu Arg Lys Lys Leu Gly Cys
                430                 435                 440

aaa tca ttt aaa tgg tat ttg gat aat gta tac cca gag atg cag ata     1518
Lys Ser Phe Lys Trp Tyr Leu Asp Asn Val Tyr Pro Glu Met Gln Ile
            445                 450                 455

tct ggg tcc cac gcc aaa ccc caa caa ccc att ttt gtc aat aga ggg     1566
Ser Gly Ser His Ala Lys Pro Gln Gln Pro Ile Phe Val Asn Arg Gly
        460                 465                 470

cca aaa cga ccc aaa gtc ctt caa cgt gga agg ctc tat cac ctc cag     1614
Pro Lys Arg Pro Lys Val Leu Gln Arg Gly Arg Leu Tyr His Leu Gln
    475                 480                 485

acc aac aaa tgc ctg gtg gcc cag ggc cgc cca agt cag aag gga ggt     1662
Thr Asn Lys Cys Leu Val Ala Gln Gly Arg Pro Ser Gln Lys Gly Gly
490                 495                 500                 505

ctc gtg gtg ctt aag gcc tgt gac tac agt gac cca aat cag atc tgg     1710
Leu Val Val Leu Lys Ala Cys Asp Tyr Ser Asp Pro Asn Gln Ile Trp
                510                 515                 520
```

-continued

```
atc tat aat gaa gag cat gaa ttg gtt tta aat agt ctc ctt tgt cta     1758
Ile Tyr Asn Glu Glu His Glu Leu Val Leu Asn Ser Leu Leu Cys Leu
            525                 530                 535

gat atg tca gag act cgc tca tca gac ccg cca cgg ctc atg aaa tgc     1806
Asp Met Ser Glu Thr Arg Ser Ser Asp Pro Pro Arg Leu Met Lys Cys
        540                 545                 550

cac ggg tca gga gga tcc cag cag tgg acc ttt ggg aaa aac aat cgg     1854
His Gly Ser Gly Gly Ser Gln Gln Trp Thr Phe Gly Lys Asn Asn Arg
    555                 560                 565

cta tac cag gtg tcg gtt gga cag tgc ctg aga gca gtg gat ccc ctg     1902
Leu Tyr Gln Val Ser Val Gly Gln Cys Leu Arg Ala Val Asp Pro Leu
570                 575                 580                 585

ggt cag aag ggc tct gtc gcc atg gcg atc tgc gat ggc tcc tct tca     1950
Gly Gln Lys Gly Ser Val Ala Met Ala Ile Cys Asp Gly Ser Ser Ser
                590                 595                 600

cag cag tgg cat ttg gaa ggt taa ggtggatgct gtggcgggaa cgttgcttca    2004
Gln Gln Trp His Leu Glu Gly  *
            605

tcaggcgttg cctccggtgt ggagtttggg gctttaggaa agcctgggtt gggtggagca   2064

gaaccatctt ggagaagatg acagttccct gtcctcccgg agatgcctgg gtgtgttagc   2124

agaggtgaca cgtgtctgac agagacggga gctctgagtg tccacgggtg aagaagtgag   2184

tgtccacggg tgaagaagtg agtatgtttc acctggacat taaggtgatg tttgagctgc   2244

tgttaaggaa tttcttgctt atagaggcaa accacagtat cattttaact ctagaattgg   2304

gcttgtacct cggccgcgac cac                                           2327


<210> SEQ ID NO 8
<211> LENGTH: 608
<212> TYPE: PRT
<213> ORGANISM: Homo sapiens

<400> SEQUENCE: 8

Met Gly Ser Val Thr Val Arg Tyr Phe Cys Tyr Gly Cys Leu Phe Thr
 1               5                  10                  15

Ser Ala Thr Trp Thr Val Leu Leu Phe Val Tyr Phe Asn Phe Ser Glu
            20                  25                  30

Val Thr Gln Pro Leu Lys Asn Val Pro Val Lys Gly Ser Gly Pro His
        35                  40                  45

Gly Pro Ser Pro Lys Lys Phe Tyr Pro Arg Phe Thr Arg Gly Pro Ser
    50                  55                  60

Arg Val Leu Glu Pro Gln Phe Lys Ala Asn Lys Ile Asp Asp Val Ile
65                  70                  75                  80

Asp Ser Arg Val Glu Asp Pro Glu Glu Gly His Leu Lys Phe Ser Ser
                85                  90                  95

Glu Leu Gly Met Ile Phe Asn Glu Arg Asp Gln Glu Leu Arg Asp Leu
            100                 105                 110

Gly Tyr Gln Lys His Ala Phe Asn Met Leu Ile Ser Asp Arg Leu Gly
        115                 120                 125

Tyr His Arg Asp Val Pro Asp Thr Arg Asn Ala Ala Cys Lys Glu Lys
    130                 135                 140

Phe Tyr Pro Pro Asp Leu Pro Ala Ala Ser Val Val Ile Cys Phe Tyr
145                 150                 155                 160

Asn Glu Ala Phe Ser Ala Leu Leu Arg Thr Val His Ser Val Ile Asp
                165                 170                 175

Arg Thr Pro Ala His Leu Leu His Glu Ile Ile Leu Val Asp Asp Asp
```

-continued

```
            180                 185                 190

Ser Asp Phe Asp Asp Leu Lys Gly Glu Leu Asp Glu Tyr Val Gln Lys
        195                 200                 205

Tyr Leu Pro Gly Lys Ile Lys Val Ile Arg Asn Thr Lys Arg Glu Gly
    210                 215                 220

Leu Ile Arg Gly Arg Met Ile Gly Ala Ala His Ala Thr Gly Glu Val
225                 230                 235                 240

Leu Val Phe Leu Asp Ser His Cys Glu Val Asn Val Met Trp Leu Gln
                245                 250                 255

Pro Leu Leu Ala Ala Ile Arg Glu Asp Arg His Thr Val Val Cys Pro
            260                 265                 270

Val Ile Asp Ile Ile Ser Ala Asp Thr Leu Ala Tyr Ser Ser Ser Pro
        275                 280                 285

Val Val Arg Gly Gly Phe Asn Trp Gly Leu His Phe Lys Trp Asp Leu
    290                 295                 300

Val Pro Leu Ser Glu Leu Gly Arg Ala Glu Gly Ala Thr Ala Pro Ile
305                 310                 315                 320

Lys Ser Pro Thr Met Ala Gly Gly Leu Phe Ala Met Asn Arg Gln Tyr
                325                 330                 335

Phe His Glu Leu Gly Gln Tyr Asp Ser Gly Met Asp Ile Trp Gly Gly
            340                 345                 350

Glu Asn Leu Glu Ile Ser Phe Arg Ile Trp Met Cys Gly Gly Lys Leu
        355                 360                 365

Phe Ile Ile Pro Cys Ser Arg Val Gly His Ile Phe Arg Lys Arg Arg
    370                 375                 380

Pro Tyr Gly Ser Pro Glu Gly Gln Asp Thr Met Thr His Asn Ser Leu
385                 390                 395                 400

Arg Leu Ala His Val Trp Leu Asp Glu Tyr Lys Glu Gln Tyr Phe Ser
                405                 410                 415

Leu Arg Pro Asp Leu Lys Thr Lys Ser Tyr Gly Asn Ile Ser Glu Arg
            420                 425                 430

Val Glu Leu Arg Lys Lys Leu Gly Cys Lys Ser Phe Lys Trp Tyr Leu
        435                 440                 445

Asp Asn Val Tyr Pro Glu Met Gln Ile Ser Gly Ser His Ala Lys Pro
    450                 455                 460

Gln Gln Pro Ile Phe Val Asn Arg Gly Pro Lys Arg Pro Lys Val Leu
465                 470                 475                 480

Gln Arg Gly Arg Leu Tyr His Leu Gln Thr Asn Lys Cys Leu Val Ala
                485                 490                 495

Gln Gly Arg Pro Ser Gln Lys Gly Gly Leu Val Val Leu Lys Ala Cys
            500                 505                 510

Asp Tyr Ser Asp Pro Asn Gln Ile Trp Ile Tyr Asn Glu Glu His Glu
        515                 520                 525

Leu Val Leu Asn Ser Leu Leu Cys Leu Asp Met Ser Glu Thr Arg Ser
    530                 535                 540

Ser Asp Pro Pro Arg Leu Met Lys Cys His Gly Ser Gly Gly Ser Gln
545                 550                 555                 560

Gln Trp Thr Phe Gly Lys Asn Asn Arg Leu Tyr Gln Val Ser Val Gly
                565                 570                 575

Gln Cys Leu Arg Ala Val Asp Pro Leu Gly Gln Lys Gly Ser Val Ala
            580                 585                 590

Met Ala Ile Cys Asp Gly Ser Ser Ser Gln Gln Trp His Leu Glu Gly
        595                 600                 605
```

-continued

<210> SEQ ID NO 9
<211> LENGTH: 1827
<212> TYPE: DNA
<213> ORGANISM: Homo sapiens
<220> FEATURE:
<221> NAME/KEY: CDS
<222> LOCATION: (1)...(1827)

<400> SEQUENCE: 9

```
atg gga agt gtc aca gtt cgg tat ttc tgt tat ggg tgc ctt ttt aca       48
Met Gly Ser Val Thr Val Arg Tyr Phe Cys Tyr Gly Cys Leu Phe Thr
 1               5                  10                  15

tct gcg acc tgg aca gtt ttg ctt ttt gtt tat ttc aac ttc agt gaa       96
Ser Ala Thr Trp Thr Val Leu Leu Phe Val Tyr Phe Asn Phe Ser Glu
            20                  25                  30

gtg act cag cca ctt aag aat gtg ccc gtc aag ggg tct ggg ccc cac      144
Val Thr Gln Pro Leu Lys Asn Val Pro Val Lys Gly Ser Gly Pro His
        35                  40                  45

gga cca tct cca aaa aaa ttc tat ccc cgt ttc act cga ggc cca agt      192
Gly Pro Ser Pro Lys Lys Phe Tyr Pro Arg Phe Thr Arg Gly Pro Ser
    50                  55                  60

cga gtg ctc gag cca cag ttc aaa gca aac aaa att gac gat gtg ata      240
Arg Val Leu Glu Pro Gln Phe Lys Ala Asn Lys Ile Asp Asp Val Ile
 65                  70                  75                  80

gac agt cgt gtt gaa gat cca gaa gaa ggc cac ttg aaa ttc tct tct      288
Asp Ser Arg Val Glu Asp Pro Glu Glu Gly His Leu Lys Phe Ser Ser
                 85                  90                  95

gaa tta ggt atg att ttt aat gaa cgc gat caa gag ttg aga gac ttg      336
Glu Leu Gly Met Ile Phe Asn Glu Arg Asp Gln Glu Leu Arg Asp Leu
            100                 105                 110

ggc tat cag aaa cat gct ttt aat atg ctt atc agt gac cgc ttg ggc      384
Gly Tyr Gln Lys His Ala Phe Asn Met Leu Ile Ser Asp Arg Leu Gly
        115                 120                 125

tac cac aga gat gtg cca gac aca agg aat gca gca tgt aaa gaa aag      432
Tyr His Arg Asp Val Pro Asp Thr Arg Asn Ala Ala Cys Lys Glu Lys
    130                 135                 140

ttc tac cca cct gac ctg cca gct gct agt gtt gtt atc tgt ttc tat      480
Phe Tyr Pro Pro Asp Leu Pro Ala Ala Ser Val Val Ile Cys Phe Tyr
145                 150                 155                 160

aat gaa gcg ttt tct gcc ttg ctt cgg aca gtg cac agt gtc ata gac      528
Asn Glu Ala Phe Ser Ala Leu Leu Arg Thr Val His Ser Val Ile Asp
                165                 170                 175

cgc acg cca gca cac ctg ctt cat gag atc atc ctt gtg gat gat gat      576
Arg Thr Pro Ala His Leu Leu His Glu Ile Ile Leu Val Asp Asp Asp
            180                 185                 190

agt gac ttt gat gat ttg aaa gga gaa cta gat gaa tat gtc caa aaa      624
Ser Asp Phe Asp Asp Leu Lys Gly Glu Leu Asp Glu Tyr Val Gln Lys
        195                 200                 205

tac ctc cct gga aaa att aaa gtc ata aga aat aca aag cgt gag ggg      672
Tyr Leu Pro Gly Lys Ile Lys Val Ile Arg Asn Thr Lys Arg Glu Gly
    210                 215                 220

ttg att cga ggg aga atg att ggc gcg gcc cac gcg aca gga gaa gtc      720
Leu Ile Arg Gly Arg Met Ile Gly Ala Ala His Ala Thr Gly Glu Val
225                 230                 235                 240

ctt gtg ttc ctg gac agc cac tgt gaa gtg aat gtg atg tgg ctg cag      768
Leu Val Phe Leu Asp Ser His Cys Glu Val Asn Val Met Trp Leu Gln
                245                 250                 255

ccc ttg ctg gcc gcc atc cgt gag gac cgg cac acc gtg gtg tgc cca      816
Pro Leu Leu Ala Ala Ile Arg Glu Asp Arg His Thr Val Val Cys Pro
            260                 265                 270
```

-continued

```
gtg att gac atc atc agc gcc gac acg ctg gcc tac agc tcg tcc cct      864
Val Ile Asp Ile Ile Ser Ala Asp Thr Leu Ala Tyr Ser Ser Ser Pro
        275                 280                 285

gtc gtc cgc gga ggg ttc aac tgg gga ctg cac ttc aaa tgg gat ctt      912
Val Val Arg Gly Gly Phe Asn Trp Gly Leu His Phe Lys Trp Asp Leu
    290                 295                 300

gtc ccc ctt tct gag cta gga cga gcg gag gga gcc act gca cca ata      960
Val Pro Leu Ser Glu Leu Gly Arg Ala Glu Gly Ala Thr Ala Pro Ile
305                 310                 315                 320

aag tca cca aca atg gct gga ggt ttg ttt gcc atg aac aga cag tat     1008
Lys Ser Pro Thr Met Ala Gly Gly Leu Phe Ala Met Asn Arg Gln Tyr
                325                 330                 335

ttc cat gaa ctt gga cag tat gat agt ggc atg gat atc tgg gga gga     1056
Phe His Glu Leu Gly Gln Tyr Asp Ser Gly Met Asp Ile Trp Gly Gly
            340                 345                 350

gaa aat ttg gaa ata tca ttt cgg atc tgg atg tgt ggc ggt aag ctc     1104
Glu Asn Leu Glu Ile Ser Phe Arg Ile Trp Met Cys Gly Gly Lys Leu
        355                 360                 365

ttc atc atc cct tgc tct aga gta gga cac att ttc cga aaa agg cga     1152
Phe Ile Ile Pro Cys Ser Arg Val Gly His Ile Phe Arg Lys Arg Arg
    370                 375                 380

cca tat gga tct ccc gaa ggc cag gac acc atg aca cac aac tct ttg     1200
Pro Tyr Gly Ser Pro Glu Gly Gln Asp Thr Met Thr His Asn Ser Leu
385                 390                 395                 400

cgg ctg gca cat gtc tgg ttg gat gaa tac aag gag cag tat ttt tcc     1248
Arg Leu Ala His Val Trp Leu Asp Glu Tyr Lys Glu Gln Tyr Phe Ser
                405                 410                 415

tta aga cct gac ctg aag acg aaa agc tat ggc aat atc agt gag cgt     1296
Leu Arg Pro Asp Leu Lys Thr Lys Ser Tyr Gly Asn Ile Ser Glu Arg
            420                 425                 430

gtg gaa ctg aga aag aag ttg ggc tgt aaa tca ttt aaa tgg tat ttg     1344
Val Glu Leu Arg Lys Lys Leu Gly Cys Lys Ser Phe Lys Trp Tyr Leu
        435                 440                 445

gat aat gta tac cca gag atg cag ata tct ggg tcc cac gcc aaa ccc     1392
Asp Asn Val Tyr Pro Glu Met Gln Ile Ser Gly Ser His Ala Lys Pro
    450                 455                 460

caa caa ccc att ttt gtc aat aga ggg cca aaa cga ccc aaa gtc ctt     1440
Gln Gln Pro Ile Phe Val Asn Arg Gly Pro Lys Arg Pro Lys Val Leu
465                 470                 475                 480

caa cgt gga agg ctc tat cac ctc cag acc aac aaa tgc ctg gtg gcc     1488
Gln Arg Gly Arg Leu Tyr His Leu Gln Thr Asn Lys Cys Leu Val Ala
                485                 490                 495

cag ggc cgc cca agt cag aag gga ggt ctc gtg gtg ctt aag gcc tgt     1536
Gln Gly Arg Pro Ser Gln Lys Gly Gly Leu Val Val Leu Lys Ala Cys
            500                 505                 510

gac tac agt gac cca aat cag atc tgg atc tat aat gaa gag cat gaa     1584
Asp Tyr Ser Asp Pro Asn Gln Ile Trp Ile Tyr Asn Glu Glu His Glu
        515                 520                 525

ttg gtt tta aat agt ctc ctt tgt cta gat atg tca gag act cgc tca     1632
Leu Val Leu Asn Ser Leu Leu Cys Leu Asp Met Ser Glu Thr Arg Ser
    530                 535                 540

tca gac ccg cca cgg ctc atg aaa tgc cac ggg tca gga gga tcc cag     1680
Ser Asp Pro Pro Arg Leu Met Lys Cys His Gly Ser Gly Gly Ser Gln
545                 550                 555                 560

cag tgg acc ttt ggg aaa aac aat cgg cta tac cag gtg tcg gtt gga     1728
Gln Trp Thr Phe Gly Lys Asn Asn Arg Leu Tyr Gln Val Ser Val Gly
                565                 570                 575

cag tgc ctg aga gca gtg gat ccc ctg ggt cag aag ggc tct gtc gcc     1776
Gln Cys Leu Arg Ala Val Asp Pro Leu Gly Gln Lys Gly Ser Val Ala
```

-continued

```
            580                 585                 590

atg gcg atc tgc gat ggc tcc tct tca cag cag tgg cat ttg gaa ggt     1824
Met Ala Ile Cys Asp Gly Ser Ser Ser Gln Gln Trp His Leu Glu Gly
        595                 600                 605

taa                                                                 1827
 *


<210> SEQ ID NO 10
<211> LENGTH: 2172
<212> TYPE: DNA
<213> ORGANISM: Homo sapiens
<220> FEATURE:
<221> NAME/KEY: CDS
<222> LOCATION: (31)...(2019)

<400> SEQUENCE: 10

gcgctgcgct gctgggggc gcgggcgagg atg gcg gcg gag aac gag gcc agc      54
                                  Met Ala Ala Glu Asn Glu Ala Ser
                                   1               5

cag gag agc gcc ctg ggc gcc tac tcg cca gtg gac tac atg agc atc     102
Gln Glu Ser Ala Leu Gly Ala Tyr Ser Pro Val Asp Tyr Met Ser Ile
     10                  15                  20

acc agc ttc ccg cgg ctg ccc gag gac gag ccg gcg ccc gcg gcc ccg     150
Thr Ser Phe Pro Arg Leu Pro Glu Asp Glu Pro Ala Pro Ala Ala Pro
 25                  30                  35                  40

ctg agg ggc cgc aag gac gag gac gcc ttt ctg gga gac ccc gac acc     198
Leu Arg Gly Arg Lys Asp Glu Asp Ala Phe Leu Gly Asp Pro Asp Thr
                 45                  50                  55

gac ccg gac tcc ttc ctg aag tct gca cgg ctg cag cgg ctg cca tcg     246
Asp Pro Asp Ser Phe Leu Lys Ser Ala Arg Leu Gln Arg Leu Pro Ser
            60                  65                  70

tcg tcg tcg gag atg ggc agc caa gac ggg tcg ccg cta cgc gag acg     294
Ser Ser Ser Glu Met Gly Ser Gln Asp Gly Ser Pro Leu Arg Glu Thr
        75                  80                  85

cgc aaa gac ccg ttc tcc gcc gca gcg gcc gag tgc tcc tgc cgc cag     342
Arg Lys Asp Pro Phe Ser Ala Ala Ala Ala Glu Cys Ser Cys Arg Gln
     90                  95                 100

gat ggg ctc acg gtc atc gtc acg gcc tgt ctc acc ttc gct acc ggt     390
Asp Gly Leu Thr Val Ile Val Thr Ala Cys Leu Thr Phe Ala Thr Gly
105                 110                 115                 120

gtc acc gtg gcg ctg gtc atg cag atc tac ttc ggg gac ccc cag atc     438
Val Thr Val Ala Leu Val Met Gln Ile Tyr Phe Gly Asp Pro Gln Ile
                125                 130                 135

ttc cag cag ggt gcc gtg gtg acc gat gct gcc cgc tgc act tca ctg     486
Phe Gln Gln Gly Ala Val Val Thr Asp Ala Ala Arg Cys Thr Ser Leu
            140                 145                 150

ggc atc gag gtg ctc agt aaa cag gga tct tct gtg gac gca gcg gtg     534
Gly Ile Glu Val Leu Ser Lys Gln Gly Ser Ser Val Asp Ala Ala Val
        155                 160                 165

gca gca gcc ttg tgt ttg ggt atc gtg gct cca cac agt tct ggc ctg     582
Ala Ala Ala Leu Cys Leu Gly Ile Val Ala Pro His Ser Ser Gly Leu
    170                 175                 180

ggc ggt ggg ggc gtg atg ctg gta cat gac atc cga cga aat gag agc     630
Gly Gly Gly Gly Val Met Leu Val His Asp Ile Arg Arg Asn Glu Ser
185                 190                 195                 200

cac cta att gat ttc cgg gag tcc gca cca ggg gcc ctc agg gaa gag     678
His Leu Ile Asp Phe Arg Glu Ser Ala Pro Gly Ala Leu Arg Glu Glu
                205                 210                 215

acc ctg caa aga tcc tgg gag acc aag cct ggg ctc ttg gtg ggg gtt     726
Thr Leu Gln Arg Ser Trp Glu Thr Lys Pro Gly Leu Leu Val Gly Val
            220                 225                 230
```

-continued

```
ccc gga atg gtg aag ggg cta cat gaa gct cac cag ctc tat ggc agg      774
Pro Gly Met Val Lys Gly Leu His Glu Ala His Gln Leu Tyr Gly Arg
        235                 240                 245

ctg cca tgg tcc caa gtc ctg gcc ttt gca gca gct gtg gcc caa gat      822
Leu Pro Trp Ser Gln Val Leu Ala Phe Ala Ala Ala Val Ala Gln Asp
    250                 255                 260

ggc ttc aac gtg act cat gat cta gcc cgt gcc ctg gct gaa cag ctg      870
Gly Phe Asn Val Thr His Asp Leu Ala Arg Ala Leu Ala Glu Gln Leu
265                 270                 275                 280

cca ccc aac atg tcc gag cgc ttc cgg gag acg ttc ctg cca tcg ggc      918
Pro Pro Asn Met Ser Glu Arg Phe Arg Glu Thr Phe Leu Pro Ser Gly
                285                 290                 295

cgc ccg cca cta cct ggc tcg ttg ctg cat cgg ccc gac ctg gct gag      966
Arg Pro Pro Leu Pro Gly Ser Leu Leu His Arg Pro Asp Leu Ala Glu
            300                 305                 310

gtg ctg gat gta ctt ggc acc tcc ggc ccg gct gcc ttc tac gca ggt     1014
Val Leu Asp Val Leu Gly Thr Ser Gly Pro Ala Ala Phe Tyr Ala Gly
        315                 320                 325

ggc aac ctc aca ctg gag atg gtg gcc gag gct cag cac gca ggg ggt     1062
Gly Asn Leu Thr Leu Glu Met Val Ala Glu Ala Gln His Ala Gly Gly
    330                 335                 340

gtc ata acc gaa gag gac ttc agc aat tac agc gcc ctt gtg gag aag     1110
Val Ile Thr Glu Glu Asp Phe Ser Asn Tyr Ser Ala Leu Val Glu Lys
345                 350                 355                 360

cct gtg tgt ggc gtg tac aga ggc cac ctg gtt ctt agt ccc cca cct     1158
Pro Val Cys Gly Val Tyr Arg Gly His Leu Val Leu Ser Pro Pro Pro
                365                 370                 375

ccg cac acg ggc cct gcc ctc atc agt gct ctc aac atc ctg gag ggc     1206
Pro His Thr Gly Pro Ala Leu Ile Ser Ala Leu Asn Ile Leu Glu Gly
            380                 385                 390

ttc aat ctc acc agc ctg gta tcc cga gaa cag gct ctt cac tgg gtg     1254
Phe Asn Leu Thr Ser Leu Val Ser Arg Glu Gln Ala Leu His Trp Val
        395                 400                 405

gca gag acc ctg aag att gca tta gcc ctg gcc agc aga ctg gga gat     1302
Ala Glu Thr Leu Lys Ile Ala Leu Ala Leu Ala Ser Arg Leu Gly Asp
    410                 415                 420

ccc gtc tat gat tct acc atc act gag agc atg gat gac atg ctc agc     1350
Pro Val Tyr Asp Ser Thr Ile Thr Glu Ser Met Asp Asp Met Leu Ser
425                 430                 435                 440

aag gtg gag gcc gcc tac ctc cgg ggc cat atc aat gac tcc cag gca     1398
Lys Val Glu Ala Ala Tyr Leu Arg Gly His Ile Asn Asp Ser Gln Ala
                445                 450                 455

gcc cct gcc cca ctc ctg cct gtc tat gaa cta gac gga gct ccc acg     1446
Ala Pro Ala Pro Leu Leu Pro Val Tyr Glu Leu Asp Gly Ala Pro Thr
            460                 465                 470

gct gcc cag gtg ctg atc atg gga cct gat gac ttc att gtg gcc atg     1494
Ala Ala Gln Val Leu Ile Met Gly Pro Asp Asp Phe Ile Val Ala Met
        475                 480                 485

gtt agc tcc ctg aac cag ccc ttt ggc agc ggc ctt atc acc ccc tcg     1542
Val Ser Ser Leu Asn Gln Pro Phe Gly Ser Gly Leu Ile Thr Pro Ser
    490                 495                 500

ggg atc ctg ctc aac agc cag atg ctg gac ttc tcc tgg ccc aac cgg     1590
Gly Ile Leu Leu Asn Ser Gln Met Leu Asp Phe Ser Trp Pro Asn Arg
505                 510                 515                 520

aca gct aac cac tct gca ccc agc ctg gag aat tca gtg cag cca ggg     1638
Thr Ala Asn His Ser Ala Pro Ser Leu Glu Asn Ser Val Gln Pro Gly
                525                 530                 535

aag cgg cca ctc tct ttc ctg ctg ccc aca gtg gtc cga ccc gcg gag     1686
Lys Arg Pro Leu Ser Phe Leu Leu Pro Thr Val Val Arg Pro Ala Glu
```

-continued

```
            540                 545                 550

ggg ctc tgt gga acc tac ctc gct ctg ggg gcc aat gga gct gcg cgg      1734
Gly Leu Cys Gly Thr Tyr Leu Ala Leu Gly Ala Asn Gly Ala Ala Arg
        555                 560                 565

ggc ctc agc ggc ctg aca cag gtt ctg ctg aat gtc ctg acc ttg aac      1782
Gly Leu Ser Gly Leu Thr Gln Val Leu Leu Asn Val Leu Thr Leu Asn
    570                 575                 580

cgg aac ctg agt gac agc ctg gcc cgc ggc cgc cta cac ccg gac ctg      1830
Arg Asn Leu Ser Asp Ser Leu Ala Arg Gly Arg Leu His Pro Asp Leu
585                 590                 595                 600

cag tcc aac ctc ctg cag gtg gac agt gag ttc aca gag gaa gag att      1878
Gln Ser Asn Leu Leu Gln Val Asp Ser Glu Phe Thr Glu Glu Glu Ile
                605                 610                 615

gag ttc ctg gaa gcc agg ggt cac cac gtg gag aaa gta gat gtc tta      1926
Glu Phe Leu Glu Ala Arg Gly His His Val Glu Lys Val Asp Val Leu
            620                 625                 630

tcc tgg gtc cat ggc agc cga agg acc aac aac ttc atc atc gct gtt      1974
Ser Trp Val His Gly Ser Arg Arg Thr Asn Asn Phe Ile Ile Ala Val
        635                 640                 645

aag gac cct cgg agc cca gat gca gct gga gcc acc atc ctg tag          2019
Lys Asp Pro Arg Ser Pro Asp Ala Ala Gly Ala Thr Ile Leu  *
    650                 655                 660

agcagcgggg tggggcgggg tctctgctcc cccactttgc atgttcccag agtccctcct   2079

tctcccaggt ttggtctcag gggacccca gggatgcccc agatcagggg ccagaggga     2139

tgcttagcaa acccaatccc agagtaactg gaa                                 2172


<210> SEQ ID NO 11
<211> LENGTH: 662
<212> TYPE: PRT
<213> ORGANISM: Homo sapiens

<400> SEQUENCE: 11

Met Ala Ala Glu Asn Glu Ala Ser Gln Glu Ser Ala Leu Gly Ala Tyr
 1               5                  10                  15

Ser Pro Val Asp Tyr Met Ser Ile Thr Ser Phe Pro Arg Leu Pro Glu
            20                  25                  30

Asp Glu Pro Ala Pro Ala Ala Pro Leu Arg Gly Arg Lys Asp Glu Asp
        35                  40                  45

Ala Phe Leu Gly Asp Pro Asp Thr Asp Pro Asp Ser Phe Leu Lys Ser
    50                  55                  60

Ala Arg Leu Gln Arg Leu Pro Ser Ser Ser Ser Glu Met Gly Ser Gln
65                  70                  75                  80

Asp Gly Ser Pro Leu Arg Glu Thr Arg Lys Asp Pro Phe Ser Ala Ala
                85                  90                  95

Ala Ala Glu Cys Ser Cys Arg Gln Asp Gly Leu Thr Val Ile Val Thr
            100                 105                 110

Ala Cys Leu Thr Phe Ala Thr Gly Val Thr Val Ala Leu Val Met Gln
        115                 120                 125

Ile Tyr Phe Gly Asp Pro Gln Ile Phe Gln Gln Gly Ala Val Val Thr
    130                 135                 140

Asp Ala Ala Arg Cys Thr Ser Leu Gly Ile Glu Val Leu Ser Lys Gln
145                 150                 155                 160

Gly Ser Ser Val Asp Ala Ala Val Ala Ala Ala Leu Cys Leu Gly Ile
                165                 170                 175

Val Ala Pro His Ser Ser Gly Leu Gly Gly Gly Gly Val Met Leu Val
            180                 185                 190
```

-continued

```
His Asp Ile Arg Arg Asn Glu Ser His Leu Ile Asp Phe Arg Glu Ser
        195                 200                 205

Ala Pro Gly Ala Leu Arg Glu Glu Thr Leu Gln Arg Ser Trp Glu Thr
    210                 215                 220

Lys Pro Gly Leu Leu Val Gly Val Pro Gly Met Val Lys Gly Leu His
225                 230                 235                 240

Glu Ala His Gln Leu Tyr Gly Arg Leu Pro Trp Ser Gln Val Leu Ala
                245                 250                 255

Phe Ala Ala Ala Val Ala Gln Asp Gly Phe Asn Val Thr His Asp Leu
            260                 265                 270

Ala Arg Ala Leu Ala Glu Gln Leu Pro Pro Asn Met Ser Glu Arg Phe
        275                 280                 285

Arg Glu Thr Phe Leu Pro Ser Gly Arg Pro Pro Leu Pro Gly Ser Leu
    290                 295                 300

Leu His Arg Pro Asp Leu Ala Glu Val Leu Asp Val Leu Gly Thr Ser
305                 310                 315                 320

Gly Pro Ala Ala Phe Tyr Ala Gly Gly Asn Leu Thr Leu Glu Met Val
                325                 330                 335

Ala Glu Ala Gln His Ala Gly Gly Val Ile Thr Glu Glu Asp Phe Ser
            340                 345                 350

Asn Tyr Ser Ala Leu Val Glu Lys Pro Val Cys Gly Val Tyr Arg Gly
        355                 360                 365

His Leu Val Leu Ser Pro Pro Pro Pro His Thr Gly Pro Ala Leu Ile
    370                 375                 380

Ser Ala Leu Asn Ile Leu Glu Gly Phe Asn Leu Thr Ser Leu Val Ser
385                 390                 395                 400

Arg Glu Gln Ala Leu His Trp Val Ala Glu Thr Leu Lys Ile Ala Leu
                405                 410                 415

Ala Leu Ala Ser Arg Leu Gly Asp Pro Val Tyr Asp Ser Thr Ile Thr
            420                 425                 430

Glu Ser Met Asp Asp Met Leu Ser Lys Val Glu Ala Ala Tyr Leu Arg
        435                 440                 445

Gly His Ile Asn Asp Ser Gln Ala Ala Pro Ala Pro Leu Leu Pro Val
    450                 455                 460

Tyr Glu Leu Asp Gly Ala Pro Thr Ala Ala Gln Val Leu Ile Met Gly
465                 470                 475                 480

Pro Asp Asp Phe Ile Val Ala Met Val Ser Ser Leu Asn Gln Pro Phe
                485                 490                 495

Gly Ser Gly Leu Ile Thr Pro Ser Gly Ile Leu Leu Asn Ser Gln Met
            500                 505                 510

Leu Asp Phe Ser Trp Pro Asn Arg Thr Ala Asn His Ser Ala Pro Ser
        515                 520                 525

Leu Glu Asn Ser Val Gln Pro Gly Lys Arg Pro Leu Ser Phe Leu Leu
    530                 535                 540

Pro Thr Val Val Arg Pro Ala Glu Gly Leu Cys Gly Thr Tyr Leu Ala
545                 550                 555                 560

Leu Gly Ala Asn Gly Ala Ala Arg Gly Leu Ser Gly Leu Thr Gln Val
                565                 570                 575

Leu Leu Asn Val Leu Thr Leu Asn Arg Asn Leu Ser Asp Ser Leu Ala
            580                 585                 590

Arg Gly Arg Leu His Pro Asp Leu Gln Ser Asn Leu Leu Gln Val Asp
        595                 600                 605
```

-continued

```
Ser Glu Phe Thr Glu Glu Glu Ile Glu Phe Leu Glu Ala Arg Gly His
    610                 615                 620

His Val Glu Lys Val Asp Val Leu Ser Trp Val His Gly Ser Arg Arg
625                 630                 635                 640

Thr Asn Asn Phe Ile Ile Ala Val Lys Asp Pro Arg Ser Pro Asp Ala
                645                 650                 655

Ala Gly Ala Thr Ile Leu
            660


<210> SEQ ID NO 12
<211> LENGTH: 1989
<212> TYPE: DNA
<213> ORGANISM: Homo sapiens
<220> FEATURE:
<221> NAME/KEY: CDS
<222> LOCATION: (1)...(1989)

<400> SEQUENCE: 12

atg gcg gcg gag aac gag gcc agc cag gag agc gcc ctg ggc gcc tac       48
Met Ala Ala Glu Asn Glu Ala Ser Gln Glu Ser Ala Leu Gly Ala Tyr
 1               5                  10                  15

tcg cca gtg gac tac atg agc atc acc agc ttc ccg cgg ctg ccc gag       96
Ser Pro Val Asp Tyr Met Ser Ile Thr Ser Phe Pro Arg Leu Pro Glu
            20                  25                  30

gac gag ccg gcg ccc gcg gcc ccg ctg agg ggc cgc aag gac gag gac      144
Asp Glu Pro Ala Pro Ala Ala Pro Leu Arg Gly Arg Lys Asp Glu Asp
        35                  40                  45

gcc ttt ctg gga gac ccc gac acc gac ccg gac tcc ttc ctg aag tct      192
Ala Phe Leu Gly Asp Pro Asp Thr Asp Pro Asp Ser Phe Leu Lys Ser
    50                  55                  60

gca cgg ctg cag cgg ctg cca tcg tcg tcg tcg gag atg ggc agc caa      240
Ala Arg Leu Gln Arg Leu Pro Ser Ser Ser Ser Glu Met Gly Ser Gln
 65                  70                  75                  80

gac ggg tcg ccg cta cgc gag acg cgc aaa gac ccg ttc tcc gcc gca      288
Asp Gly Ser Pro Leu Arg Glu Thr Arg Lys Asp Pro Phe Ser Ala Ala
                85                  90                  95

gcg gcc gag tgc tcc tgc cgc cag gat ggg ctc acg gtc atc gtc acg      336
Ala Ala Glu Cys Ser Cys Arg Gln Asp Gly Leu Thr Val Ile Val Thr
            100                 105                 110

gcc tgt ctc acc ttc gct acc ggt gtc acc gtg gcg ctg gtc atg cag      384
Ala Cys Leu Thr Phe Ala Thr Gly Val Thr Val Ala Leu Val Met Gln
        115                 120                 125

atc tac ttc ggg gac ccc cag atc ttc cag cag ggt gcc gtg gtg acc      432
Ile Tyr Phe Gly Asp Pro Gln Ile Phe Gln Gln Gly Ala Val Val Thr
    130                 135                 140

gat gct gcc cgc tgc act tca ctg ggc atc gag gtg ctc agt aaa cag      480
Asp Ala Ala Arg Cys Thr Ser Leu Gly Ile Glu Val Leu Ser Lys Gln
145                 150                 155                 160

gga tct tct gtg gac gca gcg gtg gca gca gcc ttg tgt ttg ggt atc      528
Gly Ser Ser Val Asp Ala Ala Val Ala Ala Ala Leu Cys Leu Gly Ile
                165                 170                 175

gtg gct cca cac agt tct ggc ctg ggc ggt ggg ggc gtg atg ctg gta      576
Val Ala Pro His Ser Ser Gly Leu Gly Gly Gly Gly Val Met Leu Val
            180                 185                 190

cat gac atc cga cga aat gag agc cac cta att gat ttc cgg gag tcc      624
His Asp Ile Arg Arg Asn Glu Ser His Leu Ile Asp Phe Arg Glu Ser
        195                 200                 205

gca cca ggg gcc ctc agg gaa gag acc ctg caa aga tcc tgg gag acc      672
Ala Pro Gly Ala Leu Arg Glu Glu Thr Leu Gln Arg Ser Trp Glu Thr
    210                 215                 220
```

-continued

```
aag cct ggg ctc ttg gtg ggg gtt ccc gga atg gtg aag ggg cta cat       720
Lys Pro Gly Leu Leu Val Gly Val Pro Gly Met Val Lys Gly Leu His
225                 230                 235                 240

gaa gct cac cag ctc tat ggc agg ctg cca tgg tcc caa gtc ctg gcc       768
Glu Ala His Gln Leu Tyr Gly Arg Leu Pro Trp Ser Gln Val Leu Ala
                245                 250                 255

ttt gca gca gct gtg gcc caa gat ggc ttc aac gtg act cat gat cta       816
Phe Ala Ala Ala Val Ala Gln Asp Gly Phe Asn Val Thr His Asp Leu
            260                 265                 270

gcc cgt gcc ctg gct gaa cag ctg cca ccc aac atg tcc gag cgc ttc       864
Ala Arg Ala Leu Ala Glu Gln Leu Pro Pro Asn Met Ser Glu Arg Phe
        275                 280                 285

cgg gag acg ttc ctg cca tcg ggc cgc ccg cca cta cct ggc tcg ttg       912
Arg Glu Thr Phe Leu Pro Ser Gly Arg Pro Pro Leu Pro Gly Ser Leu
    290                 295                 300

ctg cat cgg ccc gac ctg gct gag gtg ctg gat gta ctt ggc acc tcc       960
Leu His Arg Pro Asp Leu Ala Glu Val Leu Asp Val Leu Gly Thr Ser
305                 310                 315                 320

ggc ccg gct gcc ttc tac gca ggt ggc aac ctc aca ctg gag atg gtg      1008
Gly Pro Ala Ala Phe Tyr Ala Gly Gly Asn Leu Thr Leu Glu Met Val
                325                 330                 335

gcc gag gct cag cac gca ggg ggt gtc ata acc gaa gag gac ttc agc      1056
Ala Glu Ala Gln His Ala Gly Gly Val Ile Thr Glu Glu Asp Phe Ser
            340                 345                 350

aat tac agc gcc ctt gtg gag aag cct gtg tgt ggc gtg tac aga ggc      1104
Asn Tyr Ser Ala Leu Val Glu Lys Pro Val Cys Gly Val Tyr Arg Gly
        355                 360                 365

cac ctg gtt ctt agt ccc cca cct ccg cac acg ggc cct gcc ctc atc      1152
His Leu Val Leu Ser Pro Pro Pro Pro His Thr Gly Pro Ala Leu Ile
    370                 375                 380

agt gct ctc aac atc ctg gag ggc ttc aat ctc acc agc ctg gta tcc      1200
Ser Ala Leu Asn Ile Leu Glu Gly Phe Asn Leu Thr Ser Leu Val Ser
385                 390                 395                 400

cga gaa cag gct ctt cac tgg gtg gca gag acc ctg aag att gca tta      1248
Arg Glu Gln Ala Leu His Trp Val Ala Glu Thr Leu Lys Ile Ala Leu
                405                 410                 415

gcc ctg gcc agc aga ctg gga gat ccc gtc tat gat tct acc atc act      1296
Ala Leu Ala Ser Arg Leu Gly Asp Pro Val Tyr Asp Ser Thr Ile Thr
            420                 425                 430

gag agc atg gat gac atg ctc agc aag gtg gag gcc gcc tac ctc cgg      1344
Glu Ser Met Asp Asp Met Leu Ser Lys Val Glu Ala Ala Tyr Leu Arg
        435                 440                 445

ggc cat atc aat gac tcc cag gca gcc cct gcc cca ctc ctg cct gtc      1392
Gly His Ile Asn Asp Ser Gln Ala Ala Pro Ala Pro Leu Leu Pro Val
    450                 455                 460

tat gaa cta gac gga gct ccc acg gct gcc cag gtg ctg atc atg gga      1440
Tyr Glu Leu Asp Gly Ala Pro Thr Ala Ala Gln Val Leu Ile Met Gly
465                 470                 475                 480

cct gat gac ttc att gtg gcc atg gtt agc tcc ctg aac cag ccc ttt      1488
Pro Asp Asp Phe Ile Val Ala Met Val Ser Ser Leu Asn Gln Pro Phe
                485                 490                 495

ggc agc ggc ctt atc acc ccc tcg ggg atc ctg ctc aac agc cag atg      1536
Gly Ser Gly Leu Ile Thr Pro Ser Gly Ile Leu Leu Asn Ser Gln Met
            500                 505                 510

ctg gac ttc tcc tgg ccc aac cgg aca gct aac cac tct gca ccc agc      1584
Leu Asp Phe Ser Trp Pro Asn Arg Thr Ala Asn His Ser Ala Pro Ser
        515                 520                 525

ctg gag aat tca gtg cag cca ggg aag cgg cca ctc tct ttc ctg ctg      1632
Leu Glu Asn Ser Val Gln Pro Gly Lys Arg Pro Leu Ser Phe Leu Leu
    530                 535                 540
```

-continued

| | |
|---|---|
| ccc aca gtg gtc cga ccc gcg gag ggg ctc tgt gga acc tac ctc gct<br>Pro Thr Val Val Arg Pro Ala Glu Gly Leu Cys Gly Thr Tyr Leu Ala<br>545                       550                    555                      560 | 1680 |
| ctg ggg gcc aat gga gct gcg cgg ggc ctc agc ggc ctg aca cag gtt<br>Leu Gly Ala Asn Gly Ala Ala Arg Gly Leu Ser Gly Leu Thr Gln Val<br>                       565                    570                      575 | 1728 |
| ctg ctg aat gtc ctg acc ttg aac cgg aac ctg agt gac agc ctg gcc<br>Leu Leu Asn Val Leu Thr Leu Asn Arg Asn Leu Ser Asp Ser Leu Ala<br>            580                    585                    590 | 1776 |
| cgc ggc cgc cta cac ccg gac ctg cag tcc aac ctc ctg cag gtg gac<br>Arg Gly Arg Leu His Pro Asp Leu Gln Ser Asn Leu Leu Gln Val Asp<br>                   595                    600                    605 | 1824 |
| agt gag ttc aca gag gaa gag att gag ttc ctg gaa gcc agg ggt cac<br>Ser Glu Phe Thr Glu Glu Glu Ile Glu Phe Leu Glu Ala Arg Gly His<br>610                       615                    620 | 1872 |
| cac gtg gag aaa gta gat gtc tta tcc tgg gtc cat ggc agc cga agg<br>His Val Glu Lys Val Asp Val Leu Ser Trp Val His Gly Ser Arg Arg<br>625                       630                    635                    640 | 1920 |
| acc aac aac ttc atc atc gct gtt aag gac cct cgg agc cca gat gca<br>Thr Asn Asn Phe Ile Ile Ala Val Lys Asp Pro Arg Ser Pro Asp Ala<br>                       645                    650                    655 | 1968 |
| gct gga gcc acc atc ctg tag<br>Ala Gly Ala Thr Ile Leu *<br>660 | 1989 |

<210> SEQ ID NO 13
<211> LENGTH: 1252
<212> TYPE: DNA
<213> ORGANISM: Homo sapiens
<220> FEATURE:
<221> NAME/KEY: CDS
<222> LOCATION: (18)...(1187)

<400> SEQUENCE: 13

| | |
|---|---|
| ccacgcgtcc ggaggcg atg agg gtg ttg gtg cgg cgc tgt tgg ggt cct<br>                        Met Arg Val Leu Val Arg Arg Cys Trp Gly Pro<br>                        1                5                        10 | 50 |
| ccg ctg gct cat ggc gcc agg cgt ggg agg ccg agt ccc cag tgg cga<br>Pro Leu Ala His Gly Ala Arg Arg Gly Arg Pro Ser Pro Gln Trp Arg<br>               15                    20                    25 | 98 |
| gca ctg gcc cga ctc ggc tgg gag gac tgc cgg gac tcc aga gtc cgc<br>Ala Leu Ala Arg Leu Gly Trp Glu Asp Cys Arg Asp Ser Arg Val Arg<br>             30                      35                    40 | 146 |
| gag aag cct ccc tgg cgg gtg ctc ttc ttc ggc acg gac cag ttc gcc<br>Glu Lys Pro Pro Trp Arg Val Leu Phe Phe Gly Thr Asp Gln Phe Ala<br>45                       50                    55 | 194 |
| cgc gag gcg ctg cgg gcg ctg cac gcc gcc agg gaa aac aaa gaa gaa<br>Arg Glu Ala Leu Arg Ala Leu His Ala Ala Arg Glu Asn Lys Glu Glu<br>  60                    65                    70                    75 | 242 |
| gag tta atc gac aaa ctg gag gtg gtc aca atg cct tcc cca tca cca<br>Glu Leu Ile Asp Lys Leu Glu Val Val Thr Met Pro Ser Pro Ser Pro<br>                80                    85                    90 | 290 |
| aaa gga ctg cca gtg aag caa tat gct gtg cag tct cag ctt ccc gta<br>Lys Gly Leu Pro Val Lys Gln Tyr Ala Val Gln Ser Gln Leu Pro Val<br>             95                     100                  105 | 338 |
| tat gag tgg ccg gat gtg gga tct gga gaa tat gat gtt gga gta gtg<br>Tyr Glu Trp Pro Asp Val Gly Ser Gly Glu Tyr Asp Val Gly Val Val<br>110                      115                    120 | 386 |
| gct tcg ttt ggc cga ctt ttg aat gag gct ctt att ctt aaa ttt ccc<br>Ala Ser Phe Gly Arg Leu Leu Asn Glu Ala Leu Ile Leu Lys Phe Pro<br>125                      130                    135 | 434 |

-continued

```
tat ggc ata ttg aat gtt cat ccc agt tgc ctc ccg aga tgg cgt ggc      482
Tyr Gly Ile Leu Asn Val His Pro Ser Cys Leu Pro Arg Trp Arg Gly
140                 145                 150                 155

cca gcc cct gta atc cat aca gtg ctt cac gga gac aca gtt act gga      530
Pro Ala Pro Val Ile His Thr Val Leu His Gly Asp Thr Val Thr Gly
                160                 165                 170

gta aca att atg caa att aga cct aaa agg ttt gat gta ggc cca att      578
Val Thr Ile Met Gln Ile Arg Pro Lys Arg Phe Asp Val Gly Pro Ile
            175                 180                 185

ctc aaa caa gaa act gtt cct gtg cca ccc aag agc act gca aag gaa      626
Leu Lys Gln Glu Thr Val Pro Val Pro Pro Lys Ser Thr Ala Lys Glu
        190                 195                 200

ttg gaa gca gtg ttg tca aga ctg ggt gcc aac atg ctc att tca gtt      674
Leu Glu Ala Val Leu Ser Arg Leu Gly Ala Asn Met Leu Ile Ser Val
    205                 210                 215

ttg aaa aat ttg cct gaa agt ctg agc aat gga agg cag cag cca atg      722
Leu Lys Asn Leu Pro Glu Ser Leu Ser Asn Gly Arg Gln Gln Pro Met
220                 225                 230                 235

gag ggg gcg act tac gcc cct aag att tct gct ggt acc agt tgt ata      770
Glu Gly Ala Thr Tyr Ala Pro Lys Ile Ser Ala Gly Thr Ser Cys Ile
                240                 245                 250

aaa tgg gag gaa caa act tca gaa caa ata ttc aga ctt tac cgt gcc      818
Lys Trp Glu Glu Gln Thr Ser Glu Gln Ile Phe Arg Leu Tyr Arg Ala
            255                 260                 265

att gga aat ata att ccg ttg cag acg ctc tgg atg gcg aat acc att      866
Ile Gly Asn Ile Ile Pro Leu Gln Thr Leu Trp Met Ala Asn Thr Ile
        270                 275                 280

aaa ctt ctg gat ttg gta gaa gtt aac agt tca gtc ctt gct gat cca      914
Lys Leu Leu Asp Leu Val Glu Val Asn Ser Ser Val Leu Ala Asp Pro
    285                 290                 295

aaa tta acg gga cag gct ctt att cca gga tca gta ata tac cac aaa      962
Lys Leu Thr Gly Gln Ala Leu Ile Pro Gly Ser Val Ile Tyr His Lys
300                 305                 310                 315

cag tca caa ata cta ttg gtt tat tgc aag gat ggt tgg att ggt gtt     1010
Gln Ser Gln Ile Leu Leu Val Tyr Cys Lys Asp Gly Trp Ile Gly Val
                320                 325                 330

cga tca gtg atg ctc aag aaa tca cta aca gct act gac ttc tac aat     1058
Arg Ser Val Met Leu Lys Lys Ser Leu Thr Ala Thr Asp Phe Tyr Asn
            335                 340                 345

gga tat ttg cac ccc tgg tac cag aaa aat tcc caa gct caa cca agc     1106
Gly Tyr Leu His Pro Trp Tyr Gln Lys Asn Ser Gln Ala Gln Pro Ser
        350                 355                 360

caa tgc aga ttt cag act ctc aga ctt cca aca aag aag aag cag aaa     1154
Gln Cys Arg Phe Gln Thr Leu Arg Leu Pro Thr Lys Lys Lys Gln Lys
    365                 370                 375

aaa act gtt gct atg caa caa tgc att gag tag ttaggaagaa gatggataaa   1207
Lys Thr Val Ala Met Gln Gln Cys Ile Glu  *
380                 385

aacctattac atatttgtaa tttattaaaa accttattta caagg                   1252
```

<210> SEQ ID NO 14
<211> LENGTH: 389
<212> TYPE: PRT
<213> ORGANISM: Homo sapiens

<400> SEQUENCE: 14

```
Met Arg Val Leu Val Arg Arg Cys Trp Gly Pro Pro Leu Ala His Gly
 1               5                  10                  15

Ala Arg Arg Gly Arg Pro Ser Pro Gln Trp Arg Ala Leu Ala Arg Leu
```

-continued

```
            20                  25                  30

Gly Trp Glu Asp Cys Arg Asp Ser Arg Val Arg Glu Lys Pro Pro Trp
        35                  40                  45

Arg Val Leu Phe Phe Gly Thr Asp Gln Phe Ala Arg Glu Ala Leu Arg
    50                  55                  60

Ala Leu His Ala Ala Arg Glu Asn Lys Glu Glu Glu Leu Ile Asp Lys
65                  70                  75                  80

Leu Glu Val Val Thr Met Pro Ser Pro Ser Pro Lys Gly Leu Pro Val
                85                  90                  95

Lys Gln Tyr Ala Val Gln Ser Gln Leu Pro Val Tyr Glu Trp Pro Asp
            100                 105                 110

Val Gly Ser Gly Glu Tyr Asp Val Gly Val Val Ala Ser Phe Gly Arg
        115                 120                 125

Leu Leu Asn Glu Ala Leu Ile Leu Lys Phe Pro Tyr Gly Ile Leu Asn
    130                 135                 140

Val His Pro Ser Cys Leu Pro Arg Trp Arg Gly Pro Ala Pro Val Ile
145                 150                 155                 160

His Thr Val Leu His Gly Asp Thr Val Thr Gly Val Thr Ile Met Gln
                165                 170                 175

Ile Arg Pro Lys Arg Phe Asp Val Gly Pro Ile Leu Lys Gln Glu Thr
            180                 185                 190

Val Pro Val Pro Pro Lys Ser Thr Ala Lys Glu Leu Glu Ala Val Leu
        195                 200                 205

Ser Arg Leu Gly Ala Asn Met Leu Ile Ser Val Leu Lys Asn Leu Pro
    210                 215                 220

Glu Ser Leu Ser Asn Gly Arg Gln Gln Pro Met Glu Gly Ala Thr Tyr
225                 230                 235                 240

Ala Pro Lys Ile Ser Ala Gly Thr Ser Cys Ile Lys Trp Glu Glu Gln
                245                 250                 255

Thr Ser Glu Gln Ile Phe Arg Leu Tyr Arg Ala Ile Gly Asn Ile Ile
            260                 265                 270

Pro Leu Gln Thr Leu Trp Met Ala Asn Thr Ile Lys Leu Leu Asp Leu
        275                 280                 285

Val Glu Val Asn Ser Ser Val Leu Ala Asp Pro Lys Leu Thr Gly Gln
    290                 295                 300

Ala Leu Ile Pro Gly Ser Val Ile Tyr His Lys Gln Ser Gln Ile Leu
305                 310                 315                 320

Leu Val Tyr Cys Lys Asp Gly Trp Ile Gly Val Arg Ser Val Met Leu
                325                 330                 335

Lys Lys Ser Leu Thr Ala Thr Asp Phe Tyr Asn Gly Tyr Leu His Pro
            340                 345                 350

Trp Tyr Gln Lys Asn Ser Gln Ala Gln Pro Ser Gln Cys Arg Phe Gln
        355                 360                 365

Thr Leu Arg Leu Pro Thr Lys Lys Lys Gln Lys Lys Thr Val Ala Met
    370                 375                 380

Gln Gln Cys Ile Glu
385
```

<210> SEQ ID NO 15
<211> LENGTH: 1170
<212> TYPE: DNA
<213> ORGANISM: Homo sapiens
<220> FEATURE:
<221> NAME/KEY: CDS
<222> LOCATION: (1)...(1170)

-continued

<400> SEQUENCE: 15

```
atg agg gtg ttg gtg cgg cgc tgt tgg ggt cct ccg ctg gct cat ggc       48
Met Arg Val Leu Val Arg Arg Cys Trp Gly Pro Pro Leu Ala His Gly
 1               5                  10                  15

gcc agg cgt ggg agg ccg agt ccc cag tgg cga gca ctg gcc cga ctc       96
Ala Arg Arg Gly Arg Pro Ser Pro Gln Trp Arg Ala Leu Ala Arg Leu
            20                  25                  30

ggc tgg gag gac tgc cgg gac tcc aga gtc cgc gag aag cct ccc tgg      144
Gly Trp Glu Asp Cys Arg Asp Ser Arg Val Arg Glu Lys Pro Pro Trp
        35                  40                  45

cgg gtg ctc ttc ttc ggc acg gac cag ttc gcc cgc gag gcg ctg cgg      192
Arg Val Leu Phe Phe Gly Thr Asp Gln Phe Ala Arg Glu Ala Leu Arg
    50                  55                  60

gcg ctg cac gcc gcc agg gaa aac aaa gaa gaa gag tta atc gac aaa      240
Ala Leu His Ala Ala Arg Glu Asn Lys Glu Glu Glu Leu Ile Asp Lys
 65                  70                  75                  80

ctg gag gtg gtc aca atg cct tcc cca tca cca aaa gga ctg cca gtg      288
Leu Glu Val Val Thr Met Pro Ser Pro Ser Pro Lys Gly Leu Pro Val
                 85                  90                  95

aag caa tat gct gtg cag tct cag ctt ccc gta tat gag tgg ccg gat      336
Lys Gln Tyr Ala Val Gln Ser Gln Leu Pro Val Tyr Glu Trp Pro Asp
            100                 105                 110

gtg gga tct gga gaa tat gat gtt gga gta gtg gct tcg ttt ggc cga      384
Val Gly Ser Gly Glu Tyr Asp Val Gly Val Val Ala Ser Phe Gly Arg
        115                 120                 125

ctt ttg aat gag gct ctt att ctt aaa ttt ccc tat ggc ata ttg aat      432
Leu Leu Asn Glu Ala Leu Ile Leu Lys Phe Pro Tyr Gly Ile Leu Asn
    130                 135                 140

gtt cat ccc agt tgc ctc ccg aga tgg cgt ggc cca gcc cct gta atc      480
Val His Pro Ser Cys Leu Pro Arg Trp Arg Gly Pro Ala Pro Val Ile
145                 150                 155                 160

cat aca gtg ctt cac gga gac aca gtt act gga gta aca att atg caa      528
His Thr Val Leu His Gly Asp Thr Val Thr Gly Val Thr Ile Met Gln
                165                 170                 175

att aga cct aaa agg ttt gat gta ggc cca att ctc aaa caa gaa act      576
Ile Arg Pro Lys Arg Phe Asp Val Gly Pro Ile Leu Lys Gln Glu Thr
            180                 185                 190

gtt cct gtg cca ccc aag agc act gca aag gaa ttg gaa gca gtg ttg      624
Val Pro Val Pro Pro Lys Ser Thr Ala Lys Glu Leu Glu Ala Val Leu
        195                 200                 205

tca aga ctg ggt gcc aac atg ctc att tca gtt ttg aaa aat ttg cct      672
Ser Arg Leu Gly Ala Asn Met Leu Ile Ser Val Leu Lys Asn Leu Pro
    210                 215                 220

gaa agt ctg agc aat gga agg cag cag cca atg gag ggg gcg act tac      720
Glu Ser Leu Ser Asn Gly Arg Gln Gln Pro Met Glu Gly Ala Thr Tyr
225                 230                 235                 240

gcc cct aag att tct gct ggt acc agt tgt ata aaa tgg gag gaa caa      768
Ala Pro Lys Ile Ser Ala Gly Thr Ser Cys Ile Lys Trp Glu Glu Gln
                245                 250                 255

act tca gaa caa ata ttc aga ctt tac cgt gcc att gga aat ata att      816
Thr Ser Glu Gln Ile Phe Arg Leu Tyr Arg Ala Ile Gly Asn Ile Ile
            260                 265                 270

ccg ttg cag acg ctc tgg atg gcg aat acc att aaa ctt ctg gat ttg      864
Pro Leu Gln Thr Leu Trp Met Ala Asn Thr Ile Lys Leu Leu Asp Leu
        275                 280                 285

gta gaa gtt aac agt tca gtc ctt gct gat cca aaa tta acg gga cag      912
Val Glu Val Asn Ser Ser Val Leu Ala Asp Pro Lys Leu Thr Gly Gln
    290                 295                 300
```

-continued

```
gct ctt att cca gga tca gta ata tac cac aaa cag tca caa ata cta      960
Ala Leu Ile Pro Gly Ser Val Ile Tyr His Lys Gln Ser Gln Ile Leu
305                 310                 315                 320

ttg gtt tat tgc aag gat ggt tgg att ggt gtt cga tca gtg atg ctc     1008
Leu Val Tyr Cys Lys Asp Gly Trp Ile Gly Val Arg Ser Val Met Leu
                325                 330                 335

aag aaa tca cta aca gct act gac ttc tac aat gga tat ttg cac ccc     1056
Lys Lys Ser Leu Thr Ala Thr Asp Phe Tyr Asn Gly Tyr Leu His Pro
            340                 345                 350

tgg tac cag aaa aat tcc caa gct caa cca agc caa tgc aga ttt cag     1104
Trp Tyr Gln Lys Asn Ser Gln Ala Gln Pro Ser Gln Cys Arg Phe Gln
        355                 360                 365

act ctc aga ctt cca aca aag aag aag cag aaa aaa act gtt gct atg     1152
Thr Leu Arg Leu Pro Thr Lys Lys Lys Gln Lys Lys Thr Val Ala Met
    370                 375                 380

caa caa tgc att gag tag                                             1170
Gln Gln Cys Ile Glu  *
385


<210> SEQ ID NO 16
<211> LENGTH: 1797
<212> TYPE: DNA
<213> ORGANISM: Homo sapiens
<220> FEATURE:
<221> NAME/KEY: CDS
<222> LOCATION: (215)...(1189)

<400> SEQUENCE: 16

cgtccgcttt cacacgggtt gcttcggagg aatccgccgt gcaaatctgt ccgccccctt     60

ggccactgat cccccgaaga gcttctgtcg ccgctctagg aatacagaca ttgaagtttg    120

ggacaagata tttatctaac ttctgtgtca aaattagcga cctgctatgg caatgaagaa    180

agaaactgaa tttgtcattt tcacctgaag aaaa atg ata gac aaa aat caa acc    235
                                      Met Ile Asp Lys Asn Gln Thr
                                       1               5

tgt ggt gta gga cag gat tct gtg ccc tat atg att tgt ctg att cac      283
Cys Gly Val Gly Gln Asp Ser Val Pro Tyr Met Ile Cys Leu Ile His
         10                  15                  20

ata ctc gaa gaa tgg ttt ggt gtg gag cag ttg gag gac tat ttg aat      331
Ile Leu Glu Glu Trp Phe Gly Val Glu Gln Leu Glu Asp Tyr Leu Asn
     25                  30                  35

ttt gca aac tat ctc ttg tgg gtt ttt aca cca cta ata ctt tta ata      379
Phe Ala Asn Tyr Leu Leu Trp Val Phe Thr Pro Leu Ile Leu Leu Ile
 40                  45                  50                  55

ctt cct tac ttt act atc ttt ctt ctc tac ctt act att att ttc tta      427
Leu Pro Tyr Phe Thr Ile Phe Leu Leu Tyr Leu Thr Ile Ile Phe Leu
                 60                  65                  70

cac att tat aag aga aag aat gta ttg aaa gaa gcc tac tct cat aat      475
His Ile Tyr Lys Arg Lys Asn Val Leu Lys Glu Ala Tyr Ser His Asn
             75                  80                  85

tta tgg gat ggt gca agg aaa aca gtg gca act ctg tgg gat gga cat      523
Leu Trp Asp Gly Ala Arg Lys Thr Val Ala Thr Leu Trp Asp Gly His
         90                  95                 100

gca gcc gtt tgg cat ggt tat gaa gtt cat gga atg gaa aaa ata cca      571
Ala Ala Val Trp His Gly Tyr Glu Val His Gly Met Glu Lys Ile Pro
    105                 110                 115

gaa gat gga cca gca ctt ata att ttt tat cat gga gct att cct ata      619
Glu Asp Gly Pro Ala Leu Ile Ile Phe Tyr His Gly Ala Ile Pro Ile
120                 125                 130                 135

gat ttt tac tat ttc atg gct aaa ata ttt ata cac aaa ggc aga act      667
Asp Phe Tyr Tyr Phe Met Ala Lys Ile Phe Ile His Lys Gly Arg Thr
```

-continued

```
                140                 145                 150

tgc cga gta gta gct gat cac ttt gtc ttt aaa att cca ggg ttt agt      715
Cys Arg Val Val Ala Asp His Phe Val Phe Lys Ile Pro Gly Phe Ser
            155                 160                 165

tta tta ctg gat gtg ttt tgt gct cta cat gga cca aga gaa aaa tgt      763
Leu Leu Leu Asp Val Phe Cys Ala Leu His Gly Pro Arg Glu Lys Cys
        170                 175                 180

gtt gaa att ctg agg agt ggc cac ttg tta gct atc tca cca ggt gga      811
Val Glu Ile Leu Arg Ser Gly His Leu Leu Ala Ile Ser Pro Gly Gly
    185                 190                 195

gtt cga gaa gcc cta att agt gat gaa act tat aac atc gta tgg ggt      859
Val Arg Glu Ala Leu Ile Ser Asp Glu Thr Tyr Asn Ile Val Trp Gly
200                 205                 210                 215

cat cgc aga ggc ttt gct cag gtt gca att gat gca aaa gtg ccc att      907
His Arg Arg Gly Phe Ala Gln Val Ala Ile Asp Ala Lys Val Pro Ile
                220                 225                 230

att cct atg ttt aca caa aat att cga gaa gga ttt aga tca ctt gga      955
Ile Pro Met Phe Thr Gln Asn Ile Arg Glu Gly Phe Arg Ser Leu Gly
            235                 240                 245

gga aca agg tta ttt agg tgg ctt tat gaa aaa ttc cgc tat cca ttt     1003
Gly Thr Arg Leu Phe Arg Trp Leu Tyr Glu Lys Phe Arg Tyr Pro Phe
        250                 255                 260

gct cca atg tat gga ggt ttt cca gtg aag tta cgg acc tat tta ggc     1051
Ala Pro Met Tyr Gly Gly Phe Pro Val Lys Leu Arg Thr Tyr Leu Gly
    265                 270                 275

gac ccc att ccg tat gac cca cag ata aca gcg gaa gaa tta gct gaa     1099
Asp Pro Ile Pro Tyr Asp Pro Gln Ile Thr Ala Glu Glu Leu Ala Glu
280                 285                 290                 295

aag acg aag aat gct gtt caa gct ttg att gat aag cac caa aga ata     1147
Lys Thr Lys Asn Ala Val Gln Ala Leu Ile Asp Lys His Gln Arg Ile
                300                 305                 310

cca gga aac att atg agt gct ttg tta gaa cgt ttt cat tga             1189
Pro Gly Asn Ile Met Ser Ala Leu Leu Glu Arg Phe His  *
            315                 320

taacaaaggg tcaactagaa gatgatttag tacatttata ttaaatgttt gtatctaagg   1249

tactgtcttc tgaattttgt aggtcctata attagtattt tttaaaaaaa tcatgttaat   1309

aagcatcttt cacagaattc gtttctttaa aatagtcaat tttgtttttg caattgtgtc   1369

aaatactaac aaattacaca cctagtaatt cagaaaaaga tgtcttattt gtaaattcct   1429

aacaatttat gctaaacata tagattctta agtttattaa taacagcagt ttaggttaaa   1489

caaacattcc tggataatgc gttaaatttc tgtatctgtc gccctgagct gattttgaaa   1549

gatggtataa gctaggggtt agtatagttg tttaagttag aaaaaacatg ctgttgtctg   1609

cccctcattc ccttcatgac cttgggcaag tcacgtaatg tttttgtgcc tcaacaattc   1669

actttttaaa aacatgatcg tatgatgaat gatattattt tgttatttat atttactgtg   1729

attgataact gttgaaccaa aataataaaa taattaattt aaacaatgtc aaaaaaaaaa   1789

aaaaaaaa                                                            1797


<210> SEQ ID NO 17
<211> LENGTH: 324
<212> TYPE: PRT
<213> ORGANISM: Homo sapiens

<400> SEQUENCE: 17

Met Ile Asp Lys Asn Gln Thr Cys Gly Val Gly Gln Asp Ser Val Pro
 1               5                  10                  15
```

-continued

```
Tyr Met Ile Cys Leu Ile His Ile Leu Glu Glu Trp Phe Gly Val Glu
            20                  25                  30

Gln Leu Glu Asp Tyr Leu Asn Phe Ala Asn Tyr Leu Leu Trp Val Phe
        35                  40                  45

Thr Pro Leu Ile Leu Leu Ile Leu Pro Tyr Phe Thr Ile Phe Leu Leu
    50                  55                  60

Tyr Leu Thr Ile Ile Phe Leu His Ile Tyr Lys Arg Lys Asn Val Leu
65                  70                  75                  80

Lys Glu Ala Tyr Ser His Asn Leu Trp Asp Gly Ala Arg Lys Thr Val
                85                  90                  95

Ala Thr Leu Trp Asp Gly His Ala Ala Val Trp His Gly Tyr Glu Val
            100                 105                 110

His Gly Met Glu Lys Ile Pro Glu Asp Gly Pro Ala Leu Ile Ile Phe
        115                 120                 125

Tyr His Gly Ala Ile Pro Ile Asp Phe Tyr Tyr Phe Met Ala Lys Ile
    130                 135                 140

Phe Ile His Lys Gly Arg Thr Cys Arg Val Val Ala Asp His Phe Val
145                 150                 155                 160

Phe Lys Ile Pro Gly Phe Ser Leu Leu Leu Asp Val Phe Cys Ala Leu
                165                 170                 175

His Gly Pro Arg Glu Lys Cys Val Glu Ile Leu Arg Ser Gly His Leu
            180                 185                 190

Leu Ala Ile Ser Pro Gly Gly Val Arg Glu Ala Leu Ile Ser Asp Glu
        195                 200                 205

Thr Tyr Asn Ile Val Trp Gly His Arg Arg Gly Phe Ala Gln Val Ala
    210                 215                 220

Ile Asp Ala Lys Val Pro Ile Ile Pro Met Phe Thr Gln Asn Ile Arg
225                 230                 235                 240

Glu Gly Phe Arg Ser Leu Gly Gly Thr Arg Leu Phe Arg Trp Leu Tyr
                245                 250                 255

Glu Lys Phe Arg Tyr Pro Phe Ala Pro Met Tyr Gly Gly Phe Pro Val
            260                 265                 270

Lys Leu Arg Thr Tyr Leu Gly Asp Pro Ile Pro Tyr Asp Pro Gln Ile
        275                 280                 285

Thr Ala Glu Glu Leu Ala Glu Lys Thr Lys Asn Ala Val Gln Ala Leu
    290                 295                 300

Ile Asp Lys His Gln Arg Ile Pro Gly Asn Ile Met Ser Ala Leu Leu
305                 310                 315                 320

Glu Arg Phe His


<210> SEQ ID NO 18
<211> LENGTH: 975
<212> TYPE: DNA
<213> ORGANISM: Homo sapiens
<220> FEATURE:
<221> NAME/KEY: CDS
<222> LOCATION: (1)...(975)

<400> SEQUENCE: 18

atg ata gac aaa aat caa acc tgt ggt gta gga cag gat tct gtg ccc       48
Met Ile Asp Lys Asn Gln Thr Cys Gly Val Gly Gln Asp Ser Val Pro
 1               5                  10                  15

tat atg att tgt ctg att cac ata ctc gaa gaa tgg ttt ggt gtg gag       96
Tyr Met Ile Cys Leu Ile His Ile Leu Glu Glu Trp Phe Gly Val Glu
             20                  25                  30

cag ttg gag gac tat ttg aat ttt gca aac tat ctc ttg tgg gtt ttt      144
```

-continued

```
Gln Leu Glu Asp Tyr Leu Asn Phe Ala Asn Tyr Leu Leu Trp Val Phe
        35                  40                  45

aca cca cta ata ctt tta ata ctt cct tac ttt act atc ttt ctt ctc      192
Thr Pro Leu Ile Leu Leu Ile Leu Pro Tyr Phe Thr Ile Phe Leu Leu
    50                  55                  60

tac ctt act att att ttc tta cac att tat aag aga aag aat gta ttg      240
Tyr Leu Thr Ile Ile Phe Leu His Ile Tyr Lys Arg Lys Asn Val Leu
65                  70                  75                  80

aaa gaa gcc tac tct cat aat tta tgg gat ggt gca agg aaa aca gtg      288
Lys Glu Ala Tyr Ser His Asn Leu Trp Asp Gly Ala Arg Lys Thr Val
                85                  90                  95

gca act ctg tgg gat gga cat gca gcc gtt tgg cat ggt tat gaa gtt      336
Ala Thr Leu Trp Asp Gly His Ala Ala Val Trp His Gly Tyr Glu Val
            100                 105                 110

cat gga atg gaa aaa ata cca gaa gat gga cca gca ctt ata att ttt      384
His Gly Met Glu Lys Ile Pro Glu Asp Gly Pro Ala Leu Ile Ile Phe
        115                 120                 125

tat cat gga gct att cct ata gat ttt tac tat ttc atg gct aaa ata      432
Tyr His Gly Ala Ile Pro Ile Asp Phe Tyr Tyr Phe Met Ala Lys Ile
    130                 135                 140

ttt ata cac aaa ggc aga act tgc cga gta gta gct gat cac ttt gtc      480
Phe Ile His Lys Gly Arg Thr Cys Arg Val Val Ala Asp His Phe Val
145                 150                 155                 160

ttt aaa att cca ggg ttt agt tta tta ctg gat gtg ttt tgt gct cta      528
Phe Lys Ile Pro Gly Phe Ser Leu Leu Leu Asp Val Phe Cys Ala Leu
                165                 170                 175

cat gga cca aga gaa aaa tgt gtt gaa att ctg agg agt ggc cac ttg      576
His Gly Pro Arg Glu Lys Cys Val Glu Ile Leu Arg Ser Gly His Leu
            180                 185                 190

tta gct atc tca cca ggt gga gtt cga gaa gcc cta att agt gat gaa      624
Leu Ala Ile Ser Pro Gly Gly Val Arg Glu Ala Leu Ile Ser Asp Glu
        195                 200                 205

act tat aac atc gta tgg ggt cat cgc aga ggc ttt gct cag gtt gca      672
Thr Tyr Asn Ile Val Trp Gly His Arg Arg Gly Phe Ala Gln Val Ala
    210                 215                 220

att gat gca aaa gtg ccc att att cct atg ttt aca caa aat att cga      720
Ile Asp Ala Lys Val Pro Ile Ile Pro Met Phe Thr Gln Asn Ile Arg
225                 230                 235                 240

gaa gga ttt aga tca ctt gga gga aca agg tta ttt agg tgg ctt tat      768
Glu Gly Phe Arg Ser Leu Gly Gly Thr Arg Leu Phe Arg Trp Leu Tyr
                245                 250                 255

gaa aaa ttc cgc tat cca ttt gct cca atg tat gga ggt ttt cca gtg      816
Glu Lys Phe Arg Tyr Pro Phe Ala Pro Met Tyr Gly Gly Phe Pro Val
            260                 265                 270

aag tta cgg acc tat tta ggc gac ccc att ccg tat gac cca cag ata      864
Lys Leu Arg Thr Tyr Leu Gly Asp Pro Ile Pro Tyr Asp Pro Gln Ile
        275                 280                 285

aca gcg gaa gaa tta gct gaa aag acg aag aat gct gtt caa gct ttg      912
Thr Ala Glu Glu Leu Ala Glu Lys Thr Lys Asn Ala Val Gln Ala Leu
    290                 295                 300

att gat aag cac caa aga ata cca gga aac att atg agt gct ttg tta      960
Ile Asp Lys His Gln Arg Ile Pro Gly Asn Ile Met Ser Ala Leu Leu
305                 310                 315                 320

gaa cgt ttt cat tga                                                  975
Glu Arg Phe His  *
```

<210> SEQ ID NO 19
<211> LENGTH: 114
<212> TYPE: PRT
<213> ORGANISM: Artificial Sequence -continued
<220> FEATURE:
<223> OTHER INFORMATION: Amino acid consensus sequence

<400> SEQUENCE: 19

Ser Ser Ile Gly Thr Pro Val Arg Ile Arg Glu Phe Asn Asn Ser Asn
1 5 10 15

Gly Val Ser Val Ile Leu Trp Pro Cys Ser Gly Thr Thr Gly Ser Val
20 25 30

Val Trp Asp Ala Gly Val Val Leu Ser Lys Tyr Leu Leu Ser Ser Thr
35 40 45

Gln Pro His Ala Leu Ser His Ser Leu Asn Gly Lys Lys Lys Val Leu
50 55 60

Glu Leu Gly Ser Gly Thr Gly Leu Val Gly Ile Ala Ala Ala Leu Cys
65 70 75 80

Leu Gly Gly Ala Asn Val Val Leu Thr Asp Leu Pro Asp Val Leu Pro
85 90 95

Leu Leu Lys Lys Asn Val Glu Ala Asn Lys His Leu Val Gly Asn Asn
100 105 110

Ile Lys

<210> SEQ ID NO 20
<211> LENGTH: 102
<212> TYPE: PRT
<213> ORGANISM: Artificial Sequence
<220> FEATURE:
<223> OTHER INFORMATION: Amino acid consensus sequence

<400> SEQUENCE: 20

Ile Val Tyr Trp Asn Asn Arg Asp Gln Ile Ser Ala Leu Lys Pro Pro
1 5 10 15

Phe Asp Leu Val Ile Ala Ala Asp Val Val Tyr Ile Glu Glu Ser Val
20 25 30

Gly Gln Leu Val Thr Ala Met Glu Leu Leu Val Ala Asp Asp Gly Ala
35 40 45

Val Leu Leu Gly Tyr Gln Ile Arg Ser Pro Glu Ala Asp Lys Leu Phe
50 55 60

Trp Glu Leu Cys Asp Ile Val Phe Lys Ile Glu Lys Val Pro His Glu
65 70 75 80

His Leu His Ser Asp Tyr Ala Tyr Glu Glu Thr Asp Val Tyr Ile Phe
85 90 95

Arg Lys Lys Val Lys Lys
100

<210> SEQ ID NO 21
<211> LENGTH: 211
<212> TYPE: PRT
<213> ORGANISM: Artificial Sequence
<220> FEATURE:
<223> OTHER INFORMATION: Amino acid consensus sequence

<400> SEQUENCE: 21

Ser Ile Val Arg Tyr Phe Glu Leu Arg Asn Leu Ser Thr Ser Ile Pro
1 5 10 15

Leu His Glu Pro Ser Leu Thr Ala Asp Asn Leu Gly Trp Lys Thr Trp
20 25 30

Gly Ser Ser Leu Ile Leu Ser Gln Leu Val Val Asp His Leu Asp Tyr
35 40 45

Leu His Thr Thr Asn Val Asn Met Leu Ala Asn Ser Asp Ile Lys Gln

-continued

```
    50                  55                  60

Ile Lys Val Leu Glu Leu Gly Ala Gly Thr Gly Leu Val Gly Leu Ser
65                  70                  75                  80

Trp Ala Leu Lys Trp Lys Glu Leu Tyr Gly Thr Glu Asn Ile Glu Ile
                85                  90                  95

Phe Val Thr Asp Leu Pro Glu Ile Val Thr Asn Leu Lys Lys Asn Val
            100                 105                 110

Ser Leu Asn Asn Leu Gly Asp Phe Val Gln Ala Glu Ile Leu Asp Trp
        115                 120                 125

Thr Asn Pro His Asp Phe Ile Asp Lys Phe Gly His Glu Asn Glu Phe
    130                 135                 140

Asp Val Ile Leu Ile Ala Asp Pro Ile Tyr Ser Pro Gln His Pro Glu
145                 150                 155                 160

Trp Val Val Asn Met Ile Ser Lys Phe Leu Ala Ala Ser Gly Thr Cys
                165                 170                 175

His Leu Glu Ile Pro Leu Arg Ala Lys Tyr Ala Lys Glu Arg Glu Val
            180                 185                 190

Leu Lys Leu Leu Leu Lys Glu Ser Asp Leu Lys Val Val Glu Glu Arg
        195                 200                 205

His Ser Glu
    210


<210> SEQ ID NO 22
<211> LENGTH: 191
<212> TYPE: PRT
<213> ORGANISM: Artificial Sequence
<220> FEATURE:
<223> OTHER INFORMATION: Amino acid consensus sequence

<400> SEQUENCE: 22

Asp Arg Glu Glu Ile Arg Lys Lys Leu Gly Ile Lys Glu Asp Lys Lys
 1               5                  10                  15

Ile Ile Leu Phe Val Gly Arg Leu Val Pro Glu Lys Gly Ile Asp Leu
            20                  25                  30

Leu Ile Glu Ala Phe Lys Lys Leu Lys Lys Lys Pro Lys Leu Leu Lys
        35                  40                  45

Leu Asn Pro Asn Leu Lys Leu Val Ile Val Gly Gly Pro Tyr Asp Ser
    50                  55                  60

Glu Asp Gly Glu Glu Glu Asp Glu Leu Lys Lys Leu Ala Glu Lys Leu
65                  70                  75                  80

Gly Leu Glu Asp Asn Val Ile Phe Leu Gly Phe Val Pro Asp Glu Asp
                85                  90                  95

Leu Pro Glu Leu Tyr Lys Ser Ala Asp Val Phe Val Leu Pro Ser Arg
            100                 105                 110

Tyr Glu Gly Phe Gly Ile Val Leu Leu Glu Ala Met Ala Cys Gly Leu
        115                 120                 125

Pro Val Ile Ala Thr Asn Cys Val Gly Gly Ile Pro Glu Val Val Lys
    130                 135                 140

Asp Gly Glu Thr Gly Leu Leu Val Glu Pro Gly Gln Asp Pro Glu Ala
145                 150                 155                 160

Leu Ala Glu Ala Ile Glu Lys Leu Leu Lys Asp Glu Glu Lys Lys Asp
                165                 170                 175

Leu Leu Glu Leu Arg Lys Arg Leu Gly Glu Asn Ala Arg Lys Arg
            180                 185                 190
```

-continued

<210> SEQ ID NO 23
<211> LENGTH: 49
<212> TYPE: PRT
<213> ORGANISM: Artificial Sequence
<220> FEATURE:
<223> OTHER INFORMATION: Amino acid consensus sequence

<400> SEQUENCE: 23

```
Val His Phe Ser Glu Ala Met Glu Lys Phe Ile His Glu Pro Ser Leu
 1               5                  10                  15

Lys Ala Thr Met Gly Leu Ala Gly Arg Ala Arg Val Lys Glu Lys Phe
            20                  25                  30

Ser Pro Asp Ala Phe Thr Asp Gln Leu Tyr Arg Tyr Val Thr Lys Leu
        35                  40                  45

Leu
```

<210> SEQ ID NO 24
<211> LENGTH: 81
<212> TYPE: PRT
<213> ORGANISM: Artificial Sequence
<220> FEATURE:
<223> OTHER INFORMATION: Amino acid consensus sequence

<400> SEQUENCE: 24

```
Val Ala Phe Ile His Pro Asp Leu Gly Ile Gly Gly Ala Glu Arg Leu
 1               5                  10                  15

Val Val Asp Ala Ala Val Gly Leu Gln Glu Arg Gly His Gln Val Lys
            20                  25                  30

Ile Phe Thr Ser His His Asp Lys Ser His Cys Phe Glu Glu Thr Arg
        35                  40                  45

Asp Gly Thr Leu Lys Val Gln Val Tyr Gly Asp Trp Leu Pro Arg Ser
    50                  55                  60

Ile Phe Trp Gly Gly Arg Phe His Ala Ile Cys Ala Tyr Leu Arg Met
65                  70                  75                  80
Ile
```

<210> SEQ ID NO 25
<211> LENGTH: 144
<212> TYPE: PRT
<213> ORGANISM: Artificial Sequence
<220> FEATURE:
<223> OTHER INFORMATION: Amino acid consensus sequence

<400> SEQUENCE: 25

```
Asn Tyr Glu Glu Lys Leu Lys Lys Leu Val Lys Glu Leu Gly Leu Glu
 1               5                  10                  15

Asn Arg Val His Phe Leu Gly Gly Met Gly Asp Glu Glu Asp Val Ser
            20                  25                  30

Glu Tyr Leu Lys Ser Ser Asp Ile Ile Ile Tyr Pro Ser Pro Ser Arg
        35                  40                  45

Ser Glu Gly Phe Pro Met Val Leu Leu Glu Ala Met Ala Cys Gly Leu
    50                  55                  60

Pro Val Ile Ala Thr Thr Thr Asp Gly Gly Gly Cys Glu Glu Ile Ile
65                  70                  75                  80

Glu Asp Gly Glu Asn Gly Leu Leu Val Glu Pro Asn Asn Ser Asp Val
                85                  90                  95

Glu Glu Leu Ala Glu Ala Leu Glu Lys Leu Leu Glu Asn Glu Glu Leu
            100                 105                 110

Arg Arg Lys Met Met Gly Lys Asn Ala Arg Arg Leu Val Glu Glu Met
        115                 120                 125
```

-continued

```
Phe Thr Ala Glu His Met Ala Lys Ala Tyr Glu Arg Phe Met Glu Lys
    130                 135                 140


<210> SEQ ID NO 26
<211> LENGTH: 46
<212> TYPE: PRT
<213> ORGANISM: Artificial Sequence
<220> FEATURE:
<223> OTHER INFORMATION: Amino acid consensus sequence

<400> SEQUENCE: 26

Phe Val Ala Leu Cys Val Leu Leu Gly Trp Ser Ser Phe Asp Val Val
 1               5                  10                  15

Leu Ala Asp Gln Val Ser Val Val Val Pro Leu Leu Lys Leu Lys Arg
            20                  25                  30

Ser Ser Lys Val Val Phe Tyr Cys His Phe Pro Asp Leu Leu
        35                  40                  45


<210> SEQ ID NO 27
<211> LENGTH: 46
<212> TYPE: PRT
<213> ORGANISM: Artificial Sequence
<220> FEATURE:
<223> OTHER INFORMATION: Amino acid consensus sequence

<400> SEQUENCE: 27

Tyr Gln Leu Ile Ile Ile Asp Gln Leu Ser Thr Cys Ile Pro Leu Leu
 1               5                  10                  15

His Ile Phe Ser Ser Ala Thr Leu Met Phe Tyr Cys His Phe Pro Asp
            20                  25                  30

Gln Leu Leu Ala Gln Arg Ala Gly Leu Leu Lys Lys Ile Tyr
        35                  40                  45


<210> SEQ ID NO 28
<211> LENGTH: 157
<212> TYPE: PRT
<213> ORGANISM: Artificial Sequence
<220> FEATURE:
<223> OTHER INFORMATION: Amino acid consensus sequence

<400> SEQUENCE: 28

Leu Arg His Leu Val Glu Lys Gly Leu Val Ala Ala Gln Phe Leu Leu
 1               5                  10                  15

Val Leu Gly Ala Ser Tyr Ser His Lys Asn Arg Asp Leu Ala Ile Leu
            20                  25                  30

Ala Trp Lys Glu Leu Arg Arg Arg Gly His Asn Ile Ala Leu Val Met
        35                  40                  45

Ala Gly Ala Val Val Ala Lys Gly Ser Ser Arg Gln Glu Glu Ala Val
    50                  55                  60

Ala Arg Trp Gly Ala Asp Glu Glu Gln Leu Val Ile Met Pro Asp Val
65                  70                  75                  80

Ser Ser Ala Val Arg Asn Trp Leu Leu Arg His Ala Ser Ile Val Leu
                85                  90                  95

Tyr Pro Thr Ser Ala Glu Gly Phe Gly Leu Val Pro Phe Glu Ala Ala
            100                 105                 110

Ser Met Gly Thr Pro Thr Ala His Val Ser Phe Gly Pro Leu Arg Glu
        115                 120                 125

Leu Ile Asp Ser Pro Glu Leu Pro Gln Asp Trp Asp Pro Leu Arg Met
    130                 135                 140
```

-continued

```
Ala Asp His Cys Gln Gln Leu Leu Gln Asp Pro Gln Leu
145                 150                 155
```

<210> SEQ ID NO 29
<211> LENGTH: 150
<212> TYPE: PRT
<213> ORGANISM: Artificial Sequence
<220> FEATURE:
<223> OTHER INFORMATION: Amino acid consensus sequence

<400> SEQUENCE: 29

```
Ser Ile Ile Ile Pro Thr Tyr Asn Glu Glu Lys Tyr Leu Glu Glu Cys
 1               5                  10                  15

Leu Glu Ser Leu Leu Asn Gln Thr Thr Tyr Glu Asn Phe Glu Ile Ile
            20                  25                  30

Val Val Asp Asp Gly Ser Thr Asp Gly Thr Val Glu Ile Leu Glu Glu
        35                  40                  45

Tyr Ala Lys Asp Pro Arg Ile Arg Val Ile Arg Leu Glu Glu Asn Leu
    50                  55                  60

Gly Leu Ala Ala Ala Arg Asn Ala Gly Leu Lys His Ala Thr Gly Asp
65                  70                  75                  80

Tyr Asp Tyr Ile Ala Phe Leu Asp Ala Asp Asp Glu Val Pro Asp Trp
                85                  90                  95

Leu Glu Lys Leu Leu Glu Leu Leu Glu Lys Asn Gly Ala Asp Ile Val
            100                 105                 110

Ile Gly Arg Val Ile Asn Glu Asn Lys Gly Arg Leu Asn Gly Lys Leu
        115                 120                 125

Arg Leu Leu Val Phe Leu Ile Gly Ser Asn Ala Leu Tyr Arg Arg Glu
    130                 135                 140

Ala Leu Glu Lys Leu Leu
145                 150
```

<210> SEQ ID NO 30
<211> LENGTH: 44
<212> TYPE: PRT
<213> ORGANISM: Artificial Sequence
<220> FEATURE:
<223> OTHER INFORMATION: Amino acid consensus sequence

<400> SEQUENCE: 30

```
Gly Thr Ile Arg Asn Leu Lys Ser Gly Leu Cys Leu Asp Val Ala Gly
 1               5                  10                  15

Gly Ser Thr Ala Asp Gly Thr Pro Val Gln Leu Tyr Thr Cys His Gly
            20                  25                  30

Asn Asp Gly Asn Gln Lys Trp Thr Leu Glu Lys Asp
        35                  40
```

<210> SEQ ID NO 31
<211> LENGTH: 44
<212> TYPE: PRT
<213> ORGANISM: Artificial Sequence
<220> FEATURE:
<223> OTHER INFORMATION: Amino acid consensus sequence

<400> SEQUENCE: 31

```
Gly Thr Ile Arg Asn Leu Lys Ser Gly Leu Cys Leu Asp Val Ala Gly
 1               5                  10                  15

Gly Ser Thr Ala Asp Gly Thr Pro Val Gln Leu Tyr Thr Cys His Gly
            20                  25                  30

Asn Asp Gly Asn Gln Lys Trp Thr Leu Glu Lys Asp
```

35 40

<210> SEQ ID NO 32
<211> LENGTH: 44
<212> TYPE: PRT
<213> ORGANISM: Artificial Sequence
<220> FEATURE:
<223> OTHER INFORMATION: Amino acid consensus sequence

<400> SEQUENCE: 32

```
Gly Thr Ile Arg Asn Leu Lys Ser Gly Leu Cys Leu Asp Val Ala Gly
 1               5                  10                  15

Gly Ser Thr Ala Asp Gly Thr Pro Val Gln Leu Tyr Thr Cys His Gly
            20                  25                  30

Asn Asp Gly Asn Gln Lys Trp Thr Leu Glu Lys Asp
        35                  40
```

<210> SEQ ID NO 33
<211> LENGTH: 102
<212> TYPE: PRT
<213> ORGANISM: Artificial Sequence
<220> FEATURE:
<223> OTHER INFORMATION: Amino acid consensus sequence

<400> SEQUENCE: 33

```
Met Gly Ser Val Thr Val Arg Tyr Phe Cys Tyr Gly Cys Leu Phe Thr
 1               5                  10                  15
Ser Ala Thr Trp Thr Val Leu Leu Phe Val Tyr Phe Asn Phe Ser Glu
            20                  25                  30
Val Thr Gln Pro Leu Lys Asn Val Pro Val Lys Gly Ser Gly Pro His
        35                  40                  45
Gly Pro Ser Pro Lys Lys Phe Tyr Pro Arg Phe Thr Arg Gly Pro Ser
    50                  55                  60

Arg Val Leu Glu Pro Gln Phe Lys Ala Asn Lys Ile Asp Asp Val Ile
65                  70                  75                  80

Asp Ser Arg Val Glu Asp Pro Glu Glu Gly His Leu Lys Phe Ser Ser
                85                  90                  95

Glu Leu Gly Met Ile Phe
            100
```

<210> SEQ ID NO 34
<211> LENGTH: 129
<212> TYPE: PRT
<213> ORGANISM: Artificial Sequence
<220> FEATURE:
<223> OTHER INFORMATION: Amino acid consensus sequence

<400> SEQUENCE: 34

```
Asn Glu Glu Glu Met Lys Ala Ala Glu Glu Ser Tyr Lys Lys Tyr Ala
 1               5                  10                  15
Phe Asn Ala Tyr Val Ser Asp Arg Ile Ser Leu Asn Arg Ser Ile Pro
            20                  25                  30
Asp Thr Arg His Pro Glu Cys Lys Asn Lys Lys Tyr Tyr Ser Asp Asn
        35                  40                  45
Leu Pro Thr Thr Ser Val Ile Ile Val Phe His Asn Glu Ala Trp Ser
    50                  55                  60
Thr Leu Leu Arg Thr Val His Ser Val Ile Asn Arg Thr Pro Pro His
65                  70                  75                  80
Leu Leu Lys Glu Ile Ile Leu Val Asp Asp Phe Ser Asp Arg Pro His
                85                  90                  95
Leu Leu Lys Gln Lys Leu Glu Glu Tyr Val Lys Lys Lys Phe Pro Gly
            100                 105                 110
Lys Val Lys Ile Leu Arg Asn Glu Glu Arg Glu Gly Leu Ile Arg Ala
        115                 120                 125
Arg
```

<210> SEQ ID NO 35

-continued

<211> LENGTH: 62
<212> TYPE: PRT
<213> ORGANISM: Artificial Sequence
<220> FEATURE:
<223> OTHER INFORMATION: Amino acid consensus sequence

<400> SEQUENCE: 35

Met Asp Ile Trp Gly Gly Glu Asn Leu Glu Leu Ser Phe Arg Val Trp
1 5 10 15

Gln Cys Gly Gly Lys Leu Glu Ile Val Pro Cys Ser Arg Val Gly His
20 25 30

Ile Phe Arg Lys Gln Ser Pro Tyr Thr Phe Pro Ser Gly Ser Ser Ser
35 40 45

Asn Val Ile Ser Arg Asn Tyr Lys Arg Val Ala Glu Val Trp
50 55 60

<210> SEQ ID NO 36
<211> LENGTH: 41
<212> TYPE: PRT
<213> ORGANISM: Artificial Sequence
<220> FEATURE:
<223> OTHER INFORMATION: Amino acid consensus sequence

<400> SEQUENCE: 36

Asn Arg Leu Tyr Gln Val Ser Val Gly Gln Cys Leu Arg Ala Val Asp
1 5 10 15

Pro Leu Gly Gln Lys Gly Ser Val Ala Met Ala Ile Cys Asp Gly Ser
20 25 30

Ser Ser Gln Gln Trp His Leu Glu Gly
35 40

<210> SEQ ID NO 37
<211> LENGTH: 36
<212> TYPE: PRT
<213> ORGANISM: Artificial Sequence
<220> FEATURE:
<223> OTHER INFORMATION: Amino acid consensus sequence

<400> SEQUENCE: 37

Arg Leu Tyr Gln Val Ser Val Gly Gln Cys Leu Arg Ala Val Asp Pro
1 5 10 15

Leu Gly Gln Lys Gly Ser Val Ala Met Ala Ile Cys Asp Gly Ser Ser
20 25 30

Ser Gln Gln Trp
35

<210> SEQ ID NO 38
<211> LENGTH: 80
<212> TYPE: PRT
<213> ORGANISM: Artificial Sequence
<220> FEATURE:
<223> OTHER INFORMATION: Amino acid consensus sequence

<400> SEQUENCE: 38

Val Ile Asp Val Ile Asp Asp Asn Thr Phe Glu Tyr His Lys Ser Lys
1 5 10 15

Ser Ser Asp Thr Ser Arg Gly Gly Phe Asp Trp Gly Leu His Phe Lys
20 25 30

Trp His Pro Ile Pro Glu Glu Glu Arg Lys Arg Lys Lys Arg Arg Glu
35 40 45

Asp Pro Thr Glu Pro Ile Arg Ser Pro Thr Met Ala Gly Gly Leu Phe
50 55 60

-continued

Ala Ile Asp Arg Glu Tyr Phe Trp Glu Leu Gly Ser Tyr Asp Pro Gly
65 70 75 80

<210> SEQ ID NO 39
<211> LENGTH: 578
<212> TYPE: PRT
<213> ORGANISM: Artificial Sequence
<220> FEATURE:
<223> OTHER INFORMATION: Amino acid consensus sequence

<400> SEQUENCE: 39

Arg Arg Val Leu Lys Asp Ala His Ala Gly Gly Asn Ala Val Asp Ala
1 5 10 15

Ala Val Ala Ala Leu Phe Cys Leu Gly Val Val Glu Pro His Ala Ser
20 25 30

Gly Ile Gly Gly Gly Gly Phe Met Leu Ile Tyr Asn Leu Ala Thr Gly
35 40 45

Lys Ala Thr Val Ile Asp Phe Arg Glu Thr Ala Pro Ala Ala Ala Thr
50 55 60

Pro Asn Met Phe Leu Asp Lys Ser Gly Glu Ala Ser Lys Gln Ser Ala
65 70 75 80

Thr Gly Gly Leu Leu Ala Ile Gly Val Pro Gly Glu Val Ala Gly Leu
85 90 95

Glu Glu Ala His Lys Lys Tyr Gly Ser Thr Thr Leu Pro Trp Ala Asp
100 105 110

Leu Leu Glu Pro Ala Ile Lys Leu Ala Arg Gly Gly Phe Pro Val Ser
115 120 125

Pro Ala Leu Ala Ala Ala Leu Asp Leu Ala Glu Pro Leu Leu Leu Ser
130 135 140

Asp Ile Leu Asp Pro Gly Leu Lys Asp Ile Phe Leu Pro Asn Gly Glu
145 150 155 160

Pro Val Leu Arg Pro Gly Glu Arg Leu Val Gln Pro Asp Leu Ala Lys
165 170 175

Thr Leu Glu Leu Ile Ala Lys Glu Glu Gly Ala Asp Ala Phe Tyr Asn
180 185 190

Gly Ile Ala Ala Ser Phe Glu Leu Ala Ala Ala Leu Val Ala Asp Ile
195 200 205

Ala Lys Asn Gly Gly Ile Ile Thr Leu Glu Asp Leu Ala Asn Tyr Arg
210 215 220

Val Glu Val Arg Glu Pro Leu Ser Gly Asp Tyr Arg Gly Ala Asp Ile
225 230 235 240

Tyr Glu Val Leu Thr Met Pro Pro Pro Ser Ser Gly Gly Pro Val Leu
245 250 255

Leu Gln Ile Leu Asn Ile Leu Glu Gly Phe Asp Leu Ser Lys Tyr Ser
260 265 270

Val Gly Ser Ala Glu Tyr Lys Gly Leu Thr Val His Leu Leu Val Glu
275 280 285

Ala Met Lys Leu Ala Tyr Ala Asp Arg Asp Ala Tyr Leu Gly Asp Pro
290 295 300

Asp Phe Val Asp Val Pro Lys Val Leu Ala Lys Leu Leu Asp Lys Lys
305 310 315 320

Tyr Ala Lys Gln Arg Arg Ala Leu Ile Ser Leu Glu Lys Ala Lys Gly
325 330 335

Asp Ile Pro Ser Ser Gly Ser Leu Asp Tyr Tyr Lys Pro Gly Glu Ala
340 345 350

-continued

```
Ala Glu Ala Gln Asp Leu Pro Lys Glu His Gly Glu Trp Met Thr Thr
        355                 360                 365

His Leu Ser Val Val Asp Ala Asp Gly Asn Ala Val Ser Leu Thr Ser
    370                 375                 380

Thr Ile Asn Leu Leu Phe Gly Ser Lys Val Leu Ser Pro Gly Thr Pro
385                 390                 395                 400

Ser Phe Gly Ile Leu Leu Asn Asn Glu Met Asp Asp Phe Ser Ser Lys
                405                 410                 415

Leu Gly Trp Ser Pro Gly Val Gly Asn Val Phe Gly Leu Ala Pro Gly
            420                 425                 430

Pro Ala Asn Phe Ile Glu Pro Gly Lys Arg Pro Leu Ser Ser Met Ser
        435                 440                 445

Pro Thr Ile Val Leu Lys Lys Ser Asp Gly Lys Pro Lys Leu Val Val
    450                 455                 460

Gly Ser Pro Gly Gly Ser Arg Ile Ile Thr Ala Val Leu Gln Thr Ile
465                 470                 475                 480

Val Asn Val Leu Asp Tyr Gly Met Asn Leu Gln Glu Ala Val Glu Ala
                485                 490                 495

Pro Arg Phe His His Gln Leu Leu Pro Ala Asp Arg Leu Glu Val Glu
            500                 505                 510

Asn Phe Pro Ile Val Val Ser Glu Glu Gly Phe Ser Lys Ala Val Leu
        515                 520                 525

Gln Glu Leu Glu Arg Arg Gly His Lys Val Glu Leu Val Pro Asp Tyr
    530                 535                 540

Asp Lys Phe Phe Gly Ser Val Gln Ala Ile Ile Val Asp Glu Asp Gly
545                 550                 555                 560

Glu Gly Ser Val Leu Tyr Gly Ala Ser Asp Pro Arg Arg Asn His Gly
                565                 570                 575

Gly Glu


<210> SEQ ID NO 40
<211> LENGTH: 135
<212> TYPE: PRT
<213> ORGANISM: Artificial Sequence
<220> FEATURE:
<223> OTHER INFORMATION: Amino acid consensus sequence

<400> SEQUENCE: 40

Met Ala Ala Glu Asn Glu Ala Ser Gln Glu Ser Ala Leu Gly Ala Tyr
 1               5                  10                  15

Ser Pro Val Asp Tyr Met Ser Ile Thr Ser Phe Pro Arg Leu Pro Glu
            20                  25                  30

Asp Glu Pro Ala Pro Ala Ala Pro Leu Arg Gly Arg Lys Asp Glu Asp
        35                  40                  45

Ala Phe Leu Gly Asp Pro Asp Thr Asp Pro Asp Ser Phe Leu Lys Ser
    50                  55                  60

Ala Arg Leu Gln Arg Leu Pro Ser Ser Ser Ser Glu Met Gly Ser Gln
65                  70                  75                  80

Asp Gly Ser Pro Leu Arg Glu Thr Arg Lys Asp Pro Phe Ser Ala Ala
                85                  90                  95

Ala Ala Glu Cys Ser Cys Arg Gln Asp Gly Leu Thr Val Ile Val Thr
            100                 105                 110

Ala Cys Leu Thr Phe Ala Thr Gly Val Thr Val Ala Leu Val Met Gln
        115                 120                 125
```

-continued

```
Ile Tyr Phe Gly Asp Pro Gln
    130                135


<210> SEQ ID NO 41
<211> LENGTH: 293
<212> TYPE: PRT
<213> ORGANISM: Artificial Sequence
<220> FEATURE:
<223> OTHER INFORMATION: Amino acid consensus sequence

<400> SEQUENCE: 41

Ala His Thr Ile Asp Ala Arg Glu Thr Ala Pro Ala Ala Ala Thr Glu
 1               5                  10                  15

Asp Met Phe Glu Asn Asn Met Asp Glu Asn Asn Ser Pro Leu Lys Lys
            20                  25                  30

Met Asp Val Thr Gly Gly Leu Ser Val Gly Val Pro Gly Glu Val Ala
        35                  40                  45

Gly Tyr Glu Glu Ala His Lys Arg Tyr Gly Arg Leu Pro Trp Ala Gln
    50                  55                  60

Leu Phe Gln Pro Ala Ile Lys Leu Ala Arg Glu Gly Phe Pro Val Ser
65                  70                  75                  80

Pro Tyr Leu Ala Arg Ala Leu Glu Ser Ser Glu Glu Arg Ile Lys Leu
                85                  90                  95

Gln Arg Pro Asp Pro Gly Trp Arg Glu Ile Phe Ala Pro Asn Gly Glu
            100                 105                 110

Pro Leu Arg Pro Gly Glu Val Leu Lys Gln Pro Asp Leu Ala Glu Thr
        115                 120                 125

Leu Glu Leu Ile Ala Glu Glu Gly Pro Glu Ala Phe Tyr Asn Gly Glu
    130                 135                 140

Arg Leu Ala Glu Gln Leu Val Lys Asp Ile Gln Lys Ser Gly Gly Ile
145                 150                 155                 160

Ile Thr Ala Glu Asp Leu Ala Asn Tyr Lys Val Lys Val Arg Glu Pro
                165                 170                 175

Val His Ser Ser Ser Tyr Ala Arg Gly Tyr Glu Val Leu Ser Met Pro
            180                 185                 190

Pro Pro Ser Ser Gly Gly Val Val Leu Ala Gln Val Leu Asn Ile Leu
        195                 200                 205

Glu Gly Tyr Asn Phe Asp Met Ser Ser Val Ala Thr Pro Glu Asn Ser
    210                 215                 220

Ala Glu Thr Tyr His Arg Leu Val Glu Ala Met Lys Phe Ala Tyr Ala
225                 230                 235                 240

Asp Arg Ser Arg Tyr Leu Gly Asp Pro Asp Phe Val Pro Val Pro Gln
                245                 250                 255

Asn Ala Val Glu Lys Leu Leu Ser Lys Asp Tyr Ala Lys Gln Arg Arg
            260                 265                 270

Ala Leu Ile Pro Ser Asn Pro Gln Arg Ala Ser Pro Ser Ser Ser Leu
        275                 280                 285

Pro Pro Gly Ala Pro
    290


<210> SEQ ID NO 42
<211> LENGTH: 114
<212> TYPE: PRT
<213> ORGANISM: Artificial Sequence
<220> FEATURE:
<223> OTHER INFORMATION: Amino acid consensus sequence

<400> SEQUENCE: 42
```

-continued

```
Arg Pro Ala Glu Gly Leu Cys Gly Thr Tyr Leu Ala Leu Gly Ala Asn
 1               5                  10                  15

Gly Ala Ala Arg Gly Leu Ser Gly Leu Thr Gln Val Leu Leu Asn Val
            20                  25                  30

Leu Thr Leu Asn Arg Asn Leu Ser Asp Ser Leu Ala Arg Gly Arg Leu
        35                  40                  45

His Pro Asp Leu Gln Ser Asn Leu Leu Gln Val Asp Ser Glu Phe Thr
    50                  55                  60

Glu Glu Glu Ile Glu Phe Leu Glu Ala Arg Gly His His Val Glu Lys
65                  70                  75                  80

Val Asp Val Leu Ser Trp Val His Gly Ser Arg Arg Thr Asn Asn Phe
                85                  90                  95

Ile Ile Ala Val Lys Asp Pro Arg Ser Pro Asp Ala Ala Gly Ala Thr
            100                 105                 110

Ile Leu


<210> SEQ ID NO 43
<211> LENGTH: 102
<212> TYPE: PRT
<213> ORGANISM: Artificial Sequence
<220> FEATURE:
<223> OTHER INFORMATION: Amino acid consensus sequence

<400> SEQUENCE: 43

Asp Leu Ile Val Leu Ala Gly Tyr Met Arg Ile Leu Pro Lys Glu Phe
 1               5                  10                  15

Leu Gln Ala Phe Pro Gly Lys Ile Leu Asn Ile His Pro Ser Leu Leu
            20                  25                  30

Pro Arg Phe Arg Gly Ala Ala Pro Ile Gln Arg Ala Leu Glu Ala Gly
        35                  40                  45

Asp Lys Glu Thr Gly Val Thr Val His Phe Val Asp Glu Glu Leu Asp
    50                  55                  60

Thr Gly Pro Ile Leu Ala Gln Lys Ala Val Pro Ile Leu Pro Thr Asp
65                  70                  75                  80

Asp Thr Ser Glu Thr Leu Glu Asn Arg Val Ala Glu Leu Glu His Lys
                85                  90                  95

Ala Leu Pro Glu Ala Leu
            100


<210> SEQ ID NO 44
<211> LENGTH: 108
<212> TYPE: PRT
<213> ORGANISM: Artificial Sequence
<220> FEATURE:
<223> OTHER INFORMATION: Amino acid consensus sequence

<400> SEQUENCE: 44

Glu Tyr Gln Pro Asp Leu Val Val Leu Ala Gly Tyr Met Arg Ile Leu
 1               5                  10                  15

Pro Pro Glu Phe Leu Glu Arg Tyr Pro His Gly Cys Ile Asn Ile His
            20                  25                  30

Pro Ser Leu Leu Pro Lys Tyr Arg Gly Ala Ser Pro Ile Gln Gln Ala
        35                  40                  45

Ile Glu Asn Gly Asp Lys Glu Thr Gly Val Thr Val His Tyr Val Asp
    50                  55                  60

Glu Glu Glu Leu Asp Thr Gly Pro Ile Ile Ala Gln Glu Thr Val Pro
65                  70                  75                  80
```

-continued

Val Glu Pro Asp Asp Thr Ala Glu Thr Thr Leu Glu Arg Val Leu Arg
85 90 95

Asp Val Glu His Glu Leu Leu Pro Glu Ala Leu Glu
100 105

<210> SEQ ID NO 45
<211> LENGTH: 114
<212> TYPE: PRT
<213> ORGANISM: Artificial Sequence
<220> FEATURE:
<223> OTHER INFORMATION: Amino acid consensus sequence

<400> SEQUENCE: 45

Ala Thr Tyr Ala Pro Lys Leu Lys Lys Glu Asp Gly Arg Ile Asp Trp
1 5 10 15

Asn Lys Pro Ala Glu Glu Ile His Asn Lys Ile Arg Ala Phe Ser Pro
20 25 30

Pro Trp Pro Gly Ala Trp Thr Tyr Phe Asn Gly Gln Lys Gln Lys Leu
35 40 45

Lys Ile Trp Gln Ala Lys Leu Val Asp Glu Ser Ala Ser Ser Gln Ala
50 55 60

Pro Gly Gly Thr Val Leu Ser Val Asp Lys Asn Gly Leu Leu Val Ala
65 70 75 80

Cys Gly Glu Gly Ser Val Leu Arg Leu Leu Gln Ile Gln Pro Pro Gly
85 90 95

Lys Lys Pro Met Ser Ala Lys Asp Phe Leu Asn Gly Lys Arg Glu Trp
100 105 110

Phe Lys

<210> SEQ ID NO 46
<211> LENGTH: 195
<212> TYPE: PRT
<213> ORGANISM: Artificial Sequence
<220> FEATURE:
<223> OTHER INFORMATION: Amino acid consensus sequence

<400> SEQUENCE: 46

Leu Glu Asn Leu Pro Lys Lys Gly Pro Ala Ile Val Val Ser Asn His
1 5 10 15

Arg Ser Tyr Leu Asp Ile Leu Val Leu Ser Ala Ala Leu Pro Arg Arg
20 25 30

Gly Pro Trp Leu Val Arg Arg Leu Val Phe Ile Ala Lys Lys Glu Leu
35 40 45

Leu Lys Val Pro Leu Leu Phe Gly Trp Leu Met Arg Leu Ala Gly Ala
50 55 60

Ile Phe Ile Asp Arg Asn Asn Arg Ala Lys Asp Ala Leu Ala Ala Ala
65 70 75 80

Asp Glu Leu Val Arg Val Leu Glu Leu Leu Arg Lys Gly Arg Ser Val
85 90 95

Leu Ile Phe Pro Glu Gly Thr Arg Ser Arg Ser Gly Glu Leu Leu Pro
100 105 110

Pro Phe Lys Lys Gly Ile Ala Ala Phe Arg Leu Ala Leu Lys Ala Gly
115 120 125

Val Pro Ile Val Pro Val Val Ile Val Ser Gly Thr Glu Glu Leu Glu
130 135 140

Pro Lys Asn Glu Ala Gly Lys Leu Leu Arg Leu Ala Arg Lys Lys Gly
145 150 155 160

-continued

Pro Val Thr Val Arg Val Leu Pro Pro Ile Pro Leu Asp Pro Glu Asp
                165                 170                 175

Ile Lys Glu Leu Ala Glu Arg Leu Arg Asp Ile Leu Val Gln Ala Leu
            180                 185                 190

Glu Glu Leu
        195

<210> SEQ ID NO 47
<211> LENGTH: 216
<212> TYPE: PRT
<213> ORGANISM: Artificial Sequence
<220> FEATURE:
<223> OTHER INFORMATION: Amino acid consensus sequence

<400> SEQUENCE: 47

Gly Thr Thr Gln Arg Leu Met Pro Phe Trp Arg Trp Phe Tyr Lys Ile
 1               5                  10                  15

Tyr His Gly Tyr Gln Val Ile Gly Leu Glu Asn Ile Pro Pro Gly Gly
            20                  25                  30

Pro Leu Leu Val Val Tyr His His Gly Gly Ile Phe Pro Pro Pro Ile
        35                  40                  45

Asp Met Tyr Tyr Leu Asp Trp Tyr Met Leu Leu Gly Arg Glu Arg Pro
    50                  55                  60

Val Tyr Thr Leu Gly His Arg Phe Leu Phe Lys Gly Leu Pro Gly Trp
65                  70                  75                  80

Gly Thr Leu Ser Glu Ala Phe His Val Ser Pro Gly Thr Val Gln Ser
                85                  90                  95

Cys Val Ser Ala Leu Arg Asp Gly Asn Leu Val Ala Val Tyr Pro Gly
            100                 105                 110

Gly Val Tyr Asp Ala Tyr Arg Pro Gly Asp His Tyr Tyr Glu Ile Leu
        115                 120                 125

Trp Arg Gly Arg Lys Gly Phe Val Lys Val Ala Ile Glu Ala Gly Val
    130                 135                 140

Pro Ile Val Pro Cys Phe Thr Gln Gly Leu Arg Glu Gly Phe Arg Gln
145                 150                 155                 160

Val Gly Asp Cys Tyr Asp Gly Thr Trp Ile Phe Arg Thr Phe Gly Met
                165                 170                 175

Arg Trp Tyr Asn Lys Val Asp Ile Pro Val Tyr Pro Ile Tyr Gly Gly
            180                 185                 190

Phe Pro Trp Gly Phe Arg Thr Tyr Leu Gly Pro Pro Ile Pro Tyr Pro
        195                 200                 205

Glu Asn Leu Thr Pro Gln Asp Leu
    210                 215

<210> SEQ ID NO 48
<211> LENGTH: 23
<212> TYPE: PRT
<213> ORGANISM: Artificial Sequence
<220> FEATURE:
<223> OTHER INFORMATION: Amino acid consensus sequence

<400> SEQUENCE: 48

Ala Ile Glu Asp Leu Ile Asn Gln His Gln Arg Leu Pro Gly Ser Ile
 1               5                  10                  15

Leu Leu Ala Leu Leu Asp Arg
            20

-continued

<210> SEQ ID NO 49
<211> LENGTH: 12
<212> TYPE: PRT
<213> ORGANISM: Artificial Sequence
<220> FEATURE:
<223> OTHER INFORMATION: Acyltransferase family motif
<220> FEATURE:
<221> NAME/KEY: VARIANT
<222> LOCATION: (2)...(2)
<223> OTHER INFORMATION: Xaa = Any amino acid
<220> FEATURE:
<221> NAME/KEY: VARIANT
<222> LOCATION: (7)...(7)
<223> OTHER INFORMATION: Xaa = Any amino acid

<400> SEQUENCE: 49

Asn Xaa His Arg Gln Ser Xaa Leu Tyr Ile Met Asp
1               5                   10

<210> SEQ ID NO 50
<211> LENGTH: 9
<212> TYPE: PRT
<213> ORGANISM: Artificial Sequence
<220> FEATURE:
<223> OTHER INFORMATION: Acyltransferase family motif
<220> FEATURE:
<221> NAME/KEY: VARIANT
<222> LOCATION: (2)...(2)
<223> OTHER INFORMATION: Xaa = Any amino acid

<400> SEQUENCE: 50

Gly Xaa Ile Phe Phe Ile Arg Asp Arg
1               5

<210> SEQ ID NO 51
<211> LENGTH: 13
<212> TYPE: PRT
<213> ORGANISM: Artificial Sequence
<220> FEATURE:
<223> OTHER INFORMATION: Acyltransferase family motif
<220> FEATURE:
<221> NAME/KEY: VARIANT
<222> LOCATION: (11)...(11)
<223> OTHER INFORMATION: Xaa = Any amino acid
<220> FEATURE:
<221> NAME/KEY: VARIANT
<222> LOCATION: (13)...(13)
<223> OTHER INFORMATION: Xaa = Any amino acid

<400> SEQUENCE: 51

Phe Pro Leu Ile Glu Gly Thr Gly Arg Ser Xaa Arg Xaa
1               5                   10

<210> SEQ ID NO 52
<211> LENGTH: 12
<212> TYPE: PRT
<213> ORGANISM: Artificial Sequence
<220> FEATURE:
<223> OTHER INFORMATION: Acyltransferase family motif
<220> FEATURE:
<221> NAME/KEY: VARIANT
<222> LOCATION: (4)...(4)
<223> OTHER INFORMATION: Xaa = Any amino acid

<400> SEQUENCE: 52

Val Ile Pro Xaa Ile Val Leu Ile Val Pro Val Ile
1               5                   10

<210> SEQ ID NO 53
<211> LENGTH: 3030
<212> TYPE: DNA

-continued

```
<213> ORGANISM: Homo sapiens
<220> FEATURE:
<221> NAME/KEY: CDS
<222> LOCATION: (238)...(2580)

<400> SEQUENCE: 53

ggagaattga aacccgaaca cacattgggc tcttttggca cttgactaga gctaaaacct      60

cgggattcag cgggcaagcg ttgctcagca acggcgcgta ggctgtgtgc ggttggctgg     120

agccagaccc caccccggcc tcggcccatg ctctagaggg gacgttgccc caatcctgaa     180

ggacttcggc actcgagacc tgtggatgcc gcgttgctgt ggcctgcggg ggtgatc atg    240
                                                                Met
                                                                 1

aag cca ggt gct act ggc gag tcc gat ttg gcc gaa gtg ctg ccc cag      288
Lys Pro Gly Ala Thr Gly Glu Ser Asp Leu Ala Glu Val Leu Pro Gln
            5                  10                  15

cac aag ttc gac agc aag tcc ctg gag gcc tac cta aac cag cac ttg      336
His Lys Phe Asp Ser Lys Ser Leu Glu Ala Tyr Leu Asn Gln His Leu
        20                  25                  30

tct ggc ttt ggg gcc gaa cgt gag gct acg ctg acc att gcc cag tac      384
Ser Gly Phe Gly Ala Glu Arg Glu Ala Thr Leu Thr Ile Ala Gln Tyr
    35                  40                  45

aga gca gga aag tcc aat cca acc ttt tat ctc cag aag ggc ttt caa      432
Arg Ala Gly Lys Ser Asn Pro Thr Phe Tyr Leu Gln Lys Gly Phe Gln
 50                  55                  60                  65

aca tat gtg ctc agg aaa aaa cca cca ggt tca ctt ctt cct aaa gca      480
Thr Tyr Val Leu Arg Lys Lys Pro Pro Gly Ser Leu Leu Pro Lys Ala
                70                  75                  80

cat cag att gat aga gaa ttt aaa gtc cag aaa gcc ttg ttt tca att      528
His Gln Ile Asp Arg Glu Phe Lys Val Gln Lys Ala Leu Phe Ser Ile
            85                  90                  95

gga ttc ccc gtt ccc aag cct ata ctg tac tgc agt gat act tct gtc      576
Gly Phe Pro Val Pro Lys Pro Ile Leu Tyr Cys Ser Asp Thr Ser Val
        100                 105                 110

att gga aca gaa ttt tac gta atg gaa cat gtg cag ggt cga atc ttc      624
Ile Gly Thr Glu Phe Tyr Val Met Glu His Val Gln Gly Arg Ile Phe
    115                 120                 125

cgt gat tta aca att cct gga ctt agc cca gca gaa cgt tca gcc ata      672
Arg Asp Leu Thr Ile Pro Gly Leu Ser Pro Ala Glu Arg Ser Ala Ile
130                 135                 140                 145

tat gtg gcc acg gta gaa aca ttg gct cag tta cat tcc ttg aat ata      720
Tyr Val Ala Thr Val Glu Thr Leu Ala Gln Leu His Ser Leu Asn Ile
                150                 155                 160

cag tca ctg cag ctg gaa gga tat ggt ata ggt gct ggg tac tgc aaa      768
Gln Ser Leu Gln Leu Glu Gly Tyr Gly Ile Gly Ala Gly Tyr Cys Lys
            165                 170                 175

aga cag gta tca acc tgg aca aag caa tat caa gct gca gct cat cag      816
Arg Gln Val Ser Thr Trp Thr Lys Gln Tyr Gln Ala Ala Ala His Gln
        180                 185                 190

gac atc cct gcc atg caa cag cta tcg gag tgg cta atg aag aac ttg      864
Asp Ile Pro Ala Met Gln Gln Leu Ser Glu Trp Leu Met Lys Asn Leu
    195                 200                 205

ccc gat aat gac aat gaa gag aat ttg att cat gga gat ttc aga cta      912
Pro Asp Asn Asp Asn Glu Glu Asn Leu Ile His Gly Asp Phe Arg Leu
210                 215                 220                 225

gat aac ata gtt ttc cac cct aaa gag tgt cga gtt ata gca gtg ctg      960
Asp Asn Ile Val Phe His Pro Lys Glu Cys Arg Val Ile Ala Val Leu
                230                 235                 240

gat tgg gag ctg tca acc att ggt cat cct ttg tca gac tta gct cat     1008
Asp Trp Glu Leu Ser Thr Ile Gly His Pro Leu Ser Asp Leu Ala His
```

-continued

```
            245                 250                 255

ttt tcc ctg ttc tac ttt tgg cca agg aca gtt cca atg ata aat caa     1056
Phe Ser Leu Phe Tyr Phe Trp Pro Arg Thr Val Pro Met Ile Asn Gln
        260                 265                 270

ggt tct tat agt gaa aac tca ggg ata cca tca atg gaa gaa ctg att     1104
Gly Ser Tyr Ser Glu Asn Ser Gly Ile Pro Ser Met Glu Glu Leu Ile
    275                 280                 285

tca ata tat tgc cgc tgc agg gga att aat tct att ctt cct aac tgg     1152
Ser Ile Tyr Cys Arg Cys Arg Gly Ile Asn Ser Ile Leu Pro Asn Trp
290                 295                 300                 305

aat ttc ttt ctt gcc ctt tca tat ttt aag atg gct gga ata gca cag     1200
Asn Phe Phe Leu Ala Leu Ser Tyr Phe Lys Met Ala Gly Ile Ala Gln
                310                 315                 320

gga gta tat agc aga tat ctt ctg gga aat aat tca tct gag gat agc     1248
Gly Val Tyr Ser Arg Tyr Leu Leu Gly Asn Asn Ser Ser Glu Asp Ser
            325                 330                 335

ttt tta ttt gcc aat att gtg caa cct ctg gca gaa act gga cta caa     1296
Phe Leu Phe Ala Asn Ile Val Gln Pro Leu Ala Glu Thr Gly Leu Gln
        340                 345                 350

ctc tcc aaa cga act ttc agt act gta cta cca cag att gat act act     1344
Leu Ser Lys Arg Thr Phe Ser Thr Val Leu Pro Gln Ile Asp Thr Thr
    355                 360                 365

gga cag ttg ttt gta cag act cgg aaa ggt cag gaa gtt ctt att aag     1392
Gly Gln Leu Phe Val Gln Thr Arg Lys Gly Gln Glu Val Leu Ile Lys
370                 375                 380                 385

gtg aag cat ttc atg aaa caa cac att ctt cca gct gaa aag gag gta     1440
Val Lys His Phe Met Lys Gln His Ile Leu Pro Ala Glu Lys Glu Val
                390                 395                 400

act gag ttc tat gtt caa aat gaa aat tca gtg gac aag tgg gga aaa     1488
Thr Glu Phe Tyr Val Gln Asn Glu Asn Ser Val Asp Lys Trp Gly Lys
            405                 410                 415

cct tta gtg att gat aaa ctc aag gaa atg gcc aaa gtc gag ggt ctc     1536
Pro Leu Val Ile Asp Lys Leu Lys Glu Met Ala Lys Val Glu Gly Leu
        420                 425                 430

tgg aac ttg ttt ttg cca gct gtc agc gga ctc agc cac gtg gac tat     1584
Trp Asn Leu Phe Leu Pro Ala Val Ser Gly Leu Ser His Val Asp Tyr
    435                 440                 445

gcc ttg att gct gaa gaa aca gga aaa tgc ttt ttt gct cca gat gtc     1632
Ala Leu Ile Ala Glu Glu Thr Gly Lys Cys Phe Phe Ala Pro Asp Val
450                 455                 460                 465

ttt aac tgc caa gca cca gac aca ggg aat atg gag gtt ctg cac ctg     1680
Phe Asn Cys Gln Ala Pro Asp Thr Gly Asn Met Glu Val Leu His Leu
                470                 475                 480

tat gga agt gag gaa cag aag aaa cag tgg ctt gag cct ctt ctt caa     1728
Tyr Gly Ser Glu Glu Gln Lys Lys Gln Trp Leu Glu Pro Leu Leu Gln
            485                 490                 495

ggg aac att acc tct tgc ttc tgt atg aca gaa cct gat gta gct tca     1776
Gly Asn Ile Thr Ser Cys Phe Cys Met Thr Glu Pro Asp Val Ala Ser
        500                 505                 510

agt gat gcc acg aat att gaa tgc agc atc caa cga gat gaa gat agc     1824
Ser Asp Ala Thr Asn Ile Glu Cys Ser Ile Gln Arg Asp Glu Asp Ser
    515                 520                 525

tat gta att aac ggc aaa aaa tgg tgg agc agt gga gct ggg aat ccc     1872
Tyr Val Ile Asn Gly Lys Lys Trp Trp Ser Ser Gly Ala Gly Asn Pro
530                 535                 540                 545

aag tgc aaa att gca att gtt ttg gga aga act caa aat act tct ctc     1920
Lys Cys Lys Ile Ala Ile Val Leu Gly Arg Thr Gln Asn Thr Ser Leu
                550                 555                 560

tcc aga cac aaa cag cac agc atg att ctt gtt ccc atg aac aca cct     1968
```

-continued

```
Ser Arg His Lys Gln His Ser Met Ile Leu Val Pro Met Asn Thr Pro
            565                 570                 575

gga gta aaa ata ata agg cct ttg tca gtt ttt ggc tac aca gat aat      2016
Gly Val Lys Ile Ile Arg Pro Leu Ser Val Phe Gly Tyr Thr Asp Asn
        580                 585                 590

ttt cat gga gga cat ttt gag atc cat ttt aat caa gtg cga gtt cct      2064
Phe His Gly Gly His Phe Glu Ile His Phe Asn Gln Val Arg Val Pro
    595                 600                 605

gcc aca aat cta ata cta ggt gaa ggt agg gga ttt gaa att tcc caa      2112
Ala Thr Asn Leu Ile Leu Gly Glu Gly Arg Gly Phe Glu Ile Ser Gln
610                 615                 620                 625

ggc cgc ctt gga cct ggc aga atc cac cac tgt atg aga aca gta ggt      2160
Gly Arg Leu Gly Pro Gly Arg Ile His His Cys Met Arg Thr Val Gly
                630                 635                 640

ttg gcg gaa cgc gct ttg cag atc atg tgt gag cgg gca aca caa agg      2208
Leu Ala Glu Arg Ala Leu Gln Ile Met Cys Glu Arg Ala Thr Gln Arg
            645                 650                 655

ata gct ttc aag aag aag ttg tat gca cat gag gtt gtg gct cac tgg      2256
Ile Ala Phe Lys Lys Lys Leu Tyr Ala His Glu Val Val Ala His Trp
        660                 665                 670

att gct gaa agc cgc att gcc att gag aag atc cgc ttg ttg act ctg      2304
Ile Ala Glu Ser Arg Ile Ala Ile Glu Lys Ile Arg Leu Leu Thr Leu
    675                 680                 685

aaa gct gct cac agc atg gac act ctg ggc agt gct ggc gct aag aaa      2352
Lys Ala Ala His Ser Met Asp Thr Leu Gly Ser Ala Gly Ala Lys Lys
690                 695                 700                 705

gag att gca atg atc aaa gtg gct gcc cca cgg gct gtc agc aaa atc      2400
Glu Ile Ala Met Ile Lys Val Ala Ala Pro Arg Ala Val Ser Lys Ile
                710                 715                 720

gtt gac tgg gcc atc cag gtg tgc gga ggt gct ggt gtt tcc cag gat      2448
Val Asp Trp Ala Ile Gln Val Cys Gly Gly Ala Gly Val Ser Gln Asp
            725                 730                 735

tac cct ctg gct aac atg tat gct ata acc cga gtt ttg cgt tta gca      2496
Tyr Pro Leu Ala Asn Met Tyr Ala Ile Thr Arg Val Leu Arg Leu Ala
        740                 745                 750

gat gga cct gac gaa gtt cat ctt tca gca atc gca aca atg gag ctg      2544
Asp Gly Pro Asp Glu Val His Leu Ser Ala Ile Ala Thr Met Glu Leu
    755                 760                 765

cgg gac caa gcc aaa aga ctg aca gcc aag ata taa ggagggtggc           2590
Arg Asp Gln Ala Lys Arg Leu Thr Ala Lys Ile  *
770                 775                 780

actgccacat cccactggca gaaactctcc tttatacaaa cttcattggc tccaacattt   2650

gaatctcata tttttgtagc agtttgagca cagggttaat tattcatttg tggtaaagat   2710

tatagcatct attttgatca gtgggtttta ttatttcaag ggtcacacag ggttaagttc   2770

agtaagaaat gctgtagctg ttgtcattca atctagtgcc tccttgaggc caggagttca   2830

ggaccagcct gggcaacata gcgagacccc cattgctaca aaaaatttaa aaatgaaaca   2890

agtgtggtgg cacatgcttg tagtcctagc tacttgggag gctgaggcag gaggattgct   2950

tgagtctagg agtttgaggt tacagtaagc tgtgatcgtg acatggcctc cagcctgggt   3010

gaccgagtga gactgtttct                                               3030


<210> SEQ ID NO 54
<211> LENGTH: 780
<212> TYPE: PRT
<213> ORGANISM: Homo sapiens

<400> SEQUENCE: 54
```

-continued

```
Met Lys Pro Gly Ala Thr Gly Glu Ser Asp Leu Ala Glu Val Leu Pro
 1               5                  10                  15

Gln His Lys Phe Asp Ser Lys Ser Leu Glu Ala Tyr Leu Asn Gln His
            20                  25                  30

Leu Ser Gly Phe Gly Ala Glu Arg Glu Ala Thr Leu Thr Ile Ala Gln
        35                  40                  45

Tyr Arg Ala Gly Lys Ser Asn Pro Thr Phe Tyr Leu Gln Lys Gly Phe
    50                  55                  60

Gln Thr Tyr Val Leu Arg Lys Lys Pro Pro Gly Ser Leu Leu Pro Lys
65                  70                  75                  80

Ala His Gln Ile Asp Arg Glu Phe Lys Val Gln Lys Ala Leu Phe Ser
                85                  90                  95

Ile Gly Phe Pro Val Pro Lys Pro Ile Leu Tyr Cys Ser Asp Thr Ser
            100                 105                 110

Val Ile Gly Thr Glu Phe Tyr Val Met Glu His Val Gln Gly Arg Ile
        115                 120                 125

Phe Arg Asp Leu Thr Ile Pro Gly Leu Ser Pro Ala Glu Arg Ser Ala
    130                 135                 140

Ile Tyr Val Ala Thr Val Glu Thr Leu Ala Gln Leu His Ser Leu Asn
145                 150                 155                 160

Ile Gln Ser Leu Gln Leu Glu Gly Tyr Gly Ile Gly Ala Gly Tyr Cys
                165                 170                 175

Lys Arg Gln Val Ser Thr Trp Thr Lys Gln Tyr Gln Ala Ala Ala His
            180                 185                 190

Gln Asp Ile Pro Ala Met Gln Gln Leu Ser Glu Trp Leu Met Lys Asn
        195                 200                 205

Leu Pro Asp Asn Asp Asn Glu Glu Asn Leu Ile His Gly Asp Phe Arg
    210                 215                 220

Leu Asp Asn Ile Val Phe His Pro Lys Glu Cys Arg Val Ile Ala Val
225                 230                 235                 240

Leu Asp Trp Glu Leu Ser Thr Ile Gly His Pro Leu Ser Asp Leu Ala
                245                 250                 255

His Phe Ser Leu Phe Tyr Phe Trp Pro Arg Thr Val Pro Met Ile Asn
            260                 265                 270

Gln Gly Ser Tyr Ser Glu Asn Ser Gly Ile Pro Ser Met Glu Glu Leu
        275                 280                 285

Ile Ser Ile Tyr Cys Arg Cys Arg Gly Ile Asn Ser Ile Leu Pro Asn
    290                 295                 300

Trp Asn Phe Phe Leu Ala Leu Ser Tyr Phe Lys Met Ala Gly Ile Ala
305                 310                 315                 320

Gln Gly Val Tyr Ser Arg Tyr Leu Leu Gly Asn Asn Ser Ser Glu Asp
                325                 330                 335

Ser Phe Leu Phe Ala Asn Ile Val Gln Pro Leu Ala Glu Thr Gly Leu
            340                 345                 350

Gln Leu Ser Lys Arg Thr Phe Ser Thr Val Leu Pro Gln Ile Asp Thr
        355                 360                 365

Thr Gly Gln Leu Phe Val Gln Thr Arg Lys Gly Gln Glu Val Leu Ile
    370                 375                 380

Lys Val Lys His Phe Met Lys Gln His Ile Leu Pro Ala Glu Lys Glu
385                 390                 395                 400

Val Thr Glu Phe Tyr Val Gln Asn Glu Asn Ser Val Asp Lys Trp Gly
                405                 410                 415

Lys Pro Leu Val Ile Asp Lys Leu Lys Glu Met Ala Lys Val Glu Gly
```

-continued

```
            420                 425                 430

Leu Trp Asn Leu Phe Leu Pro Ala Val Ser Gly Leu Ser His Val Asp
        435                 440                 445

Tyr Ala Leu Ile Ala Glu Glu Thr Gly Lys Cys Phe Phe Ala Pro Asp
    450                 455                 460

Val Phe Asn Cys Gln Ala Pro Asp Thr Gly Asn Met Glu Val Leu His
465                 470                 475                 480

Leu Tyr Gly Ser Glu Glu Gln Lys Lys Gln Trp Leu Glu Pro Leu Leu
                485                 490                 495

Gln Gly Asn Ile Thr Ser Cys Phe Cys Met Thr Glu Pro Asp Val Ala
            500                 505                 510

Ser Ser Asp Ala Thr Asn Ile Glu Cys Ser Ile Gln Arg Asp Glu Asp
        515                 520                 525

Ser Tyr Val Ile Asn Gly Lys Lys Trp Trp Ser Ser Gly Ala Gly Asn
    530                 535                 540

Pro Lys Cys Lys Ile Ala Ile Val Leu Gly Arg Thr Gln Asn Thr Ser
545                 550                 555                 560

Leu Ser Arg His Lys Gln His Ser Met Ile Leu Val Pro Met Asn Thr
                565                 570                 575

Pro Gly Val Lys Ile Ile Arg Pro Leu Ser Val Phe Gly Tyr Thr Asp
            580                 585                 590

Asn Phe His Gly Gly His Phe Glu Ile His Phe Asn Gln Val Arg Val
        595                 600                 605

Pro Ala Thr Asn Leu Ile Leu Gly Glu Gly Arg Gly Phe Glu Ile Ser
    610                 615                 620

Gln Gly Arg Leu Gly Pro Gly Arg Ile His His Cys Met Arg Thr Val
625                 630                 635                 640

Gly Leu Ala Glu Arg Ala Leu Gln Ile Met Cys Glu Arg Ala Thr Gln
                645                 650                 655

Arg Ile Ala Phe Lys Lys Lys Leu Tyr Ala His Glu Val Val Ala His
            660                 665                 670

Trp Ile Ala Glu Ser Arg Ile Ala Ile Glu Lys Ile Arg Leu Leu Thr
        675                 680                 685

Leu Lys Ala Ala His Ser Met Asp Thr Leu Gly Ser Ala Gly Ala Lys
    690                 695                 700

Lys Glu Ile Ala Met Ile Lys Val Ala Ala Pro Arg Ala Val Ser Lys
705                 710                 715                 720

Ile Val Asp Trp Ala Ile Gln Val Cys Gly Gly Ala Gly Val Ser Gln
                725                 730                 735

Asp Tyr Pro Leu Ala Asn Met Tyr Ala Ile Thr Arg Val Leu Arg Leu
            740                 745                 750

Ala Asp Gly Pro Asp Glu Val His Leu Ser Ala Ile Ala Thr Met Glu
        755                 760                 765

Leu Arg Asp Gln Ala Lys Arg Leu Thr Ala Lys Ile
    770                 775                 780
```

<210> SEQ ID NO 55
<211> LENGTH: 2343
<212> TYPE: DNA
<213> ORGANISM: Homo sapiens
<220> FEATURE:
<221> NAME/KEY: CDS
<222> LOCATION: (1)...(2343)

<400> SEQUENCE: 55

-continued

```
atg aag cca ggt gct act ggc gag tcc gat ttg gcc gaa gtg ctg ccc       48
Met Lys Pro Gly Ala Thr Gly Glu Ser Asp Leu Ala Glu Val Leu Pro
 1               5                  10                  15

cag cac aag ttc gac agc aag tcc ctg gag gcc tac cta aac cag cac       96
Gln His Lys Phe Asp Ser Lys Ser Leu Glu Ala Tyr Leu Asn Gln His
            20                  25                  30

ttg tct ggc ttt ggg gcc gaa cgt gag gct acg ctg acc att gcc cag      144
Leu Ser Gly Phe Gly Ala Glu Arg Glu Ala Thr Leu Thr Ile Ala Gln
        35                  40                  45

tac aga gca gga aag tcc aat cca acc ttt tat ctc cag aag ggc ttt      192
Tyr Arg Ala Gly Lys Ser Asn Pro Thr Phe Tyr Leu Gln Lys Gly Phe
    50                  55                  60

caa aca tat gtg ctc agg aaa aaa cca cca ggt tca ctt ctt cct aaa      240
Gln Thr Tyr Val Leu Arg Lys Lys Pro Pro Gly Ser Leu Leu Pro Lys
 65                  70                  75                  80

gca cat cag att gat aga gaa ttt aaa gtc cag aaa gcc ttg ttt tca      288
Ala His Gln Ile Asp Arg Glu Phe Lys Val Gln Lys Ala Leu Phe Ser
                85                  90                  95

att gga ttc ccc gtt ccc aag cct ata ctg tac tgc agt gat act tct      336
Ile Gly Phe Pro Val Pro Lys Pro Ile Leu Tyr Cys Ser Asp Thr Ser
            100                 105                 110

gtc att gga aca gaa ttt tac gta atg gaa cat gtg cag ggt cga atc      384
Val Ile Gly Thr Glu Phe Tyr Val Met Glu His Val Gln Gly Arg Ile
        115                 120                 125

ttc cgt gat tta aca att cct gga ctt agc cca gca gaa cgt tca gcc      432
Phe Arg Asp Leu Thr Ile Pro Gly Leu Ser Pro Ala Glu Arg Ser Ala
    130                 135                 140

ata tat gtg gcc acg gta gaa aca ttg gct cag tta cat tcc ttg aat      480
Ile Tyr Val Ala Thr Val Glu Thr Leu Ala Gln Leu His Ser Leu Asn
145                 150                 155                 160

ata cag tca ctg cag ctg gaa gga tat ggt ata ggt gct ggg tac tgc      528
Ile Gln Ser Leu Gln Leu Glu Gly Tyr Gly Ile Gly Ala Gly Tyr Cys
                165                 170                 175

aaa aga cag gta tca acc tgg aca aag caa tat caa gct gca gct cat      576
Lys Arg Gln Val Ser Thr Trp Thr Lys Gln Tyr Gln Ala Ala Ala His
            180                 185                 190

cag gac atc cct gcc atg caa cag cta tcg gag tgg cta atg aag aac      624
Gln Asp Ile Pro Ala Met Gln Gln Leu Ser Glu Trp Leu Met Lys Asn
        195                 200                 205

ttg ccc gat aat gac aat gaa gag aat ttg att cat gga gat ttc aga      672
Leu Pro Asp Asn Asp Asn Glu Glu Asn Leu Ile His Gly Asp Phe Arg
    210                 215                 220

cta gat aac ata gtt ttc cac cct aaa gag tgt cga gtt ata gca gtg      720
Leu Asp Asn Ile Val Phe His Pro Lys Glu Cys Arg Val Ile Ala Val
225                 230                 235                 240

ctg gat tgg gag ctg tca acc att ggt cat cct ttg tca gac tta gct      768
Leu Asp Trp Glu Leu Ser Thr Ile Gly His Pro Leu Ser Asp Leu Ala
                245                 250                 255

cat ttt tcc ctg ttc tac ttt tgg cca agg aca gtt cca atg ata aat      816
His Phe Ser Leu Phe Tyr Phe Trp Pro Arg Thr Val Pro Met Ile Asn
            260                 265                 270

caa ggt tct tat agt gaa aac tca ggg ata cca tca atg gaa gaa ctg      864
Gln Gly Ser Tyr Ser Glu Asn Ser Gly Ile Pro Ser Met Glu Glu Leu
        275                 280                 285

att tca ata tat tgc cgc tgc agg gga att aat tct att ctt cct aac      912
Ile Ser Ile Tyr Cys Arg Cys Arg Gly Ile Asn Ser Ile Leu Pro Asn
    290                 295                 300

tgg aat ttc ttt ctt gcc ctt tca tat ttt aag atg gct gga ata gca      960
Trp Asn Phe Phe Leu Ala Leu Ser Tyr Phe Lys Met Ala Gly Ile Ala
305                 310                 315                 320
```

-continued

```
cag gga gta tat agc aga tat ctt ctg gga aat aat tca tct gag gat      1008
Gln Gly Val Tyr Ser Arg Tyr Leu Leu Gly Asn Asn Ser Ser Glu Asp
                325                 330                 335

agc ttt tta ttt gcc aat att gtg caa cct ctg gca gaa act gga cta      1056
Ser Phe Leu Phe Ala Asn Ile Val Gln Pro Leu Ala Glu Thr Gly Leu
            340                 345                 350

caa ctc tcc aaa cga act ttc agt act gta cta cca cag att gat act      1104
Gln Leu Ser Lys Arg Thr Phe Ser Thr Val Leu Pro Gln Ile Asp Thr
        355                 360                 365

act gga cag ttg ttt gta cag act cgg aaa ggt cag gaa gtt ctt att      1152
Thr Gly Gln Leu Phe Val Gln Thr Arg Lys Gly Gln Glu Val Leu Ile
    370                 375                 380

aag gtg aag cat ttc atg aaa caa cac att ctt cca gct gaa aag gag      1200
Lys Val Lys His Phe Met Lys Gln His Ile Leu Pro Ala Glu Lys Glu
385                 390                 395                 400

gta act gag ttc tat gtt caa aat gaa aat tca gtg gac aag tgg gga      1248
Val Thr Glu Phe Tyr Val Gln Asn Glu Asn Ser Val Asp Lys Trp Gly
                405                 410                 415

aaa cct tta gtg att gat aaa ctc aag gaa atg gcc aaa gtc gag ggt      1296
Lys Pro Leu Val Ile Asp Lys Leu Lys Glu Met Ala Lys Val Glu Gly
            420                 425                 430

ctc tgg aac ttg ttt ttg cca gct gtc agc gga ctc agc cac gtg gac      1344
Leu Trp Asn Leu Phe Leu Pro Ala Val Ser Gly Leu Ser His Val Asp
        435                 440                 445

tat gcc ttg att gct gaa gaa aca gga aaa tgc ttt ttt gct cca gat      1392
Tyr Ala Leu Ile Ala Glu Glu Thr Gly Lys Cys Phe Phe Ala Pro Asp
    450                 455                 460

gtc ttt aac tgc caa gca cca gac aca ggg aat atg gag gtt ctg cac      1440
Val Phe Asn Cys Gln Ala Pro Asp Thr Gly Asn Met Glu Val Leu His
465                 470                 475                 480

ctg tat gga agt gag gaa cag aag aaa cag tgg ctt gag cct ctt ctt      1488
Leu Tyr Gly Ser Glu Glu Gln Lys Lys Gln Trp Leu Glu Pro Leu Leu
                485                 490                 495

caa ggg aac att acc tct tgc ttc tgt atg aca gaa cct gat gta gct      1536
Gln Gly Asn Ile Thr Ser Cys Phe Cys Met Thr Glu Pro Asp Val Ala
            500                 505                 510

tca agt gat gcc acg aat att gaa tgc agc atc caa cga gat gaa gat      1584
Ser Ser Asp Ala Thr Asn Ile Glu Cys Ser Ile Gln Arg Asp Glu Asp
        515                 520                 525

agc tat gta att aac ggc aaa aaa tgg tgg agc agt gga gct ggg aat      1632
Ser Tyr Val Ile Asn Gly Lys Lys Trp Trp Ser Ser Gly Ala Gly Asn
    530                 535                 540

ccc aag tgc aaa att gca att gtt ttg gga aga act caa aat act tct      1680
Pro Lys Cys Lys Ile Ala Ile Val Leu Gly Arg Thr Gln Asn Thr Ser
545                 550                 555                 560

ctc tcc aga cac aaa cag cac agc atg att ctt gtt ccc atg aac aca      1728
Leu Ser Arg His Lys Gln His Ser Met Ile Leu Val Pro Met Asn Thr
                565                 570                 575

cct gga gta aaa ata ata agg cct ttg tca gtt ttt ggc tac aca gat      1776
Pro Gly Val Lys Ile Ile Arg Pro Leu Ser Val Phe Gly Tyr Thr Asp
            580                 585                 590

aat ttt cat gga gga cat ttt gag atc cat ttt aat caa gtg cga gtt      1824
Asn Phe His Gly Gly His Phe Glu Ile His Phe Asn Gln Val Arg Val
        595                 600                 605

cct gcc aca aat cta ata cta ggt gaa ggt agg gga ttt gaa att tcc      1872
Pro Ala Thr Asn Leu Ile Leu Gly Glu Gly Arg Gly Phe Glu Ile Ser
    610                 615                 620

caa ggc cgc ctt gga cct ggc aga atc cac cac tgt atg aga aca gta      1920
Gln Gly Arg Leu Gly Pro Gly Arg Ile His His Cys Met Arg Thr Val
```

-continued

```
625                 630                 635                 640

ggt ttg gcg gaa cgc gct ttg cag atc atg tgt gag cgg gca aca caa      1968
Gly Leu Ala Glu Arg Ala Leu Gln Ile Met Cys Glu Arg Ala Thr Gln
            645                 650                 655

agg ata gct ttc aag aag aag ttg tat gca cat gag gtt gtg gct cac      2016
Arg Ile Ala Phe Lys Lys Lys Leu Tyr Ala His Glu Val Val Ala His
            660                 665                 670

tgg att gct gaa agc cgc att gcc att gag aag atc cgc ttg ttg act      2064
Trp Ile Ala Glu Ser Arg Ile Ala Ile Glu Lys Ile Arg Leu Leu Thr
        675                 680                 685

ctg aaa gct gct cac agc atg gac act ctg ggc agt gct ggc gct aag      2112
Leu Lys Ala Ala His Ser Met Asp Thr Leu Gly Ser Ala Gly Ala Lys
    690                 695                 700

aaa gag att gca atg atc aaa gtg gct gcc cca cgg gct gtc agc aaa      2160
Lys Glu Ile Ala Met Ile Lys Val Ala Ala Pro Arg Ala Val Ser Lys
705                 710                 715                 720

atc gtt gac tgg gcc atc cag gtg tgc gga ggt gct ggt gtt tcc cag      2208
Ile Val Asp Trp Ala Ile Gln Val Cys Gly Gly Ala Gly Val Ser Gln
            725                 730                 735

gat tac cct ctg gct aac atg tat gct ata acc cga gtt ttg cgt tta      2256
Asp Tyr Pro Leu Ala Asn Met Tyr Ala Ile Thr Arg Val Leu Arg Leu
            740                 745                 750

gca gat gga cct gac gaa gtt cat ctt tca gca atc gca aca atg gag      2304
Ala Asp Gly Pro Asp Glu Val His Leu Ser Ala Ile Ala Thr Met Glu
        755                 760                 765
ctg cgg gac caa gcc aaa aga ctg aca gcc aag ata taa                2343
Leu Arg Asp Gln Ala Lys Arg Leu Thr Ala Lys Ile  *
    770                 775                 780
```

<210> SEQ ID NO 56
<211> LENGTH: 21
<212> TYPE: PRT
<213> ORGANISM: Artificial Sequence
<220> FEATURE:
<223> OTHER INFORMATION: Amino acid consensus sequence

<400> SEQUENCE: 56

```
Gly Ser Glu Glu Gln Lys Lys Lys Tyr Leu Pro Gln Leu Thr Ser Gly
 1               5                  10                  15

Asp Leu Ile Gly Ala
            20
```

<210> SEQ ID NO 57
<211> LENGTH: 80
<212> TYPE: PRT
<213> ORGANISM: Artificial Sequence
<220> FEATURE:
<223> OTHER INFORMATION: Amino acid consensus sequence

<400> SEQUENCE: 57

```
Ala Leu Thr Glu Pro Gly Ala Gly Ser Asp Val Gly Ser Leu Lys Thr
 1               5                  10                  15

Thr Ala Glu Lys Lys Glu Gly Asp Asp Tyr Ile Leu Asn Gly Ser Lys
            20                  25                  30

Met Trp Ile Thr Asn Gly Gly Gln Ala Asp Trp Tyr Ile Val Leu Ala
        35                  40                  45

Val Thr Asp Pro Ala Lys Lys Val Pro Gly Lys Lys Gly Ile Thr Ala
    50                  55                  60

Phe Leu Val Glu Lys Asp Thr Pro Gly Phe Ser Ile Gly Lys Lys Glu
65                  70                  75                  80
```

-continued

<210> SEQ ID NO 58
<211> LENGTH: 128
<212> TYPE: PRT
<213> ORGANISM: Artificial Sequence
<220> FEATURE:
<223> OTHER INFORMATION: Amino acid consensus sequence

<400> SEQUENCE: 58

```
Gly Lys Gly Phe Lys Tyr Ala Met Lys Glu Leu Asp Met Glu Arg Leu
 1               5                  10                  15

Val Ile Ala Ala Gln Ala Leu Gly Leu Ala Gln Gly Ala Leu Asp Glu
            20                  25                  30

Ala Ile Asn Tyr Ala Lys Gln Arg Lys Gln Phe Gly Lys Pro Leu Ala
        35                  40                  45

Asp Phe Gln Leu Ile Gln Phe Lys Leu Ala Asp Met Ala Thr Lys Leu
    50                  55                  60

Glu Ala Ala Arg Leu Leu Val Tyr Arg Ala Ala Trp Leu Ala Asp Arg
65                  70                  75                  80

Gly Glu Asp Ala Lys Glu Ala Leu Pro Thr Ser Lys Glu Ala Ala Met
                85                  90                  95

Ala Lys Leu Phe Ala Ser Glu Ala Ala Met Gln Val Ala Thr Asp Ala
            100                 105                 110

Val Gln Ile Leu Gly Gly Val Gly Tyr Thr Lys Asp Tyr Pro Val Glu
        115                 120                 125
```

<210> SEQ ID NO 59
<211> LENGTH: 13
<212> TYPE: PRT
<213> ORGANISM: Artificial Sequence
<220> FEATURE:
<223> OTHER INFORMATION: Amino acid consensus sequence
<220> FEATURE:
<221> NAME/KEY: VARIANT
<222> LOCATION: (1)...(1)
<223> OTHER INFORMATION: Xaa at position 1 can be G, A or C
<220> FEATURE:
<221> NAME/KEY: VARIANT
<222> LOCATION: (2)...(2)
<223> OTHER INFORMATION: Xaa at position 2 can be I, V, L or M
<220> FEATURE:
<221> NAME/KEY: VARIANT
<222> LOCATION: (3)...(3)
<223> OTHER INFORMATION: Xaa at position 3 can be S or T
<220> FEATURE:
<221> NAME/KEY: VARIANT
<222> LOCATION: (5)...(6)
<223> OTHER INFORMATION: Xaa = Any amino acid
<220> FEATURE:
<221> NAME/KEY: VARIANT
<222> LOCATION: (7)...(7)
<223> OTHER INFORMATION: Xaa at position 7 can be G, S, A or N
<220> FEATURE:
<221> NAME/KEY: VARIANT
<222> LOCATION: (9)...(9)
<223> OTHER INFORMATION: Xaa at position 9 can be S or T
<220> FEATURE:
<221> NAME/KEY: VARIANT
<222> LOCATION: (11)...(12)
<223> OTHER INFORMATION: Xaa = Any amino acid
<220> FEATURE:
<221> NAME/KEY: VARIANT
<222> LOCATION: (13)...(13)
<223> OTHER INFORMATION: Xaa at position 13 can be S, G or A

<400> SEQUENCE: 59

```
Xaa Xaa Xaa Glu Xaa Xaa Xaa Gly Xaa Asp Xaa Xaa Xaa
 1               5                  10
```

-continued

<210> SEQ ID NO 60
<211> LENGTH: 20
<212> TYPE: PRT
<213> ORGANISM: Artificial Sequence
<220> FEATURE:
<223> OTHER INFORMATION: Amino acid consensus sequence
<220> FEATURE:
<221> NAME/KEY: VARIANT
<222> LOCATION: (1)...(1)
<223> OTHER INFORMATION: Xaa at position 1 can be Q, D or E
<220> FEATURE:
<221> NAME/KEY: VARIANT
<222> LOCATION: (2)...(3)
<223> OTHER INFORMATION: Xaa = Any amino acid
<220> FEATURE:
<221> NAME/KEY: VARIANT
<222> LOCATION: (5)...(5)
<223> OTHER INFORMATION: Xaa at position 5 can be G or S
<220> FEATURE:
<221> NAME/KEY: VARIANT
<222> LOCATION: (6)...(6)
<223> OTHER INFORMATION: Xaa = Any amino acid
<220> FEATURE:
<221> NAME/KEY: VARIANT
<222> LOCATION: (8)...(8)
<223> OTHER INFORMATION: Xaa at position 8 can be L, I, V, M, F or Y
<220> FEATURE:
<221> NAME/KEY: VARIANT
<222> LOCATION: (9)...(10)
<223> OTHER INFORMATION: Xaa = Any amino acid
<220> FEATURE:
<221> NAME/KEY: VARIANT
<222> LOCATION: (11)...(11)
<223> OTHER INFORMATION: Xaa at position 11 can be D, E or N
<220> FEATURE:
<221> NAME/KEY: VARIANT
<222> LOCATION: (12)...(15)
<223> OTHER INFORMATION: Xaa = Any amino acid
<220> FEATURE:
<221> NAME/KEY: VARIANT
<222> LOCATION: (16)...(16)
<223> OTHER INFORMATION: Xaa at position 16 can be K or R
<220> FEATURE:
<221> NAME/KEY: VARIANT
<222> LOCATION: (17)...(19)
<223> OTHER INFORMATION: Xaa = Any amino acid
<220> FEATURE:
<221> NAME/KEY: VARIANT
<222> LOCATION: (20)...(20)
<223> OTHER INFORMATION: Xaa at position 20 can be D, E or N

<400> SEQUENCE: 60

```
Xaa Xaa Xaa Gly Xaa Xaa Gly Xaa Xaa Xaa Xaa Xaa Xaa Xaa Xaa Xaa
 1               5                  10                  15

Xaa Xaa Xaa Xaa
            20
```

<210> SEQ ID NO 61
<211> LENGTH: 2004
<212> TYPE: DNA
<213> ORGANISM: Homo sapiens
<220> FEATURE:
<221> NAME/KEY: CDS
<222> LOCATION: (119)...(1717)

<400> SEQUENCE: 61

```
gcactggact tgtaaacgaa aagcttcata agtccctctt tgcttagtac ttttctcgtc      60

ctttccccag ggtgcacgta accctcaagc actaggaccg tgcggaatcc aggctgcg       118

atg gca cct tca ttt acc gcc cgc att cag ttg ttc ctc ttg cgg gcg       166
Met Ala Pro Ser Phe Thr Ala Arg Ile Gln Leu Phe Leu Leu Arg Ala
 1               5                  10                  15

cta ggc ttt ctc ata ggc tta gta ggc cga gca gct tta gtc tta ggg       214
```

-continued

```
Leu Gly Phe Leu Ile Gly Leu Val Gly Arg Ala Ala Leu Val Leu Gly
             20                  25                  30

ggt cca aag ttt gcc tca aag acc cct cgg ccg gtg act gaa cca ttg      262
Gly Pro Lys Phe Ala Ser Lys Thr Pro Arg Pro Val Thr Glu Pro Leu
         35                  40                  45

ctt ctg ctt tcg ggg atg cag ctg gcc aag ctg atc cga cag aga aag      310
Leu Leu Leu Ser Gly Met Gln Leu Ala Lys Leu Ile Arg Gln Arg Lys
     50                  55                  60

gtg aaa tgt ata gat gtt gtt cag gct tat atc aac aga atc aag gac      358
Val Lys Cys Ile Asp Val Val Gln Ala Tyr Ile Asn Arg Ile Lys Asp
 65                  70                  75                  80

gtg aac cca atg atc aat gga att gtc aag tac agg ttt gag gaa gcg      406
Val Asn Pro Met Ile Asn Gly Ile Val Lys Tyr Arg Phe Glu Glu Ala
                 85                  90                  95

atg aag gag gct cat gct gta gat caa aag ctt gca gag aag cag gaa      454
Met Lys Glu Ala His Ala Val Asp Gln Lys Leu Ala Glu Lys Gln Glu
            100                 105                 110

gat gaa gcc acc ctg gaa aat aaa tgg ccc ttc ctt ggg gtt cct ttg      502
Asp Glu Ala Thr Leu Glu Asn Lys Trp Pro Phe Leu Gly Val Pro Leu
        115                 120                 125

aca gtc aag gaa gct ttc cag cta caa gga atg ccc aat tct tct gga      550
Thr Val Lys Glu Ala Phe Gln Leu Gln Gly Met Pro Asn Ser Ser Gly
    130                 135                 140

ctc atg aac cgt cgt gat gcc att gcc aaa aca gat gcc act gtg gtg      598
Leu Met Asn Arg Arg Asp Ala Ile Ala Lys Thr Asp Ala Thr Val Val
145                 150                 155                 160

gca tta ctg aag gga gct ggt gcc att cct ctt ggc ata acc aac tgt      646
Ala Leu Leu Lys Gly Ala Gly Ala Ile Pro Leu Gly Ile Thr Asn Cys
                165                 170                 175

agt gag ttg tgt atg tgg tat gaa tcc agt aac aag atc tat ggc cga      694
Ser Glu Leu Cys Met Trp Tyr Glu Ser Ser Asn Lys Ile Tyr Gly Arg
            180                 185                 190

tca aac aac cca tat gat tta cag cat att gta ggt gga agt tct ggt      742
Ser Asn Asn Pro Tyr Asp Leu Gln His Ile Val Gly Gly Ser Ser Gly
        195                 200                 205

ggt gag ggc tgc aca ctg gca gct gcc tgc tca gtt att ggt gtg ggc      790
Gly Glu Gly Cys Thr Leu Ala Ala Ala Cys Ser Val Ile Gly Val Gly
    210                 215                 220

tct gat att ggt ggt agc att cga atg cct gct ttc ttc aat ggt ata      838
Ser Asp Ile Gly Gly Ser Ile Arg Met Pro Ala Phe Phe Asn Gly Ile
225                 230                 235                 240

ttt gga cac aag cct tct cca ggt gtg gtt ccc aac aaa ggt cag ttt      886
Phe Gly His Lys Pro Ser Pro Gly Val Val Pro Asn Lys Gly Gln Phe
                245                 250                 255

ccc ttg gct gtg gga gcc cag gag ttg ttt ctg tgc act ggt cct atg      934
Pro Leu Ala Val Gly Ala Gln Glu Leu Phe Leu Cys Thr Gly Pro Met
            260                 265                 270

tgc cgc tat gct gaa gac ctg gcc ccc atg ttg aag gtc atg gca gga      982
Cys Arg Tyr Ala Glu Asp Leu Ala Pro Met Leu Lys Val Met Ala Gly
        275                 280                 285

cct ggg atc aaa agg tta aaa cta gac aca aag gta cat tta aaa gac     1030
Pro Gly Ile Lys Arg Leu Lys Leu Asp Thr Lys Val His Leu Lys Asp
    290                 295                 300

tta aaa ttt tac tgg atg gaa cat gat gga ggc tca ttt tta atg tcc     1078
Leu Lys Phe Tyr Trp Met Glu His Asp Gly Gly Ser Phe Leu Met Ser
305                 310                 315                 320

aaa gtg gac caa gat ctc att atg act cag aaa aag gtt gtg gtt cac     1126
Lys Val Asp Gln Asp Leu Ile Met Thr Gln Lys Lys Val Val Val His
                325                 330                 335
```

-continued

```
ctt gaa act att cta gga gcc tca gtt caa cat gtt aaa ctg aag aaa      1174
Leu Glu Thr Ile Leu Gly Ala Ser Val Gln His Val Lys Leu Lys Lys
            340                 345                 350

atg aag tac tct ttt cag ttg tgg atc gca atg atg tca gca aag gga      1222
Met Lys Tyr Ser Phe Gln Leu Trp Ile Ala Met Met Ser Ala Lys Gly
        355                 360                 365

cat gat ggg aag gaa cct gtg aaa ttt gta gat ttg ctt ggt gac cat      1270
His Asp Gly Lys Glu Pro Val Lys Phe Val Asp Leu Leu Gly Asp His
    370                 375                 380

ggg aaa cat gtc agt cct ctg tgg gag ttg atc aaa tgg tgc ctg ggt      1318
Gly Lys His Val Ser Pro Leu Trp Glu Leu Ile Lys Trp Cys Leu Gly
385                 390                 395                 400

ctg tca gtg tac acc atc cct tcc att gga ctg gct ttg ttg gaa gaa      1366
Leu Ser Val Tyr Thr Ile Pro Ser Ile Gly Leu Ala Leu Leu Glu Glu
                405                 410                 415

aag ctc aga tat agc aat gag aaa tac caa aag ttt aag gca gtg gaa      1414
Lys Leu Arg Tyr Ser Asn Glu Lys Tyr Gln Lys Phe Lys Ala Val Glu
            420                 425                 430

gaa agc ctg cgt aaa gag ctg gtg gat atg cta ggt gat gat ggt gtg      1462
Glu Ser Leu Arg Lys Glu Leu Val Asp Met Leu Gly Asp Asp Gly Val
        435                 440                 445

ttc tta tat ccc tca cat ccc aca gtg gca cct aag cat cat gtc cct      1510
Phe Leu Tyr Pro Ser His Pro Thr Val Ala Pro Lys His His Val Pro
    450                 455                 460

cta aca cgg ccc ttc aac ttt gct tac aca ggt gtc ttc agt gcc ctg      1558
Leu Thr Arg Pro Phe Asn Phe Ala Tyr Thr Gly Val Phe Ser Ala Leu
465                 470                 475                 480

ggt ttg cct gtg acc caa tgc cca ctg gga ctg aat gcc aaa gga ctc      1606
Gly Leu Pro Val Thr Gln Cys Pro Leu Gly Leu Asn Ala Lys Gly Leu
                485                 490                 495

cct tta ggc atc cag gtt gtg gct gga ccc ttt aat gat cat ctg acc      1654
Pro Leu Gly Ile Gln Val Val Ala Gly Pro Phe Asn Asp His Leu Thr
            500                 505                 510

ctg gct gtg gcc cag tac ttg gag aaa act ttt ggg ggc tgg gtc tgt      1702
Leu Ala Val Ala Gln Tyr Leu Glu Lys Thr Phe Gly Gly Trp Val Cys
        515                 520                 525

cca gga aag ttt tag gaggaccttc tgcaaggtta atgtgtgtgt gtgtttgtgt      1757
Pro Gly Lys Phe  *
    530

tcgtgtggtg gtgtttctat taattgggtg aaaccaagca ccagcagaca agcagagaaa   1817

caactgggga atttattgac tcatttagtt attctttcta cttttatttc cttctctaac   1877

tgttggtctt actaaaatgg taatatttgc ttcttgcttt tatgttactg gaaaattagg   1937

acatgtaaat ggataagtgc aataaagttt cctaaatgct gaaaaaaaaa aaaaaaaaaa   1997

aggccgc                                                             2004


<210> SEQ ID NO 62
<211> LENGTH: 532
<212> TYPE: PRT
<213> ORGANISM: Homo sapiens

<400> SEQUENCE: 62

Met Ala Pro Ser Phe Thr Ala Arg Ile Gln Leu Phe Leu Leu Arg Ala
 1               5                  10                  15

Leu Gly Phe Leu Ile Gly Leu Val Gly Arg Ala Ala Leu Val Leu Gly
            20                  25                  30

Gly Pro Lys Phe Ala Ser Lys Thr Pro Arg Pro Val Thr Glu Pro Leu
        35                  40                  45
```

-continued

```
Leu Leu Leu Ser Gly Met Gln Leu Ala Lys Leu Ile Arg Gln Arg Lys
    50                  55                  60

Val Lys Cys Ile Asp Val Val Gln Ala Tyr Ile Asn Arg Ile Lys Asp
65                  70                  75                  80

Val Asn Pro Met Ile Asn Gly Ile Val Lys Tyr Arg Phe Glu Glu Ala
                85                  90                  95

Met Lys Glu Ala His Ala Val Asp Gln Lys Leu Ala Glu Lys Gln Glu
            100                 105                 110

Asp Glu Ala Thr Leu Glu Asn Lys Trp Pro Phe Leu Gly Val Pro Leu
        115                 120                 125

Thr Val Lys Glu Ala Phe Gln Leu Gln Gly Met Pro Asn Ser Ser Gly
    130                 135                 140

Leu Met Asn Arg Arg Asp Ala Ile Ala Lys Thr Asp Ala Thr Val Val
145                 150                 155                 160

Ala Leu Leu Lys Gly Ala Gly Ala Ile Pro Leu Gly Ile Thr Asn Cys
                165                 170                 175

Ser Glu Leu Cys Met Trp Tyr Glu Ser Ser Asn Lys Ile Tyr Gly Arg
            180                 185                 190

Ser Asn Asn Pro Tyr Asp Leu Gln His Ile Val Gly Gly Ser Ser Gly
        195                 200                 205

Gly Glu Gly Cys Thr Leu Ala Ala Ala Cys Ser Val Ile Gly Val Gly
    210                 215                 220

Ser Asp Ile Gly Gly Ser Ile Arg Met Pro Ala Phe Phe Asn Gly Ile
225                 230                 235                 240

Phe Gly His Lys Pro Ser Pro Gly Val Val Pro Asn Lys Gly Gln Phe
                245                 250                 255

Pro Leu Ala Val Gly Ala Gln Glu Leu Phe Leu Cys Thr Gly Pro Met
            260                 265                 270

Cys Arg Tyr Ala Glu Asp Leu Ala Pro Met Leu Lys Val Met Ala Gly
        275                 280                 285

Pro Gly Ile Lys Arg Leu Lys Leu Asp Thr Lys Val His Leu Lys Asp
    290                 295                 300

Leu Lys Phe Tyr Trp Met Glu His Asp Gly Gly Ser Phe Leu Met Ser
305                 310                 315                 320

Lys Val Asp Gln Asp Leu Ile Met Thr Gln Lys Lys Val Val Val His
                325                 330                 335

Leu Glu Thr Ile Leu Gly Ala Ser Val Gln His Val Lys Leu Lys Lys
            340                 345                 350

Met Lys Tyr Ser Phe Gln Leu Trp Ile Ala Met Met Ser Ala Lys Gly
        355                 360                 365

His Asp Gly Lys Glu Pro Val Lys Phe Val Asp Leu Leu Gly Asp His
    370                 375                 380

Gly Lys His Val Ser Pro Leu Trp Glu Leu Ile Lys Trp Cys Leu Gly
385                 390                 395                 400

Leu Ser Val Tyr Thr Ile Pro Ser Ile Gly Leu Ala Leu Leu Glu Glu
                405                 410                 415

Lys Leu Arg Tyr Ser Asn Glu Lys Tyr Gln Lys Phe Lys Ala Val Glu
            420                 425                 430

Glu Ser Leu Arg Lys Glu Leu Val Asp Met Leu Gly Asp Asp Gly Val
        435                 440                 445

Phe Leu Tyr Pro Ser His Pro Thr Val Ala Pro Lys His His Val Pro
    450                 455                 460

Leu Thr Arg Pro Phe Asn Phe Ala Tyr Thr Gly Val Phe Ser Ala Leu
```

-continued 465 470 475 480

Gly Leu Pro Val Thr Gln Cys Pro Leu Gly Leu Asn Ala Lys Gly Leu
485 490 495

Pro Leu Gly Ile Gln Val Val Ala Gly Pro Phe Asn Asp His Leu Thr
500 505 510

Leu Ala Val Ala Gln Tyr Leu Glu Lys Thr Phe Gly Gly Trp Val Cys
515 520 525

Pro Gly Lys Phe
530

<210> SEQ ID NO 63
<211> LENGTH: 1599
<212> TYPE: DNA
<213> ORGANISM: Homo sapiens
<220> FEATURE:
<221> NAME/KEY: CDS
<222> LOCATION: (1)...(1599)

<400> SEQUENCE: 63 atg gca cct tca ttt acc gcc cgc att cag ttg ttc ctc ttg cgg gcg 48
Met Ala Pro Ser Phe Thr Ala Arg Ile Gln Leu Phe Leu Leu Arg Ala
1 5 10 15 cta ggc ttt ctc ata ggc tta gta ggc cga gca gct tta gtc tta ggg 96
Leu Gly Phe Leu Ile Gly Leu Val Gly Arg Ala Ala Leu Val Leu Gly
20 25 30 ggt cca aag ttt gcc tca aag acc cct cgg ccg gtg act gaa cca ttg 144
Gly Pro Lys Phe Ala Ser Lys Thr Pro Arg Pro Val Thr Glu Pro Leu
35 40 45 ctt ctg ctt tcg ggg atg cag ctg gcc aag ctg atc cga cag aga aag 192
Leu Leu Leu Ser Gly Met Gln Leu Ala Lys Leu Ile Arg Gln Arg Lys
50 55 60 gtg aaa tgt ata gat gtt gtt cag gct tat atc aac aga atc aag gac 240
Val Lys Cys Ile Asp Val Val Gln Ala Tyr Ile Asn Arg Ile Lys Asp
65 70 75 80 gtg aac cca atg atc aat gga att gtc aag tac agg ttt gag gaa gcg 288
Val Asn Pro Met Ile Asn Gly Ile Val Lys Tyr Arg Phe Glu Glu Ala
85 90 95 atg aag gag gct cat gct gta gat caa aag ctt gca gag aag cag gaa 336
Met Lys Glu Ala His Ala Val Asp Gln Lys Leu Ala Glu Lys Gln Glu
100 105 110 gat gaa gcc acc ctg gaa aat aaa tgg ccc ttc ctt ggg gtt cct ttg 384
Asp Glu Ala Thr Leu Glu Asn Lys Trp Pro Phe Leu Gly Val Pro Leu
115 120 125 aca gtc aag gaa gct ttc cag cta caa gga atg ccc aat tct tct gga 432
Thr Val Lys Glu Ala Phe Gln Leu Gln Gly Met Pro Asn Ser Ser Gly
130 135 140 ctc atg aac cgt cgt gat gcc att gcc aaa aca gat gcc act gtg gtg 480
Leu Met Asn Arg Arg Asp Ala Ile Ala Lys Thr Asp Ala Thr Val Val
145 150 155 160 gca tta ctg aag gga gct ggt gcc att cct ctt ggc ata acc aac tgt 528
Ala Leu Leu Lys Gly Ala Gly Ala Ile Pro Leu Gly Ile Thr Asn Cys
165 170 175 agt gag ttg tgt atg tgg tat gaa tcc agt aac aag atc tat ggc cga 576
Ser Glu Leu Cys Met Trp Tyr Glu Ser Ser Asn Lys Ile Tyr Gly Arg
180 185 190 tca aac aac cca tat gat tta cag cat att gta ggt gga agt tct ggt 624
Ser Asn Asn Pro Tyr Asp Leu Gln His Ile Val Gly Gly Ser Ser Gly
195 200 205 ggt gag ggc tgc aca ctg gca gct gcc tgc tca gtt att ggt gtg ggc 672
Gly Glu Gly Cys Thr Leu Ala Ala Ala Cys Ser Val Ile Gly Val Gly -continued

```
    210                 215                 220

tct gat att ggt ggt agc att cga atg cct gct ttc ttc aat ggt ata      720
Ser Asp Ile Gly Gly Ser Ile Arg Met Pro Ala Phe Phe Asn Gly Ile
225                 230                 235                 240

ttt gga cac aag cct tct cca ggt gtg gtt ccc aac aaa ggt cag ttt      768
Phe Gly His Lys Pro Ser Pro Gly Val Val Pro Asn Lys Gly Gln Phe
                245                 250                 255

ccc ttg gct gtg gga gcc cag gag ttg ttt ctg tgc act ggt cct atg      816
Pro Leu Ala Val Gly Ala Gln Glu Leu Phe Leu Cys Thr Gly Pro Met
            260                 265                 270

tgc cgc tat gct gaa gac ctg gcc ccc atg ttg aag gtc atg gca gga      864
Cys Arg Tyr Ala Glu Asp Leu Ala Pro Met Leu Lys Val Met Ala Gly
        275                 280                 285

cct ggg atc aaa agg tta aaa cta gac aca aag gta cat tta aaa gac      912
Pro Gly Ile Lys Arg Leu Lys Leu Asp Thr Lys Val His Leu Lys Asp
    290                 295                 300

tta aaa ttt tac tgg atg gaa cat gat gga ggc tca ttt tta atg tcc      960
Leu Lys Phe Tyr Trp Met Glu His Asp Gly Gly Ser Phe Leu Met Ser
305                 310                 315                 320

aaa gtg gac caa gat ctc att atg act cag aaa aag gtt gtg gtt cac     1008
Lys Val Asp Gln Asp Leu Ile Met Thr Gln Lys Lys Val Val Val His
                325                 330                 335

ctt gaa act att cta gga gcc tca gtt caa cat gtt aaa ctg aag aaa     1056
Leu Glu Thr Ile Leu Gly Ala Ser Val Gln His Val Lys Leu Lys Lys
            340                 345                 350

atg aag tac tct ttt cag ttg tgg atc gca atg atg tca gca aag gga     1104
Met Lys Tyr Ser Phe Gln Leu Trp Ile Ala Met Met Ser Ala Lys Gly
        355                 360                 365

cat gat ggg aag gaa cct gtg aaa ttt gta gat ttg ctt ggt gac cat     1152
His Asp Gly Lys Glu Pro Val Lys Phe Val Asp Leu Leu Gly Asp His
    370                 375                 380

ggg aaa cat gtc agt cct ctg tgg gag ttg atc aaa tgg tgc ctg ggt     1200
Gly Lys His Val Ser Pro Leu Trp Glu Leu Ile Lys Trp Cys Leu Gly
385                 390                 395                 400

ctg tca gtg tac acc atc cct tcc att gga ctg gct ttg ttg gaa gaa     1248
Leu Ser Val Tyr Thr Ile Pro Ser Ile Gly Leu Ala Leu Leu Glu Glu
                405                 410                 415

aag ctc aga tat agc aat gag aaa tac caa aag ttt aag gca gtg gaa     1296
Lys Leu Arg Tyr Ser Asn Glu Lys Tyr Gln Lys Phe Lys Ala Val Glu
            420                 425                 430

gaa agc ctg cgt aaa gag ctg gtg gat atg cta ggt gat gat ggt gtg     1344
Glu Ser Leu Arg Lys Glu Leu Val Asp Met Leu Gly Asp Asp Gly Val
        435                 440                 445

ttc tta tat ccc tca cat ccc aca gtg gca cct aag cat cat gtc cct     1392
Phe Leu Tyr Pro Ser His Pro Thr Val Ala Pro Lys His His Val Pro
    450                 455                 460

cta aca cgg ccc ttc aac ttt gct tac aca ggt gtc ttc agt gcc ctg     1440
Leu Thr Arg Pro Phe Asn Phe Ala Tyr Thr Gly Val Phe Ser Ala Leu
465                 470                 475                 480

ggt ttg cct gtg acc caa tgc cca ctg gga ctg aat gcc aaa gga ctc     1488
Gly Leu Pro Val Thr Gln Cys Pro Leu Gly Leu Asn Ala Lys Gly Leu
                485                 490                 495

cct tta ggc atc cag gtt gtg gct gga ccc ttt aat gat cat ctg acc     1536
Pro Leu Gly Ile Gln Val Val Ala Gly Pro Phe Asn Asp His Leu Thr
            500                 505                 510

ctg gct gtg gcc cag tac ttg gag aaa act ttt ggg ggc tgg gtc tgt     1584
Leu Ala Val Ala Gln Tyr Leu Glu Lys Thr Phe Gly Gly Trp Val Cys
        515                 520                 525

cca gga aag ttt tag                                                 1599
```

-continued

```
Pro Gly Lys Phe  *
    530


<210> SEQ ID NO 64
<211> LENGTH: 218
<212> TYPE: PRT
<213> ORGANISM: Artificial Sequence
<220> FEATURE:
<223> OTHER INFORMATION: Amino acid consensus sequence

<400> SEQUENCE: 64

Glu Leu Val Glu Ala Phe Leu Ala Arg Ile Glu Ala Ala Asn Pro Lys
 1               5                  10                  15

Leu Asn Val Thr Ala Phe Val Thr Val Phe Phe Glu Glu Ala Leu Ala
            20                  25                  30

Ala Ala Lys Ala Ala Asp Lys Arg Arg Ala Arg Lys Arg Gly Gly Glu
        35                  40                  45

Lys Gly Pro Leu His Gly Val Pro Ile Ala Leu Lys Asp Asn Ile Asp
    50                  55                  60

Val Lys Gly Val Pro Thr Thr Ala Gly Ser Lys Ala Leu Glu Gly Tyr
65                  70                  75                  80

Pro Pro Pro Tyr Asp Ala Thr Val Val Glu Arg Leu Arg Ala Ala Gly
                85                  90                  95

Ala Val Ile Leu Gly Lys Thr Asn Met Asp Glu Phe Ala Met Gly Ser
            100                 105                 110

Thr Thr Glu Asn Ser Ala Phe Gly Pro Thr Arg Asn Pro Trp Asp Leu
        115                 120                 125

Ser Arg Thr Pro Gly Gly Ser Ser Gly Gly Ser Ala Ala Ala Val Ala
    130                 135                 140

Ala Gly Leu Val Pro Leu Ala Ile Gly Thr Asp Thr Gly Gly Ser Ile
145                 150                 155                 160

Arg Ile Pro Ala Ala Phe Cys Gly Leu Val Gly Leu Lys Pro Thr Tyr
                165                 170                 175

Gly Arg Val Ser Arg Tyr Gly Val Val Gly Ser Val Glu Pro Leu Ser
            180                 185                 190

Ser Ser Leu Asp Gln Val Gly Pro Leu Ala Arg Ser Val Glu Asp Ala
        195                 200                 205

Ala Leu Leu Leu Asp Val Ile Ala Gly Tyr
    210                 215


<210> SEQ ID NO 65
<211> LENGTH: 127
<212> TYPE: PRT
<213> ORGANISM: Artificial Sequence
<220> FEATURE:
<223> OTHER INFORMATION: Amino acid consensus sequence

<400> SEQUENCE: 65

Gly Tyr Ser Asp Ala Tyr Glu Tyr Leu Lys Ala Gln Lys Val Arg Arg
 1               5                  10                  15

Leu Leu Arg Arg Glu Phe Asp Gly Leu Phe Glu Glu His Gly Val Asp
            20                  25                  30

Val Leu Ile Ser Pro Thr Thr Pro Thr Pro Ala Pro Arg Ile Gly Glu
        35                  40                  45

Pro Asp Lys Leu Ile Ser Glu Ala Asp Asp Tyr Thr Val Leu Tyr Leu
    50                  55                  60

Leu Asp Asp Phe Thr Ala Asn Thr Val Pro Ala Asn Leu Ala Gly Leu
65                  70                  75                  80
```

-continued

```
Pro Ala Ile Ser Val Pro Val Gly Phe Ser Pro Glu Asp Ser Trp Asp
                85                  90                  95

Ala Leu Val Lys Glu Tyr Leu Pro Glu Gly Tyr Val Gly Leu Pro Val
            100                 105                 110

Gly Leu Gln Ile Ile Gly Lys Pro Gly Asp Glu Glu Thr Leu Leu
        115                 120                 125
```

<210> SEQ ID NO 66
<211> LENGTH: 22
<212> TYPE: PRT
<213> ORGANISM: Artificial Sequence
<220> FEATURE:
<223> OTHER INFORMATION: Amidase signature motif
<220> FEATURE:
<221> NAME/KEY: VARIANT
<222> LOCATION: (2)...(2)
<223> OTHER INFORMATION: Xaa at position2 can be G or A
<220> FEATURE:
<221> NAME/KEY: VARIANT
<222> LOCATION: (4)...(5)
<223> OTHER INFORMATION: Xaa at positions 4 and 5 can be G or S
<220> FEATURE:
<221> NAME/KEY: VARIANT
<222> LOCATION: (7)...(7)
<223> OTHER INFORMATION: Xaa = Any amino acid
<220> FEATURE:
<221> NAME/KEY: VARIANT
<222> LOCATION: (8)...(8)
<223> OTHER INFORMATION: Xaa at position 8 can be G, S or A
<220> FEATURE:
<221> NAME/KEY: VARIANT
<222> LOCATION: (9)...(9)
<223> OTHER INFORMATION: Xaa at position 9 can be G, S, A, V or Y
<220> FEATURE:
<221> NAME/KEY: VARIANT
<222> LOCATION: (10)...(10)
<223> OTHER INFORMATION: Xaa = Any amino acid
<220> FEATURE:
<221> NAME/KEY: VARIANT
<222> LOCATION: (11)...(11)
<223> OTHER INFORMATION: Xaa at position 11 can be G or A
<220> FEATURE:
<221> NAME/KEY: VARIANT
<222> LOCATION: (12)...(12)
<223> OTHER INFORMATION: Xaa = Any amino acid
<220> FEATURE:
<221> NAME/KEY: VARIANT
<222> LOCATION: (13)...(13)
<223> OTHER INFORMATION: Xaa at position 13 can be D or E
<220> FEATURE:
<221> NAME/KEY: VARIANT
<222> LOCATION: (14)...(14)
<223> OTHER INFORMATION: Xaa = Any amino acid
<220> FEATURE:
<221> NAME/KEY: VARIANT
<222> LOCATION: (15)...(15)
<223> OTHER INFORMATION: Xaa at position 15 can be G or A
<220> FEATURE:
<221> NAME/KEY: VARIANT
<222> LOCATION: (16)...(16)
<223> OTHER INFORMATION: Xaa = Any amino acid
<220> FEATURE:
<221> NAME/KEY: VARIANT
<222> LOCATION: (18)...(18)
<223> OTHER INFORMATION: Xaa at position 18 can be L, I, V or M
<220> FEATURE:
<221> NAME/KEY: VARIANT
<222> LOCATION: (20)...(20)
<223> OTHER INFORMATION: Xaa = Any amino acid
<220> FEATURE:
<221> NAME/KEY: VARIANT
<222> LOCATION: (22)...(22)
<223> OTHER INFORMATION: Xaa at position 22 can be G, S, A or C

<400> SEQUENCE: 66

-continued

```
Gly Xaa Ser Xaa Xaa Gly Xaa Xaa Xaa Xaa Xaa Xaa Xaa Xaa Xaa Xaa
 1               5                  10                  15

Ser Xaa Arg Xaa Pro Xaa
            20


<210> SEQ ID NO 67
<211> LENGTH: 1816
<212> TYPE: DNA
<213> ORGANISM: Homo sapiens
<220> FEATURE:
<221> NAME/KEY: CDS
<222> LOCATION: (84)...(1436)

<400> SEQUENCE: 67

cacgcgtccg gggccttgg aggcccagcc cgcgcggcga cgtctccgcg tggcgtcacg      60

gcaccgactg acggccaccc acc atg gcc gca gac cag cgc ccg aag gcc gac    113
                          Met Ala Ala Asp Gln Arg Pro Lys Ala Asp
                           1               5                  10

acg ctg gcc ctg agg caa cgg ctc atc agc tct tcc tgc aga ccc ttt      161
Thr Leu Ala Leu Arg Gln Arg Leu Ile Ser Ser Ser Cys Arg Pro Phe
                 15                  20                  25

ttt ccc gag gat cct gtt aag att gtc cgg gcc caa ggg cag tac atg      209
Phe Pro Glu Asp Pro Val Lys Ile Val Arg Ala Gln Gly Gln Tyr Met
             30                  35                  40

tac gat gaa cag ggg gca gaa tac atc gat tgc atc agc aat gtg gcg      257
Tyr Asp Glu Gln Gly Ala Glu Tyr Ile Asp Cys Ile Ser Asn Val Ala
         45                  50                  55

cac gtt ggg cac tgc cac cct ctc gtg gtc caa gca gca cat gag cag      305
His Val Gly His Cys His Pro Leu Val Val Gln Ala Ala His Glu Gln
     60                  65                  70

aac cag gtg ctc aac acc aac agc cgg tac ctg cat gac aac atc gtg      353
Asn Gln Val Leu Asn Thr Asn Ser Arg Tyr Leu His Asp Asn Ile Val
 75                  80                  85                  90

gac tat gcg cag agg ctg tca gag acc ctg ccg gag cag ctc tgt gtg      401
Asp Tyr Ala Gln Arg Leu Ser Glu Thr Leu Pro Glu Gln Leu Cys Val
                 95                 100                 105

ttc tat ttc ctg aat tct ggg tca gaa gcc aat gac ctg gcc ctg agg      449
Phe Tyr Phe Leu Asn Ser Gly Ser Glu Ala Asn Asp Leu Ala Leu Arg
            110                 115                 120

ctg gct cgc cac tac acg gga cac cag gac gtg gtg gta tta gat cat      497
Leu Ala Arg His Tyr Thr Gly His Gln Asp Val Val Val Leu Asp His
        125                 130                 135

gcg tat cac ggc cac ctg agc tcc ctg att gac atc agt ccc tac aag      545
Ala Tyr His Gly His Leu Ser Ser Leu Ile Asp Ile Ser Pro Tyr Lys
    140                 145                 150

ttc cgc aac ctg gat ggc cag aag gag tgg gtc cac gtg gca cct ctc      593
Phe Arg Asn Leu Asp Gly Gln Lys Glu Trp Val His Val Ala Pro Leu
155                 160                 165                 170

cca gac acc tac cgg ggc ccc tac cgg gag gac cac ccc aac cca gct      641
Pro Asp Thr Tyr Arg Gly Pro Tyr Arg Glu Asp His Pro Asn Pro Ala
                175                 180                 185

atg gcc tat gcc aac gag gtg aaa cgt gtg gtc agc agt gca cag gag      689
Met Ala Tyr Ala Asn Glu Val Lys Arg Val Val Ser Ser Ala Gln Glu
            190                 195                 200

aag ggc agg aag att gca gcc ttc ttc gct gag tct ctg ccc agt gtg      737
Lys Gly Arg Lys Ile Ala Ala Phe Phe Ala Glu Ser Leu Pro Ser Val
        205                 210                 215

gga ggg cag atc att ccc cct gct ggc tac ttc tcc caa gtg gca gag      785
Gly Gly Gln Ile Ile Pro Pro Ala Gly Tyr Phe Ser Gln Val Ala Glu
    220                 225                 230
```

-continued

```
cac atc cgc aag gcc gga ggg gtc ttt gtt gca gat gag atc cag gtt      833
His Ile Arg Lys Ala Gly Gly Val Phe Val Ala Asp Glu Ile Gln Val
235                 240                 245                 250

ggc ttt ggc cgg gta ggc aag cac ttc tgg gcc ttc cag ctc cag gga      881
Gly Phe Gly Arg Val Gly Lys His Phe Trp Ala Phe Gln Leu Gln Gly
                255                 260                 265

aaa gac ttc gtc cct gac atc gtc acc atg ggc aag tcc att ggc aac      929
Lys Asp Phe Val Pro Asp Ile Val Thr Met Gly Lys Ser Ile Gly Asn
            270                 275                 280

ggc cac cct gtt gcc tgc gtg gcc gca acc cag cct gtg gcg agg gca      977
Gly His Pro Val Ala Cys Val Ala Ala Thr Gln Pro Val Ala Arg Ala
        285                 290                 295

ttt gaa gcc acc ggc gtt gag tac ttc aac acg ttt ggg ggc agc cca     1025
Phe Glu Ala Thr Gly Val Glu Tyr Phe Asn Thr Phe Gly Gly Ser Pro
    300                 305                 310

gtg tcc tgc gct gtg ggg ctg gcc gtc ctg aat gtc ttg gag aag gag     1073
Val Ser Cys Ala Val Gly Leu Ala Val Leu Asn Val Leu Glu Lys Glu
315                 320                 325                 330

cag ctc cag gat cat gcc acc agt gta ggc agc ttc ctg atg cag ctc     1121
Gln Leu Gln Asp His Ala Thr Ser Val Gly Ser Phe Leu Met Gln Leu
                335                 340                 345

ctc ggg cag caa aaa atc aaa cat ccc atc gtc ggg gat gtc agg ggt     1169
Leu Gly Gln Gln Lys Ile Lys His Pro Ile Val Gly Asp Val Arg Gly
            350                 355                 360

gtt ggg ctc ttc att ggt gtg gat ctg atc aaa gat gag gcc aca agg     1217
Val Gly Leu Phe Ile Gly Val Asp Leu Ile Lys Asp Glu Ala Thr Arg
        365                 370                 375

aca cca gca act gaa gag gct gcc tac ttg gta tca agg ctg aag gag     1265
Thr Pro Ala Thr Glu Glu Ala Ala Tyr Leu Val Ser Arg Leu Lys Glu
    380                 385                 390

aac tac gtt ttg ctg agc act gat ggc cct ggg agg aac atc ctg aag     1313
Asn Tyr Val Leu Leu Ser Thr Asp Gly Pro Gly Arg Asn Ile Leu Lys
395                 400                 405                 410

ttt aag ccc cca atg tgc ttc agc ctg gac aat gca cgg cag gtg gtg     1361
Phe Lys Pro Pro Met Cys Phe Ser Leu Asp Asn Ala Arg Gln Val Val
                415                 420                 425

gca aag ctg gat gcc att ctg act gac atg gaa gag aag gtg aga agt     1409
Ala Lys Leu Asp Ala Ile Leu Thr Asp Met Glu Glu Lys Val Arg Ser
            430                 435                 440

tgt gaa acg ctg agg ctc cag ccc taa gccagccctg ctctgcctaa           1456
Cys Glu Thr Leu Arg Leu Gln Pro  *
        445                 450

gtgtactcca gaagaaactc atctcatcca aatacacgct attgagaagg cgagcctgac   1516

ctccctctta cagataaagt cagctttcag aggctcaggg tggggggccc tgcccgaggc   1576

cataatgcta cccacccccct cctcctaacc actggtctgt tggaataacc cagatgtctg   1636

catcccctca agtcagtcaa tttcctttct gtccactggg ggtggaatgg ggtagggtgg   1696

gatactttaa agtgctcctg cttaaataaa ttagaccaga ccagtgtatt tctaaagaaa   1756

atcctgacat gcacacccat taaaaatagt acattttaca gtgaaaaaaa aaaaaaaagg   1816
```

<210> SEQ ID NO 68
<211> LENGTH: 450
<212> TYPE: PRT
<213> ORGANISM: Homo sapiens

<400> SEQUENCE: 68

```
Met Ala Ala Asp Gln Arg Pro Lys Ala Asp Thr Leu Ala Leu Arg Gln
 1               5                  10                  15
```

-continued

```
Arg Leu Ile Ser Ser Ser Cys Arg Pro Phe Phe Pro Glu Asp Pro Val
            20                  25                  30

Lys Ile Val Arg Ala Gln Gly Gln Tyr Met Tyr Asp Glu Gln Gly Ala
        35                  40                  45

Glu Tyr Ile Asp Cys Ile Ser Asn Val Ala His Val Gly His Cys His
    50                  55                  60

Pro Leu Val Val Gln Ala Ala His Glu Gln Asn Gln Val Leu Asn Thr
65                  70                  75                  80

Asn Ser Arg Tyr Leu His Asp Asn Ile Val Asp Tyr Ala Gln Arg Leu
                85                  90                  95

Ser Glu Thr Leu Pro Glu Gln Leu Cys Val Phe Tyr Phe Leu Asn Ser
            100                 105                 110

Gly Ser Glu Ala Asn Asp Leu Ala Leu Arg Leu Ala Arg His Tyr Thr
        115                 120                 125

Gly His Gln Asp Val Val Val Leu Asp His Ala Tyr His Gly His Leu
    130                 135                 140

Ser Ser Leu Ile Asp Ile Ser Pro Tyr Lys Phe Arg Asn Leu Asp Gly
145                 150                 155                 160

Gln Lys Glu Trp Val His Val Ala Pro Leu Pro Asp Thr Tyr Arg Gly
                165                 170                 175

Pro Tyr Arg Glu Asp His Pro Asn Pro Ala Met Ala Tyr Ala Asn Glu
            180                 185                 190

Val Lys Arg Val Val Ser Ser Ala Gln Glu Lys Gly Arg Lys Ile Ala
        195                 200                 205

Ala Phe Phe Ala Glu Ser Leu Pro Ser Val Gly Gly Gln Ile Ile Pro
    210                 215                 220

Pro Ala Gly Tyr Phe Ser Gln Val Ala Glu His Ile Arg Lys Ala Gly
225                 230                 235                 240

Gly Val Phe Val Ala Asp Glu Ile Gln Val Gly Phe Gly Arg Val Gly
                245                 250                 255

Lys His Phe Trp Ala Phe Gln Leu Gln Gly Lys Asp Phe Val Pro Asp
            260                 265                 270

Ile Val Thr Met Gly Lys Ser Ile Gly Asn Gly His Pro Val Ala Cys
        275                 280                 285

Val Ala Ala Thr Gln Pro Val Ala Arg Ala Phe Glu Ala Thr Gly Val
    290                 295                 300

Glu Tyr Phe Asn Thr Phe Gly Gly Ser Pro Val Ser Cys Ala Val Gly
305                 310                 315                 320

Leu Ala Val Leu Asn Val Leu Glu Lys Glu Gln Leu Gln Asp His Ala
                325                 330                 335

Thr Ser Val Gly Ser Phe Leu Met Gln Leu Leu Gly Gln Gln Lys Ile
            340                 345                 350

Lys His Pro Ile Val Gly Asp Val Arg Gly Val Gly Leu Phe Ile Gly
        355                 360                 365

Val Asp Leu Ile Lys Asp Glu Ala Thr Arg Thr Pro Ala Thr Glu Glu
    370                 375                 380

Ala Ala Tyr Leu Val Ser Arg Leu Lys Glu Asn Tyr Val Leu Leu Ser
385                 390                 395                 400

Thr Asp Gly Pro Gly Arg Asn Ile Leu Lys Phe Lys Pro Pro Met Cys
                405                 410                 415

Phe Ser Leu Asp Asn Ala Arg Gln Val Val Ala Lys Leu Asp Ala Ile
            420                 425                 430
```

-continued

```
Leu Thr Asp Met Glu Glu Lys Val Arg Ser Cys Glu Thr Leu Arg Leu
        435                 440                 445

Gln Pro
    450


<210> SEQ ID NO 69
<211> LENGTH: 1353
<212> TYPE: DNA
<213> ORGANISM: Homo sapiens
<220> FEATURE:
<221> NAME/KEY: CDS
<222> LOCATION: (1)...(1353)

<400> SEQUENCE: 69

atg gcc gca gac cag cgc ccg aag gcc gac acg ctg gcc ctg agg caa       48
Met Ala Ala Asp Gln Arg Pro Lys Ala Asp Thr Leu Ala Leu Arg Gln
 1               5                  10                  15

cgg ctc atc agc tct tcc tgc aga ccc ttt ttt ccc gag gat cct gtt       96
Arg Leu Ile Ser Ser Ser Cys Arg Pro Phe Phe Pro Glu Asp Pro Val
            20                  25                  30

aag att gtc cgg gcc caa ggg cag tac atg tac gat gaa cag ggg gca      144
Lys Ile Val Arg Ala Gln Gly Gln Tyr Met Tyr Asp Glu Gln Gly Ala
        35                  40                  45

gaa tac atc gat tgc atc agc aat gtg gcg cac gtt ggg cac tgc cac      192
Glu Tyr Ile Asp Cys Ile Ser Asn Val Ala His Val Gly His Cys His
    50                  55                  60

cct ctc gtg gtc caa gca gca cat gag cag aac cag gtg ctc aac acc      240
Pro Leu Val Val Gln Ala Ala His Glu Gln Asn Gln Val Leu Asn Thr
 65                  70                  75                  80

aac agc cgg tac ctg cat gac aac atc gtg gac tat gcg cag agg ctg      288
Asn Ser Arg Tyr Leu His Asp Asn Ile Val Asp Tyr Ala Gln Arg Leu
                85                  90                  95

tca gag acc ctg ccg gag cag ctc tgt gtg ttc tat ttc ctg aat tct      336
Ser Glu Thr Leu Pro Glu Gln Leu Cys Val Phe Tyr Phe Leu Asn Ser
            100                 105                 110

ggg tca gaa gcc aat gac ctg gcc ctg agg ctg gct cgc cac tac acg      384
Gly Ser Glu Ala Asn Asp Leu Ala Leu Arg Leu Ala Arg His Tyr Thr
        115                 120                 125

gga cac cag gac gtg gtg gta tta gat cat gcg tat cac ggc cac ctg      432
Gly His Gln Asp Val Val Val Leu Asp His Ala Tyr His Gly His Leu
    130                 135                 140

agc tcc ctg att gac atc agt ccc tac aag ttc cgc aac ctg gat ggc      480
Ser Ser Leu Ile Asp Ile Ser Pro Tyr Lys Phe Arg Asn Leu Asp Gly
145                 150                 155                 160

cag aag gag tgg gtc cac gtg gca cct ctc cca gac acc tac cgg ggc      528
Gln Lys Glu Trp Val His Val Ala Pro Leu Pro Asp Thr Tyr Arg Gly
                165                 170                 175

ccc tac cgg gag gac cac ccc aac cca gct atg gcc tat gcc aac gag      576
Pro Tyr Arg Glu Asp His Pro Asn Pro Ala Met Ala Tyr Ala Asn Glu
            180                 185                 190

gtg aaa cgt gtg gtc agc agt gca cag gag aag ggc agg aag att gca      624
Val Lys Arg Val Val Ser Ser Ala Gln Glu Lys Gly Arg Lys Ile Ala
        195                 200                 205

gcc ttc ttc gct gag tct ctg ccc agt gtg gga ggg cag atc att ccc      672
Ala Phe Phe Ala Glu Ser Leu Pro Ser Val Gly Gly Gln Ile Ile Pro
    210                 215                 220

cct gct ggc tac ttc tcc caa gtg gca gag cac atc cgc aag gcc gga      720
Pro Ala Gly Tyr Phe Ser Gln Val Ala Glu His Ile Arg Lys Ala Gly
225                 230                 235                 240

ggg gtc ttt gtt gca gat gag atc cag gtt ggc ttt ggc cgg gta ggc      768
Gly Val Phe Val Ala Asp Glu Ile Gln Val Gly Phe Gly Arg Val Gly
```

-continued

```
            245                 250                 255

aag cac ttc tgg gcc ttc cag ctc cag gga aaa gac ttc gtc cct gac      816
Lys His Phe Trp Ala Phe Gln Leu Gln Gly Lys Asp Phe Val Pro Asp
        260                 265                 270

atc gtc acc atg ggc aag tcc att ggc aac ggc cac cct gtt gcc tgc      864
Ile Val Thr Met Gly Lys Ser Ile Gly Asn Gly His Pro Val Ala Cys
    275                 280                 285

gtg gcc gca acc cag cct gtg gcg agg gca ttt gaa gcc acc ggc gtt      912
Val Ala Ala Thr Gln Pro Val Ala Arg Ala Phe Glu Ala Thr Gly Val
    290                 295                 300

gag tac ttc aac acg ttt ggg ggc agc cca gtg tcc tgc gct gtg ggg      960
Glu Tyr Phe Asn Thr Phe Gly Gly Ser Pro Val Ser Cys Ala Val Gly
305                 310                 315                 320

ctg gcc gtc ctg aat gtc ttg gag aag gag cag ctc cag gat cat gcc     1008
Leu Ala Val Leu Asn Val Leu Glu Lys Glu Gln Leu Gln Asp His Ala
                325                 330                 335

acc agt gta ggc agc ttc ctg atg cag ctc ctc ggg cag caa aaa atc     1056
Thr Ser Val Gly Ser Phe Leu Met Gln Leu Leu Gly Gln Gln Lys Ile
            340                 345                 350

aaa cat ccc atc gtc ggg gat gtc agg ggt gtt ggg ctc ttc att ggt     1104
Lys His Pro Ile Val Gly Asp Val Arg Gly Val Gly Leu Phe Ile Gly
        355                 360                 365

gtg gat ctg atc aaa gat gag gcc aca agg aca cca gca act gaa gag     1152
Val Asp Leu Ile Lys Asp Glu Ala Thr Arg Thr Pro Ala Thr Glu Glu
    370                 375                 380

gct gcc tac ttg gta tca agg ctg aag gag aac tac gtt ttg ctg agc     1200
Ala Ala Tyr Leu Val Ser Arg Leu Lys Glu Asn Tyr Val Leu Leu Ser
385                 390                 395                 400

act gat ggc cct ggg agg aac atc ctg aag ttt aag ccc cca atg tgc     1248
Thr Asp Gly Pro Gly Arg Asn Ile Leu Lys Phe Lys Pro Pro Met Cys
                405                 410                 415

ttc agc ctg gac aat gca cgg cag gtg gtg gca aag ctg gat gcc att     1296
Phe Ser Leu Asp Asn Ala Arg Gln Val Val Ala Lys Leu Asp Ala Ile
            420                 425                 430

ctg act gac atg gaa gag aag gtg aga agt tgt gaa acg ctg agg ctc     1344
Leu Thr Asp Met Glu Glu Lys Val Arg Ser Cys Glu Thr Leu Arg Leu
        435                 440                 445

cag ccc taa                                                         1353
Gln Pro  *
    450


<210> SEQ ID NO 70
<211> LENGTH: 483
<212> TYPE: PRT
<213> ORGANISM: Artificial Sequence
<220> FEATURE:
<223> OTHER INFORMATION: Amino acid consensus sequence
<220> FEATURE:
<221> NAME/KEY: VARIANT
<222> LOCATION: (293)...(295)
<223> OTHER INFORMATION: Xaa = Any amino acid

<400> SEQUENCE: 70

Ser Val Ala Arg Gly Asn Tyr Gly Pro Leu Pro Val Leu Ile Thr Arg
 1               5                  10                  15

Ala Lys Gly Val Trp Leu Thr Asp Val Asp Gly Arg Glu Tyr Leu Asp
            20                  25                  30

Phe Leu Ser Gly Ile Ala Val Ala Asn Leu Gly His Cys His Pro Lys
        35                  40                  45

Val Val Gln Ala Val Lys Glu Gln Ala Asp Lys Leu Thr His Thr Ser
    50                  55                  60
```

-continued

```
Arg Ala Phe Leu Thr His Glu Pro Ala Leu Asp Phe Val Glu Lys Leu
65                  70                  75                  80

Ala Glu Lys Leu Ala Ser Leu Thr Pro Gly Asp Gly Leu Asp Arg Val
                85                  90                  95

Phe Phe Met Asn Ser Gly Ser Glu Ala Asn Glu Thr Ala Leu Lys Leu
            100                 105                 110

Ala Arg Ala Tyr Ala Arg Gln Lys Gly Lys Val Pro Glu Lys Phe Ser
        115                 120                 125

Glu Glu Leu Glu Ser Met Leu Asn Gln Pro Gly Thr Gly Lys Thr Lys
    130                 135                 140

Ile Ile Ala Phe Ser Gly Ala Phe His Gly Arg Thr Leu Gly Ala Leu
145                 150                 155                 160

Ser Val Thr Gly Ser Lys Lys Gly Tyr Arg Lys Leu Phe Gly Pro Leu
                165                 170                 175

Leu Pro Gly Val Val Tyr Ala Ala Ala Asp Thr Leu Phe Ala Pro Tyr
            180                 185                 190

Asn Asp Pro Ser Leu Tyr Arg Pro Pro Phe Glu Glu Gly Lys Glu Asn
        195                 200                 205

Ala Ser Glu Gly Leu Glu Ala Lys Leu Glu Glu Ala Leu Glu Asp Leu
    210                 215                 220

Ile Glu Glu Tyr Lys Lys Lys Asp Asp Glu Ile Ala Ala Val Ile Val
225                 230                 235                 240

Glu Pro Ile Val Gln Gly Glu Gly Gly Val Ile Pro Pro Pro Pro Gly
                245                 250                 255

Phe Leu Ala Gly Leu Arg Glu Leu Cys Lys Lys His Gly Val Leu Leu
            260                 265                 270

Ile Ala Asp Glu Val Gln Thr Gly Phe Gly Arg Thr Gly Lys Leu Phe
        275                 280                 285

Ala Cys Glu His Xaa Xaa Xaa Asp Gly Val Thr Pro Pro Asp Ile Met
    290                 295                 300

Thr Leu Ala Lys Ala Leu Gly Gly Gly Val Leu Pro Leu Ala Ala Val
305                 310                 315                 320

Ile Gly Arg Ala Glu Ile Met Gln Ala Phe Phe Asp Ala Pro Gly Gly
                325                 330                 335

Glu Ala Lys Pro Phe Leu His Gly Thr Thr Phe Gly Gly Asn Pro Leu
            340                 345                 350

Ala Cys Ala Ala Ala Leu Ala Thr Leu Lys Val Leu Glu Glu Glu Asn
        355                 360                 365

Leu Leu Gln Asn Ala Gln Glu Lys Gly Asp Tyr Leu Arg Lys Gly Leu
    370                 375                 380

Leu Glu Leu Ala Lys Lys Tyr Pro Asp Val Ile Gly Asp Val Arg Gly
385                 390                 395                 400

Lys Gly Leu Met Ile Gly Ile Glu Ile Val Glu Asp Arg Val Thr Lys
                405                 410                 415

Glu Pro Ala Ala Lys Pro Ser Asp Glu Glu Leu Val Ala Asp Ile Ile
            420                 425                 430

Lys Ala Ala Leu Glu Lys Gly Leu Leu Ile Leu Pro Ala Gly Tyr Val
        435                 440                 445

Arg Asn Gly Gly Asn Val Ile Arg Phe Ala Pro Pro Leu Thr Ile Thr
    450                 455                 460

Asp Glu Glu Ile Asp Glu Gly Leu Asp Ala Leu Lys Lys Ala Leu Ala
465                 470                 475                 480
```

-continued

Lys Ala Leu

<210> SEQ ID NO 71
<211> LENGTH: 166
<212> TYPE: PRT
<213> ORGANISM: Artificial Sequence
<220> FEATURE:
<223> OTHER INFORMATION: Amino acid consensus sequence
<220> FEATURE:
<221> NAME/KEY: VARIANT
<222> LOCATION: (77)...(77)
<223> OTHER INFORMATION: Xaa = Any amino acid
<220> FEATURE:
<221> NAME/KEY: VARIANT
<222> LOCATION: (105)...(108)
<223> OTHER INFORMATION: Xaa = Any amino acid
<220> FEATURE:
<221> NAME/KEY: VARIANT
<222> LOCATION: (115)...(115)
<223> OTHER INFORMATION: Xaa = Any amino acid
<220> FEATURE:
<221> NAME/KEY: VARIANT
<222> LOCATION: (125)...(125)
<223> OTHER INFORMATION: Xaa = Any amino acid

<400> SEQUENCE: 71

```
Tyr Leu His His Glu Ile His Asp Tyr Ala Glu Arg Leu Thr Ala Lys
 1               5                  10                  15

Met Pro Gly Pro Leu Lys Val Val Phe Phe Val Asn Ser Gly Ser Glu
            20                  25                  30

Ala Asn Asp Leu Ala Met Met Met Ala Arg Asn Tyr Thr Gly His Gln
        35                  40                  45

Asp Val Ile Ser Leu Arg Asn Ala Tyr His Gly Met Ser Pro Thr Thr
    50                  55                  60

Met Gly Leu Thr Asn Leu Gly Thr Trp Lys Tyr Pro Xaa Leu Pro Gly
65                  70                  75                  80

Val Gln Ser Gly Ile His His Val Met Asn Pro Asp Pro Tyr Arg Gly
                85                  90                  95

Ile Trp Gly Ser Asp Gly Glu Lys Xaa Xaa Xaa Xaa Tyr Ala Lys Asp
            100                 105                 110

Val Gln Xaa Thr Phe Lys Tyr Tyr Gly Pro Arg Gly Xaa Lys Val Ala
        115                 120                 125

Ala Phe Ile Ala Glu Ser Ile Gln Gly Val Gly Gly Thr Val Gln Leu
    130                 135                 140

Pro Pro Gly Tyr Leu Lys Ala Val Tyr Asp Ile Val Arg Ser Ala Gly
145                 150                 155                 160

Gly Val Cys Ile Ala Asp
                165
```

<210> SEQ ID NO 72
<211> LENGTH: 57
<212> TYPE: PRT
<213> ORGANISM: Artificial Sequence
<220> FEATURE:
<223> OTHER INFORMATION: Amino acid consensus sequence

<400> SEQUENCE: 72

```
Ser Thr Tyr Gly Gly Asn Pro Leu Ala Cys Ala Ala Ala Leu Ala Thr
 1               5                  10                  15

Leu Glu Ile Ile Glu Glu Glu Asn Leu Val Glu Arg Ala Gln Glu Leu
            20                  25                  30

Gly Glu Tyr Leu Arg Glu Arg Leu Leu Glu Met Gln Glu Glu His His
        35                  40                  45
```

-continued

Pro Ile Val Gly Asp Val Arg Thr Val
50 55

<210> SEQ ID NO 73
<211> LENGTH: 1971
<212> TYPE: DNA
<213> ORGANISM: Homo sapiens
<220> FEATURE:
<221> NAME/KEY: misc_feature
<222> LOCATION: (1)...(1971)
<223> OTHER INFORMATION: n = A,T,C or G

<400> SEQUENCE: 73
nnnnnnnnnn nnnnnnnnnn nnaccaggac cgctcggcgn nnnnnnnnnn nnnnnnnnnn 60
nnnnnnnnnn nnnnnnnnnc nncatggccg cggacacggc gccnnaaggc cgtcactctg 120
gacctgagac gtcggctgct cagctcttcc tgcagactct tttttcctga ggatcctgtt 180
aagattatcc gaggccaagg gcagtacctg tacgatgagc aagggcgaga gtacctggac 240
tgtatcaaca acgtggctca tgttgggcac tgccacccta ccgtggtcca agccgcacat 300
gaacagaacc tagtgctcaa caccaacagc cgctacctgc atggcaacat cgtggactat 360
gcccagaggc tgtcggagac cctgccggag cagctctctg tgttttactt cttgaattct 420
gggtcagaag ccaacgacct ggccttgaga ctagctcgac agtacacggg acaccaggat 480
gtggtggtat tagaccatgc ttatcatggt cacctgagct ccctgatcga catcagtccc 540
tacaagttcc ggaatctggg tggccagaag gaatgggtcc atgtggctcc tctcccagac 600
acctaccggg gcccttacag ggaggaccac cccaacccag cagaggccta tgccaacgag 660
gtgaagcacg tcatcagcag tgcacagcag aagggcagga agatcgcagc cttcttcgct 720
gagtctctgc ccagtgtgag tggacagatc attcctcctg ctggctactt ctcccaggtg 780
gctgagcaca tccacagagc tccgcaaggc cggagggctc tttgtggcag atgagatcca 840
ggttggtttt ggccgcatag gcaagcactt ttgggccttc cagctggagg gagaagactt 900
tgttcccgac attgtcacca tgggcaagtc catcggcaat ggtcaccctg ttgcctgcat 960
ggccactacc caagctgtgt caagggcatt tgaagctacc ggtgtagaat acttcaacac 1020
gtttggtggc aaccccgtat cctgtgctgt ggggctagca gtcctagatg tcttgaaaac 1080
agaacagctc caggctcacg ccactaatgt ccaccagtgt gggcagtttc cttctggagc 1140
acctcaccca gcagaaagcc aagcacccta tcattggaga tgtcaggggc actggactct 1200
tcatcggtgt ggatctcatc aaagatgaga ccctgaggac accagcaact gaagaggcgg 1260
aatatttggt ctccaggcta aaggaaaact acattttact gagcattgat ggccctggaa 1320
agaatattct gaagttcaag cccccaatgt gcttcaacgt tgacaatgca caacatgtgg 1380
tagcaaagct ggatgacatt ctaacagaca tggaagaaaa agtaagaagt tgtgagaccc 1440
tgaggatcaa gcnnnacnnn nnncccnnnn nnnnnnnnnn nnnnccagaa gatactcatc 1500
ctactcaaat actcnctaac aagacagcaa gattgacacc caccttacag ataaaacaag 1560
ntgtgtgagg cttcactgga ttggtgaact actgatnnag gctttatttc taaatcaaaa 1620
caagacccag tcagactttt atgcctgaaa actttgagga tggtgtacat gcttcaaaag 1680
aacatgtttt aaagacagac ctgacatact cccattttta aaaaaaaaaa aaaaaggtaa 1740
aaaatgagct ggccatggca catgccttta gtctcatctc actgggaggt agaaacaggc 1800
agannnnnnn actcttaagt ttgagaccag cctggttttg tatagggcag ccagggcagc 1860
agtagggtga tctctcaaaa gggggtggaa agataaactt tatctnnnct ccctatcaag 1920
ctatgacttt tatttcatct gaattaaaga cactgaataa tttgagtatt t 1971

<210> SEQ ID NO 74
<211> LENGTH: 1951
<212> TYPE: DNA
<213> ORGANISM: Homo sapiens
<220> FEATURE:
<221> NAME/KEY: misc_feature
<222> LOCATION: (1)...(1952)
<223> OTHER INFORMATION: n = A,T,C or G

<400> SEQUENCE: 74
nnnnnnnnnn nnnnnnnnnn nnnnnncgcc cgcgcggcga cgtctccgcg aggcgtcacg 60
gcaccgactg acggccaccc accatggccg cagacncagc gcccgaaggc cgacaccctg 120
gccctgaggc aacggctcat cagctcttcc tgcagactct tttttcccga ggatcctgtt 180
aagattgtcc gggcccaagg gcagtacatg tacgatgaac agggggcaga atacatcgat 240
tgcatcagca atgtggcgca cgttgggcac tgccaccctc tcgtggtcca agcagcacat 300
gagcagaacc aggtgctcaa caccaacagc cggtacctgc atgacaacat cgtggactat 360
gcgcagaggc tgtcagagac cctgccggag cagctctgtg tgttctattt cctgaattct 420
gggtcagaag ccaatgacct ggccctgagg ctggctcgcc actacacggg acaccaggac 480
gtggtggtat tagatcatgc gtatcacggc cacctgagct ccctgattga catcagtccc 540
tacaagttcc gcaacctgga tggccagaag gagtgggtcc acgtggcacc tctcccagac 600
acctaccggg gcccctaccg ggaggaccac cccaacccag ctatggccta tgccaacgag 660
gtgaaacgtg tggtcagcag tgcacaggag aagggcagga agattgcagc cttcttcgct 720
gagtctctgc ccagtgtggg agggcagatc attcccccctg ctggctactt ctcccaagtg 780
gcagagcaca tccgcaaggc cggaggggtc tttgttgcag atgagatcca ggttggcttt 840
ggccgggtag gcaagcactt ctgggccttc cagctccagg gaaaagactt cgtccctgac 900
atcgtcacca tgggcaagtc cattggcaac ggccaccctg ttgcctgcgt ggccgcaacc 960
cagcctgtgg cgagggcatt tgaagccacc ggcgttgagt acttcaacac gtttgggggc 1020
agcccagtgt cctgcgctgt ggggctggcc gtcctgaatg tcttggagaa ggagcagctc 1080
caggatcatg ccaccagtgt aggcagcttc ctgatgcagc tcctcgggca gcaaaaaatc 1140
aaacatccca tcgtcgggga tgtcaggggt gttgggctct tcattggtgt ggatctgatc 1200
aaagatgagg ccacaaggac accagcaact gaagaggctg cctacttggt atcaaggctg 1260
aaggagaact acgttttgct gagcactgat ggccctggga ggaacatcct gaagtttaag 1320
cccccaatgt gcttcagcct ggacaatgca cggcaggtgg tggcaaagct ggatgccatt 1380
ctgactgaca tggaagagaa ggtgagaagt tgtgaaacgc tgaggctcca gccctaagcc 1440
agccctgctc tgcctaagtg tactccagaa gaaactcatc tcatccaaat acacgctatt 1500
gagaaggcga gcctgacctc cctcttacag ataaagtcag ctttcagagg ctnnncaggg 1560 tggggggcn nctgcccgag gccataatgc tannnnnnnn nnnnncccac cccctcctnn 1620
nnncctaacc actgnnngtc tgttggganat nnnnnnaacc cagatgtnnn nnnnnnnnnn 1680
ctgncatccc ctcannnnnn nnnnnnnnnn nnnnagtcag tcaatnnnnn nnnnnnnnnn 1740
nnttcctttc ntgtcnnnnc actgggnggt ggaatggggt agggtgggat actttaaagt 1800
gctnnnnnnn cctgcttaaa taaattagan ccagnnnacc agtnnngtna tttctnnnnn 1860
nnnnnnnnaa agaaaatcct gacatgcaca cccattaaaa atagtacatt tnntacagnt 1920

-continued

```
gaaaaaaaaa aannnaannn nnnnnnnnnn n                                  1951


<210> SEQ ID NO 75
<211> LENGTH: 532
<212> TYPE: PRT
<213> ORGANISM: Homo sapiens
<220> FEATURE:
<221> NAME/KEY: VARIANT
<222> LOCATION: (1)...(9)
<223> OTHER INFORMATION: Xaa = Any amino acid
<220> FEATURE:
<221> NAME/KEY: VARIANT
<222> LOCATION: (41)...(46)
<223> OTHER INFORMATION: Xaa = Any amino acid
<220> FEATURE:
<221> NAME/KEY: VARIANT
<222> LOCATION: (129)...(134)
<223> OTHER INFORMATION: Xaa = Any amino acid
<220> FEATURE:
<221> NAME/KEY: VARIANT
<222> LOCATION: (160)...(160)
<223> OTHER INFORMATION: Xaa = Any amino acid
<220> FEATURE:
<221> NAME/KEY: VARIANT
<222> LOCATION: (180)...(188)
<223> OTHER INFORMATION: Xaa = Any amino acid
<220> FEATURE:
<221> NAME/KEY: VARIANT
<222> LOCATION: (208)...(212)
<223> OTHER INFORMATION: Xaa = Any amino acid
<220> FEATURE:
<221> NAME/KEY: VARIANT
<222> LOCATION: (247)...(270)
<223> OTHER INFORMATION: Xaa = Any amino acid
<220> FEATURE:
<221> NAME/KEY: VARIANT
<222> LOCATION: (284)...(285)
<223> OTHER INFORMATION: Xaa = Any amino acid
<220> FEATURE:
<221> NAME/KEY: VARIANT
<222> LOCATION: (338)...(340)
<223> OTHER INFORMATION: Xaa = Any amino acid
<220> FEATURE:
<221> NAME/KEY: VARIANT
<222> LOCATION: (384)...(385)
<223> OTHER INFORMATION: Xaa = Any amino acid
<220> FEATURE:
<221> NAME/KEY: VARIANT
<222> LOCATION: (422)...(422)
<223> OTHER INFORMATION: Xaa = Any amino acid
<220> FEATURE:
<221> NAME/KEY: VARIANT
<222> LOCATION: (430)...(431)
<223> OTHER INFORMATION: Xaa = Any amino acid
<220> FEATURE:
<221> NAME/KEY: VARIANT
<222> LOCATION: (450)...(455)
<223> OTHER INFORMATION: Xaa = Any amino acid
<220> FEATURE:
<221> NAME/KEY: VARIANT
<222> LOCATION: (487)...(488)
<223> OTHER INFORMATION: Xaa = Any amino acid
<220> FEATURE:
<221> NAME/KEY: VARIANT
<222> LOCATION: (519)...(532)
<223> OTHER INFORMATION: Xaa = Any amino acid

<400> SEQUENCE: 75

Xaa Xaa Xaa Xaa Xaa Xaa Xaa Xaa Xaa Met Phe Ser Lys Leu Ala His
 1               5                  10                  15

Leu Gln Arg Phe Ala Val Leu Ser Arg Gly Val His Ser Ser Val Ala
            20                  25                  30

Ser Ala Thr Ser Val Ala Thr Lys Xaa Xaa Xaa Xaa Xaa Xaa Lys Thr
        35                  40                  45
```

-continued

```
Val Gln Gly Pro Pro Thr Ser Asp Asp Ile Phe Glu Arg Glu Tyr Lys
    50                  55                  60

Tyr Gly Ala His Asn Tyr His Pro Leu Pro Val Ala Leu Glu Arg Gly
65                  70                  75                  80

Lys Gly Ile Tyr Leu Trp Asp Val Glu Gly Arg Lys Tyr Phe Asp Phe
                85                  90                  95

Leu Ser Ser Tyr Ser Ala Val Asn Gln Gly His Cys His Pro Lys Ile
            100                 105                 110

Val Asn Ala Leu Lys Ser Gln Val Asp Lys Leu Thr Leu Thr Ser Arg
        115                 120                 125

Xaa Xaa Xaa Xaa Xaa Xaa Ala Phe Tyr Asn Asn Val Leu Gly Glu Tyr
    130                 135                 140

Glu Glu Tyr Ile Thr Lys Leu Phe Asn Tyr His Lys Val Leu Pro Xaa
145                 150                 155                 160

Met Asn Thr Gly Val Glu Ala Gly Glu Thr Ala Cys Lys Leu Ala Arg
                165                 170                 175

Lys Trp Gly Xaa Xaa Xaa Xaa Xaa Xaa Xaa Xaa Xaa Tyr Thr Val Lys
            180                 185                 190

Gly Ile Gln Lys Tyr Lys Ala Lys Ile Val Phe Ala Ala Gly Asn Xaa
        195                 200                 205

Xaa Xaa Xaa Xaa Phe Trp Gly Arg Thr Leu Ser Ala Ile Ser Ser Ser
    210                 215                 220

Thr Asp Pro Thr Ser Tyr Asp Gly Xaa Phe Gly Pro Phe Met Pro Gly
225                 230                 235                 240

Phe Asp Ile Ile Pro Tyr Xaa Xaa Xaa Xaa Xaa Xaa Xaa Xaa Xaa Xaa
                245                 250                 255

Xaa Xaa Xaa Xaa Xaa Xaa Xaa Xaa Xaa Xaa Xaa Xaa Xaa Xaa Asn Asp
            260                 265                 270

Leu Pro Ala Leu Glu Arg Ala Leu Gln Asp Pro Xaa Xaa Asn Val Ala
        275                 280                 285

Ala Phe Met Val Glu Pro Ile Gln Gly Glu Ala Gly Val Val Val Pro
    290                 295                 300

Asp Pro Gly Tyr Leu Met Gly Val Arg Glu Leu Cys Thr Arg His Gln
305                 310                 315                 320

Val Leu Phe Ile Ala Asp Glu Ile Gln Thr Gly Leu Ala Arg Thr Gly
                325                 330                 335

Arg Xaa Xaa Xaa Trp Leu Ala Val Asp Tyr Glu Asn Val Arg Pro Asp
            340                 345                 350

Ile Val Leu Leu Gly Lys Ala Leu Ser Gly Gly Leu Tyr Pro Val Ser
        355                 360                 365

Ala Val Leu Cys Asp Asp Asp Ile Met Leu Thr Ile Lys Pro Gly Xaa
    370                 375                 380

Xaa Glu His Gly Ser Thr Tyr Gly Gly Asn Pro Leu Gly Cys Arg Val
385                 390                 395                 400

Ala Ile Ala Ala Leu Glu Val Leu Glu Glu Glu Asn Leu Ala Glu Asn
                405                 410                 415

Ala Asp Lys Leu Gly Xaa Ile Ile Leu Arg Asn Glu Leu Xaa Xaa Met
            420                 425                 430

Lys Leu Pro Ser Asp Val Val Thr Ala Val Arg Gly Lys Gly Leu Leu
        435                 440                 445

Asn Xaa Xaa Xaa Xaa Xaa Xaa Ala Ile Val Ile Lys Glu Thr Lys Asp
    450                 455                 460

Trp Asp Ala Trp Lys Val Cys Leu Arg Leu Arg Asp Asn Gly Leu Leu
```

-continued 465 470 475 480

Ala Lys Pro Thr His Gly Xaa Xaa Asp Ile Ile Arg Phe Ala Pro Pro
485 490 495

Leu Val Ile Lys Glu Asp Glu Leu Arg Glu Ser Ile Glu Ile Ile Asn
500 505 510

Lys Thr Ile Leu Ser Phe Xaa Xaa Xaa Xaa Xaa Xaa Xaa Xaa Xaa Xaa
515 520 525

Xaa Xaa Xaa Xaa
530

<210> SEQ ID NO 76
<211> LENGTH: 532
<212> TYPE: PRT
<213> ORGANISM: Homo sapiens
<220> FEATURE:
<221> NAME/KEY: VARIANT
<222> LOCATION: (378)...(386)
<223> OTHER INFORMATION: Xaa = Any amino acid
<220> FEATURE:
<221> NAME/KEY: VARIANT
<222> LOCATION: (451)...(458)
<223> OTHER INFORMATION: Xaa = Any amino acid
<220> FEATURE:
<221> NAME/KEY: VARIANT
<222> LOCATION: (487)...(488)
<223> OTHER INFORMATION: Xaa = Any amino acid
<220> FEATURE:
<221> NAME/KEY: VARIANT
<222> LOCATION: (520)...(532)
<223> OTHER INFORMATION: Xaa = Any amino acid

<400> SEQUENCE: 76

Met Ala Ser Met Leu Leu Ala Gln Arg Leu Ala Cys Ser Phe Gln His
1 5 10 15

Thr Tyr Arg Leu Leu Val Pro Gly Ser Arg His Ile Ser Gln Ala Ala
20 25 30

Ala Lys Val Asp Val Glu Phe Asp Tyr Asp Gly Pro Leu Met Lys Thr
35 40 45

Glu Val Pro Gly Pro Arg Ser Gln Glu Leu Met Lys Gln Leu Asn Ile
50 55 60

Ile Gln Asn Ala Glu Ala Val His Phe Phe Cys Asn Tyr Glu Glu Ser
65 70 75 80

Arg Gly Asn Tyr Leu Val Asp Val Asp Gly Asn Arg Met Leu Asp Leu
85 90 95

Tyr Ser Gln Ile Ser Ser Val Pro Ile Gly Tyr Ser Asp Pro Ala Leu
100 105 110

Val Lys Leu Ile Gln Gln Pro Gln Asn Ala Ser Met Phe Val Asn Arg
115 120 125

Pro Ala Leu Glu Ile Leu Pro Pro Glu Asn Phe Val Glu Lys Leu Arg
130 135 140

Gln Ser Leu Leu Ser Val Ala Pro Lys Gly Met Ser Gln Leu Ile Thr
145 150 155 160

Met Ala Cys Gly Ser Cys Ser Asn Glu Asn Ala Leu Lys Thr Ile Phe
165 170 175

Met Trp Tyr Arg Ser Lys Glu Arg Gly Gln Arg Gly Phe Ser Lys Glu
180 185 190

Glu Leu Glu Thr Cys Met Ile Asn Gln Ala Pro Trp Cys Pro Asp Tyr
195 200 205

Ser Ile Leu Ser Phe Met Gly Ser Phe His Gly Arg Thr Met Gly Cys
210 215 220

-continued

```
Leu Ala Thr Thr His Ser Lys Ala Ile His Lys Ile Asp Ile Pro Ser
225                 230                 235                 240

Phe Asp Trp Pro Ile Ala Pro Phe Pro Arg Leu Lys Tyr Pro Leu Glu
                245                 250                 255

Glu Phe Val Lys Glu Asn Gln Gln Glu Glu Ala Gly Cys Leu Glu Glu
            260                 265                 270

Val Glu Asp Leu Ile Val Lys Tyr Arg Lys Lys Lys Lys Thr Val Ala
        275                 280                 285

Gly Ile Ile Val Glu Pro Ile Gln Ser Glu Gly Gly Asp Asn His Ala
    290                 295                 300

Ser Asp Asp Phe Phe Arg Lys Leu Arg Asp Ile Ala Arg Lys His Cys
305                 310                 315                 320

Cys Ala Phe Leu Val Asp Glu Val Gln Thr Gly Gly Gly Cys Thr Gly
                325                 330                 335

Lys Phe Trp Ala His Glu His Trp Gly Leu Asp Asp Pro Ala Asp Val
            340                 345                 350

Met Thr Phe Ser Lys Lys Met Met Thr Gly Gly Phe Phe Leu Lys Glu
        355                 360                 365

Glu Phe Arg Pro Asn Ala Pro Tyr Arg Xaa Xaa Xaa Xaa Xaa Xaa Xaa
    370                 375                 380

Xaa Xaa Ile Phe Asn Thr Trp Leu Gly Asp Pro Ser Lys Asn Leu Leu
385                 390                 395                 400

Leu Ala Glu Val Ile Asn Ile Ile Lys Arg Glu Asp Leu Leu Asn Asn
                405                 410                 415

Ala Ala His Ala Gly Lys Ala Leu Leu Thr Gly Leu Leu Asp Leu Gln
            420                 425                 430

Ala Arg Tyr Pro Gln Phe Ile Ser Arg Val Arg Gly Arg Gly Thr Phe
        435                 440                 445

Cys Ser Xaa Xaa Xaa Xaa Xaa Xaa Xaa Xaa Phe Asp Thr Pro Asp Asp
    450                 455                 460

Ser Ile Arg Asn Lys Leu Ile Leu Ile Ala Arg Asn Lys Gly Val Val
465                 470                 475                 480

Leu Gly Gly Cys Gly Asp Xaa Xaa Lys Ser Ile Arg Phe Arg Pro Thr
                485                 490                 495

Leu Val Phe Arg Asp His His Ala His Leu Phe Leu Asn Ile Phe Ser
            500                 505                 510

Asp Ile Leu Ala Asp Phe Lys Xaa Xaa Xaa Xaa Xaa Xaa Xaa Xaa Xaa
        515                 520                 525

Xaa Xaa Xaa Xaa
    530
```

<210> SEQ ID NO 77
<211> LENGTH: 27
<212> TYPE: PRT
<213> ORGANISM: Artificial Sequence
<220> FEATURE:
<223> OTHER INFORMATION: Aminotransferase class III pyridoxal-phosphate attachment site consensus sequence
<220> FEATURE:
<221> NAME/KEY: VARIANT
<222> LOCATION: (1)...(2)
<223> OTHER INFORMATION: Xaa at positions 1 and 2 can be L, I, V, M, F, Y, W or C
<220> FEATURE:
<221> NAME/KEY: VARIANT
<222> LOCATION: (3)...(3)
<223> OTHER INFORMATION: Xaa = Any amino acid
<220> FEATURE:

-continued

```
<221> NAME/KEY: VARIANT
<222> LOCATION: (6)...(6)
<223> OTHER INFORMATION: Xaa at position 6 can be I, V or A
<220> FEATURE:
<221> NAME/KEY: VARIANT
<222> LOCATION: (7)...(8)
<223> OTHER INFORMATION: Xaa = Any amino acid
<220> FEATURE:
<221> NAME/KEY: VARIANT
<222> LOCATION: (10)...(10)
<223> OTHER INFORMATION: Xaa at position 10 can be L, I, V, M, F, A, G
      or C
<220> FEATURE:
<221> NAME/KEY: VARIANT
<222> LOCATION: (11)...(11)
<223> OTHER INFORMATION: Xaa at position 11 can be 0 or 1 residues of
      any amino acid
<220> FEATURE:
<221> NAME/KEY: VARIANT
<222> LOCATION: (12)...(12)
<223> OTHER INFORMATION: Xaa at position 12 can be R, S, A, C, L or I
<220> FEATURE:
<221> NAME/KEY: VARIANT
<222> LOCATION: (13)...(13)
<223> OTHER INFORMATION: Xaa = Any amino acid
<220> FEATURE:
<221> NAME/KEY: VARIANT
<222> LOCATION: (14)...(14)
<223> OTHER INFORMATION: Xaa at position 14 can be G, S, A or D
<220> FEATURE:
<221> NAME/KEY: VARIANT
<222> LOCATION: (15)...(15)
<223> OTHER INFORMATION: Xaa at position 15 can be 12 to 16 residues of
      any amino acid
<220> FEATURE:
<221> NAME/KEY: VARIANT
<222> LOCATION: (17)...(17)
<223> OTHER INFORMATION: Xaa at position 17 can be L, I, V, M, F or C
<220> FEATURE:
<221> NAME/KEY: VARIANT
<222> LOCATION: (18)...(18)
<223> OTHER INFORMATION: Xaa at position 18 can be L, I, V, M, F, Y,
      S, T or A
<220> FEATURE:
<221> NAME/KEY: VARIANT
<222> LOCATION: (19)...(20)
<223> OTHER INFORMATION: Xaa = Any amino acid
<220> FEATURE:
<221> NAME/KEY: VARIANT
<222> LOCATION: (21)...(21)
<223> OTHER INFORMATION: Xaa at position 21 can be G, S or A
<220> FEATURE:
<221> NAME/KEY: VARIANT
<222> LOCATION: (23)...(25)
<223> OTHER INFORMATION: Xaa = Any amino acid
<220> FEATURE:
<221> NAME/KEY: VARIANT
<222> LOCATION: (26)...(26)
<223> OTHER INFORMATION: Xaa at position 26 can be G, S, T, A, D, N or V
<220> FEATURE:
<221> NAME/KEY: VARIANT
<222> LOCATION: (27)...(27)
<223> OTHER INFORMATION: Xaa at position 27 can be G, S, A or C

<400> SEQUENCE: 77

Xaa Xaa Xaa Asp Glu Xaa Xaa Xaa Gly Xaa Xaa Xaa Xaa Xaa Xaa Asp
 1               5                  10                  15

Xaa Xaa Xaa Xaa Xaa Lys Xaa Xaa Xaa Xaa Xaa
            20                  25


<210> SEQ ID NO 78
<211> LENGTH: 1687
<212> TYPE: DNA
<213> ORGANISM: Homo sapiens
<220> FEATURE:
<221> NAME/KEY: CDS
```

-continued

```
<222> LOCATION: (160)...(1470)
<220> FEATURE:
<221> NAME/KEY: misc_feature
<222> LOCATION: (1)...(1687)
<223> OTHER INFORMATION: n = A,T,C or G

<400> SEQUENCE: 78

cccacgcgtn cgggcatgtg ggagccacat gctgggtgcc ccagacagcc taatgctcat      60

tctcaggccg ggctttccag cctctaggtg ctgtgctgtc ctgaggcctg ggccatggtg     120

cccaaggaaa gcccctgaag ctcaccagga ggaagaagc atg cag ggc act cct       174
                                           Met Gln Gly Thr Pro
                                            1               5

gga ggc ggg acg cgc cct ggg cca tcc ccc gtg gac agg cgg acg ctc      222
Gly Gly Gly Thr Arg Pro Gly Pro Ser Pro Val Asp Arg Arg Thr Leu
                10                  15                  20

ctg gtc ttc agc ttt atc ctg gca gca gct ttg ggc caa atg aat ttc      270
Leu Val Phe Ser Phe Ile Leu Ala Ala Ala Leu Gly Gln Met Asn Phe
            25                  30                  35

aca ggg gac cag gtt ctt cga gtc ctg gcc aaa gat gag aag cag ctt      318
Thr Gly Asp Gln Val Leu Arg Val Leu Ala Lys Asp Glu Lys Gln Leu
        40                  45                  50

tca ctt ctc ggg gat ctg gag ggc ctg aaa ccc cag aag gtg gac ttc      366
Ser Leu Leu Gly Asp Leu Glu Gly Leu Lys Pro Gln Lys Val Asp Phe
    55                  60                  65

tgg cgt ggc cca gcc agg ccc agc ctc cct gtg gat atg aga gtt cct      414
Trp Arg Gly Pro Ala Arg Pro Ser Leu Pro Val Asp Met Arg Val Pro
 70                  75                  80                  85

ttc tcc gaa ctg aaa gac atc aaa gct tat ctg gag tct cat gga ctt      462
Phe Ser Glu Leu Lys Asp Ile Lys Ala Tyr Leu Glu Ser His Gly Leu
                90                  95                  100

gct tac agc atc atg ata aag gac atc cag gtg ctg ctg gat gag gaa      510
Ala Tyr Ser Ile Met Ile Lys Asp Ile Gln Val Leu Leu Asp Glu Glu
            105                 110                 115

aga cag gcc atg gcg aaa tcc cgc cgg ctg gag cgc agc acc aac agc      558
Arg Gln Ala Met Ala Lys Ser Arg Arg Leu Glu Arg Ser Thr Asn Ser
        120                 125                 130

ttc agt tac tca tca tac cac acc ctg gag gag ata tat agc tgg att      606
Phe Ser Tyr Ser Ser Tyr His Thr Leu Glu Glu Ile Tyr Ser Trp Ile
    135                 140                 145

gac aac ttt gta atg gag cat tcc gat att gtc tca aaa att cag att      654
Asp Asn Phe Val Met Glu His Ser Asp Ile Val Ser Lys Ile Gln Ile
150                 155                 160                 165

ggc aac agc ttt gaa aac cag tcc att ctt gtc ctg aag ttc agc act      702
Gly Asn Ser Phe Glu Asn Gln Ser Ile Leu Val Leu Lys Phe Ser Thr
                170                 175                 180

gga ggt tct cgg cac cca gcc atc tgg atc gac act gga att cac tcc      750
Gly Gly Ser Arg His Pro Ala Ile Trp Ile Asp Thr Gly Ile His Ser
            185                 190                 195

cgg gag tgg atc acc cat gcc acc ggc atc tgg act gcc aat aag att      798
Arg Glu Trp Ile Thr His Ala Thr Gly Ile Trp Thr Ala Asn Lys Ile
        200                 205                 210

gtc agt gat tat ggc aaa gac cgt gtc ctg aca gac ata ctg aat gcc      846
Val Ser Asp Tyr Gly Lys Asp Arg Val Leu Thr Asp Ile Leu Asn Ala
    215                 220                 225

atg gac atc ttc ata gag ctc gtc aca aac cct gat ggg ttt gct ttt      894
Met Asp Ile Phe Ile Glu Leu Val Thr Asn Pro Asp Gly Phe Ala Phe
230                 235                 240                 245

acc cac agc atg aac cgc tta tgg cgg aag aac aag tcc atc aga cct      942
Thr His Ser Met Asn Arg Leu Trp Arg Lys Asn Lys Ser Ile Arg Pro
                250                 255                 260
```

-continued

```
gga atc ttc tgc atc ggc gtg gat ctc aac agg aac tgg aag tcg ggt      990
Gly Ile Phe Cys Ile Gly Val Asp Leu Asn Arg Asn Trp Lys Ser Gly
            265                 270                 275

ttt gga gga aat ggt tct aac agc aac ccc tgc tca gaa act tat cac     1038
Phe Gly Gly Asn Gly Ser Asn Ser Asn Pro Cys Ser Glu Thr Tyr His
        280                 285                 290

ggg ccc tcc cct cag tcg gag tcg gag gtg gct gcc ata gtg aac ttc     1086
Gly Pro Ser Pro Gln Ser Glu Ser Glu Val Ala Ala Ile Val Asn Phe
    295                 300                 305

atc aca gcc cat ggc aac ttc aag gct ctg atc tcc atc cac agc tac     1134
Ile Thr Ala His Gly Asn Phe Lys Ala Leu Ile Ser Ile His Ser Tyr
310                 315                 320                 325

tct cag atg ctt atg tac cct tac ggc cga ttg ctg gag ccc gtt tca     1182
Ser Gln Met Leu Met Tyr Pro Tyr Gly Arg Leu Leu Glu Pro Val Ser
                330                 335                 340

aat cag agg gag ttg tac gat ctt gcc aag gat gcg gtg gag gcc ttg     1230
Asn Gln Arg Glu Leu Tyr Asp Leu Ala Lys Asp Ala Val Glu Ala Leu
            345                 350                 355

tat aag gtc cat ggg atc gag tac att ttt ggc agc atc agc acc acc     1278
Tyr Lys Val His Gly Ile Glu Tyr Ile Phe Gly Ser Ile Ser Thr Thr
        360                 365                 370

ctc tat gtg gcc agt ggg atc acc gtc gac tgg gcc tat gac agt ggc     1326
Leu Tyr Val Ala Ser Gly Ile Thr Val Asp Trp Ala Tyr Asp Ser Gly
    375                 380                 385

atc aag tac gcc ttc agc ttt gag ctc cgg gac act ggg cag tat ggc     1374
Ile Lys Tyr Ala Phe Ser Phe Glu Leu Arg Asp Thr Gly Gln Tyr Gly
390                 395                 400                 405

ttc ctg ctg ccg gcc aca cag atc atc ccc acg gcc cag gag acg tgg     1422
Phe Leu Leu Pro Ala Thr Gln Ile Ile Pro Thr Ala Gln Glu Thr Trp
                410                 415                 420

atg gcg ctt cgg acc atc atg gag cac acc ctg aat cac ccc tac tag     1470
Met Ala Leu Arg Thr Ile Met Glu His Thr Leu Asn His Pro Tyr  *
            425                 430                 435

cagcacgact gagggcagga ggctccatcc ttctccccaa ggtctgtggc tcctcccgaa   1530

acccaagtta tgcatcccca tccccatgcc ctcatcccga cctcttagaa aataaataca   1590

agtttgaaca ggcaaaaaaa aaaaaaaaaa aaaaaattgg cggccgcaag cttattcctt   1650

taagtgaggg ttaattttag cttggcactg gccgncg                            1687
```

```
<210> SEQ ID NO 79
<211> LENGTH: 436
<212> TYPE: PRT
<213> ORGANISM: Homo sapiens

<400> SEQUENCE: 79

Met Gln Gly Thr Pro Gly Gly Gly Thr Arg Pro Gly Pro Ser Pro Val
 1               5                  10                  15

Asp Arg Arg Thr Leu Leu Val Phe Ser Phe Ile Leu Ala Ala Ala Leu
            20                  25                  30

Gly Gln Met Asn Phe Thr Gly Asp Gln Val Leu Arg Val Leu Ala Lys
        35                  40                  45

Asp Glu Lys Gln Leu Ser Leu Leu Gly Asp Leu Glu Gly Leu Lys Pro
    50                  55                  60

Gln Lys Val Asp Phe Trp Arg Gly Pro Ala Arg Pro Ser Leu Pro Val
65                  70                  75                  80

Asp Met Arg Val Pro Phe Ser Glu Leu Lys Asp Ile Lys Ala Tyr Leu
                85                  90                  95
```

-continued

```
Glu Ser His Gly Leu Ala Tyr Ser Ile Met Ile Lys Asp Ile Gln Val
            100                 105                 110

Leu Leu Asp Glu Glu Arg Gln Ala Met Ala Lys Ser Arg Arg Leu Glu
        115                 120                 125

Arg Ser Thr Asn Ser Phe Ser Tyr Ser Ser Tyr His Thr Leu Glu Glu
    130                 135                 140

Ile Tyr Ser Trp Ile Asp Asn Phe Val Met Glu His Ser Asp Ile Val
145                 150                 155                 160

Ser Lys Ile Gln Ile Gly Asn Ser Phe Glu Asn Gln Ser Ile Leu Val
                165                 170                 175

Leu Lys Phe Ser Thr Gly Gly Ser Arg His Pro Ala Ile Trp Ile Asp
            180                 185                 190

Thr Gly Ile His Ser Arg Glu Trp Ile Thr His Ala Thr Gly Ile Trp
        195                 200                 205

Thr Ala Asn Lys Ile Val Ser Asp Tyr Gly Lys Asp Arg Val Leu Thr
    210                 215                 220

Asp Ile Leu Asn Ala Met Asp Ile Phe Ile Glu Leu Val Thr Asn Pro
225                 230                 235                 240

Asp Gly Phe Ala Phe Thr His Ser Met Asn Arg Leu Trp Arg Lys Asn
                245                 250                 255

Lys Ser Ile Arg Pro Gly Ile Phe Cys Ile Gly Val Asp Leu Asn Arg
            260                 265                 270

Asn Trp Lys Ser Gly Phe Gly Gly Asn Gly Ser Asn Ser Asn Pro Cys
        275                 280                 285

Ser Glu Thr Tyr His Gly Pro Ser Pro Gln Ser Glu Ser Glu Val Ala
    290                 295                 300

Ala Ile Val Asn Phe Ile Thr Ala His Gly Asn Phe Lys Ala Leu Ile
305                 310                 315                 320

Ser Ile His Ser Tyr Ser Gln Met Leu Met Tyr Pro Tyr Gly Arg Leu
                325                 330                 335

Leu Glu Pro Val Ser Asn Gln Arg Glu Leu Tyr Asp Leu Ala Lys Asp
            340                 345                 350

Ala Val Glu Ala Leu Tyr Lys Val His Gly Ile Glu Tyr Ile Phe Gly
        355                 360                 365

Ser Ile Ser Thr Thr Leu Tyr Val Ala Ser Gly Ile Thr Val Asp Trp
    370                 375                 380

Ala Tyr Asp Ser Gly Ile Lys Tyr Ala Phe Ser Phe Glu Leu Arg Asp
385                 390                 395                 400

Thr Gly Gln Tyr Gly Phe Leu Leu Pro Ala Thr Gln Ile Ile Pro Thr
                405                 410                 415

Ala Gln Glu Thr Trp Met Ala Leu Arg Thr Ile Met Glu His Thr Leu
            420                 425                 430

Asn His Pro Tyr
        435


<210> SEQ ID NO 80
<211> LENGTH: 1311
<212> TYPE: DNA
<213> ORGANISM: Homo sapiens
<220> FEATURE:
<221> NAME/KEY: CDS
<222> LOCATION: (1)...(1311)

<400> SEQUENCE: 80

atg cag ggc act cct gga ggc ggg acg cgc cct ggg cca tcc ccc gtg       48
Met Gln Gly Thr Pro Gly Gly Gly Thr Arg Pro Gly Pro Ser Pro Val
```

-continued

```
 1               5                   10                  15

gac agg cgg acg ctc ctg gtc ttc agc ttt atc ctg gca gca gct ttg        96
Asp Arg Arg Thr Leu Leu Val Phe Ser Phe Ile Leu Ala Ala Ala Leu
            20                  25                  30

ggc caa atg aat ttc aca ggg gac cag gtt ctt cga gtc ctg gcc aaa       144
Gly Gln Met Asn Phe Thr Gly Asp Gln Val Leu Arg Val Leu Ala Lys
        35                  40                  45

gat gag aag cag ctt tca ctt ctc ggg gat ctg gag ggc ctg aaa ccc       192
Asp Glu Lys Gln Leu Ser Leu Leu Gly Asp Leu Glu Gly Leu Lys Pro
    50                  55                  60

cag aag gtg gac ttc tgg cgt ggc cca gcc agg ccc agc ctc cct gtg       240
Gln Lys Val Asp Phe Trp Arg Gly Pro Ala Arg Pro Ser Leu Pro Val
65                  70                  75                  80

gat atg aga gtt cct ttc tcc gaa ctg aaa gac atc aaa gct tat ctg       288
Asp Met Arg Val Pro Phe Ser Glu Leu Lys Asp Ile Lys Ala Tyr Leu
                85                  90                  95

gag tct cat gga ctt gct tac agc atc atg ata aag gac atc cag gtg       336
Glu Ser His Gly Leu Ala Tyr Ser Ile Met Ile Lys Asp Ile Gln Val
            100                 105                 110

ctg ctg gat gag gaa aga cag gcc atg gcg aaa tcc cgc cgg ctg gag       384
Leu Leu Asp Glu Glu Arg Gln Ala Met Ala Lys Ser Arg Arg Leu Glu
        115                 120                 125

cgc agc acc aac agc ttc agt tac tca tca tac cac acc ctg gag gag       432
Arg Ser Thr Asn Ser Phe Ser Tyr Ser Ser Tyr His Thr Leu Glu Glu
    130                 135                 140

ata tat agc tgg att gac aac ttt gta atg gag cat tcc gat att gtc       480
Ile Tyr Ser Trp Ile Asp Asn Phe Val Met Glu His Ser Asp Ile Val
145                 150                 155                 160

tca aaa att cag att ggc aac agc ttt gaa aac cag tcc att ctt gtc       528
Ser Lys Ile Gln Ile Gly Asn Ser Phe Glu Asn Gln Ser Ile Leu Val
                165                 170                 175

ctg aag ttc agc act gga ggt tct cgg cac cca gcc atc tgg atc gac       576
Leu Lys Phe Ser Thr Gly Gly Ser Arg His Pro Ala Ile Trp Ile Asp
            180                 185                 190

act gga att cac tcc cgg gag tgg atc acc cat gcc acc ggc atc tgg       624
Thr Gly Ile His Ser Arg Glu Trp Ile Thr His Ala Thr Gly Ile Trp
        195                 200                 205

act gcc aat aag att gtc agt gat tat ggc aaa gac cgt gtc ctg aca       672
Thr Ala Asn Lys Ile Val Ser Asp Tyr Gly Lys Asp Arg Val Leu Thr
    210                 215                 220

gac ata ctg aat gcc atg gac atc ttc ata gag ctc gtc aca aac cct       720
Asp Ile Leu Asn Ala Met Asp Ile Phe Ile Glu Leu Val Thr Asn Pro
225                 230                 235                 240

gat ggg ttt gct ttt acc cac agc atg aac cgc tta tgg cgg aag aac       768
Asp Gly Phe Ala Phe Thr His Ser Met Asn Arg Leu Trp Arg Lys Asn
                245                 250                 255

aag tcc atc aga cct gga atc ttc tgc atc ggc gtg gat ctc aac agg       816
Lys Ser Ile Arg Pro Gly Ile Phe Cys Ile Gly Val Asp Leu Asn Arg
            260                 265                 270

aac tgg aag tcg ggt ttt gga gga aat ggt tct aac agc aac ccc tgc       864
Asn Trp Lys Ser Gly Phe Gly Gly Asn Gly Ser Asn Ser Asn Pro Cys
        275                 280                 285

tca gaa act tat cac ggg ccc tcc cct cag tcg gag tcg gag gtg gct       912
Ser Glu Thr Tyr His Gly Pro Ser Pro Gln Ser Glu Ser Glu Val Ala
    290                 295                 300

gcc ata gtg aac ttc atc aca gcc cat ggc aac ttc aag gct ctg atc       960
Ala Ile Val Asn Phe Ile Thr Ala His Gly Asn Phe Lys Ala Leu Ile
305                 310                 315                 320

tcc atc cac agc tac tct cag atg ctt atg tac cct tac ggc cga ttg      1008
```

-continued

```
Ser Ile His Ser Tyr Ser Gln Met Leu Met Tyr Pro Tyr Gly Arg Leu
                325                 330                 335

ctg gag ccc gtt tca aat cag agg gag ttg tac gat ctt gcc aag gat     1056
Leu Glu Pro Val Ser Asn Gln Arg Glu Leu Tyr Asp Leu Ala Lys Asp
            340                 345                 350

gcg gtg gag gcc ttg tat aag gtc cat ggg atc gag tac att ttt ggc     1104
Ala Val Glu Ala Leu Tyr Lys Val His Gly Ile Glu Tyr Ile Phe Gly
        355                 360                 365

agc atc agc acc acc ctc tat gtg gcc agt ggg atc acc gtc gac tgg     1152
Ser Ile Ser Thr Thr Leu Tyr Val Ala Ser Gly Ile Thr Val Asp Trp
    370                 375                 380

gcc tat gac agt ggc atc aag tac gcc ttc agc ttt gag ctc cgg gac     1200
Ala Tyr Asp Ser Gly Ile Lys Tyr Ala Phe Ser Phe Glu Leu Arg Asp
385                 390                 395                 400

act ggg cag tat ggc ttc ctg ctg ccg gcc aca cag atc atc ccc acg     1248
Thr Gly Gln Tyr Gly Phe Leu Leu Pro Ala Thr Gln Ile Ile Pro Thr
                405                 410                 415

gcc cag gag acg tgg atg gcg ctt cgg acc atc atg gag cac acc ctg     1296
Ala Gln Glu Thr Trp Met Ala Leu Arg Thr Ile Met Glu His Thr Leu
            420                 425                 430

aat cac ccc tac tag                                                 1311
Asn His Pro Tyr  *
        435
```

```
<210> SEQ ID NO 81
<211> LENGTH: 304
<212> TYPE: PRT
<213> ORGANISM: Artificial Sequence
<220> FEATURE:
<223> OTHER INFORMATION: Amino acid consensus sequence

<400> SEQUENCE: 81

Tyr His Asn Leu Glu Glu Ile Tyr Ala Trp Leu Asp Leu Leu Val Ser
 1               5                  10                  15

Asn Phe Pro Asp Leu Val Ser Lys Val Ser Ile Gly Lys Ser Tyr Glu
            20                  25                  30

Gly Arg Asp Leu Lys Val Leu Lys Ile Ser Asp Asn Pro Ala Thr Gly
        35                  40                  45

Glu Asn Glu Pro Glu Val Phe Ala Val Ala Gly Trp Ile His Ala Arg
    50                  55                  60

Glu Trp Val Thr Ser Ala Thr Leu Leu Trp Leu Leu Lys Glu Leu Val
65                  70                  75                  80

Ala Asn Tyr Gly Ser Asp Lys Thr Ile Thr Lys Leu Leu Asp Gly Leu
                85                  90                  95

Asp Leu Phe Tyr Ile Leu Pro Val Phe Asn Pro Asp Gly Tyr Ala Tyr
            100                 105                 110

Ser Ile Thr Thr Asp Ser Tyr Arg Met Trp Arg Lys Thr Arg Ser Pro
        115                 120                 125

Asn Ala Gly Ser Phe Cys Val Gly Thr Asp Pro Asn Arg Asn Trp Tyr
    130                 135                 140

Ala Gln Trp Gly Gly Met Gly Ala Ser Ser Tyr Ser Pro Cys Ser Glu
145                 150                 155                 160

Thr Tyr Glu Gly Thr Ala Pro Phe Ser Glu Pro Glu Thr Lys Ala Val
                165                 170                 175

Glu Asp Phe Ile Arg Ser Trp Leu Gly Gly Gly Lys Gln Asn Ile Lys
            180                 185                 190

Ala Tyr Ile Thr Phe His Ser Tyr Ser Gln Leu Leu Leu Tyr Pro Tyr
        195                 200                 205
```

Gly Tyr Asp Tyr Asn Leu Asn Pro Asp Ala Asn Asp Leu Asp Glu Leu
210 215 220

Ser Asp Leu Lys Ile Ala Ala Asp Ala Leu Ser Ala Arg His Gly Thr
225 230 235 240

Tyr Tyr Thr Leu Gly Leu Pro Gly Ser Ser Thr Ile Tyr Pro Ala Ser
245 250 255

Ala Gly Gly Ser Asp Asp Trp Ala Tyr Asp Val Gly Ile Ile Lys Tyr
260 265 270

Ala Phe Thr Phe Glu Leu Arg Pro Asp Thr Gly Ser Tyr Gly Asn Pro
275 280 285

Cys Phe Leu Leu Pro Glu Glu Gln Ile Ile Pro Thr Gly Ser Glu Glu
290 295 300

<210> SEQ ID NO 82
<211> LENGTH: 324
<212> TYPE: PRT
<213> ORGANISM: Artificial Sequence
<220> FEATURE:
<223> OTHER INFORMATION: Amino acid consensus sequence

<400> SEQUENCE: 82

Tyr His Ser Tyr Glu Glu Ile Asn Ala Trp Leu Asp Asp Leu Ala Arg
1 5 10 15

Asn Tyr Pro Asp Leu Thr Ser Val Ser Leu Ile Ser Ile Gly Lys Ser
20 25 30

Tyr Glu Gly Arg Pro Ile Lys Val Leu Lys Ile Lys Pro Ala Val Phe
35 40 45

Ile Asp Ala Gly Ile His Ala Arg Glu Trp Ile Ala Pro Ala Thr Ala
50 55 60

Leu Tyr Leu Ile Asn Gln Leu Leu Thr Asn Glu Thr Glu Tyr Ser Lys
65 70 75 80

Asp Pro Asp Asp Glu Gly Ser Val Thr Lys Leu Leu Asp Lys Leu Asp
85 90 95

Trp Tyr Ile Val Pro Val Met Asn Pro Asp Gly Tyr Glu Tyr Thr His
100 105 110

Thr Ser Thr Asp Arg Leu Trp Arg Lys Asn Arg Ser Pro Asn Gly Ala
115 120 125

Ser Gly Ser Gln Gly Thr Trp Tyr Asn Cys Tyr Gly Val Asp Leu Asn
130 135 140

Arg Asn Phe Asp Phe His Asn Trp Gly Glu Ile Gly Gly Ser Ser Ser
145 150 155 160

Leu Pro Cys Ser Glu Thr Tyr Ala Gly Ser Ser Pro Phe Ser Glu Trp
165 170 175

Glu Pro Glu Thr Lys Ala Leu Leu Asp Phe Ile Leu Ser Asn Glu Ile
180 185 190

Gly Lys Gly Arg Ile Lys Ala Tyr Ile Ser Leu His Ser Tyr Ser Gln
195 200 205

Leu Leu Leu Tyr Pro Tyr Gly Tyr Thr Asn Ala Thr Val Pro Pro Asn
210 215 220

Gly Glu Asp Leu His Lys Glu Val Ala Lys Ala Ala Ala Lys Ala Ile
225 230 235 240

Gly Asp Tyr Tyr Phe Gly Gly Thr Leu Tyr Thr Pro Gly Ser Ser Ser
245 250 255

Ala Asp Pro Asp Leu Asp Ile Thr Leu Tyr Pro Ala Ser Gly Gly Ser
260 265 270

-continued

```
Asp Asp Trp Ala Tyr Gly Thr Leu Lys Gly Val Lys Tyr Ser Tyr Thr
        275                 280                 285

Ile Glu Leu Arg Asp Thr Gly Asp Asp Ala Gly Arg Tyr Gly Phe Leu
    290                 295                 300

Leu Pro Pro Ser Cys Val Lys Pro Val Arg Met Glu Gln Ile Ile Pro
305                 310                 315                 320

Thr Gly Glu Glu


<210> SEQ ID NO 83
<211> LENGTH: 82
<212> TYPE: PRT
<213> ORGANISM: Artificial Sequence
<220> FEATURE:
<223> OTHER INFORMATION: Amino acid consensus sequence

<400> SEQUENCE: 83

Gln Val Leu Arg Val Lys Val Ala Asp Glu Asp Gln Val Lys Leu Leu
 1               5                  10                  15

Lys Asp Leu Glu Asn Thr Glu His Leu Glu Leu Asp Phe Trp Lys Pro
            20                  25                  30

Asp Ser Ala Thr Pro Ile Lys Pro Gly Ser Thr Val Asp Phe Arg Val
        35                  40                  45

Pro Ala Glu Asp Ile Gln Ala Val Lys Ser Phe Leu Glu Gln Ser Gly
    50                  55                  60

Ile His Tyr Glu Val Leu Ile Glu Asp Val Gln Glu Leu Leu Glu Glu
65                  70                  75                  80

Gln Phe


<210> SEQ ID NO 84
<211> LENGTH: 23
<212> TYPE: PRT
<213> ORGANISM: Artificial Sequence
<220> FEATURE:
<223> OTHER INFORMATION: Zinc carboxypeptidase zinc-binding region 1
      signature consensus sequence
<220> FEATURE:
<221> NAME/KEY: VARIANT
<222> LOCATION: (1)...(1)
<223> OTHER INFORMATION: Xaa at position 1 can be P or K
<220> FEATURE:
<221> NAME/KEY: VARIANT
<222> LOCATION: (2)...(2)
<223> OTHER INFORMATION: Xaa = Any amino acid
<220> FEATURE:
<221> NAME/KEY: VARIANT
<222> LOCATION: (3)...(3)
<223> OTHER INFORMATION: Xaa at position 3 can be L, I, V, M, F or Y
<220> FEATURE:
<221> NAME/KEY: VARIANT
<222> LOCATION: (4)...(4)
<223> OTHER INFORMATION: Xaa = Any amino acid
<220> FEATURE:
<221> NAME/KEY: VARIANT
<222> LOCATION: (5)...(5)
<223> OTHER INFORMATION: Xaa at position 5 can be L, I, V, M, F or Y
<220> FEATURE:
<221> NAME/KEY: VARIANT
<222> LOCATION: (6)...(9)
<223> OTHER INFORMATION: Xaa = Any amino acid
<220> FEATURE:
<221> NAME/KEY: VARIANT
<222> LOCATION: (11)...(11)
<223> OTHER INFORMATION: Xaa at position 11 can be S, T, A or G
<220> FEATURE:
<221> NAME/KEY: VARIANT
<222> LOCATION: (12)...(12)
<223> OTHER INFORMATION: Xaa = Any amino acid
```

-continued

```
<220> FEATURE:
<221> NAME/KEY: VARIANT
<222> LOCATION: (14)...(14)
<223> OTHER INFORMATION: Xaa = Any amino acid
<220> FEATURE:
<221> NAME/KEY: VARIANT
<222> LOCATION: (15)...(15)
<223> OTHER INFORMATION: Xaa at position 15 can be L, I, V or M
<220> FEATURE:
<221> NAME/KEY: VARIANT
<222> LOCATION: (16)...(16)
<223> OTHER INFORMATION: Xaa at position 16 can be S, T, A or G
<220> FEATURE:
<221> NAME/KEY: VARIANT
<222> LOCATION: (17)...(22)
<223> OTHER INFORMATION: Xaa = Any amino acid
<220> FEATURE:
<221> NAME/KEY: VARIANT
<222> LOCATION: (23)...(23)
<223> OTHER INFORMATION: Xaa at position 23 can be L, I, V, M, F, Y, T
      or A

<400> SEQUENCE: 84

Xaa Xaa Xaa Xaa Xaa Xaa Xaa Xaa Xaa His Xaa Xaa Glu Xaa Xaa Xaa
 1               5                  10                  15

Xaa Xaa Xaa Xaa Xaa Xaa Xaa
            20


<210> SEQ ID NO 85
<211> LENGTH: 11
<212> TYPE: PRT
<213> ORGANISM: Artificial Sequence
<220> FEATURE:
<223> OTHER INFORMATION: Zinc carboxypeptidase zinc-binding region 2
      signature consensus sequence
<220> FEATURE:
<221> NAME/KEY: VARIANT
<222> LOCATION: (2)...(2)
<223> OTHER INFORMATION: Xaa at position 2 can be S, T, A or G
<220> FEATURE:
<221> NAME/KEY: VARIANT
<222> LOCATION: (3)...(5)
<223> OTHER INFORMATION: Xaa = Any amino acid
<220> FEATURE:
<221> NAME/KEY: VARIANT
<222> LOCATION: (6)...(6)
<223> OTHER INFORMATION: Xaa at position 6 can be L, I, V, M or E
<220> FEATURE:
<221> NAME/KEY: VARIANT
<222> LOCATION: (7)...(8)
<223> OTHER INFORMATION: Xaa = Any amino acid
<220> FEATURE:
<221> NAME/KEY: VARIANT
<222> LOCATION: (9)...(9)
<223> OTHER INFORMATION: Xaa at position 9 can be L, I, V, M, F, Y or W
<220> FEATURE:
<221> NAME/KEY: VARIANT
<222> LOCATION: (11)...(11)
<223> OTHER INFORMATION: Xaa at position 11 can be F, Y or W

<400> SEQUENCE: 85

His Xaa Xaa Xaa Xaa Xaa Xaa Xaa Xaa Pro Xaa
 1               5                  10


<210> SEQ ID NO 86
<211> LENGTH: 22
<212> TYPE: PRT
<213> ORGANISM: Artificial Sequence
<220> FEATURE:
<223> OTHER INFORMATION: Zinc carboxypeptidase zinc-binding region 1
      signature

<400> SEQUENCE: 86
```

-continued

```
Pro Ala Ile Trp Ile Asp Thr Gly His Ser Arg Glu Trp Ile Thr His
 1               5                  10                  15

Ala Thr Gly Ile Trp Thr
            20
```

<210> SEQ ID NO 87
<211> LENGTH: 11
<212> TYPE: PRT
<213> ORGANISM: Artificial Sequence
<220> FEATURE:
<223> OTHER INFORMATION: Zinc carboxypeptidase zinc-binding region 2 signature

<400> SEQUENCE: 87

```
His Ser Tyr Ser Gln Met Leu Met Tyr Pro Tyr
 1               5                  10
```

<210> SEQ ID NO 88
<211> LENGTH: 5389
<212> TYPE: DNA
<213> ORGANISM: Homo sapiens
<220> FEATURE:
<221> NAME/KEY: CDS
<222> LOCATION: (6)...(3638)

<400> SEQUENCE: 88

```
ttggt atg gca tca cag ctg caa gtg ttt tcg ccc cca tca gtg tcg tcg      50
      Met Ala Ser Gln Leu Gln Val Phe Ser Pro Pro Ser Val Ser Ser
       1               5                  10                  15

agt gcc ttc tgc agt gcg aag aaa ctg aaa ata gag ccc tct ggc tgg        98
Ser Ala Phe Cys Ser Ala Lys Lys Leu Lys Ile Glu Pro Ser Gly Trp
                20                  25                  30

gat gtt tca gga cag agt agc aac gac aaa tat tat acc cac agc aaa       146
Asp Val Ser Gly Gln Ser Ser Asn Asp Lys Tyr Tyr Thr His Ser Lys
            35                  40                  45

acc ctc cca gcc aca caa ggg caa gcc aac tcc tct cac cag gta gca       194
Thr Leu Pro Ala Thr Gln Gly Gln Ala Asn Ser Ser His Gln Val Ala
        50                  55                  60

aat ttc aac atc cct gct tac gac cag ggc ctc ctc ctc cca gct cct       242
Asn Phe Asn Ile Pro Ala Tyr Asp Gln Gly Leu Leu Leu Pro Ala Pro
    65                  70                  75

gca gtg gag cat att gtt gta aca gcc gct gat agc tcg ggc agt gct       290
Ala Val Glu His Ile Val Val Thr Ala Ala Asp Ser Ser Gly Ser Ala
 80                  85                  90                  95

gct aca tca acc ttc caa agc agc cag acc ctg act ccc aga agc aac       338
Ala Thr Ser Thr Phe Gln Ser Ser Gln Thr Leu Thr Pro Arg Ser Asn
               100                 105                 110

gtt tct ttg ctt gag cca tat caa aaa tgt gga ttg aaa cga aaa agt       386
Val Ser Leu Leu Glu Pro Tyr Gln Lys Cys Gly Leu Lys Arg Lys Ser
           115                 120                 125

gag gaa gtt gac agc aac ggt agt gtg cag atc ata gaa gaa cat ccc       434
Glu Glu Val Asp Ser Asn Gly Ser Val Gln Ile Ile Glu Glu His Pro
       130                 135                 140

cct ctc atg ctg caa aac agg act gtg gtg ggt gct gct gcc aca acc       482
Pro Leu Met Leu Gln Asn Arg Thr Val Val Gly Ala Ala Ala Thr Thr
    145                 150                 155

acc act gtg acc aca aag agt agc agt tcc agc gga gaa ggg gat tac       530
Thr Thr Val Thr Thr Lys Ser Ser Ser Ser Ser Gly Glu Gly Asp Tyr
160                 165                 170                 175

cag ctg gtc cag cat gag atc ctt tgc tct atg acc aat agc tat gaa       578
Gln Leu Val Gln His Glu Ile Leu Cys Ser Met Thr Asn Ser Tyr Glu
                180                 185                 190
```

-continued

```
gtc ttg gag ttc cta ggc cgg ggg aca ttt gga cag gtg gct aag tgc      626
Val Leu Glu Phe Leu Gly Arg Gly Thr Phe Gly Gln Val Ala Lys Cys
            195                 200                 205

tgg aag agg agc acc aag gaa att gtg gct att aaa atc ttg aag aac      674
Trp Lys Arg Ser Thr Lys Glu Ile Val Ala Ile Lys Ile Leu Lys Asn
        210                 215                 220

cac ccc tcc tat gcc aga caa gga cag att gaa gtg agc atc ctt tcc      722
His Pro Ser Tyr Ala Arg Gln Gly Gln Ile Glu Val Ser Ile Leu Ser
    225                 230                 235

cgc cta agc agt gaa aat gct gat gag tat aat ttt gtc cgt tca tac      770
Arg Leu Ser Ser Glu Asn Ala Asp Glu Tyr Asn Phe Val Arg Ser Tyr
240                 245                 250                 255

gag tgc ttt cag cat aag aat cac acc tgc ctt gtt ttt gaa atg ttg      818
Glu Cys Phe Gln His Lys Asn His Thr Cys Leu Val Phe Glu Met Leu
                260                 265                 270

gag cag aac tta tat gat ttt cta aag caa aac aaa ttt agc cca ctg      866
Glu Gln Asn Leu Tyr Asp Phe Leu Lys Gln Asn Lys Phe Ser Pro Leu
            275                 280                 285

cca ctc aag tac atc aga cca atc ttg cag cag gtg gcc aca gcc ttg      914
Pro Leu Lys Tyr Ile Arg Pro Ile Leu Gln Gln Val Ala Thr Ala Leu
        290                 295                 300

atg aag ctc aag agt ctt ggt ctg atc cac gct gac ctt aag cct gaa      962
Met Lys Leu Lys Ser Leu Gly Leu Ile His Ala Asp Leu Lys Pro Glu
    305                 310                 315

aac atc atg ctg gtt gat cca gtt cgc cag ccc tac cga gtg aag gtc     1010
Asn Ile Met Leu Val Asp Pro Val Arg Gln Pro Tyr Arg Val Lys Val
320                 325                 330                 335

ttt gac ttt ggt tct gct agt cac gtt tcc aaa gct gtg tgc tca acc     1058
Phe Asp Phe Gly Ser Ala Ser His Val Ser Lys Ala Val Cys Ser Thr
                340                 345                 350

tac tta cag tca cgt tac tac aga gct cct gaa att att ctt ggg tta     1106
Tyr Leu Gln Ser Arg Tyr Tyr Arg Ala Pro Glu Ile Ile Leu Gly Leu
            355                 360                 365

cca ttt tgt gaa gct att gat atg tgg tca ctg ggc tgt gtg ata gct     1154
Pro Phe Cys Glu Ala Ile Asp Met Trp Ser Leu Gly Cys Val Ile Ala
        370                 375                 380

gag ctg ttc ctg gga tgg cct ctt tat cct ggt gct tca gaa tat gat     1202
Glu Leu Phe Leu Gly Trp Pro Leu Tyr Pro Gly Ala Ser Glu Tyr Asp
    385                 390                 395

cag att cgt tat att tca caa aca caa ggc ttg cca gct gaa tat ctt     1250
Gln Ile Arg Tyr Ile Ser Gln Thr Gln Gly Leu Pro Ala Glu Tyr Leu
400                 405                 410                 415

ctc agt gcc gga aca aaa aca acc agg ttt ttc aac aga gat cct aat     1298
Leu Ser Ala Gly Thr Lys Thr Thr Arg Phe Phe Asn Arg Asp Pro Asn
                420                 425                 430

ttg ggg tac cca ctg tgg agg ctt aag aca cct gaa gaa cat gaa ctg     1346
Leu Gly Tyr Pro Leu Trp Arg Leu Lys Thr Pro Glu Glu His Glu Leu
            435                 440                 445

gag act gga ata aaa tca aaa gaa gct cgg aag tac att ttt aat tgc     1394
Glu Thr Gly Ile Lys Ser Lys Glu Ala Arg Lys Tyr Ile Phe Asn Cys
        450                 455                 460

tta gat gac atg gct cag gtg aat atg tct aca gac ctg gag gga aca     1442
Leu Asp Asp Met Ala Gln Val Asn Met Ser Thr Asp Leu Glu Gly Thr
    465                 470                 475

gac atg ttg gca gag aag gca gac cga aga gaa tac att gat ctg tta     1490
Asp Met Leu Ala Glu Lys Ala Asp Arg Arg Glu Tyr Ile Asp Leu Leu
480                 485                 490                 495

aag aaa atg ctc aca att gat gca gat aag aga att acc cct cta aaa     1538
Lys Lys Met Leu Thr Ile Asp Ala Asp Lys Arg Ile Thr Pro Leu Lys
                500                 505                 510
```

-continued

```
act ctt aac cat cag ttt gtg aca atg act cac ctt ttg gat ttt cca     1586
Thr Leu Asn His Gln Phe Val Thr Met Thr His Leu Leu Asp Phe Pro
            515                 520                 525

cat agc aat cat gtt aag tct tgt ttt cag aac atg gag atc tgc aag     1634
His Ser Asn His Val Lys Ser Cys Phe Gln Asn Met Glu Ile Cys Lys
        530                 535                 540

cgg agg gtt cac atg tat gat aca gtg agt cag atc aag agt ccc ttc     1682
Arg Arg Val His Met Tyr Asp Thr Val Ser Gln Ile Lys Ser Pro Phe
    545                 550                 555

act aca cat gtt gcc cca aat aca agc aca aat cta acc atg agc ttc     1730
Thr Thr His Val Ala Pro Asn Thr Ser Thr Asn Leu Thr Met Ser Phe
560                 565                 570                 575

agc aat cag ctc aat aca gtg cac aat cag gcc agt gtt cta gct tcc     1778
Ser Asn Gln Leu Asn Thr Val His Asn Gln Ala Ser Val Leu Ala Ser
                580                 585                 590

agt tct act gca gca gct gct act ctt tct ctg gct aat tca gat gtc     1826
Ser Ser Thr Ala Ala Ala Ala Thr Leu Ser Leu Ala Asn Ser Asp Val
            595                 600                 605

tca cta cta aac tac cag tca gct ttg tac cca tca tct gct gca cca     1874
Ser Leu Leu Asn Tyr Gln Ser Ala Leu Tyr Pro Ser Ser Ala Ala Pro
        610                 615                 620

gtt cct gga gtt gcc cag cag ggt gtt tcc ttg cag cct gga acc acc     1922
Val Pro Gly Val Ala Gln Gln Gly Val Ser Leu Gln Pro Gly Thr Thr
    625                 630                 635

cag att tgc act cag aca gat cca ttc caa cag aca ttt ata gta tgt     1970
Gln Ile Cys Thr Gln Thr Asp Pro Phe Gln Gln Thr Phe Ile Val Cys
640                 645                 650                 655

cca cct gcg ttt caa act gga cta caa gca aca aca aag cat tct gga     2018
Pro Pro Ala Phe Gln Thr Gly Leu Gln Ala Thr Thr Lys His Ser Gly
                660                 665                 670

ttc cct gtg agg atg gat aat gct gta ccg att gta ccc cag gca cca     2066
Phe Pro Val Arg Met Asp Asn Ala Val Pro Ile Val Pro Gln Ala Pro
            675                 680                 685

gct gct cag cca cta cag att cag tca gga gtt ctc acg cag gga agc     2114
Ala Ala Gln Pro Leu Gln Ile Gln Ser Gly Val Leu Thr Gln Gly Ser
        690                 695                 700

tgt aca cca cta atg gta gca act ctc cac cct caa gta gcc acc atc     2162
Cys Thr Pro Leu Met Val Ala Thr Leu His Pro Gln Val Ala Thr Ile
    705                 710                 715

aca ccg cag tat gcg gtg ccc ttt act ctg agc tgc gca gcc ggc cgg     2210
Thr Pro Gln Tyr Ala Val Pro Phe Thr Leu Ser Cys Ala Ala Gly Arg
720                 725                 730                 735

ccg gcg ctg gtt gaa cag act gcc gct gta ctg cag gcg tgg cct gga     2258
Pro Ala Leu Val Glu Gln Thr Ala Ala Val Leu Gln Ala Trp Pro Gly
                740                 745                 750

ggg act cag caa att ctc ctg cct tca act tgg caa cag ttg cct ggg     2306
Gly Thr Gln Gln Ile Leu Leu Pro Ser Thr Trp Gln Gln Leu Pro Gly
            755                 760                 765

gta gct cta cac aac tct gtc cag ccc aca gca atg att cca gag gcc     2354
Val Ala Leu His Asn Ser Val Gln Pro Thr Ala Met Ile Pro Glu Ala
        770                 775                 780

atg ggg agt gga cag cag cta gct gac tgg agg aat gcc cac tct cat     2402
Met Gly Ser Gly Gln Gln Leu Ala Asp Trp Arg Asn Ala His Ser His
    785                 790                 795

ggc aac cag tac agc act atc atg cag cag cca tcc ttg ctg act aac     2450
Gly Asn Gln Tyr Ser Thr Ile Met Gln Gln Pro Ser Leu Leu Thr Asn
800                 805                 810                 815

cat gtg aca ttg gcc act gct cag cct ctg aat gtt ggt gtt gcc cat     2498
His Val Thr Leu Ala Thr Ala Gln Pro Leu Asn Val Gly Val Ala His
```

-continued

```
                820                 825                 830

gtt gtc aga caa caa caa tcc agt tcc ctc cct tcg aag aag aat aag      2546
Val Val Arg Gln Gln Gln Ser Ser Ser Leu Pro Ser Lys Lys Asn Lys
            835                 840                 845

cag tca gct cca gtc tct tcc aag tcc tct cta gat gtt ctg cct tcc      2594
Gln Ser Ala Pro Val Ser Ser Lys Ser Ser Leu Asp Val Leu Pro Ser
        850                 855                 860

caa gtc tat tct ctg gtt ggg agc agt ccc ctc cgc acc aca tct tct      2642
Gln Val Tyr Ser Leu Val Gly Ser Ser Pro Leu Arg Thr Thr Ser Ser
    865                 870                 875

tat aat tcc ttg gtc cct gtc caa gat cag cat cag ccc atc atc att      2690
Tyr Asn Ser Leu Val Pro Val Gln Asp Gln His Gln Pro Ile Ile Ile
880                 885                 890                 895

cca gat act ccc agc cct cct gtg agt gtc atc act atc cga agt gac      2738
Pro Asp Thr Pro Ser Pro Pro Val Ser Val Ile Thr Ile Arg Ser Asp
                900                 905                 910

act gat gag gaa gag gac aac aaa tac aag ccc agt agc tct gga ctg      2786
Thr Asp Glu Glu Glu Asp Asn Lys Tyr Lys Pro Ser Ser Ser Gly Leu
            915                 920                 925

aag cca agg tct aat gtc atc agt tat gtc act gtc aat gat tct cca      2834
Lys Pro Arg Ser Asn Val Ile Ser Tyr Val Thr Val Asn Asp Ser Pro
        930                 935                 940

gac tct gac tct tct ttg agc agc cct tat tcc act gat acc ctg agt      2882
Asp Ser Asp Ser Ser Leu Ser Ser Pro Tyr Ser Thr Asp Thr Leu Ser
    945                 950                 955

gct ctc cga ggc aat agt gga tcc gtt ttg gag ggg cct ggc aga gtt      2930
Ala Leu Arg Gly Asn Ser Gly Ser Val Leu Glu Gly Pro Gly Arg Val
960                 965                 970                 975

gtg gca gat ggc act ggc acc cgc act atc att gtg cct cca ctg aaa      2978
Val Ala Asp Gly Thr Gly Thr Arg Thr Ile Ile Val Pro Pro Leu Lys
                980                 985                 990

act cag ctt ggt gac tgc act gta gca acc cag gcc tca ggt ctc ctg      3026
Thr Gln Leu Gly Asp Cys Thr Val Ala Thr Gln Ala Ser Gly Leu Leu
            995                 1000                1005

agc aat aag act aag cca gtc gct tca gtg agt ggg cag tca tct gga      3074
Ser Asn Lys Thr Lys Pro Val Ala Ser Val Ser Gly Gln Ser Ser Gly
        1010                1015                1020

tgc tgt atc acc ccc aca ggg tat cga gct caa cgc ggg ggg acc agt      3122
Cys Cys Ile Thr Pro Thr Gly Tyr Arg Ala Gln Arg Gly Gly Thr Ser
    1025                1030                1035

gca gca caa cca ctc aat ctt agc cag aac cag cag tca tcg gcg gct      3170
Ala Ala Gln Pro Leu Asn Leu Ser Gln Asn Gln Gln Ser Ser Ala Ala
1040                1045                1050                1055

cca acc tca cag gag aga agc agc aac cca gcc ccc cgc agg cag cag      3218
Pro Thr Ser Gln Glu Arg Ser Ser Asn Pro Ala Pro Arg Arg Gln Gln
                1060                1065                1070

gcg ttt gtg gcc cct ctc tcc caa gcc ccc tac acc ttc cag cat ggc      3266
Ala Phe Val Ala Pro Leu Ser Gln Ala Pro Tyr Thr Phe Gln His Gly
            1075                1080                1085

agc ccg cta cac tcg aca ggg cac cca cac ctt gcc ccg gcc cct gct      3314
Ser Pro Leu His Ser Thr Gly His Pro His Leu Ala Pro Ala Pro Ala
        1090                1095                1100

cac ctg cca agc cag gct cat ctg tat acg tat gct gcc ccg act tct      3362
His Leu Pro Ser Gln Ala His Leu Tyr Thr Tyr Ala Ala Pro Thr Ser
    1105                1110                1115

gct gct gca ctg ggc tca acc agc tcc att gct cat ctt ttc tcc cca      3410
Ala Ala Ala Leu Gly Ser Thr Ser Ser Ile Ala His Leu Phe Ser Pro
1120                1125                1130                1135

cag ggt tcc tca agg cat gct gca gcc tat acc act cac cct agc act      3458
```

-continued

```
Gln Gly Ser Ser Arg His Ala Ala Ala Tyr Thr Thr His Pro Ser Thr
                1140                1145                1150

ttg gtg cac cag gtc cct gtc agt gtt ggg ccc agc ctc ctc act tct     3506
Leu Val His Gln Val Pro Val Ser Val Gly Pro Ser Leu Leu Thr Ser
            1155                1160                1165

gcc agc gtg gcc cct gct cag tac caa cac cag ttt gcc acc caa tcc     3554
Ala Ser Val Ala Pro Ala Gln Tyr Gln His Gln Phe Ala Thr Gln Ser
        1170                1175                1180

tac att ggg tct tcc cga ggc tca aca att tac act gga tac ccg ctg     3602
Tyr Ile Gly Ser Ser Arg Gly Ser Thr Ile Tyr Thr Gly Tyr Pro Leu
    1185                1190                1195

agt cct acc aag atc agc cag tat tcc tac tta tag ttggtgagca          3648
Ser Pro Thr Lys Ile Ser Gln Tyr Ser Tyr Leu  *
1200                1205                1210

tgagggagga ggaatcatgg ctaccttctc ctggccctgc gttcttaata ttgggctatg   3708

gagagatcct cctttaccct cttgaaattt cttagccagc aacttgttct gcaggggccc   3768

actgaagcag aaggtttttc tctgggggaa cctgtctcag tgttgactgc attgttgtag   3828

tcttcccaaa gtttgcccta tttttaaatt cattattttt gtgacagtaa ttttggtact   3888

tggaagagtt cagatgccca tcttctgcag ttaccaagga agagagattg ttctgaagtt   3948

accctctgaa aaatattttg tctctctgac ttgatttcta taaatgcttt taaaaacaag   4008

tgaagcccct ctttatttca ttttgtgtta ttgtgattgc tggtcaggaa aaatgctgat   4068

agaaggagtt gaaatctgat gacaaaaaaa gaaaaattac tttttgtttg tttataaact   4128

cagacttgcc tattttattt taaaagcggc ttacacaatc tccctttttgt ttattggaca   4188

tttaaactta cagagtttca gttttgtttt aatgtcatat tatacttaat gggcaattgt   4248

tatttttgca aaactggtta cgtattactc tgtgttacta ttgagattct ctcaattgct   4308

cctgtgtttg ttataaagta gtgtttaaaa ggcagctcac catttgctgg taacttaatg   4368

tgagagaatc catatctgcg tgaaaacacc aagtattctt tttaaatgaa gcaccatgaa   4428

ttcttttttta aattattttt taaaagtctt tctctctctg attcagctta aattttttta   4488

tcgaaaaagc cattaaggtg gttattatta catggtggtg gtggttttat tatatgcaaa   4548

atctctgtct attatgagat actggcattg atgagctttg cctaaagatt agtatgaatt   4608

ttcagtaata cacctctgtt ttgctcatct ctcccttctg ttttatgtga tttgtttggg   4668

gagaaagcta aaaaaacctg aaaccagata agaacatttc ttgtgtatag cttttatact   4728

tcaaagtagc ttcctttgta tgccagcagc aaattgaatg ctctcttatt aagacttata   4788

taataagtgc atgtaggaat tgcaaaaaat attttaaaaa tttattactg aatttaaaaa   4848

tattttagaa gttttgtaat ggtggtgttt taatatttta cataattaaa tatgtacata   4908

ttgattagaa aaatataaca agcaattttt cctgctaacc caaaatgtta tttgtaatca   4968

aatgtgtagt gattacactt gaattgtgta cttagtgtgt atgtgatcct ccagtgttat   5028

cccggagatg gattgatgtc tccattgtat ttaaaccaaa atgaactgat acttgttgga   5088

atgtatgtga actaattgca attatattag agcatattac tgtagtgctg aatgagcagg   5148

ggcattgcct gcaaggagag gagacccttg gaattgtttt gcacaggtgt gtctggtgag   5208

gagtttttca gtgtgtgtct cttccttccc tttcttcctc cttcccttat tgagtgcctt   5268

atatgataat gtagtggtta atagagttta cagtgagctt gccttaggat ggaccagcaa   5328

gcccccgggg accctaagtt gttcaccggg atttatcaga acaggattag tagctggatt   5388

g                                                                   5389
```

<210> SEQ ID NO 89
<211> LENGTH: 1210
<212> TYPE: PRT
<213> ORGANISM: Homo sapiens

<400> SEQUENCE: 89

```
Met Ala Ser Gln Leu Gln Val Phe Ser Pro Pro Ser Val Ser Ser Ser
 1               5                  10                  15

Ala Phe Cys Ser Ala Lys Lys Leu Lys Ile Glu Pro Ser Gly Trp Asp
            20                  25                  30

Val Ser Gly Gln Ser Ser Asn Asp Lys Tyr Tyr Thr His Ser Lys Thr
        35                  40                  45

Leu Pro Ala Thr Gln Gly Gln Ala Asn Ser Ser His Gln Val Ala Asn
    50                  55                  60

Phe Asn Ile Pro Ala Tyr Asp Gln Gly Leu Leu Leu Pro Ala Pro Ala
65                  70                  75                  80

Val Glu His Ile Val Val Thr Ala Ala Asp Ser Ser Gly Ser Ala Ala
                85                  90                  95

Thr Ser Thr Phe Gln Ser Ser Gln Thr Leu Thr Pro Arg Ser Asn Val
            100                 105                 110

Ser Leu Leu Glu Pro Tyr Gln Lys Cys Gly Leu Lys Arg Lys Ser Glu
        115                 120                 125

Glu Val Asp Ser Asn Gly Ser Val Gln Ile Ile Glu Glu His Pro Pro
    130                 135                 140

Leu Met Leu Gln Asn Arg Thr Val Val Gly Ala Ala Ala Thr Thr Thr
145                 150                 155                 160

Thr Val Thr Thr Lys Ser Ser Ser Ser Ser Gly Glu Gly Asp Tyr Gln
                165                 170                 175

Leu Val Gln His Glu Ile Leu Cys Ser Met Thr Asn Ser Tyr Glu Val
            180                 185                 190

Leu Glu Phe Leu Gly Arg Gly Thr Phe Gly Gln Val Ala Lys Cys Trp
        195                 200                 205

Lys Arg Ser Thr Lys Glu Ile Val Ala Ile Lys Ile Leu Lys Asn His
    210                 215                 220

Pro Ser Tyr Ala Arg Gln Gly Gln Ile Glu Val Ser Ile Leu Ser Arg
225                 230                 235                 240

Leu Ser Ser Glu Asn Ala Asp Glu Tyr Asn Phe Val Arg Ser Tyr Glu
                245                 250                 255

Cys Phe Gln His Lys Asn His Thr Cys Leu Val Phe Glu Met Leu Glu
            260                 265                 270

Gln Asn Leu Tyr Asp Phe Leu Lys Gln Asn Lys Phe Ser Pro Leu Pro
        275                 280                 285

Leu Lys Tyr Ile Arg Pro Ile Leu Gln Gln Val Ala Thr Ala Leu Met
    290                 295                 300

Lys Leu Lys Ser Leu Gly Leu Ile His Ala Asp Leu Lys Pro Glu Asn
305                 310                 315                 320

Ile Met Leu Val Asp Pro Val Arg Gln Pro Tyr Arg Val Lys Val Phe
                325                 330                 335

Asp Phe Gly Ser Ala Ser His Val Ser Lys Ala Val Cys Ser Thr Tyr
            340                 345                 350

Leu Gln Ser Arg Tyr Tyr Arg Ala Pro Glu Ile Ile Leu Gly Leu Pro
        355                 360                 365

Phe Cys Glu Ala Ile Asp Met Trp Ser Leu Gly Cys Val Ile Ala Glu
    370                 375                 380
```

-continued

```
Leu Phe Leu Gly Trp Pro Leu Tyr Pro Gly Ala Ser Glu Tyr Asp Gln
385                 390                 395                 400

Ile Arg Tyr Ile Ser Gln Thr Gln Gly Leu Pro Ala Glu Tyr Leu Leu
                405                 410                 415

Ser Ala Gly Thr Lys Thr Thr Arg Phe Phe Asn Arg Asp Pro Asn Leu
            420                 425                 430

Gly Tyr Pro Leu Trp Arg Leu Lys Thr Pro Glu Glu His Glu Leu Glu
        435                 440                 445

Thr Gly Ile Lys Ser Lys Glu Ala Arg Lys Tyr Ile Phe Asn Cys Leu
    450                 455                 460

Asp Asp Met Ala Gln Val Asn Met Ser Thr Asp Leu Glu Gly Thr Asp
465                 470                 475                 480

Met Leu Ala Glu Lys Ala Asp Arg Arg Glu Tyr Ile Asp Leu Leu Lys
                485                 490                 495

Lys Met Leu Thr Ile Asp Ala Asp Lys Arg Ile Thr Pro Leu Lys Thr
            500                 505                 510

Leu Asn His Gln Phe Val Thr Met Thr His Leu Leu Asp Phe Pro His
        515                 520                 525

Ser Asn His Val Lys Ser Cys Phe Gln Asn Met Glu Ile Cys Lys Arg
    530                 535                 540

Arg Val His Met Tyr Asp Thr Val Ser Gln Ile Lys Ser Pro Phe Thr
545                 550                 555                 560

Thr His Val Ala Pro Asn Thr Ser Thr Asn Leu Thr Met Ser Phe Ser
                565                 570                 575

Asn Gln Leu Asn Thr Val His Asn Gln Ala Ser Val Leu Ala Ser Ser
            580                 585                 590

Ser Thr Ala Ala Ala Ala Thr Leu Ser Leu Ala Asn Ser Asp Val Ser
        595                 600                 605

Leu Leu Asn Tyr Gln Ser Ala Leu Tyr Pro Ser Ser Ala Ala Pro Val
    610                 615                 620

Pro Gly Val Ala Gln Gln Gly Val Ser Leu Gln Pro Gly Thr Thr Gln
625                 630                 635                 640

Ile Cys Thr Gln Thr Asp Pro Phe Gln Gln Thr Phe Ile Val Cys Pro
                645                 650                 655

Pro Ala Phe Gln Thr Gly Leu Gln Ala Thr Thr Lys His Ser Gly Phe
            660                 665                 670

Pro Val Arg Met Asp Asn Ala Val Pro Ile Val Pro Gln Ala Pro Ala
        675                 680                 685

Ala Gln Pro Leu Gln Ile Gln Ser Gly Val Leu Thr Gln Gly Ser Cys
    690                 695                 700

Thr Pro Leu Met Val Ala Thr Leu His Pro Gln Val Ala Thr Ile Thr
705                 710                 715                 720

Pro Gln Tyr Ala Val Pro Phe Thr Leu Ser Cys Ala Ala Gly Arg Pro
                725                 730                 735

Ala Leu Val Glu Gln Thr Ala Ala Val Leu Gln Ala Trp Pro Gly Gly
            740                 745                 750

Thr Gln Gln Ile Leu Leu Pro Ser Thr Trp Gln Gln Leu Pro Gly Val
        755                 760                 765

Ala Leu His Asn Ser Val Gln Pro Thr Ala Met Ile Pro Glu Ala Met
    770                 775                 780

Gly Ser Gly Gln Gln Leu Ala Asp Trp Arg Asn Ala His Ser His Gly
785                 790                 795                 800
```

-continued

```
Asn Gln Tyr Ser Thr Ile Met Gln Gln Pro Ser Leu Leu Thr Asn His
                805                 810                 815

Val Thr Leu Ala Thr Ala Gln Pro Leu Asn Val Gly Val Ala His Val
            820                 825                 830

Val Arg Gln Gln Gln Ser Ser Ser Leu Pro Ser Lys Lys Asn Lys Gln
        835                 840                 845

Ser Ala Pro Val Ser Ser Lys Ser Ser Leu Asp Val Leu Pro Ser Gln
    850                 855                 860

Val Tyr Ser Leu Val Gly Ser Ser Pro Leu Arg Thr Thr Ser Ser Tyr
865                 870                 875                 880

Asn Ser Leu Val Pro Val Gln Asp Gln His Gln Pro Ile Ile Ile Pro
                885                 890                 895

Asp Thr Pro Ser Pro Pro Val Ser Val Ile Thr Ile Arg Ser Asp Thr
            900                 905                 910

Asp Glu Glu Glu Asp Asn Lys Tyr Lys Pro Ser Ser Ser Gly Leu Lys
        915                 920                 925

Pro Arg Ser Asn Val Ile Ser Tyr Val Thr Val Asn Asp Ser Pro Asp
    930                 935                 940

Ser Asp Ser Ser Leu Ser Ser Pro Tyr Ser Thr Asp Thr Leu Ser Ala
945                 950                 955                 960

Leu Arg Gly Asn Ser Gly Ser Val Leu Glu Gly Pro Gly Arg Val Val
                965                 970                 975

Ala Asp Gly Thr Gly Thr Arg Thr Ile Ile Val Pro Pro Leu Lys Thr
            980                 985                 990

Gln Leu Gly Asp Cys Thr Val Ala Thr Gln Ala Ser Gly Leu Leu Ser
        995                 1000                1005

Asn Lys Thr Lys Pro Val Ala Ser Val Ser Gly Gln Ser Ser Gly Cys
    1010                1015                1020

Cys Ile Thr Pro Thr Gly Tyr Arg Ala Gln Arg Gly Gly Thr Ser Ala
1025                1030                1035                1040

Ala Gln Pro Leu Asn Leu Ser Gln Asn Gln Gln Ser Ser Ala Ala Pro
                1045                1050                1055

Thr Ser Gln Glu Arg Ser Ser Asn Pro Ala Pro Arg Arg Gln Gln Ala
            1060                1065                1070

Phe Val Ala Pro Leu Ser Gln Ala Pro Tyr Thr Phe Gln His Gly Ser
        1075                1080                1085

Pro Leu His Ser Thr Gly His Pro His Leu Ala Pro Ala Pro Ala His
    1090                1095                1100

Leu Pro Ser Gln Ala His Leu Tyr Thr Tyr Ala Ala Pro Thr Ser Ala
1105                1110                1115                1120

Ala Ala Leu Gly Ser Thr Ser Ser Ile Ala His Leu Phe Ser Pro Gln
                1125                1130                1135

Gly Ser Ser Arg His Ala Ala Ala Tyr Thr Thr His Pro Ser Thr Leu
            1140                1145                1150

Val His Gln Val Pro Val Ser Val Gly Pro Ser Leu Leu Thr Ser Ala
        1155                1160                1165

Ser Val Ala Pro Ala Gln Tyr Gln His Gln Phe Ala Thr Gln Ser Tyr
    1170                1175                1180

Ile Gly Ser Ser Arg Gly Ser Thr Ile Tyr Thr Gly Tyr Pro Leu Ser
1185                1190                1195                1200

Pro Thr Lys Ile Ser Gln Tyr Ser Tyr Leu
                1205                1210
```

-continued

<210> SEQ ID NO 90
<211> LENGTH: 3633
<212> TYPE: DNA
<213> ORGANISM: Homo sapiens
<220> FEATURE:
<221> NAME/KEY: CDS
<222> LOCATION: (1)...(3633)

<400> SEQUENCE: 90

```
atg gca tca cag ctg caa gtg ttt tcg ccc cca tca gtg tcg tcg agt       48
Met Ala Ser Gln Leu Gln Val Phe Ser Pro Pro Ser Val Ser Ser Ser
 1               5                  10                  15

gcc ttc tgc agt gcg aag aaa ctg aaa ata gag ccc tct ggc tgg gat       96
Ala Phe Cys Ser Ala Lys Lys Leu Lys Ile Glu Pro Ser Gly Trp Asp
            20                  25                  30

gtt tca gga cag agt agc aac gac aaa tat tat acc cac agc aaa acc      144
Val Ser Gly Gln Ser Ser Asn Asp Lys Tyr Tyr Thr His Ser Lys Thr
        35                  40                  45

ctc cca gcc aca caa ggg caa gcc aac tcc tct cac cag gta gca aat      192
Leu Pro Ala Thr Gln Gly Gln Ala Asn Ser Ser His Gln Val Ala Asn
    50                  55                  60

ttc aac atc cct gct tac gac cag ggc ctc ctc ctc cca gct cct gca      240
Phe Asn Ile Pro Ala Tyr Asp Gln Gly Leu Leu Leu Pro Ala Pro Ala
 65                  70                  75                  80

gtg gag cat att gtt gta aca gcc gct gat agc tcg ggc agt gct gct      288
Val Glu His Ile Val Val Thr Ala Ala Asp Ser Ser Gly Ser Ala Ala
                85                  90                  95

aca tca acc ttc caa agc agc cag acc ctg act ccc aga agc aac gtt      336
Thr Ser Thr Phe Gln Ser Ser Gln Thr Leu Thr Pro Arg Ser Asn Val
            100                 105                 110

tct ttg ctt gag cca tat caa aaa tgt gga ttg aaa cga aaa agt gag      384
Ser Leu Leu Glu Pro Tyr Gln Lys Cys Gly Leu Lys Arg Lys Ser Glu
        115                 120                 125

gaa gtt gac agc aac ggt agt gtg cag atc ata gaa gaa cat ccc cct      432
Glu Val Asp Ser Asn Gly Ser Val Gln Ile Ile Glu Glu His Pro Pro
    130                 135                 140

ctc atg ctg caa aac agg act gtg gtg ggt gct gct gcc aca acc acc      480
Leu Met Leu Gln Asn Arg Thr Val Val Gly Ala Ala Ala Thr Thr Thr
145                 150                 155                 160

act gtg acc aca aag agt agc agt tcc agc gga gaa ggg gat tac cag      528
Thr Val Thr Thr Lys Ser Ser Ser Ser Ser Gly Glu Gly Asp Tyr Gln
                165                 170                 175

ctg gtc cag cat gag atc ctt tgc tct atg acc aat agc tat gaa gtc      576
Leu Val Gln His Glu Ile Leu Cys Ser Met Thr Asn Ser Tyr Glu Val
            180                 185                 190

ttg gag ttc cta ggc cgg ggg aca ttt gga cag gtg gct aag tgc tgg      624
Leu Glu Phe Leu Gly Arg Gly Thr Phe Gly Gln Val Ala Lys Cys Trp
        195                 200                 205

aag agg agc acc aag gaa att gtg gct att aaa atc ttg aag aac cac      672
Lys Arg Ser Thr Lys Glu Ile Val Ala Ile Lys Ile Leu Lys Asn His
    210                 215                 220

ccc tcc tat gcc aga caa gga cag att gaa gtg agc atc ctt tcc cgc      720
Pro Ser Tyr Ala Arg Gln Gly Gln Ile Glu Val Ser Ile Leu Ser Arg
225                 230                 235                 240

cta agc agt gaa aat gct gat gag tat aat ttt gtc cgt tca tac gag      768
Leu Ser Ser Glu Asn Ala Asp Glu Tyr Asn Phe Val Arg Ser Tyr Glu
                245                 250                 255

tgc ttt cag cat aag aat cac acc tgc ctt gtt ttt gaa atg ttg gag      816
Cys Phe Gln His Lys Asn His Thr Cys Leu Val Phe Glu Met Leu Glu
            260                 265                 270

cag aac tta tat gat ttt cta aag caa aac aaa ttt agc cca ctg cca      864
```

-continued

```
Gln Asn Leu Tyr Asp Phe Leu Lys Gln Asn Lys Phe Ser Pro Leu Pro
        275                 280                 285

ctc aag tac atc aga cca atc ttg cag cag gtg gcc aca gcc ttg atg      912
Leu Lys Tyr Ile Arg Pro Ile Leu Gln Gln Val Ala Thr Ala Leu Met
    290                 295                 300

aag ctc aag agt ctt ggt ctg atc cac gct gac ctt aag cct gaa aac      960
Lys Leu Lys Ser Leu Gly Leu Ile His Ala Asp Leu Lys Pro Glu Asn
305                 310                 315                 320

atc atg ctg gtt gat cca gtt cgc cag ccc tac cga gtg aag gtc ttt     1008
Ile Met Leu Val Asp Pro Val Arg Gln Pro Tyr Arg Val Lys Val Phe
            325                 330                 335

gac ttt ggt tct gct agt cac gtt tcc aaa gct gtg tgc tca acc tac   1056
Asp Phe Gly Ser Ala Ser His Val Ser Lys Ala Val Cys Ser Thr Tyr

            340                 345                 350
tta cag tca cgt tac tac aga gct cct gaa att att ctt ggg tta cca   1104

Leu Gln Ser Arg Tyr Tyr Arg Ala Pro Glu Ile Ile Leu Gly Leu Pro
        355                 360                 365

ttt tgt gaa gct att gat atg tgg tca ctg ggc tgt gtg ata gct gag   1152
Phe Cys Glu Ala Ile Asp Met Trp Ser Leu Gly Cys Val Ile Ala Glu

    370                 375                 380
ctg ttc ctg gga tgg cct ctt tat cct ggt gct tca gaa tat gat cag   1200

Leu Phe Leu Gly Trp Pro Leu Tyr Pro Gly Ala Ser Glu Tyr Asp Gln
385                 390                 395                 400

att cgt tat att tca caa aca caa ggc ttg cca gct gaa tat ctt ctc   1248
Ile Arg Tyr Ile Ser Gln Thr Gln Gly Leu Pro Ala Glu Tyr Leu Leu

                405                 410                 415
agt gcc gga aca aaa aca acc agg ttt ttc aac aga gat cct aat ttg   1296

Ser Ala Gly Thr Lys Thr Thr Arg Phe Phe Asn Arg Asp Pro Asn Leu
            420                 425                 430

ggg tac cca ctg tgg agg ctt aag aca cct gaa gaa cat gaa ctg gag   1344
Gly Tyr Pro Leu Trp Arg Leu Lys Thr Pro Glu Glu His Glu Leu Glu

        435                 440                 445
act gga ata aaa tca aaa gaa gct cgg aag tac att ttt aat tgc tta   1392

Thr Gly Ile Lys Ser Lys Glu Ala Arg Lys Tyr Ile Phe Asn Cys Leu
    450                 455                 460

gat gac atg gct cag gtg aat atg tct aca gac ctg gag gga aca gac   1440
Asp Asp Met Ala Gln Val Asn Met Ser Thr Asp Leu Glu Gly Thr Asp

465                 470                 475                 480
atg ttg gca gag aag gca gac cga aga gaa tac att gat ctg tta aag   1488

Met Leu Ala Glu Lys Ala Asp Arg Arg Glu Tyr Ile Asp Leu Leu Lys
                485                 490                 495

aaa atg ctc aca att gat gca gat aag aga att acc cct cta aaa act   1536
Lys Met Leu Thr Ile Asp Ala Asp Lys Arg Ile Thr Pro Leu Lys Thr

            500                 505                 510
ctt aac cat cag ttt gtg aca atg act cac ctt ttg gat ttt cca cat   1584

Leu Asn His Gln Phe Val Thr Met Thr His Leu Leu Asp Phe Pro His
        515                 520                 525

agc aat cat gtt aag tct tgt ttt cag aac atg gag atc tgc aag cgg   1632
Ser Asn His Val Lys Ser Cys Phe Gln Asn Met Glu Ile Cys Lys Arg

    530                 535                 540
agg gtt cac atg tat gat aca gtg agt cag atc aag agt ccc ttc act   1680

Arg Val His Met Tyr Asp Thr Val Ser Gln Ile Lys Ser Pro Phe Thr
545                 550                 555                 560

aca cat gtt gcc cca aat aca agc aca aat cta acc atg agc ttc agc   1728
```

-continued

```
Thr His Val Ala Pro Asn Thr Ser Thr Asn Leu Thr Met Ser Phe Ser

                565                 570                 575
aat cag ctc aat aca gtg cac aat cag gcc agt gtt cta gct tcc agt    1776

Asn Gln Leu Asn Thr Val His Asn Gln Ala Ser Val Leu Ala Ser Ser
            580                 585                 590

tct act gca gca gct gct act ctt tct ctg gct aat tca gat gtc tca    1824
Ser Thr Ala Ala Ala Ala Thr Leu Ser Leu Ala Asn Ser Asp Val Ser

        595                 600                 605
cta cta aac tac cag tca gct ttg tac cca tca tct gct gca cca gtt    1872

Leu Leu Asn Tyr Gln Ser Ala Leu Tyr Pro Ser Ser Ala Ala Pro Val
    610                 615                 620

cct gga gtt gcc cag cag ggt gtt tcc ttg cag cct gga acc acc cag    1920
Pro Gly Val Ala Gln Gln Gly Val Ser Leu Gln Pro Gly Thr Thr Gln

625                 630                 635                 640
att tgc act cag aca gat cca ttc caa cag aca ttt ata gta tgt cca    1968

Ile Cys Thr Gln Thr Asp Pro Phe Gln Gln Thr Phe Ile Val Cys Pro
                645                 650                 655

cct gcg ttt caa act gga cta caa gca aca aca aag cat tct gga ttc    2016
Pro Ala Phe Gln Thr Gly Leu Gln Ala Thr Thr Lys His Ser Gly Phe

            660                 665                 670
cct gtg agg atg gat aat gct gta ccg att gta ccc cag gca cca gct    2064

Pro Val Arg Met Asp Asn Ala Val Pro Ile Val Pro Gln Ala Pro Ala
        675                 680                 685

gct cag cca cta cag att cag tca gga gtt ctc acg cag gga agc tgt    2112
Ala Gln Pro Leu Gln Ile Gln Ser Gly Val Leu Thr Gln Gly Ser Cys

    690                 695                 700
aca cca cta atg gta gca act ctc cac cct caa gta gcc acc atc aca    2160

Thr Pro Leu Met Val Ala Thr Leu His Pro Gln Val Ala Thr Ile Thr
705                 710                 715                 720

ccg cag tat gcg gtg ccc ttt act ctg agc tgc gca gcc ggc cgg ccg    2208
Pro Gln Tyr Ala Val Pro Phe Thr Leu Ser Cys Ala Ala Gly Arg Pro

                725                 730                 735
gcg ctg gtt gaa cag act gcc gct gta ctg cag gcg tgg cct gga ggg    2256

Ala Leu Val Glu Gln Thr Ala Ala Val Leu Gln Ala Trp Pro Gly Gly
            740                 745                 750

act cag caa att ctc ctg cct tca act tgg caa cag ttg cct ggg gta    2304
Thr Gln Gln Ile Leu Leu Pro Ser Thr Trp Gln Gln Leu Pro Gly Val

        755                 760                 765
gct cta cac aac tct gtc cag ccc aca gca atg att cca gag gcc atg    2352

Ala Leu His Asn Ser Val Gln Pro Thr Ala Met Ile Pro Glu Ala Met
    770                 775                 780

ggg agt gga cag cag cta gct gac tgg agg aat gcc cac tct cat ggc    2400
Gly Ser Gly Gln Gln Leu Ala Asp Trp Arg Asn Ala His Ser His Gly

785                 790                 795                 800
aac cag tac agc act atc atg cag cag cca tcc ttg ctg act aac cat    2448

Asn Gln Tyr Ser Thr Ile Met Gln Gln Pro Ser Leu Leu Thr Asn His
                805                 810                 815

gtg aca ttg gcc act gct cag cct ctg aat gtt ggt gtt gcc cat gtt    2496
Val Thr Leu Ala Thr Ala Gln Pro Leu Asn Val Gly Val Ala His Val

            820                 825                 830
gtc aga caa caa caa tcc agt tcc ctc cct tcg aag aag aat aag cag    2544

Val Arg Gln Gln Gln Ser Ser Ser Leu Pro Ser Lys Lys Asn Lys Gln
        835                 840                 845
```

-continued

```
tca gct cca gtc tct tcc aag tcc tct cta gat gtt ctg cct tcc caa   2592
Ser Ala Pro Val Ser Ser Lys Ser Ser Leu Asp Val Leu Pro Ser Gln
    850                 855                 860
gtc tat tct ctg gtt ggg agc agt ccc ctc cgc acc aca tct tct tat   2640
Val Tyr Ser Leu Val Gly Ser Ser Pro Leu Arg Thr Thr Ser Ser Tyr
865                 870                 875                 880
aat tcc ttg gtc cct gtc caa gat cag cat cag ccc atc atc att cca   2688
Asn Ser Leu Val Pro Val Gln Asp Gln His Gln Pro Ile Ile Ile Pro
                885                 890                 895
gat act ccc agc cct cct gtg agt gtc atc act atc cga agt gac act   2736
Asp Thr Pro Ser Pro Pro Val Ser Val Ile Thr Ile Arg Ser Asp Thr
            900                 905                 910
gat gag gaa gag gac aac aaa tac aag ccc agt agc tct gga ctg aag   2784
Asp Glu Glu Glu Asp Asn Lys Tyr Lys Pro Ser Ser Ser Gly Leu Lys
        915                 920                 925
cca agg tct aat gtc atc agt tat gtc act gtc aat gat tct cca gac   2832
Pro Arg Ser Asn Val Ile Ser Tyr Val Thr Val Asn Asp Ser Pro Asp
    930                 935                 940
tct gac tct tct ttg agc agc cct tat tcc act gat acc ctg agt gct   2880
Ser Asp Ser Ser Leu Ser Ser Pro Tyr Ser Thr Asp Thr Leu Ser Ala
945                 950                 955                 960
ctc cga ggc aat agt gga tcc gtt ttg gag ggg cct ggc aga gtt gtg   2928
Leu Arg Gly Asn Ser Gly Ser Val Leu Glu Gly Pro Gly Arg Val Val
                965                 970                 975
gca gat ggc act ggc acc cgc act atc att gtg cct cca ctg aaa act   2976
Ala Asp Gly Thr Gly Thr Arg Thr Ile Ile Val Pro Pro Leu Lys Thr
            980                 985                 990
cag ctt ggt gac tgc act gta gca acc cag gcc tca ggt ctc ctg agc   3024
Gln Leu Gly Asp Cys Thr Val Ala Thr Gln Ala Ser Gly Leu Leu Ser
        995                 1000                1005
aat aag act aag cca gtc gct tca gtg agt ggg cag tca tct gga tgc   3072
Asn Lys Thr Lys Pro Val Ala Ser Val Ser Gly Gln Ser Ser Gly Cys
    1010                1015                1020
tgt atc acc ccc aca ggg tat cga gct caa cgc ggg ggg acc agt gca   3120
Cys Ile Thr Pro Thr Gly Tyr Arg Ala Gln Arg Gly Gly Thr Ser Ala
1025                1030                1035                1040
gca caa cca ctc aat ctt agc cag aac cag cag tca tcg gcg gct cca   3168
Ala Gln Pro Leu Asn Leu Ser Gln Asn Gln Gln Ser Ser Ala Ala Pro
                1045                1050                1055
acc tca cag gag aga agc agc aac cca gcc ccc cgc agg cag cag gcg   3216
Thr Ser Gln Glu Arg Ser Ser Asn Pro Ala Pro Arg Arg Gln Gln Ala
            1060                1065                1070
ttt gtg gcc cct ctc tcc caa gcc ccc tac acc ttc cag cat ggc agc   3264
Phe Val Ala Pro Leu Ser Gln Ala Pro Tyr Thr Phe Gln His Gly Ser
        1075                1080                1085
ccg cta cac tcg aca ggg cac cca cac ctt gcc ccg gcc cct gct cac   3312
Pro Leu His Ser Thr Gly His Pro His Leu Ala Pro Ala Pro Ala His
    1090                1095                1100
ctg cca agc cag gct cat ctg tat acg tat gct gcc ccg act tct gct   3360
Leu Pro Ser Gln Ala His Leu Tyr Thr Tyr Ala Ala Pro Thr Ser Ala
1105                1110                1115                1120
gct gca ctg ggc tca acc agc tcc att gct cat ctt ttc tcc cca cag   3408
```

-continued

```
Ala Ala Leu Gly Ser Thr Ser Ser Ile Ala His Leu Phe Ser Pro Gln
                1125                1130                1135

ggt tcc tca agg cat gct gca gcc tat acc act cac cct agc act ttg   3456
Gly Ser Ser Arg His Ala Ala Ala Tyr Thr Thr His Pro Ser Thr Leu

            1140                1145                1150
gtg cac cag gtc cct gtc agt gtt ggg ccc agc ctc ctc act tct gcc   3504

Val His Gln Val Pro Val Ser Val Gly Pro Ser Leu Leu Thr Ser Ala
        1155                1160                1165

agc gtg gcc cct gct cag tac caa cac cag ttt gcc acc caa tcc tac   3552
Ser Val Ala Pro Ala Gln Tyr Gln His Gln Phe Ala Thr Gln Ser Tyr

    1170                1175                1180
att ggg tct tcc cga ggc tca aca att tac act gga tac ccg ctg agt   3600

Ile Gly Ser Ser Arg Gly Ser Thr Ile Tyr Thr Gly Tyr Pro Leu Ser
1185                1190                1195                1200

cct acc aag atc agc cag tat tcc tac tta tag                       3633
Pro Thr Lys Ile Ser Gln Tyr Ser Tyr Leu  *
                1205                1210
```

<210> SEQ ID NO 91
<211> LENGTH: 270
<212> TYPE: PRT
<213> ORGANISM: Artificial Sequence
<220> FEATURE:
<223> OTHER INFORMATION: Ser/Thr kinase site consensus sequence
<220> FEATURE:
<221> NAME/KEY: VARIANT
<222> LOCATION: (1)...(9)
<223> OTHER INFORMATION: Xaa = Any amino acid
<220> FEATURE:
<221> NAME/KEY: VARIANT
<222> LOCATION: (11)...(11)
<223> OTHER INFORMATION: Xaa = Any amino acid
<220> FEATURE:
<221> NAME/KEY: VARIANT
<222> LOCATION: (13)...(16)
<223> OTHER INFORMATION: Xaa = Any amino acid
<220> FEATURE:
<221> NAME/KEY: VARIANT
<222> LOCATION: (18)...(29)
<223> OTHER INFORMATION: Xaa = Any amino acid
<220> FEATURE:
<221> NAME/KEY: VARIANT
<222> LOCATION: (31)...(49)
<223> OTHER INFORMATION: Xaa = Any amino acid
<220> FEATURE:
<221> NAME/KEY: VARIANT
<222> LOCATION: (51)...(116)
<223> OTHER INFORMATION: Xaa = Any amino acid
<220> FEATURE:
<221> NAME/KEY: VARIANT
<222> LOCATION: (118)...(125)
<223> OTHER INFORMATION: Xaa = Any amino acid
<220> FEATURE:
<221> NAME/KEY: VARIANT
<222> LOCATION: (129)...(129)
<223> OTHER INFORMATION: Xaa = Any amino acid
<220> FEATURE:
<221> NAME/KEY: VARIANT
<222> LOCATION: (131)...(132)
<223> OTHER INFORMATION: Xaa = Any amino acid
<220> FEATURE:
<221> NAME/KEY: VARIANT
<222> LOCATION: (134)...(150)
<223> OTHER INFORMATION: Xaa = Any amino acid
<220> FEATURE:
<221> NAME/KEY: VARIANT
<222> LOCATION: (152)...(153)
<223> OTHER INFORMATION: Xaa = Any amino acid
<220> FEATURE:
<221> NAME/KEY: VARIANT
<222> LOCATION: (157)...(177)

-continued

<223> OTHER INFORMATION: Xaa = Any amino acid
<220> FEATURE:
<221> NAME/KEY: VARIANT
<222> LOCATION: (179)...(191)
<223> OTHER INFORMATION: Xaa = Any amino acid
<220> FEATURE:
<221> NAME/KEY: VARIANT
<222> LOCATION: (193)...(195)
<223> OTHER INFORMATION: Xaa = Any amino acid
<220> FEATURE:
<221> NAME/KEY: VARIANT
<222> LOCATION: (197)...(251)
<223> OTHER INFORMATION: Xaa = Any amino acid
<220> FEATURE:
<221> NAME/KEY: VARIANT
<222> LOCATION: (253)...(266)
<223> OTHER INFORMATION: Xaa = Any amino acid
<220> FEATURE:
<221> NAME/KEY: VARIANT
<222> LOCATION: (268)...(270)
<223> OTHER INFORMATION: Xaa = Any amino acid

<400> SEQUENCE: 91

```
Xaa Xaa Xaa Xaa Xaa Xaa Xaa Xaa Xaa Gly Xaa Gly Xaa Xaa Xaa Xaa
 1               5                  10                  15

Val Xaa Xaa Xaa Xaa Xaa Xaa Xaa Xaa Xaa Xaa Xaa Xaa Lys Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa Glu Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa Xaa
                85                  90                  95

Xaa Xaa Xaa Xaa Xaa Xaa Xaa Xaa Xaa Xaa Xaa Xaa Xaa Xaa Xaa Xaa
            100                 105                 110

Xaa Xaa Xaa Xaa His Xaa Xaa Xaa Xaa Xaa Xaa Xaa Xaa His Arg Asp
        115                 120                 125

Xaa Lys Xaa Xaa Asn Xaa Xaa Xaa Xaa Xaa Xaa Xaa Xaa Xaa Xaa Xaa
    130                 135                 140

Xaa Xaa Xaa Xaa Xaa Xaa Lys Xaa Xaa Asp Phe Gly Xaa Xaa Xaa Xaa
145                 150                 155                 160

Xaa Xaa Xaa Xaa Xaa Xaa Xaa Xaa Xaa Xaa Xaa Xaa Xaa Xaa Xaa Xaa
                165                 170                 175

Xaa Pro Xaa Xaa Xaa Xaa Xaa Xaa Xaa Xaa Xaa Xaa Xaa Xaa Xaa Trp
            180                 185                 190

Xaa Xaa Xaa Gly Xaa Xaa Xaa Xaa Xaa Xaa Xaa Xaa Xaa Xaa Xaa Xaa
        195                 200                 205

Xaa Xaa Xaa Xaa Xaa Xaa Xaa Xaa Xaa Xaa Xaa Xaa Xaa Xaa Xaa Xaa
    210                 215                 220

Xaa Xaa Xaa Xaa Xaa Xaa Xaa Xaa Xaa Xaa Xaa Xaa Xaa Xaa Xaa Xaa
225                 230                 235                 240

Xaa Xaa Xaa Xaa Xaa Xaa Xaa Xaa Xaa Xaa Xaa Arg Xaa Xaa Xaa Xaa
                245                 250                 255

Xaa Xaa Xaa Xaa Xaa Xaa Xaa Xaa Xaa Xaa His Xaa Xaa Xaa
            260                 265                 270
```

<210> SEQ ID NO 92
<211> LENGTH: 30
<212> TYPE: PRT

-continued

<213> ORGANISM: Artificial Sequence
<220> FEATURE:
<223> OTHER INFORMATION: ATP-binding region consensus sequence
<220> FEATURE:
<221> NAME/KEY: VARIANT
<222> LOCATION: (2)...(2)
<223> OTHER INFORMATION: Xaa = Any amino acid
<220> FEATURE:
<221> NAME/KEY: VARIANT
<222> LOCATION: (4)...(5)
<223> OTHER INFORMATION: Xaa = Any amino acid
<220> FEATURE:
<221> NAME/KEY: VARIANT
<222> LOCATION: (7)...(29)
<223> OTHER INFORMATION: Xaa = Any amino acid

<400> SEQUENCE: 92

```
Gly Xaa Gly Xaa Xaa Gly Xaa Xaa Xaa Xaa Xaa Xaa Xaa Xaa Xaa Xaa
 1               5                  10                  15

Xaa Xaa Xaa Xaa Xaa Xaa Xaa Xaa Xaa Xaa Xaa Xaa Xaa Lys
            20                  25                  30
```

<210> SEQ ID NO 93
<211> LENGTH: 214
<212> TYPE: PRT
<213> ORGANISM: Artificial Sequence
<220> FEATURE:
<223> OTHER INFORMATION: Amino acid consensus sequence

<400> SEQUENCE: 93

```
Tyr Glu Leu Leu Glu Lys Leu Gly Glu Gly Ser Phe Gly Lys Val Tyr
 1               5                  10                  15

Lys Ala Lys His Lys Thr Gly Lys Ile Val Ala Val Lys Ile Leu Lys
            20                  25                  30

Lys Glu Ser Leu Ser Leu Arg Glu Ile Gln Ile Leu Lys Arg Leu Ser
        35                  40                  45

His Pro Asn Ile Val Arg Leu Leu Gly Val Phe Glu Asp Thr Asp Asp
    50                  55                  60

His Leu Tyr Leu Val Met Glu Tyr Met Glu Gly Gly Asp Leu Phe Asp
65                  70                  75                  80

Tyr Leu Arg Arg Asn Gly Pro Leu Ser Glu Lys Glu Ala Lys Lys Ile
                85                  90                  95

Ala Leu Gln Ile Leu Arg Gly Leu Glu Tyr Leu His Ser Asn Gly Ile
            100                 105                 110

Val His Arg Asp Leu Lys Pro Glu Asn Ile Leu Leu Asp Glu Asn Gly
        115                 120                 125

Thr Val Lys Ile Ala Asp Phe Gly Leu Ala Arg Leu Leu Glu Lys Leu
    130                 135                 140

Thr Thr Phe Val Gly Thr Pro Trp Tyr Met Met Ala Pro Glu Val Ile
145                 150                 155                 160

Leu Glu Gly Arg Gly Tyr Ser Ser Lys Val Asp Val Trp Ser Leu Gly
                165                 170                 175

Val Ile Leu Tyr Glu Leu Leu Thr Gly Gly Pro Leu Phe Pro Gly Ala
            180                 185                 190

Asp Leu Pro Ala Phe Thr Gly Gly Asp Glu Val Asp Gln Leu Ile Ile
        195                 200                 205

Phe Val Leu Lys Leu Pro
    210
```

<210> SEQ ID NO 94
<211> LENGTH: 30

-continued

<212> TYPE: PRT
<213> ORGANISM: Artificial Sequence
<220> FEATURE:
<223> OTHER INFORMATION: Amino acid consensus sequence

<400> SEQUENCE: 94

Lys Asp Leu Leu Lys Lys Cys Leu Asn Lys Asp Pro Ser Lys Arg Pro
1               5                   10                  15

Gly Ser Ala Thr Ala Lys Glu Ile Leu Asn His Pro Trp Phe
            20                  25                  30

<210> SEQ ID NO 95
<211> LENGTH: 158
<212> TYPE: PRT
<213> ORGANISM: Artificial Sequence
<220> FEATURE:
<223> OTHER INFORMATION: Amino acid consensus sequence

<400> SEQUENCE: 95

Leu Asn Ala Gly Thr Lys Thr Thr Arg Phe Phe Asn Arg Val Lys Ser
1               5                   10                  15

Glu Ser Pro Asn Asp Thr Asp Met Gly His Ser Tyr Trp Arg Leu Lys
            20                  25                  30

Thr Pro Glu Glu His Glu Ala Glu Thr Gly Thr Ala Lys Ser Lys Glu
        35                  40                  45

Ala Arg Lys Tyr Ile Phe Asn Cys Leu Asp Asp Ile Ala His Val Asn
    50                  55                  60

Met Thr Met Asp Leu Glu Gly Ser Asp Met Leu Cys Glu Lys Ala Asp
65                  70                  75                  80

Arg Arg Glu Phe Val Asp Leu Leu Lys Lys Met Leu Thr Ile Asp Ala
                85                  90                  95

Asp Phe Arg Ile Thr Pro Ile Glu Thr Leu Asn His Pro Phe Val Thr
            100                 105                 110

Met Thr His Leu Leu Asp Phe Pro His Ser Asn His Val Lys Ser Cys
        115                 120                 125

Phe His Asn Met Glu Ile Cys Lys Lys Pro Gly Asn Ser Cys Asp Thr
    130                 135                 140

Pro Asn His Ser Lys Thr Asn Leu Leu Thr Pro Val Ala Pro
145                 150                 155

<210> SEQ ID NO 96
<211> LENGTH: 135
<212> TYPE: PRT
<213> ORGANISM: Artificial Sequence
<220> FEATURE:
<223> OTHER INFORMATION: Amino acid consensus sequence

<400> SEQUENCE: 96

Pro Thr Ser Tyr Ser Ile Arg Pro Glu Asn Ala Val Pro Phe Val Thr
1               5                   10                  15

Gln Ala Pro Ala Ala Gln Pro Leu Gln Ile Gln Pro Gly Val Leu Ala
            20                  25                  30

Gln Gln Ala Trp Pro Gly Gly Thr Gln Gln Ile Leu Leu Pro Pro Ala
        35                  40                  45

Trp Gln Gln Leu Thr Gly Val Ala Pro His Thr Ser Val Gln Pro Ala
    50                  55                  60

Ala Val Ile Pro Glu Ala Met Ala Gly Ser Gln Gln Leu Ala Asp Trp
65                  70                  75                  80

Arg Asn Met His Ser His Gly Asn His Tyr Asn Thr Ile Met Gln Gln

-continued

```
                85                  90                  95

Pro Ser Leu Leu Thr Asn His Val Thr Leu Ser Ala Ala Gln Pro Leu
            100                 105                 110

Asn Val Gly Val Ala His Val Val Trp Gln Gln Pro Ser Ser Thr Lys
        115                 120                 125

Pro Ser Lys Lys Cys Lys Gln
    130                 135


<210> SEQ ID NO 97
<211> LENGTH: 162
<212> TYPE: PRT
<213> ORGANISM: Artificial Sequence
<220> FEATURE:
<223> OTHER INFORMATION: Amino acid consensus sequence

<400> SEQUENCE: 97

Thr Gln Gln Ile Leu Leu Pro Pro Ala Trp Gln Gln Leu Thr Gly Val
 1               5                  10                  15

Ala Pro His Thr Ser Val Gln Pro Ala Ala Val Ile Pro Glu Ala Met
            20                  25                  30

Ala Gly Ser Gln Gln Leu Ala Asp Trp Arg Asn Met His Ser His Gly
        35                  40                  45

Asn His Tyr Asn Thr Ile Met Gln Gln Pro Ser Leu Leu Thr Asn His
    50                  55                  60

Val Thr Leu Ser Ala Ala Gln Pro Leu Asn Val Gly Val Ala His Val
65                  70                  75                  80

Val Trp Gln Gln Pro Ser Ser Thr Lys Pro Ser Lys Lys Cys Lys Gln
                85                  90                  95

His Gln Ile Leu Val Lys Leu Met Glu Trp Glu Pro Gly Arg Glu Glu
            100                 105                 110

Ile Asn Ala Phe Ser Pro Val Asn Ser Leu Ser Asn Cys Glu Val Pro
        115                 120                 125

His Ser Gln Phe Ile Ser Pro Pro Ile Ile Ser Gly Lys Glu Val Glu
    130                 135                 140

Glu Ser Ser Pro Ile Arg Thr Thr Asp Asn His Asn Ser Pro Gly Pro
145                 150                 155                 160

Cys Gln


<210> SEQ ID NO 98
<211> LENGTH: 55
<212> TYPE: PRT
<213> ORGANISM: Artificial Sequence
<220> FEATURE:
<223> OTHER INFORMATION: Amino acid consensus sequence

<400> SEQUENCE: 98

Ser Ile Arg Pro Glu Asn Ala Val Pro Phe Val Thr Gln Ala Pro Ala
 1               5                  10                  15

Ala Gln Pro Leu Gln Ile Gln Pro Gly Val Leu Ala Gln Gln Ala Trp
            20                  25                  30

Pro Gly Gly Thr Gln Gln Ile Leu Leu Pro Pro Ala Trp Gln Gln Leu
        35                  40                  45

Thr Gly Val Ala Pro His Thr
    50                  55


<210> SEQ ID NO 99
<211> LENGTH: 188
<212> TYPE: PRT
```

-continued

<213> ORGANISM: Artificial Sequence
<220> FEATURE:
<223> OTHER INFORMATION: Amino acid consensus sequence

<400> SEQUENCE: 99

```
Gly Tyr Arg Gln Gln Arg Pro Gly Pro His Phe Gln Gln Gln Gln Pro
 1               5                  10                  15

Leu Asn Leu Ser Gln Ala Gln His His Gly Ser Ala His Gln Glu Trp
            20                  25                  30

Asn His Ser Ser Asn Phe Gly His Arg Arg Gln Gln Ala Tyr Ile Pro
        35                  40                  45

Pro Thr Met Thr Gln Ala Pro Tyr Thr Phe Pro His Gly Ser Pro Asn
    50                  55                  60

His Ser Thr Val His Pro His Leu Ala Gly Ala Pro Ala His Leu Pro
65                  70                  75                  80

Gly Gln Pro His Leu Tyr Thr Tyr Pro Ala Pro Thr Ser Ala Ala Ala
                85                  90                  95

Leu Gly Ser Thr Gly Pro Val Ala His Leu Leu Ala Ser Gln Gly Ser
            100                 105                 110

Ser Arg His Met Val Gln His Thr Thr Tyr Asn Ile Ser His Pro Ser
        115                 120                 125

Gly Ile Val His Gln Val Pro Val Ser Met Gly Pro Arg Leu Leu Pro
    130                 135                 140

Ser Pro Thr Ile His Pro Thr Gln Tyr Lys Pro Gln Phe Ala Pro Gln
145                 150                 155                 160

Ser Tyr Ile Ala Ala Ser Pro Ala Ser Thr Val Tyr Thr Gly Tyr Pro
                165                 170                 175

Leu Ser Pro Thr Lys Ile Ser Gln Tyr Pro Tyr Met
            180                 185
```

<210> SEQ ID NO 100
<211> LENGTH: 1281
<212> TYPE: DNA
<213> ORGANISM: Homo sapiens
<220> FEATURE:
<221> NAME/KEY: CDS
<222> LOCATION: (49)...(1239)

<400> SEQUENCE: 100

```
ctgcccggat agtataaatc gaggatccag gtctgggcag attcaacc atg gga gcc      57
                                                     Met Gly Ala
                                                      1

aac act tca aga aaa cca cca gtg ttt gat gaa aat gaa gat gtc aac      105
Asn Thr Ser Arg Lys Pro Pro Val Phe Asp Glu Asn Glu Asp Val Asn
     5                  10                  15

ttt gac cac ttt gaa att ttg cga gcc att ggg aaa ggc agt ttt ggg      153
Phe Asp His Phe Glu Ile Leu Arg Ala Ile Gly Lys Gly Ser Phe Gly
 20                  25                  30                  35

aag gtc tgc att gta cag aag aat gat acc aag aag atg tac gca atg      201
Lys Val Cys Ile Val Gln Lys Asn Asp Thr Lys Lys Met Tyr Ala Met
                 40                  45                  50

aag tac atg aat aaa caa aag tgc gtg gag cgc aat gaa gtg aga aat      249
Lys Tyr Met Asn Lys Gln Lys Cys Val Glu Arg Asn Glu Val Arg Asn
             55                  60                  65

gtc ttc aag gaa ctc cag atc atg cag ggt ctg gag cac cct ttc ctg      297
Val Phe Lys Glu Leu Gln Ile Met Gln Gly Leu Glu His Pro Phe Leu
         70                  75                  80

gtt aat ttg tgg tat tcc ttc caa gat gag gaa gac atg ttc atg gtg      345
Val Asn Leu Trp Tyr Ser Phe Gln Asp Glu Glu Asp Met Phe Met Val
```

-continued

```
    85                  90                  95

gtg gac ctc ctg ctg ggt gga gac ctg cgt tat cac ctg caa cag aac      393
Val Asp Leu Leu Leu Gly Gly Asp Leu Arg Tyr His Leu Gln Gln Asn
100                 105                 110                 115

gtc cac ttc aag gaa gaa aca gtg aag ctc ttc atc tgt gag ctg gtc      441
Val His Phe Lys Glu Glu Thr Val Lys Leu Phe Ile Cys Glu Leu Val
                120                 125                 130

atg gcc ctg gac tac ctg cag aac cag cgc atc att cac agg gat atg      489
Met Ala Leu Asp Tyr Leu Gln Asn Gln Arg Ile Ile His Arg Asp Met
            135                 140                 145

aag cct gac aat att tta ctt gac gaa cat ggg cac gtg cac atc aca      537
Lys Pro Asp Asn Ile Leu Leu Asp Glu His Gly His Val His Ile Thr
        150                 155                 160

gat ttc aac att gct gcg atg ctg ccc agg gag ata cag att acc acc      585
Asp Phe Asn Ile Ala Ala Met Leu Pro Arg Glu Ile Gln Ile Thr Thr
    165                 170                 175

atg gct ggc acc aag cct tac atg gca cct gag atg ttc agc tcc aga      633
Met Ala Gly Thr Lys Pro Tyr Met Ala Pro Glu Met Phe Ser Ser Arg
180                 185                 190                 195

aaa gga gca ggc tat tcc ttt gct gtt gac tgg tgg tcc ctg gga gtg      681
Lys Gly Ala Gly Tyr Ser Phe Ala Val Asp Trp Trp Ser Leu Gly Val
                200                 205                 210

acg gca tat gaa ctg ctg aga ggc cgg aga ccg tat cat att cgc tcc      729
Thr Ala Tyr Glu Leu Leu Arg Gly Arg Arg Pro Tyr His Ile Arg Ser
            215                 220                 225

agt act tcc agc aag gaa att gta cac acg ttt gag acg act gtt gta      777
Ser Thr Ser Ser Lys Glu Ile Val His Thr Phe Glu Thr Thr Val Val
        230                 235                 240

act tac cct tct gcc tgg tca cag gaa atg gtg tca ctt ctt aaa aag      825
Thr Tyr Pro Ser Ala Trp Ser Gln Glu Met Val Ser Leu Leu Lys Lys
    245                 250                 255

cta ctc gaa cct aat cca gac caa cga ttt tct cag tta tct gat gtc      873
Leu Leu Glu Pro Asn Pro Asp Gln Arg Phe Ser Gln Leu Ser Asp Val
260                 265                 270                 275

cag aac ttc ccg tat atg aat gat ata aac tgg gat gca gtt ttt cag      921
Gln Asn Phe Pro Tyr Met Asn Asp Ile Asn Trp Asp Ala Val Phe Gln
                280                 285                 290

aag agg ctc att cca ggt ttc att cct aat aaa ggc agg ctg aat tgt      969
Lys Arg Leu Ile Pro Gly Phe Ile Pro Asn Lys Gly Arg Leu Asn Cys
            295                 300                 305

gat cct acc ttt gaa ctt gag gaa atg att ttg gag tcc aaa cct cta     1017
Asp Pro Thr Phe Glu Leu Glu Glu Met Ile Leu Glu Ser Lys Pro Leu
        310                 315                 320

cat aag aaa aaa aag cgt ctg gca aag aag gag aag gat atg agg aaa     1065
His Lys Lys Lys Lys Arg Leu Ala Lys Lys Glu Lys Asp Met Arg Lys
    325                 330                 335

tgc gat tct tct cag aca tgt ctt ctt caa gag cac ctt gac tct gtc     1113
Cys Asp Ser Ser Gln Thr Cys Leu Leu Gln Glu His Leu Asp Ser Val
340                 345                 350                 355

cag aag gag ttc ata att ttc aac aga gaa aaa gta aac agg gac ttt     1161
Gln Lys Glu Phe Ile Ile Phe Asn Arg Glu Lys Val Asn Arg Asp Phe
                360                 365                 370

aac aaa aga caa cca aat cta gcc ttg gaa caa acc aaa gac cca caa     1209
Asn Lys Arg Gln Pro Asn Leu Ala Leu Glu Gln Thr Lys Asp Pro Gln
            375                 380                 385

ggt gag gat ggt cag aat aac aac ttg taa aggcctcatg tcttcttctt       1259
Gly Glu Asp Gly Gln Asn Asn Asn Leu  *
        390                 395

gggacaatct catgccagaa ac                                             1281
```

-continued

<210> SEQ ID NO 101
<211> LENGTH: 396
<212> TYPE: PRT
<213> ORGANISM: Homo sapiens

<400> SEQUENCE: 101

```
Met Gly Ala Asn Thr Ser Arg Lys Pro Pro Val Phe Asp Glu Asn Glu
 1               5                  10                  15

Asp Val Asn Phe Asp His Phe Glu Ile Leu Arg Ala Ile Gly Lys Gly
            20                  25                  30

Ser Phe Gly Lys Val Cys Ile Val Gln Lys Asn Asp Thr Lys Lys Met
        35                  40                  45

Tyr Ala Met Lys Tyr Met Asn Lys Gln Lys Cys Val Glu Arg Asn Glu
    50                  55                  60

Val Arg Asn Val Phe Lys Glu Leu Gln Ile Met Gln Gly Leu Glu His
65                  70                  75                  80

Pro Phe Leu Val Asn Leu Trp Tyr Ser Phe Gln Asp Glu Glu Asp Met
                85                  90                  95

Phe Met Val Val Asp Leu Leu Leu Gly Gly Asp Leu Arg Tyr His Leu
            100                 105                 110

Gln Gln Asn Val His Phe Lys Glu Glu Thr Val Lys Leu Phe Ile Cys
        115                 120                 125

Glu Leu Val Met Ala Leu Asp Tyr Leu Gln Asn Gln Arg Ile Ile His
    130                 135                 140

Arg Asp Met Lys Pro Asp Asn Ile Leu Leu Asp Glu His Gly His Val
145                 150                 155                 160

His Ile Thr Asp Phe Asn Ile Ala Ala Met Leu Pro Arg Glu Ile Gln
                165                 170                 175

Ile Thr Thr Met Ala Gly Thr Lys Pro Tyr Met Ala Pro Glu Met Phe
            180                 185                 190

Ser Ser Arg Lys Gly Ala Gly Tyr Ser Phe Ala Val Asp Trp Trp Ser
        195                 200                 205

Leu Gly Val Thr Ala Tyr Glu Leu Leu Arg Gly Arg Arg Pro Tyr His
    210                 215                 220

Ile Arg Ser Ser Thr Ser Ser Lys Glu Ile Val His Thr Phe Glu Thr
225                 230                 235                 240

Thr Val Val Thr Tyr Pro Ser Ala Trp Ser Gln Glu Met Val Ser Leu
                245                 250                 255

Leu Lys Lys Leu Leu Glu Pro Asn Pro Asp Gln Arg Phe Ser Gln Leu
            260                 265                 270

Ser Asp Val Gln Asn Phe Pro Tyr Met Asn Asp Ile Asn Trp Asp Ala
        275                 280                 285

Val Phe Gln Lys Arg Leu Ile Pro Gly Phe Ile Pro Asn Lys Gly Arg
    290                 295                 300

Leu Asn Cys Asp Pro Thr Phe Glu Leu Glu Glu Met Ile Leu Glu Ser
305                 310                 315                 320

Lys Pro Leu His Lys Lys Lys Lys Arg Leu Ala Lys Lys Glu Lys Asp
                325                 330                 335

Met Arg Lys Cys Asp Ser Ser Gln Thr Cys Leu Leu Gln Glu His Leu
            340                 345                 350

Asp Ser Val Gln Lys Glu Phe Ile Ile Phe Asn Arg Glu Lys Val Asn
        355                 360                 365

Arg Asp Phe Asn Lys Arg Gln Pro Asn Leu Ala Leu Glu Gln Thr Lys
```

-continued

```
    370                 375                 380

Asp Pro Gln Gly Glu Asp Gly Gln Asn Asn Asn Leu
385                 390                 395


<210> SEQ ID NO 102
<211> LENGTH: 1191
<212> TYPE: DNA
<213> ORGANISM: Homo sapiens
<220> FEATURE:
<221> NAME/KEY: CDS
<222> LOCATION: (1)...(1191)

<400> SEQUENCE: 102

atg gga gcc aac act tca aga aaa cca cca gtg ttt gat gaa aat gaa       48
Met Gly Ala Asn Thr Ser Arg Lys Pro Pro Val Phe Asp Glu Asn Glu
 1               5                  10                  15

gat gtc aac ttt gac cac ttt gaa att ttg cga gcc att ggg aaa ggc       96
Asp Val Asn Phe Asp His Phe Glu Ile Leu Arg Ala Ile Gly Lys Gly
            20                  25                  30

agt ttt ggg aag gtc tgc att gta cag aag aat gat acc aag aag atg      144
Ser Phe Gly Lys Val Cys Ile Val Gln Lys Asn Asp Thr Lys Lys Met
        35                  40                  45

tac gca atg aag tac atg aat aaa caa aag tgc gtg gag cgc aat gaa      192
Tyr Ala Met Lys Tyr Met Asn Lys Gln Lys Cys Val Glu Arg Asn Glu
    50                  55                  60

gtg aga aat gtc ttc aag gaa ctc cag atc atg cag ggt ctg gag cac      240
Val Arg Asn Val Phe Lys Glu Leu Gln Ile Met Gln Gly Leu Glu His
 65                 70                  75                  80

cct ttc ctg gtt aat ttg tgg tat tcc ttc caa gat gag gaa gac atg      288
Pro Phe Leu Val Asn Leu Trp Tyr Ser Phe Gln Asp Glu Glu Asp Met
                85                  90                  95

ttc atg gtg gtg gac ctc ctg ctg ggt gga gac ctg cgt tat cac ctg      336
Phe Met Val Val Asp Leu Leu Leu Gly Gly Asp Leu Arg Tyr His Leu
            100                 105                 110

caa cag aac gtc cac ttc aag gaa gaa aca gtg aag ctc ttc atc tgt      384
Gln Gln Asn Val His Phe Lys Glu Glu Thr Val Lys Leu Phe Ile Cys
        115                 120                 125

gag ctg gtc atg gcc ctg gac tac ctg cag aac cag cgc atc att cac      432
Glu Leu Val Met Ala Leu Asp Tyr Leu Gln Asn Gln Arg Ile Ile His
    130                 135                 140

agg gat atg aag cct gac aat att tta ctt gac gaa cat ggg cac gtg      480
Arg Asp Met Lys Pro Asp Asn Ile Leu Leu Asp Glu His Gly His Val
145                 150                 155                 160

cac atc aca gat ttc aac att gct gcg atg ctg ccc agg gag ata cag      528
His Ile Thr Asp Phe Asn Ile Ala Ala Met Leu Pro Arg Glu Ile Gln
                165                 170                 175

att acc acc atg gct ggc acc aag cct tac atg gca cct gag atg ttc      576
Ile Thr Thr Met Ala Gly Thr Lys Pro Tyr Met Ala Pro Glu Met Phe
            180                 185                 190

agc tcc aga aaa gga gca ggc tat tcc ttt gct gtt gac tgg tgg tcc      624
Ser Ser Arg Lys Gly Ala Gly Tyr Ser Phe Ala Val Asp Trp Trp Ser
        195                 200                 205

ctg gga gtg acg gca tat gaa ctg ctg aga ggc cgg aga ccg tat cat      672
Leu Gly Val Thr Ala Tyr Glu Leu Leu Arg Gly Arg Arg Pro Tyr His
    210                 215                 220

att cgc tcc agt act tcc agc aag gaa att gta cac acg ttt gag acg      720
Ile Arg Ser Ser Thr Ser Ser Lys Glu Ile Val His Thr Phe Glu Thr
225                 230                 235                 240

act gtt gta act tac cct tct gcc tgg tca cag gaa atg gtg tca ctt      768
Thr Val Val Thr Tyr Pro Ser Ala Trp Ser Gln Glu Met Val Ser Leu
                245                 250                 255
```

-continued

```
ctt aaa aag cta ctc gaa cct aat cca gac caa cga ttt tct cag tta      816
Leu Lys Lys Leu Leu Glu Pro Asn Pro Asp Gln Arg Phe Ser Gln Leu
            260                 265                 270

tct gat gtc cag aac ttc ccg tat atg aat gat ata aac tgg gat gca      864
Ser Asp Val Gln Asn Phe Pro Tyr Met Asn Asp Ile Asn Trp Asp Ala
        275                 280                 285

gtt ttt cag aag agg ctc att cca ggt ttc att cct aat aaa ggc agg      912
Val Phe Gln Lys Arg Leu Ile Pro Gly Phe Ile Pro Asn Lys Gly Arg
    290                 295                 300

ctg aat tgt gat cct acc ttt gaa ctt gag gaa atg att ttg gag tcc      960
Leu Asn Cys Asp Pro Thr Phe Glu Leu Glu Glu Met Ile Leu Glu Ser
305                 310                 315                 320

aaa cct cta cat aag aaa aaa aag cgt ctg gca aag aag gag aag gat     1008
Lys Pro Leu His Lys Lys Lys Lys Arg Leu Ala Lys Lys Glu Lys Asp
                325                 330                 335

atg agg aaa tgc gat tct tct cag aca tgt ctt ctt caa gag cac ctt     1056
Met Arg Lys Cys Asp Ser Ser Gln Thr Cys Leu Leu Gln Glu His Leu
            340                 345                 350

gac tct gtc cag aag gag ttc ata att ttc aac aga gaa aaa gta aac     1104
Asp Ser Val Gln Lys Glu Phe Ile Ile Phe Asn Arg Glu Lys Val Asn
        355                 360                 365

agg gac ttt aac aaa aga caa cca aat cta gcc ttg gaa caa acc aaa     1152
Arg Asp Phe Asn Lys Arg Gln Pro Asn Leu Ala Leu Glu Gln Thr Lys
    370                 375                 380

gac cca caa ggt gag gat ggt cag aat aac aac ttg taa                 1191
Asp Pro Gln Gly Glu Asp Gly Gln Asn Asn Asn Leu  *
385                 390                 395
```

<210> SEQ ID NO 103
<211> LENGTH: 270
<212> TYPE: PRT
<213> ORGANISM: Artificial Sequence
<220> FEATURE:
<223> OTHER INFORMATION: Ser/Thr kinase site consensus sequence
<220> FEATURE:
<221> NAME/KEY: VARIANT
<222> LOCATION: (1)...(9)
<223> OTHER INFORMATION: Xaa = Any amino acid
<220> FEATURE:
<221> NAME/KEY: VARIANT
<222> LOCATION: (11)...(11)
<223> OTHER INFORMATION: Xaa = Any amino acid
<220> FEATURE:
<221> NAME/KEY: VARIANT
<222> LOCATION: (13)...(16)
<223> OTHER INFORMATION: Xaa = Any amino acid
<220> FEATURE:
<221> NAME/KEY: VARIANT
<222> LOCATION: (18)...(29)
<223> OTHER INFORMATION: Xaa = Any amino acid
<220> FEATURE:
<221> NAME/KEY: VARIANT
<222> LOCATION: (31)...(49)
<223> OTHER INFORMATION: Xaa = Any amino acid
<220> FEATURE:
<221> NAME/KEY: VARIANT
<222> LOCATION: (51)...(116)
<223> OTHER INFORMATION: Xaa = Any amino acid
<220> FEATURE:
<221> NAME/KEY: VARIANT
<222> LOCATION: (118)...(125)
<223> OTHER INFORMATION: Xaa = Any amino acid
<220> FEATURE:
<221> NAME/KEY: VARIANT
<222> LOCATION: (129)...(129)
<223> OTHER INFORMATION: Xaa = Any amino acid
<220> FEATURE:
<221> NAME/KEY: VARIANT
<222> LOCATION: (131)...(132)

-continued

<223> OTHER INFORMATION: Xaa = Any amino acid
<220> FEATURE:
<221> NAME/KEY: VARIANT
<222> LOCATION: (134)...(150)
<223> OTHER INFORMATION: Xaa = Any amino acid
<220> FEATURE:
<221> NAME/KEY: VARIANT
<222> LOCATION: (152)...(153)
<223> OTHER INFORMATION: Xaa = Any amino acid
<220> FEATURE:
<221> NAME/KEY: VARIANT
<222> LOCATION: (157)...(177)
<223> OTHER INFORMATION: Xaa = Any amino acid
<220> FEATURE:
<221> NAME/KEY: VARIANT
<222> LOCATION: (179)...(191)
<223> OTHER INFORMATION: Xaa = Any amino acid
<220> FEATURE:
<221> NAME/KEY: VARIANT
<222> LOCATION: (193)...(195)
<223> OTHER INFORMATION: Xaa = Any amino acid
<220> FEATURE:
<221> NAME/KEY: VARIANT
<222> LOCATION: (197)...(251)
<223> OTHER INFORMATION: Xaa = Any amino acid
<220> FEATURE:
<221> NAME/KEY: VARIANT
<222> LOCATION: (253)...(266)
<223> OTHER INFORMATION: Xaa = Any amino acid
<220> FEATURE:
<221> NAME/KEY: VARIANT
<222> LOCATION: (268)...(270)
<223> OTHER INFORMATION: Xaa = Any amino acid

<400> SEQUENCE: 103

```
Xaa Xaa Xaa Xaa Xaa Xaa Xaa Xaa Xaa Gly Xaa Gly Xaa Xaa Xaa Xaa
 1               5                  10                  15

Val Xaa Xaa Xaa Xaa Xaa Xaa Xaa Xaa Xaa Xaa Xaa Xaa Lys Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa Glu Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa Xaa
                85                  90                  95

Xaa Xaa Xaa Xaa Xaa Xaa Xaa Xaa Xaa Xaa Xaa Xaa Xaa Xaa Xaa Xaa
            100                 105                 110

Xaa Xaa Xaa Xaa His Xaa Xaa Xaa Xaa Xaa Xaa Xaa Xaa His Arg Asp
        115                 120                 125

Xaa Lys Xaa Xaa Asn Xaa Xaa Xaa Xaa Xaa Xaa Xaa Xaa Xaa Xaa Xaa
    130                 135                 140

Xaa Xaa Xaa Xaa Xaa Xaa Lys Xaa Xaa Asp Phe Gly Xaa Xaa Xaa Xaa
145                 150                 155                 160

Xaa Xaa Xaa Xaa Xaa Xaa Xaa Xaa Xaa Xaa Xaa Xaa Xaa Xaa Xaa Xaa
                165                 170                 175

Xaa Pro Xaa Xaa Xaa Xaa Xaa Xaa Xaa Xaa Xaa Xaa Xaa Xaa Xaa Trp
            180                 185                 190

Xaa Xaa Xaa Gly Xaa Xaa Xaa Xaa Xaa Xaa Xaa Xaa Xaa Xaa Xaa Xaa
        195                 200                 205

Xaa Xaa Xaa Xaa Xaa Xaa Xaa Xaa Xaa Xaa Xaa Xaa Xaa Xaa Xaa Xaa
    210                 215                 220

Xaa Xaa Xaa Xaa Xaa Xaa Xaa Xaa Xaa Xaa Xaa Xaa Xaa Xaa Xaa Xaa
```

-continued

```
225                 230                 235                 240

Xaa Xaa Xaa Xaa Xaa Xaa Xaa Xaa Xaa Xaa Xaa Arg Xaa Xaa Xaa Xaa
                245                 250                 255

Xaa Xaa Xaa Xaa Xaa Xaa Xaa Xaa Xaa Xaa His Xaa Xaa Xaa
            260                 265                 270


<210> SEQ ID NO 104
<211> LENGTH: 30
<212> TYPE: PRT
<213> ORGANISM: Artificial Sequence
<220> FEATURE:
<223> OTHER INFORMATION: ATP-binding region consensus sequence
<220> FEATURE:
<221> NAME/KEY: VARIANT
<222> LOCATION: (2)...(2)
<223> OTHER INFORMATION: Xaa = Any amino acid
<220> FEATURE:
<221> NAME/KEY: VARIANT
<222> LOCATION: (4)...(5)
<223> OTHER INFORMATION: Xaa = Any amino acid
<220> FEATURE:
<221> NAME/KEY: VARIANT
<222> LOCATION: (7)...(29)
<223> OTHER INFORMATION: Xaa = Any amino acid

<400> SEQUENCE: 104

Gly Xaa Gly Xaa Xaa Gly Xaa Xaa Xaa Xaa Xaa Xaa Xaa Xaa Xaa Xaa
 1               5                  10                  15

Xaa Xaa Xaa Xaa Xaa Xaa Xaa Xaa Xaa Xaa Xaa Xaa Xaa Lys
            20                  25                  30


<210> SEQ ID NO 105
<211> LENGTH: 278
<212> TYPE: PRT
<213> ORGANISM: Artificial Sequence
<220> FEATURE:
<223> OTHER INFORMATION: Eukaryotic protein kinase domain

<400> SEQUENCE: 105

Tyr Glu Leu Leu Glu Lys Leu Gly Glu Gly Ser Phe Gly Lys Val Tyr
 1               5                  10                  15

Lys Ala Lys His Lys Thr Gly Lys Ile Val Ala Val Lys Ile Leu Lys
            20                  25                  30

Lys Glu Ser Leu Ser Leu Arg Glu Ile Gln Ile Leu Lys Arg Leu Ser
        35                  40                  45

His Pro Asn Ile Val Arg Leu Leu Gly Val Phe Glu Asp Thr Asp Asp
    50                  55                  60

His Leu Tyr Leu Val Met Glu Tyr Met Glu Gly Gly Asp Leu Phe Asp
65                  70                  75                  80

Tyr Leu Arg Arg Asn Gly Pro Leu Ser Glu Lys Glu Ala Lys Lys Ile
                85                  90                  95

Ala Leu Gln Ile Leu Arg Gly Leu Glu Tyr Leu His Ser Asn Gly Ile
            100                 105                 110

Val His Arg Asp Leu Lys Pro Glu Asn Ile Leu Leu Asp Glu Asn Gly
        115                 120                 125

Thr Val Lys Ile Ala Asp Phe Gly Leu Ala Arg Leu Leu Glu Lys Leu
    130                 135                 140

Thr Thr Phe Val Gly Thr Pro Trp Tyr Met Met Ala Pro Glu Val Ile
145                 150                 155                 160

Leu Glu Gly Arg Gly Tyr Ser Ser Lys Val Asp Val Trp Ser Leu Gly
                165                 170                 175
```

-continued

```
Val Ile Leu Tyr Glu Leu Leu Thr Gly Gly Pro Leu Phe Pro Gly Ala
            180                 185                 190

Asp Leu Pro Ala Phe Thr Gly Gly Asp Glu Val Asp Gln Leu Ile Ile
        195                 200                 205

Phe Val Leu Lys Leu Pro Phe Ser Asp Glu Leu Pro Lys Thr Arg Ile
    210                 215                 220

Asp Pro Leu Glu Glu Leu Phe Arg Ile Lys Lys Arg Arg Leu Pro Leu
225                 230                 235                 240

Pro Ser Asn Cys Ser Glu Glu Leu Lys Asp Leu Leu Lys Lys Cys Leu
                245                 250                 255

Asn Lys Asp Pro Ser Lys Arg Pro Gly Ser Ala Thr Ala Lys Glu Ile
            260                 265                 270

Leu Asn His Pro Trp Phe
        275


<210> SEQ ID NO 106
<211> LENGTH: 20
<212> TYPE: PRT
<213> ORGANISM: Artificial Sequence
<220> FEATURE:
<223> OTHER INFORMATION: Protein kinase C terminal domain

<400> SEQUENCE: 106

Arg Glu Ile Asp Trp Asp Lys Leu Glu Asn Lys Glu Ile Glu Pro Pro
 1               5                  10                  15

Phe Lys Pro Lys
            20


<210> SEQ ID NO 107
<211> LENGTH: 129
<212> TYPE: PRT
<213> ORGANISM: Artificial Sequence
<220> FEATURE:
<223> OTHER INFORMATION: Kinase protein transferase ATP-binding
      serine/threonine-protein phosphorylation receptor
      tyrosine-protein precursor transmembrane

<400> SEQUENCE: 107

Pro Tyr Tyr Val Ser Met Lys Ser Met Ala Pro Glu Tyr Met Ala Pro
 1               5                  10                  15

Glu Ser Ser Ala Thr Asn Tyr Gln Lys Tyr Ser Thr Lys Ser Asp Val
            20                  25                  30

Trp Ser Phe Gly Val Ile Leu Tyr Glu Met Leu Thr Gly Lys Pro Pro
        35                  40                  45

Phe Phe Pro Gly Glu Ser Glu Val Ser Glu Glu Glu Pro Tyr Gln Ser
    50                  55                  60

Met Lys Asn Met Glu Val Leu Glu Met Gly Pro Glu Glu Thr Ile Gln
65                  70                  75                  80

Lys Val Met Ser Lys Ile Val Glu Lys Lys Gly Glu Arg Met Pro Gln
                85                  90                  95

Pro Ser Ser Ser Asn Cys Pro Glu Val Ser Gln Glu Ala Lys Asp Leu
            100                 105                 110

Leu Lys Lys Cys Leu Gln Lys Asp Pro Glu Lys Arg Arg Pro Thr Phe
        115                 120                 125

Glu


<210> SEQ ID NO 108
<211> LENGTH: 43
<212> TYPE: PRT
```

-continued

<213> ORGANISM: Artificial Sequence
<220> FEATURE:
<223> OTHER INFORMATION: Kinase protein transferase ATP-binding serine/threonine-protein phosphorylation receptor tyrosine-protein precursor transmembrane

<400> SEQUENCE: 108

```
Tyr Val His Gln Ile Ala Lys Gly Leu Glu Tyr Leu His Ser Lys Asn
 1               5                  10                  15

Gln Lys His Gln Gly Ile Ile His Arg Ala Lys Lys Val Asp Leu Lys
            20                  25                  30

Pro Glu Asn Ile Leu Leu Asp Glu Glu Ser His
        35                  40
```

<210> SEQ ID NO 109
<211> LENGTH: 53
<212> TYPE: PRT
<213> ORGANISM: Artificial Sequence
<220> FEATURE:
<223> OTHER INFORMATION: Kinase protein transferase ATP-binding serine/threonine-protein phosphorylation receptor tyrosine-protein precursor transmembrane

<400> SEQUENCE: 109

```
Tyr Glu Leu Leu Lys Lys Leu Leu Gly Lys Gly Ser Phe Gly Lys Val
 1               5                  10                  15

Tyr Lys Ala Lys His Lys Ser Thr Ser Thr Thr Gly Glu Val Val Ala
            20                  25                  30

Val Lys Val Met Lys Lys Lys Lys Val Met Glu Lys Ser Ser Lys Glu
        35                  40                  45

Ser Ser Ser Lys Lys
    50
```

<210> SEQ ID NO 110
<211> LENGTH: 31
<212> TYPE: PRT
<213> ORGANISM: Artificial Sequence
<220> FEATURE:
<223> OTHER INFORMATION: Kinase protein transferase ATP-binding serine/threonine-protein phosphorylation receptor tyrosine-protein precursor transmembrane

<400> SEQUENCE: 110

```
Ser Gln Glu Ala Lys Asp Leu Leu Lys Lys Cys Leu Gln Lys Asp Pro
 1               5                  10                  15

Glu Lys Arg Arg Pro Thr Phe Glu Glu Ile Leu Gln His Pro Trp
            20                  25                  30
```

<210> SEQ ID NO 111
<211> LENGTH: 87
<212> TYPE: PRT
<213> ORGANISM: Artificial Sequence
<220> FEATURE:
<223> OTHER INFORMATION: M03C11.1 protein

<400> SEQUENCE: 111

```
Tyr Thr Glu Arg Ile Asp Phe Lys Ser Val Phe Glu Lys Lys Pro Ser
 1               5                  10                  15

Pro Val Phe Ile Pro Cys Lys Glu Gly Leu Asn Cys Asp Pro Met Tyr
            20                  25                  30

Glu Leu Glu Glu Arg Ile Leu Val Ser Thr Pro Ile His Arg Arg Arg
        35                  40                  45

Thr Asn His Asn Asn Ser Ser Gly Arg Ser Ser Ser Glu Pro Gln Asn
```

-continued

```
    50                  55                  60

Ala Ala Leu Val Glu Val Ser Lys Ala Phe Ile Asp Phe Ser Arg His
65                  70                  75                  80

Asn Val Lys Ile Glu Pro Asn
                85
```

<210> SEQ ID NO 112
<211> LENGTH: 72
<212> TYPE: PRT
<213> ORGANISM: Artificial Sequence
<220> FEATURE:
<223> OTHER INFORMATION: F8K4.6 protein

<400> SEQUENCE: 112

```
Thr Asp Pro Ala Ile Trp Leu Lys Leu Glu Ala Ala Ile Glu Glu Phe
 1               5                  10                  15

Ile Gln Ser Asn Pro Gln Val Phe Lys Asn Val Cys Glu Arg Leu Thr
            20                  25                  30

Leu Pro Phe Leu Asn Asp Glu Lys Trp Cys Asp Asn Leu Lys Pro Arg
        35                  40                  45

Phe Met Asn Gly Lys Leu Pro Asn Ser Arg Val Glu Ser Ser Pro Ser
    50                  55                  60

Leu Gly Trp Arg Arg Asn Val Leu
65                  70
```

<210> SEQ ID NO 113
<211> LENGTH: 3577
<212> TYPE: DNA
<213> ORGANISM: Homo sapiens
<220> FEATURE:
<221> NAME/KEY: CDS
<222> LOCATION: (47)...(2386)

<400> SEQUENCE: 113

```
ctcctcagat cggtggacgt gctcgcctcc actcggggcc aggtct atg tcc cgg        55
                                                   Met Ser Arg
                                                    1

ttt ccc gca gtc gcg ggc agg gcg cca agg cgg cag gag gag ggt gag      103
Phe Pro Ala Val Ala Gly Arg Ala Pro Arg Arg Gln Glu Glu Gly Glu
     5                  10                  15

cgg tca aga gac ctc cag gaa gag cgg ctc tcg gct gtt tgc atc gcc      151
Arg Ser Arg Asp Leu Gln Glu Glu Arg Leu Ser Ala Val Cys Ile Ala
 20                  25                  30                  35

gat aga gaa gag aaa gga tgc acg tcc cag gag gga gga act act cca      199
Asp Arg Glu Glu Lys Gly Cys Thr Ser Gln Glu Gly Gly Thr Thr Pro
                40                  45                  50

act ttt cct att cag aaa caa aga aaa aag att att caa gct gtg agg      247
Thr Phe Pro Ile Gln Lys Gln Arg Lys Lys Ile Ile Gln Ala Val Arg
            55                  60                  65

gac aat tca ttc ctt att gtt act gga aat aca gga agt ggt aaa aca      295
Asp Asn Ser Phe Leu Ile Val Thr Gly Asn Thr Gly Ser Gly Lys Thr
        70                  75                  80

act caa ctc cca aaa tat cta tat gaa gca ggg ttt tca caa cat ggt      343
Thr Gln Leu Pro Lys Tyr Leu Tyr Glu Ala Gly Phe Ser Gln His Gly
     85                  90                  95

atg att ggt gta act caa cca cga aaa gta gct gct ata tca gtt gct      391
Met Ile Gly Val Thr Gln Pro Arg Lys Val Ala Ala Ile Ser Val Ala
100                 105                 110                 115

cag aga gta gct gaa gaa atg aaa tgc act ttg gga tcc aaa gta gga      439
Gln Arg Val Ala Glu Glu Met Lys Cys Thr Leu Gly Ser Lys Val Gly
                120                 125                 130
```

-continued

```
tac caa gtt cgt ttt gat gat tgc agt tct aag gag aca gca atc aaa      487
Tyr Gln Val Arg Phe Asp Asp Cys Ser Ser Lys Glu Thr Ala Ile Lys
            135                 140                 145

tat atg act gat gga tgt tta ctg aaa cat att ctg gga gac cca aat      535
Tyr Met Thr Asp Gly Cys Leu Leu Lys His Ile Leu Gly Asp Pro Asn
        150                 155                 160

ctt acc aaa ttc agt gtc att att ttg gat gaa gcc cat gaa aga act      583
Leu Thr Lys Phe Ser Val Ile Ile Leu Asp Glu Ala His Glu Arg Thr
    165                 170                 175

cta act aca gat atc tta ttt ggt tta ttg aag aag cta ttt cag gag      631
Leu Thr Thr Asp Ile Leu Phe Gly Leu Leu Lys Lys Leu Phe Gln Glu
180                 185                 190                 195

aag tct cct aat agg aag gag cat tta aaa gtg gtg gta atg tca gca      679
Lys Ser Pro Asn Arg Lys Glu His Leu Lys Val Val Val Met Ser Ala
                200                 205                 210

act atg gaa tta gcc aag ctc tct gca ttc ttt gga aat tgt cca ata      727
Thr Met Glu Leu Ala Lys Leu Ser Ala Phe Phe Gly Asn Cys Pro Ile
            215                 220                 225

ttt gat ata cct gga agg ctt tat cca gtc aga gag aaa ttc tgc aat      775
Phe Asp Ile Pro Gly Arg Leu Tyr Pro Val Arg Glu Lys Phe Cys Asn
        230                 235                 240

ttg att ggt cca cga gac aga gaa aat act gcg tat att caa gcg att      823
Leu Ile Gly Pro Arg Asp Arg Glu Asn Thr Ala Tyr Ile Gln Ala Ile
    245                 250                 255

gtg aaa gtc acc atg gat atc cat ttg aat gaa atg gct gga gac atc      871
Val Lys Val Thr Met Asp Ile His Leu Asn Glu Met Ala Gly Asp Ile
260                 265                 270                 275

ttg gtt ttt ctg act ggc cag ttt gaa ata gaa aaa agt tgt gag tta      919
Leu Val Phe Leu Thr Gly Gln Phe Glu Ile Glu Lys Ser Cys Glu Leu
                280                 285                 290

ctt ttt cag atg gca gag tct gtt gat tat gat tat gat gtt caa gat      967
Leu Phe Gln Met Ala Glu Ser Val Asp Tyr Asp Tyr Asp Val Gln Asp
            295                 300                 305

acc acc ctc gat ggc ttg tta ata ttg ccg tgt tat gga tca atg aca     1015
Thr Thr Leu Asp Gly Leu Leu Ile Leu Pro Cys Tyr Gly Ser Met Thr
        310                 315                 320

aca gat caa cag agg agg ata ttt ttg cca cca cca cct gga att aga     1063
Thr Asp Gln Gln Arg Arg Ile Phe Leu Pro Pro Pro Pro Gly Ile Arg
    325                 330                 335

aaa tgt gtc ata tcc acc aat att tct gca acg tct ttg aca ata gat     1111
Lys Cys Val Ile Ser Thr Asn Ile Ser Ala Thr Ser Leu Thr Ile Asp
340                 345                 350                 355

gga atc aga tat gtg gta gat ggt ggc ttc gtg aag cag tta aat cac     1159
Gly Ile Arg Tyr Val Val Asp Gly Gly Phe Val Lys Gln Leu Asn His
                360                 365                 370

aac ccc aga tta ggg ttg gac atc ctg gag gtg gtt cca att tca aag     1207
Asn Pro Arg Leu Gly Leu Asp Ile Leu Glu Val Val Pro Ile Ser Lys
            375                 380                 385

agc gag gca tta cag cga agt ggc cga gct ggc agg act tct tca gga     1255
Ser Glu Ala Leu Gln Arg Ser Gly Arg Ala Gly Arg Thr Ser Ser Gly
        390                 395                 400

aaa tgc ttt cgg atc tat agt aaa gat ttt tgg aac cag tgt atg cct     1303
Lys Cys Phe Arg Ile Tyr Ser Lys Asp Phe Trp Asn Gln Cys Met Pro
    405                 410                 415

gac cat gtg atc cct gaa att aag aga act agt ttg aca tct gta gtt     1351
Asp His Val Ile Pro Glu Ile Lys Arg Thr Ser Leu Thr Ser Val Val
420                 425                 430                 435

ctg acc tta aag tgc ctt gcc ata cac gat gtc ata agg ttt ccc tat     1399
Leu Thr Leu Lys Cys Leu Ala Ile His Asp Val Ile Arg Phe Pro Tyr
```

-continued

```
                440                 445                 450

ttg gat cca cct aat gag aga ctt att tta gaa gct ctt aaa caa ctt      1447
Leu Asp Pro Pro Asn Glu Arg Leu Ile Leu Glu Ala Leu Lys Gln Leu
            455                 460                 465

tac cag tgt gat gct att gac agg agt ggc cat gtc acc aga ttg ggt      1495
Tyr Gln Cys Asp Ala Ile Asp Arg Ser Gly His Val Thr Arg Leu Gly
        470                 475                 480

ttg tct atg gtg gag ttt cct ttg cct cca cat ctg aca tgt gca gta      1543
Leu Ser Met Val Glu Phe Pro Leu Pro Pro His Leu Thr Cys Ala Val
    485                 490                 495

ata aaa gct gct tcc ctg gat tgt gaa gat cta cta ctt cca ata gca      1591
Ile Lys Ala Ala Ser Leu Asp Cys Glu Asp Leu Leu Leu Pro Ile Ala
500                 505                 510                 515

gca atg ttg tct gtg gaa aac gtc ttc att aga cct gtt gat cca gag      1639
Ala Met Leu Ser Val Glu Asn Val Phe Ile Arg Pro Val Asp Pro Glu
                520                 525                 530

tac cag aag gaa gca gaa cag aga cat cga gaa ttg gca gct aaa gct      1687
Tyr Gln Lys Glu Ala Glu Gln Arg His Arg Glu Leu Ala Ala Lys Ala
            535                 540                 545

gga gga ttt aat gac ttt gca act tta gct gtc atc ttt gaa caa tgc      1735
Gly Gly Phe Asn Asp Phe Ala Thr Leu Ala Val Ile Phe Glu Gln Cys
        550                 555                 560

aaa tca agt gga gct cca gct tca tgg tgc caa aaa cac tgg att cat      1783
Lys Ser Ser Gly Ala Pro Ala Ser Trp Cys Gln Lys His Trp Ile His
    565                 570                 575

tgg agg tgc tta ttt tct gca ttt cgt gtg gaa gct caa ctt cga gaa      1831
Trp Arg Cys Leu Phe Ser Ala Phe Arg Val Glu Ala Gln Leu Arg Glu
580                 585                 590                 595

cta atc agg aag ctt aaa cag caa agt gat ttc cca aaa gag acc ttt      1879
Leu Ile Arg Lys Leu Lys Gln Gln Ser Asp Phe Pro Lys Glu Thr Phe
                600                 605                 610

gaa ggc cct aaa cat gaa gta cta cga aga tgt ctt tgt gcg ggc tat      1927
Glu Gly Pro Lys His Glu Val Leu Arg Arg Cys Leu Cys Ala Gly Tyr
            615                 620                 625

ttc aaa aat gta gct cga aga tct gtt ggg aga acg ttt tgc aca atg      1975
Phe Lys Asn Val Ala Arg Arg Ser Val Gly Arg Thr Phe Cys Thr Met
        630                 635                 640

gat ggt cgt gga agc cca gtt cac att cat cct tcc tca gca ctt cat      2023
Asp Gly Arg Gly Ser Pro Val His Ile His Pro Ser Ser Ala Leu His
    645                 650                 655

gaa cag gaa acc aaa ctt gaa tgg atc att ttt cat gag gta ttg gtt      2071
Glu Gln Glu Thr Lys Leu Glu Trp Ile Ile Phe His Glu Val Leu Val
660                 665                 670                 675

acc acc aaa gtc tac gca aga att gta tgc cca atc cgt tat gaa tgg      2119
Thr Thr Lys Val Tyr Ala Arg Ile Val Cys Pro Ile Arg Tyr Glu Trp
                680                 685                 690

gta aga gac ttg tta ccc aag ttg cat gaa ttt aat gca cat gat ttg      2167
Val Arg Asp Leu Leu Pro Lys Leu His Glu Phe Asn Ala His Asp Leu
            695                 700                 705

agc agt gtg gcc cga cgt gaa gtg aga gaa gat gca aga agg aga tgg      2215
Ser Ser Val Ala Arg Arg Glu Val Arg Glu Asp Ala Arg Arg Arg Trp
        710                 715                 720

aca aat aag gaa aat gta aag cag cta aag gat gga ata tcg aaa gac      2263
Thr Asn Lys Glu Asn Val Lys Gln Leu Lys Asp Gly Ile Ser Lys Asp
    725                 730                 735

gtc tta aag aaa atg caa aga aga aat gat gac aaa tcc ata tct gat      2311
Val Leu Lys Lys Met Gln Arg Arg Asn Asp Asp Lys Ser Ile Ser Asp
740                 745                 750                 755

gca cgg gct cgt ttc ctt gag aga aag cag cag agg acc cag gac cac      2359
```

-continued

```
Ala Arg Ala Arg Phe Leu Glu Arg Lys Gln Gln Arg Thr Gln Asp His
                760                 765                 770

agt gac aca cga aag gaa aca ggc taa ggtggtgaac cctccaattc           2406
Ser Asp Thr Arg Lys Glu Thr Gly  *
            775

aggaagtggg aaaaggagcc aggaaatgtg cttctacttt gccagttatt tcagacagca   2466

ctaccaagag gaggtggtca gcacttgtta ttggcctatg aactaaaagc aaatcaaagc   2526

tcataaatca aagctcatca gttcccataa atgcagttgt caaagaaaag atttggttgc   2586

catagtcata agcaatgata catgaaacca atgaaagaca gtacatgtaa taatattttc   2646

ctcagtacaa ttttgctggc cttaactggt atcaaacgct gtcattgaga tgttttcaaa   2706

gaacattgag ttgtatttaa tcagcgtgta ctccatttgc attgaagcat taaaaattat   2766

ttttcttaaa atctctttaa ggccttcttg ttgctgttag aatagtgcta tatatcaggt   2826

atgtgaccat ttatttcaga aggctgaaca taagaggttt ctactcagca atacttagat   2886

gtctaactgt ttaattgcta cagagcttta tagatattta gagaaaagac ttaatcaatt   2946

agtaaataaa attgcctatg gcaggattct ttcttgaatt aatattaatc cttaaattga   3006

tttttctggg attatacaaa ttccttttta tataaaagta tattgtttaa aacagtagct   3066

atagccatta accaaaggac agatgatata tatatatatg atatatatat atatataagt   3126

tctttttag ctgtacctac gtacttatat cagcaccatg tatgtaggtg tgatagtact    3186

ttcaaacagc gcctccacct ggcctactct gttatttcca cctgtttggg tagggccatt   3246

taacttccat tatgccaaac ttgggatggg attttcgaag cagacaacac tatttcatcg   3306

tgtttcaaat tggaaccttg aggctagtta gtatcacact caggccacac tcagcacttg   3366

cccactcttg tttactgcct tgtattctag ttatttgtgt atttgtctcc ctcactagat   3426

tatacgctcc ttgtgggcag ggactgtgtc ttttttcatc tttgtatctt tcatggacct   3486

agcatagtgc tttgcacata gtagtcactc agtgtttgtt aaataaagct attagtgtca   3546

ttaaaattca aaaaaaaaaa aaaaaaaaaa a                                  3577


<210> SEQ ID NO 114
<211> LENGTH: 779
<212> TYPE: PRT
<213> ORGANISM: Homo sapiens

<400> SEQUENCE: 114

Met Ser Arg Phe Pro Ala Val Ala Gly Arg Ala Pro Arg Arg Gln Glu
 1               5                  10                  15

Glu Gly Glu Arg Ser Arg Asp Leu Gln Glu Glu Arg Leu Ser Ala Val
            20                  25                  30

Cys Ile Ala Asp Arg Glu Glu Lys Gly Cys Thr Ser Gln Glu Gly Gly
        35                  40                  45

Thr Thr Pro Thr Phe Pro Ile Gln Lys Gln Arg Lys Lys Ile Ile Gln
    50                  55                  60

Ala Val Arg Asp Asn Ser Phe Leu Ile Val Thr Gly Asn Thr Gly Ser
65                  70                  75                  80

Gly Lys Thr Thr Gln Leu Pro Lys Tyr Leu Tyr Glu Ala Gly Phe Ser
                85                  90                  95

Gln His Gly Met Ile Gly Val Thr Gln Pro Arg Lys Val Ala Ala Ile
            100                 105                 110

Ser Val Ala Gln Arg Val Ala Glu Glu Met Lys Cys Thr Leu Gly Ser
        115                 120                 125
```

-continued

```
Lys Val Gly Tyr Gln Val Arg Phe Asp Asp Cys Ser Ser Lys Glu Thr
    130                 135                 140

Ala Ile Lys Tyr Met Thr Asp Gly Cys Leu Leu Lys His Ile Leu Gly
145                 150                 155                 160

Asp Pro Asn Leu Thr Lys Phe Ser Val Ile Ile Leu Asp Glu Ala His
                165                 170                 175

Glu Arg Thr Leu Thr Thr Asp Ile Leu Phe Gly Leu Leu Lys Lys Leu
            180                 185                 190

Phe Gln Glu Lys Ser Pro Asn Arg Lys Glu His Leu Lys Val Val Val
        195                 200                 205

Met Ser Ala Thr Met Glu Leu Ala Lys Leu Ser Ala Phe Phe Gly Asn
    210                 215                 220

Cys Pro Ile Phe Asp Ile Pro Gly Arg Leu Tyr Pro Val Arg Glu Lys
225                 230                 235                 240

Phe Cys Asn Leu Ile Gly Pro Arg Asp Arg Glu Asn Thr Ala Tyr Ile
                245                 250                 255

Gln Ala Ile Val Lys Val Thr Met Asp Ile His Leu Asn Glu Met Ala
            260                 265                 270

Gly Asp Ile Leu Val Phe Leu Thr Gly Gln Phe Glu Ile Glu Lys Ser
        275                 280                 285

Cys Glu Leu Leu Phe Gln Met Ala Glu Ser Val Asp Tyr Asp Tyr Asp
    290                 295                 300

Val Gln Asp Thr Thr Leu Asp Gly Leu Leu Ile Leu Pro Cys Tyr Gly
305                 310                 315                 320

Ser Met Thr Thr Asp Gln Gln Arg Arg Ile Phe Leu Pro Pro Pro Pro
                325                 330                 335

Gly Ile Arg Lys Cys Val Ile Ser Thr Asn Ile Ser Ala Thr Ser Leu
            340                 345                 350

Thr Ile Asp Gly Ile Arg Tyr Val Val Asp Gly Gly Phe Val Lys Gln
        355                 360                 365

Leu Asn His Asn Pro Arg Leu Gly Leu Asp Ile Leu Glu Val Val Pro
    370                 375                 380

Ile Ser Lys Ser Glu Ala Leu Gln Arg Ser Gly Arg Ala Gly Arg Thr
385                 390                 395                 400

Ser Ser Gly Lys Cys Phe Arg Ile Tyr Ser Lys Asp Phe Trp Asn Gln
                405                 410                 415

Cys Met Pro Asp His Val Ile Pro Glu Ile Lys Arg Thr Ser Leu Thr
            420                 425                 430

Ser Val Val Leu Thr Leu Lys Cys Leu Ala Ile His Asp Val Ile Arg
        435                 440                 445

Phe Pro Tyr Leu Asp Pro Pro Asn Glu Arg Leu Ile Leu Glu Ala Leu
    450                 455                 460

Lys Gln Leu Tyr Gln Cys Asp Ala Ile Asp Arg Ser Gly His Val Thr
465                 470                 475                 480

Arg Leu Gly Leu Ser Met Val Glu Phe Pro Leu Pro Pro His Leu Thr
                485                 490                 495

Cys Ala Val Ile Lys Ala Ala Ser Leu Asp Cys Glu Asp Leu Leu Leu
            500                 505                 510

Pro Ile Ala Ala Met Leu Ser Val Glu Asn Val Phe Ile Arg Pro Val
        515                 520                 525

Asp Pro Glu Tyr Gln Lys Glu Ala Glu Gln Arg His Arg Glu Leu Ala
    530                 535                 540

Ala Lys Ala Gly Gly Phe Asn Asp Phe Ala Thr Leu Ala Val Ile Phe
```

```
545                 550                 555                 560

Glu Gln Cys Lys Ser Ser Gly Ala Pro Ala Ser Trp Cys Gln Lys His
                565                 570                 575

Trp Ile His Trp Arg Cys Leu Phe Ser Ala Phe Arg Val Glu Ala Gln
            580                 585                 590

Leu Arg Glu Leu Ile Arg Lys Leu Lys Gln Gln Ser Asp Phe Pro Lys
        595                 600                 605

Glu Thr Phe Glu Gly Pro Lys His Glu Val Leu Arg Arg Cys Leu Cys
    610                 615                 620

Ala Gly Tyr Phe Lys Asn Val Ala Arg Arg Ser Val Gly Arg Thr Phe
625                 630                 635                 640

Cys Thr Met Asp Gly Arg Gly Ser Pro Val His Ile His Pro Ser Ser
                645                 650                 655

Ala Leu His Glu Gln Glu Thr Lys Leu Glu Trp Ile Ile Phe His Glu
            660                 665                 670

Val Leu Val Thr Thr Lys Val Tyr Ala Arg Ile Val Cys Pro Ile Arg
        675                 680                 685

Tyr Glu Trp Val Arg Asp Leu Leu Pro Lys Leu His Glu Phe Asn Ala
    690                 695                 700

His Asp Leu Ser Ser Val Ala Arg Arg Glu Val Arg Glu Asp Ala Arg
705                 710                 715                 720

Arg Arg Trp Thr Asn Lys Glu Asn Val Lys Gln Leu Lys Asp Gly Ile
                725                 730                 735

Ser Lys Asp Val Leu Lys Lys Met Gln Arg Arg Asn Asp Asp Lys Ser
            740                 745                 750

Ile Ser Asp Ala Arg Ala Arg Phe Leu Glu Arg Lys Gln Gln Arg Thr
        755                 760                 765

Gln Asp His Ser Asp Thr Arg Lys Glu Thr Gly
    770                 775


<210> SEQ ID NO 115
<211> LENGTH: 2340
<212> TYPE: DNA
<213> ORGANISM: Homo sapiens
<220> FEATURE:
<221> NAME/KEY: CDS
<222> LOCATION: (1)...(2340)

<400> SEQUENCE: 115

atg tcc cgg ttt ccc gca gtc gcg ggc agg gcg cca agg cgg cag gag      48
Met Ser Arg Phe Pro Ala Val Ala Gly Arg Ala Pro Arg Arg Gln Glu
 1               5                  10                  15

gag ggt gag cgg tca aga gac ctc cag gaa gag cgg ctc tcg gct gtt      96
Glu Gly Glu Arg Ser Arg Asp Leu Gln Glu Glu Arg Leu Ser Ala Val
            20                  25                  30

tgc atc gcc gat aga gaa gag aaa gga tgc acg tcc cag gag gga gga     144
Cys Ile Ala Asp Arg Glu Glu Lys Gly Cys Thr Ser Gln Glu Gly Gly
        35                  40                  45

act act cca act ttt cct att cag aaa caa aga aaa aag att att caa     192
Thr Thr Pro Thr Phe Pro Ile Gln Lys Gln Arg Lys Lys Ile Ile Gln
     50                  55                  60

gct gtg agg gac aat tca ttc ctt att gtt act gga aat aca gga agt     240
Ala Val Arg Asp Asn Ser Phe Leu Ile Val Thr Gly Asn Thr Gly Ser
 65                  70                  75                  80

ggt aaa aca act caa ctc cca aaa tat cta tat gaa gca ggg ttt tca     288
Gly Lys Thr Thr Gln Leu Pro Lys Tyr Leu Tyr Glu Ala Gly Phe Ser
                85                  90                  95
```

-continued

```
caa cat ggt atg att ggt gta act caa cca cga aaa gta gct gct ata      336
Gln His Gly Met Ile Gly Val Thr Gln Pro Arg Lys Val Ala Ala Ile
            100                 105                 110

tca gtt gct cag aga gta gct gaa gaa atg aaa tgc act ttg gga tcc      384
Ser Val Ala Gln Arg Val Ala Glu Glu Met Lys Cys Thr Leu Gly Ser
        115                 120                 125

aaa gta gga tac caa gtt cgt ttt gat gat tgc agt tct aag gag aca      432
Lys Val Gly Tyr Gln Val Arg Phe Asp Asp Cys Ser Ser Lys Glu Thr
    130                 135                 140

gca atc aaa tat atg act gat gga tgt tta ctg aaa cat att ctg gga      480
Ala Ile Lys Tyr Met Thr Asp Gly Cys Leu Leu Lys His Ile Leu Gly
145                 150                 155                 160

gac cca aat ctt acc aaa ttc agt gtc att att ttg gat gaa gcc cat      528
Asp Pro Asn Leu Thr Lys Phe Ser Val Ile Ile Leu Asp Glu Ala His
                165                 170                 175

gaa aga act cta act aca gat atc tta ttt ggt tta ttg aag aag cta      576
Glu Arg Thr Leu Thr Thr Asp Ile Leu Phe Gly Leu Leu Lys Lys Leu
            180                 185                 190

ttt cag gag aag tct cct aat agg aag gag cat tta aaa gtg gtg gta      624
Phe Gln Glu Lys Ser Pro Asn Arg Lys Glu His Leu Lys Val Val Val
        195                 200                 205

atg tca gca act atg gaa tta gcc aag ctc tct gca ttc ttt gga aat      672
Met Ser Ala Thr Met Glu Leu Ala Lys Leu Ser Ala Phe Phe Gly Asn
    210                 215                 220

tgt cca ata ttt gat ata cct gga agg ctt tat cca gtc aga gag aaa      720
Cys Pro Ile Phe Asp Ile Pro Gly Arg Leu Tyr Pro Val Arg Glu Lys
225                 230                 235                 240

ttc tgc aat ttg att ggt cca cga gac aga gaa aat act gcg tat att      768
Phe Cys Asn Leu Ile Gly Pro Arg Asp Arg Glu Asn Thr Ala Tyr Ile
                245                 250                 255

caa gcg att gtg aaa gtc acc atg gat atc cat ttg aat gaa atg gct      816
Gln Ala Ile Val Lys Val Thr Met Asp Ile His Leu Asn Glu Met Ala
            260                 265                 270

gga gac atc ttg gtt ttt ctg act ggc cag ttt gaa ata gaa aaa agt      864
Gly Asp Ile Leu Val Phe Leu Thr Gly Gln Phe Glu Ile Glu Lys Ser
        275                 280                 285

tgt gag tta ctt ttt cag atg gca gag tct gtt gat tat gat tat gat      912
Cys Glu Leu Leu Phe Gln Met Ala Glu Ser Val Asp Tyr Asp Tyr Asp
    290                 295                 300

gtt caa gat acc acc ctc gat ggc ttg tta ata ttg ccg tgt tat gga      960
Val Gln Asp Thr Thr Leu Asp Gly Leu Leu Ile Leu Pro Cys Tyr Gly
305                 310                 315                 320

tca atg aca aca gat caa cag agg agg ata ttt ttg cca cca cca cct     1008
Ser Met Thr Thr Asp Gln Gln Arg Arg Ile Phe Leu Pro Pro Pro Pro
                325                 330                 335

gga att aga aaa tgt gtc ata tcc acc aat att tct gca acg tct ttg     1056
Gly Ile Arg Lys Cys Val Ile Ser Thr Asn Ile Ser Ala Thr Ser Leu
            340                 345                 350

aca ata gat gga atc aga tat gtg gta gat ggt ggc ttc gtg aag cag     1104
Thr Ile Asp Gly Ile Arg Tyr Val Val Asp Gly Gly Phe Val Lys Gln
        355                 360                 365

tta aat cac aac ccc aga tta ggg ttg gac atc ctg gag gtg gtt cca     1152
Leu Asn His Asn Pro Arg Leu Gly Leu Asp Ile Leu Glu Val Val Pro
    370                 375                 380

att tca aag agc gag gca tta cag cga agt ggc cga gct ggc agg act     1200
Ile Ser Lys Ser Glu Ala Leu Gln Arg Ser Gly Arg Ala Gly Arg Thr
385                 390                 395                 400

tct tca gga aaa tgc ttt cgg atc tat agt aaa gat ttt tgg aac cag     1248
Ser Ser Gly Lys Cys Phe Arg Ile Tyr Ser Lys Asp Phe Trp Asn Gln
                405                 410                 415
```

-continued

```
tgt atg cct gac cat gtg atc cct gaa att aag aga act agt ttg aca      1296
Cys Met Pro Asp His Val Ile Pro Glu Ile Lys Arg Thr Ser Leu Thr
            420                 425                 430

tct gta gtt ctg acc tta aag tgc ctt gcc ata cac gat gtc ata agg      1344
Ser Val Val Leu Thr Leu Lys Cys Leu Ala Ile His Asp Val Ile Arg
        435                 440                 445

ttt ccc tat ttg gat cca cct aat gag aga ctt att tta gaa gct ctt      1392
Phe Pro Tyr Leu Asp Pro Pro Asn Glu Arg Leu Ile Leu Glu Ala Leu
    450                 455                 460

aaa caa ctt tac cag tgt gat gct att gac agg agt ggc cat gtc acc      1440
Lys Gln Leu Tyr Gln Cys Asp Ala Ile Asp Arg Ser Gly His Val Thr
465                 470                 475                 480

aga ttg ggt ttg tct atg gtg gag ttt cct ttg cct cca cat ctg aca      1488
Arg Leu Gly Leu Ser Met Val Glu Phe Pro Leu Pro Pro His Leu Thr
                485                 490                 495

tgt gca gta ata aaa gct gct tcc ctg gat tgt gaa gat cta cta ctt      1536
Cys Ala Val Ile Lys Ala Ala Ser Leu Asp Cys Glu Asp Leu Leu Leu
            500                 505                 510

cca ata gca gca atg ttg tct gtg gaa aac gtc ttc att aga cct gtt      1584
Pro Ile Ala Ala Met Leu Ser Val Glu Asn Val Phe Ile Arg Pro Val
        515                 520                 525

gat cca gag tac cag aag gaa gca gaa cag aga cat cga gaa ttg gca      1632
Asp Pro Glu Tyr Gln Lys Glu Ala Glu Gln Arg His Arg Glu Leu Ala
    530                 535                 540

gct aaa gct gga gga ttt aat gac ttt gca act tta gct gtc atc ttt      1680
Ala Lys Ala Gly Gly Phe Asn Asp Phe Ala Thr Leu Ala Val Ile Phe
545                 550                 555                 560

gaa caa tgc aaa tca agt gga gct cca gct tca tgg tgc caa aaa cac      1728
Glu Gln Cys Lys Ser Ser Gly Ala Pro Ala Ser Trp Cys Gln Lys His
                565                 570                 575

tgg att cat tgg agg tgc tta ttt tct gca ttt cgt gtg gaa gct caa      1776
Trp Ile His Trp Arg Cys Leu Phe Ser Ala Phe Arg Val Glu Ala Gln
            580                 585                 590

ctt cga gaa cta atc agg aag ctt aaa cag caa agt gat ttc cca aaa      1824
Leu Arg Glu Leu Ile Arg Lys Leu Lys Gln Gln Ser Asp Phe Pro Lys
        595                 600                 605

gag acc ttt gaa ggc cct aaa cat gaa gta cta cga aga tgt ctt tgt      1872
Glu Thr Phe Glu Gly Pro Lys His Glu Val Leu Arg Arg Cys Leu Cys
    610                 615                 620

gcg ggc tat ttc aaa aat gta gct cga aga tct gtt ggg aga acg ttt      1920
Ala Gly Tyr Phe Lys Asn Val Ala Arg Arg Ser Val Gly Arg Thr Phe
625                 630                 635                 640

tgc aca atg gat ggt cgt gga agc cca gtt cac att cat cct tcc tca      1968
Cys Thr Met Asp Gly Arg Gly Ser Pro Val His Ile His Pro Ser Ser
                645                 650                 655

gca ctt cat gaa cag gaa acc aaa ctt gaa tgg atc att ttt cat gag      2016
Ala Leu His Glu Gln Glu Thr Lys Leu Glu Trp Ile Ile Phe His Glu
            660                 665                 670

gta ttg gtt acc acc aaa gtc tac gca aga att gta tgc cca atc cgt      2064
Val Leu Val Thr Thr Lys Val Tyr Ala Arg Ile Val Cys Pro Ile Arg
        675                 680                 685

tat gaa tgg gta aga gac ttg tta ccc aag ttg cat gaa ttt aat gca      2112
Tyr Glu Trp Val Arg Asp Leu Leu Pro Lys Leu His Glu Phe Asn Ala
    690                 695                 700

cat gat ttg agc agt gtg gcc cga cgt gaa gtg aga gaa gat gca aga      2160
His Asp Leu Ser Ser Val Ala Arg Arg Glu Val Arg Glu Asp Ala Arg
705                 710                 715                 720

agg aga tgg aca aat aag gaa aat gta aag cag cta aag gat gga ata      2208
Arg Arg Trp Thr Asn Lys Glu Asn Val Lys Gln Leu Lys Asp Gly Ile
```

-continued

```
                725                 730                 735

tcg aaa gac gtc tta aag aaa atg caa aga aga aat gat gac aaa tcc     2256
Ser Lys Asp Val Leu Lys Lys Met Gln Arg Arg Asn Asp Asp Lys Ser
            740                 745                 750

ata tct gat gca cgg gct cgt ttc ctt gag aga aag cag cag agg acc     2304
Ile Ser Asp Ala Arg Ala Arg Phe Leu Glu Arg Lys Gln Gln Arg Thr
        755                 760                 765

cag gac cac agt gac aca cga aag gaa aca ggc taa                     2340
Gln Asp His Ser Asp Thr Arg Lys Glu Thr Gly  *
    770                 775


<210> SEQ ID NO 116
<211> LENGTH: 86
<212> TYPE: PRT
<213> ORGANISM: Artificial Sequence
<220> FEATURE:
<223> OTHER INFORMATION: Amino acid consensus sequence

<400> SEQUENCE: 116

Glu Glu Leu Lys Lys Leu Ile Leu Val Ala Thr Pro Gly Arg Leu Leu
 1               5                  10                  15

Asp His Leu Glu Asn Gly Ser Leu Leu Glu Lys Arg Leu Lys Leu Lys
            20                  25                  30

Asn Leu Lys Leu Leu Val Leu Asp Glu Ala Asp Arg Met Leu Asp Met
        35                  40                  45

Gly Lys Ala His Gly Phe Gly Pro Asp Leu Glu Glu Gln Thr Leu Leu
    50                  55                  60

Phe Ser Ala Thr Leu Pro Glu Val Glu Arg Leu Ala Lys Leu Phe Leu
65                  70                  75                  80

Leu Arg Ile Lys Gln Lys
                85


<210> SEQ ID NO 117
<211> LENGTH: 87
<212> TYPE: PRT
<213> ORGANISM: Artificial Sequence
<220> FEATURE:
<223> OTHER INFORMATION: Amino acid consensus sequence

<400> SEQUENCE: 117

Asp Glu Leu Ala Lys Phe Leu Lys Glu Leu Phe Pro Lys Leu Pro Gly
 1               5                  10                  15

Ile Lys Val Ala Arg Leu His Gly Gly Leu Ser Gln Glu Glu Arg Glu
            20                  25                  30

Glu Ile Leu Glu Lys Phe Arg Asn Gly Lys Ser Lys Val Leu Val Ala
        35                  40                  45

Thr Asp Val Ala Ala Arg Gly Ile Asp Ile Pro Asp Val Asn Leu Val
    50                  55                  60

Ile Asn Tyr Asp Leu Pro Trp Asn Pro Glu Ser Tyr Ile Gln Arg Ile
65                  70                  75                  80

Gly Arg Ala Gly Arg Ala Gly
                85


<210> SEQ ID NO 118
<211> LENGTH: 86
<212> TYPE: PRT
<213> ORGANISM: Artificial Sequence
<220> FEATURE:
<223> OTHER INFORMATION: Amino acid consensus sequence

<400> SEQUENCE: 118
```

Leu Asp Ala Glu Lys Phe Ser Glu Tyr Phe Gly Asn Cys Pro Ile Ile
1 5 10 15

Glu Val Pro Gly Arg Thr Tyr Pro Val Glu Val Tyr Tyr Thr Lys Glu
20 25 30

Thr Thr Glu Pro Glu Glu Asp Tyr Ile Glu Ala Ala Ile Arg Thr Val
35 40 45

Ile Gln Ile His Met Thr Glu Pro Ala Pro Gly Asp Ile Leu Val Phe
50 55 60

Leu Thr Gly Gln Glu Glu Ile Glu Glu Ala Cys Glu Arg Leu Lys Glu
65 70 75 80

Arg Met Lys Gln Leu Glu
85

<210> SEQ ID NO 119
<211> LENGTH: 745
<212> TYPE: PRT
<213> ORGANISM: Homo sapiens

<400> SEQUENCE: 119

Arg Glu Arg Glu Lys Glu Lys Glu Lys Glu Leu Arg Ala Ser Thr Asn
1 5 10 15

Ala Met Leu Ile Ser Ala Gly Leu Pro Pro Leu Lys Ala Ser His Ser
20 25 30

Ala His Ser Thr His Ser Ala His Ser Thr His Ser Thr His Ser Ala
35 40 45

His Ser Thr His Ala Gly His Ala Gly His Thr Ser Leu Pro Gln Cys
50 55 60

Ile Asn Pro Phe Thr Asn Leu Pro His Thr Pro Arg Tyr Tyr Asp Ile
65 70 75 80

Leu Lys Lys Arg Leu Gln Leu Pro Val Trp Glu Tyr Lys Asp Arg Phe
85 90 95

Thr Asp Ile Leu Val Arg His Gln Ser Phe Val Leu Val Gly Glu Thr
100 105 110

Gly Ser Gly Lys Thr Thr Gln Ile Pro Gln Trp Cys Val Glu Tyr Met
115 120 125

Arg Ser Leu Pro Gly Pro Lys Arg Gly Val Ala Cys Thr Gln Pro Arg
130 135 140

Arg Val Ala Ala Met Ser Val Ala Gln Arg Val Ala Asp Glu Met Asp
145 150 155 160

Val Met Leu Gly Gln Glu Val Gly Tyr Ser Ile Arg Phe Glu Asp Cys
165 170 175

Ser Ser Ala Lys Thr Ile Leu Lys Tyr Met Thr Asp Gly Met Leu Leu
180 185 190

Arg Glu Ala Met Asn Asp Pro Leu Leu Glu Arg Tyr Gly Val Ile Ile
195 200 205

Leu Asp Glu Ala His Glu Arg Thr Leu Ala Thr Asp Ile Leu Met Gly
210 215 220

Val Leu Lys Glu Val Val Arg Gln Arg Ser Asp Leu Lys Val Ile Val
225 230 235 240

Met Ser Ala Thr Leu Asp Ala Gly Lys Phe Gln Ile Tyr Phe Asp Asn
245 250 255

Cys Pro Leu Leu Thr Ile Pro Gly Arg Thr His Pro Val Glu Ile Phe
260 265 270

Tyr Thr Pro Glu Pro Glu Arg Asp Tyr Leu Glu Ala Ala Ile Arg Thr

-continued

```
        275                 280                 285

Val Ile Gln Ile His Met Cys Glu Glu Glu Glu Gly Asp Leu Leu Leu
    290                 295                 300

Phe Leu Thr Gly Gln Glu Glu Ile Asp Glu Ala Cys Lys Arg Ile Lys
305                 310                 315                 320

Arg Glu Val Asp Asp Leu Gly Pro Glu Val Gly Asp Ile Lys Ile Ile
                325                 330                 335

Pro Leu Tyr Ser Thr Leu Pro Pro Gln Gln Gln Gln Arg Ile Phe Glu
            340                 345                 350

Pro Pro Pro Pro Lys Lys Gln Asn Gly Ala Ile Gly Arg Lys Val Val
        355                 360                 365

Val Ser Thr Asn Ile Ala Glu Thr Ser Leu Thr Ile Asp Gly Val Val
    370                 375                 380

Phe Val Ile Asp Pro Gly Phe Ala Lys Gln Lys Val Tyr Asn Pro Arg
385                 390                 395                 400

Ile Arg Val Glu Ser Leu Leu Val Thr Ala Ile Ser Lys Ala Ser Ala
                405                 410                 415

Gln Gln Arg Ala Gly Arg Ala Gly Arg Thr Arg Pro Gly Lys Cys Phe
            420                 425                 430

Arg Leu Tyr Thr Glu Lys Ala Tyr Lys Thr Glu Met Gln Asp Asn Thr
        435                 440                 445

Tyr Pro Glu Ile Leu Arg Ser Asn Leu Gly Ser Val Val Leu Gln Leu
    450                 455                 460

Lys Lys Leu Gly Ile Asp Asp Leu Val His Phe Asp Phe Met Asp Pro
465                 470                 475                 480

Pro Ala Pro Glu Thr Leu Met Arg Ala Leu Glu Leu Leu Asn Tyr Leu
                485                 490                 495

Ala Ala Leu Asn Asp Asp Gly Asp Leu Thr Glu Leu Gly Ser Met Met
            500                 505                 510

Ala Glu Phe Pro Leu Asp Pro Gln Leu Ala Lys Met Val Ile Ala Ser
        515                 520                 525

Cys Asp Tyr Asn Cys Ser Asn Glu Val Leu Ser Ile Thr Ala Met Leu
    530                 535                 540

Ser Val Pro Gln Cys Phe Val Arg Pro Thr Glu Ala Lys Lys Ala Ala
545                 550                 555                 560

Asp Glu Ala Lys Met Arg Phe Ala His Ile Asp Gly Asp His Leu Thr
                565                 570                 575

Leu Leu Asn Val Tyr His Ala Phe Lys Gln Asn His Glu Ser Val Gln
            580                 585                 590

Trp Cys Tyr Asp Asn Phe Ile Asn Tyr Arg Ser Leu Met Ser Ala Asp
        595                 600                 605

Asn Val Arg Gln Gln Leu Ser Arg Ile Met Asp Arg Phe Asn Leu Pro
    610                 615                 620

Arg Arg Ser Thr Asp Phe Thr Ser Arg Asp Tyr Tyr Ile Asn Ile Arg
625                 630                 635                 640

Lys Ala Leu Val Thr Gly Tyr Phe Met Gln Val Ala His Leu Glu Arg
                645                 650                 655

Thr Gly His Tyr Leu Thr Val Lys Asp Asn Gln Val Val Gln Leu His
            660                 665                 670

Pro Ser Thr Val Leu Asp His Lys Pro Glu Trp Val Leu Tyr Asn Glu
        675                 680                 685

Phe Val Leu Thr Thr Lys Asn Tyr Ile Arg Thr Cys Thr Asp Ile Lys
    690                 695                 700
```

-continued

```
Pro Glu Trp Leu Val Lys Ile Ala Pro Gln Tyr Tyr Asp Met Ser Asn
705                 710                 715                 720

Phe Pro Gln Cys Glu Ala Lys Arg Gln Leu Asp Arg Ile Ile Ala Lys
                725                 730                 735

Leu Gln Ser Lys Glu Tyr Ser Gln Tyr
            740                 745


<210> SEQ ID NO 120
<211> LENGTH: 10
<212> TYPE: PRT
<213> ORGANISM: Artificial Sequence
<220> FEATURE:
<223> OTHER INFORMATION: DEAH-box subfamily ATP-dependent helicases
      signature
<220> FEATURE:
<221> NAME/KEY: VARIANT
<222> LOCATION: (1)...(1)
<223> OTHER INFORMATION: Xaa at position 1 can be G, S, A or H
<220> FEATURE:
<221> NAME/KEY: VARIANT
<222> LOCATION: (2)...(2)
<223> OTHER INFORMATION: Xaa = Any amino acid
<220> FEATURE:
<221> NAME/KEY: VARIANT
<222> LOCATION: (3)...(5)
<223> OTHER INFORMATION: Xaa at positions 3, 4 and 5 can be L, I, V, M
      or F
<220> FEATURE:
<221> NAME/KEY: VARIANT
<222> LOCATION: (8)...(8)
<223> OTHER INFORMATION: Xaa at position 8 can be A, L, I or V
<220> FEATURE:
<221> NAME/KEY: VARIANT
<222> LOCATION: (10)...(10)
<223> OTHER INFORMATION: Xaa at position 10 can be N, E, C or R

<400> SEQUENCE: 120

Xaa Xaa Xaa Xaa Xaa Asp Glu Xaa His Xaa
 1               5                  10


<210> SEQ ID NO 121
<211> LENGTH: 8
<212> TYPE: PRT
<213> ORGANISM: Artificial Sequence
<220> FEATURE:
<223> OTHER INFORMATION: ATP/GTP-binding motif 'A' (P-loop) signature
<220> FEATURE:
<221> NAME/KEY: VARIANT
<222> LOCATION: (1)...(1)
<223> OTHER INFORMATION: Xaa at position 1 can be A or G
<220> FEATURE:
<221> NAME/KEY: VARIANT
<222> LOCATION: (2)...(5)
<223> OTHER INFORMATION: Xaa = any amino acid
<220> FEATURE:
<221> NAME/KEY: VARIANT
<222> LOCATION: (8)...(8)
<223> OTHER INFORMATION: Xaa at position 8 can be S or T

<400> SEQUENCE: 121

Xaa Xaa Xaa Xaa Xaa Gly Lys Xaa
 1               5


<210> SEQ ID NO 122
<211> LENGTH: 1649
<212> TYPE: DNA
<213> ORGANISM: Homo sapiens
<220> FEATURE:
<221> NAME/KEY: CDS
<222> LOCATION: (213)...(1073)
```

```
<400> SEQUENCE: 122

gcgctgggtc cccgaggccc ggcccctccc cgggaggagg tgggcttcga gtcacgtgac      60

ccgtgcccta cgggaggggg tgcggtcggg gacccggcag gaggcggccg agaagagagg     120

accgtggggg cgttcgcgtg gctcccagcc cgggacccca cccccgctgg acagtggggg     180

aaactgaggc ctgagcgggc ccacacagga cc atg aag gtg ctt ctc ctc aca       233
                                    Met Lys Val Leu Leu Leu Thr
                                    1               5

ggg ctg ggg gcc ctg ttc ttc gcc tat tat tgg gat gac aac ttc gac       281
Gly Leu Gly Ala Leu Phe Phe Ala Tyr Tyr Trp Asp Asp Asn Phe Asp
        10                  15                  20

cca gcc agc ctc cag gga gcg cga gtg ctg ctg aca ggg gcc aac gct       329
Pro Ala Ser Leu Gln Gly Ala Arg Val Leu Leu Thr Gly Ala Asn Ala
    25                  30                  35

ggt gtt ggt gag gag ctg gcc tat cac tac gcg cgt ctg ggc tcc cac       377
Gly Val Gly Glu Glu Leu Ala Tyr His Tyr Ala Arg Leu Gly Ser His
40                  45                  50                  55

ctg gtg ctc act gcc cac act gag gct ctc ctg cag aag gtg gta ggg       425
Leu Val Leu Thr Ala His Thr Glu Ala Leu Leu Gln Lys Val Val Gly
                60                  65                  70

aac tgc cgg aag ctg ggc gcc ccc aag gtc ttc tac atc gcg gcg gac       473
Asn Cys Arg Lys Leu Gly Ala Pro Lys Val Phe Tyr Ile Ala Ala Asp
            75                  80                  85

atg gcc tcc cct gag gcg ccc gag agc gtg gtg cag ttt gcg ctg gac       521
Met Ala Ser Pro Glu Ala Pro Glu Ser Val Val Gln Phe Ala Leu Asp
        90                  95                  100

aag ctg ggc ggg ctg gac tac ctc gtg ctg aac cac atc ggc ggc gcc       569
Lys Leu Gly Gly Leu Asp Tyr Leu Val Leu Asn His Ile Gly Gly Ala
    105                 110                 115

ccg gcc ggc acg cga gcc cgc agc ccc cag gca act cgc tgg ctc atg       617
Pro Ala Gly Thr Arg Ala Arg Ser Pro Gln Ala Thr Arg Trp Leu Met
120                 125                 130                 135

cag gta aac ttt gtg agc tac gtg caa ctg acg tcg cgg gcg ctg ccc       665
Gln Val Asn Phe Val Ser Tyr Val Gln Leu Thr Ser Arg Ala Leu Pro
                140                 145                 150

agc ctg acg gac agc aag ggc tcc ctg gtg gtg gtg tcc tcg ctg ctc       713
Ser Leu Thr Asp Ser Lys Gly Ser Leu Val Val Val Ser Ser Leu Leu
            155                 160                 165

ggc cgc gtg ccc acg tcg ttc tcc act ccc tac tcg gcg gcc aag ttt       761
Gly Arg Val Pro Thr Ser Phe Ser Thr Pro Tyr Ser Ala Ala Lys Phe
        170                 175                 180

gcg ctg gac ggc ttc ttc ggc tcc ctg cgg cgg gag ctg gac gtg cag       809
Ala Leu Asp Gly Phe Phe Gly Ser Leu Arg Arg Glu Leu Asp Val Gln
    185                 190                 195

gac gtg aac gtg gcc atc acc atg tgc gtc ctg ggc ctc cga gat cgc       857
Asp Val Asn Val Ala Ile Thr Met Cys Val Leu Gly Leu Arg Asp Arg
200                 205                 210                 215

gcc tcc gcc gcc gag gca gtc agg gga gtc acg agg gtc aag gcg gcc       905
Ala Ser Ala Ala Glu Ala Val Arg Gly Val Thr Arg Val Lys Ala Ala
                220                 225                 230

ccg ggg ccc aag gca gcc ctg gcc gtg atc cgc ggc ggc gcc acg cgc       953
Pro Gly Pro Lys Ala Ala Leu Ala Val Ile Arg Gly Gly Ala Thr Arg
            235                 240                 245

gcg gcc ggc gtc ttc tac ccg tgg cgt ttc cgc ctg ctg tgc ttg ctc      1001
Ala Ala Gly Val Phe Tyr Pro Trp Arg Phe Arg Leu Leu Cys Leu Leu
        250                 255                 260

cgg cgc tgg cta ccg cgc ccg cgg gcc tgg ttt atc cgc cag gag ctc      1049
Arg Arg Trp Leu Pro Arg Pro Arg Ala Trp Phe Ile Arg Gln Glu Leu
    265                 270                 275
```

-continued

```
aac gtc acg gcc gcg gca gcc tga gcaccggggg gtgcccctcc agtcccagac    1103
Asn Val Thr Ala Ala Ala Ala  *
280                 285

ggcaatgttc ctccctccaa ctgtccctgg agccagaaca ctcacagaga cacccctgag   1163

agggtggcca cagcccaaga tgaagtcatc aagacagaaa agcaaaaccg agaaaaacga   1223

cgggcacctg gaaccagtca cggcttggga ggtgcaggtg ccccgtgtta ggcgcctttg   1283

tcggggactt gcaaggcctc acctgtttgg ccatgattga tgacgtgact gcttccattt   1343

tgcagatgag gaaactaagg ctcagagagg ccacgccacc cttgagccac ccatggaccc   1403

ctctccatct cctgcctgcg cctttaagtc cctgatttat tctttccatt cattccatct   1463

gggaggaacc cccccaactc ctgccagctt cccctagctg ggtctctgg  tactcttcac   1523

acctgcaggg gcgtctacac tgttcgtcta cctggtggca gggtctgagc gggaggagga   1583

gggaaagagt gtgttctgag ctggacccag cctcttgttc gagaataaaa actcttcttc   1643

tcttgc                                                              1649


<210> SEQ ID NO 123
<211> LENGTH: 286
<212> TYPE: PRT
<213> ORGANISM: Homo sapiens

<400> SEQUENCE: 123

Met Lys Val Leu Leu Leu Thr Gly Leu Gly Ala Leu Phe Phe Ala Tyr
 1               5                  10                  15

Tyr Trp Asp Asp Asn Phe Asp Pro Ala Ser Leu Gln Gly Ala Arg Val
            20                  25                  30

Leu Leu Thr Gly Ala Asn Ala Gly Val Gly Glu Glu Leu Ala Tyr His
        35                  40                  45

Tyr Ala Arg Leu Gly Ser His Leu Val Leu Thr Ala His Thr Glu Ala
    50                  55                  60

Leu Leu Gln Lys Val Val Gly Asn Cys Arg Lys Leu Gly Ala Pro Lys
65                  70                  75                  80

Val Phe Tyr Ile Ala Ala Asp Met Ala Ser Pro Glu Ala Pro Glu Ser
                85                  90                  95

Val Val Gln Phe Ala Leu Asp Lys Leu Gly Gly Leu Asp Tyr Leu Val
            100                 105                 110

Leu Asn His Ile Gly Gly Ala Pro Ala Gly Thr Arg Ala Arg Ser Pro
        115                 120                 125

Gln Ala Thr Arg Trp Leu Met Gln Val Asn Phe Val Ser Tyr Val Gln
    130                 135                 140

Leu Thr Ser Arg Ala Leu Pro Ser Leu Thr Asp Ser Lys Gly Ser Leu
145                 150                 155                 160

Val Val Val Ser Ser Leu Leu Gly Arg Val Pro Thr Ser Phe Ser Thr
                165                 170                 175

Pro Tyr Ser Ala Ala Lys Phe Ala Leu Asp Gly Phe Phe Gly Ser Leu
            180                 185                 190

Arg Arg Glu Leu Asp Val Gln Asp Val Asn Val Ala Ile Thr Met Cys
        195                 200                 205

Val Leu Gly Leu Arg Asp Arg Ala Ser Ala Ala Glu Ala Val Arg Gly
    210                 215                 220

Val Thr Arg Val Lys Ala Ala Pro Gly Pro Lys Ala Ala Leu Ala Val
225                 230                 235                 240

Ile Arg Gly Gly Ala Thr Arg Ala Ala Gly Val Phe Tyr Pro Trp Arg
```

-continued

```
                245                 250                 255

Phe Arg Leu Leu Cys Leu Leu Arg Arg Trp Leu Pro Arg Pro Arg Ala
            260                 265                 270

Trp Phe Ile Arg Gln Glu Leu Asn Val Thr Ala Ala Ala Ala
        275                 280                 285


<210> SEQ ID NO 124
<211> LENGTH: 861
<212> TYPE: DNA
<213> ORGANISM: Homo sapiens
<220> FEATURE:
<221> NAME/KEY: CDS
<222> LOCATION: (1)...(861)

<400> SEQUENCE: 124

atg aag gtg ctt ctc ctc aca ggg ctg ggg gcc ctg ttc ttc gcc tat       48
Met Lys Val Leu Leu Leu Thr Gly Leu Gly Ala Leu Phe Phe Ala Tyr
 1               5                  10                  15

tat tgg gat gac aac ttc gac cca gcc agc ctc cag gga gcg cga gtg       96
Tyr Trp Asp Asp Asn Phe Asp Pro Ala Ser Leu Gln Gly Ala Arg Val
            20                  25                  30

ctg ctg aca ggg gcc aac gct ggt gtt ggt gag gag ctg gcc tat cac      144
Leu Leu Thr Gly Ala Asn Ala Gly Val Gly Glu Glu Leu Ala Tyr His
        35                  40                  45

tac gcg cgt ctg ggc tcc cac ctg gtg ctc act gcc cac act gag gct      192
Tyr Ala Arg Leu Gly Ser His Leu Val Leu Thr Ala His Thr Glu Ala
    50                  55                  60

ctc ctg cag aag gtg gta ggg aac tgc cgg aag ctg ggc gcc ccc aag      240
Leu Leu Gln Lys Val Val Gly Asn Cys Arg Lys Leu Gly Ala Pro Lys
 65                  70                  75                  80

gtc ttc tac atc gcg gcg gac atg gcc tcc cct gag gcg ccc gag agc      288
Val Phe Tyr Ile Ala Ala Asp Met Ala Ser Pro Glu Ala Pro Glu Ser
                85                  90                  95

gtg gtg cag ttt gcg ctg gac aag ctg ggc ggg ctg gac tac ctc gtg      336
Val Val Gln Phe Ala Leu Asp Lys Leu Gly Gly Leu Asp Tyr Leu Val
            100                 105                 110

ctg aac cac atc ggc ggc gcc ccg gcc ggc acg cga gcc cgc agc ccc      384
Leu Asn His Ile Gly Gly Ala Pro Ala Gly Thr Arg Ala Arg Ser Pro
        115                 120                 125

cag gca act cgc tgg ctc atg cag gta aac ttt gtg agc tac gtg caa      432
Gln Ala Thr Arg Trp Leu Met Gln Val Asn Phe Val Ser Tyr Val Gln
    130                 135                 140

ctg acg tcg cgg gcg ctg ccc agc ctg acg gac agc aag ggc tcc ctg      480
Leu Thr Ser Arg Ala Leu Pro Ser Leu Thr Asp Ser Lys Gly Ser Leu
145                 150                 155                 160

gtg gtg gtg tcc tcg ctg ctc ggc cgc gtg ccc acg tcg ttc tcc act      528
Val Val Val Ser Ser Leu Leu Gly Arg Val Pro Thr Ser Phe Ser Thr
                165                 170                 175

ccc tac tcg gcg gcc aag ttt gcg ctg gac ggc ttc ttc ggc tcc ctg      576
Pro Tyr Ser Ala Ala Lys Phe Ala Leu Asp Gly Phe Phe Gly Ser Leu
            180                 185                 190

cgg cgg gag ctg gac gtg cag gac gtg aac gtg gcc atc acc atg tgc      624
Arg Arg Glu Leu Asp Val Gln Asp Val Asn Val Ala Ile Thr Met Cys
        195                 200                 205

gtc ctg ggc ctc cga gat cgc gcc tcc gcc gcc gag gca gtc agg gga      672
Val Leu Gly Leu Arg Asp Arg Ala Ser Ala Ala Glu Ala Val Arg Gly
    210                 215                 220

gtc acg agg gtc aag gcg gcc ccg ggg ccc aag gca gcc ctg gcc gtg      720
Val Thr Arg Val Lys Ala Ala Pro Gly Pro Lys Ala Ala Leu Ala Val
225                 230                 235                 240
```

-continued

```
atc cgc ggc ggc gcc acg cgc gcg gcc ggc gtc ttc tac ccg tgg cgt      768
Ile Arg Gly Gly Ala Thr Arg Ala Ala Gly Val Phe Tyr Pro Trp Arg
                245                 250                 255

ttc cgc ctg ctg tgc ttg ctc cgg cgc tgg cta ccg cgc ccg cgg gcc      816
Phe Arg Leu Leu Cys Leu Leu Arg Arg Trp Leu Pro Arg Pro Arg Ala
            260                 265                 270

tgg ttt atc cgc cag gag ctc aac gtc acg gcc gcg gca gcc tga          861
Trp Phe Ile Arg Gln Glu Leu Asn Val Thr Ala Ala Ala Ala  *
        275                 280                 285


<210> SEQ ID NO 125
<211> LENGTH: 206
<212> TYPE: PRT
<213> ORGANISM: Artificial Sequence
<220> FEATURE:
<223> OTHER INFORMATION: Amino acid consensus sequence

<400> SEQUENCE: 125

Lys Val Ala Leu Val Thr Gly Ala Ser Ser Gly Ile Gly Leu Ala Ile
 1               5                  10                  15

Ala Lys Arg Leu Ala Lys Glu Gly Ala Lys Val Val Val Ala Asp Arg
            20                  25                  30

Asn Glu Glu Lys Leu Glu Lys Gly Ala Val Ala Lys Glu Leu Lys Glu
        35                  40                  45

Leu Gly Gly Asn Asp Lys Asp Arg Ala Leu Ala Ile Gln Leu Asp Val
    50                  55                  60

Thr Asp Glu Glu Ser Val Lys Ala Ala Val Glu Gln Ala Val Glu Arg
65                  70                  75                  80

Leu Gly Arg Gly Leu Asp Val Leu Val Asn Asn Ala Gly Gly Ile Ile
                85                  90                  95

Leu Leu Arg Pro Gly Pro Phe Ala Glu Leu Ser Arg Thr Met Glu Glu
            100                 105                 110

Asp Trp Asp Arg Val Ile Asp Val Asn Leu Thr Gly Val Phe Leu Leu
        115                 120                 125

Thr Arg Ala Val Leu Pro Leu Met Ala Met Lys Lys Arg Gly Gly Gly
    130                 135                 140

Arg Ile Val Asn Ile Ser Ser Val Ala Gly Arg Lys Glu Gly Gly Leu
145                 150                 155                 160

Val Gly Val Pro Gly Gly Ser Ala Tyr Ser Ala Ser Lys Ala Ala Val
                165                 170                 175

Ile Gly Leu Thr Arg Ser Leu Ala Leu Glu Leu Ala Pro His Gly Gly
            180                 185                 190

Ile Arg Val Asn Ala Val Ala Pro Gly Gly Val Asp Thr Asp
        195                 200                 205


<210> SEQ ID NO 126
<211> LENGTH: 7
<212> TYPE: PRT
<213> ORGANISM: Artificial Sequence
<220> FEATURE:
<223> OTHER INFORMATION: Co-enzyme binding pattern
<220> FEATURE:
<221> NAME/KEY: VARIANT
<222> LOCATION: (2)...(4)
<223> OTHER INFORMATION: Xaa = Any amino acid
<220> FEATURE:
<221> NAME/KEY: CONFLICT
<222> LOCATION: (6)...(6)
<223> OTHER INFORMATION: Xaa = Any amino acid

<400> SEQUENCE: 126
```

-continued

```
Gly Xaa Xaa Xaa Gly Xaa Gly
 1               5


<210> SEQ ID NO 127
<211> LENGTH: 4
<212> TYPE: PRT
<213> ORGANISM: Artificial Sequence
<220> FEATURE:
<223> OTHER INFORMATION: SDR active-site pattern
<220> FEATURE:
<221> NAME/KEY: VARIANT
<222> LOCATION: (2)...(3)
<223> OTHER INFORMATION: Xaa = Any amino acid

<400> SEQUENCE: 127

Tyr Xaa Xaa Lys
 1


<210> SEQ ID NO 128
<211> LENGTH: 11
<212> TYPE: PRT
<213> ORGANISM: Artificial Sequence
<220> FEATURE:
<223> OTHER INFORMATION: Short chain dehydrogenase family signature

<400> SEQUENCE: 128

Tyr Ser Ala Ala Lys Phe Ala Leu Asp Gly Phe
 1               5                   10


<210> SEQ ID NO 129
<211> LENGTH: 839
<212> TYPE: DNA
<213> ORGANISM: Homo sapiens
<220> FEATURE:
<221> NAME/KEY: CDS
<222> LOCATION: (44)...(649)

<400> SEQUENCE: 129

cgcgagcgcg ggggccgacg ggtcgccgct gcgccgggcc ggg atg gcg gcc acc       55
                                                Met Ala Ala Thr
                                                 1

gcg ctg ctg gag gcc ggc ctg gcg cgg gtg ctc ttc tac ccg acg ctg      103
Ala Leu Leu Glu Ala Gly Leu Ala Arg Val Leu Phe Tyr Pro Thr Leu
 5                  10                  15                  20

ctc tac acc ctg ttc cgc ggg aag gtg ccg ggt cgg gcg cac cgg gac      151
Leu Tyr Thr Leu Phe Arg Gly Lys Val Pro Gly Arg Ala His Arg Asp
                25                  30                  35

tgg tac cac cgc atc gac ccc acc gtg ctg ctg ggc gcg ctg ccg ttg      199
Trp Tyr His Arg Ile Asp Pro Thr Val Leu Leu Gly Ala Leu Pro Leu
            40                  45                  50

cgg agc ttg acg cgc cag ctg gta cag gac gag aac gtg cgc ggg gtg      247
Arg Ser Leu Thr Arg Gln Leu Val Gln Asp Glu Asn Val Arg Gly Val
        55                  60                  65

atc acc atg aac gag gag tac gag acg agg ttc ctg tgc aac tct tca      295
Ile Thr Met Asn Glu Glu Tyr Glu Thr Arg Phe Leu Cys Asn Ser Ser
    70                  75                  80

cag gag tgg aag aga cta gga gtc gag cag ctg cgg ctc agc aca gta      343
Gln Glu Trp Lys Arg Leu Gly Val Glu Gln Leu Arg Leu Ser Thr Val
 85                  90                  95                 100

gac atg act ggg atc ccc acc ttg gac aac ctc cag aag gga gtc caa      391
Asp Met Thr Gly Ile Pro Thr Leu Asp Asn Leu Gln Lys Gly Val Gln
                105                 110                 115

ttt gct ctc aag tac cag tcg ctg ggc cag tgt gtt tac gtg cat tgt      439
Phe Ala Leu Lys Tyr Gln Ser Leu Gly Gln Cys Val Tyr Val His Cys
            120                 125                 130
```

-continued

```
aag gct ggg cgc tcc agg agt gcc act atg gtg gca gca tac ctg att      487
Lys Ala Gly Arg Ser Arg Ser Ala Thr Met Val Ala Ala Tyr Leu Ile
        135                 140                 145

cag gtg cac aaa tgg agt cca gag gag gct gta aga gcc atc gcc aag      535
Gln Val His Lys Trp Ser Pro Glu Glu Ala Val Arg Ala Ile Ala Lys
    150                 155                 160

atc cgg tca tac atc cac atc agg cct ggc cag ctg gat gtt ctt aaa      583
Ile Arg Ser Tyr Ile His Ile Arg Pro Gly Gln Leu Asp Val Leu Lys
165                 170                 175                 180

gag ttc cac aag cag att act gca cgg gca aca aag gat ggg act ttt      631
Glu Phe His Lys Gln Ile Thr Ala Arg Ala Thr Lys Asp Gly Thr Phe
                185                 190                 195

gtc att tca aag aca tga tgtatgggga ttagaaagaa ctcaagacac             679
Val Ile Ser Lys Thr  *
            200

tcctgcttga tacagaacaa aaagagctta acaggaccaa cagggcttaa gcccagactt    739

gacgtaacag aaatgtgcca ataggtaata ggtaattttt ctttctctga cttgttttgt    799

tttcttgaaa taacactgtt gtgtggctag aaaaaaaaaa                          839


<210> SEQ ID NO 130
<211> LENGTH: 201
<212> TYPE: PRT
<213> ORGANISM: Homo sapiens

<400> SEQUENCE: 130

Met Ala Ala Thr Ala Leu Leu Glu Ala Gly Leu Ala Arg Val Leu Phe
 1               5                  10                  15

Tyr Pro Thr Leu Leu Tyr Thr Leu Phe Arg Gly Lys Val Pro Gly Arg
            20                  25                  30

Ala His Arg Asp Trp Tyr His Arg Ile Asp Pro Thr Val Leu Leu Gly
        35                  40                  45

Ala Leu Pro Leu Arg Ser Leu Thr Arg Gln Leu Val Gln Asp Glu Asn
    50                  55                  60

Val Arg Gly Val Ile Thr Met Asn Glu Glu Tyr Glu Thr Arg Phe Leu
65                  70                  75                  80

Cys Asn Ser Ser Gln Glu Trp Lys Arg Leu Gly Val Glu Gln Leu Arg
                85                  90                  95

Leu Ser Thr Val Asp Met Thr Gly Ile Pro Thr Leu Asp Asn Leu Gln
            100                 105                 110

Lys Gly Val Gln Phe Ala Leu Lys Tyr Gln Ser Leu Gly Gln Cys Val
        115                 120                 125

Tyr Val His Cys Lys Ala Gly Arg Ser Arg Ser Ala Thr Met Val Ala
    130                 135                 140

Ala Tyr Leu Ile Gln Val His Lys Trp Ser Pro Glu Glu Ala Val Arg
145                 150                 155                 160

Ala Ile Ala Lys Ile Arg Ser Tyr Ile His Ile Arg Pro Gly Gln Leu
                165                 170                 175

Asp Val Leu Lys Glu Phe His Lys Gln Ile Thr Ala Arg Ala Thr Lys
            180                 185                 190

Asp Gly Thr Phe Val Ile Ser Lys Thr
        195                 200


<210> SEQ ID NO 131
<211> LENGTH: 606
<212> TYPE: DNA
<213> ORGANISM: Homo sapiens
```

-continued

```
<220> FEATURE:
<221> NAME/KEY: CDS
<222> LOCATION: (1)...(606)

<400> SEQUENCE: 131

atg gcg gcc acc gcg ctg ctg gag gcc ggc ctg gcg cgg gtg ctc ttc       48
Met Ala Ala Thr Ala Leu Leu Glu Ala Gly Leu Ala Arg Val Leu Phe
 1               5                  10                  15

tac ccg acg ctg ctc tac acc ctg ttc cgc ggg aag gtg ccg ggt cgg       96
Tyr Pro Thr Leu Leu Tyr Thr Leu Phe Arg Gly Lys Val Pro Gly Arg
            20                  25                  30

gcg cac cgg gac tgg tac cac cgc atc gac ccc acc gtg ctg ctg ggc      144
Ala His Arg Asp Trp Tyr His Arg Ile Asp Pro Thr Val Leu Leu Gly
        35                  40                  45

gcg ctg ccg ttg cgg agc ttg acg cgc cag ctg gta cag gac gag aac      192
Ala Leu Pro Leu Arg Ser Leu Thr Arg Gln Leu Val Gln Asp Glu Asn
    50                  55                  60

gtg cgc ggg gtg atc acc atg aac gag gag tac gag acg agg ttc ctg      240
Val Arg Gly Val Ile Thr Met Asn Glu Glu Tyr Glu Thr Arg Phe Leu
 65                  70                  75                  80

tgc aac tct tca cag gag tgg aag aga cta gga gtc gag cag ctg cgg      288
Cys Asn Ser Ser Gln Glu Trp Lys Arg Leu Gly Val Glu Gln Leu Arg
                85                  90                  95

ctc agc aca gta gac atg act ggg atc ccc acc ttg gac aac ctc cag      336
Leu Ser Thr Val Asp Met Thr Gly Ile Pro Thr Leu Asp Asn Leu Gln
            100                 105                 110

aag gga gtc caa ttt gct ctc aag tac cag tcg ctg ggc cag tgt gtt      384
Lys Gly Val Gln Phe Ala Leu Lys Tyr Gln Ser Leu Gly Gln Cys Val
        115                 120                 125

tac gtg cat tgt aag gct ggg cgc tcc agg agt gcc act atg gtg gca      432
Tyr Val His Cys Lys Ala Gly Arg Ser Arg Ser Ala Thr Met Val Ala
    130                 135                 140

gca tac ctg att cag gtg cac aaa tgg agt cca gag gag gct gta aga      480
Ala Tyr Leu Ile Gln Val His Lys Trp Ser Pro Glu Glu Ala Val Arg
145                 150                 155                 160

gcc atc gcc aag atc cgg tca tac atc cac atc agg cct ggc cag ctg      528
Ala Ile Ala Lys Ile Arg Ser Tyr Ile His Ile Arg Pro Gly Gln Leu
                165                 170                 175

gat gtt ctt aaa gag ttc cac aag cag att act gca cgg gca aca aag      576
Asp Val Leu Lys Glu Phe His Lys Gln Ile Thr Ala Arg Ala Thr Lys
            180                 185                 190

gat ggg act ttt gtc att tca aag aca tga                              606
Asp Gly Thr Phe Val Ile Ser Lys Thr  *
        195                 200


<210> SEQ ID NO 132
<211> LENGTH: 173
<212> TYPE: PRT
<213> ORGANISM: Artificial Sequence
<220> FEATURE:
<223> OTHER INFORMATION: Amino acid consensus sequence

<400> SEQUENCE: 132

Gly Pro Ser Glu Ile Leu Pro His Leu Tyr Leu Gly Ser Tyr Ser Thr
 1               5                  10                  15

Ala Ser Glu Ala Asn Leu Ala Leu Leu Lys Lys Leu Gly Ile Thr His
            20                  25                  30

Val Ile Asn Val Thr Glu Glu Val Pro Asn Pro Phe Glu Leu Asp Lys
        35                  40                  45

Lys Asn Asp Arg His Tyr Thr Asn Ala Tyr Ile Ser Lys Asn Ser Gly
    50                  55                  60
```

-continued

```
Phe Thr Tyr Leu Gln Ile Pro Asn Val Asp Asp His Ile Tyr Tyr His
65                  70                  75                  80

Ile Ala Trp Asn His Glu Thr Lys Ile Ser Lys Tyr Phe Asp Glu Ala
                85                  90                  95

Val Asp Phe Ile Asp Asp Ala Arg Gln Lys Gly Gly Lys Val Leu Val
            100                 105                 110

His Cys Gln Ala Gly Ile Ser Arg Ser Ala Thr Leu Ile Ile Ala Tyr
        115                 120                 125

Leu Met Lys Thr Arg Asn Leu Ser Leu Asn Glu Ala Tyr Asp Phe Val
    130                 135                 140

Tyr Val Tyr His Ile Lys Glu Arg Arg Cys Pro Ile Ile Ser Pro Asn
145                 150                 155                 160

Phe Gly Phe Leu Arg Gln Leu Ile Glu Tyr Glu Arg Lys
                165                 170


<210> SEQ ID NO 133
<211> LENGTH: 172
<212> TYPE: PRT
<213> ORGANISM: Artificial Sequence
<220> FEATURE:
<223> OTHER INFORMATION: Amino acid consensus sequence

<400> SEQUENCE: 133

Gly Pro Ser Glu Ile Leu Pro His Leu Tyr Leu Gly Ser Tyr Ser Asp
 1               5                  10                  15

Ala Ser Glu Ala Asn Leu Ala Leu Leu Lys Lys Leu Gly Ile Thr His
            20                  25                  30

Val Ile Asn Val Thr Glu Glu Val Pro Asn Asn Phe Glu Leu Lys Lys
        35                  40                  45

Lys Asn Asp Arg Tyr Tyr Thr Asn Glu Tyr Ile Ser Lys Gly Ser Gly
    50                  55                  60

Phe Thr Tyr Leu Gln Ile Pro Asn Val Asp Asp Ile Tyr Tyr His Ile
65                  70                  75                  80

Ala Trp Asn Thr Glu Thr Lys Ile Ser Lys Tyr Leu Glu Glu Ala Val
                85                  90                  95

Glu Phe Ile Glu Asp Ala Glu Lys Lys Gly Gly Lys Val Leu Val His
            100                 105                 110

Cys Gln Ala Gly Val Ser Arg Ser Ala Thr Leu Val Ile Ala Tyr Leu
        115                 120                 125

Met Lys Thr Arg Asn Leu Ser Leu Arg Asp Ala Tyr Asp Phe Val Tyr
    130                 135                 140

Val Tyr His Ile Lys Glu Arg Arg Cys Pro Ile Ile Ser Pro Asn Phe
145                 150                 155                 160

Gly Phe Leu Arg Gln Leu Ile Glu Tyr Glu Arg Lys
                165                 170


<210> SEQ ID NO 134
<211> LENGTH: 13
<212> TYPE: PRT
<213> ORGANISM: Artificial Sequence
<220> FEATURE:
<223> OTHER INFORMATION: Tyrosine specific protein phosphatase active
      site signature
<220> FEATURE:
<221> NAME/KEY: VARIANT
<222> LOCATION: (1)...(1)
<223> OTHER INFORMATION: Xaa at position 1 can be L, I, V, M or F
<220> FEATURE:
<221> NAME/KEY: VARIANT
```

-continued

<222> LOCATION: (4)...(5)
<223> OTHER INFORMATION: Xaa = Any amino acid
<220> FEATURE:
<221> NAME/KEY: VARIANT
<222> LOCATION: (7)...(9)
<223> OTHER INFORMATION: Xaa = Any amino acid
<220> FEATURE:
<221> NAME/KEY: VARIANT
<222> LOCATION: (10)...(10)
<223> OTHER INFORMATION: Xaa at position 10 can be S, T or C
<220> FEATURE:
<221> NAME/KEY: VARIANT
<222> LOCATION: (11)...(11)
<223> OTHER INFORMATION: Xaa at position 11 can be S, T, A, G or P
<220> FEATURE:
<221> NAME/KEY: VARIANT
<222> LOCATION: (12)...(12)
<223> OTHER INFORMATION: Xaa = Any amino acid
<220> FEATURE:
<221> NAME/KEY: VARIANT
<222> LOCATION: (13)...(13)
<223> OTHER INFORMATION: Xaa at position 13 can be L, I, V, M, F or Y

<400> SEQUENCE: 134

Xaa His Cys Xaa Xaa Gly Xaa Xaa Xaa Xaa Xaa Xaa Xaa
1 5 10

<210> SEQ ID NO 135
<211> LENGTH: 7
<212> TYPE: PRT
<213> ORGANISM: Artificial Sequence
<220> FEATURE:
<223> OTHER INFORMATION: Active site motif of the tyrosine phosphatase signature
<220> FEATURE:
<221> NAME/KEY: VARIANT
<222> LOCATION: (2)...(6)
<223> OTHER INFORMATION: Xaa = Any amino acid

<400> SEQUENCE: 135

Cys Xaa Xaa Xaa Xaa Xaa Arg
1 5

<210> SEQ ID NO 136
<211> LENGTH: 21
<212> TYPE: PRT
<213> ORGANISM: Artificial Sequence
<220> FEATURE:
<223> OTHER INFORMATION: Dual specificity phosphatase extended active site signature
<220> FEATURE:
<221> NAME/KEY: VARIANT
<222> LOCATION: (2)...(2)
<223> OTHER INFORMATION: Xaa = Any amino acid
<220> FEATURE:
<221> NAME/KEY: VARIANT
<222> LOCATION: (6)...(7)
<223> OTHER INFORMATION: Xaa = Any amino acid
<220> FEATURE:
<221> NAME/KEY: VARIANT
<222> LOCATION: (9)...(9)
<223> OTHER INFORMATION: Xaa = Any amino acid
<220> FEATURE:
<221> NAME/KEY: VARIANT
<222> LOCATION: (13)...(13)
<223> OTHER INFORMATION: Xaa = Any amino acid
<220> FEATURE:
<221> NAME/KEY: VARIANT
<222> LOCATION: (15)...(17)
<223> OTHER INFORMATION: Xaa = Any amino acid
<220> FEATURE:
<221> NAME/KEY: VARIANT
<222> LOCATION: (20)...(20)
<223> OTHER INFORMATION: Xaa at position 20 can be L or I -continued

```
<400> SEQUENCE: 136

Val Xaa Val His Cys Xaa Xaa Gly Xaa Ser Arg Ser Xaa Thr Xaa Xaa
 1              5                  10                  15

Xaa Ala Tyr Xaa Met
            20
```

26199, 33530, 33949, 47148, 50226, 58764, 62113, 32144, 32235, 23565, 13305, 14911, 86216, 25206, AND 8843 MOLECULES AND USES THEREFOR

RELATED APPLICATIONS

The present application is a continuation of U.S. patent application Ser. No. 10/410,764, filed Apr. 10, 2003 (abandoned). U.S. patent application Ser. No. 10/410,764 is a continuation-in-part of U.S. patent application Ser. No. 09/924,358, filed Aug. 6, 2001 (abandoned), which claims the benefit of U.S. Provisional Application Ser. No. 60/229,300, filed Sep. 1, 2000 (abandoned). U.S. patent application Ser. No. 10/410,764 is also a continuation-in-part of U.S. patent application Ser. No. 10/350,553, filed Jan. 24, 2003 (abandoned), which claims the benefit of U.S. Provisional Application Ser. No. 60/351,572, filed Jan. 24, 2002 (abandoned). U.S. patent application Ser. No. 10/410,764 is also a continuation-in-part of U.S. patent application Ser. No. 09/966,614, filed Sep. 27, 2001 (abandoned), which claims the benefit of U.S. Provisional Application Ser. No. 60/238,054, filed Oct. 5, 2000 (abandoned). U.S. patent application Ser. No. 10/410,764 is also a continuation-in-part of U.S. patent application Ser. No. 10/281,094, filed Oct. 25, 2002 (abandoned), which claims the benefit of U.S. Provisional Application Ser. No. 60/347,815, filed Oct. 29, 2001 (abandoned). U.S. patent application Ser. No. 10/410,764 is also a continuation-in-part of U.S. patent application Ser. No. 10/076,535, filed Feb. 15, 2002 (abandoned), which claims the benefit of U.S. Provisional Application Ser. No. 60/269,440, filed Feb. 16, 2001 (abandoned). U.S. patent application Ser. No. 10/410,764 is also a continuation-in-part of U.S. patent application Ser. No. 09/860,352, filed May 17, 2001 (abandoned), which claims the benefit of U.S. Provisional Application Ser. No. 60/205,301, filed May 19, 2000 (abandoned). U.S. patent application Ser. No. 10/410,764 is also a continuation-in-part of U.S. patent application Ser. No. 09/593,927, filed Jun. 15, 2000 (abandoned), which claims the benefit of U.S. Provisional Application Ser. No. 60/199,391, filed Apr. 25, 2000 (abandoned). U.S. patent application Ser. No. 10/410,764 is also a continuation-in-part of U.S. patent application Ser. No. 10/226,410, filed Aug. 23, 2002 (abandoned), which claims the benefit of U.S. Provisional Application Ser. No. 60/314,884, filed on Aug. 24, 2001 (abandoned). U.S. patent application Ser. No. 10/410,764 is also a continuation-in-part of U.S. patent application Ser. No. 09/997,816, filed Nov. 29, 2001 (abandoned), which claims the benefit of U.S. Provisional Application Ser. No. 60/250,186, filed Nov. 30, 2000 (abandoned). U.S. patent application Ser. No. 10/410,764 is also a continuation-in-part of U.S. patent application Ser. No. 09/686,673, filed Oct. 11, 2000 (abandoned). The entire contents of each of the above-referenced patent applications are incorporated herein by this reference.

BACKGROUND OF THE INVENTION

The enormous variety of biochemical reactions that comprise life are nearly all mediated by a series of biological catalysts known as enzymes. Enzymes are proteins which possess specific catalytic activities that enable them to catalyze a series of reactions, hence enabling metabolic pathways to degrade and to reconstruct products needed to maintain organisms. By the binding of substrates through geometrically and physically complementary reactions, enzymes are stereospecific in binding substrates as well as in catalyzing reactions. The stringency for this stereospecificity varies as some enzymes are more specific to the identity of their substrates, while others are capable of binding multiple substrates and can catalyze numerous types of reactions.

Examples of enzymes include, for example, arginine methyltransferases, glycosyltransferases, gamma-glutamyltraspeptidases, phosphoribosylglycinamide transferases, acyltransferases, acyl-CoA dehydrogenases, fatty acid amide hydrolases, aminotransferases, zinc carboxypeptidases, protein kinases, DEAD helicases, short-chain dehydrogenase/reductases and phosphatases. Such enzymes have the ability, for example: 1) to transfer an activated sugar residue to an acceptor molecule; 2) to modulate the processing, folding, and secretion of proteins; 3) to transport amino acids in the form of their gamma-glutamyl derivatives; 4) to regulate the metabolism of glutathione; 5) to regulate the synthesis of purines; 6) to modulate cell division and proliferation; 7) to modulate cell death; 8) to transfer an acyl chain to a lipid precursor; 9) to regulate lipid biosynthesis; 10) to catalyze the transfer of hydrogen and electrons from one compound to another; 11) to catalyze the I,ϑ-dehydrogenation of fatty acyl-CoA derivatives; 12) to bind and catabolize fatty acid amides; 13) to modulate metabolism, e.g., amino acid metabolism; 14) to bind an amino acid, e.g., L-alanine; 15) to bind an oxo acid, e.g., pyruvate; 16) to modulate the formation of a zinc ion complex with a carbonyl group of a substrate polypeptide and polarization of the carbon-oxygen bond; 17) to modulate formation of a tetrahedral intermediate due to attack of the carbonyl carbon by water in a reaction assisted by a carboxylate side chain of glutamate; 18) to modulate the production of a dianion intermediate by rapid ionization of the tetrahedral intermediate produced; 19) to modulate ATP dependent nucleic acid unwinding; 20) to modulate RNA metabolism (e.g., nuclear transcription, and mRNA splicing); 21) to modulate steroid biosynthesis or metabolism (breakdown); 22) to catalyze the removal of a phosphate group attached to a tyrosine residue in a protein; 23) to catalyze the removal of a phosphate group attached to a serine or threonine residue in a protein; 24) to modulate an intracellular signaling pathway, e.g., a MAP kinase or ERK kinase pathway; 25) to regulate the transmission of signals from cellular receptors, e.g., cardiac cell growth factor receptors; as well as many others. Accordingly, there exists a need to identify additional human enzymes, for example, for use as disease markers and as targets for identifying various therapeutic modulators.

SUMMARY OF THE INVENTION

The present invention is based, at least in part, on the discovery of novel nucleic acid molecules and proteins encoded by such nucleic acid molecules, referred to herein as "26199, 33530, 33949, 47148, 50226, 58764, 62113, 32144, 32235, 23565, 13305, 14911, 86216, 25206 or 8843". The 26199, 33530, 33949, 47148, 50226, 58764, 62113, 32144, 32235, 23565, 13305, 14911, 86216, 25206 or 8843 nucleic acid and protein molecules of the present invention are useful as modulating agents in regulating a variety of cellular processes, e.g., including cell proliferation, differentiation, growth and division. In particular, these nucleic acid molecules will be advantageous in the regulation of any cellular function, uncontrolled proliferation and differentiation, such as in cases of cancer. Accordingly, in one aspect, this invention provides isolated nucleic acid molecules encoding 26199, 33530, 33949, 47148, 50226, 58764, 62113, 32144, 32235, 23565, 13305, 14911, 86216, 25206 or 8843 proteins or biologically active portions thereof, as well as nucleic acid fragments suitable as primers or hybridization probes for the detection of 26199, 33530, 33949, 47148, 50226, 58764, 62113, 32144, 32235, 23565, 13305, 14911, 86216, 25206 or 8843-encoding nucleic acids.

The nucleotide sequence of the cDNA encoding 26199, 33530, 33949, 47148, 50226, 58764, 62113, 32144, 32235, 23565, 13305, 14911, 86216, 25206 or 8843, and the amino acid sequence of 26199, 33530, 33949, 47148, 50226, 58764, 62113, 32144, 32235, 23565, 13305, 14911, 86216, 25206 or 8843 polypeptides are depicted in Table 1.

TABLE 1

Sequences of the invention

| Gene Name | cDNA | Protein | Coding Region | ATCC accession number |
|---|---|---|---|---|
| 26199 | SEQ ID NO: 1 | SEQ ID NO: 2 | SEQ ID NO: 3 | N/A |
| 33530 | SEQ ID NO: 4 | SEQ ID NO: 5 | SEQ ID NO: 6 | PTA-3437 |
| 33949 | SEQ ID NO: 7 | SEQ ID NO: 8 | SEQ ID NO: 9 | N/A |
| 47148 | SEQ ID NO: 10 | SEQ ID NO: 11 | SEQ ID NO: 12 | N/A |
| 50226 | SEQ ID NO: 13 | SEQ ID NO: 14 | SEQ ID NO: 15 | N/A |
| 58764 | SEQ ID NO: 16 | SEQ ID NO: 17 | SEQ ID NO: 18 | N/A |
| 62113 | SEQ ID NO: 53 | SEQ ID NO: 54 | SEQ ID NO: 55 | N/A |
| 32144 | SEQ ID NO: 61 | SEQ ID NO: 62 | SEQ ID NO: 63 | N/A |
| 32235 | SEQ ID NO: 67 | SEQ ID NO: 68 | SEQ ID NO: 69 | N/A |
| 23565 | SEQ ID NO: 78 | SEQ ID NO: 79 | SEQ ID NO: 80 | N/A |
| 13305 | SEQ ID NO: 88 | SEQ ID NO: 89 | SEQ ID NO: 90 | N/A |
| 14911 | SEQ ID NO: 100 | SEQ ID NO: 101 | SEQ ID NO: 102 | PTA-3435 |
| 86216 | SEQ ID NO: 113 | SEQ ID NO: 114 | SEQ ID NO: 115 | N/A |
| 25206 | SEQ ID NO: 122 | SEQ ID NO: 123 | SEQ ID NO: 124 | N/A |
| 8843 | SEQ ID NO: 129 | SEQ ID NO: 130 | SEQ ID NO: 131 | N/A |

Accordingly, in one aspect, the invention features a nucleic acid molecule which encodes a 26199, 33530, 33949, 47148, 50226, 58764, 62113, 32144, 32235, 23565, 13305, 14911, 86216, 25206 or 8843 protein or polypeptide, e.g., a biologically active portion of the 26199, 33530, 33949, 47148, 50226, 58764, 62113, 32144, 32235, 23565, 13305, 14911, 86216, 25206 or 8843 protein. In a preferred embodiment, the isolated nucleic acid molecule encodes a polypeptide having the amino acid sequence of SEQ ID NO:2, 5, 8, 11, 14, 17, 54, 62, 68, 79, 89, 101, 114, 123 or 130. In other embodiments, the Invention provides isolated 26199, 33530, 33949, 47148, 50226, 58764, 62113, 32144, 32235, 23565, 13305, 14911, 86216, 25206 or 8843 nucleic acid molecules having the nucleotide sequence shown in SEQ ID NO:1, 3, 4, 6, 7, 9, 10, 12, 13, 15, 16, 18, 53, 55, 61, 63, 67, 69, 78, 80, 88, 90, 100, 102, 113, 115, 122, 124, 129 or 131 or the nucleotide sequence of the DNA insert of the plasmid deposited with ATCC Accession Number PTA-IA-3437 or PTA-3435. In still other embodiments, the invention provides nucleic acid molecules that are substantially identical (e.g., naturally occurring allelic variants) to the nucleotide sequence shown in SEQ ID NO:1, 3, 4, 6, 7, 9, 10, 12, 13, 15, 16, 18, 53, 55, 61, 63, 67, 69, 78, 80, 88, 90, 100, 102, 113, 115, 122, 124, 129 or 131 or the nucleotide sequence of the DNA insert of the plasmid deposited with ATCC Accession Number PTA-3437 or PTA-3435. In other embodiments, the invention provides a nucleic acid molecule which hybridizes under a stringent hybridization condition as described herein to a nucleic acid molecule comprising the nucleotide sequence of SEQ ID NO:1, 3, 4, 6, 7, 9, 10, 12, 13, 15, 16, 18, 53, 55, 61, 63, 67, 69, 78, 80, 88, 90, 100, 102, 113, 115, 122, 124, 129 or 131 or the nucleotide sequence of the DNA insert of the plasmid deposited with ATCC Accession Number PTA-3437 or PTA-3435, wherein the nucleic acid encodes a full length 26199, 33530, 33949, 47148, 50226, 58764, 62113, 32144, 32235, 23565, 13305, 14911, 86216, 25206 or 8843 protein or an active fragment thereof.

In a related aspect, the invention further provides nucleic acid constructs which include a 26199, 33530, 33949, 47148, 50226, 58764, 62113, 32144, 32235, 23565, 13305, 14911, 86216, 25206 or 8843 nucleic acid molecule described herein. In certain embodiments, the nucleic acid molecules of the invention are operatively linked to native or heterologous regulatory sequences. Also included are vectors and host cells containing the 26199, 33530, 33949, 47148, 50226, 58764, 62113, 32144, 32235, 23565, 13305, 14911, 86216, 25206 or 8843 nucleic acid molecules of the invention e.g., vectors and host cells suitable for producing polypeptides.

In another related aspect, the invention provides nucleic acid fragments suitable as primers or hybridization probes for the detection of 26199, 33530, 33949, 47148, 50226, 58764, 62113, 32144, 32235, 23565, 13305, 14911, 86216, 25206 or 8843-encoding nucleic acids.

In still another related aspect, isolated nucleic acid molecules that are antisense to a 26199, 33530, 33949, 47148, 50226, 58764, 62113, 32144, 32235, 23565, 13305, 14911, 86216, 25206 or 8843 encoding nucleic acid molecule are provided.

In another aspect, the invention features 26199, 33530, 33949, 47148, 50226, 58764, 62113, 32144, 32235, 23565, 13305, 14911, 86216, 25206 or 8843 polypeptides, and biologically active or antigenic fragments thereof that are useful, e.g., as reagents or targets in assays applicable to treatment and diagnosis of 26199, 33530, 33949, 47148, 50226, 58764, 62113, 32144, 32235, 23565, 13305, 14911, 86216, 25206 or 8843-associated disorders. In another embodiment, the invention provides 26199, 33530, 33949, 47148, 50226, 58764, 62113, 32144, 32235, 23565, 13305, 14911, 86216, 25206 or 8843 polypeptides having a 26199, 33530, 33949, 47148, 50226, 58764, 62113, 32144, 32235, 23565, 13305, 14911, 86216, 25206 or 8843 activity.

In other embodiments, the invention provides 26199, 33530, 33949, 47148, 50226, 58764, 62113, 32144, 32235, 23565, 13305, 14911, 86216, 25206 or 8843 polypeptides, e.g., a 26199, 33530, 33949, 47148, 50226, 58764, 62113, 32144, 32235, 23565, 13305, 14911, 86216, 25206 or 8843 polypeptide having the amino acid sequence shown in SEQ ID NO:2, 5, 8, 11, 14, 17, 54, 62, 68, 79, 89, 101, 114, 123 or 130 or the amino acid sequence encoded by the cDNA insert of the plasmid deposited with ATCC Accession Number PTA-3437 or PTA-3435; an amino acid sequence that is substantially identical to the amino acid sequence shown in SEQ ID NO:2, 5, 8, 11, 14, 17, 54, 62, 68, 79, 89, 101, 114, 123 or 130 or the amino acid sequence encoded by the cDNA insert of the plasmid deposited with ATCC Accession Number PTA-3437 or PTA-3435; or an amino acid sequence encoded by a nucleic acid molecule having a nucleotide sequence which hybridizes under a stringent hybridization condition as described herein to a nucleic acid molecule comprising the nucleotide sequence of SEQ ID NO:1, 3, 4, 6, 7, 9, 10, 12, 13, 15, 16, 18, 53, 55, 61, 63, 67, 69, 78, 80, 88, 90, 100, 102, 113, 115, 122, 124, 129 or 131 or the nucleotide sequence of the insert of the plasmid deposited with ATCC Accession Number PTA-3437 or PTA-3435, wherein the nucleic acid encodes a full length 26199, 33530, 33949, 47148, 50226, 58764, 62113, 32144, 32235, 23565, 13305, 14911, 86216, 25206 or 8843 protein or an active fragment thereof.

In a related aspect, the invention further provides nucleic acid constructs which include a 26199, 33530, 33949, 47148, 50226, 58764, 62113, 32144, 32235, 23565, 13305, 14911, 86216, 25206 or 8843 nucleic acid molecule described herein.

In a related aspect, the invention provides 26199, 33530, 33949, 47148, 50226, 58764, 62113, 32144, 32235, 23565, 13305, 14911, 86216, 25206 or 8843 polypeptides or fragments operatively linked to non-26199, 33530, 33949, 47148, 50226, 58764, 62113, 32144, 32235, 23565, 13305, 14911, 86216, 25206 or 8843 polypeptides to form fusion proteins.

In another aspect, the invention features antibodies and antigen-binding fragments thereof, that react with, or more preferably specifically or selectively bind 26199, 33530, 33949, 47148, 50226, 58764, 62113, 32144, 32235, 23565, 13305, 14911, 86216, 25206 or 8843 polypeptides.

In another aspect, the invention provides methods of screening for compounds that modulate the expression or activity of the 26199, 33530, 33949, 47148, 50226, 58764, 62113, 32144, 32235, 23565, 13305, 14911, 86216, 25206 or 8843 polypeptides or nucleic acids.

In still another aspect, the invention provides a process for modulating 26199, 33530, 33949, 47148, 50226, 58764, 62113, 32144, 32235, 23565, 13305, 14911, 86216, 25206 or 8843 polypeptide or nucleic acid expression or activity, e.g., using the compounds identified in the screens described herein. In certain embodiments, the methods involve treatment of conditions related to aberrant activity or expression of the 26199, 33530, 33949, 47148, 50226, 58764, 62113, 32144, 32235, 23565, 13305, 14911, 86216, 25206 or 8843 polypeptides or nucleic acids, such as conditions or disorders involving aberrant or deficient 26199, 33530, 33949, 47148, 50226, 58764, 62113, 32144, 32235, 23565, 13305, 14911, 86216, 25206 or 8843 expression. Examples of such disorders include, but are not limited to cellular proliferative and/or differentiative disorders, brain disorders, platelet disorders, breast disorders, colon disorders, kidney (renal) disorders, lung disorders, ovarian disorders, prostate disorders, hematopoeitic disorders, pancreatic disorders, skeletal muscle disorders, skin (dermal) disorders, disorders associated with bone metabolism, immune, e.g., inflammatory, disorders, cardiovascular disorders, endothelial cell disorders, liver disorders, viral diseases, pain disorders, metabolic disorders, neurological or CNS disorders, erythroid disorders or anemic disorders.

The invention also provides assays for determining the activity of or the presence or absence of 26199, 33530, 33949, 47148, 50226, 58764, 62113, 32144, 32235, 23565, 13305, 14911, 86216, 25206 or 8843 polypeptides or nucleic acid molecules in a biological sample, including for disease diagnosis.

In a further aspect, the invention provides assays for determining the presence or absence of a genetic alteration in a 26199, 33530, 33949, 47148, 50226, 58764, 62113, 32144, 32235, 23565, 13305, 14911, 86216, 25206 or 8843 polypeptide or nucleic acid molecule, including for disease diagnosis.

In another aspect, the invention features a two dimensional array having a plurality of addresses, each address of the plurality being positionally distinguishable from each other address of the plurality, and each address of the plurality having a unique capture probe, e.g., a nucleic acid or peptide sequence. At least one address of the plurality has a capture probe that recognizes a 26199, 33530, 33949, 47148, 50226, 58764, 62113, 32144, 32235, 23565, 13305, 14911, 86216, 25206 or 8843 molecule. In one embodiment, the capture probe is a nucleic acid, e.g., a probe complementary to a 26199, 33530, 33949, 47148, 50226, 58764, 62113, 32144, 32235, 23565, 13305, 14911, 86216, 25206 or 8843 nucleic acid sequence. In another embodiment, the capture probe is a polypeptide, e.g., an antibody specific for 26199, 33530, 33949, 47148, 50226, 58764, 62113, 32144, 32235, 23565, 13305, 14911, 86216, 25206 or 8843 polypeptides. Also featured is a method of analyzing a sample by contacting the sample to the aforementioned array and detecting binding of the sample to the array.

Other features and advantages of the invention will be apparent from the following detailed description, and from the claims.

DETAILED DESCRIPTION OF THE INVENTION

Human 26199, 33530, 33949, 47148, 50226, and 58764

The present invention is based, in part, on the discovery of novel human transferase family members, referred to herein as "26199, 33530, 33949, 47148, 50226, and 58764".

Human 26199

The human 26199 sequence (SEQ ID NO:1), which is approximately 1828 nucleotides long including untranslated regions, contains a predicted methionine-initiated coding sequence of about 687 nucleotides (nucleotides 56-742 of SEQ ID NO:1; 1-687 of SEQ ID NO:3, not including the terminal codon). The coding sequence encodes a 229 amino acid protein (SEQ ID NO:2). This mature protein form is approximately 229 amino acid residues in length (from about amino acid 1 to amino acid 229 of SEQ ID NO:2).

A BLAST alignment of human 26199 with a consensus amino acid sequence derived from a Propomain "chromosome genomic DNA 5 FIS clone:MLN1 T6D22.22 UME3-HDA1 tumor-related ZHB0014.1" (PD113097; Release 2001.1) shows amino acid residues 2 to 115 of the 119 amino acid consensus sequence (SEQ ID NO:19) aligns with the "chromosome genomic DNA 5 FIS clone:MLN1 T6D22.22 UME3-HDA1 tumor-related ZHB0014.1" domain of human 26199, amino acid residues 7 to 120 of SEQ ID NO:2.

A BLAST alignment of human 26199 with a consensus amino acid sequence derived from a Propomain "P1 genomic clone:MLN1 chromosome 5" (PD289255; Release 2001.1) shows amino acid residues 3 to 104 of the 111 amino acid consensus sequence (SEQ ID NO:20) aligns with the "P1 genomic clone:MLN1 chromosome 5" domain of human 26199, amino acid residues 123 to 226 of SEQ ID NO:2.

A BLAST alignment of human 26199 with a consensus amino acid sequence derived from a Propomain "MRPL37-

RIF1" (PD113089; Release 2001.1) shows amino acid residues 191 to 401 of the 419 amino acid consensus sequence (SEQ ID NO:21) aligns with the "MRPL37-RIF1" domain of human 26199, amino acid residues 15 to 208 of SEQ ID NO:2.

Human 26199 contains the following regions or other structural features: two predicted transmembrane domains (predicted by MEMSAT, Jones et al. (1994) *Biochemistry* 33:3038-3049) which extend from about amino acid residue 3349 and 74-94 of SEQ ID NO:2; two glycosaminoglycan attachment sites (PS00002) located at about amino acids 59-62 and 76-79 of SEQ ID NO:2; one predicted cAMP- and cGMP-dependent protein kinase phosphorylation site (PS0004) located at about amino acids 222-225 of SEQ ID NO:2; two predicted protein kinase C phosphorylation sites (PS00005) located at about amino acids 67-69 and 158-160 of SEQ ID NO:2; six predicted casein kinase II phosphorylation sites (PS00006) located at about amino 7-10, 70-73, 95-98, 135-138, 158-161 and 163-166 of SEQ ID NO:2; four predicted N-myristoylation sites (PS00008) located at about amino acids 36-41, 75-80, 82-87 and 117-122 of SEQ ID NO:2; and one predicted prokaryotic membrane lipoprotein lipid attachment site (PS00013) located at about amino acids 30-40 of SEQ ID NO:2.

In one embodiment, a 26199 family member can include at least one and preferably two transmembrane domains. Furthermore, a 26199 family member can include at least one and preferably two glycosaminoglycan attachment sites (PS00002); at least one cAMP- and cGMP-dependent protein kinase phosphorylation site (PS00004); at least one, and preferably two protein kinase C phosphorylation sites (PS00005); at least one, two, three, four, five, and preferably six casein kinase II phosphorylation sites (PS00006); at least one, two, three, and preferably four N-myristolyation sites (PS00008); at least one prokaryotic membrane lipoprotein lipid attachment site (PS00013).

26199 is overexpressed in human breast and lung carcinomas. It is expected that inhibition of this arginine methyltransferase will inhibit tumor progression.

For general information regarding PFAM identifiers, PS prefix and PF prefix domain identification numbers, refer to Sonnhammer et al. (1997) *Protein* 28:405-420.

A hydropathy plot of human 26199 was performed. Polypeptides of the invention include fragments which include: all or part of a hydrophobic sequence, e.g., the sequence from about amino acid 40 to 50, from about 80 to 100, and from about 135 to 145 of SEQ ID NO:2; all or part of a hydrophilic sequence, e.g., the sequence from about amino acid 50 to 70, from about 170 to 190, and from about 200 to 210 of SEQ ID NO:2; a sequence which includes a Cys, or a glycosylation site.

Human 33530

The human 33530 sequence (SEQ ID NO:4), which is approximately 1408 nucleotides long including untranslated regions, contains a predicted methionine-initiated coding sequence of about 1248 nucleotides (nucleotides 36-1283 of SEQ ID NO:4; 1-1248 of SEQ ID NO:6, not including the terminal codon). The coding sequence encodes a 416 amino acid protein (SEQ ID NO:5). This mature protein form is approximately 416 amino acid residues in length (from about amino acid 1 to amino acid 416 of SEQ ID NO:5).

An alignment of the "glycosyl transferase group 1" domain of human 33530 with a consensus amino acid sequence derived from a hidden Markov model (HMM) from PFAM shows the consensus amino acid sequence (SEQ ID NO:22) aligns with amino acids 211 to 393 of SEQ ID NO:5.

A BLAST alignment of human 33530 with a consensus amino acid sequence derived from a Propomain "a similar BA13B9.1 glycosyltransferase novel cDNA MNCB-5081 brain" (PD346441; Release 2001.1) shows amino acid residues 1 to 49 of the 49 amino acid consensus sequence (SEQ ID NO:23) aligns with the "a similar BA13B9.1 glycosyltransferase novel cDNA MNCB-5081 brain" domain of human 33530, amino acid residues 367 to 415 of SEQ ID NO:5.

A BLAST alignment of human 33530 with a consensus amino acid sequence derived from a Propomain "glycosyltransferase ALG2 similar musculus F9K20.16 other novel brain 2.4.1." (PD011566; Release 2001.1) shows amino acid residues 4 to 84 of the 84 amino acid consensus sequence (SEQ ID NO:24) aligns with the "glycosyltransferase ALG2 similar musculus F9K20.16 other novel brain 2.4.1." domain of human 33530, amino acid residues 17 to 95 of SEQ ID NO:5.

A BLAST alignment of human 33530 with a consensus amino acid sequence derived from a Propomain "transferase glycosyltransferase biosynthesis lipopolysaccharide galactosyltransferase glucosyltransferase mannosyl 2.4.1.-mannosyltransferase" (PD010528; Release 2001.1) shows amino acid residues 15 to 158 of the 164 amino acid consensus sequence (SEQ ID NO:25) aligns with the "transferase glycosyltransferase biosynthesis lipopolysaccharide galactosyltransferase glucosyltransferase mannosyl 2.4.1.-mannosyltransferase" domain of human 33530, amino acid residues 280 to 413 of SEQ ID NO:5.

A BLAST alignment of human 33530 with a consensus amino acid sequence derived from a Propomain "F9K20.16" (PD241981; Release 2001.1) shows amino acid residues 1 to 46 of the 46 amino acid consensus sequence (SEQ ID NO:26) aligns with the "F9K20.16" domain of human 33530, amino acid residues 96 to 143 of SEQ ID NO:5.

A BLAST alignment of human 33530 with a consensus amino acid sequence derived from a Propomain "glycosyltransferase 2.4.1.-ALG2 transmembrane glycoprotein" (PD258606; Release 2001.1) shows amino acid residues 15 to 60 of the 60 amino acid consensus sequence (SEQ ID NO:27) aligns with the "glycosyltransferase 2.4.1.-ALG2 transmembrane glycoprotein" domain of human 33530, amino acid residues 109 to 155 of SEQ ID NO:5.

A BLAST alignment of human 33530 with a consensus amino acid sequence derived from a Propomain "glycosyltransferase" (PD309959; Release 2001.1) shows amino acid residues 5 to 161 of the 199 amino acid consensus sequence (SEQ ID NO:28) aligns with the "glycosyltransferase" domain of human 33530, amino acid residues 216 to 382 of SEQ ID NO:5.

Human 33530 contains the following regions or other structural features: one predicted glycosyl transferase group 1 domain (PFAM Accession Number PF00534) located at about amino acid residues 211-393 of SEQ ID NO:5; one predicted transmembrane domain (predicted by MEMSAT, Jones et al. (1994) *Biochemistry* 33:3038-3049) which extends from about amino acid residue 85-105 of SEQ ID NO:5; two predicted N-glycosylation sites (PS00001) located at about amino acids 204-207 and 239-242 of SEQ ID NO:5; one predicted cAMP- and cGMP-dependent protein kinase phosphorylation site (PS0004) located at about amino acids 146-149 of SEQ ID NO:5; five predicted protein kinase C phosphorylation sites (PS00005) located at about amino acids 46-48, 145-147, 187-189, 304-306 and 381-383 of SEQ ID NO:5; five predicted casein kinase II phosphorylation sites (PS00006) located at about amino 145-148, 192-195, 206-209, 255-258 and 302-305 of SEQ ID NO:5; five predicted N-myristoylation sites (PS00008) located at about amino acids 25-30, 78-83, 85-90, 168-173 and 294-299 of SEQ ID NO:5; and one predicted amidation site (PS00009) located at about amino acids 222-225 of SEQ ID NO:5.

In one embodiment, a 33530 family member can include at least one glycosyl transferase group 1 domain (PFAM Accession Number PF00534) and at least one transmembrane domain. Furthermore, a 33530 family member can include at least one and preferably two N-glycosylation sites (PS00001); at least one cAMP- and cGMP-dependent protein kinase phosphorylation site (PS00004); at least one, two, three, four, and preferably five protein kinase C phosphorylation sites (PS00005); at least one, two, three, four, and preferably five casein kinase II phosphorylation sites (PS00006); at least one, two, three, four, and preferably five N-myristolyation sites (PS00008); at least one amidation site (PS00009).

For general information regarding PFAM identifiers, PS prefix and PF prefix domain identification numbers, refer to Sonnhammer et al. (1997) *Protein* 28:405-420.

A hydropathy plot of human 33530 was performed. Polypeptides of the invention include fragments which include: all or part of a hydrophobic sequence, e.g., the sequence from about amino acid 30 to 45, from about 85 to 105, and from about 115 to 125 of SEQ ID NO:5; all or part of a hydrophilic sequence, e.g., the sequence from about amino acid 55 to 70, from about 155 to 160, and from about 270 to 290 of SEQ ID NO:5; a sequence which includes a Cys, or a glycosylation site.

A plasmid containing the nucleotide sequence encoding human 33530 was deposited with American Type Culture Collection (ATCC), 10801 University Boulevard, Manassas, Va. 20110-2209, on Jun. 7, 2001 and assigned Accession Number PTA-3437. This deposit will be maintained under the terms of the Budapest Treaty on the International Recognition of the Deposit of Microorganisms for the Purposes of Patent Procedure. This deposit was made merely as a convenience for those of skill in the art and is not an admission that a deposit is required under 35 U.S.C. § 112.

Human 33949

The human 33949 sequence (SEQ ID NO:7), which is approximately 2327 nucleotides long including untranslated regions, contains a predicted methionine-initiated coding sequence of about 1824 nucleotides (nucleotides 148-1971 of SEQ ID NO:7; 1-1824 of SEQ ID NO:9, not including the terminal codon). The coding sequence encodes a 608 amino acid protein (SEQ ID NO:8). The protein contains a signal sequence from about amino acid 1 to 37 of SEQ ID NO:8. The mature protein form is approximately 571 amino acid residues in length (from about amino acid 38 to amino acid 608 of SEQ ID NO:8).

An alignment of the "glycosyl transferase group 2" domain of human 33949 with a consensus amino acid sequence derived from a hidden Markov model (HMM) from PFAM shows the consensus amino acid sequence (SEQ ID NO:29) aligns with amino acids 154 to 341 of SEQ ID NO:8.

An alignment of the "QXW lectin repeat (Ricin_B_lectin)" domain of human 33949 with a consensus amino acid sequence derived from a hidden Markov model (HMM) from PFAM shows the consensus amino acid sequence (SEQ ID NOS:30-32) aligns with amino acids 483 to 526, 527 to 567 and 568 to 606 of SEQ ID NO:8.

A BLAST alignment of human 33949 with a consensus amino acid sequence derived from a Propomain "WUGSC: H_DJ0981O07.2 cDNA: FIS COL08230 FU21634" (PD354231; Release 2001.1) shows amino acid residues 1 to 102 of the 102 amino acid consensus sequence (SEQ ID NO:33) aligns with the "WUGSC:H_DJ0981O07.2 cDNA: FIS COL08230 FLJ21634" domain of human 33949, amino acid residues 1 to 102 of SEQ ID NO:8.

A BLAST alignment of human 33949 with a consensus amino acid sequence derived from a Propomain "acetylgalactosaminyltransferase N-acetylgalactosaminyltransferase polypeptide UDP-GALNAC:polypeptide protein-glyco glycosyltransferase" (PD003677; Release 2001.1) shows amino acid residues 2 to 130 of the 130 amino acid consensus sequence (SEQ ID NO:34) aligns with the "acetylgalactosaminyltransferase N-acetylgalactosaminyltransferase polypeptide UDP-GALNAC:polypeptide protein-glyco glycosyltransferase" domain of human 33949, amino acid residues 103 to 229 of SEQ ID NO:8.

A BLAST alignment of human 33949 with a consensus amino acid sequence derived from a Propomain "acetylgalactosaminyltransferase N-acetylgalactosaminyltransferase polypeptide UDP-GALNAC:polypeptide protein-FIS GALNAC-T1" (PD003162; Release 2001.1) shows amino acid residues 1 to 62 of the 62 amino acid consensus sequence (SEQ ID NO:35) aligns with the "acetylgalactosaminyltransferase N-acetylgalactosaminyltransferase polypeptide UDP-GALNAC:polypeptide protein-FIS GALNAC-T1" domain of human 33949, amino acid residues 347 to 406 of SEQ ID NO:8.

A BLAST alignment of human 33949 with a consensus amino acid sequence derived from a Propomain "FIS cDNA: WUGSC:H_DJ0981O07.2 HRC08167 COL08230 FLJ21634 FLJ22403" (PD334332; Release 2001.1) shows amino acid residues 1 to 41 and 2 to 37 of the 41 amino acid consensus sequence (SEQ ID NOs:36-37) aligns with the "FIS cDNA: WUGSC:H_DJ0981O07.2 HRC08167 COL08230 FLJ21634 FLJ22403" domain of human 33949, amino acid residues 568 to 608 and 484 to 521 of SEQ ID NO:8.

A BLAST alignment of human 33949 with a consensus amino acid sequence derived from a Propomain "N-acetylgalactosaminyltransferase polypeptide UDP-GALNAC: polypeptide protein-glyco glycosyltransferase" (PD301297; Release 2001.1) shows amino acid residues 1 to 80 of the 80 amino acid consensus sequence (SEQ ID NO:38) aligns with the "N-acetylgalactosaminyltransferase polypeptide UDP-GALNAC:polypeptide protein-glyco glycosyltransferase" domain of human 33949, amino acid residues 273 to 346 of SEQ ID NO:8.

Human 33949 contains the following regions or other structural features: one predicted glycosyl transferase group 2 domain located at about amino acid residues 154-341 of SEQ ID NO:8; three predicted transmembrane domains (predicted by MEMSAT, Jones et al. (1994) *Biochemistry* 33:3038-3049) which extends from about amino acid residues 8-28, 150-168 and 268-284 of SEQ ID NO:8; two predicted N-glycosylation site (PS00001) located at about amino acids 29-32 and 428-431 of SEQ ID NO:8; eleven predicted protein kinase C phosphorylation sites (PS00005) located at about amino acids 5-7, 51-53, 124-126, 220-222, 358-360, 399-401, 416-418, 430-432, 443-445, 490-492 and 501-503 of SEQ ID NO:8; six predicted casein kinase II phosphorylation sites (PS00006) located at about amino 82-85, 173-176, 193-196, 220-223, 246-249 and 345-348 of SEQ ID NO:8; one predicted tyrosine kinase phosphorylation site (PS00007) located at about amino acids 445-452 of SEQ ID NO:8; and nine predicted N-myristoylation sites (PS00008) located at about amino acids 12-17, 99-104, 224-229, 232-237, 327-332, 341-346, 387-392, 555-560 and 586-591 of SEQ ID NO:8.

In one embodiment, a 33949 family member can include at least one glycosyl transferase group 2 domain (PFAM Accession Number PF00535) and at least one, two and preferably three transmembrane domains. Furthermore, a 33949 family member can include at least one and preferably two N-glycosylation sites (PS00001); at least one, two, three, four, five, six, seven, eight, nine, ten and preferably eleven protein kinase C phosphorylation sites (PS00005); at least one, two, three, four, five and preferably six casein kinase II phosphorylation sites (PS00006); at least one predicted tyrosine kinase phosphorylation site (PS00007); at least one, two, three, four, five, six, seven, eight, and preferably nine N-myristolyation sites (PS00008).

For general information regarding PFAM identifiers, PS prefix and PF prefix domain identification numbers, refer to Sonnhammer et al. (1997) *Protein* 28:405-420.

A hydropathy plot of human 33949 was performed. Polypeptides of the invention include fragments which include: all or part of a hydrophobic sequence, e.g., the sequence from about amino acid 235 to 245, from about 275 to 285, and from about 360 to 375 of SEQ ID NO:8; all or part of a hydrophilic sequence, e.g., the sequence from about amino acid 50 to 70, from about 130 to 150, and from about 385 to 400 of SEQ ID NO:8; a sequence which includes a Cys, or a glycosylation site.

The 33530 and 33949 proteins contain a significant number of structural characteristics in common with members of the glycosyltransferase family. A 33530 or 33949 polypeptide can include a “glycosyltransferase domain” or regions homologous with a “glycosyltransferase domain.”

As used herein, the term “glycosyltransferase” includes a protein or polypeptide which is capable of catalyzing the synthesis of glycoconjugates, including glycolipids, glycoproteins, and polysaccharides, by transferring an activated mono- or oligosaccharide residue to an existing acceptor molecule for the initiation or elongation of the carbohydrate chain. The acceptor can be a lipid, a protein, a heterocyclic compound, or another carbohydrate residue. Glycosyltransferases can be divided into numerous subfamilies based upon their specificity for sugar moieties and acceptor molecules. The glycosyltransferase domain of human 33530 bears similarity to a subfamily designated “group 1” glycosyltransferases. Members of this family transfer activated sugars to a variety of substrates, including glycogen, fructose-6-phosphate and lipopolysaccharides. Members of this family transfer UDP, ADP, GDP or CMP linked sugars. The glycosyltransferase domain of human 33949 bears similarity to a subfamily designated “group 2” glycosyltransferases. These enzymes comprise a diverse subfamily, whose members transfer sugar from UDP-glucose, UDP-N-acetyl-galactosamine, GDP-mannose or CDP-abequose, to a range of substrates including cellulose, dolichol phosphate and teichoic acids. Based on the sequence similarities, the 33530 or 33949 molecules of the present invention are predicted to have similar biological activities as glycosyltransferase family members.

Glycosyltransferases play roles in diverse cellular processes. For example, the major target of the natural IgM and IgG antibodies during hyperacute xenograft rejection is the terminal carbohydrate epitope Gal alpha(1,3)Gal, formed by the alpha 1,3galactosyl transferase, which places a terminal galactose residue in an alpha-linkage to another galactose (Sandrin et al. (1994) *Immunol Rev* 141:169-90). As another example, mutations in the Piga gene, the protein product of which mediates N-acetylglucosamine attachment to phosphatidylinositol, results in the clonal hematologic disorder, paroxysmal nocturnal hemoglobinuria (Ware et al. (1994) *Blood* 83:2418-22). Additionally, UDP-galactose:ceramide galactosyltransferase is the enzyme responsible for the biosynthesis of galactosylceramide, a molecule thought to play a critical role in myelin formation, signal transduction, viral and microbial adhesion, and oligodendrocyte development (Kapitonov et al. (1999) *Glycobiology* 9:961-78).

Glycosylation of glycoproteins and glycolipids is one of many molecular changes that accompany malignant transformation. GlcNAc-branched N-glycans and terminal Lewis antigen sequences have been observed to increase in some cancers, and to correlate with poor prognosis (Dennis et al. (1999) *Biochim Biophys Acta* 1473:21-34). Cellular membrane over-expression and shedding of acidic glycosphingolipids into the interstitial spaces and blood of cancer patients may play a central role in increased tumour cell growth, lack of immune cell recognition and neovascularization and could represent a molecular target for cancer therapy (Fish (1996) *Med Hypotheses* 46:140-44). Thus, the 33530 or 33949 molecules of the present invention may be involved in: 1) the transfer of an activated sugar residue to an acceptor molecule; 2) the processing, folding, and secretion of proteins; 3) the modulation of tumor cell growth and invasion; 4) myelin formation; 5) signal transduction; 6) viral and microbial adhesion; 7) oligodendrocyte development; 8) sperm-egg binding; 9) evasion of immune detection; 10) xenograft rejection; and 11) the ability to antagonize or inhibit, competitively or non-competitively, any of 1-11. Thus, the 33530 and 33949 molecules can act as novel diagnostic targets and therapeutic agents for controlling glycosyltransferase-related disorders, for example, such as those diseases associated with the activities described above. As the 33530 and 33949 molecules have homology to known glycosyltransferases, they are expected to be involved in controlling similar disorders.

33530 has been shown to be overexpressed in some human breast, lung and colon carcinomas, and underexpressed in some ovary and brain carcinomas. As such, inhibition of this gycosyltransferase may inhibit tumor progression in breast, lung and colon. Further, activation of this gycosyltransferase may inhibit tumor progression in ovary and brain.

The 33949 molecules also have similarities to bovine and murine N-acetygalactosaminyltransferase. Thus, without being bound by theory, the 33949 transferase, may be a human analogue of the bovine or murine N-acetygalactosaminyltransferase.

Further, 33949 is overexpressed in a subset of breast, ovary, lung and colon tumors. As such, inhibition of this N-acetylgalactosaminyltransferase may inhibit tumor progression.

33949 is clearly a member of the GalNAc-transferase family of glycosyl transferase type 2 enzymes. The overall sequence identity is quite high, and all of the residues known to be required for catalytic activity are present in 33949. In the lectin domain of the protein, which has been shown to be involved in glycopeptide substrate specifity, 33949 has a V where the majority of known active enzymes have a D (in the CLD motif). In one study with GalNAc-T1, this D was changed to an H and the enzyme was still active (albeit with 42% of maximum activity).

Phylogenetic analysis of 33949 indicates that both the catalytic and lectin domains may be most similar to the GalNAc-T6 and -T7 enzymes.

It is expected that 33949 will encode an active enzyme. Identification of the ‘natural’ protein substrate may not necessary for assay configuration since many GalNAc-transferases have been shown to work on various peptide substrates derived from mucin and other proteins.

As used herein, the term “glycosyltransferase domain” includes an amino acid sequence of about 100-250 amino acid residues in length and having a bit score for the alignment of the sequence to the glycosyltransferase domain (HMM) of at least 30. Preferably, a glycosyltransferase domain includes at least about 120-220 amino acids, more preferably about 120-200 amino acid residues, or about 130-180 amino acids and has a bit score for the alignment of the sequence to the glycosyltransferase domain (HMM) of at least 50 or greater. Glycosyltransferase domains (HMM) have been assigned numerous PFAM Accession Numbers, including PF00534 (group 1) and PF00535 (group 2). The glycosyltransferase domain (amino acids 211 to 393 of SEQ ID NO:5) of human 33530 aligns with a consensus amino acid sequence (group 1 glycosyltransferases) derived from a hidden Markov model. The glycosyltransferase domain (amino acids 154 to 341 of SEQ ID NO:8) of human 33949 aligns with a consensus amino acid sequence (group 2 glycosyltransferases) derived from a hidden Markov model.

In a preferred embodiment a 33530 or 33949 polypeptide or protein has a "glycosyltransferase domain" or a region which includes at least about 120-220 more preferably about 120-200 or 130-180 amino acid residues and has at least about 70% 80% 90% 95%, 99%, or 100% homology with a "glycosyltransferase domain," e.g., the glycosyltransferase domain of human 33530 or 33949 (e.g., residues 211 to 393 of SEQ ID NO:5 or residues 154 to 341 of SEQ ID NO:8).

To identify the presence of a "glycosyltransferase" domain in a 33530 or 33949 protein sequence, and make the determination that a polypeptide or protein of interest has a particular profile, the amino acid sequence of the protein can be searched against a database of HMMs Human 47148

The human 47148 sequence (SEQ ID NO:10), which is approximately 2172 nucleotides long including untranslated regions, contains a predicted methionine-initiated coding sequence of about 1986 nucleotides (nucleotides 31-2016 of SEQ ID NO:10; 1-1986 of SEQ ID NO:12, not including the terminal codon). The coding sequence encodes a 662 amino acid protein (SEQ ID NO:11). This mature protein form is approximately 662 amino acid residues in length (from about amino acid 1 to amino acid 662 of SEQ ID NO:11).

An alignment of the gamma-glutamyltranspeptidase domain of human 47148 with a consensus amino acid sequence derived from a hidden Markov model (HMM) from PFAM shows the consensus amino acid sequence (SEQ ID NO:39) aligns with amino acids 154 to 656 of SEQ ID NO:11.

A BLAST alignment of human 47148 with a consensus amino acid sequence derived from a Propomain "FGENESH repeat novel gamma-glutamyltranspeptidase locus CCA D20S101 similar predictions. DJ18C9.2" (PD297327; Release 2001.1) shows amino acid residues 1 to 135 of the 135 amino acid consensus sequence (SEQ ID NO:40) aligns with the "FGENESH repeat novel gamma-glutamyltranspeptidase locus CCA D20S101 similar predictions. DJ18C9.2" domain of human 47148, amino acid residues 1 to 135 of SEQ ID NO:11.

A BLAST alignment of human 47148 with a consensus amino acid sequence derived from a Propomain "gamma-glutamyltranspeptidase transferase acyltransferase precursor zymogen glutathione biosynthesis acylase glycoprotein" (PD127336; Release 2001.1) shows amino acid residues 2 to 294 of the 304 amino acid consensus sequence (SEQ ID NO:41) aligns with "gamma-glutamyltranspeptidase transferase acyltransferase precursor zymogen glutathione biosynthesis acylase glycoprotein" domain of human 47148, amino acid residues 200 to 471 of SEQ ID NO:11.

A BLAST alignment of human 47148 with a consensus amino acid sequence derived from a Propomain "FGENESH repeat novel gamma-glutamyltranspeptidase locus CCA D20S101 similar predictions. DJ18C9.2" (PD290211; Release 2001.1) shows amino acid residues 1 to 114 of the 114 amino acid consensus sequence (SEQ ID NO:42) aligns with the "FGENESH repeat novel gamma-glutamyltranspeptidase locus CCA D20S101 similar predictions. DJ18C9.2" domain of human 47148, amino acid residues 549 to 662 of SEQ ID NO:11.

Human 47148 contains the following regions or other structural features: one predicted gamma-glutamyltranspeptidase domain (PFAM Accession Number PF01019) located at about amino acid residues 154-656 of SEQ ID NO:11; two predicted transmembrane domains (predicted by MEMSAT, Jones et al. (1994) *Biochemistry* 33:3038-3049) which extend from about amino acid residues 106-127 and 168-192 of SEQ ID NO:11; ten predicted N-glycosylation sites (PS00001) located at about amino acids 198-201, 267-270, 283-286, 330-333, 353-356, 394-397, 452-455, 519-522, 523-526 and 586-589 of SEQ ID NO:11; one predicted glycosaminoglycan attachment site (PS00002) located at about amino acids 182-185 of SEQ ID NO:11; seven predicted protein kinase C phosphorylation sites (PS00005) located at about amino acids 64-66, 88-90, 101-103, 285-287, 295-297, 411-413 and 638-640 of SEQ ID NO:11; ten predicted casein kinase II phosphorylation sites (PS00006) located at about amino 17-20, 56-59, 73-76, 88-91, 162-165, 347-350, 430-433, 434-437, 440-443 and 612-615 of SEQ ID NO:11; one predicted tyrosine kinase phosphorylation site (PS00007) located at about amino acids 421-427 of SEQ ID NO:11; fourteen predicted N-myristoylation sites (PS00008) located at about amino acids 78-83, 120-125, 140-145, 183-188, 227-232, 234-239, 328-333, 343-348, 364-369, 469-474, 505-510, 553-558, 562-567 and 637-642 of SEQ ID NO:11; and two predicted amidation sites (PS00009) located at about amino acids 42-45 and 535-538 of SEQ ID NO:11.

In one embodiment, a 47148 family member can include at least one gamma-glutamyltranspeptidase domain (PFAM Accession Number PF01019) and at least one and preferably two transmembrane domain. Furthermore, a 47148 family member can include at least one, two, three, four, five, six, seven, eight, nine, and preferably ten N-glycosylation sites (PS00001); at least one predicted glycosaminoglycan attachment site (PS00002); at least one, two, three, four, five, six, and preferably seven protein kinase C phosphorylation sites (PS00005); at least one, two, three, four, five, six, seven, eight, nine, and preferably ten casein kinase II phosphorylation sites (PS00006); at least one predicted tyrosine kinase phosphorylation site (PS00007); at least one, two, three, four, five, six, seven, eight, nine, ten, eleven, twelve, thirteen and preferably fourteen N-myristolyation sites (PS00008); at least one and preferably two amidation sites (PS00009).

For general information regarding PFAM identifiers, PS prefix and PF prefix domain identification numbers, refer to Sonnhammer et al. (1997) *Protein* 28:405-420.

A hydropathy plot of human 47148 was performed. Polypeptides of the invention include fragments which include: all or part of a hydrophobic sequence, e.g., the sequence from about amino acid 110 to 130, from about 165 to 180, and from about 480 to 490 SEQ ID NO:11; all or part of a hydrophilic sequence, e.g., the sequence from about amino acid 70 to 90, from about 210 to 225, and from about 520 to 540 of SEQ ID NO:11; a sequence which includes a Cys, or a glycosylation site.

Gamma-glutamyltraspeptidase plays an important role in the metabolism of glutathione. Located at the external surface of epithelial cells, gamma-glutamyltraspeptidase initiates extracellular glutathione breakdown, provides cells with local cysteine supply and contributes to maintain intracellular glutathione level. Gamma-glutamyltraspeptidase expression, highly sensitive to oxidative stress, is a part of the cell anti-oxidant defense mechanisms. Chikhi, N., et al. (1999) *Comp Biochem Physiol B Biochem Mol Biol* 122(4):367-80. Glutathione plays an essential role in protecting the pulmonary system for toxic insults (Potdar, P. D., et al. (1997) Am J Physiol 273(5 Pt 1):L1082-9). Thus, the 47148 molecules of the present invention may be involved in: 1) transport of amino acids in the form of their gamma-glutamyl derivatives; 2) metabolism of glutathione; 3) maintenance of cellular cysteine levels; 4) maintenance of intracellular glutathione levels; 5) metabolism of amino acids; and 6) the ability to antagonize or inhibit, competitively or non-competitively, any of 1-5. Thus, the 47148 molecules can act as novel diagnostic targets and therapeutic agents for controlling gamma-glutamyltraspeptidase-related disorders, for example, such as those diseases (e.g. liver disease) associated with the activities described above. As the 47148 molecules have homology to known gamma-glutamyltraspeptidase, they are expected to be involved in controlling similar disorders.

Gamma-glutamyltraspeptidase is conserved among species (Chikhi, supra) and, thus without being bound by theory, the 47148 gamma-glutamyltraspeptidase may be a human analogue of rat, mouse, or pig gamma-glutamyltraspeptidase.

As used herein, the term "gamma-glutamyltraspeptidase domain" includes an amino acid sequence of about 100-500 amino acid residues in length and having a bit score for the alignment of the sequence to the gamma-glutamyltraspeptidase domain (HMM) of at least 30. Preferably, a gamma-glutamyltraspeptidase domain includes at least about 200-500 amino acids, more preferably about 300-500 amino acid residues, or about 400-500 amino acids and has a bit score for the alignment of the sequence to the gamma-glutamyltraspeptidase domain (HMM) of at least 50 or greater. The gamma-glutamyltraspeptidase domain (HMM) has been assigned PFAM Accession Numbers, including PF01019. The gamma-glutamyltranspeptidase domain (amino acids 154 to 656 of SEQ ID NO:11) of human 47148 aligns with a consensus amino acid sequence derived from a hidden Markov model.

In a preferred embodiment a 47148 polypeptide or protein has a gamma-glutamyltraspeptidase domain" or a region which includes at least about 200-500 more preferably about 300-500 or 400-500 amino acid residues and has at least about 70% 80% 90% 95%, 99%, or 100% homology with a "gamma-glutamyltraspeptidase domain," e.g., the gamma-glutamyltraspeptidase domain of human 47148 (e.g., residues 154 to 656 of SEQ ID NO:11).

To identify the presence of a "gamma-glutamyltraspeptidase" domain in a 47148 protein sequence, and make the determination that a polypeptide or protein of interest has a particular profile, the amino acid sequence of the protein can be searched against a database of HMMs Human 50226

The human 50226 sequence (SEQ ID NO:13), which is approximately 1252 nucleotides long including untranslated regions, contains a predicted methionine-initiated coding sequence of about 1167 nucleotides (nucleotides 18-1184 of SEQ ID NO:13; 1-1167 of SEQ ID NO:15, not including the terminal codon). The coding sequence encodes a 389 amino acid protein (SEQ ID NO:14). The protein contains a signal sequence from about amino acid 1 to 17 of SEQ ID NO:14. The mature protein form is approximately 372 amino acid residues in length (from about amino acid 18 to amino acid 389 of SEQ ID NO:14).

An alignment of the formyl transferase domain of human 50226 with a consensus amino acid sequence derived from a hidden Markov model (HMM) from PFAM shows the consensus amino acid sequence (SEQ ID NO:43) aligns with amino acids 119 to 220 of SEQ ID NO:14.

A BLAST alignment of human 50226 with a consensus amino acid sequence derived from a Propomain "transferase formyltransferase phosphoribosylglycinamide biosynthesis methionyl-tRNA methyltransferase purine transformylase formyltetrahydrofolate hydrolase" (PD001209; Release 2001.1) shows amino acid residues 42 to 149 of the 156 amino acid consensus sequence (SEQ ID NO:44) aligns with the "transferase formyltransferase phosphoribosylglycinamide biosynthesis methionyl-tRNA methyltransferase purine transformylase formyltetrahydrofolate hydrolase" domain of human 50226, amino acid residues 117 to 221 of SEQ ID NO:14.

A BLAST alignment of human 50226 with a consensus amino acid sequence derived from a Propomain "formyltransferase methionyl-tRNA methyltransferase biosynthesis one-carbon metabolism 10-formyltetrahydrofolate 10-FTH-FDH dehydrogenase" (PD004966; Release 2001.1) shows amino acid residues 10 to 123 of the 129 amino acid consensus sequence (SEQ ID NO:45) aligns with the "formyltransferase methionyl-tRNA methyltransferase biosynthesis one-carbon metabolism 10-formyltetrahydrofolate 10-FTHFDH dehydrogenase" domain of human 50226, amino acid residues 238 to 355 of SEQ ID NO:14.

Human 50226 contains the following regions or other structural features: one predicted formyl transferase domain (PFAM Accession Number PF00551) located at about amino acid residues 119-220 of SEQ ID NO:14; one predicted N-glycosylation site (PS00001) located at about amino acids 292-295 of SEQ ID NO:14; five predicted protein kinase C phosphorylation sites (PS00005) located at about amino acids 90-92, 200-202, 282-284, 369-371 and 374-376 of SEQ ID NO:14; two predicted casein kinase II phosphorylation sites (PS00006) located at about amino 200-203 and 341-344 of SEQ ID NO:14; two predicted N-myristoylation sites (PS00008) located at about amino acids 16-21 and 121-126 of SEQ ID NO:14; and one predicted leucine zipper pattern (PS00029) located at about amino acids 129-150 of SEQ ID NO:14.

In one embodiment, a 50226 family member can include at least one formyl transferase domain (PFAM Accession Number PF00551). Furthermore, a 50226 family member can include at least one N-glycosylation site (PS00001); at least one, two, three, four, and preferably five protein kinase C phosphorylation sites (PS00005); at least one, and preferably two casein kinase II phosphorylation sites (PS00006); at least one, and preferably two N-myristolyation sites (PS00008); at least one leucine zipper pattern (PS00029).

For general information regarding PFAM identifiers, PS prefix and PF prefix domain identification numbers, refer to Sonnhammer et al. (1997) *Protein* 28:405-420.

A hydropathy plot of human 50226 was performed. Polypeptides of the invention include fragments which include: all or part of a hydrophobic sequence, e.g., the sequence from about amino acid 122 to 130, from about 140 to 150, and from about 285 to 300 SEQ ID NO:14; all or part of a hydrophilic sequence, e.g., the sequence from about amino acid 35 to 50, from about 230 to 240, and from about 350 to 370 of SEQ ID NO:14; a sequence which includes a Cys, or a glycosylation site.

The 50226 protein has similarities to formyl transferase, specifically, phosphoribosylglycinamide transferase, which plays a role in the de novo purine biosynthetic pathway. Thus, the 50226 molecules of the present invention may be involved in: 1) synthesis of purines; 2) modulation of cell division and proliferation; 3) the modulation of cell death; and 4) the ability to antagonize or inhibit, competitively or non-competitively, any of 1-3. Thus, the 50226 molecules can act as novel diagnostic targets and therapeutic agents for controlling phosphoribosylglycinamide transferase-related disorders, for example, such as those diseases (e.g. cancer) associated with the activities described above. As the 50226 molecules have homology to known phosphoribosylglycinamide transferase, they are expected to be involved in controlling similar disorders.

Phosphoribosylglycinamide transferase is conserved among species and, thus without being bound by theory, the 50226 phosphoribosylglycinamide transferase may be a human analogue of chicken or mouse phosphoribosylglycinamide transferase.

50226 has been shown to be overexpressed in some human breast, lung and colon carcinomas, and underexpressed in some ovary carcinomas. As such, inhibition of this gycosyltransferase may inhibit tumor progression in breast, lung and colon. Further, activation of this gycosyltransferase may inhibit tumor progression in ovary.

As used herein, the term "formyl transferase domain" includes an amino acid sequence of about 20-150 amino acid residues in length and having a bit score for the alignment of the sequence to the formyl transferase domain (HMM) of at least 30. Preferably, a formyl transferase domain includes at least about 40-130 amino acids, more preferably about 60-110 amino acid residues, or about 70-100 amino acids and has a bit score for the alignment of the sequence to the glycosyltransferase domain (HMM) of at least 50 or greater. The formyl transferase domain (HMM) has been assigned PFAM Accession Number PF00551. The formyl transferase domain (amino acids 119-220 of SEQ ID NO:14) of human 50226 aligns with a consensus amino acid sequence derived from a hidden Markov model.

In a preferred embodiment a 50226 polypeptide or protein has a formyl transferase domain" or a region which includes at least about 20-150 more preferably about 50-125 or 70-100 amino acid residues and has at least about 70% 80% 90% 95%, 99%, or 100% homology with a "formyl transferase domain," e.g., the formyl transferase domain of human 50226 (e.g., residues 119 to 220 of SEQ ID NO:14).

To identify the presence of a "formyl transferase" domain in a 50226 protein sequence, and make the determination that a polypeptide or protein of interest has a particular profile, the amino acid sequence of the protein can be searched against a database of HMMs Human 58764

The human 58764 sequence (SEQ ID NO:16), which is approximately 1797 nucleotides long including untranslated regions, contains a predicted methionine-initiated coding sequence of about 972 nucleotides (nucleotides 215-1186 of SEQ ID NO:16; 1-972 of SEQ ID NO:18, not including the terminal codon). The coding sequence encodes a 324 amino acid protein (SEQ ID NO:17). The protein contains a signal sequence from about amino acids 1 to 63. This mature protein form is approximately 261 amino acid residues in length (from about amino acid 64 to amino acid 324 of SEQ ID NO:17).

An alignment of the acyltransferase domain of human 58764 with a consensus amino acid sequence derived from a hidden Markov model (HMM) from PFAM shows the consensus amino acid sequence (SEQ ID NO:46) aligns with amino acids 115 to 300 of SEQ ID NO:17.

A BLAST alignment of human 58764 with a consensus amino acid sequence derived from a Propomain "CG11757" (PD107349; Release 2001.1) shows amino acid residues 7 to 222 of the 260 amino acid consensus sequence (SEQ ID NO:47) aligns with the "CG11757" domain of human 58764, amino acid residues 91 to 293 of SEQ ID NO:17.

A BLAST alignment of human 58764 with a consensus amino acid sequence derived from a Propomain "CG11757" (PD260979; Release 2001.1) shows amino acid residues 28 to 50 of the 63 amino acid consensus sequence (SEQ ID NO:48) aligns with the "CG11757" domain of human 58764, amino acid residues 300 to 322 of SEQ ID NO:17.

Human 58764 contains the following regions or other structural features: one predicted acyltransferase domain (PFAM Accession Number PF01553) located at about amino acid residues 115-300 of SEQ ID NO:17; two or three predicted transmembrane domains (predicted by MEMSAT, Jones et al. (1994) *Biochemistry* 33:3038-3049) which extend from about amino acid residues 51-74, 124-141 and 159-176 of SEQ ID NO:17; one predicted N-glycosylation site (PS0001) located at about amino acids 5-8 of SEQ ID NO:17; one predicted protein kinase C phosphorylation site (PS00005) located at about amino acids 151-153 of SEQ ID NO:17; two predicted casein kinase II phosphorylation sites (PS00006) located at about amino 98-101 and 289-292 of SEQ ID NO:17; one predicted tyrosine kinase phosphorylation site (PS00007) located at about amino acids 23-261 of SEQ ID NO:17; three predicted N-myristoylation sites (PS00008) located at about amino acids 91-96, 199-204 and 313-318 of SEQ ID NO:17; and five predicted dileucine motifs in the tail located at about amino acids 53-54, 63-64, 168-169, 169-170 and 192-193 of SEQ ID NO:17.

In one embodiment, a 58764 family member can include at least one acyltransferase domain (PFAM Accession Number PF01553); and at least one, and preferably two or three transmembrane domains. Furthermore, a 58764 family member can include at least one N-glycosylation site (PS00001); at least one protein kinase C phosphorylation site (PS00005); at least one, and preferably two casein kinase II phosphorylation sites (PS00006); at least one predicted tyrosine kinase phosphorylation site (PS00007); at least one, two and preferably three N-myristolyation sites (PS00008); at least one, two, three, four and preferably five predicted dileucine motifs in the tail.

For general information regarding PFAM identifiers, PS prefix and PF prefix domain identification numbers, refer to Sonnhammer et al. (1997) *Protein* 28:405-420.

A hydropathy plot of human 58764 was performed. Polypeptides of the invention include fragments which include: all or part of a hydrophobic sequence, e.g., the sequence from about amino acid 125 to 140, from about 160 to 180, and from about 225 to 235 SEQ ID NO:17; all or part of a hydrophilic sequence, e.g., the sequence from about amino acid 85 to 90, from about 155 to 125, and from about 240 to 250 of SEQ ID NO:17; a sequence which includes a Cys, or a glycosylation site.

As referred to herein, acyltransferases preferably include a catalytic domain of about 100-250 amino acid residues in length, preferably about 130-200 amino acid residues in length, or more preferably about 160-200 amino acid residues in length. An acyltransferase domain typically includes at least one of four blocks of homology commonly found in members of the acyltransferase family. The four blocks are each characterized by the following motifs: (1) [NX]-H-

[RQ]-S-X-[LYIM]-D, SEQ ID NO:49; (2) G-X-[IF]-F-I-[RD]-R, SEQ ID NO:50; (3) F-[PLI]-E-G-[TG]-R-[SX]-[RX], SEQ ID NO:51; and (4) [VI]-[PX]-[IVL]-[IV]-P-[VI], SEQ ID NO:52. Specificity of an acyltransferase for acylation of a particular lipid target can be predicted by the presence of sequences within the four blocks, whereby particular amino acid residues are associated with particular classes of acyltransferases (as described in lewin et al., (1999) *Biochemistry* 38:5764-71, for example, the contents of which are incorporated herein by reference). For example, 58764 contains some residues in these blocks of homology that are typically found in LPAATs and not typically found in GPATs. Based on these sequence similarities, the 58764 molecules of the present invention are predicted to have similar biological activities as acyltransferase family members. Thus, the molecules of the present invention may be involved in one or more of: 1) the transfer of an acyl chain to a lipid precursor; 2) the regulation of lipid biosynthesis; 3) the regulation of wound healing; 4) the regulation of platelet aggregation; 5) the modulation of mitogenesis; 6) the modulation of cellular differentiation; 7) the modulation of actin cytoskleleton remodeling; 8) the regulation of monocyte chemotaxis; 9) the modulation of neurite retraction; 10) the modulation of vasoconstriction; 11) the modulation of glutamate and glucose uptake by astrocytes; 12) the modulation of tumor cell growth and invasion; or 13) the formation of synaptic-like microvesicles. Thus, the 58764 molecules can act as novel diagnostic targets and therapeutic agents for controlling acyltransferase-related disorders, for example, such as those diseases associated with the activities described above. As the 58764 molecules have homology to known acyltransferases, they are expected to be involved in controlling similar disorders.

The 26199, 33530, 33949, 47148, 50226, and 58764 proteins contain a significant number of structural characteristics in common with members of the transferase family. The present invention is based, at least in part, on the discovery of novel transferase family members, referred to herein as "transferase" nucleic acid and protein molecules.

A 26199, 33530, 33949, 47148, 50226, or 58764 polypeptide can include a "transferase domain" or regions homologous with an "transferase domain".

To identify the presence of a "transferase" domain in a 26199, 33530, 33949, 47148, 50226, or 58764 protein sequence, and make the determination that a polypeptide or protein of interest has a particular profile, the amino acid sequence of the protein can be searched against a database of HMMs (e.g., the Pfam database, release 2.1) using the default parameters. For example, the hmmsf program, which is available as part of the HMMER package of search programs, is a family specific default program for MILPAT0063 and a score of 15 is the default threshold score for determining a hit. Alternatively, the threshold score for determining a hit can be lowered (e.g., to 8 bits). A description of the Pfam database can be found in Sonhammer et al., (1997) *Proteins* 28(3):405-420 and a detailed description of HMMs can be found, for example, in Gribskov et al., (1990) *Meth. Enzymol.* 183:146-159; Gribskov et al., (1987) *Proc. Natl. Acad. Sci. USA* 84:4355-4358; Krogh et al., (1994) *J. Mol. Biol.* 235:1501-1531; and Stultz et al., (1993) *Protein Sci.* 2:305-314, the contents of which are incorporated herein by reference.

For further identification of domains in a 26199, 33530, 33949, 47148, 50226, or 58764 protein sequence, and make the determination that a polypeptide or protein of interest has a particular profile, the amino acid sequence of the protein can be searched against a database of domains, e.g., the Propom database (Corpet et al. (1999), *Nucl. Acids Res.* 27:263-267). The Propom protein domain database consists of an automatic compilation of homologous domains. Current versions of Propom are built using recursive PSI-BLAST searches (Altschul S F et al. (1997) *Nucleic Acids Res.* 25:3389-3402; Gouzy et al. (1999) 23:333-340) of the SWISS-PROT 38 and TREMBL protein databases. The database automatically generates a consensus sequence for each domain. A BLAST search was performed against the HMM database resulting in the identification of a "transferase" domain(s) in the amino acid sequence of human 26199 at about residues 7 to 120, 123 to 226, and 15 to 208 of SEQ ID NO:2 having 44%, 27% and 29% identity over those residues respectively; of human 33530 at about residues 367 to 415, 17 to 95, 280 to 413, 96 to 143, 109 to 155, and 216 to 382 of SEQ ID NO:5 having 91%, 49%, 35%, 56%, 40% and 30% identity over those residues respectively; of human 33949 at about residues 1 to 102, 103 to 229, 347 to 406, 568 to 608 and 484 to 521 (two local alignments), and 273 to 346 of SEQ ID NO:8 having 100%, 49%, 64%, 100%, 39%, and 56% identity over those residues respectively; of human 47148 at about residues 1 to 135, 200 to 471, and 549 to 662 of SEQ ID NO:11 having 80%, 37% and 64% identity over those residues respectively; of human 50226 at about residues 117 to 221 and 238 to 355 of SEQ ID NO:14 having 39% and 29% identity over those residues respectively; and of human 58764 at about residues 91 to 293 and 300 to 322 of SEQ ID NO:17 having 41% and 56% identity over those residues respectively.

An additional method to identify the presence of a "transferase" domain in a 26199, 33530, 33949, 47148, 50226, or 58764 protein sequence, and make the determination that a polypeptide or protein of interest has a particular profile, the amino acid sequence of the protein can be searched against a SMART database (Simple Modular Architecture Research Tool) of HMMs as described in Schultz et al. (1998), *Proc. Natl. Acad. Sci. USA* 95:5857 and Schultz et al. (2000) *Nucl. Acids Res* 28:231. The database contains domains identified by profiling with the hidden Markov models of the HMMer2 search program (R. Durbin et al. (1998) *Biological sequence analysis: probabilistic models of proteins and nucleic acids*. Cambridge University Press). The database also is extensively annotated and monitored by experts to enhance accuracy. For example, a search was performed against the HMM database resulting in the identification of a "ricin_3" domain in the amino acid sequence of human 33949 at about residues 476 to 607 of SEQ ID NO:8.

In one embodiment, 26199, 33530, 33949, 47148, and 58764 proteins include at least one transmembrane domain. As used herein, the term "transmembrane domain" includes an amino acid sequence of about 14 amino acid residues in length that spans a phospholipid membrane. More preferably, a transmembrane domain includes about at least 15, 16, 17, 18, 20, 21, 23 or 24 amino acid residues and spans a phospholipid membrane. Transmembrane domains are rich in hydrophobic residues, and typically have an α-helical structure. In a preferred embodiment, at least 50%, 60%, 70%, 80%, 90%, 95% or more of the amino acids of a transmembrane domain are hydrophobic, e.g., leucines, isoleucines, tyrosines, or tryptophans. Transmembrane domains are described in, for example, Zagotta W. N. et al., (1996) *Annual Rev. Neuronsci.* 19: 235-63, the contents of which are incorporated herein by reference.

In a preferred embodiment, 26199, 33530, 33949, 47148, and 58764 polypeptides or proteins have at least one transmembrane domain or a region which includes at least 15, 16, 17, 18, 20, 21, 23 or 24 amino acid residues and has at least about 60%, 70% 80% 90% 95%, 99%, or 100% homology with a "transmembrane domain," e.g., at least one transmembrane domain of human 26199, 33530, 33949, 47148, or 58764 (e.g., amino acid residues 33-49 and 74-94 of SEQ ID NO:2; amino acids 85-105 of SEQ ID NO:5; amino acids 8-28, 150-168, and 268-284 of SEQ ID NO:8; amino acids 106-127 and 168-192 of SEQ ID NO:11; and amino acids 51-74, 124-141, and 159-176 of SEQ ID NO:17).

In another embodiment, a 26199, 33530, 33949, 47148, or 58764 protein includes at least one "non-transmembrane domain." As used herein, "non-transmembrane domains" are domains that reside outside of the membrane. When referring to plasma membranes, non-transmembrane domains include extracellular domains (i.e., outside of the cell) and intracellular domains (i.e., within the cell). When referring to membrane-bound proteins found in intracellular organelles (e.g., mitochondria, endoplasmic reticulum, peroxisomes and microsomes), non-transmembrane domains include those domains of the protein that reside in the cytosol (i.e., the cytoplasm), the lumen of the organelle, or the matrix or the intermembrane space (the latter two relate specifically to mitochondria organelles). The C-terminal amino acid residue of a non-transmembrane domain is adjacent to an N-terminal amino acid residue of a transmembrane domain in a naturally-occurring 26199, 33530, 33949, 47148, or 58764, or 26199-, 33530-, 33949-, 47148-, or 58764-like protein.

In a preferred embodiment, a 26199, 33530, 33949, 47148, or 58764 polypeptide or protein has a "non-transmembrane domain" or a region which includes at least about 1-150, preferably about 5-140, more preferably about 10-130, and even more preferably about 16-120 amino acid residues, and has at least about 60%, 70% 80% 90% 95%, 99% or 100% homology with a "non-transmembrane domain", e.g., a non-transmembrane domain of human 26199, 33530, 33949, 47148, or 58764 (e.g., residues 1-32, 50-73 or 95-229 of SEQ ID NO:2; residues 1-84 and 105-416 of SEQ ID NO:5; residues 1-8, 29-149, 169-263, and 285-608 of SEQ ID NO:8; residues 1-105, 128-167 and 193-662 of SEQ ID NO:11; or residues 1-50, 75-123, 142-158, and 177-324 of SEQ ID NO:17). Preferably, a non-transmembrane domain is capable of catalytic activity.

A non-transmembrane domain located at the N-terminus of a 26199, 33530, 33949, 47148, or 58764 protein or polypeptide is referred to herein as an "N-terminal non-transmembrane domain." As used herein, an "N-terminal non-transmembrane domain" includes an amino acid sequence having about 1-150, preferably about 2-125, more preferably about 4-110, or even more preferably about 7-105 amino acid residues in length and is located outside the boundaries of a membrane. For example, an N-terminal non-transmembrane domain is located at about amino acid residues 1-32 of SEQ ID NO:2.

Similarly, a non-transmembrane domain located at the C-terminus of a 26199, 33530, 33949, 47148, or 58764 protein or polypeptide is referred to herein as a "C-terminal non-transmembrane domain." As used herein, a "C-terminal non-transmembrane domain" includes an amino acid sequence having about 1-600, preferably about 75-525, preferably about 125-475, more preferably about 134-469 amino acid residues in length and is located outside the boundaries of a membrane. For example, a C-terminal non-transmembrane domain is located at about amino acid residues 95-229 of SEQ ID NO:2.

In another embodiment, a 33949, 50226, or 58764 molecule can further include a signal sequence. As used herein, a "signal sequence" refers to a peptide of about 10-80 amino acid residues in length which occurs at the N-terminus of secretory and integral membrane proteins and which contains a majority of hydrophobic amino acid residues. For example, a signal sequence contains at least about 12-70 amino acid residues, preferably about 15-65 amino acid residues, more preferably about 17-63 amino acid residues, and has at least about 40-70%, preferably about 50-65%, and more preferably about 55-60% hydrophobic amino acid residues (e.g., alanine, valine, leucine, isoleucine, phenylalanine, tyrosine, tryptophan, or proline). Such a "signal sequence", also referred to in the art as a "signal peptide", serves to direct a protein containing such a sequence to a lipid bilayer. For example, in one embodiment, a 33949 protein contains a signal sequence of about amino acids 1-37 of SEQ ID NO:8. The "signal sequence" is cleaved during processing of the mature protein. The mature 33949 protein corresponds to amino acids 38-608 of SEQ ID NO:8. The 50226 or 58764 protein may include a signal sequence, and thus the mature 50226 or 58764 protein may correspond to amino acids 18-389 of SEQ ID NO:14 or amino acids 64-324 of SEQ ID NO:17 respectively.

As the 26199, 33530, 33949, 47148, 50226, or 58764 polypeptides of the invention may modulate 26199-, 33530-, 33949-, 47148-, 50226-, or 58764-mediated activities, they may be useful for developing novel diagnostic and therapeutic agents for 26199-, 33530-, 33949-, 47148-, 50226-, or 58764-mediated or related disorders, as described below.

As used herein, a "26199, 33530, 33949, 47148, 50226, or 58764 activity", "biological activity of 26199, 33530, 33949, 47148, 50226, or 58764" or "functional activity of 26199, 33530, 33949, 47148, 50226, or 58764", refers to an activity exerted by a 26199, 33530, 33949, 47148, 50226, or 58764 protein, polypeptide or nucleic acid molecule on e.g., a 26199-, 33530-, 33949-, 47148-, 50226-, or 58764-responsive cell or on a 26199, 33530, 33949, 47148, 50226, or 58764 substrate, e.g., a lipid or protein substrate, as determined in vivo or in vitro. In one embodiment, a 26199, 33530, 33949, 47148, 50226, or 58764 activity is a direct activity, such as an association with a 26199, 33530, 33949, 47148, 50226, or 58764 target molecule. A "target molecule" or "binding partner" is a molecule with which a 26199, 33530, 33949, 47148, 50226, or 58764 protein binds or interacts in nature, e.g., a lipid to which the 26199, 33530, 33949, 47148, 50226, or 58764 protein attaches an acyl chain. A 26199, 33530, 33949, 47148, 50226, or 58764 activity can also be an indirect activity, e.g., a cellular signaling activity mediated by interaction of the 26199, 33530, 33949, 47148, 50226, or 58764 protein with a 26199, 33530, 33949, 47148, 50226, or 58764 ligand.

The transferase molecules of the present invention are predicted to modulate and facilitate cell proliferation, differentiation, motility, and apoptosis. Thus, the transferase molecules of the present invention may play a role in cellular growth signaling mechanisms. As used herein, the term "cellular growth signaling mechanism" includes signal transmissions from cell receptors, e.g., growth factor receptors, which regulate one or more of the following: 1) cell transversal through the cell cycle, 2) cell differentiation, 3) cell migration and patterning, and 4) programmed cell death. Throughout development and in the adult organism, cell fate and activity is determined, in part, by extracellular and intracellular stimuli, e.g., growth factors, angiogenic factors, chemotactic factors, neurotrophic factors, cytokines, and hormones. These stimuli act on their target cells by initiating signal transduction cascades that alter the pattern of gene expression and metabolic activity so as to mediate the appropriate cellular response. The transferase molecules of the present invention are predicted to be involved in the initiation or modulation of cellular signal transduction pathways that modulate cell growth, differentiation, migration and/or apoptosis. Thus, the transferase molecules, by participating in cellular growth signaling mechanisms, may modulate cell behavior and act as therapeutic agents for controlling cellular proliferation, differentiation, migration, and apoptosis.

Altered expression of factors (e.g., a transferase molecule) involved in the regulation of signaling pathways associated with cell growth, differentiation, migration, and apoptosis can lead to perturbed cellular proliferation, which in turn can lead to cellular proliferative and/or differentiative disorders. As used herein, a "cellular proliferative disorder" includes a disorder, disease, or condition characterized by a deregulated, e.g., upregulated or downregulated, growth response. As used herein, a "cellular differentiative disorder" includes a disorder, disease, or condition characterized by aberrant cellular differentiation. Thus, the transferase molecules can act as novel diagnostic targets and therapeutic agents for controlling cellular proliferative and/or differentiative disorders.

Examples of cellular proliferative and/or differentiative disorders include cancer, e.g., carcinoma, sarcoma, metastatic disorders or hematopoietic neoplastic disorders, e.g., leukemias. A metastatic tumor can arise from a multitude of primary tumor types, including but not limited to those of prostate, colon, lung, breast and liver origin.

The 26199, 33530, 33949, 47148, 50226, and 58764 nucleic acid and protein of the invention can be used to treat and/or diagnose a variety of proliferative disorders. E.g., such disorders include hematopoietic neoplastic disorders.

Gene Expression Analysis of 26199, 33530, 33949, 50226 and 58764

Human 26199, 33530, 33949, 50226 or 58764 expression was measured by TaqMan® quantitative PCR (Perkin Elmer Applied Biosystems) in cDNA prepared from a variety of normal and diseased (e.g., cancerous) human tissues or cell lines.

26199 was identified as being induced in MCF10A and MCF10AT3B human breast epithelial cells, following stimulation with epidermal growth factor (EGF). Taqman results for 26199 on cDNA from untreated MCF10A, untreated MCF10AT3B cells and cells treated with 10 ng EGF/ml for 0.5, 1, 2, 4 and 8 hours is shown in the following Table 2. In the EGF treated MCF10A and MCF10AT3B panel, 26199 expression increased in MCF10A cells at 1 hour through 4 hours post EGF-treatment. This was consistent with the array data, although slightly delayed, as the array data showed an increase in 26199 expression at 30 minutes post EGF treatment.

The 25K array was profiled with probes generated from untreated MCF10A cells and MCF10A cells treated with 10 ng EGF/ml for 0.5, 1, 2, 4 and 8 hours. The 25K array was also profiled with probes generated from untreated MCF10AT3B cells and MCF10AT3B cells treated with 10 ng EGF/ml for 0.5, 1, 2, 4 and 8 hours. 26199 expression increased following EGF treatment.

The MPGv3.0 array was profiled with probes generated from 4 normal breast tissue samples, 4 ductal carcinoma in situ (DCIS) samples, 4 invasive ductal carcinoma (IDC) samples and 3 invasive lobular carcinoma (ILC) samples. A clone representing 26199 showed expression levels at 2.6-4.5 the median array intensity of the normal breast samples in 3/4 DCIS samples.

This discrepancy may be explained by the fact that RNAs from different EGF-treated MCF10A cell experiments were used for the array and Taqman experiments. MCF10AT3B cells also showed an increase in 26199 expression at 1 hour post EGF-treatment, but overall expression levels were low (Ct values ~30).

TABLE 2

26199 Expression in EGF-treated MCF10A and MCF10AT3B Cells

| | | | |
|---|---|---|---|
| MCF10A 0 hr | 27.0 | 15.7 | 0.4 |
| MCF10A 0.5 hr | 27.0 | 15.6 | 0.4 |
| MCF10A 1 hr | 25.5 | 15.9 | 1.3 |
| MCF10A 2 hr | 25.2 | 15.8 | 1.4 |
| MCF10A 4 hr | 25.7 | 15.9 | 1.1 |
| MCF10A 8 hr | 26.5 | 16.0 | 0.7 |
| MCF3B 0 hr | 30.7 | 17.8 | 0.1 |
| MCF3B 0.5 hr | 31.0 | 17.8 | 0.1 |
| MCF3B 1 hr | 29.1 | 17.3 | 0.3 |
| MCF3B 2 hr | 30.1 | 18.4 | 0.3 |
| MCF3B 4 hr | 30.1 | 18.1 | 0.2 |
| MCF3B 8 hr | 30.3 | 17.7 | 0.2 |

The following Table 3 shows the Taqman results for an oncology panel (Phase I) of human tissues. 26199 expression was upregulated by 4-16-fold in 6/6 breast tumor samples versus 3/4 normal breast samples. Lung tumors uniformly expressed increased levels of 26199 in comparison to normal lung samples.

TABLE 3

26199 Expression in Clinical Tumor Samples

| | Average 26199 | Average Beta 2 | Relative Expression |
|---|---|---|---|
| Breast N | 37.0 | 22.2 | 0.0 |
| Breast N | 38.5 | 20.6 | 0.0 |
| Breast N | 33.2 | 17.2 | 0.0 |
| Breast N | 31.3 | 19.0 | 0.6 |
| Breast T | 30.8 | 17.3 | 0.3 |
| Breast T | 31.8 | 17.9 | 0.2 |
| Breast T | 28.1 | 16.2 | 0.8 |
| Breast T | 30.0 | 16.5 | 0.3 |
| Breast T | 32.2 | 18.2 | 0.2 |
| Breast T | 32.5 | 19.3 | 0.4 |
| Ovary N | 28.9 | 17.3 | 1.1 |
| Ovary N | 30.2 | 18.7 | 1.1 |
| Ovary N | 31.2 | 19.1 | 0.8 |
| Ovary N | 34.9 | 22.3 | 0.5 |
| Ovary T | 33.1 | 18.3 | 0.1 |
| Ovary T | 32.5 | 17.6 | 0.1 |
| Ovary T | 30.3 | 16.9 | 0.3 |
| Ovary T | 32.8 | 17.8 | 0.1 |
| Ovary T | 32.3 | 17.3 | 0.1 |
| Ovary T | 35.1 | 19.2 | 0.0 |
| Ovary T | 33.3 | 20.3 | 0.4 |
| Ovary T | 33.0 | 16.5 | 0.0 |
| Lung N | 40.0 | 21.8 | 0.0 |
| Lung N | 40.0 | 18.5 | 0.0 |
| Lung N | 32.7 | 16.2 | 0.0 |
| Lung N | 38.0 | 15.6 | 0.0 |
| Lung T | 29.5 | 16.1 | 0.3 |
| Lung T | 27.1 | 16.0 | 1.4 |
| Lung T | 31.8 | 17.4 | 0.2 |
| Lung T | 31.4 | 16.5 | 0.1 |
| Lung T | 30.4 | 18.7 | 1.0 |
| Lung T | 32.3 | 18.6 | 0.3 |
| Lung T | 30.5 | 17.2 | 0.3 |

The following Table 4 shows the Taqman results for another oncology (Phase II) panel of human tissues. Breast, ovary, colon and lung tumors all expressed 26199. Differential expression between tumor and normal tissues was most significant in colon and lung tissues.

TABLE 4

| 26199 Expression in Clinical Tumor Samples | Average 26199 | Average Beta 2 | Relative Expression |
|---|---|---|---|
| Colon N | 32.2 | 16.9 | 0.0 |
| Colon N | 35.4 | 21.1 | 0.0 |
| Colon N | 30.0 | 18.0 | 0.3 |
| Colon N | 31.2 | 16.8 | 0.0 |
| Colon T | 31.0 | 16.2 | 0.0 |
| Colon T | 26.8 | 17.2 | 1.3 |
| Colon T | 31.5 | 16.0 | 0.0 |
| Colon T | 30.1 | 17.0 | 0.1 |
| Colon T | 29.7 | 16.2 | 0.1 |
| Colon T | 32.4 | 16.0 | 0.0 |
| Liver Met | 30.7 | 17.3 | 0.1 |
| Liver Met | 31.3 | 19.6 | 0.3 |
| Liver Met | 31.6 | 17.8 | 0.1 |
| Liver Met | 31.9 | 17.7 | 0.1 |
| Liver Nor | 33.0 | 16.3 | 0.0 |
| Liver Nor | 36.8 | 22.6 | 0.0 |
| Brain N | 28.3 | 19.6 | 2.5 |
| Brain N | 28.8 | 20.2 | 2.7 |
| Brain N | 30.4 | 19.5 | 0.5 |
| Brain N | 27.3 | 19.5 | 4.5 |
| Astrocytes | 33.5 | 21.1 | 0.2 |
| Brain T | 36.3 | 16.6 | 0.0 |
| Brain T | 35.6 | 17.4 | 0.0 |
| Brain T | 34.0 | 18.2 | 0.0 |
| Brain T | 32.2 | 17.0 | 0.0 |
| Brain T | 33.6 | 19.2 | 0.0 |
| HMVEC | 29.9 | 15.9 | 0.1 |
| HMVEC | 30.0 | 16.5 | 0.1 |
| Placenta | 36.3 | 22.1 | 0.0 |
| Fetal Adren | 34.9 | 23.7 | 0.4 |
| Fetal Adren | 25.4 | 16.2 | 1.7 |
| Fetal Liver | 27.9 | 19.7 | 3.3 |
| Fetal Liver | 31.5 | 18.3 | 0.1 |

For Taqman results on the phase I tissue panel, highest expression of 26199 orthologs is found in normal brain cortex as shown in the following Table 5.

TABLE 5

26199 Expression w/β2 in Normal Tissues

| Tissue Type | Mean | β2 Mean | ∂∂ Ct | Expression |
|---|---|---|---|---|
| Artery normal | 31.98 | 21.32 | 10.66 | 0.6159 |
| Vein normal | 33.19 | 19.65 | 13.54 | 0.084 |
| Aortic SMC EARLY | 29.74 | 20.91 | 8.82 | 2.205 |
| Coronary SMC | 29.25 | 21.77 | 7.48 | 5.6014 |
| Static HUVEC | 26.98 | 20.16 | 6.83 | 8.82 |
| Shear HUVEC | 26.61 | 20.43 | 6.18 | 13.7445 |
| Heart normal | 26.57 | 18.23 | 8.35 | 3.0648 |
| Heart CHF | 26.59 | 18.58 | 8.02 | 3.8658 |
| Kidney | 27.37 | 19.32 | 8.04 | 3.7863 |
| Skeletal Muscle | 27.2 | 21.36 | 5.84 | 17.4576 |
| Adipose normal | 34.56 | 19.29 | 15.28 | 0.0251 |
| Pancreas | 28.25 | 20.68 | 7.58 | 5.2444 |
| primary osteoblasts | 28.33 | 18.55 | 9.79 | 1.1335 |
| Osteoclasts (diff) | 36.87 | 16.93 | 19.94 | 0 |
| Skin normal | 30.56 | 20.45 | 10.1 | 0.9112 |
| Spinal cord normal | 30 | 20.06 | 9.94 | 1.018 |
| Brain Cortex normal | 24.36 | 20.31 | 4.04 | 60.5806 |
| Brain Hypothalamus normal | 27.36 | 20.49 | 6.88 | 8.5196 |
| Nerve | 29.99 | 23.6 | 6.39 | 11.9239 |
| DRG (Dorsal Root Ganglion) | 28.39 | 20.9 | 7.5 | 5.5435 |
| Glial Cells (Astrocytes) | 27.25 | 22.14 | 5.12 | 28.8557 |
| Glioblastoma | 30.12 | 17.41 | 12.71 | 0.1492 |
| Breast normal | 28.45 | 19.5 | 8.95 | 2.022 |
| Breast tumor | 26.3 | 17.65 | 8.64 | 2.498 |
| Ovary normal | 27.08 | 19.48 | 7.6 | 5.1543 |
| Ovary Tumor | 28.14 | 19.61 | 8.52 | 2.7241 |
| Prostate Normal | 28.88 | 18.95 | 9.93 | 1.0287 |
| Prostate Tumor | 27.23 | 17.13 | 10.11 | 0.908 |

TABLE 5-continued

26199 Expression w/β2 in Normal Tissues

| Tissue Type | Mean | β2 Mean | ∂∂ Ct | Expression |
|---|---|---|---|---|
| Epithelial Cells (Prostate) | 27.35 | 21.06 | 6.29 | 12.7797 |
| Colon normal | 30.91 | 17.58 | 13.34 | 0.0968 |
| Colon Tumor | 26.05 | 18.32 | 7.73 | 4.7102 |
| Lung normal | 33.2 | 17.39 | 15.81 | 0.0174 |
| Lung tumor | 26.78 | 18.11 | 8.66 | 2.4636 |
| Lung COPD | 31.59 | 18.16 | 13.43 | 0.0906 |
| Colon IBD | 34.27 | 17.11 | 17.16 | 0.0068 |
| Liver normal | 32.2 | 19.23 | 12.97 | 0.1251 |
| Liver fibrosis | 29.07 | 20.81 | 8.27 | 3.2508 |
| Dermal Cells-fibroblasts | 31.31 | 19.29 | 12.02 | 0.2408 |
| Spleen normal | 27.47 | 18.92 | 8.55 | 2.668 |
| Tonsil normal | 28.11 | 16.62 | 11.49 | 0.3465 |
| Lymph node | 28.27 | 18.01 | 10.26 | 0.8155 |
| Small Intestine | 31.52 | 19.39 | 12.14 | 0.2223 |
| Skin-Decubitus | 29.75 | 19.63 | 10.12 | 0.8986 |
| Synovium | 32.38 | 18.95 | 13.44 | 0.09 |
| BM-MNC (Bone marrow mononuclear cells) | 26.89 | 16.43 | 10.46 | 0.7124 |
| Activated PBMC | 30.66 | 15.45 | 15.21 | 0.0264 |

The following Table 6 shows the Taqman results of an oncology cell lines panel. 26199 is expressed in many tumor cell lines. MCF-7 human breast cancer cells is expressed at the highest levels.

TABLE 6

| 26199 Expression in Cell Lines | Average 26199 | Average B-2 | Relative Expression |
|---|---|---|---|
| MCF-7 | 24.5 | 19.0 | 45.9 |
| ZR75 | 26.6 | 18.7 | 8.6 |
| T47D | 25.5 | 18.4 | 15.6 |
| MDA 231 | 26.8 | 17.3 | 2.8 |
| MDA 435 | 27.5 | 16.3 | 0.9 |
| DLD-1 | 25.0 | 19.4 | 42.5 |
| SW 480 | 27.5 | 16.9 | 1.4 |
| SW 620 | 25.7 | 18.6 | 15.0 |
| HCT 116 | 26.5 | 18.4 | 7.7 |
| HT 29 | 27.7 | 16.1 | 0.7 |
| Colo 205 | 25.8 | 15.3 | 1.4 |
| NCIH 125 | 26.6 | 17.9 | 5.3 |
| NCIH 67 | 25.6 | 18.8 | 18.8 |
| NCIH 322 | 27.0 | 18.6 | 6.1 |
| NCIH 460 | 26.6 | 17.2 | 3.2 |
| A549 | 25.9 | 18.6 | 14.0 |
| NHBE | 27.7 | 19.0 | 5.0 |

Confirming previous Taqman results, in a breast cancer cell model panel, 26199 showed increased expression in MCF10A cells treated with EGF and high expression in MCF-7 cells as shown in the following Table 7.

TABLE 7

26199 Expression in Breast Cancer Cell Model Panel

| Tissue Type | 26199.2 Mean | β2 Mean | ∂∂ Ct | Expression |
|---|---|---|---|---|
| MCF10MS | 33.07 | 20.2 | 12.87 | 0.13 |
| MCF10A | 28.86 | 19.93 | 8.93 | 2.05 |
| MCF10AT.cl1 | 27.27 | 20 | 7.27 | 6.48 |
| MCF10AT.cl3 | 26.41 | 19.45 | 6.96 | 8.00 |
| MCF10AT1 | 28.55 | 20.47 | 8.08 | 3.70 |
| MCF10AT3B | 28.27 | 20.23 | 8.04 | 3.79 |

TABLE 7-continued

26199 Expression in Breast Cancer Cell Model Panel

| Tissue Type | 26199.2 Mean | β2 Mean | ∂∂ Ct | Expression |
|---|---|---|---|---|
| MCF10CA1a.cl1 | 33.88 | 17.32 | 16.57 | 0.01 |
| MCF10CA1a.cl1 Agar | 33.52 | 24.69 | 8.83 | 2.20 |
| MCF10A.m25 Plastic | 31.13 | 24.23 | 6.9 | 8.37 |
| MCF10CA Agar | 30.59 | 22.17 | 8.41 | 2.93 |
| MCF10CA Plastic | 29.75 | 21.52 | 8.22 | 3.35 |
| MCF3B Agar | 29.02 | 22.31 | 6.71 | 9.59 |
| MCF3B Plastic | 28.29 | 22.19 | 6.1 | 14.58 |
| MCF10A EGF 0 hr | 26.32 | 17.72 | 8.61 | 2.57 |
| MCF10A EGF 0.5 hr | 25.47 | 17.66 | 7.8 | 4.47 |
| MCF10A EGF 1 hr | 25.24 | 17.77 | 7.47 | 5.62 |
| MCF10A EGF 2 hr | 24.84 | 17.93 | 6.9 | 8.37 |
| MCF10A EGF 4 hr | 25.77 | 17.58 | 8.19 | 3.42 |
| MCF10A EGF 8 hr | 25.7 | 18.02 | 7.68 | 4.88 |
| MCF10A IGF1A 0 hr | 28.02 | 21.95 | 6.07 | 14.94 |
| MCF10A IGF1A 0.5 hr | 28.84 | 22.38 | 6.46 | 11.32 |
| MCF10A IGF1A 1 hr | 28.61 | 21.93 | 6.68 | 9.75 |
| MCF10A IGF1A 3 hr | 28.55 | 21.86 | 6.7 | 9.65 |
| MCF10A IGF1A 24 hr | 27.09 | 21.53 | 5.56 | 21.20 |
| MCF10AT3B.cl5 Plastic | 28.56 | 22.27 | 6.29 | 12.78 |
| MCF10AT3B.cl6 Plastic | 29.16 | 21.9 | 7.25 | 6.55 |
| MCF10AT3B.cl3 Plastic | 29.12 | 21.88 | 7.25 | 6.59 |
| MCF10AT3B.cl1 Plastic | 28.68 | 22.09 | 6.59 | 10.34 |
| MCF10AT3B.cl4 Plastic | 28.85 | 21.75 | 7.09 | 7.31 |
| MCF10AT3B.cl2 Plastic | 28.84 | 22.13 | 6.71 | 9.55 |
| MCF10AT3B.cl5 Agar | 31.66 | 24.07 | 7.6 | 5.15 |
| MCF10AT3B.cl6 Agar | 30.9 | 24.27 | 6.63 | 10.13 |
| MCF-7 | 27.43 | 23.34 | 4.09 | 58.52 |
| ZR-75 | 28.2 | 21.51 | 6.7 | 9.65 |
| T47D | 28.65 | 21.72 | 6.93 | 8.20 |
| MDA-231 | 29.11 | 20.47 | 8.65 | 2.49 |
| MDA-435 | 32.42 | 20.43 | 11.99 | 0.25 |
| SkBr3 | 28.41 | 20.93 | 7.47 | 5.62 |
| Hs578Bst | 30.59 | 19.98 | 10.61 | 0.64 |
| Hs578T | 28.68 | 19.93 | 8.74 | 2.33 |
| MCF10AT3B Agar | 31.95 | 26.23 | 5.71 | 19.04 |

For Taqman results in the angiogenesis panel, highest expression of 26199 orthologs is found in Wilm's tumor as shown in the following Table 8.

TABLE 8

Expression of 26199 w/β2 in the Angiogenesis Panel

| Tissue Type | 26199.2 Mean | β2 Mean | ∂∂ Ct | Expression |
|---|---|---|---|---|
| ONC 101 Hemangioma | 29.19 | 20.93 | 8.26 | 3.26 |
| ONC 102 Hemangioma | 28.2 | 19.48 | 8.72 | 2.37 |
| ONC 103 Hemangioma | 31.97 | 20.1 | 11.87 | 0.27 |
| CHT 1273 Glioblastoma | 25.92 | 20.98 | 4.95 | 32.46 |
| CHT 216 Glioblastoma | 28.43 | 18.61 | 9.82 | 1.10 |
| CHT 501 Glioblastoma | 28.2 | 21.54 | 6.66 | 9.89 |
| NDR 203 Normal Kidney | 28.88 | 21.8 | 7.08 | 7.39 |
| PIT 213 Renal Cell Carcinoma | 34.1 | 21.15 | 12.96 | 0.13 |
| CHT 732 Wilms Tumor | 25.18 | 20.18 | 5 | 31.25 |
| CHT 765 Wilms Tumor | 27.55 | 22.97 | 4.59 | 41.67 |
| NDR 295 Skin | 32.78 | 22.2 | 10.58 | 0.65 |
| CHT 1424 Uterine Adenocarcinoma | 27.2 | 19.95 | 7.25 | 6.55 |
| CHT 1238 Neuroblastoma | 28.02 | 20.8 | 7.22 | 6.68 |
| BWH 78 Fetal Adrenal | 25.25 | 19.23 | 6.02 | 15.41 |
| BWH 74 Fetal Kidney | 26.73 | 21.11 | 5.62 | 20.33 |
| BWH 4 Fetal Heart | 27.56 | 21.14 | 6.42 | 11.64 |
| MPI 849 Normal Heart | 28.16 | 20.2 | 7.96 | 4.00 |
| CLN 746 Spinal cord | 29.54 | 21.25 | 8.29 | 3.21 |

The following Table 9 shows the Taqman results for an oncology panel (Plate I) of human tissues. 33530 expression was upregulated by 3/8 breast tumor samples versus normal breast samples. 33530 expression was upregulated by 5/7 lung tumor samples versus normal lung samples. 33530 expression is found in both ovary tumors and normal ovary samples.

TABLE 9

33530 Expression in Oncology Plate I

| | Average 33530 | Average Beta 2 | Relative Expression |
|---|---|---|---|
| Brst N | 29.4 | 22.4 | 7.8 |
| Brst N | 28.9 | 21.2 | 4.8 |
| Brst N | 25.8 | 17.5 | 3.1 |
| Brst N | 26.3 | 19.9 | 11.4 |
| Brst T | 24.0 | 16.5 | 5.5 |
| Brst T | 30.0 | 24.1 | 16.7 |
| Brst T | 23.2 | 15.7 | 5.5 |
| Brst T | 31.0 | 25.0 | 16.2 |
| Brst T | 25.0 | 16.0 | 2.0 |
| Brst T | 25.5 | 16.5 | 1.9 |
| Brst T | 28.3 | 18.2 | 0.9 |
| Brst T | 26.9 | 19.5 | 6.1 |
| Ovry N | 25.4 | 17.4 | 3.9 |
| Ovry N | 28.6 | 18.4 | 0.8 |
| Ovry T | 28.4 | 18.3 | 0.9 |
| Ovry T | 27.2 | 17.6 | 1.3 |
| Ovry T | 26.6 | 16.8 | 1.1 |
| Ovry T | 28.4 | 17.6 | 0.6 |
| Ovry T | 27.9 | 17.3 | 0.7 |
| Ovry T | 30.1 | 19.2 | 0.5 |
| Lung N | 34.2 | 22.3 | 0.3 |
| Lung N | 31.2 | 18.9 | 0.2 |
| Lung N | 25.4 | 15.0 | 0.7 |
| Lung N | 28.2 | 16.2 | 0.2 |
| Lung T | 24.3 | 16.1 | 3.3 |
| Lung T | 25.9 | 17.0 | 2.0 |
| Lung T | 26.7 | 17.5 | 1.7 |
| Lung T | 27.4 | 16.6 | 0.6 |
| Lung T | 26.6 | 18.8 | 4.5 |
| Lung T | 25.9 | 17.2 | 2.4 |
| Lung T | 26.7 | 17.3 | 1.5 |

The following Table 10 shows the Taqman results for an oncology panel (Plate II) of human tissues. 33530 expression is found in both colon tumors and normal colon samples as well as normal liver and liver metastases. 33530 expression was downregulated by 6/6 glioblastoma samples versus normal brain samples.

TABLE 10

| 33530 Expression in Oncology Plate II | | | |
|---|---|---|---|
| | Average 33530 | Average Beta 2 | Relative Expression |
| Colon N | 25.6 | 16.5 | 1.9 |
| Colon N | 28.8 | 20.7 | 3.6 |
| Colon N | 25.9 | 18.1 | 4.4 |
| Colon N | 25.3 | 16.1 | 1.7 |
| Colon T | 23.2 | 15.7 | 5.5 |
| Colon T | 26.8 | 16.5 | 0.8 |
| Colon T | 24.0 | 15.7 | 3.1 |
| Colon T | 25.0 | 16.3 | 2.5 |
| Colon T | 24.5 | 16.3 | 3.4 |
| Colon T | 30.4 | 23.2 | 6.9 |
| Colon T | 25.3 | 15.7 | 1.3 |
| Liver Met | 26.7 | 16.9 | 1.1 |
| Liver Met | 28.5 | 19.3 | 1.7 |
| Liver Met | 27.7 | 17.5 | 0.9 |
| Liver Met | 28.2 | 17.3 | 0.5 |
| Liver Norm | 27.4 | 17.1 | 0.8 |
| Liver Norm | 30.7 | 22.5 | 3.6 |
| Brain N | 27.5 | 19.1 | 3.0 |
| Brain N | 26.7 | 18.6 | 3.7 |
| Brain N | 28.5 | 19.5 | 1.9 |
| Brain N | 28.0 | 19.5 | 2.7 |
| GLIO | 29.0 | 17.8 | 0.4 |
| GLIO | 28.0 | 16.5 | 0.3 |
| GLIO | 27.8 | 17.2 | 0.7 |
| GLIO | 27.9 | 17.1 | 0.6 |
| GLIO | 27.5 | 16.8 | 0.6 |
| GLIO | 29.3 | 18.9 | 0.7 |
| HMVEC | 24.9 | 15.9 | 1.9 |
| HMVEC | 24.4 | 16.6 | 4.4 |
| Placenta | 25.5 | 16.0 | 1.5 |
| Fetal Adrenal | 30.8 | 23.6 | 6.9 |
| Fetal Adrenal | 30.4 | 23.0 | 5.9 |
| Fetal Liver | 25.8 | 19.1 | 10.0 |
| Fetal Liver | 27.6 | 19.3 | 3.2 |

The following Table 11 shows the Taqman results of an oncology cell lines panel. 33530 is expressed in many tumor cell lines. NCIH67 cancer cells are expressed at the highest levels.

TABLE 11

| 33530 Expression in Xenograph Cell Lines | | | |
|---|---|---|---|
| | Average 33530 | Average B-2 | Relative Expression |
| MCF-7 | 24.5 | 19.3 | 27.5 |
| ZR75 | 24.9 | 18.0 | 8.5 |
| T47D | 24.9 | 18.3 | 10.0 |
| MDA 231 | 25.5 | 17.8 | 4.8 |
| MDA 435 | 24.4 | 16.2 | 3.4 |
| DLD-1 | 24.1 | 19.0 | 29.9 |
| SW 480 | 24.4 | 16.6 | 4.4 |
| SW 620 | 24.7 | 18.2 | 11.1 |
| HCT 116 | 24.7 | 18.2 | 11.0 |
| HT 29 | 23.5 | 15.5 | 3.8 |
| Colo 205 | 22.2 | 14.6 | 4.9 |
| NCIH 125 | 24.9 | 17.2 | 4.9 |
| NCIH 67 | 22.8 | 18.6 | 54.8 |
| NCIH 322 | 25.4 | 18.1 | 6.4 |
| NCIH 460 | 25.3 | 17.4 | 4.1 |
| A549 | 24.6 | 19.1 | 22.0 |
| NHBE | 24.9 | 18.5 | 11.4 |

For Taqman results on the phase I tissue panel, highest expression of 33530 orthologs is found in epithelial cells, glial cells and pancreas as shown in the following Table 12.

TABLE 12

| Phase 1.2.2 Expression of 33530 w/β2 | | | | |
|---|---|---|---|---|
| Tissue Type | Mean | β2 Mean | ∂∂Ct | Expression |
| Aorta/normal | 37.40 | 24.33 | 13.07 | 0.00 |
| Fetal heart/normal | 26.36 | 20.76 | 5.60 | 20.69 |
| Heart normal | 28.15 | 19.80 | 8.36 | 3.05 |
| Heart/CHF | 28.75 | 21.82 | 6.93 | 8.23 |
| Vein/Normal | 31.44 | 20.27 | 11.17 | 0.43 |
| Spinal cord/Normal | 29.60 | 19.98 | 9.62 | 1.27 |
| Brain cortex/Normal | 27.74 | 21.97 | 5.77 | 18.39 |
| Brain hypothalamus/Normal | 27.36 | 21.03 | 6.33 | 12.43 |
| Glial cells (Astrocytes) | 26.81 | 22.55 | 4.26 | 52.19 |
| Brain/Glioblastoma | 27.58 | 19.24 | 8.34 | 3.09 |
| Breast/Normal | 30.40 | 20.10 | 10.31 | 0.79 |
| Breast tumor/IDC | 27.78 | 19.53 | 8.26 | 3.27 |
| OVARY/Normal | 29.29 | 21.91 | 7.38 | 6.00 |
| OVARY/Tumor | 29.68 | 20.37 | 9.32 | 1.57 |
| Pancreas | 29.50 | 25.16 | 4.34 | 49.38 |
| Prostate/Normal | 28.56 | 20.13 | 8.44 | 2.89 |
| Prostate/Tumor | 26.51 | 18.99 | 7.52 | 5.45 |
| Colon/normal | 31.80 | 18.59 | 13.21 | 0.11 |
| Colon/tumor | 25.95 | 19.55 | 6.40 | 11.88 |
| Colon/IBD | 29.96 | 19.32 | 10.64 | 0.63 |
| Kidney/normal | 28.40 | 21.43 | 6.97 | 7.98 |
| Liver/normal | 28.56 | 19.72 | 8.84 | 2.18 |
| Liver fibrosis | 28.54 | 20.98 | 7.56 | 5.30 |
| Fetal Liver/normal | 27.48 | 22.30 | 5.18 | 27.58 |
| Lung/normal | 30.84 | 18.76 | 12.08 | 0.23 |
| Lung/tumor | 28.44 | 19.05 | 9.39 | 1.49 |
| Lung/COPD | 27.78 | 19.06 | 8.73 | 2.36 |
| Spleen/normal | 32.91 | 21.51 | 11.40 | 0.37 |
| Tonsil/normal | 30.34 | 19.01 | 11.33 | 0.39 |
| Lymph node/normal | 30.65 | 19.50 | 11.15 | 0.44 |
| Thymus/normal | 28.21 | 20.28 | 7.93 | 4.11 |
| Epithelial Cells (prostate) | 24.93 | 21.34 | 3.60 | 82.76 |
| Endothelial Cells (aortic) | 29.20 | 21.77 | 7.43 | 5.80 |
| Skeletal Muscle/Normal | 30.83 | 21.49 | 9.35 | 1.54 |
| Fibroblasts (Dermal) | 27.80 | 19.85 | 7.95 | 4.06 |
| Skin/normal | 30.89 | 22.13 | 8.76 | 2.31 |
| Adipose/Normal | 30.81 | 19.69 | 11.12 | 0.45 |
| Osteoblasts (primary) | 29.02 | 21.13 | 7.89 | 4.23 |
| Osteoblasts (Undiff) | 26.95 | 19.97 | 6.98 | 7.92 |
| Osteoblasts(Diff) | 26.73 | 19.10 | 7.63 | 5.07 |
| Osteoclasts | 30.45 | 18.45 | 12.01 | 0.24 |
| Aortic SMC Early | 26.91 | 21.36 | 5.55 | 21.42 |
| Aortic SMC Late | 28.93 | 24.16 | 4.78 | 36.52 |
| shear HUVEC | 26.17 | 21.42 | 4.76 | 37.03 |
| static HUVEC | 27.71 | 21.97 | 5.75 | 18.65 |
| Osteoclasts(Undiff) | 32.78 | 17.43 | 15.35 | 0.02 |

Table 13 below shows Taqman results for an oncology cell lines panel. 33949 was expressed at high levels in many tumor cell lines, including DLD-1, ZR-75, SW620, NCIH125 and MCF-7.

TABLE 13

| 33949 Expression in Xenograph Panel | | | | |
|---|---|---|---|---|
| | Average 33949 | Average B-2 | DCt | Relative Expression |
| MCF-7 | 22.0 | 23.1 | −1.1 | 2166.0 |
| ZR75 | 21.2 | 23.1 | −1.9 | 3823.8 |
| T47D | 21.6 | 22.0 | −0.5 | 1375.5 |
| MDA 231 | 21.6 | 21.0 | 0.7 | 619.9 |
| MDA 435 | 21.8 | 19.7 | 2.1 | 238.2 |
| DLD-1 | 21.3 | 25.0 | −3.7 | 12996.0 |
| SW 480 | 21.7 | 19.4 | 2.3 | 203.1 |
| SW 620 | 20.9 | 22.3 | −1.4 | 2657.4 |
| HCT 116 | 22.1 | 22.1 | 0.0 | 993.1 |
| HT 29 | 22.2 | 19.6 | 2.6 | 162.1 |
| Colo 205 | 22.3 | 18.7 | 3.6 | 84.2 |
| NCIH 125 | 21.1 | 21.7 | −0.6 | 1489.7 |
| NCIH 67 | 21.0 | 22.3 | −1.2 | 2329.5 |

TABLE 13-continued

| 33949 Expression in Xenograph Panel | | | | |
|---|---|---|---|---|
| | Average 33949 | Average B-2 | DCt | Relative Expression |
| NCIH 322 | 22.6 | 22.2 | 0.4 | 737.1 |
| NCIH 460 | 20.9 | 21.6 | −0.7 | 1613.3 |
| A549 | 22.2 | 23.1 | −0.9 | 1859.6 |
| NHBE | 23.2 | 23.0 | 0.2 | 858.6 |
| SKOV-3 | 24.4 | 20.8 | 3.6 | 82.2 |
| OVCAR-3 | 24.4 | 23.9 | 0.4 | 732.0 |
| 293 | 22.9 | 23.9 | −1.0 | 2013.9 |
| 293T | 22.9 | 25.3 | −2.4 | 5259.8 |

In an oncology phase I panel of human tissues, Taqman results showed highest expression of 33949 in the normal brain cortex and kidney pools as shown in the following Table 14. Breast, colon and lung tumor pools expressed higher levels of 33949 than their respective normal tissue counterparts.

TABLE 14

| Phase 1.3.3 Expression of 33949 | | | | |
|---|---|---|---|---|
| Tissue Type | Mean | β2 Mean | ∂∂Ct | Expression |
| Artery normal | 31.23 | 22.2 | 9.03 | 1.91 |
| Vein normal | 32.41 | 20.47 | 11.95 | 0.25 |
| Aortic SMC EARLY | 28.88 | 21.97 | 6.91 | 8.34 |
| Coronary SMC | 28.32 | 23.06 | 5.26 | 26.01 |
| Static HUVEC | 25.88 | 20.7 | 5.18 | 27.49 |
| Shear HUVEC | 26.43 | 21.16 | 5.26 | 26.01 |
| Heart normal | 27.95 | 19.02 | 8.92 | 2.06 |
| Heart CHF | 26.23 | 19.27 | 6.96 | 8.06 |
| Kidney | 24.45 | 20.72 | 3.73 | 75.36 |
| Skeletal Muscle | 28.6 | 21.41 | 7.18 | 6.87 |
| Adipose normal | 31.28 | 19.6 | 11.68 | 0.30 |
| Pancreas | 26.29 | 21.61 | 4.67 | 39.15 |
| primary osteoblasts | 27.75 | 19.37 | 8.38 | 3.00 |
| Osteoclasts (diff) | 40 | 17.53 | 22.47 | 0.00 |
| Skin normal | 29.98 | 21.37 | 8.62 | 2.55 |
| Spinal cord normal | 29.07 | 19.88 | 9.2 | 1.71 |
| Brain Cortex normal | 23.39 | 21.23 | 2.15 | 225.31 |
| Brain Hypothalamus normal | 26.27 | 21.24 | 5.03 | 30.71 |
| Nerve | 33.73 | 23.85 | 9.88 | 1.06 |
| DRG (Dorsal Root Ganglion) | 27.38 | 21.94 | 5.43 | 23.12 |
| Glial Cells (Astrocytes) | 27.7 | 22.29 | 5.41 | 23.60 |
| Glioblastoma | 25.72 | 18.29 | 7.43 | 5.78 |
| Breast normal | 28.07 | 20.45 | 7.62 | 5.10 |
| Breast tumor | 24.44 | 18.28 | 6.16 | 13.98 |
| Ovary normal | 25.82 | 20.36 | 5.45 | 22.88 |
| Ovary Tumor | 31.1 | 20.29 | 10.81 | 0.56 |
| Prostate Normal | 26.41 | 19.45 | 6.95 | 8.09 |
| Prostate Tumor | 24.09 | 17.93 | 6.16 | 13.98 |
| Epithelial Cells (Prostate) | 26.16 | 21.29 | 4.87 | 34.20 |
| Colon normal | 31.93 | 18.18 | 13.76 | 0.07 |
| Colon Tumor | 25.5 | 19.03 | 6.46 | 11.32 |
| Lung normal | 33.51 | 18.43 | 15.07 | 0.03 |
| Lung tumor | 25.87 | 18.64 | 7.24 | 6.64 |
| Lung COPD | 28.28 | 18.41 | 9.87 | 1.07 |
| Colon IBD | 35.7 | 18.15 | 17.56 | 0.00 |
| Liver normal | 32.31 | 20.04 | 12.27 | 0.20 |
| Liver fibrosis | 30.41 | 21.65 | 8.77 | 2.30 |
| Dermal Cells-fibroblasts | 29.56 | 20.88 | 8.69 | 2.43 |
| Spleen normal | 31.32 | 19.43 | 11.9 | 0.26 |
| Tonsil normal | 28.16 | 17.18 | 10.98 | 0.49 |
| Lymph node | 30.18 | 18.55 | 11.64 | 0.31 |
| Small Intestine | 32.89 | 19.52 | 13.37 | 0.09 |
| Skin-Decubitus | 29.54 | 20.52 | 9.02 | 1.93 |
| Synovium | 33.65 | 20.19 | 13.46 | 0.09 |
| BM-MNC (Bone marrow mononuclear cells) | 31.97 | 16.69 | 15.28 | 0.03 |
| Activated PBMC | 32.12 | 15.93 | 16.18 | 0.01 |

Table 15 below shows Taqman results for oncology phase II panels of human tissues. 33949 was expressed at high levels in a subset of breast, lung, colon, ovarian and brain tumors. Differential expression between tumors and respective normal tissues was most significant in lung tissue. Confirming phase I expression patterns, normal brain tissue expressed very high levels of 33949.

TABLE 15

| 33949 Expression in Oncology Plate | | | | |
|---|---|---|---|---|
| Tissue Type | Mean | β2 Mean | ∂∂Ct | Expression |
| PIT 400 Breast N | 24.57 | 18.06 | 6.28 | 12.8686 |
| PIT 271 Breast N | 30.05 | 24.81 | 5.01 | 31.0341 |
| PIT 56 Breast N | 29.92 | 21.97 | 7.71 | 4.7594 |
| MDA 106 Breast T | 26.18 | 20.25 | 5.68 | 19.4377 |
| MDA 234 Breast T | 26.1 | 17.11 | 8.76 | 2.3146 |
| NDR 57 Breast T | 25.75 | 18.3 | 7.21 | 6.7542 |
| MDA 304 Breast T | 28.6 | 18.4 | 9.96 | 1.0005 |
| NDR 58 Breast T | 23.85 | 17.22 | 6.4 | 11.8415 |
| NDR 132 Breast T | 24.95 | 20.3 | 4.42 | 46.5524 |
| NDR 07 Breast T | 29.02 | 18.8 | 9.98 | 0.9868 |
| NDR 12 Breast T | 26.93 | 20.73 | 5.96 | 16.0087 |
| PIT 208 Ovary N | 23.66 | 18.22 | 5.21 | 27.1106 |
| CHT 620 Ovary N | 25.61 | 19.01 | 6.37 | 12.0904 |
| CHT 619 Ovary N | 24.16 | 19.19 | 4.74 | 37.4212 |
| CLN 03 Ovary T | 26.27 | 19.18 | 6.84 | 8.6986 |
| CLN 05 Ovary T | 26.7 | 18.09 | 8.37 | 3.0331 |
| CLN 17 Ovary T | 24.8 | 19.27 | 5.29 | 25.471 |
| CLN 07 Ovary T | 27.07 | 18.56 | 8.28 | 3.2283 |
| CLN 08 Ovary T | 27.11 | 18.23 | 8.64 | 2.498 |
| MDA 216 Ovary T | 29.27 | 20.16 | 8.88 | 2.1299 |
| CLN 012 Ovary T | 24.94 | 20.36 | 4.34 | 49.3776 |
| MDA 25 Ovary T | 25.53 | 20.97 | 4.33 | 49.721 |
| MDA 183 Lung N | 28.27 | 17.23 | 10.81 | 0.557 |
| CLN 930 Lung N | 29.38 | 20.37 | 8.78 | 2.2828 |
| MDA 185 Lung N | 28.19 | 19.45 | 8.5 | 2.7621 |
| MDI 215 Lung T | 24.5 | 18.5 | 5.76 | 18.3892 |
| MDA 259 Lung T | 23.52 | 18.9 | 4.39 | 47.6956 |
| CHT 832 Lung T | 23.47 | 18.11 | 5.12 | 28.8557 |
| MDA 253 Lung T | 26.18 | 17.5 | 8.46 | 2.8496 |
| CHT 814 Lung T | 23.95 | 16.45 | 7.27 | 6.4791 |
| CHT 911 Lung T | 24.47 | 18.52 | 5.72 | 18.9718 |
| CHT 726 Lung T | 24.97 | 16.82 | 7.92 | 4.1433 |
| MDA 253 Lung T | 24.09 | 19.9 | 3.96 | 64.0348 |
| CHT 845 Lung T | 23.81 | 19.38 | 4.2 | 54.5983 |
| NHBE | 38.42 | 18.29 | 19.9 | 0 |
| CHT 396 Colon N | 32 | 18.5 | 13.27 | 0.10 |
| CHT 519 Colon N | 35.76 | 19.97 | 15.56 | 0.00 |
| CHT 416 Colon N | 29.23 | 19.16 | 9.83 | 1.10 |
| CHT 452 Colon N | 34.25 | 17.43 | 16.59 | 0.01 |
| CHT 398 Colon T | 25.08 | 19.49 | 5.36 | 24.43 |
| CHT 805 Colon T | 26.63 | 18.18 | 8.21 | 3.38 |
| CHT 528 Colon T | 25.23 | 18.18 | 6.83 | 8.82 |
| CHT 368 Colon T | 27.58 | 17.29 | 10.06 | 0.94 |
| CHT 372 Colon T | 28.23 | 19.59 | 8.4 | 2.95 |
| CHT 01 Liver Met | 32.19 | 18.34 | 13.61 | 0.08 |
| CHT 896 Liver Met | 28.47 | 19.28 | 8.95 | 2.02 |
| NDR 217 Liver Met | 30.55 | 18.48 | 11.82 | 0.28 |
| PIT 260 Liver N | 34.7 | 17.28 | 17.19 | 0.01 |
| PIT 229 Liver N | 29.16 | 24.06 | 4.87 | 34.20 |
| MGH 16 Brain N | 27.71 | 23.88 | 3.6 | 82.76 |
| MCL 53 Brain N | 25.63 | 23.82 | 1.58 | 335.64* |
| MCL 377 Brain N | 28.52 | 24.89 | 3.4 | 94.73 |
| MCL 390 Brain N | 25.23 | 23.19 | 1.8 | 287.17* |
| MPI 665 Astrocytes | 24.72 | 19.84 | 4.65 | 39.83 |
| CHT 201 Brain T | 35.55 | 20.35 | 14.97 | 0.00 |
| CHT 216 Brain T | 24.07 | 17.25 | 6.58 | 10.45 |
| CHT 501 Brain T | 26.57 | 20.53 | 5.8 | 17.89 |
| CHT 1273 Brain T | 24.31 | 21.39 | 2.69 | 155.50* |
| CHT 828 Brian T | 30.73 | 21.98 | 8.52 | 2.72 |
| A24 HMVEC-Arr | 25.1 | 18.09 | 6.78 | 9.13 |
| C48 HMVEC-Prol | 25.8 | 20.19 | 5.38 | 24.10 |
| CHT 50 Placenta | 28.98 | 24.77 | 3.98 | 63.37 |
| BWH 75 Fetal Liver | 26.2 | 19.39 | 6.58 | 10.49 |
| BWH 54 Fetal Liver | 27.23 | 21.57 | 5.42 | 23.36 |
| PIT 213 Rnal Tumor | 36.71 | 24.85 | 11.63 | 0.00 |
| CHT 1424 Endometrial AC | 30.24 | 23.34 | 6.66 | 9.89 |

TABLE 15-continued

33949 Expression in Oncology Plate

| Tissue Type | Mean | β2 Mean | ∂∂Ct | Expression |
|---|---|---|---|---|
| BWH 58 Fetal Adrenal | 32.01 | 26.05 | 5.73 | 18.84 |
| PIT 251 Fetal Adrenal | 32.1 | 26.06 | 5.81 | 17.82 |

∂∂Ct value less than 3 so data may be inaccurate

Table 16 below shows Taqman results for an MCF10 variants cell model panel (breast cancer cell model panel). Confirming transcription profiling data, 33949 was expressed at highest levels in MCF10AT3B cells grown on agar vs. plastic. 33949 was first identified by transcription profiling as being expressed at higher levels in MCF10AT3B cells grown anchorage-independently vs. anchorage-dependently.

In microarray expression experiments, a human MPGv3.0 array was hybridized with probes generated from various MCF10 cells:

MCF10A (10A)—normal human breast epithelial cell, nontransformed, nontumorigenic MCF10A.m25 (10A.m25)—clone of MCF10A MCF10AT.cl1 (CL.1)—activated-ras-expressing nontumorigenic clone MCF10AT.cl3 (CL.3)—activated-ras-expressing nontumorigenic clone MCF10AT1 (AT1)—activated-ras-expressing tumorigenic line, derived from passage of MCF10AT cells through immunocompromised mice MCF10AT3B (3B)—activated ras-expressing tumorigenic line, derived from two additional serial passages of MCF10AT1 through immunocompromised mice Cells were cultured anchorage-dependently on plastic unless indicated by the word 'agar' in which case the cells were cultured anchorage-independently in soft agar. 33949 was expressed at the highest levels in MCF10AT3B cells grown anchorage-independently vs. anchorage-dependently.

This result was repeated in independently prepared MCF10AT3B plastic and agar samples as shown in the Taqman results below.

TABLE 16

33949 Expression in MCF10A Variant Cells

| | Average 33949 | Average Beta 2 | D Ct | Relative Expression |
|---|---|---|---|---|
| MCF10A-NT | 23.7 | 17.7 | 6.0 | 15.7 |
| MCF10AT.c11-NT | 23.1 | 17.3 | 5.8 | 18.5 |
| MCF10AT.c13-NT | 23.4 | 17.5 | 6.0 | 15.8 |
| MCF10MS-NT | 23.8 | 17.5 | 6.3 | 12.4 |
| MCF10CA1a.c11-T | 22.3 | 15.1 | 7.3 | 6.4 |
| MCF10AT1-T | 23.9 | 18.0 | 5.9 | 17.0 |
| MCF10AT3B-T | 24.1 | 18.0 | 6.2 | 13.8 |
| MCF10AT3B-agar | 27.3 | 23.7 | 3.6 | 84.5 |
| MCF10CA1a.cl1-agar | 27.1 | 22.0 | 5.1 | 30.0 |
| MCF10A-m25-plastic | 27.7 | 22.1 | 5.6 | 21.0 |
| MCF CA-agar | 24.0 | 18.9 | 5.1 | 28.9 |
| MCF CA-plastic | 23.5 | 18.3 | 5.2 | 27.2 |
| MCF 3B-agar | 24.2 | 20.0 | 4.2 | 53.1 |
| MCF 3B-plastic | 24.8 | 19.4 | 5.4 | 23.2 |

The following Table 17 depicts a Taq Man array of 50226 RNA expression relative to the progression of cells through the cell cycle of human colon cancer cells, HCT166 and HCT116 Noc Cells.

TABLE 17

50226 Expression in HCT166 and HCT116 Noc Cells

| | Average 50226.1 | Average Beta 2 | D Ct | Relative Expression |
|---|---|---|---|---|
| HCT116 t = 0 | 23.92 | 20.28 | 3.64 | 80.21 |
| HCT116 t = 3 | 20.82 | 17.08 | 3.74 | 74.84 |
| HCT116 t = 6 | 21.26 | 17.42 | 3.84 | 69.83 |
| HCT116 t = 9 | 21.57 | 17.78 | 3.79 | 72.29 |
| HCT116 t = 12 | 20.46 | 16.37 | 4.09 | 58.72 |
| HCT116 t = 15 | 29.10 | 21.57 | 7.53 | 5.43 |
| HCT116 t = 18 | 21.19 | 17.26 | 3.93 | 65.61 |
| HCT116 t = 21 | 21.09 | 17.60 | 3.49 | 89.00 |
| HCT116 t = 24 | 21.27 | 17.41 | 3.87 | 68.63 |
| HCT116 NOC t = 0 | 23.64 | 21.51 | 2.13 | 228.46 |
| HCT116 Noc t = 3 | 24.25 | 22.02 | 2.23 | 213.16 |
| HCT116 Noc t = 6 | 24.07 | 21.39 | 2.68 | 156.04 |
| HCT116 Noc t = 9 | 23.60 | 20.77 | 2.83 | 140.63 |
| HCT116 Noc t = 15 | 24.51 | 22.45 | 2.06 | 240.65 |
| HCT116 Noc t = 18 | 23.95 | 21.32 | 2.63 | 161.54 |
| HCT116 Noc t = 21 | 24.09 | 20.99 | 3.10 | 116.63 |
| HCT116 Noc t = 24 | 24.51 | 21.69 | 2.83 | 141.12 |

For Taqman results on the phase I tissue panel, highest expression of 50226 orthologs is found in normal brain cortex as shown in the following Table 18. Breast, prostate, colon and lung tumor pools expressed higher levels of 50226 than their respective normal tissue counterparts. Normal ovary and prostate pools expressed higher levels of 50226 than their respective tumor tissue counterparts.

TABLE 18

Phase 1.4.3 Expression of 50226.1

| Tissue Type | Mean | β2 Mean | ∂∂Ct | Expression |
|---|---|---|---|---|
| Artery normal | 30.18 | 23.23 | 6.95 | 8.088 |
| Vein normal | 31.3 | 21.28 | 10.02 | 0.9665 |
| Aortic SMC EARLY | 29.36 | 22.54 | 6.82 | 8.8507 |
| Coronary SMC | 29.88 | 23.15 | 6.73 | 9.4204 |
| Static HUVEC | 27.09 | 21.57 | 5.53 | 21.7175 |
| Shear HUVEC | 27.27 | 22.45 | 4.82 | 35.4026 |
| Heart normal | 26.66 | 19.45 | 7.21 | 6.7542 |
| Heart CHF | 26.14 | 19.93 | 6.21 | 13.5553 |
| Kidney | 28 | 20.84 | 7.16 | 7.0167 |
| Skeletal Muscle | 29.7 | 23.25 | 6.46 | 11.3986 |
| Adipose normal | 32.58 | 23.22 | 9.36 | 1.5271 |
| Pancreas | 30.8 | 23.16 | 7.63 | 5.0483 |
| primary osteoblasts | 27.09 | 20.11 | 6.98 | 7.9216 |
| Osteoclasts (diff) | 29.05 | 18.11 | 10.93 | 0.5126 |
| Skin normal | 31.93 | 23.18 | 8.76 | 2.3146 |
| Spinal cord normal | 31.09 | 21.81 | 9.28 | 1.6142 |
| Brain Cortex normal | 27.18 | 23.11 | 4.07 | 59.7466 |
| Brain Hypothalamus normal | 29.58 | 22.89 | 6.7 | 9.6517 |
| Nerve | 30.18 | 22.61 | 7.57 | 5.2626 |
| DRG (Dorsal Root Ganglion) | 29.32 | 22.54 | 6.78 | 9.1311 |
| Resting PBMC | 28.56 | 16.98 | 11.59 | 0.3255 |
| Glioblastoma | 28.11 | 19.28 | 8.84 | 2.1898 |
| Breast normal | 31.39 | 23.15 | 8.23 | 3.3191 |
| Breast tumor | 27.75 | 20 | 7.75 | 4.6615 |
| Ovary normal | 27.11 | 20.98 | 6.12 | 14.3779 |
| Ovary Tumor | 29.52 | 20.84 | 8.67 | 2.4551 |
| Prostate Normal | 28.54 | 21.18 | 7.36 | 6.1084 |
| Prostate Tumor | 28.86 | 21.33 | 7.54 | 5.3919 |
| Colon normal | 29.94 | 20.62 | 9.32 | 1.5646 |
| Colon Tumor | 25.78 | 19.79 | 5.99 | 15.7337 |
| Lung normal | 28.98 | 19.22 | 9.77 | 1.1453 |
| Lung tumor | 27 | 19.61 | 7.4 | 5.9208 |
| Lung COPD | 30.52 | 20.83 | 9.69 | 1.2107 |
| Colon IBD | 31.5 | 19.93 | 11.57 | 0.3278 |

TABLE 18-continued

| Phase 1.4.3 Expression of 50226.1 | | | | |
|---|---|---|---|---|
| Tissue Type | Mean | β2 Mean | ∂∂Ct | Expression |
| Liver normal | 30.23 | 21.82 | 8.41 | 2.9298 |
| Liver fibrosis | 29.7 | 22.08 | 7.62 | 5.0834 |
| Dermal Cells-fibroblasts | 27.83 | 19.76 | 8.07 | 3.7212 |
| Spleen normal | 30.41 | 20.82 | 9.59 | 1.302 |
| Tonsil normal | 28.18 | 18.33 | 9.85 | 1.0836 |
| Lymph node | 30.59 | 20.27 | 10.32 | 0.7796 |
| Skin-Decubitus | 29.86 | 21.06 | 8.8 | 2.2358 |
| Synovium | 30.67 | 20.34 | 10.34 | 0.7742 |
| BM-MNC (Bone marrow mononuclear cells) | 26.86 | 17.29 | 9.57 | 1.3111 |
| Activated PBMC | 30.02 | 19.17 | 10.85 | 0.5437 |
| Epithelial Cells (Prostate) | 30.75 | 26.5 | 4.25 | 52.556 |
| small Intestine | 32.32 | 24.07 | 8.25 | 3.2848 |

The Taqman results in the following Table 19 also show highest expression of 50226 orthologs in normal brain cortex.

TABLE 19

| Phase 1.3.3 Expression of 50226 w/β2 | | | | |
|---|---|---|---|---|
| Tissue Type | Mean | β2 Mean | ∂∂Ct | Expression |
| Artery normal | 30.93 | 21.29 | 9.65 | 1.2447 |
| Vein normal | 30.26 | 19.26 | 11 | 0.4883 |
| Aortic SMC EARLY | 25.3 | 19.11 | 6.2 | 13.6496 |
| Coronary SMC | 27.07 | 21.04 | 6.03 | 15.3566 |
| Static HUVEC | 25.16 | 19.84 | 5.31 | 25.2076 |
| Shear HUVEC | 24.94 | 19.89 | 5.05 | 30.0811 |
| Heart normal | 25.16 | 18.14 | 7.02 | 7.7049 |
| Heart CHF | 24.55 | 18.68 | 5.87 | 17.0983 |
| Kidney | 26.04 | 19.78 | 6.26 | 13.0482 |
| Skeletal Muscle | 27.34 | 20.53 | 6.82 | 8.8814 |
| Adipose normal | 29.99 | 18.93 | 11.07 | 0.4668 |
| Pancreas | 28.31 | 20.91 | 7.4 | 5.9208 |
| primary osteoblasts | 25.76 | 18.66 | 7.11 | 7.2641 |
| Osteoclasts (diff) | 32.91 | 17.1 | 15.81 | 0.0174 |
| Skin normal | 29.99 | 20.32 | 9.66 | 1.2318 |
| Spinal cord normal | 28.36 | 19.06 | 9.29 | 1.5919 |

TABLE 19-continued

| Phase 1.3.3 Expression of 50226 w/β2 | | | | |
|---|---|---|---|---|
| Tissue Type | Mean | β2 Mean | ∂∂Ct | Expression |
| Brain Cortex normal | 24.93 | 20.15 | 4.79 | 36.272 |
| Brain Hypothalamus normal | 27.38 | 20.47 | 6.92 | 8.2866 |
| Nerve | 31.3 | 23.34 | 7.96 | 4.03 |
| DRG (Dorsal Root Ganglion) | 28.2 | 21.32 | 6.87 | 8.5492 |
| Glial Cells (Astrocytes) | 27.02 | 21.56 | 5.46 | 22.6397 |
| Glioblastoma | 27.93 | 17.18 | 10.74 | 0.5827 |
| Breast normal | 30.11 | 19.61 | 10.51 | 0.6881 |
| Breast tumor | 26.22 | 17.66 | 8.56 | 2.6405 |
| Ovary normal | 25.93 | 19.54 | 6.39 | 11.9239 |
| Ovary Tumor | 30.86 | 19.39 | 11.48 | 0.3501 |
| Prostate Normal | 28.35 | 18.9 | 9.46 | 1.4248 |
| Prostate Tumor | 25.82 | 17.18 | 8.64 | 2.498 |
| Epithelial Cells (Prostate) | 25.31 | 20.23 | 5.08 | 29.6669 |
| Colon normal | 28.63 | 17.5 | 11.14 | 0.4447 |
| Colon Tumor | 24.52 | 18.2 | 6.32 | 12.5602 |
| Lung normal | 32.88 | 18 | 14.88 | 0.0332 |
| Lung tumor | 26.56 | 17.91 | 8.65 | 2.4894 |
| Lung COPD | 30.25 | 17.91 | 12.35 | 0.1915 |
| Colon IBD | 34.87 | 17.56 | 17.31 | 0.0062 |
| Liver normal | 28.68 | 19.39 | 9.29 | 1.5919 |
| Liver fibrosis | 28.52 | 21.29 | 7.24 | 6.6382 |
| Dermal Cells-fibroblasts | 26.73 | 18.81 | 7.92 | 4.1147 |
| Spleen normal | 31.04 | 18.86 | 12.18 | 0.2163 |
| Tonsil normal | 27.56 | 16.65 | 10.91 | 0.5197 |
| Lymph node | 29.31 | 18.07 | 11.23 | 0.4149 |
| Small intestine | 29.88 | 19.14 | 10.74 | 0.5847 |
| Skin-Decubitus | 29.5 | 19.95 | 9.55 | 1.334 |
| Synovium | 37.22 | 20.08 | 17.14 | 0 |
| BM-MNC (Bone marrow mononuclear cells) | 26.81 | 16.31 | 10.49 | 0.6929 |
| Activated PBMC | 28.93 | 15.64 | 13.29 | 0.0998 |

The following Table 20 shows the Taqman results for an oncology panel (Phase II) of human tissues. 50226 expression was upregulated by in 6/6 colon tumor or colon metastases samples versus normal colon samples. 50226 expression was upregulated by in 5/6 lung tumor samples versus normal lung samples. 50226 expression was found in both breast and ovary tumors and normal breast and ovary samples.

TABLE 20

| 50226.2 Expression in Oncology Phase II Panel | | | | |
|---|---|---|---|---|
| Tissue Type | 50226.2 Mean | β2 Mean | ∂∂Ct | Expression |
| PIT 400 Breast N | 29.77 | 20.4 | 9.38 | 1.50 |
| PIT 372 Breast N | 30.78 | 21.07 | 9.71 | 1.19 |
| CHT 559 Breast N | 35.76 | 22.82 | 12.94 | 0.00 |
| MDA 304 Breast T: MD-IDC | 30.93 | 19.61 | 11.32 | 0.39 |
| CHT 2002 Breast T: IDC | 29.42 | 20.3 | 9.13 | 1.79 |
| MDA 236-Breast T: PD-IDC(ILC?) | 32.06 | 20.57 | 11.48 | 0.35 |
| CHT 562 Breast T: IDC | 30.16 | 19.44 | 10.73 | 0.59 |
| NDR 138 Breast T ILC (LG) | 28.67 | 21.43 | 7.24 | 6.64 |
| CHT 1841 Lymph node (Breast met) | 33.12 | 22.2 | 10.91 | 0.52 |
| PIT 58 Lung (Breast met) | 33.91 | 23.27 | 10.64 | 0.63 |
| CHT 620 Ovary N | 27.41 | 20.14 | 7.27 | 6.48 |
| PIT 208 Ovary N | 26.11 | 19.45 | 6.66 | 9.89 |
| CLN 012 Ovary T | 29.97 | 22.59 | 7.38 | 5.98 |
| CLN 07 Ovary T | 29.81 | 19.73 | 10.07 | 0.93 |
| CLN 17 Ovary T | 27.32 | 20.9 | 6.42 | 11.64 |
| MDA 25 Ovary T | 30.21 | 22.52 | 7.7 | 4.83 |
| MDA 216 Ovary T | 29.27 | 19.29 | 9.98 | 0.99 |
| PIT 298 Lung N | 29.74 | 19.52 | 10.22 | 0.84 |
| MDA 185 Lung N | 32.22 | 20.52 | 11.71 | 0.30 |
| CLN 930 Lung N | 31.83 | 21.5 | 10.32 | 0.78 |
| MPI 215 Lung T-SmC | 27.18 | 19.74 | 7.45 | 5.74 |
| MDA 259 Lung T-PDNSCCL | 27.36 | 20.67 | 6.68 | 9.72 |
| CHT 832 Lung T-PDNSCCL | 29.51 | 19.36 | 10.15 | 0.88 |
| MDA 262 Lung T-SCC | 28.93 | 23.23 | 5.71 | 19.17 |

TABLE 20-continued

| 50226.2 Expression in Oncology Phase II Panel | | | | |
|---|---|---|---|---|
| Tissue Type | 50226.2 Mean | β2 Mean | ∂∂Ct | Expression |
| CHT 793 Lung T-ACA | 26.51 | 19.22 | 7.29 | 6.37 |
| CHT 331 Lung T-ACA | 28.55 | 22.22 | 6.33 | 12.43 |
| CHT 405 Colon N | 28.07 | 17.4 | 10.66 | 0.62 |
| CHT 523 Colon N | 29.19 | 19.36 | 9.82 | 1.10 |
| CHT 371 Colon N | 26.55 | 16.68 | 9.86 | 1.08 |
| CHT 382 Colon T: MD | 29.84 | 21.75 | 8.1 | 3.64 |
| CHT 528 Colon T: MD | 25.31 | 18.47 | 6.84 | 8.73 |
| CLN 609 Colon T | 27.82 | 19.79 | 8.04 | 3.81 |
| NDR 210 Colon T: MD-PD | 30.75 | 24.11 | 6.64 | 9.99 |
| CHT 340 Colon-Liver Met | 28.59 | 21.66 | 6.92 | 8.23 |
| NDR 100 Colon-Liver Met | 25.22 | 18.55 | 6.67 | 9.82 |
| PIT 260 Liver N (female) | 28.43 | 19.15 | 9.29 | 1.60 |
| CHT 1653 Cervix Squamous CC | 27.37 | 21.91 | 5.46 | 22.72 |
| CHT 569 Cervix Squamous CC | 31.57 | 19.77 | 11.8 | 0.28 |
| A24 HMVEC-Arr | 27.13 | 19.58 | 7.54 | 5.35 |
| C48 HMVEC-Prol | 26.39 | 19.91 | 6.48 | 11.20 |
| Pooled Hemangiomas | 30.27 | 20.04 | 10.23 | 0.84 |
| HCT116N22 Normoxic | 25.3 | 22.16 | 3.14 | 113.44 |
| HCT116H22 Hypoxic | 26.24 | 22.8 | 3.44 | 91.82 |

The Taqman results in the following Table 21 show highest expression of 58764 orthologs in PBL HIV-1 d1.

TABLE 21

| 58764 (agpat) Expression | | | |
|---|---|---|---|
| | 58764 | 18S | relative exp. |
| PBL mock d1 | 26.6 | 12.9 | 0.50 |
| PBL HIV-1 d1 | 24.4 | 11.3 | 0.75 |
| PBL mock d3 | 26.3 | 11.9 | 0.31 |
| PBL HIV-1 d3 | 25.7 | 11.7 | 0.40 |
| PBL mock d5 | 28.1 | 12.6 | 0.14 |
| PBL HIV-1 d5 | 27.3 | 12.1 | 0.17 |
| M/M mock d7 | 29.0 | 12.4 | 0.06 |
| M/M MOI 0.1 d7 | 29.3 | 12.1 | 0.04 |
| M/M mock d15 | 29.2 | 12.2 | 0.05 |
| M/M MOI 0.1 d15 | 30.2 | 14.1 | 0.10 |
| M/M mock d26 | 31.1 | 14.7 | 0.08 |
| M/M MOI 0.1 d26 | 30.6 | 12.4 | 0.02 |
| Chronic-TRD-Pre | 29.1 | 11.9 | 0.04 |
| Chronic-TRD-Post | 28.4 | 11.5 | 0.06 |
| Chronic-MGB-Pre | 29.0 | 12.1 | 0.05 |
| Chronic-MGB-Post | 28.9 | 11.6 | 0.04 |
| Acute-EJT-Pre | 28.3 | 11.7 | 0.07 |
| Acute-EJT-Post | 29.3 | 11.7 | 0.03 |
| Acute-KEK-Pre | 30.4 | 11.8 | 0.02 |
| Acute-KEK-Post | 28.9 | 11.4 | 0.03 |
| Acute-RKY-Pre | 31.2 | 12.1 | 0.01 |
| Acute-RKY-Post | 32.5 | 12.0 | 0.00 |
| d2 uninfect. | 29.4 | 13.7 | 0.13 |
| d2 SIV239 | 29.6 | 12.9 | 0.06 |
| d2 SIV316 | 28.0 | 12.1 | 0.10 |
| d3 uninfect. | 26.9 | 11.8 | 0.18 |
| d3 SIV239 | 28.5 | 12.8 | 0.13 |
| d3 SIV316 | 28.7 | 13.5 | 0.17 |
| II AB | 28.2 | 14.0 | 0.36 |
| II M-CSF | 30.2 | 14.7 | 0.14 |
| IV AB | 28.4 | 12.3 | 0.09 |
| IV M-CSF | 29.8 | 14.3 | 0.14 |

As seen by these results, 26199, 33530, 33949, or 50226 molecules have been found to be underexpressed or overexpressed in tumor cells, where the molecules may be inappropriately propagating either cell proliferation or cell survival signals. As such, activators or inhibitors of the 26199, 33530, 33949, or 50226 molecules are useful for the treatment of cancer, preferably ovarian, breast, colon, lung, liver or brain cancer, and useful as a diagnostic.

In Situ Hybridization of 26199 and 33949

Specific in situ localization of gene 26199 was observed in 3/3 breast tumors and 1/1 ovarian tumor. No normal tissues for breast or ovary showed staining. 3/11 angiogenic tissues were also stained for 26199, including a Wilm's tumor and a neuroblastoma. Labeling was confined to epithelial cells with no evidence of expression by stromal blood vessels.

For 33949, 1/2 normal breast tissues, 4/5 breast tumors, 0/3 normal colon tissues, 3/4 primary colon tumors, 1/2 colon metastasis, 0/2 normal lung tissues, 2/4 lung tumors, 0/1 normal ovary tissue and 2/2 ovary tumors showed positive staining.

Human 62113

The present invention is based, in part, on the discovery of a novel acyl-CoA dehydrogenase family member, referred to herein as "62113".

The human 62113 sequence (SEQ ID NO:53), which is approximately 3030 nucleotides long including untranslated regions, contains a predicted methionine-initiated coding sequence of about 2340 nucleotides, not including the termination codon (nucleotides 238-2577 of SEQ ID NO:53, 1-2340 of SEQ ID NO:55). The coding sequence encodes a 780 amino acid protein (SEQ ID NO:54).

Human 62113 contains the following regions or other structural features (for general information regarding PFAM identifiers, PS prefix and PF prefix domain identification numbers, refer to Sonnhammer et al. (1997) *Protein* 28:405-420): an acyl-CoA dehydrogenase N-terminal domain (PFAM Accession Number PF02771) located at about amino acid residues 483 to 503 of SEQ ID NO:54; an acyl-CoA dehydrogenase middle domains (PFAM Accession Number PF02770) located at about amino acid residues 505 to 585 of SEQ ID NO:54; an acyl-CoA dehydrogenase C-terminal domain (PFAM Accession Number PF00441) located at about amino acid residues 618 to 741 of SEQ ID NO:54; an acyl-CoA dehydrogenase signature 1-like sequence (Prosite PS00072) located at about amino acid residues 505 to 518 of SEQ ID NO:54; an acyl-CoA dehydrogenase signature 2-like sequence (Prosite PS00073) located at about amino acid residues 622 to 642 of SEQ ID NO:54; three N-glycosylation sites (Prosite PS00001) located at about amino acids 331 to 334, 499 to 502, and 558 to 561 of SEQ ID NO:54; two glycosaminoglycan attachment sites (Prosite PS00002)

located at about amino acids 34 to 37, and 540 to 543 of SEQ ID NO:54; one cAMP/cGMP-dependent protein kinase phosphorylation site (Prosite PS00004) located at about amino acids 774 to 777 of SEQ ID NO:54; six protein kinase C phosphorylation sites (Prosite PS00005) located at about amino acids 355 to 357, 376 to 378, 456 to 458, 655 to 657, 688 to 690, and 777 to 779 of SEQ ID NO:54; seven casein kinase II phosphorylation sites (Prosite PS00006) located at about amino acids 138 to 141, 275 to 278, 284 to 287, 333 to 336, 445 to 448, 507 to 510, and 517 to 520 of SEQ ID NO:54; nine N-myristoylation sites (Prosite PS00008) located at about amino acids 136 to 141, 170 to 175, 318 to 323, 330 to 335, 351 to 356,498 to 503, 543 to 548, 699 to 704, 731 to 736 of SEQ ID NO:54; one amidation site (Prosite PS00009) located at about amino acids 533 to 536 of SEQ ID NO:54; one ATP/GTP-binding site motif A (P-loop; Prosite PS00017) located at about amino acids 47 to 54 of SEQ ID NO:54; one tyrosine protein kinase specific active-site signature sequence (Prosite PS00109) located at about amino acids 218 to 230 of SEQ ID NO:54; one microbodies C-terminal targeting signal sequence (Prosite PS00342) located at about amino acids 778 to 781 of SEQ ID NO:54; and two eukaryotic thiol (cysteine) proteases histidien active site signature sequence (Prosite PS 00639) located at about amino acids 633 to 643 and 691 to 701 of SEQ ID NO:54.

A hydropathy plot of human 62113 was peformed. Polypeptides of the invention include fragments which include: all or part of a hydrophobic sequence; all or part of a hydrophilic sequence; and a sequence which includes a cysteine residue or a glycosylation site.

The 62113 protein contains a significant number of structural characteristics in common with members of the acyl-CoA dehydrogenase family. The acyl-CoA dehydrogenase family comprises a number of related enzymes that share high structural homology and a common catalytic mechanism which involves abstraction of an I-proton from the substrate (Thorpe and Kim (1995) *FASEB J* 9: 718-25). For example, acyl-CoA dehydrogenases catalyze the conversion of a fatty acyl thioester substrate to the corresponding I,ϑ-enoyl-CoA product. Thus, this family includes enzymes critical for the proper function of many physiological systems, including fatty acid oxidation, amino acid metabolism, and cellular proliferation and differentiation.

A 62113 polypeptide can include an "acyl-CoA dehydrogenase domain" or regions homologous with an "acyl-CoA dehydrogenase domain."

As used herein, the term "acyl-CoA dehydrogenase domain" includes an amino acid sequence of about 50 to 500 amino acid residues in length, more preferably about 100 to 400 amino acid residues, or about 200 to 300 amino acids and has a bit score for the alignment of the sequence to the acyl-CoA dehydrogenase domain (HMM) of at least 4.9 or greater. The acyl-CoA dehydrogenase domain includes an amino acid sequence which has an all-alpha, four helical up-and-down bundle conformation at the C-terminal portion of the acyl-CoA dehydrogenase domain, e.g., an acyl-CoA dehydrogenase C-terminal domain (Pfam Accession Number PF00441). The acyl-CoA dehydrogenase domain also includes an amino acid sequence which has a beta-barrel fold conformation and is found in the central domain of an acyl-CoA dehydrogenase, e.g., an acyl-CoA dehydrogenase middle domain (Pfam Accession Number PF02770). Preferably, the acyl-CoA middle domain includes an amino acid residue capable of providing a catalytic function to the active site, for example, an aspartate (D), at about amino acid 515 of SEQ ID NO:54. The acyl-CoA dehydrogenase domain also includes an amino acid sequence which has an all-alpha conformation and is found at the N-terminal portion of the acyl-CoA dehydrogenase domain, e.g., an acyl-CoA dehydrogenase N-terminal domain (Pfam Accession Number PF02771).

An alignment of the acyl-CoA dehydrogenase N-terminal domain (amino acids 483 to 503 of SEQ ID NO:54) of human 62113 with a consensus amino acid sequence derived from a hidden Markov model derived from Pfam (Pfam Accession Number PF02771; SEQ ID NO:56) has a bit score of 5.5 and E-value of 3.7.

An alignment of the acyl-CoA dehydrogenase middle domain (amino acids 505 to 585 of SEQ ID NO:54) of human 62113 with a consensus amino acid sequence derived from a hidden Markov model derived from Pfam (Pfam Accession Number PF02770; SEQ ID NO:57) has a bit score of 25.6 and E-value of 6.6e-06.

An alignment of the acyl-CoA dehydrogenase C-terminal domain (amino acids 618 to 741 of SEQ ID NO:54) of human 62113 with a consensus amino acid sequence derived from a hidden Markov model derived from Pfam (Pfam Accession Number PF00441; SEQ ID NO:58) has a bit score of 24.6 and E-value of 1.5e-05.

A 62113 polypeptide can include a "acyl-CoA dehydrogenase domain", e.g., an acyl-CoA dehydrogenase N-terminal domain, an acyl-CoA dehydrogenase middle domain, or an acyl-CoA dehydrogenase C-terminal domain, or regions homologous thereto.

As used herein, the term "acyl-CoA dehydrogenase N-terminal domain" includes an amino acid sequence of about 5 to 50 amino acid residues in length and having a bit score for the alignment of the sequence to the acyl-CoA dehydrogenase domain (HMM; Pfam Accession Number PF02771) of at least 5 and E-value of less than 4. Preferably, an acyl-CoA dehydrogenase N-terminal domain includes at least about 5 to 50 amino acids, more preferably about 10 to 40 amino acid residues, or about 15 to 25 amino acids and has a bit score for the alignment of the sequence to the acyl-CoA dehydrogenase N-terminal domain (HMM) of at least 3, preferably 4, more preferably 5, or greater and E-value of 6, preferably 5, more preferably 4 or less.

In a preferred embodiment, a 62113 polypeptide or protein has a "acyl-CoA dehydrogenase N-terminal domain" or a region which includes at least about 5 to 50, more preferably about 10 to 40, or 15 to 25 amino acid residues and has at least about 60%, 70%, 80%, 90%, 95%, 99%, or 100% homology with an "acyl-CoA dehydrogenase N-terminal domain," e.g., the acyl-CoA dehydrogenase N-terminal domain of human 62113 (e.g., residues 483 to 503 of SEQ ID NO:54).

As used herein, the term "acyl-CoA dehydrogenase middle domain" includes an amino acid sequence of about 50 to 200 amino acid residues in length and having a bit score for the alignment of the sequence to the acyl-CoA dehydrogenase middle domain (HMM; Pfam Accession Number PF00441) of at least 20 and E-value of less than 1e-05. Preferably, an acyl-CoA dehydrogenase middle domain includes at least about 20 to 120 amino acids, more preferably about 50 to 100 amino acid residues, or about 75 to 90 amino acids and has a bit score for the alignment of the sequence to the acyl-CoA dehydrogenase middle domain (HMM) of at least 10, preferably 15, more preferably 20, or greater, and E-value of 1e-05, preferably 5e-05, more preferably 1e-06, or less.

The acyl-CoA dehydrogenase middle domain can include an acyl-CoA dehydrogenase signature 1 sequence pattern, or sequence patterns homologous thereto. A consensus sequence for this pattern is as follows: [GAC]-[LIVM]-[ST]-E-x(2)-[GSAN]-G-[ST]-D-x(2)-[GSA] (Prosite Accession No. PS00072; SEQ ID NO:59). The aspartate residue in the tenth position of the consensus sequence is a conserved residue in the active site of the enzyme and is important for its catalytic activity.

In the above conserved signature sequence, and other motifs or signature sequences described herein, the standard IUPAC one-letter code for the amino acids is used. Each element in the pattern is separated by a dash (-); square brackets ([ ]) indicate the particular residues that are accepted at that position; x indicates that any residue is accepted at that position; and numbers in parentheses (( )) indicate the number of residues represented by the accompanying amino acid.

A sequence pattern homologous to an acyl-CoA dehydrogenase signature 1 sequence pattern includes an acyl-CoA dehydrogenase signature 1-like sequence pattern which differs from the consensus sequence of Prosite Accession No. PS00072 by less than six, preferably less than five, more preferably less than four elements in the sequence. An acyl-CoA dehydrogenase signature 1-like sequence is located within the acyl-CoA dehydrogenase middle domain of human 62113 polypeptide, corresponding to amino acid residues at about 505 to 518 of SEQ ID NO:54. This acyl-CoA dehydrogenase signature 1-like sequence differs from an acyl-CoA dehydrogenase signature 1 sequence (e.g., Prosite Accession Number PS00072) in the fifth element, which consists of three amino acids, in the eighth element, which is a serine residue instead of glycine, and in the thirteenth element, which is an asparagine residue instead of glycine, serine, or alanine. The aspartate residue in the tenth position is a conserved residue and corresponds to the aspartate residue at about position 515 in SEQ ID NO:54.

In a preferred embodiment, a 62113 polypeptide or protein has an "acyl-CoA dehydrogenase middle domain" or a region which includes at least about 50 to 200, more preferably about 100 to 150, or about 115 to 135 amino acid residues and has at least about 60%, 70%, 80%, 90%, 95%, 99%, or 100% homology with an "acyl-CoA dehydrogenase middle domain," e.g., the acyl-CoA dehydrogenase middle domain of human 62113 (e.g., residues 505 to 585 of SEQ ID NO:54).

In another preferred embodiment, a 62113 polypeptide or protein has an acyl-CoA dehydrogenase middle domain which includes an acyl-CoA dehydrogenase signature 1-like sequence pattern which differs from the consensus sequence (e.g., Prosite Accession No. PS00072) by less than six, preferably less than five, more preferably less than four elements in the sequence and has at least about 60%, 70%, 80%, 90%, 95%, 99%, or 100% homology with an acyl-CoA dehydrogenase signature 1-like sequence pattern, e.g., the acyl-CoA dehydrogenase signature 1-like sequence pattern of human 62113 (e.g., residues 505 to 518 of SEQ ID NO:54)

As used herein, the term "acyl-CoA dehydrogenase C-terminal domain" includes an amino acid sequence of about 50 to 200 amino acid residues in length and having a bit score for the alignment of the sequence to the acyl-CoA dehydrogenase domain (HMM) of at least 20 and E-value of less than 1e-04. Preferably, an acyl-CoA dehydrogenase C-terminal domain includes at least about 50 to 200 amino acids, more preferably about 80 to 150 amino acid residues, or about 110 to 140 amino acid residues and has a bit score for the alignment of the sequence to the acyl-CoA dehydrogenase domain (HMM) of at least 5, preferably 10, more preferably 15, or greater, and E-value of 1e-04, preferably 5e-04, more preferably 1e-05, or less.

The acyl-CoA dehydrogenase C-terminal domain can include an acyl-CoA dehydrogenase signature 2 sequence pattern, or sequence patterns homologus thereto. A consensus sequence for this pattern is as follows: [QDE]-x(2)-G-[GS]-x-G-[LIVMFY]-x(2)-[DEN]-x(4)-[KR]-x(3)-[DEN] (Prosite Accession No. PS00073; SEQ ID NO:60).

A sequence pattern homologous to an acyl-CoA dehydrogenase signature 2 sequence pattern includes an acyl-CoA dehydrogenase signature 2-like sequence pattern which differs from the consensus sequence of Prosite Accession No. PS00073 by less than six, preferably less than five, more preferably less than four elements in the sequence. An acyl-CoA dehydrogenase signature 2-like sequence is located within the acyl-CoA dehydrogenase C-terminal domain of human 62113 polypeptide, corresponding to amino acid residues at about 618 to 741 of SEQ ID NO:54. This acyl-CoA dehydrogenase signature 2-like sequence differs from an acyl-CoA dehydrogenase signature 2 sequence (e.g., Prosite Accession Number PS00073) in the second element, which consists of three amino acids, in the fifth element, which is an arginine residue instead of glycine or serine, in the eighth element, which is a proline residue instead of leucine, isoleucine, valine, methionine, phenylalanine, or tyrosine, and in the eleventh element, which is an isoleucine residue instead of aspartate, glutamate, or asparagine.

In a preferred embodiment, a 62113 polypeptide or protein has an "acyl-CoA dehydrogenase C-terminal domain" or a region which includes at least about 50 to 200, more preferably about 80 to 150, or about 110 to 140 amino acid residues and has at least about 60%, 70%, 80%, 90%, 95%, 99%, or 100% homology with an "acyl-CoA dehydrogenase C-terminal domain," e.g., the acyl-CoA dehydrogenase C-terminal domain of human 62113 (e.g., residues 618 to 741 of SEQ ID NO:54).

In another preferred embodiment, a 62113 polypeptide or protein has an acyl-CoA dehydrogenase C-terminal domain which includes an acyl-CoA dehydrogenase signature 2-like sequence pattern which differs from the consensus sequence (e.g., Prosite Accession No. PS00073) by less than seven, preferably less than six, more preferably less than five elements in the sequence and has at least about 60%, 70%, 80%, 90%, 95%, 99%, or 100% homology with an acyl-CoA dehydrogenase signature 2-like sequence pattern, e.g., the acyl-CoA dehydrogenase signature 1-like sequence pattern of human 62113 (e.g., residues 618 to 741 of SEQ ID NO:54).

To identify the presence of an "acyl-CoA dehydrogenase N-terminal domain", an "acyl-CoA dehydrogenase middle domain", or an "acyl-CoA dehydrogenase C-terminal domain" in a 62113 protein sequence, and make the determination that a polypeptide or protein of interest has a particular profile, the amino acid sequence of the protein can be searched against the Pfam database of HMMs (e.g., the Pfam database, version 6.6) using the default parameters. For example, the hmmsf program, which is available as part of the HMMER package of search programs, is a family specific default program for MILPAT0063 and a score of 15 is the default threshold score for determining a hit. Alternatively, the threshold score for determining a hit can be lowered (e.g., to 8 bits). A description of the Pfam database can be found in Sonhammer et al. (1997) *Proteins* 28:405-420 and a detailed description of HMMs can be found, for example, in Gribskov et al. (1990) *Meth. Enzymol.* 183:146-159; Gribskov et al. (1987) *Proc. Natl. Acad. Sci. USA* 84:4355-4358; Krogh et al. (1994) *J. Mol. Biol.* 235:1501-1531; and Stultz et al. (1993) *Protein Sci.* 2:305-314, the contents of which are incorporated herein by reference. A search was performed against the HMM database resulting in the identification of the "acyl-CoA dehydrogenase N-terminal domain" described above in the amino acid sequence of human 62113 at about residues 483 to 503 of SEQ ID NO:54, the "acyl-CoA dehydrogenase middle domain" described above in the amino acid sequence of human 62113 at about residues 505 to 585 of SEQ ID NO:54; and the "acyl-CoA dehydrogenase C-terminal domain" described above in the amino acid sequence of human 62113 at about residues 618 to 741 of SEQ ID NO:54.

A 62113 family member can include at least one acyl-CoA dehydrogenase N-terminal domain; at least one acyl-CoA dehydrogenase middle domain; and at least one acyl-CoA dehydrogenase C-terminal domain. A 62113 family member can include an acyl-CoA dehydrogenase middle domain with an acyl-CoA dehydrogenase signature 1-like sequence. A 62113 family member can also include an acyl-CoA dehydrogenase C-terminal domain with an acyl-CoA dehydrogenase signature 2-like sequence. Furthermore, a 62113 family member can include at least one, two, preferably three N-glycosylation site (Prosite PS00001); at least one, preferably two glycosaminoglycan attachment sites (Prosite PS00002); at least one cAMP/cGMP protein kinase phosphorylation sites (Prosite PS00004); at least one, two, three, four, five, preferably six protein kinase C phosphorylation sites (Prosite PS00005); at least one, two, three, four, five, six, preferably seven [as appropriate] casein kinase II phosphorylation sites (Prosite PS00006); at least one, two, three, four, five, six, seven, eight, preferably nine N-myristoylation sites (Prosite PS00008); at least one amidation site (Prosite PS00009); at least one ATP/GTP binding site motif A (P-loop; Prosite PS00017); at least one tyrosine protein kinase specific active site signature sequence (Prosite PS00109); at least one microbodies C-terminal targeting signal (Prosite PS00342); and at least one, preferably two eukaryotic thiol (cysteine) protease histidine active site (Prosite PS00639).

Based on the above-described sequence similarities, the 62113 molecules of the present invention are predicted to have similar biological activities as acyl-CoA dehydrogenase family members. For example, the 62113 protein is predicted to have one or more of the following activities: (1) the ability to catalyze the transfer of hydrogen and electrons from one compound to another; (2) the ability to catalyze the I,ϑ-dehydrogenation of fatty acyl-CoA derivatives; (3) the ability to catalyze the dehydrogenation of branched short-chain acyl-CoAs in the metabolism of the branched-chain amino acids; (4) the ability to modulate the oxidation of fatty acids; (5) the ability to modulate the metabolism of amino acids; (6) the ability to modulate a cardiovascular activity; (7) the ability to modulate a renal activity; or (8) the ability to modulate a hepatic activity. As a result, the 62113 protein may have a critical function in one or more of the following physiological processes: (1) fatty acid metabolism; (2) amino acid metabolism; (3) modulation (stimulation or inhibition) of cell proliferation and differentiation; (4) modulation of tumorigenesis and tumor invasion; (5) cardiovascular activity; (6) renal activity; or (7) hepatic activity.

As the 62113 polypeptides of the invention can modulate 62113-mediated activities, they can be useful for developing novel diagnostic and therapeutic agents for acyl-CoA dehydrogenase-associated or other 62113-associated disorders, as described below.

As used herein, a "62113 activity", "biological activity of 62113" or "functional activity of 62113", refers to an activity exerted by a 62113 protein, polypeptide or nucleic acid molecule on e.g., a 62113-responsive cell or on a 62113 substrate, e.g., a protein substrate, as determined in vivo or in vitro. In one embodiment, a 62113 activity is a direct activity, such as an association with a 62113 target molecule. A "target molecule" or "binding partner" is a molecule with which a 62113 protein binds or interacts in nature. In an exemplary embodiment, 62113 is an enzyme that metabolizes fatty acyl-CoA substrates.

A 62113 activity can also be an indirect activity, e.g., a cellular signaling activity mediated by interaction of the 62113 protein with a 62113 receptor.

The 62113 molecules of the invention can modulate the activities of cells in tissues where they are expressed. For example, 62113 mRNA is expressed in tumors and metastases of the lung, colon, prostate, breast, and ovaries; heart, kidney, liver, and prostate. Accordingly, the 62113 molecules of the invention can act as therapeutic or diagnostic agents for tumors and metastases of the lung, colon, prostate, breast, and ovaries; and cardiovascular, renal, hepatic, and prostate disorders.

Examples of cellular proliferative and/or differentiative disorders include cancer, e.g., carcinoma, sarcoma, metastatic disorders or hematopoietic neoplastic disorders, e.g., leukemias. A metastatic tumor can arise from a multitude of primary tumor types, including but not limited to those of prostate, colon, lung, breast, ovarian, and liver origin.

The 62113 molecules of the invention can be used to monitor, treat and/or diagnose a variety of proliferative disorders. Such disorders include hematopoietic neoplastic disorders.

Gene Expression Analysis of 62113

Human 62113 expression was measured by TaqMan® quantitative PCR (Perkin Elmer Applied Biosystems) in cDNA prepared from a variety of normal and diseased (e.g., cancerous) human tissues or cell lines.

The results indicate significant 62113 expression in normal liver and in liver fibrosis samples; normal breast and breast tumor; normal ovary and ovarian tumor; normal prostate and prostate tumor; upregulated expression in lung tumor (e.g., adenocarcinoma) when compared to normal lung; upregulated expression in colon tumor (e.g., adenocarcinoma) when compared to normal colon; upregulated expression in diseased heart when compared to normal heart; and upregulated expression in diseased kidney (including hypertensive kidney) when compared to normal kidney.

Additional TaqMan panels showed the following patterns of 62113 expression: high levels of 62113 expression in HUVEC (human umbilical vein endothelial cells), normal adrenal gland, normal brain cortex and brain hypothalamus, dorsal root ganglia, and diseased aoartic tissue; and moderate levels of 62113 expression in pancreas, normal spinal cord and hemangiomas.

Human 32144

The present invention is based, in part, on the discovery of a novel fatty acid amide hydrolase family member, referred to herein as "32144".

The human 32144 sequence (SEQ ID NO:61), which is approximately 2004 nucleotides long including untranslated regions, contains a predicted methionine-initiated coding sequence of about 1596 nucleotides, (nucleotides 119-1714 of SEQ ID NO:61; 1-1596 of SEQ ID NO:63) not including the termination codon. The coding sequence encodes a 532 amino acid protein (SEQ ID NO:62).

Portions of the fatty acid amide hydrolase domain of human 32144 align with consensus amino acid sequences derived from a hidden Markov model (HMM) from PFAM. The two distinct and non-overlapping consensus amino acid sequences correspond to portions of the PFAM amidase domain, PF01425. The scores for the two individual alignments were: 219.6 (E-value=4.8e-62) and 38.4 (E-value=6.6e-10), and the combined score for the two alignments was: 258.0 (E-value=1.3e-73). In the first alignment, the consensus amino acid sequence (residues 1-218 of the domain or SEQ ID NO:64) of an N-terminal portion of the amidase domain aligns with amino acids 69 to 289 of SEQ ID NO:62. In the second alignment, the consensus amino acid sequence (residues 395-521 of the domain or SEQ ID NO:65) of a C-terminal portion of the amidase domain aligns with amino acids 419 to 513 of SEQ ID NO:62.

Human 32144 contains the following regions or other structural features: an amidase domain (PFAM Accession Number PF01425) located at about amino acid residues 69 to 289 and 419 to 513 of SEQ ID NO:62; an amidase signature motif (PS00571) located at about amino acid residues 204 to 235 of SEQ ID NO:62; a transmembrane domain located at about amino acid residues 11 to 33 of SEQ ID NO:62; eight predicted Protein Kinase C phosphorylation sites (PS00005) located at about amino acid residues 6 to 8, and 40 to 42, 129 to 131, 186 to 188, 230 to 232, 329 to 331, 365 to 367, and 434 to 436 of SEQ ID NO:62; three predicted Casein Kinase II phosphorylation sites (PS00006) located at about amino acid residues 129 to 132, 207 to 210, and 320 to 323 of SEQ ID NO:62; eleven predicted N-myristoylation sites (PS00008) located at about amino acid residues 53 to 58, 125 to 130, 138 to 143, 172 to 177, 204 to 209, 211 to 216, 224 to 229, 248 to 253, 475 to 480, 481 to 486, and 495 to 500 of SEQ ID NO:62; two predicted N-glycosylation sites (PS00001) at about amino acids 141 to 144 and 175 to 178 of SEQ ID NO:62; and one predicted microbodies C-terminal targeting signal (PS00342) at about amino acid 530 to 532 of SEQ ID NO:62.

For general information regarding PFAM identifiers, PS prefix and PF prefix domain identification numbers, refer to Sonnhammer et al. (1997) *Protein* 28:405-420.

A hydropathy plot of human 32144 was performed. Polypeptides of the invention include fragments which include: all or part of a hydrophobic sequence, e.g., the sequence from about amino acid 157 to 182, from about 388 to 414, and from about 471 to 491 of SEQ ID NO:62; all or part of a hydrophilic sequence, e.g., the sequence of from about amino acid 104 to 120, from about 183 to 201, and from about 415 to 438 of SEQ ID NO:62.

The 32144 protein contains a significant number of structural characteristics in common with members of the amidase family. An amidase family of proteins, also referred to as fatty acid amidase hydrolases (FAAH), is characterized by the ability to hydrolyze fatty acid amides, e.g., neuromodulatory fatty acid amides, such as oleamide, anandamide and myristic amide. Representative amidases include fatty acid amide hydrolases (FAAH) from human and mouse (Giang, D. K. et al. (1997) Proc. Natl. Acad. Sci. 94: 2238-2242). Typically, amidases possess substrate specificity based on chain length and degree of saturation of fatty acid amides. Fatty acid amides, e.g., oleamide and ananadmide, are known to have sleep-inducing and analgesic properties, as well as the ability to regulate cellular proliferation. This family of proteins typically contains a highly conserved region rich in glycine, serine and alanine residues. Fatty acid amide hydrolases have been described in Ueda et al. (2000), supra, the contents of which are incorporated herein by reference.

A 32144 polypeptide can include at least one "amidase domain" or "fatty acid amid hydrolase domain", which contains one and preferably two "amidase subdomains" or regions homologous with an "amidase domain".

As used herein, the term "amidase subdomain" or "first amidase subdomain" includes an amino acid sequence of about 100 to 500 amino acid residues in length and having a bit score for the alignment of the sequence to the amidase domain (HMM) of at least 100. Preferably, an amidase domain includes at least about 150 to 450 amino acids, more preferably about 200 to 300 amino acid residues, or about 220 amino acids and has a bit score for the alignment of the sequence to the amidase domain (HMM) of at least 150, preferably 200 or greater. The amidase domain (HMM) has been assigned the PFAM Accession Number PF01425. The first amidase domain (amino acids 69 to 289 of SEQ ID NO:62) of human 32144 aligns with a consensus amino acid sequence derived from a hidden Markov model.

The term "amidase subdomain" or "second amidase subdomain" includes an amino acid sequence of about 40 to 300 in length and having a bit score for the alignment of the sequence to the amidase domain (HMM) of at least 10. Preferably, an amidase domain includes at least about 60 to 200 amino acids, more preferably about 80 to 100 amino acid residues, or about 94 amino acids and has a bit score for the alignment of the sequence to the amidase domain (HMM) of at least 20, preferably 30 or greater. The amidase domain (HMM) has been assigned the PFAM Accession Number PF01425. The second amidase subdomain (amino acid residues 419 to 513 of SEQ ID NO:62) of human 32144 aligns with a consensus amino acid sequence derived from a hidden Markov model.

In a preferred embodiment, a 32144 polypeptide or protein has at least one "amidase subdomain" or a region that includes at least the size ranges described above and has at least about 60%, 70% 80% 90% 95%, 99%, or 100% homology with an "amidase domain," e.g., the amidase subdomain of human 32144 (e.g., residues 69 to 289 or 419 to 513 of SEQ ID NO:62).

To identify the presence of an "amidase" or "fatty acid amide hydrolase" domain in a 32144 protein sequence, and make the determination that a polypeptide or protein of interest has a particular profile, the amino acid sequence of the protein can be searched against the PFAM database of HMMs (e.g., the Pfam database, release 2.1) using the default parameters. For example, the hmmsf program, which is available as part of the HMMER package of search programs, is a family specific default program for MILPAT0063 and a score of 15 is the default threshold score for determining a hit. Alternatively, the threshold score for determining a hit can be lowered (e.g., to 8 bits). A description of the PFAM database can be found in Sonhammer et al. (1997) *Proteins* 28(3):405-420 and a detailed description of HMMs can be found, for example, in Gribskov et al. (1990) *Meth. Enzymol.* 183:146-159; Gribskov et al. (1987) *Proc. Natl. Acad. Sci. USA* 84:4355-4358; Krogh et al. (1994) *J. Mol. Biol.* 235:1501-1531; and Stultz et al. (1993) *Protein Sci.* 2:305-314, the contents of which are incorporated herein by reference. A search was performed against the HMM database resulting in the identification of a "amidase" domain in the amino acid sequence of human 32144, which includes two amidase subdomains located at about amino acid residues 69 to 289 and 419 to 513 of SEQ ID NO:62.

In one embodiment, a 32144 protein includes at least one amidase signature motif. As used herein, an "amidase signature motif" includes a sequence of at least nineteen amino acid residues defined by the sequence: G-[G/A]-S-[G/S]-[GIS]-G-X-[G/S/A]-[G/S/A/V/Y]-X-[G/A]-X-[D/E]-X-[G/A]-X-S-[L/I/V/M]-R-X-P-[G/S/A/C] (SEQ ID NO:66). An amidase signature motif, as defined, can be involved in the enzymatic hydrolysis of a fatty acid amide. More preferably, an amidase signature motif includes 25, 29, or even more preferably 32 amino acid residues. Amidase signature motifs have been described in, e.g., Mayaux et al. (1990), *J Bacteriology* 172:6764-73, the contents of which are incorporated herein by reference. Human 32144 contains a sequence (about amino acid residues 204-235 of SEQ ID NO:62) which matches the sequence of an amide signature motif at 18/19 of the conserved positions. The single discrepancy occurs at position 9 ([G/S/A/V/Y]) of the amidase signature sequence, where there is a conservative cystein substitution (located at about amino acid residue 212 of SEQ ID NO:62) observed in human 32144.

In a preferred embodiment, a 32144 polypeptide or protein has at least one amidase signature motif, or a region which includes at least 19, 25, 29, or even 32 amino acid residues and has at least 70%, 80%, 90%, or 100% homology with an "amidase signature motif" or the variant amidase signature motif observed in human 32225, e.g., about amino acid residues 204 to 235 of SEQ ID NO:62.

A 32144 molecule can further include a transmembrane region. As used herein, the term "transmembrane domain" includes an amino acid sequence of at least about 14 amino acid residues in length that spans a phospholipid membrane. More preferably, a transmembrane domain includes at least about 14, 16, 18, 20, 22, or 24 amino acid residues and spans a phospholipid membrane. Transmembrane domains are rich in hydrophobic residues, and typically have an I-helical structure. In a preferred embodiment, at least 50%, 60%, 70%, 80%, 90%, 95% or more of the amino acids of a transmembrane domain are hydrophobic, e.g., leucines, valines, alanines, phenylalanines, methionines, isoleucines, tyrosines, or tryptophans. Transmembrane domains are described in, for example, Zagotta W. N. et al., (1996) Annual Rev. Neuronsci. 19:235-63.

In a preferred embodiment, a 32144 polypeptide or protein has at least one transmembrane domain or a region which includes at least 18, 19, or 20 amino acid residues and has at least about 60%, 70%, 80%, 90%, 95%, 99%, or 100% homology with a "transmembrane domain," e.g., at least one transmembrane domain of human 32144 (e.g., from about amino acid residues 11 to 33 of SEQ ID NO:62). In one embodiment, the transmembrane domain of a 32144 molecule is able to interact with transmembrane domains of other molecules, e.g. other 32144 molecules, such that the 32144 forms an oligomer, e.g., a homooligomer. The self-association of fatty acid amide hydrolases via N-terminal transmembrane domains has been described in Ueda et al. (2000), supra.

A 32144 family member can include at least one, and preferably two amidase subdomains. Furthermore, a 32144 family member can include at least one amidase signature motif; at least one transmembrane domain; at least one, two, three, four, five, six, seven, and preferably eight predicted protein kinase C phosphorylation sites (PS00005); at least one, two, and preferably three predicted casein kinase II phosphorylation sites (PS00006); at least one, two, three, four, five, six, seven, eight, nine, ten, and preferably eleven predicted N-myristylation sites (PS00008); at least one, and preferably two predicted N-glycosylation sites (PS00001); and at least one predicted Microbodies C-terminal targeting signal (PS00342).

As the 32144 polypeptides of the invention may modulate 32144-mediated activities, they may be useful as of for developing novel diagnostic and therapeutic agents for 32144-mediated or related disorders, as described below.

As used herein, a "32144 activity", "biological activity of 32144" or "functional activity of 32144", refers to an activity exerted by a 32144 protein, polypeptide or nucleic acid molecule. For example, a 32144 activity can be an activity exerted by 32144 in a physiological milieu on, e.g., a 32144-responsive cell or on a 32144 substrate, e.g., a protein substrate. A 32144 activity can be determined in vivo or in vitro. In one embodiment, a 32144 activity is a direct activity, such as an association with a 32144 target molecule. A "target molecule" or "binding partner" is a molecule with which a 32144 protein binds or interacts in nature. In an exemplary embodiment, 32144 is an enzyme that hydrolyses fatty acid amides, e.g., anandamide or ethanolamides of oleic (e.g., oleamide), linoleic, or palmitic acids.

A 32144 activity can also be an indirect activity, e.g., a cellular signaling activity mediated by interaction of the 32144 protein with a 32144 receptor. The features of the 32144 molecules of the present invention can provide similar biological activities as fatty acid amide hydrolase family members. For example, the 32144 proteins of the present invention can have one or more of the following activities: (1) bind and catabolize fatty acid amides; (2) regulate neuronal signaling; (3) regulate ion channel function, e.g., $5\text{-HT}_3$ ion channel function; (4) regulate cannabinoid receptor signaling; (5) regulate seratonin signaling, e.g., $5\text{-HT}_2$ response to seratonin; (6) regulate gap junction activity; (7) regulate pain reception; (8) regulate development; (9) regulate cellular proliferation and/or migration; (10) regulate focal adhesion kinase activity; or (11) regulate the induction of sleep.

Thus, the 32144 molecules can act as novel diagnostic targets and therapeutic agents for controlling cellular proliferation and/or differentiation disorders, disorders of the brain, CNS, or peripheral nervous system, metabolic and pain disorders, or sleep disorders, e.g., narcolepsy.

Examples of cellular proliferation and/or differentiation disorders include cancer, e.g., carcinoma, sarcoma, metastatic disorders or hematopoietic neoplastic disorders, e.g., leukemias. A metastatic tumor can arise from a multitude of primary tumor types, including but not limited to those of prostate, colon, lung, breast and liver origin.

Tissue Distribution of 32144 mRNA

Endogenous human 32144 gene expression was determined using the Perkin-Elmer/ABI 7700 Sequence Detection System which employs TaqMan technology. Tissues tested include the human tissues and several cell lines shown in Tables 22-25. 32144 mRNA was detected in a number of tissues, including the kidney, pancreas, brain, and liver (Table 22). Importantly, 32144 expression was upregulated in most of the lung, colon, breast, and ovarian tumors tested (Tables 22-24). 32144 mRNA was also detected in several tumor cell lines, whether grown in vivo (Table 25) or in vitro (Table 26), and growth of breast tumor cell lines on agar correlated with increased expression of 32144 mRNA as compared to growth on plastic (Table 26).

The incidence of tumor-associated expression of 32144 mRNA in lung, ovary, breast, and colon tissues was further evaluated by in situ hybridization (Table 27). Notable tumor-associated expression of 32144 is seen in all of the different tumor types tested. This data, like the Taqman data, suggests a role for 32144 in tumor development. In addition, expression of 32144 mRNA in invasive indolent breast carcinomas vs. metastatic breast carcinomas was evaluated by hybridizing tumor cell RNA to microarray chips that were capable of detecting 32144 nucleic acids (Table 28). All of the tumors tested expressed 32144 mRNA, while 2/5 metastatic tumors and 0/3 invasive indolent tumors displayed a relative increase in 32144 expression. This data, along with the colon tumor in-situ hybridization data reveals a positive correlation between 32144 expression and tumor metastasis, at least for breast and colon tumors.

TABLE 22

| Tissue Type | 32144 Mean | β2 Mean | Relative Expression |
|---|---|---|---|
| Artery normal | 34.72 | 22.38 | 0.19 |
| Aorta diseased | 33.33 | 23.00 | 0.78 |
| Vein normal | 35.26 | 20.66 | 0.00 |
| Coronary SMC | 35.06 | 21.18 | 0.00 |
| HUVBC | 31.24 | 21.50 | 1.17 |

TABLE 22-continued

| Tissue Type | 32144 Mean | β2 Mean | Relative Expression |
|---|---|---|---|
| Hemangioma | 31.99 | 20.05 | 0.25 |
| Heart normal | 33.42 | 20.90 | 0.17 |
| Heart CHF | 31.20 | 20.26 | 0.51 |
| Kidney | 27.57 | 20.53 | 7.60 |
| Skeletal Muscle | 40.00 | 28.39 | 0.00 |
| Adipose normal | 37.55 | 29.80 | 0.00 |
| Pancreas | 28.33 | 22.43 | 16.69 |
| primary osteoblasts | 35.35 | 21.07 | 0.00 |
| Osteoclasts (diff) | 34.77 | 17.92 | 0.01 |
| Skin normal | 31.45 | 22.34 | 1.81 |
| Spinal cord normal | 32.28 | 21.36 | 0.52 |
| Brain Cortex normal | 29.65 | 22.56 | 7.37 |
| Brain Hypothalamusnormal | 30.93 | 22.57 | 3.02 |
| Nerve | 34.01 | 22.24 | 0.29 |
| DRG (Dorsal Root Ganglion) | 33.84 | 22.35 | 0.35 |
| Breast normal | 30.32 | 21.55 | 2.28 |
| Breast tumor | 28.50 | 20.88 | 5.05 |
| Ovary normal | 29.64 | 20.07 | 1.32 |
| Ovary Tumor | 29.09 | 20.02 | 1.85 |
| Salivary glands | 28.74 | 19.91 | 2.19 |
| Colon normal | 28.41 | 18.40 | 0.97 |
| Colon Tumor | 28.68 | 21.98 | 9.62 |
| Lung normal | 28.62 | 18.32 | 0.79 |
| Lung tumor | 25.91 | 20.45 | 22.72 |
| Lung COPD | 28.17 | 18.70 | 1.41 |
| Colon IBD | 27.64 | 18.00 | 1.26 |
| Liver normal | 27.31 | 20.34 | 7.98 |
| Liver fibrosis | 27.41 | 20.89 | 10.82 |
| Spleen normal | 30.79 | 19.91 | 0.53 |
| Tonsil normal | 25.54 | 17.77 | 4.60 |
| Lymph node normal | 28.48 | 19.77 | 2.40 |
| Small intestine normal | 30.61 | 20.50 | 0.91 |
| Macrophages | 31.80 | 17.40 | 0.05 |
| Synovium | 31.52 | 19.78 | 0.29 |
| BM-MNC | 33.83 | 19.09 | 0.04 |
| Activated PBMC | 28.09 | 18.29 | 1.12 |
| Neutrophils | 36.31 | 19.26 | 0.00 |
| Megakaryocytes | 32.13 | 19.11 | 0.12 |
| Eythroid | 33.20 | 22.05 | 0.44 |
| positive control | 28.92 | 20.59 | 3.12 |

As shown in the "Relative Expression" column of Table 22, 32144 mRNA is expressed in the pancreas, kidney, liver, cerebral cortex, hypothalamus, tonsils, lymph nodes, breast, salivary gland, skin, and ovary. Weak expression is observed in the heart and blood vessels, dorsal root gaglia, colon, lung, spleen, small intestine, and blood cells. In addition, 32144 expression is highly upregulated in lung, colon, and breast tumors, and slightly upregulated in ovarian tumors. Abbreviations used in Table 22: SMC, smooth muscle cell; HUVEC, human umbilical vein endothelial cells; CHF, congestive heart failure; diff, differentiated; COPD, chronic obstructive pulmonary disease; IBD, inflammatory bowel disease; BM-MNC, bone marrow mononuclear cell; PBMC, pre-bone marrow cell.

TABLE 23

| Tissue Type | 32144.1 Mean | β2 Mean | Relative Expression |
|---|---|---|---|
| PIT400 Breast N | 31.85 | 20.18 | 0.31 |
| PIT 372 Breast N | 32.09 | 20.92 | 0.43 |
| PIT 271 Breast N | 35.4 | 25.48 | 0.00 |
| MDA 106 Breast T | 31.93 | 21.11 | 0.55 |
| MDA 234 Breast T | 29.27 | 18.77 | 0.69 |
| NDR 57 Breast T | 30.98 | 19.75 | 0.41 |
| MDA 304 Breast T | 29.8 | 19.34 | 0.71 |
| NDR 58 Breast T | 26.43 | 17.88 | 2.66 |
| NDR 132 Breast T | 30.15 | 21.54 | 2.57 |
| NDR 07 Breast T | 30 | 19.65 | 0.76 |

TABLE 23-continued

| Tissue Type | 32144.1 Mean | β2 Mean | Relative Expression |
|---|---|---|---|
| NDR 12 Breast T | 28.84 | 21.69 | 7.02 |
| PIT 208 Ovary N | 32.35 | 19.52 | 0.14 |
| CHT 620 Ovary N | 34.23 | 20.1 | 0.06 |
| CHT 619 Ovary N | 34.7 | 20.6 | 0.06 |
| CLN 03 Ovary T | 29.57 | 20.08 | 1.39 |
| CLN 17 Ovary T | 27.84 | 20.35 | 5.58 |
| CLN 07 Ovary T | 30.43 | 19.66 | 0.57 |
| CLN 08 Ovary T | 29.87 | 18.9 | 0.50 |
| MDA 216 Ovary T | 33.05 | 21.04 | 0.24 |
| CLN 012 Ovary T | 31.83 | 22.16 | 1.22 |
| MDA 25 Ovary T | 29.89 | 22.62 | 6.50 |
| MDA 183 Lung N | 30.52 | 18.43 | 0.23 |
| CLN 930 Lung N | 32.03 | 19.36 | 0.15 |
| MDA 185 Lung N | 34.11 | 19.88 | 0.05 |
| CHT 816 Lung N | 30.36 | 17.2 | 0.11 |
| MPI 215 Lung T--SmC | 31.25 | 18.91 | 0.19 |
| MDA 259 Lung T-PDNSCCL | 27.37 | 19.87 | 5.52 |
| CHT 832 Lung T-PDNSCCL | 28.59 | 19.36 | 1.68 |
| MDA 253 Lung T-PDNSCCL | 29.66 | 19 | 0.62 |
| CHT 911 Lung T-SCC | 28.73 | 19.3 | 1.45 |
| CHT 793 Lung T-ACA (?) | 29.3 | 19.2 | 0.91 |
| MDA 262 Lung T-SCC | 31.18 | 23.35 | 4.38 |
| CHT 211 Lung T-AC | 28.01 | 19.86 | 3.53 |
| NHBE | 30.45 | 21.66 | 2.27 |
| MDA 127 N Ovarian Epithelial Cells | 34.08 | 16.97 | 0.01 |
| MDA 224 N Ovarian Epithelial Cells | 36.37 | 16.62 | 0.00 |
| MDA 124 Ovarian Ascites | 28.13 | 15.52 | 0.16 |
| MDA 126 Ovarian Ascites | 26.59 | 17.4 | 1.71 |

As shown in the "Relative Expression" column of Table 23, 32144 mRNA expression is slightly upregulated in 4/8 of the breast tumor samples tested, as compared to normal breast tissue, and dramatically upregulated in 3/8 of the breast tumor samples. Likewise, 7/7 ovary tumor samples displayed an increase in 32144 expression relative to normal ovary tissue, while 2/7 contained dramatically upregulated levels of 32144 mRNA. Amongst lung tumor samples tested, 8/9 displayed an increase in 32144 expression relative to normal lung tissue, with 4/9 containing highly elevated levels of 32144 mRNA. Abbreviations used in Table 23: N, normal tissue; T, tumor; 5 mC, small cell carcinoma; PDNSCCL, poorly differentiated non-small cell carcinoma; SCC, squamous cell carcinoma; AC, adenocarcinoma; NHBE, lung cell line.

TABLE 24

| Tissue Type | 32144.1 Mean | β2 Mean | Relative Expression |
|---|---|---|---|
| CHT 523 Colon N | 31.64 | 19 | 0.16 |
| NDR 104 Colon N | 28.39 | 19.09 | 1.59 |
| CHT 416 Colon N | 30.23 | 19.48 | 0.58 |
| CHT 452 Colon N | 32 | 18.7 | 0.10 |
| NDR 210 Colon T | 32.7 | 24.07 | 2.51 |
| CHT 398 Colon T | 27.32 | 19.91 | 5.84 |
| CHT 382 Colon T | 26.62 | 18.97 | 4.96 |
| CHT 944 Colon T | 28.61 | 18.84 | 1.15 |
| CHT 528 Colon T | 26.5 | 19.07 | 5.78 |
| CHT 1365 Colon T | 27.56 | 19.2 | 3.05 |
| CHT 372 Colon T | 30.31 | 20.27 | 0.95 |
| CLN 609 Colon T | 28.55 | 20.02 | 2.70 |
| CHT 01 Liver Met | 28.29 | 18.11 | 0.87 |
| NDR 100 Liver Met | 26.37 | 18.59 | 4.53 |
| CHT 340 Liver Met | 30.07 | 20.79 | 1.60 |
| NDR 217 Liver Met | 29.04 | 19.2 | 1.10 |
| PIT 260 Liver N | 27.5 | 17.77 | 1.17 |
| CHT 320 Liver N | 30.67 | 23.56 | 7.21 |
| C48 HMVEC-Prol | 36.87 | 20.74 | 0.00 |
| ONC 102 Hemangioma | 33.59 | 20.15 | 0.09 |

As shown in the "Relative Expression" column of Table 24, 6/8 of the tested colon tumors had an elevated level of 32144 expression as compared to normal colon tissue, with 3/8 displaying a dramatic increase in 32144 mRNA expression. All liver metastases tested expressed 32144 mRNA. Abbreviations used in Table 24: N, normal tissue; T, tumor; Met, metastasis; HMVEC, human vascular endothelial cells; prol, proliferating.

TABLE 25

| Cell Line | 32144.1 Mean | B-2 Mean | Relative Expression |
|---|---|---|---|
| MCF-7 Breast T | 25.21 | 18.88 | 12.43 |
| ZR75 Breast T | 26.34 | 20.29 | 15.09 |
| T47D Breast T | 25.98 | 18.00 | 3.96 |
| MDA 231 Breast T | 33.38 | 17.35 | 0.01 |
| MDA 435 Breast T | 30.20 | 15.89 | 0.05 |
| SKBr3 Breast | 28.63 | 18.99 | 1.25 |
| DLD 1 ColonT (stageC) | 24.36 | 19.44 | 33.03 |
| SW620 ColonT (stageC | 25.12 | 18.26 | 8.58 |
| HCT116 | 25.33 | 18.00 | 6.22 |
| HT29 | 25.09 | 15.88 | 1.68 |
| Colo 205 | 24.23 | 14.83 | 1.48 |
| NCIH125 | 30.26 | 17.38 | 0.13 |
| NCIH322 | 25.66 | 18.36 | 6.37 |
| NCIH460 | 32.71 | 17.33 | 0.02 |
| A549 | 32.39 | 18.62 | 0.07 |
| NHBE | 30.14 | 21.37 | 2.29 |
| SKOV-3 ovary | 28.29 | 17.24 | 0.47 |
| OVCAR-3 ovary | 26.55 | 20.31 | 13.23 |
| 293 baby kidney | 27.04 | 20.28 | 9.23 |
| 293T baby kidney | 32.24 | 21.60 | 0.63 |

Table 25 depicts the relative expression of 32144 mRNA in cell lines that have been xenographed into mice and allowed to form tumors. Several of the lines display high levels of 32144 expression when grown under such conditions. Most notable is one of the Stage C colon tumor lines, a couple of the breast tumor lines, one of the ovary carcinoma lines, and a baby kidney fibroblast line. Many of the other cell lines also express 32144 mRNA when xenographed into mice. Abbreviation used in Table 25: T, tumor; HCT116, HT29, and Colo 205, colon carcinoma cell lines; NCIH125, NCIH322, NCIH460, A549, and NHBE, lung carcinoma cell lines.

TABLE 26

| Tissue Type | 32144.1 Mean | β2 Mean | Relative Expression |
|---|---|---|---|
| MCF10MS | 31.31 | 19.84 | 0.35 |
| MCF10A | 37.33 | 19.75 | 0.00 |
| MCF10AT.cl1 | 39.96 | 19.48 | 0.00 |
| MCF10AT.cl3 | 38.22 | 18.86 | 0.00 |
| MCF10AT1 | 31.68 | 19.94 | 0.29 |
| MCF10AT3B | 39.88 | 19.47 | 0.00 |
| MCF10CA1a.cl1 | 34.26 | 17.09 | 0.01 |
| MCF10AT3B Agar | 32.53 | 25.9 | 10.10 |
| MCF10CA1a.cl1 Agar | 33.95 | 24.5 | 1.43 |
| MCF10A.m25 Plastic | 37.11 | 24.54 | 0.00 |
| MCF10CA Agar | 33.07 | 21.5 | 0.33 |
| MCF10CA Plastic | 33.27 | 21.56 | 0.30 |
| MCF3B Agar | 29.58 | 21.84 | 4.68 |
| MCF3B Plastic | 30.32 | 21.58 | 2.35 |
| MCF10A EGF 0 hr | 32.59 | 17.23 | 0.02 |
| MCF10A EGF 0.5 hr | 32.2 | 17.45 | 0.04 |
| MCF10A EGF 1 hr | 32.63 | 17.6 | 0.03 |
| MCF10A EGF 2 hr | 32.83 | 17.63 | 0.03 |
| MCF10A EGF 4 hr | 33.52 | 17.63 | 0.02 |
| MCF10A EGF 8 hr | 33.31 | 17.52 | 0.02 |
| MCF10A IGF1A 0 hr | 31.05 | 21.58 | 1.41 |
| MCF10A IGF1A 0.5 hr | 31.36 | 21.75 | 1.27 |
| MCF10A IGF1A 1 hr | 30.93 | 21.84 | 1.84 |
| MCF10A IGF1A 3 hr | 30.78 | 21.88 | 2.09 |

TABLE 26-continued

| Tissue Type | 32144.1 Mean | β2 Mean | Relative Expression |
|---|---|---|---|
| MCF10A IGF1A 24 hr | 29.32 | 21.84 | 5.62 |
| MCF10AT3B.cl5 Plastic | 35.42 | 21.82 | 0.00 |
| MCF10AT3B.cl6 Plastic | 35.7 | 21.85 | 0.00 |
| MCF10AT3B.cl3 Plastic | 36.19 | 21.63 | 0.00 |
| MCF10AT3B.cl1 Plastic | 35.02 | 21.72 | 0.00 |
| MCF10AT3B.cl4 Plastic | 35.09 | 21.47 | 0.00 |
| MCF10AT3B.cl2 Plastic | 36.45 | 21.84 | 0.00 |
| MCF10AT3B.cl5 Agar | 31.91 | 24.06 | 4.33 |
| MCF10AT3B.cl6 Agar | 32.32 | 24.05 | 3.23 |
| MCF-7 | 30.1 | 23.27 | 8.76 |
| ZR--75 | 28.29 | 21.59 | 9.65 |
| T47D | 29.61 | 21.64 | 3.97 |
| MDA-231 | 36.9 | 20.45 | 0.00 |
| MDA-435 | 36.16 | 20.55 | 0.00 |
| SkBr3 | 30.81 | 20.93 | 1.06 |
| Hs578Bst | 36.78 | 19.85 | 0.00 |
| Hs578T | 38.49 | 19.66 | 0.00 |

Table 26 depicts the relative expression of 32144 mRNA in breast carcinoma cell lines grown under various conditions. Growth of the cell lines on agar correlates with an increase in 32144 expression, as shown by the MCF10AT3B, MCF3B, MCF10AT3B clone 5 and MCT10AT3B clone 6 cell lines. MCF10A cells did not display a change in 32144 expression in response to epidermal growth factor (EGF), while they did respond to insulin growth factor 1A (IGF-1A) by gradually increasing 32144 mRNA expression over the course of 24 hours.

TABLE 27

| Spectrum | Tissue | Expression |
|---|---|---|
| CHT 800 | Lung - PD-NSC | +/− |
| CHT 813 | Lung - MD-SCC | −/− |
| CHT 726 | Lung - MD-SCC | +/− |
| CHT 331 | Lung - MD-AC | −/− |
| MPI 216 | Lung - Normal | −/− |
| (LUNG: 0/1 normals; 2/4 tumors) | | |
| MDA 28 | Ovary - Malignant | −/− |
| MDA 300 | Ovary - MD-AC | +/− |
| MDA 202 | Ovary - Normal | −/− |
| (OVARY: 0/1 normals; 1/2 tumors) | | |
| NDR 7 | Breast - IDC | +/− |
| NDR 12 | Breast - IDC | +++/+ |
| NDR 57 | Breast - PD-Ductal AC | +/− |
| CLN 662 | Breast - IDC/IDL | +/− |
| MDA 156 | Breast - DCIS | ++/+ |
| CLN 156 | Breast - PD-IDC | +/+ |
| MDA 91 | Breast - AC | +++/+ |
| PIT 58 | Breast - PD-AC(lung) | −/− |
| CHT 1841 | Breast - Met AC(lymph) | +/− |
| PIT 116 | Breast - Met AC(lung) | +/− |
| MDA 405 | Breast - normal | −/− |
| (BREAST: 0/1 normals; 7/7 tumors; 2/3 metastasis) | | |
| CLN 609 | Colon - Invasive | −/− |
| NDR 99 | Colon - Invasive | +/− |
| NDR 100 | Colon - AC(liver) | +/+ |
| CHT 1 | Colon - Met AC | ++/+ |
| (Colon: 1/2 tumors; 2/2 metastasis) | | |

Expression of 32144 mRNA was analyzed by in-situ hybridization in both normal and tumor tissue samples. Expression of 32144 mRNA was consistently observed in the tumors, suggesting a role for 32144 in tumor development. Furthermore, in colon tumor samples, expression of 32144 mRNA was more prevalent in metastatic tumors, indicating a possible link between 32144 expression and tumor metastasis in some tissues. Abbreviations used in Table 27 include: PD, poorly differentiated; MD, moderately differentiated; NSCC, non-small cell carcinoma; SCC, squamous cell carcinoma; AC, adenocarcinoma; IDC, invasive ductal carcinoma; ILC, invasive lobular carcinoma; Met, metastasis. Parenthesis indicates the tissue in which the tumor was found, if other than the tissue of origin.

TABLE 28

| Spectrum | Tissue | Relative Expression |
|---|---|---|
| MPM51 | Breast - IIC | 1.29 |
| MPM66 | Breast - IIC | 2.25 |
| MPM67 | Breast - IIC | 1.80 |
| MPM81 | Breast - MetC | 2.50 |
| MPM50 | Breast - MetC | 1.24 |
| MPM68 | Breast - MetC | 10.23 |
| MPM70 | Breast - MetC | 10.22 |
| MPM71 | Breast - MetC | 1.92 |

Expression array-based analysis of human 32144 mRNA expression in invasive indolent breast carcinomas (IIC) and metastatic breast carcinomas (MetC). 2/5 metastatic breast carcinomas displayed an elevated level of 32144 expression, while 0/3 invasive indolent breast carcinomas displayed an elevation in 32144 expression, suggesting a correlation between elevated 32144 expression and tumor metastasis.

Human 32235

The present invention is based, in part, on the discovery of a novel aminotransferase family member, referred to herein as "32235".

The human 32235 sequence (SEQ ID NO:67), which is approximately 1816 nucleotides long including untranslated regions, contains a predicted methionine-initiated coding sequence of about 1350 nucleotides, not including the termination codon (nucleotides 84-1433 of SEQ ID NO:67; 1-1350 of SEQ ID NO:69). The coding sequence encodes a 450 amino acid protein (SEQ ID NO:68).

An alignment of the aminotransferase class III domain of human 32235 with a consensus amino acid sequence derived from a hidden Markov model (HMM) from PFAM shows the consensus amino acid sequence (SEQ ID NO:70) aligns with amino acids 23 to 437 of SEQ ID NO:68.

A BLAST alignment of a first region of the aminotransferase class III domain of human 32235 with a consensus amino acid sequence of a domain derived from the Propomain database ("AMINOTRANSFERASE CG8745 CG11241 PHOSPHATE PYRIDOXAL AMINOTRANSFERASES PRECURSOR BETA-ALAAT BETA-ALANINE-PYRUVATE;" No. PD082189; Propomain Release 2001.1) shows amino acid residues 1 to 159 of the amino acid PD082189 consensus sequence (SEQ ID NO:71) aligns the first region of the human 32235 sequence (amino acid residues 84 to 246 of SEQ ID NO:68).

A BLAST alignment of a second region of the aminotransferase class III domain of human 32235 with a consensus amino acid sequence of a domain derived from the Propomain database ("AMINOTRANSFERASE PYRIDOXAL ADENOSYLMETHIONINE-8-AMINO-7-OXONONANOATE PHOSPHATE TRANSAMINASE BIOSYNTHESIS ACID DAPA 78-DIAMINO-PELARGONIC;" No. PD000519; Propomain Release 2001.1) shows amino acid residues 12 to 68 of the amino acid PD000519 consensus sequence (SEQ ID NO:72), while the upper amino acid sequence corresponds to the second region of the human 32235 sequence (amino acid residues 308 to 363 of SEQ ID NO:68).

A CLUSTAL W alignment of human 32235 with human and mouse beta-alanine pyruvate aminotransferase (Accession No. AR105920 in GenBank, and BAB28878 in GenPept, respectively) shows nucleotides 1 to 1844 of BAB28878 (SEQ ID NO:73) and nucleotides 1 to 1786 of AR105920 (SEQ ID NO:74) align with nucleotides 1 to 1816 of human 32235 (SEQ ID NO:69). CLUSTAL W (v 1.74; Thompson et al. (1994) *Nuc. Acids Res.* 22:4673-80) uses dynamically varied gap penalties for progressive sequence alignments.

A CLUSTAL W alignment of human 32235 with human ornithine aminotransferase (Accession No. P04181 in Swissprot) and human 4-aminobutyrate aminotransferase (Accession No. P80404 in Swissprot) shows amino acids 1 to 439 of P04181 (SEQ ID NO:75) aligns with amino acids 1 to 450 of human 32235 and amino acids 1 to 500 of P80404 (SEQ ID NO:76).

Human 32235 contains the following regions or other structural features (for general information regarding PFAM identifiers, PS prefix and PF prefix domain identification numbers, refer to Sonnhammer et al. (1997) *Protein* 28:405-420): an aminotransferase class III domain (PFAM Accession No. PF00202) located at about amino acid residues 23 to 437 of SEQ ID NO:68; one coiled coil structure (PSORT) located at about amino acids 416 to 446 of SEQ ID NO:68; one aminotransferase class III pyridoxal-phosphate attachment site (ProSite PS00600) located at about amino acids 203 to 206 of SEQ ID NO:68; three protein kinase C phosphorylation sites (ProSite PS00005) located at about amino acids 22 to 24, 173 to 175, and 445 to 447 of SEQ ID NO:68; six casein kinase II phosphorylation sites (ProSite PS00006) located at about amino acids 99 to 102, 112 to 115, 146 to 149, 199 to 202, 302 to 305, and 434 to 437 of SEQ ID NO:68; four N-myristoylation sites (ProSite PS00008) located at about amino acids 113 to 118, 241 to 246, 312 to 317, and 364 to 369 of SEQ ID NO:68; and one amidation site (ProSite PS00009) located at about amino acids 203 to 206 of SEQ ID NO:68.

A hydropathy plot of human 32235 was performed. Polypeptides of the invention include fragments which include: all or part of a hydrophobic sequence; all or part of a hydrophilic sequence; or a sequence which includes a cysteine residue.

The 32235 protein contains a significant number of structural characteristics in common with members of the aminotransferase family. As used herein, the term "aminotransferase" includes a protein or polypeptide which is capable of transferring an amino group from an amino acid to an oxo acid.

Members of the aminotransferase family of proteins are generally cytoplasmic or mitochondrial and play a pivotal role in the metabolism of amino acids. An alignment of the 32235 protein with human beta-alanine pyruvate aminotransferase (Accession No. in GenBank AR105920) demonstrates about 99% sequence identity between the two sequences (as calculated by CLUSTAL W). An alignment of the 32235 protein with a mouse ortholog of human beta-alanine pyruvate aminotransferase (Accession No. in GenPept BAB28878) demonstrates about 87% sequence identity between the two sequences (as calculated by CLUSTAL W).

A 32235 polypeptide can include an "aminotransferase class III domain" or regions homologous with an "aminotransferase class III domain". A 32235 polypeptide can further include a "coiled coil structure" or regions homologous with a "coiled coil structure," and at least one aminotransferase class III pyridoxal-phosphate attachment site.

As used herein, the term "aminotransferase class III domain" includes an amino acid sequence of about 400 to 500 amino acid residues in length and having a bit score for the alignment of the sequence to the aminotransferase class III domain (HMM) of at least 150. Preferably an aminotransferase class III domain mediates the transfer of an amino group from an amino acid to an oxo acid. Preferably, an aminotransferase class III domain includes at least about 400 to 500 amino acids, more preferably about 425 to 475 amino acid residues, or about 440 to 460 amino acids and has a bit score for the alignment of the sequence to the aminotransferase class III domain (HMM) of at least 150, more preferably at least 200, most preferably 250 or greater.

The aminotransferase class III domain can include a ProSite aminotransferase class III pyridoxal-phosphate attachment site (signature sequence ProSite PS00600), or sequences homologous thereto. The ProSite aminotransferase class III pyridoxal-phosphate attachment site has the following consensus sequence: [LIVMFYWC](2)-x-D-E-[IVA]-x(2)-G-[LIVMFAGC]-x(0,1)-[RSACLI]-x-[GSAD]-x(12,16)-D-[LIVMFC]-[LIVMFYSTA]-x(2)-[GSA]-K-x (3)-[GSTADNV]-[GSAC] (SEQ ID NO:77). In the above conserved signature sequence, and other motifs or signature sequences described herein, the standard IUPAC one-letter code for the amino acids is used. Each element in the pattern is separated by a dash (–); square brackets ([ ]) indicate the particular residues that are accepted at that position; x indicates that any residue is accepted at that position; and numbers in parentheses (O) indicate the number of residues represented by the accompanying amino acid.

The aminotransferase class III domain preferably includes the following highly conserved residues and regions: a nucleotide binding region (amino acids 251 to 256 of SEQ ID NO:68); a glutamic acid residue that may interact with the 3'-OH of pyridoxal-5'-phosphate (E213 in SEQ ID NO:68); an aspartate residue that may interact with the N1 nitrogen of pyridoxal-5'-phosphate (D246 in SEQ ID NO:68); and a lysine residue that may form a Schiff base with pyridoxal-5'-phosphate (K278 in SEQ ID NO:68). In certain embodiments, the aminotransferase class III domain may also include the following conserved residues: G39, Y41, D44, G47, D52, S55, G61, V68, R83, G113, A120, P183, A208, G220, F243, E247, Q249, G251, G256, G283, T309, G312, P314, E330, L332, A336, G340, L343, L347, V360, R361, G362, G364, F411, and P413 in SEQ ID NO:2 that may play a catalytic and/or structural role.

The aminotransferase class III domain (HMM) has been assigned the PFAM Accession Number PF00202. The aminotransferase class III domain (amino acids 23 to 437 of SEQ ID NO:68) of human 32235 aligns with the PFAM aminotransferase class III domain consensus amino acid sequence (SEQ ID NO:70) derived from a hidden Markov model.

In a preferred embodiment, a 32235 polypeptide or protein has an "aminotransferase class III domain" or a region which includes at least about 400 to 500 amino acids, more preferably about 425 to 475 amino acid residues, or about 440 to 460 amino acid residues and has at least about 60%, 70%, 80%, 90%, 95%, 99%, or 100% homology with an "aminotransferase class III domain," e.g., the aminotransferase class III domain of human 32235 (e.g., residues 23 to 437 of SEQ ID NO:68).

To identify the presence of an "aminotransferase class III domain" in a 32235 protein sequence, and make the determination that a polypeptide or protein of interest has a particular profile, the amino acid sequence of the protein can be searched against the Pfam database of HMMs (e.g., the Pfam database, release 2.1) using the default parameters. For example, the hmmsf program, which is available as part of the HMMER package of search programs, is a family specific default program for MILPAT0063 and a score of 15 is the default threshold score for determining a hit. Alternatively, the threshold score for determining a hit can be lowered (e.g., to 8 bits). A description of the Pfam database can be found in Sonhammer et al. (1997) *Proteins* 28:405-420 and a detailed description of HMMs can be found, for example, in Gribskov et al. (1990) *Meth. Enzymol.* 183:146-159; Gribskov et al. (1987) *Proc. Natl. Acad. Sci. USA* 84:4355-4358; Krogh et al. (1994) *J. Mol. Biol.* 235:1501-1531; and Stultz et al. (1993) *Protein Sci.* 2:305-314, the contents of which are incorporated herein by reference. A search was performed against the HMM database resulting in the identification of an "aminotransferase class III domain" in the amino acid sequence of human 32235 at about residues 23 to 437 of SEQ ID NO:68.

For further identification of an "aminotransferase class III domain" in a 32235 protein sequence, and make the determination that a polypeptide or protein of interest has a particular profile, the amino acid sequence of the protein can be searched against a database of domains, e.g., the Propom database (Corpet et al. (1999), *Nucl. Acids Res.* 27:263-267). The Propom protein domain database consists of an automatic compilation of homologous domains. Current versions of Propom are built using recursive PSI-BLAST searches (Altschul et al. (1997) *Nucleic Acids Res.* 25:3389-3402; Gouzy et al. (1999) *Computers and Chemistry* 23:333-340) of the SWISS-PROT 38 and TREMBL protein databases. The database automatically generates a consensus sequence for each domain. A BLAST search was performed against the HMM database resulting in the identification of a first and second region of an "aminotransferase class III domain" domain in the amino acid sequence of human 32235 at about residues 84 to 246 and 308 to 363 of SEQ ID NO:68.

A 32235 family member can include at least one amino transferase class III domain. A 32235 family member can further include a coiled coil structure and an aminotransferase class III pyridoxal-phosphate attachment site (ProSite PS00600). Furthermore, a 32235 family member can include at least one, two, preferably three protein kinase C phosphorylation sites (ProSite PS00005); at least one, two, three, four, five, preferably six casein kinase II phosphorylation sites (ProSite PS00006); at least one, two, three, and preferably four N-myristoylation sites (ProSite PS00008); and at least one amidation site (ProSite PS00009).

As the 32235 polypeptides of the invention can modulate 32235-mediated activities, they can be useful for developing novel diagnostic and therapeutic agents for aminotransferase-associated or other 32235-associated disorders, as described below.

As used herein, an "aminotransferase-associated activity" includes an activity which involves transfer of an amino group from an amino acid to an oxo acid. Members of the family can play a role in metabolic disorders, e.g., disorders of amino acid metabolism.

As used herein, a "32235 activity", "biological activity of 32235" or "functional activity of 32235", refers to an activity exerted by a 32235 protein, polypeptide or nucleic acid molecule on e.g., a 32235-responsive cell or on a 32235 substrate, e.g., a protein substrate, as determined in vivo or in vitro. In one embodiment, a 32235 activity is a direct activity, such as an association with a 32235 target molecule. A "target molecule" or "binding partner" is a molecule with which a 32235 protein binds or interacts in nature. In an exemplary embodiment, 32235 is an enzyme for a substrate, e.g., an amino acid substrate such as L-alanine or an oxo acid substrate such as pyruvate.

A 32235 activity can also be an indirect activity, e.g., a cellular signaling activity mediated by interaction of the 32235 protein with a 32235 receptor. Based on the above-described sequence structures and similarities to molecules of known function, the 32235 molecules of the present invention can have similar biological activities as aminotransferase family members. For example, the 32235 proteins of the present invention can have one or more of the following activities: (1) the ability to modulate metabolism, e.g., amino acid metabolism; (2) the ability to bind an amino acid, e.g., L-alanine; (3) the ability to bind an oxo acid, e.g., pyruvate; (4) the ability to bind a co-factor, e.g., pyridoxal-5'-phosphate; and (5) the ability to catalyze the transfer of an amino group from an amino acid to an oxo acid, e.g., from L-alanine to pyruvate.

The 32235 molecules of the invention can modulate the activities of cells in tissues where they are expressed. For example, 32235 mRNA is expressed in lung tumors, prostate tumors, ovarian tumors, colon tumors, breast tumors, normal artery, normal heart, heart under congestive heart failure, kidney, skeletal muscle, pancreas, normal brain hypothalamus, and nerve. Accordingly, the 32235 molecules of the invention can act as therapeutic or diagnostic agents for cellular proliferative, cardiovascular, renal, muscular, pancreatic, neurological disorders, and metabolic.

The 32235 molecules can be used to treat cellular proliferative and/or differentiative disorders in part because 32235 mRNA is expressed in tumor tissues, e.g., breast tumors, lung tumors, prostate tumors, ovarian tumors and colon tumors. Examples of cellular proliferative and/or differentiative disorders include cancer, e.g., carcinoma, sarcoma, metastatic disorders or hematopoietic neoplastic disorders, e.g., leukemias. A metastatic tumor can arise from a multitude of primary tumor types, including but not limited to those of prostate, colon, lung, breast and liver origin.

The 32235 molecules can be used to treat pancreatic disorders in part because 32235 mRNA is expressed in the pancreas.

The 32235 molecules can be used to treat endothelial cell disorders in part because 32235 mRNA is expressed in endothelial tissues, e.g., human umbilical vein endothelial cells (HUVEC) and human microvascular endothelial cells (HMVEC).

The 32235 molecules can be used to treat pain disorders because 32235 mRNA is expressed in neurological tissues, e.g., nerves and the hypothalamus.

Thus, the 32235 molecules can act as novel diagnostic targets and therapeutic agents for controlling one or more cellular proliferative, cardiovascular, renal, muscular, pancreatic, neurological or other aminotransferase disorder. As used herein, "aminotransferase disorders" are diseases or disorders whose pathogenesis is caused by, is related to, or is associated with aberrant or deficient aminotransferase protein function or expression. Examples of such disorders, e.g., aminotransferase-associated or other 32235-associated disorders, include but are not limited to metabolic disorders.

The 32235 molecules can be used to treat metabolic disorders in part because aberrant or deficient function or expression of aminotransferase family members results in the inability to fully degrade essential amino acids. Diseases of metabolic imbalance include, but are not limited to, obesity, anorexia nervosa, cachexia, lipid disorders, and diabetes.

Gene Expression Analysis of 32235

Human 32235 expression was measured by TaqMan® quantitative PCR (Perkin Elmer Applied Biosystems) in cDNA prepared from a variety of normal and diseased (e.g., cancerous) human tissues or cell lines.

The results indicate significant 32235 expression in tumors, cardiovascular, renal, muscular, pancreatic, and neurological tissues.

Tables 32235 was first identified from a TxP experiment which profiled three distinct ovarian carcinoma cell lines that were grown on plastic, soft agar, and as subcutaneous xenograft tumors (see Table 29). 32235 was found to be upregulated when the cells were grown either on soft agar or as xenograft tumors compared to growth on plastic.

TABLE 29

TxP analysis

| Cell line | 32235 expression |
|---|---|
| HEY (plastic) | 1.4841 |
| HEY (soft agar) | 1.6636 |
| SKOV-3 #1 (plastic) | 1.0752 |
| SKOV-3 #1 (soft agar) | 1.4575 |
| SKOV-3 #1 (tumor) | 1.7173 |
| SKOV-3 #2 (plastic) | 1.4160 |
| SKOV-3 #2 (soft agar) | 1.9042 |
| SKOV-3 #2 (tumor) | 2.1054 |
| SKOV-3 variant #1 (plastic) | 1.2800 |
| SKOV-3 variant #1 (soft agar) | 1.4000 |
| SKOV-3 variant #1 (tumor) | 1.9748 |
| SKOV-3 variant #2 (plastic) | 1.4500 |
| SKOV-3 variant #2 (soft agar) | 1.3626 |
| SKOV-3 variant #2 (tumor) | 1.5179 |

The expression of 32235 was also increased with addition of the growth factor EGF to serum free culture media of the SKOV-3 cell line for 15, 30, or 60 minutes (see Table 30). Clinical data comparing expression of 32235 in isolated ovarian epithelial cells vs. ascites (see Table 31), across a range of tissues (see Table 32), and expression in normal and diseased tissues (see Table 33), all indicate that 32235 is upregulated in tumor tissues compared to normal tissues. 32235 is also expressed in several xenograft friendly cell lines (see Table 34).

TABLE 30

TaqMan ® analysis of the ovarian carcinoma cell line SKOV-3 ± EGF

| Cell line | Relative 32235 expression |
|---|---|
| SKOV-3 (without EGF) | 4.2 |
| SKOV-3 (with EGF 15') | 5.8 |
| SKOV-3 (with EGF 30') | 5.0 |
| SKOV-3 (with EGF 60') | 5.8 |

TABLE 31

TaqMan ® analysis of clinical human isolated ovarian epithelial cells compared to clinical ovarian ascites

| Tissue | Relative 32235 expression |
|---|---|
| Ovary (normal) | 0.9 |
| Ovary (normal) | 0.5 |
| Ovary (ascites) | 1.1 |
| Ovary (ascites) | 1.6 |

TABLE 32

TaqMan ® organ recital

| Tissue | Relative 32235 expression |
|---|---|
| Artery (normal) | 22.9 |
| Aorta (diseased) | 10.7 |

TABLE 32-continued

TaqMan ® organ recital

| Tissue | Relative 32235 expression |
|---|---|
| Vein (normal) | 4.0 |
| Coronary smooth muscle | 11.6 |
| HUVEC[1] | 28.6 |
| Hemangioma | 11.4 |
| Heart (normal) | 17.1 |
| Heart (CHF[2]) | 18.3 |
| Kidney | 17.9 |
| Skeletal muscle | 24.0 |
| Adipose (normal) | 4.8 |
| Pancreas | 15.8 |
| Primary osteoblasts | 5.5 |
| Osteoclasts (differentiated) | 0.9 |
| Skin (normal) | 7.0 |
| Spinal cord (normal) | 8.8 |
| Brain hypothalamus (normal) | 19.2 |
| Nerve | 27.6 |
| Dorsal root ganglion | 11.1 |
| Breast (normal) | 10.9 |
| Breast (tumor) | 6.6 |
| Ovary (normal) | 13.5 |
| Ovary (tumor) | 2.8 |
| Prostate (normal) | 11.5 |
| Prostate (tumor) | 15.6 |
| Salivary glands | 2.7 |
| Colon (normal) | 4.7 |
| Colon (tumor) | 10.3 |
| Lung (normal) | 3.0 |
| Lung (tumor) | 10.4 |
| Lung (COPD[3]) | 11.6 |
| Colon (IBD[4]) | 2.8 |
| Liver (normal) | 8.5 |
| Liver (fibrosis) | 11.2 |
| Spleen (normal) | 5.4 |
| Tonsil (normal) | 8.1 |
| Lymph node (normal) | 6.3 |
| Small intestine (normal) | 3.5 |
| Macrophages | 0.5 |
| Synovium | 1.8 |
| Bone marrow MNC[5] | 4.4 |
| Activated peripheral blood MNC[5] | 1.9 |
| Neutrophils | 5.3 |
| Megakaryocytes | 8.9 |
| Erythroid | 11.7 |

[1]Human umbilical vein endothelial cells,
[2]congestive heart failure,
[3]chronic obstructive pulmonary disease,
[4]inflammatory bowel disease,
[5]mononuclear cells.

TABLE 33

TaqMan ® analysis comparing clinical tumors with their normal tissue counterparts

| Source | Tissue | Relative 32235 expression |
|---|---|---|
| PIT 400 | Breast (normal) | 32.7 |
| PIT 372 | Breast (normal) | 18.8 |
| CHT 559 | Breast (normal) | 0.7 |
| CLN 168 | Breast (tumor, IDC[1]) | 5.5 |
| MDA 304 | Breast (tumor, MD-IDC[2]) | 3.1 |
| CHT 2002 | Breast (tumor, IDC[1]) | 8.3 |
| CHT 562 | Breast (tumor, IDC[1]) | 4.0 |
| NDR 138 | Breast (tumor, ILC[3]) | 10.2 |
| CHT 1841 | Lymph node (breast met.) | 18.9 |
| PIT 58 | Lung (breast met.) | 5.0 |
| CHT 620 | Ovary (normal) | 6.7 |
| PIT 208 | Ovary (normal) | 11.2 |
| CLN 012 | Ovary (tumor) | 10.8 |
| CLN 07 | Ovary (tumor) | 2.9 |
| CLN 17 | Ovary (tumor) | 12.7 |
| MDA 25 | Ovary (tumor) | 24.3 |

TABLE 33-continued

TaqMan ® analysis comparing clinical tumors with their normal tissue counterparts

| Source | Tissue | Relative 32235 expression |
|---|---|---|
| MDA 216 | Ovary (tumor) | 2.9 |
| PIT 298 | Lung (normal) | 4.4 |
| MDA 185 | Lung (normal) | 6.3 |
| CLN 930 | Lung (normal) | 6.6 |
| MPI 215 | Lung (tumor, SmC[4]) | 7.3 |
| MDA 259 | Lung (tumor, PD-NSCC[5]) | 23.9 |
| CHT 832 | Lung (tumor, PD-NSCC[5]) | 6.4 |
| MDA 262 | Lung (tumor, SCC[6]) | 9.6 |
| CHT 793 | Lung (tumor, ACA[7]) | 4.6 |
| CHT 331 | Lung (tumor, ACA[7]) | 19.0 |
| CHT 405 | Colon (normal) | 9.4 |
| CHT 523 | Colon (normal) | 10.7 |
| CHT 371 | Colon (normal) | 6.5 |
| CHT 382 | Colon (tumor, MD[8]) | 7.0 |
| CHT 528 | Colon (tumor, MD[8]) | 11.8 |
| CLN 609 | Colon (tumor) | 11.2 |
| NDR 210 | Colon (tumor, PD[9]) | 36.4 |
| CHT 340 | Colon (liver met.) | 26.8 |
| NDR 100 | Colon (liver met.) | 15.8 |
| PIT 260 | Liver (normal, female) | 6.3 |
| CHT 1653 | Cervix (SCC[6]) | 8.5 |
| CHT 569 | Cervix (SCC[6]) | 1.7 |
| A24 | HMVEC[10] (arrested) | 10.0 |
| C48 | HMVEC[10] (proliferating) | 14.7 |
| Pooled | Hemangiomas | 3.6 |
| HCT 116 N22 | Normoxic | 30.0 |
| HCT 116 H22 | Hypoxic | 14.4 |

[1]Invasive ductal carcinoma,
[2]moderately differentiated invasive ductal carcinoma,
[3]invasive lobular carcinoma,
[4]small cell papillary carcinoma,
[5]poorly differentiated non squamous cell carcinoma,
[6]squamous cell carcinoma,
[7]acinic cell adenocarcinoma,
[8]moderately differentiated,
[9]poorly differentiated,
[10]human microvascular endothelial cells.

TABLE 34

TaqMan ® analysis of xenograft friendly cell lines

| Cell line | Tissue | Relative 32235 expression |
|---|---|---|
| MCF-7 | Breast (tumor) | 115.8 |
| ZR75 | Breast (tumor) | 62.9 |
| T47D | Breast (tumor) | 40.4 |
| MDA231 | Breast (tumor) | 16.9 |
| MDA435 | Breast (tumor) | 20.5 |
| SKBr3 | Breast (tumor) | 31.8 |
| DLD1 | Colon (tumor, stage C) | 397.8 |
| SW480 | Colon (tumor, stage B) | 42.2 |
| HCT116 | Colon (tumor) | 45.6 |
| HT29 | Colon (tumor) | 27.5 |
| Colo 205 | Colon (tumor) | 65.4 |
| NCIH125 | | 69.8 |
| NCIH67 | | 44.0 |
| NCIH322 | | 44.5 |
| NCIH460 | | 56.1 |
| A549 | Lung (tumor) | 122.9 |
| NHBE[1] | Lung | 60.2 |
| SKOV-3 | Ovary (tumor) | 11.8 |
| OVCAR-3 | Ovary (tumor) | 22.7 |
| 293 | Baby kidney | 116.2 |
| 293T | Baby kidney | 289.2 |

In situ hybridization (ISH) localized 32235 to the epithelial tumor component of 7/8 ovarian tumors and 3/3 lung tumors. No expression was found in normal ovarian surface epithelium (see Table 35).

TABLE 35

| Tissue | Diagnosis | Results |
|---|---|---|
| | In situ hybridization | |
| | Ovary: 7/8 Tumors; 1/1 Met; 0/2 Normals | |
| Ovary T | Endometrial adenocarcinoma | (−/−) |
| Ovary T | Endometrial adenocarcinoma | (+++/+) |
| Ovary T | Endometrial adenocarcinoma | (+/+) |
| Ovary T | PD-Serous | (+++/+) |
| Ovary T | MD-Adenocarcinoma | (+/+) |
| Ovary T | Serous carcinoma | (++/+) |
| Ovary T | PD-Serous carcinoma | (++/+) |
| Ovary T | PD-Clear cell | (++/+) |
| Ovary M | Ovarian met | (+++/+) |
| Ovary N | Normal | (−/−) |
| Ovary N | Normal ovarian stroma | (−/−) |
| | Lung: 3/3 Tumors | |
| Lung T | Non-small | (++/+) |
| Lung T | Small cell | (++/+) |
| Lung T | Small cell | (+/+) |

Human 23565

The present invention is based, in part, on the discovery of a novel zinc carboxypeptidase family member, referred to herein as “23565”.

The human 23565 sequence (SEQ ID NO:78), which is approximately 1687 nucleotides long including untranslated regions, contains a predicted methionine-initiated coding sequence of about 1308 nucleotides, (nucleotides 160-1467 of SEQ ID NO:78, 1-1308 of SEQ ID NO:80) not including the termination codon. The coding sequence encodes a 436 amino acid protein (SEQ ID NO:79).

The human 23565 protein of SEQ ID NO:79 includes an amino-terminal hydrophobic amino acid sequence, consistent with a signal sequence, of about 34 amino acids (from amino acid 1 to about amino acid 34 of SEQ ID NO:79), which upon cleavage results in the production of a mature protein form. The mature protein form is approximately 402 amino acid residues in length (from about amino acid 35 to amino acid 436 of SEQ ID NO:79).

An alignment of the zinc carboxypeptidase domain of human 23565 with a consensus amino acid sequence derived from a hidden Markov model (HMM) from PFAM shows the consensus amino acid sequence (SEQ ID NO:81) aligns with amino acids 139 to 419 of SEQ ID NO:79.

An alignment of the zinc carboxypeptidase domain of human 23565 with a consensus amino acid sequence derived from a hidden Markov model (HMM) from SMART shows the consensus amino acid sequence (SEQ ID NO:82) aligns with amino acids 139 to 419 of SEQ ID NO:79.

An alignment of the carboxypeptidase activation peptide of human 23565 with a consensus amino acid sequence derived from a hidden Markov model (HMM) from PFAM shows the consensus amino acid sequence (SEQ ID NO:83), while the lower amino acid sequence corresponds to amino acids 41 to 118 of SEQ ID NO:79.

Human 23565 contains the following regions or other structural features: one zinc carboxypeptidase domain (PFAM Accession Number PF00246) located at about amino acid residues 139 to 419 of SEQ ID NO:79, which includes one predicted zinc carboxypeptidase zinc-binding region 1 signature from about amino acid residues 187 to 209 of SEQ ID NO:79; and one predicted zinc carboxypeptidase zinc-binding region 2 signature from about amino acid residues 323 to 333 of SEQ ID NO:79; one carboxypeptidase activation peptide (PFAM Accession Number PF02244) located at about amino acid residues 41 to 118 of SEQ ID NO:79; one signal peptide located at about amino acids 1 to 34 of SEQ ID NO:79; four N-Glycosylation sites (PS00001) at about amino acids 36 to 39, 171 to 174, 256 to 259, and 281 to 284 of SEQ ID NO:79; one Glycosaminoglycan attachment site (PS00002) at about amino acid 276 to 279 of SEQ ID NO:79; two Protein Kinase C phosphorylation sites (PS00005) at about amino acids 124 to 126, and 258 to 260 of SEQ ID NO:79; seven Casein Kinase II phosphorylation sites (PS00006) at about amino 14 to 17, 141 to 144, 147 to 150, 238 to 241, 299 to 302, 416 to 419, and 426 to 429 of SEQ ID NO:79; one Tyrosine kinase phosphorylation site (PS00007) at about amino acid 351 to 358 of SEQ ID NO:79; and eight N-myristylation sites (PS00008) at about amino acid 3 to 8, 100 to 105, 206 to 211, 267 to 272, 279 to 284, 314 to 319, 368 to 373, and 389 to 394 of SEQ ID NO:79.

For general information regarding PFAM identifiers, PS prefix and PF prefix domain identification numbers, refer to Sonnhammer et al. (1997) *Protein* 28: 405-420.

A hydropathy plot of human 23565 was performed. Polypeptides of the invention include fragments which include: all or part of a hydrophobic sequence, e.g., the sequence from about amino acid 105 to 119, from about 222 to 235, from about 260 to 267 and from about 200 to 310 of SEQ ID NO:79; all or part of a hydrophilic sequence, e.g., the sequence of from about amino acid 115 to 142, from about 245 to 258, and from about 280 to 301 of SEQ ID NO:79; a sequence which includes a Cys, or a glycosylation site.

The 23565 protein contains a significant number of structural characteristics in common with members of the zinc carboxypeptidase family. The zinc carboxypeptidase family of proteins are structurally and functionally related, and are characterized by the following signature patterns: a zinc carboxypeptidase zinc-binding region 1 signature [PK]-x-[LIVMFY]-x-[LIVMFY]-x(4)-H-[STAG]-x-E-x-[LIVM]-[STAG]-x(6)-[LIVMFYTA] (SEQ ID NO:84), wherein H and E are zinc ligands, and a zinc carboxypeptidase zinc-binding region 2 signature H-[STAG]-x(3)-[LIVME]-x(2)-[LIVMFYW]-P-[FYW] (SEQ ID NO:85), wherein H is a zinc ligand. 23565, a member of the carboxypeptidase family shows good homology with critical residues of known family members. A 23565 protein typically contains one or more sequences that conform to each of the signature patterns. For example, a 23565 protein contains the sequence PAIWIDTGHSREWITHATGIWT (SEQ ID NO:86) located at amino acids 187 to 209 of SEQ ID NO:79, which corresponds to the zinc carboxypeptidase zinc-binding region 1 signature. A 23565 protein can also include the sequence HSYSQMLMYPY (SEQ ID NO:87) located at amino acids 323 to 333 of SEQ ID NO:79, which corresponds to the zinc carboxypeptidease zinc-binding region 2 signature. Carboxypeptidases are known to degrade peptide hormone and growth factors.

A 23565 polypeptide can include a “zinc carboxypeptidase domain” or regions homologous with a “zinc carboxypeptidase domain”. As used herein, the term “zinc carboxypeptidase domain” includes an amino acid sequence of about 100 to 400 amino acid residues in length and having a bit score for the alignment of the sequence to the zinc carboxypeptidase domain (HMM) of at least 200. Preferably, a zinc carboxypeptidase domain includes at least about 200 to 350 amino acids, more preferably about 250 to 300 amino acid residues, or about 275 to 285 amino acids and has a bit score for the alignment of the sequence to the zinc carboxypeptidase domain (HMM) of at least 250, 300, 350, 400 or greater. In one embodiment, a zinc carboxypeptidase domain includes one zinc carboxypeptidase zinc-binding region 1 signature: PAIWIDTGHSREWITHATGIWT (SEQ ID NO:86) located at amino acids 187 to 209 of SEQ ID NO:79, wherein the H and E residues are zinc ligands; and one zinc carboxypeptidase zinc-binding region 2 signature: HSYSQMLMYPY (SEQ ID NO:87) located at amino acids 323 to 333 of SEQ ID NO:79, wherein the H is a zinc ligand. The zinc carboxypeptidase domain (HMM) has been assigned the PFAM Accession Number PF00246. The zinc carboxypeptidase domain (HMM) has also been assigned the SMART identifier zn_carb. The zinc carboxypeptidase domain (amino acids 139 to 419 of SEQ ID NO:79) of human 23565 aligns with a consensus amino acid sequence (SEQ ID NOs:81 and 82) derived from a hidden Markov model.

In a preferred embodiment 23565 polypeptide or protein has a "zinc carboxypeptidase domain" or a region which includes at least about 200 to 350 more preferably about 250 to 300, or 275 to 285 amino acid residues and has at least about 60%, 70% 80% 90% 95%, 99%, or 100% homology with a "zinc carboxypeptidase domain," e.g., the zinc carboxypeptidase domain of human 23565 (e.g., residues 139 to 419 of SEQ ID NO:79).

The zinc carboxypeptidase family member may also include a carboxypeptidase activation peptide, which is a pro-segment motif accounting for up to about a quarter of the total length of the peptidase and responsible for modulation of folding and activity of the enzyme. Preferably, the carboxypeptidase activation peptide includes at least about 20 to 200 amino acids, more preferably about 50 to 100 amino acid residues, or about 70 to 80 amino acids and has a bit score for the alignment of the sequence to the carboxypeptidase activation peptide (HMM) of at least 50, 70, 90, 100, or greater. The carboxypeptidase activation peptide motif has been assigned the PFAM Accession Number PF02244. The zinc carboxypeptidase domain (amino acids 41 to 118 of SEQ ID NO:79) of human 23565 aligns with a consensus amino acid sequence derived from a hidden Markov model.

In a preferred embodiment 23565 polypeptide or protein has a "carboxypeptidase activation peptide" or a region which includes at least about 20 to 200 more preferably about 50 to 100 or 70 to 80 amino acid residues and has at least about 50%, 60%, 70% 80% 90% 95%, 99%, or 100% homology with a "carboxypeptidase activation peptide," e.g., the carboxypeptidase activation peptide of human 23565 (e.g., residues 41 to 118 of SEQ ID NO:79).

To identify the presence of a "zinc carboxypeptidase" domain or a "carboxypeptidase activation peptide" in a 23565 protein sequence, and make the determination that a polypeptide or protein of interest has a particular profile, the amino acid sequence of the protein can be searched against the Pfam database of HMMs (e.g., the Pfam database, release 2.1) using the default parameters. For example, the hmmsf program, which is available as part of the HMMER package of search programs, is a family specific default program for MILPAT0063 and a score of 15 is the default threshold score for determining a hit. Alternatively, the threshold score for determining a hit can be lowered (e.g., to 8 bits). A description of the Pfam database can be found in Sonhammer et al. (1997) *Proteins* 28(3): 405-420 and a detailed description of HMMs can be found, for example, in Gribskov et al. (1990) *Meth. Enzymol.* 183:146-159; Gribskov et al. (1987) *Proc. Natl. Acad. Sci. USA* 84:4355-4358; Krogh et al. (1994) *J. Mol. Biol.* 235:1501-1531; and Stultz et al. (1993) *Protein Sci.* 2:305-314, the contents of which are incorporated herein by reference. A search was performed against the HMM database resulting in the identification of a "zinc carboxypeptidase" domain in the amino acid sequence of human 23565 at about residues 139 to 419 of SEQ ID NO:79, and the identification of a "carboxypeptidase activation peptide" in the amino acid sequence of human 23565 at about residues 41 to 118 of SEQ ID NO:79.

To identify the presence of a "zinc carboxypeptidase" domain in a 23565 protein sequence, and make the determination that a polypeptide or protein of interest has a particular profile, the amino acid sequence of the protein can be searched against a SMART database (Simple Modular Architecture Research Tool) of HMMs as described in Schultz et al. (1998), *Proc. Natl. Acad. Sci. USA* 95: 5857 and Schultz et al. (200) *Nucl. Acids Res* 28:231. The database contains domains identified by profiling with the hidden Markov models of the HMMer2 search program (R. Durbin et al. (1998) *Biological sequence analysis: probabilistic models of proteins and nucleic acids.* Cambridge University Press). The database also is extensively annotated and monitored by experts to enhance accuracy. A search was performed against the HMM database resulting in the identification of a "zinc carboxypeptidase" domain in the amino acid sequence of human 23565 at about residues 139 to 419 of SEQ ID NO:79.

In yet another embodiment, the 23565 molecule can further include a signal sequence. As used herein, a "signal sequence" refers to a peptide of about 20 to 50 amino acid residues in length which occurs at the N-terminus of secretory and integral membrane proteins and which contains a majority of hydrophobic amino acid residues. For example, a signal sequence contains at least about 30 to 40 amino acid residues, preferably about 34 amino acid residues, and has at least about 40-70%, preferably about 50-65%, and more preferably about 55-60% hydrophobic amino acid residues (e.g., alanine, valine, leucine, isoleucine, phenylalanine, tyrosine, tryptophan, or proline). Such a "signal sequence", also referred to in the art as a "signal peptide", serves to direct a protein containing such a sequence to a lipid bilayer. For example, in one embodiment, a 23565 protein contains a signal sequence of about amino acids 1 to 34 of SEQ ID NO:79. The "signal sequence" is cleaved during processing of the mature protein. The mature 23565 protein corresponds to amino acids 35 to 436 of SEQ ID NO:79.

A 23565 polypeptide can optionally include at least one, two, preferably three N-glycosylation sites; at least one glycosaminoglycan attachment site; at least one, preferably two protein kinase C phosphorylation sites; at least one, two, three, four, five, six, preferably seven casein kinase II phosphorylation sites; at least one tyrosine kinase phosphorylation sites; and at least one, two, three, four, five, six, seven, preferably eight N-myristylation sites.

As the 23565 polypeptides of the invention may modulate 23565-mediated activities, they may be useful as of for developing novel diagnostic and therapeutic agents for 23565-mediated or related disorders, as described below.

As used herein, a "23565 activity," "biological activity of 23565" or "functional activity of 23565," refers to an activity exerted by a 23565 protein, polypeptide or nucleic acid molecule. For example, a 23565 activity can be an activity exerted by 23565 in a physiological milieu on, e.g., a 23565-responsive cell or on a 23565 substrate, e.g., a protein substrate. A 23565 activity can be determined in vivo or in vitro. In one embodiment, a 23565 activity is a direct activity, such as an association with a 23565 target molecule. A "target molecule" or "binding partner" is a molecule with which a 23565 protein binds or interacts in nature.

In an exemplary embodiment, 23565 is an enzyme for a polypeptide substrate.

A 23565 activity can also be an indirect activity, e.g., a cellular signaling activity mediated by interaction of the 23565 protein with a 23565 receptor. The features of the 23565 molecules of the present invention can provide similar biological activities as zinc carboxypeptidase family members. For example, the 23565 proteins of the present invention can have one or more of the following activities: (1) formation of a zinc ion complex with a carbonyl group of a substrate polypeptide and polarization of the carbon-oxygen bond; (2) formation of a tetrahedral intermediate due to attack of the carbonyl carbon by water in a reaction assisted by a carboxylate side chain of glutamate; (3) production of a dianion intermediate by rapid ionization of the tetrahedral intermediate produced; (4) cleavage of the C—N bond of the substrate to collapse the tetrahedral intermediate; (5) binding the carboxy-terminus of polypeptides; (6) hydrolyzing polypeptides to remove/release a carboxy-terminal residue; (7) participating in digestion of polypeptides/proteins; (8) processing prohormones; (9) regulating growth hormones; (10) modulating (e.g., stimulate) cell differentiation or proliferation, e.g., differentiation or proliferation of hematopoietic cells; (11) modulating hematopoiesis, e.g., erythropoiesis; (12) modulating apoptosis, of a cell, e.g., increase apoptosis of a cancer cell, e.g., a leukemic cell, (e.g., an erythroleukemia cell); or suppress apoptosis of a blood or erythroid cell; or (13) modulating transcriptional activity, e.g., cytokine transcriptional activity.

Taqman analysis revealed high levels of expression of 23565 mRNA in erythroid (GPA+) and megakaryocyte (CD61+) lineages in vivo, and in vitro, high levels of expression only during late megakaryocyte differentiation, low levels of expression in most tissues, and moderate expression in skeletal muscle and pituitary (Tables 36-40). Table 36 shows 23565 mRNA expression as determined by TaqMan assays in a panel of human tissues, including artery normal, aorta diseased, vein normal, coronary SMC, Human Umbilical Vein Endothelial Cells (HUVEC), heart, pancreas, skin, spinal cord, brain, adrenal glands, dorsal root gland (DRG), nerve, breast, ovary, colon, lung, liver, megakaryocytes, and erythroid. The highest 23565 mRNA expression was observed in megakaryocytes, followed by skeletal muscle, lymphnode, tonsil, and pituitary gland. Its expression is further enhanced in the erythroid lineage and increases as blood cell differentiation proceeds. Tables 37-40 show relative 23565 mRNA expression as determined by TaqMan assays on mRNA most derived from human hematological samples, e.g., bone marrow (BM), erythroid cells (Eryth), megakaryocytes (Meg), neutrophils (Neut), or a negative reference sample (NTC). 23565 mRNA was highly expressed in pooled megakaryocytes, glycophorin A (GPA) expressing cells, and BM CD 61+ cell. In Table 39, mRNA expression was detected at the indicated times in culture (e.g., 24 hrs., 48 hrs., days in culture). High levels of 23565 mRNA expression were observed in one sample of erythroid cells, especially day 7 (erythroid burst forming units (BFU) Eryth D7). In Table 40, high levels of 23565 mRNA expressions were observed in two samples of megakaryocyte cells, especially day 6 and day 10. This pattern of expression suggests a role for 23565 in the regulation of cytokine signaling during the development of cells of the erythroid lineage. Thus, inhibition of 23565 expression is expected to accelerate megakaryopoiesis by inhibiting degradation of growth factors critical for megakaryocyte growth. Accordingly, the 23565 molecules can act as novel diagnostic targets and therapeutic agents for controlling hematopoietic disorders.

As used herein, a "CD61-positive cell" or a "CD61-expressing cell" refers to a cell that expresses detectable levels of the CD61 antigen, preferably human CD61 antigen. CD61 recognizes a Mr 110-kilodalton (kDa) protein, also known as gpIIIa, the common β-subunit (integrin β3-chain) of the gpIIb/IIIa complex and the vitronectin receptor. The CD61 antigen is typically present on hematopoietic cells and hematopoietic colony-forming cells in the bone marrow.

As the 23565 polypeptides of the invention may modulate 23565-mediated activities, they may be useful as of for developing novel diagnostic and therapeutic agents for 23565-mediated or related disorders, e.g., blood cell- (e.g., erythroid-) associated disorders and other hematopoietic disorders.

Agents that modulate 23565 polypeptide or nucleic acid activity or expression can be used to treat anemias, in particular, drug-induced anemias or anemias associated with cancer chemotherapy, chronic renal failure, malignancies, adult and juvenile rheumatoid arthritis, disorders of hemoglobin synthesis, prematurity, and zidovudine treatment of HIV infection. A subject receiving the treatment can be additionally treated with a second agent, e.g., erythropoietin, to further ameliorate the condition.

As used herein, the term "erythropoietin" or "EPO" refers to a glycoprotein produced in the kidney, which is the principal hormone responsible for stimulating red blood cell production (erythrogenesis). EPO stimulates the division and differentiation of committed erythroid progenitors in the bone marrow. Normal plasma erythropoietin levels range from 0.01 to 0.03 Units/mL, and can increase up to 100 to 1,000-fold during hypoxia or anemia. Graber and Krantz, *Ann. Rev. Med.* 29: 51 (1978); Eschbach and Adamson, *Kidney Intl.* 28:1 (1985). Recombinant human erythropoietin (rHuEpo or epoietin alpha) is commercially available as EPOGEN.RTM. (epoietin alpha, recombinant human erythropoietin) (Amgen Inc., Thousand Oaks, Calif.) and as PROCRIT.RTM. (epoietin alpha, recombinant human erythropoietin) (Ortho Biotech Inc., Raritan, N.J.).

Aberrant expression or activity of the 23565 molecules may be involved in neoplastic disorders. Accordingly, treatment, prevention and diagnosis of cancer or neoplastic disorders related to hematopoietic cells and, in particular, cells of the erythroid lineage are also included in the present invention.

The 23565 nucleic acid and protein of the invention can also be used to treat and/or diagnose a variety of immune disorders.

The molecules of the invention may also modulate the activity of tissues in which they are expressed, e.g., skeletal muscle or pituitary, as well as other neoplastic tissues. For example, increase expression of 23565 molecules is detected on lung tumors compared to the normal lung. Accordingly, the 23565 molecules can act as novel diagnostic targets and therapeutic agents for controlling one or more of cellular proliferative and/or differentiative disorders.

Examples of cellular proliferative and/or differentiative disorders include cancer, e.g., carcinoma, sarcoma, metastatic disorders or hematopoietic neoplastic disorders, e.g., leukemias. A metastatic tumor can arise from a multitude of primary tumor types, including but not limited to those of prostate, colon, lung, breast and liver origin.

Tissue Distribution of 23565 mRNA by TagMan Analysis

Endogenous human 23565 gene expression was determined using the Perkin-Elmer/ABI 7700 Sequence Detection System which employs TaqMan technology. Tissues tested include the human tissues and several cell lines shown in Tables 36-40.

TABLE 36

| | 23565 mRNA Expression | | | |
|---|---|---|---|---|
| Tissue Type | Mean | β2 Mean | ∂∂ Ct | Expression |
| Artery normal | 40.0 | 20.1 | 19.9 | 0.0 |
| Aorta diseased | 39.9 | 22.9 | 17.0 | 0.0 |
| Vein normal | 40.0 | 20.2 | 19.8 | 0.0 |
| Coronary SMC | 38.7 | 19.7 | 18.9 | 0.0 |
| HUVEC | 40.0 | 21.2 | 18.9 | 0.0 |
| Hemangioma | 40.0 | 20.1 | 19.9 | 0.0 |

TABLE 36-continued

| 23565 mRNA Expression | | | | |
|---|---|---|---|---|
| Tissue Type | Mean | β2 Mean | ∂∂ Ct | Expression |
| Heart normal | 38.6 | 19.5 | 19.1 | 0.0 |
| Heart CHF | 40.0 | 21.3 | 18.7 | 0.0 |
| Kidney | 37.0 | 20.7 | 16.3 | 0.0 |
| Skeletal Muscle | 33.8 | 22.2 | 11.6 | 0.3 |
| Liver normal | 40.0 | 19.7 | 20.3 | 0.0 |
| Small intestine normal | 40.0 | 20.5 | 19.5 | 0.0 |
| Adipose normal | 36.7 | 19.2 | 17.5 | 0.0 |
| Pancreas | 35.8 | 22.2 | 13.6 | 0.0 |
| primary osteoblast | 38.5 | 19.8 | 18.7 | 0.0 |
| Bladder | 40.0 | 19.4 | 20.6 | 0.0 |
| Adrenal Gland normal | 36.0 | 19.4 | 16.6 | 0.0 |
| Pituitary Gland normal | 32.7 | 20.2 | 12.6 | 0.2 |
| Spinal cord normal | 38.7 | 22.0 | 16.6 | 0.0 |
| Brain Cortex normal | 36.2 | 22.2 | 14.0 | 0.0 |
| Brain Hypothalamus normal | 38.1 | 21.2 | 16.8 | 0.0 |
| Nerve | 40.0 | 20.9 | 19.1 | 0.0 |
| DRG (Dorsal Root Ganglion) | 39.4 | 21.6 | 17.9 | 0.0 |
| Breast normal | 34.8 | 20.3 | 14.5 | 0.0 |
| Breast Tumor | 33.9 | 19.6 | 14.3 | 0.0 |
| Ovary normal | 39.3 | 20.2 | 19.1 | 0.0 |
| Ovary Tumor | 37.1 | 19.9 | 17.2 | 0.0 |
| Prostate BPH | 37.5 | 20.1 | 17.4 | 0.0 |

TABLE 36-continued

| 23565 mRNA Expression | | | | |
|---|---|---|---|---|
| Tissue Type | Mean | β2 Mean | ∂∂ Ct | Expression |
| Prostate Tumor | 39.2 | 20.6 | 18.6 | 0.0 |
| Colon normal | 39.2 | 19.6 | 19.6 | 0.0 |
| Colon Tumor | 37.5 | 20.2 | 17.4 | 0.0 |
| Lung normal | 38.9 | 18.1 | 20.9 | 0.0 |
| Lung tumor | 38.6 | 20.2 | 18.4 | 0.0 |
| Lung COPD | 37.6 | 19.4 | 18.2 | 0.0 |
| Colon IBD | 40.0 | 20.5 | 19.5 | 0.0 |
| Synovium | 38.1 | 19.6 | 18.6 | 0.0 |
| Tonsil normal | 30.5 | 18.6 | 11.9 | 0.3 |
| Lymph node normal | 32.3 | 20.4 | 11.8 | 0.3 |
| Liver fibrosis | 38.4 | 21.2 | 17.3 | 0.0 |
| Spleen normal | 34.8 | 18.2 | 16.6 | 0.0 |
| Macrophages | 40.0 | 17.1 | 22.9 | 0.0 |
| Progenitors (erythroid, megakaryocyte, neutrophil) | 35.7 | 19.5 | 16.2 | 0.0 |
| Megakaryocytes | 28.3 | 19.3 | 9.1 | 1.8 |
| Activated PBMC | 37.0 | 18.1 | 18.9 | 0.0 |
| Neutrophils | 40.0 | 18.6 | 21.4 | 0.0 |
| Erythroid | 40.0 | 21.0 | 19.1 | 0.0 |
| positive control | 27.5 | 21.5 | 6.0 | 15.2 |

TABLE 37

| 23565 mRNA expression | | | | | | | |
|---|---|---|---|---|---|---|---|
| | 23565 | Beta | Avg 23565 | Avg Beta | ΔCT | ΔΔCT | Rel exp Rel exp |
| Heart PT 262 | 40 | 20.22 | 40.0 | 20.2 | 19.8 | 19.8 | 0.0 |
| Brain MCL 400 | 33.83 | 20.49 | 33.8 | 20.5 | 13.3 | 13.3 | 0.1 |
| Lung CHT 330 | 32.69 | 17.7 | 32.7 | 17.7 | 15.0 | 15.0 | 0.0 |
| Liver NDR 379 | 35.89 | 21.6 | 35.9 | 21.6 | 14.3 | 14.3 | 0.0 |
| Spleen 380 | 31.04 | 19.22 | 31.0 | 19.2 | 11.8 | 11.8 | 0.3 |
| Kidney 27 | 31.13 | 19.96 | 31.1 | 20.0 | 11.2 | 11.2 | 0.4 |
| CD3 4 hr Rest LF164 | 30.31 | 18.56 | 30.3 | 18.6 | 11.8 | 11.8 | 0.3 |
| CD3 4 hr Act LF164 | 31.72 | 19.49 | 31.7 | 19.5 | 12.2 | 12.2 | 0.2 |
| CD3 24 hr Rest LF164 | 29.13 | 18.43 | 29.1 | 18.4 | 10.7 | 10.7 | 0.6 |
| CD3 24 hr Act LF164 | 29.12 | 17.59 | 29.1 | 17.6 | 11.5 | 11.5 | 0.3 |
| CD4 4 hr Rest LF164 | 33.04 | 20.24 | 33.0 | 20.2 | 12.8 | 12.8 | 0.1 |
| CD4 4 hr Act LF164 | 31.06 | 18.77 | 31.1 | 18.8 | 12.3 | 12.3 | 0.2 |
| CD4 24 hr Rest LF164 | 32.13 | 20.07 | 32.1 | 20.1 | 12.1 | 12.1 | 0.2 |
| CD4 24 hr Act LF164 | 30.61 | 18.01 | 30.6 | 18.0 | 12.6 | 12.6 | 0.2 |
| CD8 4 hr Rest LF164 | 28.92 | 18.7 | 28.9 | 18.7 | 10.2 | 10.2 | 0.8 |
| CD8 4 hr Act LF164 | 32.51 | 20.5 | 32.5 | 20.5 | 12.0 | 12.0 | 0.2 |
| CD8 24 hr Rest LF164 | 28.93 | 18.59 | 28.9 | 18.6 | 10.3 | 10.3 | 0.8 |
| CD8 24 hr Act LF164 | 36.01 | 23.11 | 36.0 | 23.1 | 12.9 | 12.9 | 0.1 |
| CD14−/19+ LF136 | 40 | 20.08 | 40.0 | 20.1 | 19.9 | 19.9 | 0.0 |
| CD14 LF129 | 37.82 | 18.91 | 37.8 | 18.9 | 18.9 | 18.9 | 0.0 |
| mBM CD14−/11b−/15+ LF120 | 34.97 | 19.25 | 35.0 | 19.3 | 15.7 | 15.7 | 0.0 |
| mBM MNC LP7 | 37.55 | 18.97 | 37.6 | 19.0 | 18.6 | 18.6 | 0.0 |
| mBM CD34+ LP92 | 35.16 | 20.25 | 35.2 | 20.3 | 14.9 | 14.9 | 0.0 |
| BM CD34+ LF75 | 32.97 | 19.31 | 33.0 | 19.3 | 13.7 | 13.7 | 0.1 |
| Cord Blood CD34+ LF101 | 34.37 | 19.86 | 34.4 | 19.9 | 14.5 | 14.5 | 0.0 |
| GPA Hi LF156 | 29.57 | 20.25 | 29.6 | 20.3 | 9.3 | 9.3 | 1.6 |
| Pooled Neut D6 | 32.24 | 19.17 | 32.2 | 19.2 | 13.1 | 13.1 | 0.1 |
| Pooled Neut D10/12 | 36.43 | 18.97 | 36.4 | 19.0 | 17.5 | 17.5 | 0.0 |
| Pooled Eryth D10/12 | 37.32 | 21.54 | 37.3 | 21.5 | 15.8 | 15.8 | 0.0 |
| Pooled Meg D10/12 | 27.46 | 19.58 | 27.5 | 19.6 | 7.9 | 7.9 | 4.2 |
| BM CD14−/15+ LF32 | 34.4 | 18.3 | 34.4 | 18.3 | 16.1 | 16.1 | 0.0 |
| Grans LF157 | 37.43 | 17.11 | 37.4 | 17.1 | 20.3 | 20.3 | 0.0 |
| K562 | 33.12 | 22.29 | 33.1 | 22.3 | 10.8 | 10.8 | 0.5 |
| HL60 | 32.7 | 20.12 | 32.7 | 20.1 | 12.6 | 12.6 | 0.2 |
| MF11 Stromal D32 post irrad | 35.7 | 18.12 | 35.7 | 18.1 | 17.6 | 17.6 | 0.0 |
| MF12 Stromal cntl | 31.17 | 16.94 | 31.2 | 16.9 | 14.2 | 14.2 | 0.1 |
| MF13 Stromal D2 post irrad | 32.31 | 17.36 | 32.3 | 17.4 | 15.0 | 15.0 | 0.0 |
| NTC | 40 | 40 | 40.0 | 40.0 | 0.0 | 0.0 | |

TABLE 38

| | 23565 mRNA expression | | | | | | |
|---|---|---|---|---|---|---|---|
| | 23565 | Beta | AVG 23565 | AVG Beta | ΔCT | ΔΔCT | Rel exp Rel exp |
| Lung CHT 330 | 33.82 | 18.22 | 33.8 | 18.2 | 15.6 | 15.6 | 0.0 |
| Heart PT 262 | 37.86 | 20.47 | 37.9 | 20.5 | 17.4 | 17.4 | 0.0 |
| Spleen 380 | 30.16 | 19.77 | 30.2 | 19.8 | 10.4 | 10.4 | 0.7 |
| Kidney 27 | 32.55 | 21.02 | 32.6 | 21.0 | 11.5 | 11.5 | 0.3 |
| Liver NDR 379 | 37.86 | 22.64 | 37.9 | 22.6 | 15.2 | 15.2 | 0.0 |
| Fetal Liver BWH 54 | 35.04 | 23.3 | 35.0 | 23.3 | 11.7 | 11.7 | 0.3 |
| Brain MCL 400 | 34.35 | 20.75 | 34.4 | 20.8 | 13.6 | 13.6 | 0.1 |
| Colon PIT 259 | 38.03 | 22.89 | 38.0 | 22.9 | 15.1 | 15.1 | 0.0 |
| mBM MNC LP7 | 38.68 | 19.38 | 38.7 | 19.4 | 19.3 | 19.3 | 0.0 |
| mBM CD34+ LP92 | 35.59 | 21.08 | 35.6 | 21.1 | 14.5 | 14.5 | 0.0 |
| mPB CD34+ LP350 | 34.41 | 20.35 | 34.4 | 20.4 | 14.1 | 14.1 | 0.1 |
| mPB CD34+ LF53 | 32.51 | 19.51 | 32.5 | 19.5 | 13.0 | 13.0 | 0.1 |
| BM CD34+ LF89 | 35.96 | 20.88 | 36.0 | 20.9 | 15.1 | 15.1 | 0.0 |
| BM CD34+ LF75 | 40 | 24.06 | 40.0 | 24.1 | 15.9 | 15.9 | 0.0 |
| Cord Blood CD34+ MF1 | 36.37 | 21.18 | 36.4 | 21.2 | 15.2 | 15.2 | 0.0 |
| Cord Blood CD34+ LF101 | 40 | 20.09 | 40.0 | 20.1 | 19.9 | 19.9 | 0.0 |
| GPA Hi LF154 | 33.87 | 22.39 | 33.9 | 22.4 | 11.5 | 11.5 | 0.4 |
| GPA Hi LF156 | 30.53 | 21.14 | 30.5 | 21.1 | 9.4 | 9.4 | 1.5 |
| GPA Lo LF154 | 37.86 | 23.44 | 37.9 | 23.4 | 14.4 | 14.4 | 0.0 |
| GPA Lo LF156 | 33.39 | 22.02 | 33.4 | 22.0 | 11.4 | 11.4 | 0.4 |
| MF11 Stromal D32 post irrad | 38.27 | 19.03 | 38.3 | 19.0 | 19.2 | 19.2 | 0.0 |
| MF13 Stromal D2 post irrad | 33.62 | 18.11 | 33.6 | 18.1 | 15.5 | 15.5 | 0.0 |

TABLE 39

| | 23565 mRNA expression | | | | | | |
|---|---|---|---|---|---|---|---|
| | 69039 | Beta | Avg 23565 | Avg Beta | ΔCT | ΔΔCT | Rel exp Rel exp |
| BM CD61+ LP196 | 31.11 | 22.28 | 31.1 | 22.3 | 8.8 | 8.8 | 2.2 |
| Platelets LP57 | 33.89 | 17.1 | 33.9 | 17.1 | 16.8 | 16.8 | 0.0 |
| mBM CD14−/11b−/15+ LF120 | 38.31 | 20.66 | 38.3 | 20.7 | 17.7 | 17.7 | 0.0 |
| BM CD14−/11b−/15+ LF54 | 35.53 | 20.71 | 35.5 | 20.7 | 14.8 | 14.8 | 0.0 |
| BM CD14−/11b−/15+ LF128 | 34.01 | 19.9 | 34.0 | 19.9 | 14.1 | 14.1 | 0.1 |
| BM CD14−/11b−/15+ LF145 | 33.97 | 20.15 | 34.0 | 20.2 | 13.8 | 13.8 | 0.1 |
| mBM CD14−/11b+/15+ LF120 | 36.12 | 20.22 | 36.1 | 20.2 | 15.9 | 15.9 | 0.0 |
| BM CD14−/11b+/15+ LF106 | 36.95 | 20.32 | 37.0 | 20.3 | 16.6 | 16.6 | 0.0 |
| BM-1 CD15+ ench LP41 | 35.23 | 19.32 | 35.2 | 19.3 | 15.9 | 15.9 | 0.0 |
| Eryth D0 LF143 | 34.53 | 20.35 | 34.5 | 20.4 | 14.2 | 14.2 | 0.1 |
| Eryth 48 hr LF143 | 33.67 | 21.44 | 33.7 | 21.4 | 12.2 | 12.2 | 0.2 |
| Eryth D6 LF143 | 36.71 | 24.18 | 36.7 | 24.2 | 12.5 | 12.5 | 0.2 |
| Eryth D12 LF143 | 35.15 | 22.74 | 35.2 | 22.7 | 12.4 | 12.4 | 0.2 |
| Eryth D0 LF139 | 34.69 | 21.85 | 34.7 | 21.9 | 12.8 | 12.8 | 0.1 |
| Eryth 24 hr LF139 | 40 | 23.77 | 40.0 | 23.8 | 16.2 | 16.2 | 0.0 |
| Eryth D6 LF139 | 40 | 21.93 | 40.0 | 21.9 | 18.1 | 18.1 | 0.0 |
| Eryth D12 LF139 | 36.39 | 23.5 | 36.4 | 23.5 | 12.9 | 12.9 | 0.1 |
| BFU Eryth D7 LP79 | 31.51 | 22.07 | 31.5 | 22.1 | 9.4 | 9.4 | 1.4 |
| BFU Eryth D7 LP95 | 33.39 | 22.97 | 33.4 | 23.0 | 10.4 | 10.4 | 0.7 |
| BFU Eryth D7 +3epo LP81 | 35.44 | 22.62 | 35.4 | 22.6 | 12.8 | 12.8 | 0.1 |
| BFU Eryth D7 +3epo LP104 | 34.41 | 23.22 | 34.4 | 23.2 | 11.2 | 11.2 | 0.4 |
| Mast Cell LP118 | 40 | 21.18 | 40.0 | 21.2 | 18.8 | 18.8 | 0.0 |

TABLE 40

| | 23565 mRNA expression | | | | | | |
|---|---|---|---|---|---|---|---|
| | 69039 | Beta | Avg 55503 | Avg Beta | ΔCT | ΔΔCT | Rel exp Rel exp |
| Meg D0 LF140 | 33.87 | 19.13 | 33.87 | 19.13 | 14.74 | 14.74 | 0.036544 |
| Meg 48 hr LF140 | 33.27 | 20.41 | 33 | 20 | 13 | 13 | 0 |
| Meg D6 LF140 | 31.13 | 20.49 | 31 | 20 | 11 | 11 | 1 |
| Meg D0 LF166 | 34.46 | 19.43 | 34 | 19 | 15 | 15 | 0 |
| Meg 24 hr LF166 | 34.3 | 19.56 | 34 | 20 | 15 | 15 | 0 |
| Meg 48 hr LF166 | 34.21 | 20.08 | 34 | 20 | 14 | 14 | 0 |
| Meg D6 LF166 | 32.69 | 19.79 | 33 | 20 | 13 | 13 | 0 |
| Meg D10 LF166 | 29.81 | 19.65 | 30 | 20 | 10 | 10 | 1 |
| Neut D0 LF141 | 34.94 | 20.64 | 35 | 21 | 14 | 14 | 0 |

TABLE 40-continued

| | 23565 mRNA expression | | | | | | |
|---|---|---|---|---|---|---|---|
| | 69039 | Beta | Avg 55503 | Avg Beta | ΔCT | ΔΔCT | Rel exp Rel exp |
| Neut 48 hr LF141 | 33.5 | 20.58 | 34 | 21 | 13 | 13 | 0 |
| Neut D6 LF141 | 33.08 | 20.34 | 33 | 20 | 13 | 13 | 0 |
| Neut D12 LF141 | 40 | 18.75 | 40 | 19 | 21 | 21 | 0 |
| Neut D0 LF144 | 37.66 | 21.89 | 38 | 22 | 16 | 16 | 0 |
| Neut 48 hr LF144 | 35.37 | 20.48 | 35 | 20 | 15 | 15 | 0 |
| Neut D6 LF144 | 35.67 | 20.55 | 36 | 21 | 15 | 15 | 0 |
| Neut D12 LF144 | 40 | 20.54 | 40 | 21 | 19 | 19 | 0 |
| NTC | 40 | 40 | 40 | 40 | 0 | 0 | |
| NTC | 40 | 40 | 40 | 40 | 0 | 0 | |

Human 13305

The present invention is based, at least in part, on the discovery of novel molecules, referred to herein as "13305" nucleic acid and polypeptide molecules, which have homologies to known serine/threonine kinases at their active sites and in regions relating to ATP binding. Thus, 13305 proteins are expected to play a role in or function in signalling pathways associated with cellular growth.

The nucleotide sequence of the isolated human 13305 cDNA (SEQ ID NO:88), which is approximately 5389 nucleotides in length including untranslated regions, contains a predicted methionine-initiated coding sequence of about 3630 nucleotides, not including the termination codon (nucleotides 6-3635 of SEQ ID NO:88; 1-3630 of SEQ ID NO:90). The coding sequence encodes a 1210 amino acid protein (SEQ ID NO:89).

An alignment of the protein kinase family domain of human 13305 with a consensus amino acid sequence derived from a hidden Markov model (HMM) from PFAM shows the consensus amino acid sequence (SEQ ID NOs:93-94) aligns with amino acids 190 to 411 and 492 to 518 of SEQ ID NO:89.

A BLAST alignment of human 13305 with a consensus amino acid sequence derived from a Propomain "protein kinase nuclear serine/threonine-protein homeodomain-interacting homeobox DNA-binding serine/threonine F20B6.8" (Release 1999.2; see also Propomain Release 2000.1) shows amino acid residues 1 to 158 of the 158 amino acid consensus sequence (SEQ ID NO:95) aligns with the "protein kinase nuclear serine/threonine-protein homeodomain-interacting homeobox DNA-binding serine/threonine F20B6.8" domain of human 13305, amino acid residues 416 to 565 of SEQ ID NO:89.

A BLAST alignment of human 13305 with a consensus amino acid sequence derived from a Propomain "protein kinase nuclear homeodomain-interacting homeobox DNA-binding serine/threonine serine/threonine-protein" (Release 1999.2; see also Propomain Release 2000.1) shows amino acid residues 72 to 272 of the amino acid consensus sequence (SEQ ID NOs:96-98) aligns with the "protein kinase nuclear homeodomain-interacting homeobox DNA-binding serine/threonine serine/threonine-protein" domain of human 13305, amino acid residues 714 to 848, 720 to 887 an 615 to 667 of SEQ ID NO:89. The BLAST algorithm identifies multiple local alignments between the consensus amino acid sequence and human 13305.

A BLAST alignment of human 13305 with a consensus amino acid sequence derived from a Propomain "protein kinase nuclear homeodomain-interacting homeobox DNA-binding serine/threonine serine/threonine-protein" (Release 1999.2; see also Propomain Release 2000.1) shows amino acid residues 3 to 190 of the 190 amino acid consensus sequence (SEQ ID NO:99) aligns with the "protein kinase nuclear homeodomain-interacting homeobox DNA-binding serine/threonine serine/threonine-protein" domain of human 13305, amino acid residues 1030 to 1210 of SEQ ID NO:89.

Human 13305 contains the following regions or other structural features (for general information regarding PFAM identifiers, PS prefix and PF prefix domain identification numbers, refer to Sonnhammer et al. (1997) *Protein* 28:405-420: a eukaryotic protein kinase domain (PFAM Accession Number PF00069) located at about amino acid residues 190 to 411 and 492 to 518 of SEQ ID NO:89; three transmembrane domains (predicted by MEMSAT, Jones et al. (1994) Biochemistry 33:3038-3049) at about amino acids 73 to 89, 363 to 387, and 1156 to 1173 of SEQ ID NO:89; ten N-glycosylation sites (Prosite PS00001) from about amino acids 57 to 60, 111 to 114, 133 to 136, 149 to 152, 262 to 265, 471 to 474, 566 to 569, 570 to 573, 1009 to 1012 and 1045 to 1048 of SEQ ID NO:89; one glycosaminoglycan attachment sites (Prosite PS00002) from about amino acids 170 to 173 of SEQ ID NO:89; three cAMP/cGMP-dependent protein kinase phosphorylation sites (Prosite PS00004) located at about amino acids 124 to 127, 209 to 212, and 505 to 508 of SEQ ID NO:89; twelve protein kinase C phosphorylation sites (Prosite PS00005) at about amino acids 20 to 22, 107 to 109, 163 to 165, 211 to 213, 422 to 424, 666 to 668, 843 to 845, 853 to 855, 907 to 909, 1008 to 1010, 1138 to 1140 and 1187 to 1189 of SEQ ID NO:89; fifteen casein kinase II phosphorylation sites (Prosite PS00006) located at about amino acids 29 to 32, 37 to 40, 87 to 90, 113 to 116, 169 to 172, 211 to 214, 396 to 399, 441 to 444, 474 to 477, 643 to 646, 856 to 859, 910 to 913, 938 to 941, 967 to 970, and 1057 to 1060 of SEQ ID NO:89; one tyrosine kinase phosphorylation site (Prosite PS00007) from about amino acids 452 to 459 of SEQ ID NO:89; seventeen N-myristoylation sites (Prosite PS00008) from about amino acids 35-40, 54-59, 93-98, 154-159, 310-315, 366-371, 379-384, 419-424, 662-667, 787-792, 800-805, 963-968, 1005-1010, 1019-1024, 1036-1041, 1124-1129 and 1186-1191 of SEQ ID NO:89; one ATP protein kinases ATP-binding region signature (Prosite PS00107) from about amino acids 196-204 of SEQ ID NO:89; and one serine-threonine protein kinases active site signature (Prosite PS00108) from about amino acids 311-323 of SEQ ID NO:89.

A hydropathy plot of human 13305 was performed. Polypeptides of the invention include fragments which include: all or part of a hydrophobic sequence, e.g., the sequence from about amino acid 300 to 310, from about 361 to 391, and from about 585 to 605 of SEQ ID NO:89; all or part of a hydrophilic sequence, e.g., the sequence from about amino acid 20 to 60, from about 245 to 265, and from about 220 to 260 of SEQ ID NO:89; a sequence which includes a Cys, or a glycosylation site.

The present invention is based, at least in part, on the discovery of novel molecules, referred to herein as 13305 protein and nucleic acid molecules, which comprise a family of molecules having certain conserved structural and functional features.

One embodiment of the invention features 13305 nucleic acid molecules, preferably human 13305 molecules, e.g., 13305. The 13305 nucleic acid and protein molecules of the invention are described in further detail in the following subsections.

In another embodiment, the isolated proteins of the present invention, preferably 13305 proteins, are identified based on the presence of at least Ser/Thr kinase site and at least one ATP-binding region.

As used herein, the term "Ser/Thr kinase site" includes an amino acid sequence of about 200-400 amino acid residues in length, preferably 200-300 amino acid residues in length, and more preferably 250-300 amino acid residues in length, which is conserved in kinases which phosphorylate serine and threonine residues and found in the catalytic domain of Ser/Thr kinases. Preferably, the Ser/Thr kinase site includes the following amino acid consensus sequence $X_9$-g-X-G-$X_4$-V-$X_{12}$-K-X-$_{(10-19)}$-E-$X_{66}$-h-$X_8$-h-r-D-X-K-$X_2$-N-$X_{17}$-K-$X_2$-D-f-g-$X_{21}$-p-$X_{13}$-w-$X_3$-g-$X_{55}$-R-$X_{14}$-h-$X_3$ (SEQ ID NO:91) (where invariant residues are indicated by upper case letters and nearly invariant residues are indicated by lower case letters). The nearly invariant residues are usually found in most Ser/Tbr kinase sites, but can be replaced by other amino acids which, preferably, have similar characteristics. For example, a nearly invariant hydrophobic amino acid in the above amino acid consensus sequence would most likely be replaced by another hydrophobic amino acid. Ser/Thr kinase domains are described in, for example, Levin D. E. et al. (1990) *Proc. Natl. Acad. Sci. USA* 87:8272-76, the contents of which are incorporated herein by reference.

As used herein, the term "ATP-binding region" includes an amino acid sequence of about 20-40, preferably 20-30, and more preferably 25-30 amino acid residues in length, present in enzymes which activate their substrates by phosphorylation, and involved in binding adenosine triphosphate (ATP). ATP-binding regions preferably include the following amino acid consensus sequence: G-X-G-X-X-G-X(15-23)-K (SEQ ID NO:92). ATP-binding regions are described in, for example, Samuel K. P. et al. (1987) *FEBS Let.* 218(1): 81-86, the contents of which are incorporated herein by reference. Amino acid residues 196 to 204 of SEQ ID NO:89 comprise an ATP-binding region. Amino acid residues 311-323 of the 13305 protein (SEQ ID NO:89) comprise a Ser/Thr kinase domain.

Isolated proteins of the present invention, preferably 13305 proteins, have an amino acid sequence sufficiently homologous to the amino acid sequence of SEQ ID NO:89 or are encoded by a nucleotide sequence sufficiently homologous to SEQ ID NO:88 or SEQ ID NO:89. The 13305 nucleic acid encodes a polypeptide with similarities to previously characterized protein kinases. Thus the 13305 encoded polypeptide is expected to be a kinase and function in the phosphorylation of protein substrates. The 13305 nucleic acid also encodes a polypeptide with similarities to previously identified homeodomains. Thus the 13305 encoded polypeptide is expected to be a kinase and function in the phosphorylation of proteins involved in interactions with DNA. The homeodomain of 13305 proteins may also be substituted for the homeodomains of other proteins in known assays based on the "swapping" of such domains.

As used interchangeably herein a "13305 activity", "biological activity of 13305" or "functional activity of 13305", refers to an activity exerted by a 13305 protein, polypeptide or nucleic acid molecule on a 13305 responsive cell or a 13305 protein substrate as determined in vivo, or in vitro, according to standard techniques. The biological activity of 13305 is described herein.

Accordingly, another embodiment of the invention features isolated 13305 proteins and polypeptides having a 13305 activity. Preferred proteins are 13305 proteins having at least one Ser/Thr kinase and at least one ATP-binding region. Additional preferred proteins have at least one Ser/Thr kinase site, at least one ATP-binding region, and preferably a 13305 activity. Additional preferred proteins have at least one Ser/Thr kinase site, at least one ATP-binding region, and are, preferably, encoded by a nucleic acid molecule having a nucleotide sequence which hybridizes under stringent hybridization conditions to a nucleic acid molecule comprising the nucleotide sequence of SEQ ID NO:88 or SEQ ID NO:90.

A 13305 polypeptide can include at least one, two, preferably three "transmembrane domains" or regions homologous with a "transmembrane domain". As used herein, the term "transmembrane domain" includes an amino acid sequence of about 10 to 40 amino acid residues in length and spans the plasma membrane. Transmembrane domains are rich in hydrophobic residues, e.g., at least 50%, 60%, 70%, 80%, 90%, 95% or more of the amino acids of a transmembrane domain are hydrophobic, e.g., leucines, isoleucines, tyrosines, or tryptophans. Transmembrane domains typically have alpha-helical structures and are described in, for example, Zagotta, W. N. et al., (1996) *Annual Rev. Neurosci.* 19:235-263, the contents of which are incorporated herein by reference.

In a preferred embodiment, a 13305 polypeptide or protein has at least one, two, preferably three "transmembrane domains" or regions which includes at least about 12 to 35 more preferably about 14 to 30 or 15 to 25 amino acid residues and has at least about 60%, 70% 80% 90% 95%, 99%, or 100% homology with a "transmembrane domain," e.g., the transmembrane domains of human 13305 (e.g., residues 73-89, 363-387, and 1156-1173 of SEQ ID NO:89). The transmembrane domain of human 13305 can be visualized in a hydropathy plot as regions of about 15 to 25 amino acids where the hydropathy trace is mostly above the horizontal line.

To identify the presence of a "transmembrane" domain in a 13305 protein sequence, and make the determination that a polypeptide or protein of interest has a particular profile, the amino acid sequence of the protein can be analyzed by a transmembrane prediction method that predicts the secondary structure and topology of integral membrane proteins based on the recognition of topological models (MEMSAT, Jones et al., (1994) Biochemistry 33:3038-3049).

A 13305 polypeptide can include at least one, two, three, preferably four "non-transmembrane regions." As used herein, the term "non-transmembrane region" includes an amino acid sequence not identified as a transmembrane domain. The non-transmembrane regions in 13305 are located at about amino acids 1-72, 90-362, 388-1155, and 1174-1210 of SEQ ID NO:89.

The non-transmembrane regions of 13305 include at least one, preferably two cytoplasmic regions. In one embodiment, a cytoplasmic region of a 13305 protein can include the C-terminus and can be a “C-terminal cytoplasmic domain,” also referred to herein as a “C-terminal cytoplasmic tail.” As used herein, a “C-terminal cytoplasmic domain” includes an amino acid sequence having a length of at least about 5, preferably about 5 to 40, more preferably about 10 to 37 amino acid residues and is located inside of a cell or within the cytoplasm of a cell. The N-terminal amino acid residue of a “C-terminal cytoplasmic domain” is adjacent to a C-terminal amino acid residue of a transmembrane domain in a 13305 protein. For example, a C-terminal cytoplasmic domain is located at about amino acid residues 1174 to 1210 of SEQ ID NO:89.

In a preferred embodiment, a 13305 polypeptide or protein has a C-terminal cytoplasmic domain or a region which includes at least about 5, preferably about 5 to 40, and more preferably about 10 to 37 amino acid residues and has at least about 60%, 70% 80% 90% 95%, 99%, or 100% homology with a C-terminal cytoplasmic domain,” e.g., the C-terminal cytoplasmic domain of human 13305 (e.g., residues 1174 to 1210 of SEQ ID NO:89).

In another embodiment, a 13305 protein includes at least one, cytoplasmic loop. As used herein, the term “loop” includes an amino acid sequence that resides outside of a phospholipid membrane, having a length of at least about 5, preferably about 100 to 300, more preferably about 100 to 273 amino acid residues, and has an amino acid sequence that connects two transmembrane domains within a protein or polypeptide. Accordingly, the N-terminal amino acid of a loop is adjacent to a C-terminal amino acid of a transmembrane domain in a 13305 molecule, and the C-terminal amino acid of a loop is adjacent to an N-terminal amino acid of a transmembrane domain in a 13305 molecule. As used herein, a “cytoplasmic loop” includes a loop located inside of a cell or within the cytoplasm of a cell. For example, a “cytoplasmic loop” can be found at about amino acid residues 90-362 of SEQ ID NO:89.

In a preferred embodiment, a 13305 polypeptide or protein has a cytoplasmic loop or a region which includes at least about 4, preferably about 5, preferably about 100 to 300, more preferably about 100 to 273 amino acid residues and has at least about 60%, 70% 80% 90% 95%, 99%, or 100% homology with a cytoplasmic loop,” e.g., a cytoplasmic loop of human 13305 (e.g., residues 90-362 of SEQ ID NO:89).

In another embodiment, a 13305 protein includes at least one non-cytoplasmic loop. As used herein, a “non-cytoplasmic loop” includes an amino acid sequence located outside of a cell or within an intracellular organelle. Non-cytoplasmic loops include extracellular domains (i.e., outside of the cell) and intracellular domains (i.e., within the cell). When referring to membrane-bound proteins found in intracellular organelles (e.g., mitochondria, endoplasmic reticulum, peroxisomes microsomes, vesicles, endosomes, and lysosomes), non-cytoplasmic loops include those domains of the protein that reside in the lumen of the organelle or the matrix or the intermembrane space. For example, a “non-cytoplasmic loop” can be found at about amino acid residues 388-1155 of SEQ ID NO:89.

In a preferred embodiment, a 13305 polypeptide or protein has at least one non-cytoplasmic loop or a region which includes at least about 5, preferably about 100 to 800, more preferably about 100 to 768 amino acid residues and has at least about 60%, 70% 80% 90% 95%, 99%, or 100% homology with a “non-cytoplasmic loop,” e.g., at least one non-cytoplasmic loop of human 13305 (e.g., residues 388-1155 of SEQ ID NO:89).

The non-transmembrane regions of 13305 include at least one, “N-terminal extracellular domain.” As used herein, an “N-terminal extracellular domain” includes an amino acid sequence having about 1 to 100, preferably about 1 to 80, more preferably about 1 to 75, or even more preferably about 1 to 72 amino acid residues in length and is located outside of a cell or outside the cytoplasm of a cell. The C-terminal amino acid residue of an “N-terminal extracellular domain” is adjacent to an N-terminal amino acid residue of a transmembrane domain in a 13305 protein. For example, an N-terminal extracellular domain is located at about amino acid residues 1 to 72 of SEQ ID NO:89.

In a preferred embodiment, a polypeptide or protein has an N-terminal extracellular domain or a region which includes at least about 1 to 100, preferably about 1 to 80, more preferably about 1 to 72 amino acid residues and has at least about 60%, 70% 80% 90% 95%, 99%, or 100% homology with an “N-terminal extracellular domain,” e.g., the N-terminal extracellular domain of human 13305 (e.g., residues 1 to 72 of SEQ ID NO:89).

A 13305 family member can include at least one protein kinase domain; and at least one, two, three, four, five, six, preferably seven transmembrane and non-transmembrane domains. Furthermore, a 13305 family member can include at least one, two, three, four, five, six, seven, eight, nine, preferably ten N-glycosylation sites (PS00001); at least one glycosaminoglycan attachment site (PS00002); at least one, two, preferably three cAMP/cGMP-dependent protein kinase phosphorylation sites (Prosite PS00004); at least one, two, three, four, five, six, seven, eight, nine, ten, eleven, preferably twelve protein kinase C phosphorylation sites (PS00005); at least one, two, three, preferably four casein kinase II phosphorylation sites (PS00006); at least one tyrosine kinase phosphorylation site (PS00007); at least one, two, three, four, five, six, seven, eight, nine, ten, eleven, twelve, thirteen, fourteen and preferably fifteen N-myristoylation sites (PS00008); at least one ATP protein kinases ATP-binding region signature (PS00107); and at least one serine-threonine protein kinases active site signature (PS00108).

As used herein, the term “kinase domain” includes an amino acid sequence of about 100 to 275 amino acid residues in length and having a bit score for the alignment of the sequence to the kinase domain (HMM) of at least 100. Preferably a kinase domain mediates intracellular signal transduction. Preferably, a kinase domain includes at least about 100 to 275 amino acids, more preferably about 150 to 275 amino acid residues, or about 200 to 275 amino acids and has a bit score for the alignment of the sequence to the kinase domain (HMM) of at least 100, 150, 200, 250 or greater. The kinase domain (amino acids 190-411 and 492-518 of SEQ ID NO:89) of human 13305 align with a consensus amino acid sequence (SEQ ID NO:93-94) derived from a hidden Markov model. The “protein kinase” domain (HMM) has been assigned the PFAM Accession Number PF00069 and corresponds to about amino acids 190-411 and 492-518 of SEQ ID NO:89.

In a preferred embodiment, a 13305 polypeptide or protein has a “kinase domain” or a region which includes at least about 100 to 215 more preferably about 150 to 275 or 200 to 275 amino acid residues and has at least about 60%, 70% 80% 90% 95%, 99%, or 100% homology with a “kinase domain,” e.g., the kinase domain of human 13305 (e.g., residues 190-411 and 492-518 of SEQ ID NO:89).

To identify the presence of a “kinase” domain in a 13305 protein sequence, and make the determination that a polypeptide or protein of interest has a particular profile, the amino acid sequence of the protein can be searched against the Pfam database of HMMs (e.g., the Pfam database, release 2.1) using the default parameters. For example, the hmmsf program, which is available as part of the HMMER package of search programs, is a family specific default program for MILPAT0063 and a score of 15 is the default threshold score for determining a hit. Alternatively, the threshold score for determining a hit can be lowered (e.g., to 8 bits). A description of the Pfam database can be found in Sonhammer et al. (1997) Proteins 28:405-420 and a detailed description of HMMs can be found, for example, in Gribskov et al. (1990) Meth. Enzymol. 183:146-159; Gribskov et al. (1987) Proc. Natl. Acad. Sci. USA 84:4355-4358; Krogh et al. (1994) J. Mol. Biol. 235:1501-1531; and Stultz et al. (1993) Protein Sci. 2:305-314, the contents of which are incorporated herein by reference. A search was performed against the HMM database resulting in the identification of a "kinase domain" domain in the amino acid sequence of human 13305 at about residues 190-411 and 492-518 of SEQ ID NO:89.

To identify the presence of a "kinase" domain in a 13305 protein sequence, and make the determination that a polypeptide or protein of interest has a particular profile, the amino acid sequence of the protein can be searched against a database of domains, e.g., the Propom database (Corpet et al. (1999), Nucl. Acids Res. 27:263-267). The Propom protein domain database consists of an automatic compilation of homologous domains. Current versions of Propom are built using recursive PSI-BLAST searches (Altschul S F et al. (1997) Nucleic Acids Res. 25:3389-3402; Gouzy et al. (1999) Computers and Chemistry 23:333-340) of the SWISS-PROT 38 and TREMBL protein databases. The database automatically generates a consensus sequence for each domain. A BLAST search was performed against the HMM database resulting in the identification of a "kinase" domain in the amino acid sequence of human 13305 at about residues 416-465 of SEQ ID NO:89. The kinase domain is homologous to Propom family "protein kinase nuclear serine/threonine-protein homeodomain-interacting homeobox DNA-binding serine/threonine F20B6.8," SEQ ID NO:95, (Propomain Release 1999.2). The consensus sequence for SEQ ID NO:95 is 72% identical over amino acids 416-465 of SEQ ID NO: 89. The kinase domain is also homologous to Propom family "protein kinase nuclear homeodomain-interacting homeobox DNA-binding serine/threonine serine/threonine-protein," SEQ ID NO:96-98, (Propomain Release 1999.2). The consensus sequences for SEQ ID NOs:96-98 are 67%, 25% and 31% identical over amino acids 714 to 848, 720 to 887 and 615 to 667 of SEQ ID NO:89 respectively. The consensus sequences for SEQ ID NO:99 is 51% identical over amino acids 1030 to 1210 of SEQ ID NO:89.

In one embodiment, the 13305 molecules modulate the activity of one or more proteins involved in cellular growth or differentiation, e.g., brain, thymus, prostate epithelium, and fetal liver growth or differentiation. In another embodiment, the 13305 molecules of the present invention are capable of modulating the phosphorylation state of a 13305 molecule or one or more proteins involved in cellular growth or differentiation.

Additionally, 13305 nucleic acids and proteins have homology to known homeoboxes and homeodomains, respectively. Thus 13305 proteins are expected to exhibit DNA binding activity, in addition to kinase activity, under appropriate conditions. Without being bound by theory, 13305 protein may play a role in cellular function by being directed to appropriate locations based on the presence of the homeodomain, followed by providing its kinase activity to phosphorylate particular polypeptides at such locations. Possible roles for 13305 protein include developmental regulation.

Since the 13305 nucleic acid was found by TaqMan analysis to be expressed in cells of the brain, thymus, prostate epithelium, and fetal liver, the encoded protein kinase is at least expected to catalyze cell type specific phosphorylation reactions in those cells.

Additionally, the 13305 encoded protein kinase has homology to a mouse kinase orthologue. Thus, without being bound by theory, the 13305 kinase may be a human analogue of the mouse kinase.

As used herein, the term "protein kinase" includes a protein or polypeptide which is capable of modulating its own phosphorylation state or the phosphorylation state of another protein or polypeptide. Protein kinases can have a specificity for (i.e., a specificity to phosphorylate) serine/threonine residues, tyrosine residues, or both serine/threonine and tyrosine residues, e.g., the dual specificity kinases. As referred to herein, protein kinases preferably include a catalytic domain of about 200-400 amino acid residues in length, preferably about 200-300 amino acid residues in length, or more preferably about 250-300 amino acid residues in length, which includes preferably 5-20, more preferably 5-15, or preferably 11 highly conserved motifs or subdomains separated by sequences of amino acids with reduced or minimal conservation. Specificity of a protein kinase for phosphorylation of either tyrosine or serine/threonine can be predicted by the sequence of two of the subdomains (VIb and VIII) in which different residues are conserved in each class (as described in, for example, Hanks et al. (1988) *Science* 241:42-52) the contents of which are incorporated herein by reference). These subdomains are also described in further detail herein. Preferably, the kinases of the invention are serine/threonine kinases.

Protein kinases play a role in signalling pathways associated with cellular growth. For example, protein kinases are involved in the regulation of signal transmission from cellular receptors, e.g., growth-factor receptors; entry of cells into mitosis; and the regulation of cytoskeleton function, e.g., actin bundling. Thus, the 13305 molecules of the present invention may be involved in: 1) the regulation of transmission of signals from cellular receptors, e.g., cardiac cell growth factor receptors; 2) the modulation of the entry of cells into mitosis; 3) the modulation of cellular differentiation; 4) the modulation of cell death; and 5) the regulation of cytoskeleton function, e.g., actin bundling.

Further, 13305 molecules have been found by TaqMan analysis to be highly expressed in human bone marrow erythrocytes (GPA+ cells) and the human erythroleukemia cell line, K562, and has significant expression in GPA (low), erythroid progenitor cells. During erythroid differentiation, the expression of 13305 is regulated and 13305 has highest expression in terminally differentiated erythrocytes, which is expected for a kinase that negatively regulates cell growth. Inhibition of some dual-specificity kinases has been shown to enhance erythroid cell differentiation. As such, the 13305 molecules of the invention may play role in the regulation of erythroid cell growth, differentiation or both. For example, and without being bound by theory, it is expected that inhibition of 13305 activity in human bone marrow progenitor cells may lead to enhanced erythroid cell differentiation.

Additionally, 13305 molecules have been found to be overexpressed in tumor cells. Specifically, TaqMan analysis can be used to compare the expression levels in lung tumor cell lines versus a normal control and in multiple tumor cells versus normal tissue. Also, 13305 has shown increased expression in the A549 tumor cell line in S-phase (t=3). Without being bound by theory, it is likely that 13305 may be mutated and rendered inactive in tumor cells. Increased cell proliferation seen in tumor cells may be result of inactivity of 13305. Further, 13305 molecules may serve as specific and novel identifiers of such tumor cells.

Further, inhibition or over stimulation of the activity of protein kinases involved in signalling pathways associated with cellular growth can lead to perturbed cellular growth, which can in turn lead to cellular growth related disorders. As used herein, a "cellular growth related disorder" includes a disorder, disease, or condition characterized by a deregulation, e.g., an upregulation or a downregulation, of cellular growth. Cellular growth deregulation may be due to a deregulation of cellular proliferation, cell cycle progression, cellular differentiation and/or cellular hypertrophy.

Aberrant expression and/or activity of 13305 molecules may mediate disorders associated with bone metabolism The 13305 nucleic acid and protein of the invention can be used to treat and/or diagnose a variety of immune disorders.

Disorders which may be treated or diagnosed by methods described herein include, but are not limited to, disorders associated with an accumulation in the liver of fibrous tissue, such as that resulting from an imbalance between production and degradation of the extracellular matrix accompanied by the collapse and condensation of preexisting fibers.

Additionally, 13305 may play an important role in the etiology of certain viral diseases and in the regulation of metabolism.

The 13305 molecules provide novel diagnostic targets and therapeutic agents to control pain in a variety of disorders, diseases, or conditions which are characterized by a deregulated, e.g., upregulated or downregulated, pain response.

Expression and Tissue Distribution of 13305

TaqMan real-time quantitative RT-PCR was used to detect the presence of RNA transcript corresponding to human 13305 in several tissues. It was found that the corresponding orthologs of 13305 are expressed in a variety of tissues. The presence of RNA transcript corresponding to human 13305 in RNA prepared from tumor and normal tissues was detected.

Transcriptional profiling results show an increased expression of 13305 mRNA in the lung tumor cell line, H460, in comparison with a normal human bronchial epithelium (NHBE) control. They also show the differential expression of 13305 RNA, in comparison with a NHBE control, in various lung tumor cell lines.

The expression of 13305 relative to the progression of cells through the cell cycle shows increased expression of 13305 RNA in S-phase (t=3) of the cell cycle in A549 cells.

Reverse Transcriptase PCR (RT-PCR) was used to detect the presence of RNA transcript corresponding to human 13305 in RNA prepared from tumor and normal tissues. Relative expression levels of the 13305 was assessed in breast, lung, colon and brain cells using TaqMan PCR and increased expression was found in 6/6 lung tumors, 3/8 breast tumors, and 3/4 colon tumor metastases in comparison to normal tissue controls. There is ubiquitous relative expression levels of 13305 in various tissues with significant expression in human fetal liver, thymus, prostate epithelial and brain cells.

In a hematology panel, there was expression of 13305 in human bone marrow erythrocytes (GPA+ cells), erythroid cells and the human erythroleukemia cell line, K562.

In another hematology panel, there was expression of 13305 in human bone marrow GPA+ cells and significant expression in GPA (low), erythroid progenitor cells.

Expression profiling results using in situ hybridization techniques have shown that 13305 mRNA has been detected in human lung and colon tumors. Low to moderate positive expression of 13305 has been shown in 3/3 lung tumor samples in comparison with 1/1 in normal lung tissue samples. Also, 13305 has been shown to be highly expressed in 4/4 primary colon tumor samples, and 2/3 colon tumor metastases, but not normal colon tissue samples (0/2).

As seen by these results, 13305 molecules have been found to be overexpressed in some tumor cells, and is presumably present in a mutated state and thus inactive. As such, 13305 molecules may serve as specific and novel identifiers of such tumor cells. Further, inhibitors of the 13305 molecules are also useful for the treatment of cancer, preferably lung cancer, and useful as a diagnostic.

Human 14911

The present invention is based, at least in part, on the discovery of novel molecules, referred to herein as "14911" nucleic acid and polypeptide molecules, which play a role in or function in the transduction of signals for cell proliferation, differentiation and apoptosis.

The human 14911 sequence (SEQ ID NO:100), which is approximately 1281 nucleotides in length, contains a predicted methionine-initiated coding sequence of about 1188 nucleotides, not including the termination codon (nucleotides 49-1236 of SEQ ID NO:100; 1-1188 of SEQ ID NO:102. The coding sequence encodes a 396 amino acid protein (SEQ ID NO:101).

A plasmid containing the nucleotide sequence encoding human 14911 was deposited with American Type Culture Collection (ATCC), 10801 University Boulevard, Manassas, Va. 20110-2209, on Jun. 7, 2001 and assigned Accession Number PTA-3435. This deposit will be maintained under the terms of the Budapest Treaty on the International Recognition of the Deposit of Microorganisms for the Purposes of Patent Procedure. This deposit was made merely as a convenience for those of skill in the art and is not an admission that a deposit is required under 35 U.S.C. § 112.

A hydropathy plot of human 14911 shows relative hydrophobic residues and relative hydrophilic residues. The cysteine residues (cys) and N-glycosylation sites (Ngly) are also indicated.

The prediction of protein subcellular localization sites using PSORT software predicts the protein to be nuclear, followed by cytoplasmic or mitochondrial.

Results from the Prosite database of protein families and domains identify biologically significant sites. Human 14911 contains the following regions or other structural features: two N-glycosylation sites (PS00001) located at about amino acid residues 4 to 7 and 43 to 46 of SEQ ID NO:101; five protein kinase C phosphorylation sites (PS00005) located at about amino acid residues 5 to 7, 45 to 47, 122 to 124, 193 to 195 and 230 to 232 of SEQ ID NO:101; three casein kinase II phosproylation sites (PS00006) located at about amino acid residues 89 to 92, 212 to 215 and 230 to 233; three N-myristoylation sties (PS00008) located at about amino acid residues 2 to 7, 197 to 202 and 391 to 396 of SEQ ID NO:101; one amidation site (PS00009) located at about amino acid residues 218 to 221 of SEQ ID NO:101; one protein kinases ATP-binding region signature (PS00107) located at about amino acid residues 29 to 37 of SEQ ID NO:101; and one serine/threonine protein kinases active site signature (PS00108) located at about amino acid residues 142 to 154 of SEQ ID NO:101.

A PFAM search finds an "eukaryotic protein kinase domain" and a "protein kinase C terminal domain" within human 14911. Amino acid residues 1 to 278 of the "eukaryotic protein kinase domain" consensus amino acid sequence (SEQ ID NO:105) align with amino acid residues 23 to 281 of SEQ ID NO:101. Amino acid residues 1 to 20 of the "protein kinase C terminal domain" consensus amino acid sequence (SEQ ID NO:106) align with amino acid residues 282 to 301 of SEQ ID NO:101.

Finally, a search of the Propom protein domain database identifies homologous domains. The "kinase protein transferase ATP-binding serine/threonine-protein phosphorylation receptor tyrosine-protein precursor transmembrane" consensus amino acid sequence (SEQ ID NOs:107-110) align with amino acid residues 23 to 71, 126 to 159, 172 to 312 and 250 to 280 of SEQ ID NO:101 over four HSPs. The "M03C11.1 protein" consensus amino acid sequence (SEQ ID NO:111) aligns with amino acid residues 280 to 372 of SEQ ID NO:101. The "F8K4.6 protein" consensus amino acid sequence (SEQ ID NO:112) aligns with amino acid residues 244 to 318 of SEQ ID NO:101.

In one embodiment, the 14911 molecules modulate the activity of one or more proteins involved in cellular growth or differentiation, e.g., cell growth or differentiation. In another embodiment, the 14911 molecules of the present invention are capable of modulating the phosphorylation state of a 14911 molecule or one or more proteins involved in cellular growth or differentiation.

In another embodiment, the isolated proteins of the present invention, preferably 14911 proteins, are identified based on the presence of at least one Ser/Thr kinase site and at least one ATP binding region.

As used herein, the term "Ser/Thr kinase site" includes an amino acid sequence of about 200-400 amino acid residues in length, preferably 200-300 amino acid residues in length, and more preferably 250-300 amino acid residues in length, which is conserved in kinases which phosphorylate serine and threonine residues and found in the catalytic domain of Ser/Thr kinases. Preferably, the Ser/Tbr kinase site includes the following amino acid consensus sequence $X_9$-g-X-G-$X_4$-V-$X_{12}$-K-X-$_{(10-19)}$-E-$X_{66}$-h-$X_8$-h-r-D-X-K-$X_2$-N-$X_{17}$-K-$X_2$-D-f-g-$X_{21}$-p-$X_{13}$-w-$X_3$-g-$X_{55}$-R-$X_{14}$-h-$X_3$ (SEQ ID NO:103) (where invariant residues are indicated by upper case letters and nearly invariant residues are indicated by lower case letters). The nearly invariant residues are usually found in most Ser/Thr kinase sites, but can be replaced by other amino acids which, preferably, have similar characteristics. For example, a nearly invariant hydrophobic amino acid in the above amino acid consensus sequence would most likely be replaced by another hydrophobic amino acid. Ser/Thr kinase domains are described in, for example, Levin D. E. et al. (1990) *Proc. Natl. Acad. Sci. USA* 87:8272-76, the contents of which are incorporated herein by reference.

As used herein, the term "ATP-binding region" includes an amino acid sequence of about 20-40, preferably 20-30, and more preferably 25-30 amino acid residues in length, present in enzymes which activate their substrates by phosphorylation, and involved in binding adenosine triphosphate (ATP). ATP-binding regions preferably include the following amino acid consensus sequence: G-X-G-X-X-G-X(15-23)-K (SEQ ID NO:104). ATP-binding regions are described in, for example, Samuel K. P. et al. (1987) *FEBS Let.* 218(1): 81-86, the contents of which are incorporated herein by reference. Amino acid residues 31 to 39 of SEQ ID NO:101 comprise an ATP-binding region. Amino acid residues 144-156 of the 14911 protein (SEQ ID NO:101) comprise a Ser/Thr kinase domain.

The nucleic acid encodes a polypeptide with similarities known Ser/Thr kinases. Thus the 14911 encoded polypeptide is expected to be a kinase and function in the phosphorylation of protein substrates. Additionally, the 14911 nucleic acids can be used in known or novel screens and assays for kinase encoding nucleic acids to distinguish it from other distinct nucleic acids. Alternatively, the nucleic acid sequences can be used in the preparation of phylogenetic trees and relationships between organisms.

As used interchangeably herein a "14911 activity", "biological activity of 14911" or "functional activity of 14911", refers to an activity exerted by a 14911 protein, polypeptide or nucleic acid molecule on a 14911 responsive cell or a 14911 protein substrate as determined in vivo, or in vitro, according to standard techniques. The biological activity of 14911 is described herein.

Accordingly, another embodiment of the invention features isolated 14911 proteins and polypeptides having a 14911 activity. Preferred proteins are 14911 proteins having at least one Ser/Thr kinase and at least one ATP-binding region. Additional preferred proteins have at least one Ser/Thr kinase site, at least one ATP-binding region, and preferably a 14911 activity. Additional preferred proteins have at least one Ser/Thr kinase site, at least one ATP-binding region, and are, preferably, encoded by a nucleic acid molecule having a nucleotide sequence which hybridizes under stringent hybridization conditions to a nucleic acid molecule comprising the nucleotide sequence of SEQ ID NO:100 or SEQ ID NO:102.

As used herein, the term "protein kinase" includes a protein or polypeptide which is capable of modulating its own phosphorylation state or the phosphorylation state of another protein or polypeptide. Protein kinases can have a specificity for (i.e., a specificity to phosphorylate) serine/threonine residues, tyrosine residues, or both serine/threonine and tyrosine residues, e.g., the dual specificity kinases. As referred to herein, protein kinases preferably include a catalytic domain of about 200-400 amino acid residues in length, preferably about 200-300 amino acid residues in length, or more preferably about 250-300 amino acid residues in length, which includes preferably 5-20, more preferably 5-15, or preferably 11 highly conserved motifs or subdomains separated by sequences of amino acids with reduced or minimal conservation. Specificity of a protein kinase for phosphorylation of either tyrosine or serine/threonine can be predicted by the sequence of two of the subdomains (VIb and VIII) in which different residues are conserved in each class (as described in, for example, Hanks et al. (1988) *Science* 241:42-52) the contents of which are incorporated herein by reference). These subdomains are also described in further detail herein.

Protein kinases play a role in signaling pathways associated with cellular growth. For example, protein kinases are involved in the regulation of signal transmission from cellular receptors, e.g., growth-factor receptors; entry of cells into mitosis; and the regulation of cytoskeleton function, e.g., actin bundling. Thus, the 14911 molecules of the present invention may be involved in: 1) the regulation of transmission of signals from cellular receptors, e.g., growth factor receptors; 2) the modulation of the entry of cells into mitosis; 3) the modulation of cellular differentiation; 4) the modulation of cell death; and 5) the regulation of cytoskeleton function.

Additionally, and without being bound by theory, 14911 molecules have been found by TaqMan analysis to be overexpressed in tumor cells, where the molecules may be inappropriately propagating either cell proliferation or cell survival signals. As such, 14911 molecules may serve as specific and novel identifiers of such tumor cells. Further, inhibitors of the 14911 molecules are also useful for the treatment of cancer, preferably lung cancer, and useful as a diagnostic.

Inhibition or over stimulation of the activity of protein kinases involved in signaling pathways associated with cellular growth can lead to perturbed cellular growth, which can in turn lead to cellular growth related disorders. As used herein, a "cellular growth related disorder" includes a disorder, disease, or condition characterized by a deregulation, e.g., an upregulation or a downregulation, of cellular growth. Cellular growth deregulation may be due to a deregulation of cellular proliferation, cell cycle progression, cellular differentiation and/or cellular hypertrophy.

The present invention is based, at least in part, on the discovery of novel molecules, referred to herein as 14911 protein and nucleic acid molecules, which comprise a family of molecules having certain conserved structural and functional features.

One embodiment of the invention features 14911 nucleic acid molecules, preferably human 14911 molecules, e.g., 14911. The 14911 nucleic acid and protein molecules of the invention are described in further detail in the following subsections.

Expression and Tissue Distribution of 14911

TaqMan real-time quantitative RT-PCR was used to detect the presence of RNA transcript corresponding to human 14911 in several tissues. It was found that the corresponding orthologs of 14911 are expressed in a variety of tissues.

Relative expression levels of the 14911 was assessed in brain and lung cells using TaqMan PCR and increased expression was found in 2/5 lung tumor cell lines in comparison to a normal human bronchial epithelium (NHBE) control; 5/8 lung tumor samples in comparison to normal lung tissues; and 3/3 glioma samples in comparison to normal brain tissues. The relative expression levels and tissue distribution of the 14911 RNA was also assessed in a panel of human tissues or cells, including but not limited to heart, brain, breast, ovary, pancreas, prostate, colon, kidney, liver, fetal liver, lung, spleen, tonsil, lymph node, epithelial, endothelial, skeletal, fibroblasts, skin, adipose, bone cells (e.g., osteoclasts and osteoblasts), among others.

Expression profiling results using in situ hybridization techniques have shown that 14911 mRNA has been detected in human colon, lung, brain and breast tumors. Positive expression of 14911 has been shown in 2/4 lung tumors in comparison with lack of expression, 0/2, in normal lung tissue samples. Further, 14911 has been shown to be expressed both in tumors and normal tissues, specifically in 1/4 colon tumors and 1/1 normal colon tissue samples; 1/2 breast tumors and 1/1 normal breast tissue samples; and 1/3 brain tumors and 2/2 normal brain tissue samples.

As seen by these results, 14911 molecules have been found to be overexpressed in some tumor cells, where the molecules may be inappropriately propagating either cell proliferation or cell survival signals. As such, 14911 molecules may serve as specific and novel identifiers of such tumor cells. Further, inhibitors of the 14911 molecules are also useful for the treatment of cancer, preferably lung cancer, and useful as a diagnostic.

Human 86216

The present invention is based, in part, on the discovery of a novel DEAD helicase family member, referred to herein as "86216".

The human 86216 sequence (SEQ ID NO:113), which is approximately 3577 nucleotides long including untranslated regions, contains a predicted methionine-initiated coding sequence of about 2337 nucleotides, not including the termination codon (nucleotides 47-2383 of SEQ ID NO:113; 1-2337 of SEQ ID NO:115). The coding sequence encodes a 779 amino acid protein (SEQ ID NO:114).

Human 86216 contains the following regions or other structural features (for general information regarding PFAM identifiers, PS prefix and PF prefix domain identification numbers, refer to Sonnhammer et al. (1997) *Protein* 28:405-420: a DEAD domain (PFAM Accession Number PF00270) located at about amino acid residues 117 to 231 of SEQ ID NO:114; a helicase c domain (PFAM Accession Number PF00271) located at about amino acid residues 300 to 401 of SEQ ID NO:114; a helicase RNA ATP dependent splicing domain (Propom No. PD117102) located at about amino acid residues 213 to 300 of SEQ ID NO:114; one DEAH-box subfamily ATP-dependent helicases signature (SEQ ID NO:120) located at about amino acids 168 to 177 of SEQ ID NO:114; one ATP/GTP binding site motif A (P-loop) located at about amino acids 76 to 83 of SEQ ID NO:114; two N-glycosylation sites (Prosite PS00001) located at about amino acids 163 to 166 and 346 to 349 of SEQ ID NO:114; three cAMP/cGMP-dependent protein kinase phosphorylation sites (Prosite PS00004) located at about amino acids 427 to 430, 721 to 724, and 775 to 778 of SEQ ID NO:114; eight protein kinase C phosphorylation sites (Prosite PS00005) located at about amino acids 80 to 82, and 140 to 142, 394 to 396, 402 to 404, 437 to 439, 676 to 678, 724 to 726, and 774 to 776 of SEQ ID NO:114; nine casein kinase II phosphorylation sites (Prosite PS00006) located at about amino acids 43 to 46, 140 to 143, 308 to 311, 386 to 389, 485 to 488, 663 to 666, 724 to 727, 752 to 755, and 774 to 777 of SEQ ID NO:114; two tyrosine kinase phosphorylation sites (Prosite PS00007) located at about amino acids 248 to 255, and 526 to 532 of SEQ ID NO:114; six N-myristoylation sites (Prosite PS00008) located at about amino acids 48 to 53, 76 to 81, 127 to 132, 320 to 325, 337 to 342, and 567 to 572 of SEQ ID NO:114.

A hydropathy plot of human 86216 was performed. Polypeptides of the invention include fragments which include: all or part of a hydrophobic sequence, e.g., the sequence from about amino acid 205 to 225, from about 425 to 435, and from about 505 to 515 of SEQ ID NO:114; all or part of a hydrophilic sequence, e.g., the sequence from about amino acid 190 to 200, from about 530 to 540, and from about 710 to 730 of SEQ ID NO:114; a sequence which includes a Cys, or a glycosylation site.

The 86216 protein contains a significant number of structural characteristics in common with members of the DEAD helicase family. For example 86216 polypeptides of the invention contain at least one DEAD domain, and at least one helicase-c domain.

As used herein, the term "DEAD helicase" includes a protein or polypeptide which is capable of ATP-dependent nucleic acid unwinding in eukaryotic cells.

Members of a DEAD helicase family of proteins in addition to their ability to unwind nucleic acids, are also involved in RNA metabolism, nuclear transcription, pre mRNA splicing, ribosome biogenesis, nucleocytoplasmic transport, translation, RNA decay, and organellar gene expression. The members of the DEAD superfamily share a number of conserved sequence motifs with those of the helicases superfamily. One of these motifs is the D-E-A-D- box, which is a version of a motif of ATP-binding proteins. Another subfamily of the ATP-dependent helicases has a conserved histidine instead of aspartic acid, and is referred to as a D-E-A-H box.

In addition, many proteins that bind ATP or GTP (e.g., DEAD helicases) share a glycine-rich region, which typically forms a flexible loop between a beta-strand and an alpha-helix. This loop interacts with one of the phosphate groups of the nucleotide. This sequence motif is generally referred to as the 'A' consensus sequence or the 'P-loop'.

An alignment of the 86216 protein with a human RNA helicase gene of the DEAH-box protein family (SwissProt accession number O43143, corresponding to O43143 in Genbank) demonstrates about 38.1% sequence identity between the two sequences (as calculated in matblas from the blosum62.iij matrix).

A 86216 polypeptide can include a "DEAD domain" or regions homologous with a "DEAD domain". A 86216 polypeptide can further include a "helicase-c domain" or regions homologous with a "helicase-c," and at least one DEAH-box subfamily ATP-dependent helicases signature region.

A CLUSTAL W alignment shows amino acids 1 to 780 of human 86216 (SEQ ID NO:114) aligns with a human RNA helicase gene of the DEAH-box protein family, corresponding to amino acid residues 51 to 795 of SwissProt accession number O43143 in Genbank (SEQ ID NO:119). CLUSTAL W (v 1.74; Thompson et al. (1994) *Nuc. Acids Res.* 22:4673-80) uses dynamically varied gap penalties for progressive sequence alignments.

As used herein, the term "DEAD domain" includes an amino acid sequence of at least about 50 amino acid residues in length and having a bit score for the alignment of the sequence to the DEAD domain (HMM) of at least 1. Preferably a DEAD domain mediates ATP-dependent unwinding of nucleic acid. Preferably, a DEAD domain includes at least about 50 to 200 amino acids, more preferably about 75 to 150 amino acid residues, or most preferably about 90 to 120 amino acids and has a bit score for the alignment of the sequence to the DEAD domain (HMM) of at least 1, more preferably 3, and most preferably 4 or greater. A characteristic of the DEAD domain is the D-E-A-D- box, which is a conserved region characteristic of ATP-dependent helicases.

The DEAD domain can include a DEAH-box subfamily ATP-dependent helicases signature: [GSAH]-X-[LIVMF](3)-D-E-[ALIV]-H-[NECR] (SEQ ID NO:120).

In addition to the DEAH box subfamily ATP-dependent helicases signature in the DEAD domain, proteins belonging to this family of helicases also have an ATP/GTP-binding motif 'A' (P-loop) signature: [AG]-X(4)-G-K-[ST] (SEQ ID NO:121).

In the above conserved signature sequences, and other motifs or signature sequences described herein, the standard IUPAC one-letter code for the amino acids is used. Each element in the pattern is separated by a dash (–); square brackets ([ ]) indicate the particular residues that are accepted at that position; x indicates that any residue is accepted at that position; and numbers in parentheses (O) indicate the number of residues represented by the accompanying amino acid.

The DEAD domain (HMM) has been assigned the PFAM Accession Number PF00270. An alignment of the DEAD domain of human 86216 with a consensus amino acid sequence derived from a hidden Markov model (HMM) from PFAM (SEQ ID NO:116) is derived from the hidden Markov model from Pfam and has a has a bit score of about 4.3.

The consensus amino acid sequence (SEQ ID NO:116), corresponds to amino acids 117 to 231 of SEQ ID NO:114.

In a preferred embodiment, a 86216 polypeptide or protein has a "DEAD domain" or a region which includes at least about 50 to 200 amino acids, more preferably about 75 to 150 amino acid residues, or most preferably about 90 to 120 amino acid residues and has at least about 60%, 70% 80% 90% 95%, 99%, or 100% homology with a "DEAD domain," e.g., the DEAD domain of human 86216 (e.g., residues 117 to 231 of SEQ ID NO:114).

A 86216 polypeptide can include a "helicase-c domain" or regions homologous with a "helicase-c domain". As used herein, the term "helicase-c domain" includes an amino acid sequence of at least about 50 amino acid residues in length and having a bit score for the alignment of the sequence to the helicase-c domain (HMM) of at least 1. Preferably a helicase-c domain is not restricted to the DEAD/DEAH helicases, and may be found in a wide variety of helicases and helicase related proteins. Preferably, a helicase-c domain includes at least about 50 to 150 amino acids, more preferably about 75 to 125 amino acid residues, or most preferably about 90 to 110 amino acids and has a bit score for the alignment of the sequence to the helicase-c domain (HMM) of at least −15, more preferably −10, and most preferably −5 or greater.

The helicase-c domain (HMM) has been assigned the PFAM Accession Number PF00271. An alignment of the helicase-c domain (amino acids 300 to 401 of SEQ ID NO:114) of human 86216 with the Pfam helicase-c consensus amino acid sequence (SEQ ID NO:117) derived from a hidden Markov model yields a bit score of about −5.3

In a preferred embodiment, a 86216 polypeptide or protein has a "helicase-c domain" or a region which includes at least about 50 to 150 amino acids, more preferably about 75 to 125 amino acid residues, or most preferably about 90 to 110 amino acid residues and has at least about 60%, 70% 80% 90% 95%, 99%, or 100% homology with a "helicase-c domain," e.g., the helicase-c domain of human 86216 (e.g., residues 300 to 401 of SEQ ID NO:114).

To identify the presence of a "helicase-c" domain, and a "DEAD" domain in a 86216 protein sequence, and make the determination that a polypeptide or protein of interest has a particular profile, the amino acid sequence of the protein can be searched against the Pfam database of HMMs (e.g., the Pfam database, release 2.1) using the default parameters. For example, the hmmsf program, which is available as part of the HMMER package of search programs, is a family specific default program for MILPAT0063 and a score of 15 is the default threshold score for determining a hit. Alternatively, the threshold score for determining a hit can be lowered (e.g., to 8 bits). A description of the Pfam database can be found in Sonhammer et al. (1997) *Proteins* 28:405-420 and a detailed description of HMMs can be found, for example, in Gribskov et al. (1990) *Meth. Enzymol.* 183:146-159; Gribskov et al. (1987) *Proc. Natl. Acad. Sci. USA* 84:4355-4358; Krogh et al. (1994) *J. Mol. Biol.* 235:1501-1531; and Stultz et al. (1993) *Protein Sci.* 2:305-314, the contents of which are incorporated herein by reference. A search was performed against the HMM database resulting in the identification of a "helicase-c" domain in the amino acid sequence of human 86216 at about residues 300-401 of SEQ ID NO:114, and a "DEAD" domain in the sequence of human 86216 at about amino acid residues 117 to 231 of SEQ ID NO:114.

For further identification of domains, to identify the presence of a "helicase-c" domain in a 86216 protein sequence, and make the determination that a polypeptide or protein of interest has a particular profile, the amino acid sequence of the protein can be searched against a database of domains, e.g., the Propom database (Corpet et al. (1999), *Nucl. Acids Res.* 27:263-267). The Propom protein domain database consists of an automatic compilation of homologous domains. Current versions of Propom are built using recursive PSI-BLAST searches (Altschul et al. (1997) *Nucleic Acids Res.* 25:3389-3402; Gouzy et al. (1999) *Computers and Chemistry* 23:333-340) of the SWISS-PROT 38 and TREMBL protein databases. The database automatically generates a consensus sequence for each domain.

A BLAST search was performed against the HMM database Propomain Release 2001.1; resulting in the identification of a "Helicase RNA ATP-independent" No. PD117102 domain (SEQ ID NO:118) in the amino acid sequence of human 86216 at about residues 213 to 301 of SEQ ID NO:114.

A 86216 family member can include at least one DEAD domain, and at least one helicase c domain. A 86216 family member can include at least one ATP/GTP binding site motif 'A' (P-loop) (Prosite PS00017), and at least one DEAH-box subfamily ATP-dependent helicase signature (Prosite PS00690).

Furthermore, a 86216 family member can include at least one, preferably two N-glycosylation site (Prosite PS00001); at least one, two, three, preferably four cAMP/cGMP protein kinase phosphorylation sites (Prosite PS00004); at least one, two, three, five, six, seven, preferably protein kinase C phosphorylation sites (Prosite PS00005); at least one, two, three, four, five, six, seven, eight, preferably nine casein kinase II phosphorylation sites (Prosite PS00006); at least one, preferably two tyrosine kinase phosphorylation sites (Prosite PS00007) and at least one, two, three, four, five, preferably six N-myristoylation sites (Prosite PS00008).

As the 86216 polypeptides of the invention can modulate 86216-mediated activities, they can be useful for developing novel diagnostic and therapeutic agents for DEAD helicase-associated or other 86216-associated disorders, as described below.

As used herein, a "DEAD helicase-associated activity" includes an activity which involves ATP-dependent, nucleic acid unwinding. Members of the DEAD helicase family can play a role in Bloom's syndrome, which is an autosomal recessive disorder associated with a predisposition to cancers of many types. Cells from those afflicted with Bloom's syndrome display extreme genomic instability. Helicase also may be implicated in Werner's syndrome (WS) another rare autosomal recessive disorder characterized by premature aging. Helicases may also have a role in breast cancer, wherein a member of the DEAH helicase family bearing a mutation in a residue (a residue known to be essential for catalytic function in other helicases), interferes with normal double-strand break repair.

As used herein, a "86216 activity", "biological activity of 86216" or "functional activity of 86216", refers to an activity exerted by a 86216 protein, polypeptide or nucleic acid molecule on e.g., a 86216-responsive cell or on a 86216 substrate, e.g., a protein substrate, as determined in vivo or in vitro. In one embodiment, a 86216 activity is a direct activity, such as an association with a 86216 target molecule. A "target molecule" or "binding partner" is a molecule with which a 86216 protein binds or interacts in nature. In an exemplary embodiment, 86216 is a helicase, e.g., a BACH1 helicase-like protein, which interacts directly with BRCA1 and contributes to its DNA repair (Cantor, S B et. al., (2001) *Cell* Apr 6; 105(1): 149-60) and thus binds to or interacts in nature with a molecule (or protein substrate), e.g., a nucleic acid binding protein.

A 86216 activity can also be an indirect activity, e.g., a cellular signaling activity mediated by interaction of the 86216 protein with a 86216 receptor. Based on the above-described sequence structures and similarities to molecules of known function, the 86216 molecules of the present invention can have similar biological activities as DEAD helicase family members. For example, the 86216 proteins of the present invention can have the ability to modulate any one or more of the following activities: (1) ATP dependent nucleic acid unwinding (2) the ability to modulate cellular proliferative disorders (e.g., proliferative disorders of the breast (e.g., breast cancer (e.g., proliferative disorders of mammary epithelial cells) Bloom's syndrome, or Werners syndrome)); (3) RNA metabolism (e.g., nuclear transcription, and mRNA splicing); (4) nucleocytoplasmic transport; and (5) RNA decay and organellar expression.

The 86216 molecules of the invention can modulate the activities of cells in tissues where they are expressed. For example, TaqMan analysis shows 86216 mRNA is expressed in the mammary epithelial cell line MCF10A. Thus, the 86216 molecules can be used to treat breast disorders (i.e., proliferative cell disorders of the breast) in part because the 86216 mRNA is expressed in breast derived cells.

Thus, the 86216 molecules can act as novel diagnostic targets and therapeutic agents for controlling one or more disorders of the breast or other DEAD helicase disorders. As used herein, "DEAD helicase disorders" are diseases or disorders whose pathogenesis is caused by, is related to, or is associated with aberrant or deficient DEAD helicase protein function or expression. Examples of such disorders, e.g., DEAD helicase-associated or other 86216-associated disorders, include but are not limited to breast disorders and cellular proliferative and/or differentiative disorders.

The 86216 molecules can be used to treat breast disorders in part because DEAD helicase family members are found in mammary epithelial cells.

Examples of cellular proliferative and/or differentiative disorders include cancer, e.g., carcinoma, sarcoma, metastatic disorders or hematopoietic neoplastic disorders, e.g., leukemias. A metastatic tumor can arise from a multitude of primary tumor types, including but not limited to those of prostate, colon, lung, breast and liver origin.

The 86216 molecules of the invention can be used to monitor, treat and/or diagnose a variety of proliferative disorders. Such disorders include hematopoietic neoplastic disorders.

Gene Expression Analysis of 86216

Human 86216 expression was measured by TaqMan® quantitative PCR (Perkin Elmer Applied Biosystems) in cDNA prepared from a variety of normal and diseased (e.g., cancerous) human tissues or cell lines.

The results indicate significant 86216 expression in the mammary epithelial cell line MCF10a.

Human 25206

The present invention is based, in part, on the discovery of a novel short-chain dehydrogenase/reductase, referred to herein as "25206".

The human 25206 sequence (SEQ ID NO:122), which is approximately 1649 nucleotides long including untranslated regions, contains a predicted methionine-initiated coding sequence of about 858 nucleotides (nucleotides 213-1070 of SEQ ID NO:122; 1-858 of SEQ ID NO:124), not including the termination codon. The coding sequence encodes a 286 amino acid protein (SEQ ID NO:123).

The human 25206 protein of SEQ ID NO:123 includes an amino-terminal hydrophobic amino acid sequence, consistent with a signal sequence, of about 19 amino acids (from amino acid 1 to about amino acid 19 of SEQ ID NO:123), which upon cleavage results in the production of a mature protein form of 267 amino acids (from about amino acid 20 to about amino acid 286 of SEQ ID NO:123).

An alignment of the short-chain dehydrogenase/reductase domain of human 25206 with a consensus amino acid sequence derived from a hidden Markov model (HMM) from PFAM shows the consensus amino acid sequence (SEQ ID NO:125) aligns with amino acids 30 to 216 of SEQ ID NO:123.

Human 25206 contains the following regions or other structural features: a short-chain dehydrogenase/reductase domain (PFAM Accession Number PF00106) located at about amino acid residues 30 to 216 of SEQ ID NO:123, which includes a short-chain alcohol dehydrogenase family signature (PS00061) located at about amino acid residues 178 to 188 of SEQ ID NO:123; a signal peptide from about amino acids 1-19 of SEQ ID NO:123; two predicted Protein Kinase C phosphorylation sites (PS00005) at about amino acids 146 to 148 and 191 to 193 of SEQ ID NO:123; two predicted Casein Kinase II phosphorylation sites (PS00006) located at about amino acids 152 to 155 and 217 to 220 of SEQ ID NO:123; one predicted N-glycosylation site (PS00001) from about amino acids 280 to 283 of SEQ ID NO:123; and three predicted N-myristoylation sites (PS00008) from about amino acids 36 to 41, 117 to 122, and 244 to 249 of SEQ ID NO:123.

For general information regarding PFAM identifiers, PS prefix and PF prefix domain identification numbers, refer to Sonnhammer et al. (1997) *Protein* 28:405-420.

A hydropathy plot of human 25206 was performed. Polypeptides of the invention include fragments which include: all or part of a hydrophobic sequence, e.g., the sequence from about amino acid 76 to 88, from about 155 to 170, and from about 198 to 211 of SEQ ID NO:123; all or part of a hydrophilic sequence, e.g., the sequence of from about amino acid 120 to 131, from about 190 to 197, and from about 265 to 279 of SEQ ID NO:123.

The 25206 protein contains a significant number of structural characteristics in common with members of the short-chain dehydrogenase/reductase family.

Dehydrogenases typically contain at least two domains, the first binds a coenzyme, such as NAD or NADP, and the second binds substrate. Sequence of the coenzyme domain does not appear to be conserved among dehydrogenases. The second domain determines substrate specificity and contains amino acids involved in catalysis. Members of this family include alchohol dehydrognase, 3-β-hydroxysteroid dehydrogenase, estradiol 17-β-dehydrogenase, retinal dehydrogenase, and NADPH-dependent carbonyl reductase.

Short-chain dehydrogenases/reductases (SDRs) typically function as dimers or tetramers. The subunits are composed of approximately 250 to 300 amino acid residues, an N-terminal co-enzyme binding pattern of GxxxGxG (SEQ ID NO:126), and an active-site pattern of YxxK (SEQ ID NO:127) (Opperman et al. (1999) Enzymology and Molecular Biology of Carbonyl Metabolism 7 ed. Weiner et al., Plenum Publishers, NY p. 373-377). Although identity between different SDR members is at the 15-30% level, three-dimensional structures thus far analyzed reveal a highly similar conformation with a one-domain subunit with seven to eight β-strands.

25206 polypeptides are homologous to 11-beta hydroxysteroid dehydrogenase (11 beta-HSD), alternatively known as corticosteroid 11-beta dehydrogenase. Two isoforms of 11-beta HSD are known (Krozowski, Z. et al. (1999) *J. Steroid Biochem. Mol. Biol.* 69(1-6):391-401). These enzymes catalyze the interconversion of cortisol and the inactive glucocorticoid metabolite cortisone in an NADPH-dependent manner. 25206 polypeptide is closely related to the type I isoform, which is a bi-directional enzyme acting predominantly as a reductase to convert inactive cortisone to active cortisol. The type II isoform acts unidirectionally to inactivate cortisol.

A 25206 polypeptide can include a "short chain dehydrogenase domain" or regions homologous with a "short chain dehydrogenase domain". Short chain dehydrogenases have the ability to directly or indirectly remove a hydride from a substrate, e.g., an alcohol; an aldehyde; a steroid, e.g., a glucocorticoid, cortisone; a sugar. Typically, after removal of a hydride from a substrate, electrons of the hydride are transferred to NAD+, NADP+, or other coenzyme (e.g., 3-acetylpyridine adenine dinucleotide phosphate) or hydride acceptor. For example, if the substrate has hydroxyl, dehydrogenation converts the hydroxyl to a keto group and produces NADH or NADPH and a proton. Hydride removal from substrate however does not require the presence of an acceptor. Free hydride can be detected, for example, optically by H+ binding to a dye molecule.

A 25206 polypeptide can include a "short-chain dehydrogenase/reductase domain" or regions homologous with a "short-chain dehydrogenase/reductase domain".

As used herein, the term "short chain dehydrogenase domain" includes an amino acid sequence of about 50 to 400 amino acid residues in length and having a bit score for the alignment of the sequence to the short chain dehydrogenase domain (HMM) of at least 50. Preferably, a short chain dehydrogenase domain includes at least about 100 to 300 amino acids, more preferably about 140 to 250 amino acid residues, or about 180 to 190 amino acids and has a bit score for the alignment of the sequence to the short chain dehydrogenase domain (HMM) of at least 80, 100, 110 or greater. The short chain dehydrogenase domain (HMM) has been assigned the PFAM Accession Number PF00106. The short chain dehydrogenase domain (amino acids 30 to 216 of SEQ ID NO:123) of human 25206 aligns with a consensus amino acid sequence (SEQ ID NO:125) derived from a hidden Markov model.

In a preferred embodiment, 25206 polypeptide or protein has a "short chain dehydrogenase domain" or a region that includes at least about 100 to 300 amino acids, more preferably about 140 to 250 amino acid residues, or about 180 to 190 amino acid residues and has at least about 60%, 70% 80% 90% 95%, 99%, or 100% homology with a "short chain dehydrogenase domain," e.g., the short chain dehydrogenase domain of human 25206 (e.g., residues 30 to 216 of SEQ ID NO:123).

Preferably, the short chain dehydrogenase domain of a 25206 polypeptide includes a short chain dehydrogenase family signature, YSAAKFALDGF (SEQ ID NO:128), which corresponds to amino acids 178-188 of SEQ ID NO:123.

To identify the presence of a "short-chain dehydrogenase/reductase" domain in a 25206 protein sequence, and make the determination that a polypeptide or protein of interest has a particular profile, the amino acid sequence of the protein can be searched against the Pfam database of HMMs (e.g., the Pfam database, release 2.1) using the default parameters. For example, the hmmsf program, which is available as part of the HMMER package of search programs, is a family specific default program for MILPAT0063 and a score of 15 is the default threshold score for determining a hit. Alternatively, the threshold score for determining a hit can be lowered (e.g., to 8 bits). A description of the Pfam database can be found in Sonhammer et al. (1997) *Proteins* 28(3):405-420 and a detailed description of HMMs can be found, for example, in Gribskov et al. (1990) *Meth. Enzymol.* 183:146-159; Oribskov et al. (1987) *Proc. Natl. Acad. Sci. USA* 84:4355-4358; Krogh et al. (1994) *J. Mol. Biol.* 235:1501-1531; and Stultz et al. (1993) *Protein Sci.* 2:305-314, the contents of which are incorporated herein by reference. A search was performed against the HMM database resulting in the identification of a "short-chain dehydrogenase/reductase" domain in the amino acid sequence of human 25206 at about residues 30 to 216 of SEQ ID NO:123.

A 25206 family member can include one or more of: a short chain dehydrogenase domain or a short chain alcohol dehydrogenase family signature. Furthermore, a 25206 family member can include a signal peptide; at least one, and preferably two, protein kinase C phosphorylation sites (PS00005); at least one, and preferably two, predicted casein kinase II phosphorylation sites (PS00006); and at least one predicted N-myristoylation sites (PS00008).

In yet another embodiment, the 25206 molecule can further include a signal sequence. As used herein, a "signal sequence" refers to a peptide of about 10-40 amino acid residues in length which occurs at the N-terminus of secretory and integral membrane proteins and which contains a majority of hydrophobic amino acid residues. For example, a signal sequence contains at least about 15-30 amino acid residues, preferably about 19 amino acid residues, and has at least about 40-70%, preferably about 50-65%, and more preferably about 55-60% hydrophobic amino acid residues (e.g., alanine, valine, leucine, isoleucine, phenylalanine, tyrosine, tryptophan, or proline). Such a "signal sequence", also referred to in the art as a "signal peptide", serves to direct a protein containing such a sequence to a lipid bilayer. For example, in one embodiment, a 25206 protein contains a signal sequence of about amino acids 1-19 of SEQ ID NO:123. The "signal sequence" is cleaved during processing of the mature protein. The mature 25206 protein corresponds to amino acids 20 to 286 of SEQ ID NO:123.

As the 25206 polypeptides of the invention may modulate 25206-mediated activities, they may be useful for developing novel diagnostic and therapeutic agents for 25206-mediated or related disorders, as described below.

As used herein, a "25206 activity", "biological activity of 25206" or "functional activity of 25206", refers to an activity exerted by a 25206 protein, polypeptide or nucleic acid molecule. For example, a 25206 activity can be an activity exerted by 25206 in a physiological milieu on, e.g., a 25206-responsive cell or on a 25206 substrate, e.g., a protein substrate. A 25206 activity can be determined in vivo or in vitro. In one embodiment, a 25206 activity can be an indirect activity, e.g., a cellular signaling activity mediated by interaction of the 25206 protein with a 25206 receptor.

In other embodiments, the 25206 activity is a direct activity, such as an association with a 25206 target molecule. A "target molecule" or "binding partner" is a molecule with which a 25206 protein binds or interacts in nature. For example, a 25206 binding partner is a substrate, e.g., an alcohol; an aldehyde; a steroid, e.g., a glucocorticoid, cortisone; a sugar. As the 25206 polypeptides show structural similarity to 111-beta-HSD, these polypeptides may be involved in the metabolism of steroids, e.g., glucocorticoids. Glucocorticoids have been shown to have an antiproliferative effect on some breast cancer cell lines in vitro (Hundertmark, S. et al. (1997) *J. Endocrinol.* 155(1):171-180). Accordingly, the 25206 molecules of the present invention may be involved in regulating cellular proliferation and differentiation.

Based on the above-described sequence similarities, the 25206 molecules of the present invention are predicted to have similar biological activities as short chain dehydrogenase family members. For example, the 25206 proteins of the present invention can have one or more of the following activities: (1) steroid biosynthesis or metabolism (breakdown); (2) changes associated with steroid biosynthesis or metabolism (e.g., sex trait development); (3) metabolism or removal of natural or xenobiotic substances (e.g., ethanol, toxins, etc.); (4) cellular proliferation or differentiation; or (5) cellular survival and/or degeneration (e.g., neurodegeneration).

As described below, TaqMan analysis shows 25206 mRNA is expressed in cancerous tissues, e.g., cancerous tissues from the breast, brain, lung, colon, liver, as well as neural (e.g., brain) or reproductive, e.g., ovarian, tissues. Thus, the 25206 molecules can act as novel diagnostic targets and therapeutic agents for controlling one or more of cellular proliferative, differentiative, neural, e.g., neurodegenerative, and reproductive, disorders.

Examples of cellular proliferative and/or differentiative disorders include cancer, e.g., carcinoma, sarcoma, metastatic disorders or hematopoietic neoplastic disorders, e.g., leukemias. A metastatic tumor can arise from a multitude of primary tumor types, including but not limited to those of prostate, colon, lung, brain, breast and liver origin.

Additional examples of proliferative disorders include hematopoietic neoplastic disorders.

Tissue Distribution of 25206 mRNA by TaqMan Analysis

Endogenous human 25206 gene expression was determined using the Perkin-Elmer/ABI 7700 Sequence Detection System which employs TaqMan technology.

Tissues tested include the human tissues and several cell lines shown in Tables 41-44. 25206 mRNA was detected in brain tissue (normal and tumorigenic), breast tissue (normal and tumorigenic), ovarian tissue (normal and tumorigenic), lung tissue (normal and tumorigenic), a host of xenograft cells and a host of breast cell clones (Tables 41-44). More specifically, as depicted in Tables 41-44, 25206 mRNA expression was increased 1.5-3.6 fold at all timepoints following IGF1 treatment. Additionally, 25206 mRNA was significantly upregulated in two MCF10AT3B tumor cell clones grown in soft agar vs. grown on plastic. 25206 mRNA was upregulated about 3 fold in 2/7 breast tumors vs. 3/4 normal breast tissues, and 3/7 lung tumors vs. 4/4 normal lung tissues. Phase I Taqman panel showed highest expression in brain tissue. 25206 showed expression in many tumor cell lines (NCIH67>A549>T47D). Each of these tables is described in more detail below.

Table 41 depicts the relative expression of 25206 mRNA in a panel of human tissues indicated below. Tissues depicted with as MET are metastatic tissue; HMVEC cells are human microvascular endothelial cells. 25206 mRNA is overexpressed in normal brain tissue and to some extent in tumorigenic brain (glioma) tissue.

TABLE 41

| Tissue source | Tissue Type | Relative Expression |
|---|---|---|
| CHT 396 | Colon Normal | 0.0 |
| CHT 519 | Colon Normal | 0.0 |
| CHT 416 | Colon Normal | 0.1 |
| CHT 452 | Colon Normal | 0.0 |
| CHT 398 | Colon Tumor | 0.2 |
| CHT 807 | Colon Tumor | 0.0 |
| CHT 805 | Colon Tumor | 0.3 |
| CHT 528 | Colon Tumor | 0.1 |
| CHT 368 | Colon Tumor | 0.0 |
| CHT 372 | Colon Tumor | 0.3 |
| CHT 01 | Liver Met | 0.1 |
| CHT 3 | Liver Met | 0.4 |
| CHT 896 | Liver Met | 0.1 |
| CHT 340 | Liver Met | 0.5 |
| PIT 260 | Liver Normal | 0.0 |
| PIT 229 | Liver Normal | 2.4 |
| MGH 16 | Brain Normal | 29.8 |
| MCL 53 | Brain Normal | 99.4 |
| MCL 377 | Brain Normal | 26.8 |
| MCL 390 | Brain Normal | 67.9 |
| MPI 665 | Astrocytes | 6.7 |
| CHT 201 | Glio | 0.6 |
| CHT 216 | Glio | 5.7 |
| CHT 501 | Glio | 5.6 |
| CHT 1273 | Glio | 37.4 |

TABLE 41-continued

| Tissue source | Tissue Type | Relative Expression |
|---|---|---|
| CHT 828 | Glio | 2.9 |
| A24 | HMVEC-Arr | 1.1 |
| C48 | HMVEC-Prol | 1.0 |
| CHT 50 | Placenta | 0.4 |
| BWH 58 | Fetal Adrenal | 8.9 |
| PIT 251 | Fetal Adrenal | 1.7 |
| BWH 54 | Fetal Liver | 0.7 |
| BWH 75 | Fetal Liver | 0.4 |
| | NTC | 1000.0 |

Table 42 depicts the relative expression of 25206 mRNA in a panel of human tissues indicated below. 25206 mRNA is relatively overexpressed in breast, ovary, and lung tumorigenic tissue, while the gene is also overexpressed in normal ovary tissue.

TABLE 42

| Tissue | Relative Expression |
|---|---|
| Breast Normal | 0.8 |
| Breast Normal | 1.4 |
| Breast Normal | 2.9 |
| Breast Normal | 0.7 |
| Breast Tumor | 2.1 |
| Breast Tumor | 0.9 |
| Breast Tumor | 0.3 |
| Breast Tumor | 0.4 |
| Breast Tumor | 1.8 |
| Breast Tumor | 5.0 |
| Breast Tumor | 4.1 |
| Ovary Normal | 6.9 |
| Ovary Normal | 6.1 |
| Ovary Normal | 7.5 |
| Ovary Normal | 7.9 |
| Ovary Tumor | 0.6 |
| Ovary Tumor | 0.6 |
| Ovary Tumor | 6.1 |
| Ovary Tumor | 1.5 |
| Ovary Tumor | 2.2 |
| Ovary Tumor | 0.2 |
| Ovary Tumor | 7.3 |
| Ovary Tumor | 0.4 |
| Lung Norm | 0.3 |
| Lung Norm | 0.9 |
| Lung Norm | 0.3 |
| Lung Norm | 0.5 |
| Lung Tumor | 3.0 |
| Lung Tumor | 3.1 |
| Lung Tumor | 2.2 |
| Lung Tumor | 1.4 |
| Lung Tumor | 14.5 |
| Lung Tumor | 1.7 |
| Lung Tumor | 0.3 |

Table 43 depicts the relative expression of 25206 mRNA in a panel of human breast cell lines indicated below. Breast carcinoma cell lines are represented by MCF10, MCF-7, ZR, T47, MDA, and SKBr3. Normal breast cells are represented by the cell line Hs578. Expression of 25206 mRNA is upregulated in breast carcinoma cells grown in soft agar compared to breast carcinoma cells grown on plastic. Exposure of the MCF10 carcinoma line with insulin-like growth factor 1 (IGF-1) or epidermal growth factor (EGF) had some effect on the expression of 25206 mRNA.

TABLE 43

| Tissue Type | Expression |
|---|---|
| MCF10MS | 1.09 |
| MCF10A | 1.23 |
| MCF10AT.cl1 | 0.42 |
| MCF10AT.cl3 | 0.63 |
| MCF10AT1 | 0.49 |
| MCF10AT3B | 0.73 |
| MCF10CA1a.cl1 | 0.41 |
| MCF10AT3B Agar | 11.13 |
| MCF10CA1a.cl1 Agar | 2.03 |
| MCF10A.m25 Plastic | 2.13 |
| MCF10CA Agar | 1.52 |
| MCF10CA Plastic | 0.46 |
| MCF3B Agar | 6.24 |
| MCF3B Plastic | 0.92 |
| MCF10A EGF 0 hr | 0.50 |
| MCF10A EGF 0.5 hr | 0.42 |
| MCF10A EGF 1 hr | 0.37 |
| MCF10A EGF 2 hr | 0.37 |
| MCF10A EGF 4 hr | 0.43 |
| MCF10A EGF 8 hr | 0.41 |
| MCF10A IGF1A 0 hr | 0.76 |
| MCF10A IGF1A 0.5 hr | 1.09 |
| MCF10A IGF1A 1 hr | 1.02 |
| MCF10A IGF1A 3 hr | 1.46 |
| MCF10A IGE1A 24 hr | 2.74 |
| MCF10AT3B.cl5 Plastic | 1.54 |
| MCF10AT3B.cl6 Plastic | 0.95 |
| MCF10AT3B.cl3 Plastic | 0.95 |
| MCF10AT3B.cl1 Plastic | 0.88 |
| MCF10AT3B.cl4 Plastic | 0.75 |
| MCF10AT3B.cl2 Plastic | 0.67 |
| MCF10AT3B.cl5 Agar | 9.49 |
| MCF10AT3B.cl6 Agar | 10.49 |
| MCF-7 | 0.75 |
| ZR--75 | 1.58 |
| T47D | 1.31 |
| MDA-231 | 0.35 |
| MDA-435 | 1.12 |
| SkBr3 | 0.13 |
| Hs578Bst | 0.68 |
| Hs578T | 0.62 |

Table 44 depicts the relative expression of 25206 mRNA in panel of human cancer cell lines after transplantation into mice. Human breast carcinoma cells lines are represented by MCF, ZR75, T47D, MDA, and SKBr3 cell lines; colon carcinoma cell lines are represented by DLD, SW620, HCT116 and Colo205 cell lines; lung adenosquamous carcinoma cell lines are represented by NCIH125, NCIH67, NCIH 322, and NCIH460 cell lines; a lung carcinoma cell line is represented by A549 cell line; a lung cell line is represented by NHBE cell lines; ovarian carcinoma cells are represented by SKOV and OVCAR cell lines; and baby kidney cells which are indicated below. 25206 mRNA shows a slight increase in expression in all lung cell lines (both cancerous and normal), but is greatly overexpressed in baby kidney cells.

TABLE 44

| Tissue Type | Relative Expression |
|---|---|
| MCF-7 Breast T | 4.69 |
| ZR75 Breast T | 4.61 |
| T47D Breast T | 6.87 |
| MDA 231 Breast T | 2.21 |
| MDA 435 Breast T | 6.64 |
| SKBr3 Breast | 0.94 |
| DLD 1 ColonT (stageC) | 2.98 |
| SW620 ColonT (stageC) | 2.07 |
| HCT116 | 3.33 |
| HT29 | 0.22 |

TABLE 44-continued

| Tissue Type | Relative Expression |
|---|---|
| Colo 205 | 0.13 |
| NCIH125 | 3.93 |
| NCIH67 | 10.13 |
| NCIH322 | 7.16 |
| NCIH460 | 1.58 |
| A549 | 8.91 |
| NHBE | 9.42 |
| SKOV-3 ovary | 1.28 |
| OVCAR-3 ovary | 4.74 |
| 293 baby kidney | 15.63 |
| 293T baby kidney | 24.77 |

Additional expression studies were conducted using probes generated from 4 normal breast tissue samples, 4 ductal carcinoma in situ (DCIS) samples, 4 invasive ductal carcinoma (IDC) samples and 3 invasive lobular carcinoma (ILC) samples. 25206 mRNA was expressed at about 2 fold the median value of the 4 normal breast samples in 1/4 DCIS samples, 1/4 IDC samples and 0/3 ILC samples.

25206 mRNA expression was assayed with probes generated from untreated human breast epithelial MCF10A cells or MCF10A cells treated with 10 nM IGF1 for 0.5, 1, 3 and 26 hours. 25206 mRNA expression was increased 1.5-1.8 fold at all timepoints following IGF1 treatment.

Tissue Distribution of 25206 mRNA by In Situ Hybridization

In situ hybridization studies revealed expression of 25206 mRNA in the following tissues: 0/2 normal breast tissues, 1/5 breast tumors, 0/3 normal lung tissues, 1/4 lung tumors, 0/1 normal colon tissue, 0/3 colon tumors, 0/1 normal ovary tissue, 0/2 ovary tumors and 1/1 normal brain tissue.

Human 8843

The present invention is based, in part, on the discovery of a novel dual specificity phosphatase family member, referred to herein as “8843”.

The human 8843 sequence (SEQ ID NO:129), which is approximately 839 nucleotides long including untranslated regions, contains a predicted methionine-initiated coding sequence of about 603 nucleotides, not including the termination codon (nucleotides 44-646 of SEQ ID NO:129; 1-603 of SEQ ID NO:131). The coding sequence encodes a 201 amino acid protein (SEQ ID NO:130).

An alignment of the dual specificity phosphatase domain of human 8843 with a consensus amino acid sequence derived from a hidden Markov model (HMM) from PFAM shows the consensus amino acid sequence (SEQ ID NO:132) aligns with amino acids 37 to 185 of SEQ ID NO:130.

An alignment of the dual specificity phosphatase domain of human 8843 with a consensus amino acid sequence derived from a hidden Markov model (HMM) in the SMART domain library shows the consensus amino acid sequence (SEQ ID NO:133) aligns with amino acids 37 to 185 of SEQ ID NO:130.

Human 8843 contains the following regions or other structural features: a dual specificity phosphatase domain (PFAM Accession Number PF00782) located at about amino acid residues 37 to 185 of SEQ ID NO:130; a tyrosine specific protein phosphatase active site signature (Prosite PS00383), also termed “C—$X_5$—R” motif (SEQ ID NO:135), located at about amino acid residues 130 to 142 of SEQ ID NO:130, including an active site cysteine at about amino acid 132 of SEQ ID NO:130, and an active site arginine at about amino acid 138 of SEQ ID NO:130; a dual specificity phosphatase extended active site signature (VXVHCXXGXSRSX-TXXXAY[LI]M; SEQ ID NO:136; Muda et al. (1996) *J Biol Chem* 271:27205) locate at about amino acid residues 128 to 158 of SEQ ID NO:130; a VH1-like dual specificity phosphatase loop located at about amino acid residues 106 to 110 of SEQ ID NO:130, include a conserved general acid, aspartic acid at about residue 109 of SEQ ID NO:130; one predicted N-glycosylation site (PS00001) at about amino acids 82 to 85 of SEQ ID NO:130; one predicted protein kinase C phosphorylation sites (PS00005) at about amino acids 187 to 189 of SEQ ID NO:130; four predicted casein kinase II phosphorylation sites (PS00006) located at about amino acids 70 to 73, 83 to 86, 98 to 101, and 154 to 157 of SEQ ID NO:130; and one predicted N-myristylation sites (PS00008) from about amino acid 114 to 119 of SEQ ID NO:130.

For general information regarding PFAM identifiers, PS prefix and PF prefix domain identification numbers, refer to Sonnhammer et al. (1997) *Protein* 28:405-420.

A hydropathy plot of human 8843 was performed. Polypeptides of the invention include fragments which include: all or part of a hydrophobic sequence, e.g., the sequence from about amino acid 9 to 25, from about 45 to 52, and from about 142 to 150, of SEQ ID NO:130; all or part of a hydrophilic sequence, e.g., the sequence of from about amino acid 27 to 36, from about 70 to 78, and from about 151 to 160, of SEQ ID NO:130; a sequence which includes a Cys, or a glycosylation site.

The 8843 protein contains a significant number of structural characteristics in common with members of the dual specificity phosphatase family.

Dual specificity phosphatase proteins are characterized by a common fold. Dual specificity phosphatases are exemplified by the VH1 or vaccinia virus late H1 gene protein, which hydrolyzes both phosphotyrosine, phosphothreonine, and phosphoserine. VH1 catalytic activity is required for viral replication. A human homolog of VH1, VHR, has been identified. The three dimensional structure of this family is based on models from x-ray crystallographic data of protein tyrosine phosphatases, and human VHR. The VHR structure includes a core domain consisting of a five-stranded mixed β-sheet and six α-helices. This structure closely superimposes on the structure of phosphotyrosine protein phosphatases. However, dual specificity phosphatases lack the KNRY motif, and the N-terminal structures of tyrosine protein phosphatases which endow these enzymes with a deep active site specific for aryl phosphates. Thus, dual specificity phosphatases have a shallower active site relative to tyrosine protein phosphatases and can accommodate phosphoserine and phosphothreonine substrates. Even so dual specificity phosphatases can have a greater than 50-fold faster rate of phosphatase activity for phosphotyrosine substrates than phosphothreonine or phosphoserine substrates.

Similar to the broader class of phosphatases, dual specificity phosphatases have a highly conserved active site including three catalytic residues, a cysteine, an arginine, and an aspartic acid. The active site cysteine and arginine are found in the “C—$X_5$—R” motif of the tyrosine phosphatase signature (Prosite PS00383; SEQ ID NO:135). This motif forms a binding pocket for three of the phosphate oxyanions. The cysteine acts as a nucleophile to accept the $PO_3$ group. The reaction transiently generates a phospho-cysteine intermediate before the phosphate is transferred to water. The active site arginine stabilizes the transition-state by hydrogen bonding to phosphate oxygens. In addition the histidine preceding the active site cysteine and the serine or threonine following the active site arginine are responsible for lowering the $pK_a$ of the cysteine to stabilize a negative charge on the cysteine. The active site aspartic acid accelerates the reaction by donating a protein to generate an uncharged hydroxyl (for a review, see Fauman and Saper (1996) *Trends in Biochem.* 21:412).

An 8843 polypeptide can include a "dual specificity phosphatase catalytic domain" or regions homologous with a "dual specificity phosphatase domain".

As used herein, the term "dual specificity phosphatase domain" includes an amino acid sequence of about 80 to 220 amino acids, more preferably about 100 to 180 amino acid residues, or about 130 to 160 amino acid residues in length and having a bit score for the alignment of the sequence to the dual specificity phosphatase domain (HMM) of at least 10, preferably 15, and more preferably 20. The dual specificity phosphatase catalytic domain (HMM) has been assigned the PFAM Accession Number PF00782. The dual specificity phosphatase domain (amino acids 37 to 185 of SEQ ID NO:130) of human 8843 aligns with a consensus amino acid sequence (SEQ ID NO:132) derived from a hidden Markov model, and with a consensus amino acid sequence (SEQ ID NO:133) derived from the SMART domain HMM model.

A dual specificity phosphatase domain preferably includes a perfect match to the Prosite tyrosine specific protein phosphatase active site signature (PS00383; [LIVMF]-H-C-x(2)-G-x(3)-[STC]-[STAGP]-x-[LIVMFY], wherein X is any amino acid and a number in parenthesis indicates the amino acid pattern is repeated that number of times; SEQ ID NO:134). Even more preferably, a dual specificity phosphatase includes the extended active site signature (VXVH-CXXGXSRSXTXXXAY[LI]M; SEQ ID NO:136; Muda et al. (1996) *J Biol Chem* 271: 27205). A dual specificity phosphatase domain also includes the conserved active site residues cysteine, arginine, and aspartic acid. The aspartic acid is preferably located in a loop region N-terminal to the active site signature.

In a preferred embodiment 8843 polypeptide or protein has a "dual specificity phosphatase domain" or a region which includes at least about 80 to 220 more preferably about 100 to 180 or 130 to 160, or about 148 amino acid residues in length and has at least about 50%, 60%, 70%, 80%, 90%, 95%, 99%, or 100% homology with a "dual specificity phosphatase domain," e.g., the dual specificity phosphatase domain of human 8843 (e.g., residues 37 to 185 of SEQ ID NO:130). In a preferred embodiment, the 8834 polypeptide has a tyrosine specific protein phosphatase active site signature located at about amino acids 130 to 142 of SEQ ID NO:130. The 8834 polypeptide also preferable has a conserved active site serine at about amino acid residue 132 of SEQ ID NO:130, a conserved active site arginine at about amino acid residue 138 of SEQ ID NO:130, and a conserved active site aspartic acid at about amino acid residue 109 of SEQ ID NO:130. Preferably, the active site aspartic acid is in an mobile loop, approximately 20 to 30, or preferably, 20 to 25 amino acids N-terminal to the active site cysteine.

To identify the presence of a "dual specificity phosphatase" domain in an 8843 protein sequence, and make the determination that a polypeptide or protein of interest has a particular profile, the amino acid sequence of the protein can be searched against a database of HMMs (e.g., the Pfam database, release 2.1) using the default parameters. For example, the hmmsf program, which is available as part of the HMMER package of search programs, is a family specific default program for MILPAT0063 and a score of 15 is the default threshold score for determining a hit. Alternatively, the threshold score for determining a hit can be lowered (e.g., to 8 bits). A description of the Pfam database can be found in Sonhammer et al. (1997) *Proteins* 28(3):405-420 and a detailed description of HMMs can be found, for example, in Gribskov et al. (1990) *Meth. Enzymol.* 183:146-159; Gribskov et al. (1987) *Proc. Natl. Acad. Sci. USA* 84:4355-4358; Krogh et al. (1994) *J. Mol. Biol.* 235:1501-1531; and Stultz et al. (1993) *Protein Sci.* 2:305-314, the contents of which are incorporated herein by reference. A search was performed against the HMM database resulting in the identification of a "dual specificity phosphatase" domain in the amino acid sequence of human 8843 at about residues 37 to 185 of SEQ ID NO:130.

An 8843 molecule can further include: preferably at least one N-glycosylation site; preferably at least one protein kinase C phosphorylation sites; at least one, two, three, and preferably four casein kinase II phosphorylation sites; and preferably at least one N-myristylation site.

As used herein, a "8843 activity", "biological activity of 8843" or "functional activity of 8843", refers to an activity exerted by an 8843 protein, polypeptide or nucleic acid molecule on e.g., an 8843-responsive cell or on an 8843 substrate, e.g., a protein substrate, as determined in vivo or in vitro. In one embodiment, an 8843 activity is a direct activity, such as an association with an 8843 target molecule. A "target molecule" or "binding partner" is a molecule with which an 8843 protein binds or interacts in nature. an 8843 activity can also be an indirect activity, e.g., a cellular signaling activity mediated by interaction of the 8843 protein with an 8843 receptor. Based on the above-described sequence similarities, the 8843 molecules of the present invention are predicted to have similar biological activities as dual specificity phosphatase family members. For example, the 8843 proteins of the present invention can have one or more of the following activities: (1) catalyzing the removal of a phosphate group attached to a tyrosine residue in a protein; (2) catalyzing the removal of a phosphate group attached to a serine or threonine residue in a protein; (3) modulating an intracellular signaling pathway, e.g., a MAP kinase or ERK kinase pathway; (4) modulating cell differentiation, e.g., differentiation of erythroid progenitor cells, such as, CD34+progenitors; (5) modulating cell proliferation, e.g., proliferation erythroid progenitor cells; (6) inactivating cell surface growth factor receptors, e.g., tyrosine kinase receptors; or (7) modulating apoptosis, of a cell, e.g., a leukemic cell, (e.g., an erythroleukemia cell).

As TaqMan analysis shows, 8843 mRNA is found in hematopoietic cells, and in particular, in erythroid cell lineages. The molecules of the invention can be used to develop novel agents or compounds to treat and/or diagnose disorders involving aberrant activities of those cells e.g., hematopoietic and, in particular, erythroid disorders, as described below. For example, an 8843 polypeptide is expressed in CD34 positive cells, e.g., mobilized peripheral blood CD34+ cells, normal adult bone marrow CD34+ cells, cord blood CD34+ cells, normal adult bone marrow CD34+ cells, G-CSF-treated bone marrow CD34+ cells, and fetal liver CD34+ cells; and erythroid progenitor cells, e.g., bone marrow glycophorin A positive cells and erythropoietin treated erythroid burst forming units (BFUs). 8843 mRNA is also expressed in hepatic cells, kidney, lung, and dermal cells, and thus diagnostic and therapeutic methods of using the molecules of the invention to treat/diagnose hepatic, kidney, lung, and dermal disorders are also contemplated by the present invention.

As used herein, the term "pluripotent hematopoietic stem cell" includes a cell that can give rise to a spleen colony forming unit (day 12 CFU-S), which, in turn, can give rise to progenitors of the granulocytic, monocytic, erythroid, megakaryocytic, and lymphoid lineages.

As used herein, a "CD34-positive cell" refers to a cell that expresses detectable levels of the CD34 antigen, preferably human CD34 antigen. The sequence for human CD34 is provided in SwissProt Accession Number P28906. The CD34 antigen is typically present on immature hematopoietic precursor cells and hematopoietic colony-forming cells in the bone marrow, including unipotent (CFU-GM, BFU-E) and pluripotent progenitors (CFU-GEMM, CFU-Mix and CFU-blast). The CD34 is also expressed on stromal cell precursors. Terminal deoxynucleotidyl transferase (TdT)-positive B- and T-lymphoid precursors in normal bone also are CD34+. The CD34 antigen is typically present on early myeloid cells that express the CD33 antigen, but lack the CD14 and CD15 antigens and on early erythroid cells that express the CD71 antigen and dimly express the CD45 antigen. The CD34 antigen is also found on capillary endothelial cells and approximately 1% of human thymocytes. Normal peripheral blood lymphocytes, monocytes, granulocytes and platelets do not express the CD34 antigen. CD34 antigen density is highest on early haematopoietic progenitor cells and decreases as the cells mature. The antigen is undetectably on fully differentiated haematopoietic cells. Approximately 60% of acute B-lymphoid leukemia's and acute myeloid leukemia express the CD34 antigen. The antigen is not expressed on chronic lymphoid leukemia (B or T lineage) or lymphomas.

As the 8843 polypeptides of the invention may modulate 8843-mediated activities, they may be useful for developing novel diagnostic and therapeutic agents for 8843-mediated or related disorders, e.g., erythroid-associated disorders.

As used herein, the term "erythropoietin" or "EPO" refers to a glycoprotein produced in the kidney, which is the principal hormone responsible for stimulating red blood cell production (erythrogenesis). EPO stimulates the division and differentiation of committed erythroid progenitors in the bone marrow. Normal plasma erythropoietin levels range from 0.01 to 0.03 Units/mL, and can increase up to 100 to 1,000-fold during hypoxia or anemia. Graber and Krantz, *Ann. Rev. Med.* 29:51 (1978); Eschbach and Adamson, *Kidney Intl.* 28:1 (1985). Recombinant human erythropoietin (rHuEpo or epoetin alfa) is commercially available as EPOGEN.RTM. (epoetin alfa, recombinant human erythropoietin) (Amgen Inc., Thousand Oaks, Calif.) and as PROCRIT.RTM. (epoetin alfa, recombinant human erythropoietin) (Ortho Biotech Inc., Raritan, N.J.).

Treatment, prevention and diagnosis of cancer or neoplastic disorders related to the erythroid lineage are also included in the present invention.

Tissue Distribution of 8843 mRNA

Endogenous human 8843 gene expression was determined using the Perkin-Elmer/ABI 7700 Sequence Detection System which employs TaqMan technology.

8843 mRNA levels were analyzed in a variety of samples of isolated and/or treated blood cells. High relative expression levels of 8843 mRNA, e.g., greater than 40 units, were observed for megakaryocytes, mast cells, blast forming units (BFU), especially BFUs treated with erythropoietin. Moderate relative expression levels of 8843 mRNA, between 10 and 40 units, were observed for multiple erythroid samples, and a subset of neutrophil samples.

High relative expression levels of 8843 mRNA, e.g., greater than 40 units, were observed for mobilized CD34+ peripheral blood cells (mBM), normal bone marrow CD34+ cells, as well as for glycophorin A (low levels) bone marrow cells (>60 units), which are erythroid progenitors. Moderate relative expression levels of 8843 mRNA, between 10 and 40 units, were observed for CD34+cord blood cells, CD34+fetal liver cells, and mobilized CD34+bone marrow cells.

8843 mRNA expression levels were also monitored in other hematopoietic lineages and tissues. K582 cells, an erythroid/megakaryocyte cell line, and Hep3b cells had high 8843 expression levels relative to controls.

8843 mRNA expression was also determined for mRNA derived from lung, fetal liver, and other tissues.

Definitions

The 26199, 33530, 33949, 47148, 50226, 58764, 62113, 32144, 32235, 23565, 13305, 14911, 86216, 25206 or 8843 protein, fragments thereof, and derivatives and other variants of the sequence in SEQ ID NO:2, 5, 8, 11, 14, 17, 54, 62, 68, 79, 89, 101, 114, 123 or 130 thereof are collectively referred to as "polypeptides or proteins of the invention" or "26199, 33530, 33949, 47148, 50226, 58764, 62113, 32144, 32235, 23565, 13305, 14911, 86216, 25206 or 8843 polypeptides or proteins". Nucleic acid molecules encoding such polypeptides or proteins are collectively referred to as "nucleic acids of the invention" or "26199, 33530, 33949, 47148, 50226, 58764, 62113, 32144, 32235, 23565, 13305, 14911, 86216, 25206 or 8843 nucleic acids."

As used herein, the term "nucleic acid molecule" includes DNA molecules (e.g., a cDNA or genomic DNA) and RNA molecules (e.g., an mRNA) and analogs of the DNA or RNA generated, e.g., by the use of nucleotide analogs. The nucleic acid molecule can be single-stranded or double-stranded, but preferably is double-stranded DNA.

The term "isolated or purified nucleic acid molecule" includes nucleic acid molecules which are separated from other nucleic acid molecules which are present in the natural source of the nucleic acid. For example, with regards to genomic DNA, the term "isolated" includes nucleic acid molecules which are separated from the chromosome with which the genomic DNA is naturally associated. Preferably, an "isolated" nucleic acid is free of sequences which naturally flank the nucleic acid (i.e., sequences located at the 5' and/or 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb or 0.1 kb of 5' and/or 3' nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material or culture medium when produced by recombinant techniques, or substantially free of chemical precursors or other chemicals when chemically synthesized.

As used herein, the term "hybridizes under low stringency, medium stringency, high stringency, or very high stringency conditions" describes conditions for hybridization and washing. Guidance for performing hybridization reactions can be found in *Current Protocols in Molecular Biology* (1989) John Wiley & Sons, N.Y., 6.3.1-6.3.6, which is incorporated by reference. Aqueous and nonaqueous methods are described in that reference and either can be used. Specific hybridization conditions referred to herein are as follows: 1) low stringency hybridization conditions in 6× sodium chloride/sodium citrate (SSC) at about 45° C., followed by two washes in 0.2× SSC, 0.1% SDS at least at 50° C. (the temperature of the washes can be increased to 55° C. for low stringency conditions); 2) medium stringency hybridization conditions in 6×SSC at about 45° C., followed by one or more washes in 0.2×SSC, 0.1% SDS at 60° C.; 3) high stringency hybridization conditions in 6×SSC at about 45° C., followed by one or more washes in 0.2×SSC, 0.1% SDS at 65° C.; and preferably 4) very high stringency hybridization conditions are 0.5M sodium phosphate, 7% SDS at 65° C., followed by one or more washes at 0.2×SSC, 1% SDS at 65° C. Very high stringency conditions (4) are the preferred conditions and the ones that should be used unless otherwise specified.

As used herein, a "naturally-occurring" nucleic acid molecule refers to an RNA or DNA molecule having a nucleotide sequence that occurs in nature (e.g., encodes a natural protein).

As used herein, the terms "gene" and "recombinant gene" refer to nucleic acid molecules which include an open reading frame encoding a 26199, 33530, 33949, 47148, 50226, 58764, 62113, 32144, 32235, 23565, 13305, 14911, 86216, 25206 or 8843 protein, preferably a mammalian 26199, 33530, 33949, 47148, 50226, 58764, 62113, 32144, 32235, 23565, 13305, 14911, 86216, 25206 or 8843 protein, and can further include non-coding regulatory sequences, and introns.

An "isolated" or "purified" polypeptide or protein is substantially free of cellular material or other contaminating proteins from the cell or tissue source from which the protein is derived, or substantially free from chemical precursors or other chemicals when chemically synthesized. In one embodiment, the language "substantially free" means preparation of 26199, 33530, 33949, 47148, 50226, 58764, 62113, 32144, 32235, 23565, 13305, 14911, 86216, 25206 or 8843 protein having less than about 30%, 20%, 10% and more preferably 5% (by dry weight), of non-26199, 33530, 33949, 47148, 50226, 58764, 62113, 32144, 32235, 23565, 13305, 14911, 86216, 25206 or 8843 protein (also referred to herein as a "contaminating protein"), or of chemical precursors or non-26199, 33530, 33949, 47148, 50226, 58764, 62113, 32144, 32235, 23565, 13305, 14911, 86216, 25206 or 8843 chemicals. When the 26199, 33530, 33949, 47148, 50226, 58764, 62113, 32144, 32235, 23565, 13305, 14911, 86216, 25206 or 8843 protein or biologically active portion thereof is recombinantly produced, it is also preferably substantially free of culture medium, i.e., culture medium represents less than about 20%, more preferably less than about 10%, and most preferably less than about 5% of the volume of the protein preparation. The invention includes isolated or purified preparations of at least 0.01, 0.1, 1.0, and 10 milligrams in dry weight.

A "non-essential" amino acid residue is a residue that can be altered from the wild-type sequence of 26199, 33530, 33949, 47148, 50226, 58764, 62113, 32144, 32235, 23565, 13305, 14911, 86216, 25206 or 8843 (e.g., the sequence of SEQ ID NO:1, 3, 4, 6, 7, 9, 10, 12, 13, 15, 16, 18, 53, 55, 61, 63, 67, 69, 78, 80, 88, 90, 100, 102, 113, 115, 122, 124, 129 or 131) without abolishing or more preferably, without substantially altering a biological activity, whereas an "essential" amino acid residue results in such a change. For example, amino acid residues that are conserved among the polypeptides of the present invention, e.g., those present in the conserved domains, are predicted to be particularly unamenable to alteration.

A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in a 26199, 33530, 33949, 47148, 50226, 58764, 62113, 32144, 32235, 23565, 13305, 14911, 86216, 25206 or 8843 protein is preferably replaced with another amino acid residue from the same side chain family. Alternatively, in another embodiment, mutations can be introduced randomly along all or part of a 26199, 33530, 33949, 47148, 50226, 58764, 62113, 32144, 32235, 23565, 13305, 14911, 86216, 25206 or 8843 coding sequence, such as by saturation mutagenesis, and the resultant mutants can be screened for 26199, 33530, 33949, 47148, 50226, 58764, 62113, 32144, 32235, 23565, 13305, 14911, 86216, 25206 or 8843 biological activity to identify mutants that retain activity. Following mutagenesis of SEQ ID NO:1, 3, 4, 6, 7, 9, 10, 12, 13, 15, 16, 18, 53, 55, 61, 63, 67, 69, 78, 80, 88, 90, 100, 102, 113, 115, 122, 124, 129 or 131, the encoded protein can be expressed recombinantly and the activity of the protein can be determined.

As used herein, a "biologically active portion" of a 26199, 33530, 33949, 47148, 50226, 58764, 62113, 32144, 32235, 23565, 13305, 14911, 86216, 25206 or 8843 protein includes a fragment of a 26199, 33530, 33949, 47148, 50226, 58764, 62113, 32144, 32235, 23565, 13305, 14911, 86216, 25206 or 8843 protein which participates in an interaction between a 26199, 33530, 33949, 47148, 50226, 58764, 62113, 32144, 32235, 23565, 13305, 14911, 86216, 25206 or 8843 molecule and a non-26199, 33530, 33949, 47148, 50226, 58764, 62113, 32144, 32235, 23565, 13305, 14911, 86216, 25206 or 8843 molecule. Biologically active portions of a 26199, 33530, 33949, 47148, 50226, 58764, 62113, 32144, 32235, 23565, 13305, 14911, 86216, 25206 or 8843 protein include peptides comprising amino acid sequences sufficiently homologous to or derived from the amino acid sequence of the 26199, 33530, 33949, 47148, 50226, 58764, 62113, 32144, 32235, 23565, 13305, 14911, 86216, 25206 or 8843 protein, e.g., the amino acid sequence shown in SEQ ID NO:2, 5, 8, 11, 14, 17, 54, 62, 68, 79, 89, 101, 114, 123 or 130, which include fewer amino acids than the full length 26199, 33530, 33949, 47148, 50226, 58764, 62113, 32144, 32235, 23565, 13305, 14911, 86216, 25206 or 8843 protein, and exhibit at least one activity of a 26199, 33530, 33949, 47148, 50226, 58764, 62113, 32144, 32235, 23565, 13305, 14911, 86216, 25206 or 8843 protein. Typically, biologically active portions comprise a domain or motif with at least one activity of the 26199, 33530, 33949, 47148, 50226, 58764, 62113, 32144, 32235, 23565, 13305, 14911, 86216, 25206 or 8843 protein. A biologically active portion of a 26199, 33530, 33949, 47148, 50226, 58764, 62113, 32144, 32235, 23565, 13305, 14911, 86216, 25206 or 8843 protein can be a polypeptide which is, for example, 10, 25, 50, 100, 200 or more amino acids in length. Biologically active portions of a 26199, 33530, 33949, 47148, 50226, 58764, 62113, 32144, 32235, 23565, 13305, 14911, 86216, 25206 or 8843 protein can be used as targets for developing agents which modulate a 26199, 33530, 33949, 47148, 50226, 58764, 62113, 32144, 32235, 23565, 13305, 14911, 86216, 25206 or 8843 mediated activity.

Calculations of homology or sequence identity (the terms "homology" and "identity" are used interchangeably herein) between sequences are performed as follows:

To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, 90%, 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch (1970) *J. Mol. Biol.* 48:444-453 algorithm which has been incorporated into the GAP program in the GCG software package using either a Blossum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package using a NWSgapdna.CMP matrix and a gap weight of 40, 50, 60, 70, or 80 and a length weight of 1, 2, 3, 4, 5, or 6. A particularly preferred set of parameters (and the one that should be used if the practitioner is uncertain about what parameters should be applied to determine if a molecule is within a sequence identity or homology limitation of the invention) are a Blossum 62 scoring matrix with a gap penalty of 12, a gap extend penalty of 4, and a frameshift gap penalty of 5.

The percent identity between two amino acid or nucleotide sequences can be determined using the algorithm of Meyers and Miller ((1989) CABIOS, 4:11-17) which has been incorporated into the ALIGN program (version 2.0), using a PAM120 weight residue table, a gap length penalty of 12 and a gap penalty of 4.

The nucleic acid and protein sequences described herein can be used as a "query sequence" to perform a search against public databases to, for example, identify other family members or related sequences. Such searches can be performed using the NBLAST and XBLAST programs (version 2.0) of Altschul et al. (1990) *J. Mol. Biol.* 215:403-10. BLAST nucleotide searches can be performed with the NBLAST program, score=100, wordlength=12 to obtain nucleotide sequences homologous to 26199, 33530, 33949, 47148, 50226, 58764, 62113, 32144, 32235, 23565, 13305, 14911, 86216, 25206 or 8843 nucleic acid molecules of the invention. BLAST protein searches can be performed with the XBLAST program, score=50, wordlength=3 to obtain amino acid sequences homologous to 26199, 33530, 33949, 47148, 50226, 58764, 62113, 32144, 32235, 23565, 13305, 14911, 86216, 25206 or 8843 protein molecules of the invention. To obtain gapped alignments for comparison purposes, Gapped BLAST can be utilized as described in Altschul et al., (1997) *Nucleic Acids Res.* 25:3389-3402. When utilizing BLAST and Gapped BLAST programs, the default parameters of the respective programs (e.g., XBLAST and NBLAST) can be used.

Particular 26199, 33530, 33949, 47148, 50226, 58764, 62113, 32144, 32235, 23565, 13305, 14911, 86216, 25206 or 8843 polypeptides of the present invention have an amino acid sequence substantially identical to the amino acid sequence of SEQ ID NO:2, 5, 8, 11, 14, 17, 54, 62, 68, 79, 89, 101, 114, 123 or 130. In the context of an amino acid sequence, the term "substantially identical" is used herein to refer to a first amino acid that contains a sufficient or minimum number of amino acid residues that are i) identical to, or ii) conservative substitutions of aligned amino acid residues in a second amino acid sequence such that the first and second amino acid sequences can have a common structural domain and/or common functional activity. For example, amino acid sequences that contain a common structural domain having at least about 60%, or 65% identity, likely 75% identity, more likely 85%, 90%. 91%, 92%, 93%, 94%, 95%, 96%, 97%, 98% or 99% identity to SEQ ID NO:2, 5, 8, 11, 14, 17, 54, 62, 68, 79, 89, 101, 114, 123 or 130 are termed substantially identical.

In the context of nucleotide sequence, the term "substantially identical" is used herein to refer to a first nucleic acid sequence that contains a sufficient or minimum number of nucleotides that are identical to aligned nucleotides in a second nucleic acid sequence such that the first and second nucleotide sequences encode a polypeptide having common functional activity, or encode a common structural polypeptide domain or a common functional polypeptide activity. For example, nucleotide sequences having at least about 60%, or 65% identity, likely 75% identity, more likely 85%, 90%. 91%, 92%, 93%, 94%, 95%, 96%, 97%, 98% or 99% identity to SEQ ID NO:1, 3, 4, 6, 7, 9, 10, 12, 13, 15, 16, 18, 53, 55, 61, 63, 67, 69, 78, 80, 88, 90, 100, 102, 113, 115, 122, 124, 129 or 131 are termed substantially identical.

"Misexpression or aberrant expression", as used herein, refers to a non-wild type pattern of gene expression, at the RNA or protein level. It includes: expression at non-wild type levels, i.e., over or under expression; a pattern of expression that differs from wild type in terms of the time or stage at which the gene is expressed, e.g., increased or decreased expression (as compared with wild type) at a predetermined developmental period or stage; a pattern of expression that differs from wild type in terms of decreased expression (as compared with wild type) in a predetermined cell type or tissue type; a pattern of expression that differs from wild type in terms of the splicing size, amino acid sequence, post-transitional modification, or biological activity of the expressed polypeptide; a pattern of expression that differs from wild type in terms of the effect of an environmental stimulus or extracellular stimulus on expression of the gene, e.g., a pattern of increased or decreased expression (as compared with wild type) in the presence of an increase or decrease in the strength of the stimulus.

"Subject", as used herein, can refer to a mammal, e.g., a human, or to an experimental or animal or disease model. The subject can also be a non-human animal, e.g., a horse, cow, goat, or other domestic animal.

A "purified preparation of cells", as used herein, refers to, in the case of plant or animal cells, an in vitro preparation of cells and not an entire intact plant or animal. In the case of cultured cells or microbial cells, it consists of a preparation of at least 10% and more preferably 50% of the subject cells.

As used herein, cellular proliferative and/or differentiative disorders include cancer, e.g., carcinoma, sarcoma, metastatic disorders or hematopoietic neoplastic disorders, e.g., leukemias. A metastatic tumor can arise from a multitude of primary tumor types, including but not limited to those of prostate, colon, lung, breast and liver origin.

As used herein, the term "cancer" (also used interchangeably with the terms, "hyperproliferative" and "neoplastic") refers to cells having the capacity for autonomous growth, i.e., an abnormal state or condition characterized by rapidly proliferating cell growth. Cancerous disease states may be categorized as pathologic, i.e., characterizing or constituting a disease state, e.g., malignant tumor growth, or may be categorized as non-pathologic, i.e., a deviation from normal but not associated with a disease state, e.g., cell proliferation associated with wound repair. The term is meant to include all types of cancerous growths or oncogenic processes, metastatic tissues or malignantly transformed cells, tissues, or organs, irrespective of histopathologic type or stage of invasiveness. The term "cancer" includes malignancies of the various organ systems, such as those affecting lung, breast, thyroid, lymphoid, gastrointestinal, and genito-urinary tract, as well as adenocarcinomas which include malignancies such as most colon cancers, renal-cell carcinoma, prostate cancer and/or testicular tumors, non-small cell carcinoma of the lung, cancer of the small intestine and cancer of the esophagus. The term "carcinoma" is art recognized and refers to malignancies of epithelial or endocrine tissues including respiratory system carcinomas, gastrointestinal system carcinomas, genitourinary system carcinomas, testicular carcinomas, breast carcinomas, prostatic carcinomas, endocrine system carcinomas, and melanomas. Exemplary carcinomas include those forming from tissue of the cervix, lung, prostate, breast, head and neck, colon and ovary. The term "carcinoma" also includes carcinosarcomas, e.g., which include malignant tumors composed of carcinomatous and sarcomatous tissues. An "adenocarcinoma" refers to a carcinoma derived from glandular tissue or in which the tumor cells form recognizable glandular structures. The term "sarcoma" is art recognized and refers to malignant tumors of mesenchymal derivation.

Examples of cellular proliferative and/or differentiative disorders of the lung include, but are not limited to, tumors such as bronchogenic carcinoma, including paraneoplastic syndromes, bronchioloalveolar carcinoma, neuroendocrine tumors, such as bronchial carcinoid, miscellaneous tumors, metastatic tumors, and pleural tumors, including solitary fibrous tumors (pleural fibroma) and malignant mesothelioma.

Examples of cellular proliferative and/or differentiative disorders of the breast include, but are not limited to, proliferative breast disease including, e.g., epithelial hyperplasia, sclerosing adenosis, and small duct papillomas; tumors, e.g., stromal tumors such as fibroadenoma, phyllodes tumor, and sarcomas, and epithelial tumors such as large duct papilloma; carcinoma of the breast including in situ (noninvasive) carcinoma that includes ductal carcinoma in situ (including Paget's disease) and lobular carcinoma in situ, and invasive (infiltrating) carcinoma including, but not limited to, invasive ductal carcinoma, invasive lobular carcinoma, medullary carcinoma, colloid (mucinous) carcinoma, tubular carcinoma, and invasive papillary carcinoma, and miscellaneous malignant neoplasms. Disorders in the male breast include, but are not limited to, gynecomastia and carcinoma.

Examples of cellular proliferative and/or differentiative disorders involving the colon include, but are not limited to, tumors of the colon, such as non-neoplastic polyps, adenomas, familial syndromes, colorectal carcinogenesis, colorectal carcinoma, and carcinoid tumors.

Examples of cancers or neoplastic conditions, in addition to the ones described above, include, but are not limited to, a fibrosarcoma, myosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, gastric cancer, esophageal cancer, rectal cancer, pancreatic cancer, ovarian cancer, prostate cancer, uterine cancer, cancer of the head and neck, skin cancer, brain cancer, squamous cell carcinoma, sebaceous gland carcinoma, papillary carcinoma, papillary adenocarcinoma, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular cancer, small cell lung carcinoma, non-small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma, leukemia, lymphoma, or Kaposi sarcoma.

Proliferative disorders include hematopoietic neoplastic disorders. As used herein, the term "hematopoietic neoplastic disorders" includes diseases involving hyperplastic/neoplastic cells of hematopoietic origin, e.g., arising from myeloid, lymphoid or erythroid lineages, or precursor cells thereof. Preferably, the diseases arise from poorly differentiated acute leukemias, e.g., erythroblastic leukemia and acute megakaryoblastic leukemia. Additional exemplary myeloid disorders include, but are not limited to, acute promyeloid leukemia (APML), acute myelogenous leukemia (AML) and chronic myelogenous leukemia (CML) (reviewed in Vaickus (1991) *Crit Rev. in Oncol./Hemotol.* 11:267-97); lymphoid malignancies include, but are not limited to acute lymphoblastic leukemia (ALL) which includes B-lineage ALL and T-lineage ALL, chronic lymphocytic leukemia (CLL), prolymphocytic leukemia (PLL), hairy cell leukemia (HLL) and Waldenstrom's macroglobulinemia (WM). Additional forms of malignant lymphomas include, but are not limited to non-Hodgkin lymphoma and variants thereof, peripheral T cell lymphomas, adult T cell leukemiallymphoma (ATL), cutaneous T-cell lymphoma (CTCL), large granular lymphocytic leukemia (LGF), Hodgkin's disease and Reed-Sternberg disease.

As used herein, disorders of the breast include, but are not limited to, disorders of development; inflammations, including but not limited to, acute mastitis, periductal mastitis, periductal mastitis (recurrent subareolar abscess, squamous metaplasia of lactiferous ducts), mammary duct ectasia, fat necrosis, granulomatous mastitis, and pathologies associated with silicone breast implants; fibrocystic changes; proliferative breast disease including, but not limited to, epithelial hyperplasia, sclerosing adenosis, and small duct papillomas; tumors including, but not limited to, stromal tumors such as fibroadenoma, phyllodes tumor, and sarcomas, and epithelial tumors such as large duct papilloma; carcinoma of the breast including in situ (noninvasive) carcinoma that includes ductal carcinoma in situ (including Paget's disease) and lobular carcinoma in situ, and invasive (infiltrating) carcinoma including, but not limited to, invasive ductal carcinoma, no special type, invasive lobular carcinoma, medullary carcinoma, colloid (mucinous) carcinoma, tubular carcinoma, and invasive papillary carcinoma, and miscellaneous malignant neoplasms. Disorders in the male breast include, but are not limited to, gynecomastia and carcinoma.

As used herein, disorders involving the colon include, but are not limited to, congenital anomalies, such as atresia and stenosis, Meckel diverticulum, congenital aganglionic megacolon-Hirschsprung disease; enterocolitis, such as diarrhea and dysentery, infectious enterocolitis, including viral gastroenteritis, bacterial enterocolitis, necrotizing enterocolitis, antibiotic-associated colitis (pseudomembranous colitis), and collagenous and lymphocytic colitis, miscellaneous intestinal inflammatory disorders, including parasites and protozoa, acquired immunodeficiency syndrome, transplantation, drug-induced intestinal injury, radiation enterocolitis, neutropenic colitis (typhlitis), and diversion colitis; idiopathic inflammatory bowel disease, such as Crohn disease and ulcerative colitis; tumors of the colon, such as non-neoplastic polyps, adenomas, familial syndromes, colorectal carcinogenesis, colorectal carcinoma, and carcinoid tumors.

As used herein, disorders involving the kidney (or renal disorders) include, but are not limited to, congenital anomalies including, but not limited to, cystic diseases of the kidney, that include but are not limited to, cystic renal dysplasia, autosomal dominant (adult) polycystic kidney disease, autosomal recessive (childhood) polycystic kidney disease, and cystic diseases of renal medulla, which include, but are not limited to, medullary sponge kidney, and nephronophthisis-uremic medullary cystic disease complex, acquired (dialysis-associated) cystic disease, such as simple cysts; glomerular diseases including pathologies of glomerular injury that include, but are not limited to, in situ immune complex deposition, that includes, but is not limited to, anti-GBM nephritis, Heymann nephritis, and antibodies against planted antigens, circulating immune complex nephritis, antibodies to glomerular cells, cell-mediated immunity in glomerulonephritis, activation of alternative complement pathway, epithelial cell injury, and pathologies involving mediators of glomerular injury including cellular and soluble mediators, acute glomerulonephritis, such as acute proliferative (poststreptococcal, postinfectious) glomerulonephritis, including but not limited to, poststreptococcal glomerulonephritis and nonstreptococcal acute glomerulonephritis, rapidly progressive (crescentic) glomerulonephritis, nephrotic syndrome, membranous glomerulonephritis (membranous nephropathy), minimal change disease (lipoid nephrosis), focal segmental glomerulosclerosis, membranoproliferative glomerulonephritis, IgA nephropathy (Berger disease), focal proliferative and necrotizing glomerulonephritis (focal glomerulonephritis), hereditary nephritis, including but not limited to, Alport syndrome and thin membrane disease (benign familial hematuria), chronic glomerulonephritis, glomerular lesions associated with systemic disease, including but not limited to, systemic lupus erythematosus, Henoch-Schönlein purpura, bacterial endocarditis, diabetic glomerulosclerosis, amyloidosis, fibrillary and immunotactoid glomerulonephritis, and other systemic disorders; diseases affecting tubules and interstitium, including acute tubular necrosis and tubulointerstitial nephritis, including but not limited to, pyelonephritis and urinary tract infection, acute pyelonephritis, chronic pyelonephritis and reflux nephropathy, and tubulointerstitial nephritis induced by drugs and toxins, including but not limited to, acute drug-induced interstitial nephritis, analgesic abuse nephropathy, nephropathy associated with nonsteroidal anti-inflammatory drugs, and other tubulointerstitial diseases including, but not limited to, urate nephropathy, hypercalcemia and nephrocalcinosis, and multiple myeloma; diseases of blood vessels including benign nephrosclerosis, malignant hypertension and accelerated nephrosclerosis, renal artery stenosis, and thrombotic microangiopathies including, but not limited to, classic (childhood) hemolytic-uremic syndrome, adult hemolytic-uremic syndrome/thrombotic thrombocytopenic purpura, idiopathic HUS/TTP, and other vascular disorders including, but not limited to, atherosclerotic ischemic renal disease, atheroembolic renal disease, sickle cell disease nephropathy, diffuse cortical necrosis, and renal infarcts; urinary tract obstruction (obstructive uropathy); urolithiasis (renal calculi, stones); and tumors of the kidney including, but not limited to, benign tumors, such as renal papillary adenoma, renal fibroma or hamartoma (renomedullary interstitial cell tumor), angiomyolipoma, and oncocytoma, and malignant tumors, including renal cell carcinoma (hypernephroma, adenocarcinoma of kidney), which includes urothelial carcinomas of renal pelvis.

Examples of disorders of the lung include, but are not limited to, congenital anomalies; atelectasis; diseases of vascular origin, such as pulmonary congestion and edema, including hemodynamic pulmonary edema and edema caused by microvascular injury, adult respiratory distress syndrome (diffuse alveolar damage), pulmonary embolism, hemorrhage, and infarction, and pulmonary hypertension and vascular sclerosis; chronic obstructive pulmonary disease, such as emphysema, chronic bronchitis, bronchial asthma, and bronchiectasis; diffuse interstitial (infiltrative, restrictive) diseases, such as pneumoconioses, sarcoidosis, idiopathic pulmonary fibrosis, desquamative interstitial pneumonitis, hypersensitivity pneumonitis, pulmonary eosinophilia (pulmonary infiltration with eosinophilia), *Bronchiolitis obliterans*-organizing pneumonia, diffuse pulmonary hemorrhage syndromes, including Goodpasture syndrome, idiopathic pulmonary hemosiderosis and other hemorrhagic syndromes, pulmonary involvement in collagen vascular disorders, and pulmonary alveolar proteinosis; complications of therapies, such as drug-induced lung disease, radiation-induced lung disease, and lung transplantation; tumors, such as bronchogenic carcinoma, including paraneoplastic syndromes, bronchioloalveolar carcinoma, neuroendocrine tumors, such as bronchial carcinoid, miscellaneous tumors, and metastatic tumors; pathologies of the pleura, including inflammatory pleural effusions, noninflammatory pleural effusions, pneumothorax, and pleural tumors, including solitary fibrous tumors (pleural fibroma) and malignant mesothelioma.

As used herein. disorders involving the pancreas include those of the exocrine pancreas such as congenital anomalies, including but not limited to, ectopic pancreas; pancreatitis, including but not limited to, acute pancreatitis; cysts, including but not limited to, pseudocysts; tumors, including but not limited to, cystic tumors and carcinoma of the pancreas; and disorders of the endocrine pancreas such as, diabetes mellitus; islet cell tumors, including but not limited to, insulinomas, gastrinomas, and other rare islet cell tumors.

As used herein, disorders involving the ovary include, for example, polycystic ovarian disease, Stein-leventhal syndrome, *Pseudomyxoma peritonei* and stromal hyperthecosis; ovarian tumors such as, tumors of coelomic epithelium, serous tumors, mucinous tumors, endometeriod tumors, clear cell adenocarcinoma, cystadenofibroma, brenner tumor, surface epithelial tumors; germ cell tumors such as mature (benign) teratomas, monodermal teratomas, immature malignant teratomas, dysgerminoma, endodermal sinus tumor, choriocarcinoma; sex cord-stomal tumors such as, granulosa-theca cell tumors, thecoma-fibromas, androblastomas, hill cell tumors, and gonadoblastoma; and metastatic tumors such as Krukenberg tumors.

Aberrant expression and/or activity of the molecules of the invention can mediate disorders associated with bone metabolism. "Bone metabolism" refers to direct or indirect effects in the formation or degeneration of bone structures, e.g., bone formation, bone resorption, etc., which can ultimately affect the concentrations in serum of calcium and phosphate. This term also includes activities mediated by the molecules of the invention in bone cells, e.g. osteoclasts and osteoblasts, that can in turn result in bone formation and degeneration. For example, molecules of the invention can support different activities of bone resorbing osteoclasts such as the stimulation of differentiation of monocytes and mononuclear phagocytes into osteoclasts. Accordingly, molecules of the invention that modulate the production of bone cells can influence bone formation and degeneration, and thus can be used to treat bone disorders. Examples of such disorders include, but are not limited to, osteoporosis, osteodystrophy, osteomalacia, rickets, osteitis fibrosa cystica, renal osteodystrophy, osteosclerosis, anti-convulsant treatment, osteopenia, fibrogenesis-imperfecta ossium, secondary hyperparathyroidism, hypoparathyroidism, hyperparathyroidism, cirrhosis, obstructive jaundice, drug induced metabolism, medullary carcinoma, chronic renal disease, rickets, sarcoidosis, glucocorticoid antagonism, malabsorption syndrome, steatorrhea, tropical sprue, idiopathic hypercalcemia and milk fever.

As used herein, "a prostate disorder" refers to an abnormal condition occurring in the male pelvic region characterized by, e.g., male sexual dysfunction and/or urinary symptoms. This disorder may be manifested in the form of genitourinary inflammation (e.g., inflammation of smooth muscle cells) as in several common diseases of the prostate including prostatitis, benign prostatic hyperplasia and cancer, e.g., adenocarcinoma or carcinoma, of the prostate.

Examples of immune, e.g., inflammatory, (e.g. respiratory inflammatory) disorders or diseases include, but are not limited to, autoimmune diseases (including, for example, diabetes mellitus, arthritis (including rheumatoid arthritis, juvenile rheumatoid arthritis, osteoarthritis, psoriatic arthritis), multiple sclerosis, encephalomyelitis, myasthenia gravis, systemic lupus erythematosis, autoimmune thyroiditis, dermatitis (including atopic dermatitis and eczematous dermatitis), psoriasis, Sjögren's Syndrome, inflammatory bowel disease, e.g. Crohn's disease and ulcerative colitis, aphthous ulcer, iritis, conjunctivitis, keratoconjunctivitis, asthma, allergic asthma, chronic obstructive pulmonary disease, cutaneous lupus erythematosus, scleroderma, vaginitis, proctitis, drug eruptions, leprosy reversal reactions, erythema nodosum leprosum, autoimmune uveitis, allergic encephalomyelitis, acute necrotizing hemorrhagic encephalopathy, idiopathic bilateral progressive sensorineural hearing loss, aplastic anemia, pure red cell anemia, idiopathic thrombocytopenia, polychondritis, Wegener's granulomatosis, chronic active hepatitis, Stevens-Johnson syndrome, idiopathic sprue, lichen planus, Graves' disease, sarcoidosis, primary biliary cirrhosis, uveitis posterior, and interstitial lung fibrosis), graft-versus-host disease, cases of transplantation, and allergy such as, atopic allergy.

As used herein, disorders involving the heart, or "cardiovascular disease" or a "cardiovascular disorder" includes a disease or disorder which affects the cardiovascular system, e.g., the heart, the blood vessels, and/or the blood. A cardiovascular disorder can be caused by an imbalance in arterial pressure, a malfunction of the heart, or an occlusion of a blood vessel, e.g., by a thrombus. A cardiovascular disorder includes, but is not limited to disorders such as arteriosclerosis, atherosclerosis, cardiac hypertrophy, ischemia reperfusion injury, restenosis, arterial inflammation, vascular wall remodeling, ventricular remodeling, rapid ventricular pacing, coronary microembolism, tachycardia, bradycardia, pressure overload, aortic bending, coronary artery ligation, vascular heart disease, valvular disease, including but not limited to, valvular degeneration caused by calcification, rheumatic heart disease, endocarditis, or complications of artificial valves; atrial fibrillation, long-QT syndrome, congestive heart failure, sinus node dysfunction, angina, heart failure, hypertension, atrial fibrillation, atrial flutter, pericardial disease, including but not limited to, pericardial effusion and pericarditis; cardiomyopathies, e.g., dilated cardiomyopathy or idiopathic cardiomyopathy, myocardial infarction, coronary artery disease, coronary artery spasm, ischemic disease, arrhythmia, sudden cardiac death, and cardiovascular developmental disorders (e.g., arteriovenous malformations, arteriovenous fistulae, raynaud's syndrome, neurogenic thoracic outlet syndrome, causalgia/reflex sympathetic dystrophy, hemangioma, aneurysm, cavernous angioma, aortic valve stenosis, atrial septal defects, atrioventricular canal, coarctation of the aorta, ebsteins anomaly, hypoplastic left heart syndrome, interruption of the aortic arch, mitral valve prolapse, ductus arteriosus, patent foramen ovale, partial anomalous pulmonary venous return, pulmonary atresia with ventricular septal defect, pulmonary atresia without ventricular septal defect, persistance of the fetal circulation, pulmonary valve stenosis, single ventricle, total anomalous pulmonary venous return, transposition of the great vessels, tricuspid atresia, truncus arteriosus, ventricular septal defects). A cardiovascular disease or disorder also can include an endothelial cell disorder.

As used herein, disorders involving the brain include, but are not limited to, disorders involving neurons, and disorders involving glia, such as astrocytes, oligodendrocytes, ependymal cells, and microglia; cerebral edema, raised intracranial pressure and herniation, and hydrocephalus; malformations and developmental diseases, such as neural tube defects, forebrain anomalies, posterior fossa anomalies, and syringomyelia and hydromyelia; perinatal brain injury; cerebrovascular diseases, such as those related to hypoxia, ischemia, and infarction, including hypotension, hypoperfusion, and low-flow states—global cerebral ischemia and focal cerebral ischemia—infarction from obstruction of local blood supply, intracranial hemorrhage, including intracerebral (intraparenchymal) hemorrhage, subarachnoid hemorrhage and ruptured berry aneurysms, and vascular malformations, hypertensive cerebrovascular disease, including lacunar infarcts, slit hemorrhages, and hypertensive encephalopathy; infections, such as acute meningitis, including acute pyrogenic (bacterial) meningitis and acute aseptic (viral) meningitis, acute focal suppurative infections, including brain abscess, subdural empyema, and extradural abscess, chronic bacterial meningoencephalitis, including tuberculosis and mycobacterioses, neurosyphilis, and neuroborreliosis (Lyme disease), viral meningoencephalitis, including arthropod-borne (Arbo) viral encephalitis, Herpes simplex virus Type 1, Herpes simplex virus Type 2, Varicella-zoster virus (*Herpes zoster*), cytomegalovirus, poliomyelitis, rabies, and human immunodeficiency virus 1, including HIV-1 meningoencephalitis (subacute encephalitis), vacuolar myelopathy, AIDS-associated myopathy, peripheral neuropathy, and AIDS in children, progressive multifocal leukoencephalopathy, subacute sclerosing panencephalitis, fungal meningoencephalitis, other infectious diseases of the nervous system; transmissible spongiform encephalopathies (prion diseases); demyelinating diseases, including multiple sclerosis, multiple sclerosis variants, acute disseminated encephalomyelitis and acute necrotizing hemorrhagic encephalomyelitis, and other diseases with demyelination; degenerative diseases, such as degenerative diseases affecting the cerebral cortex, including Alzheimer disease and Pick disease, degenerative diseases of basal ganglia and brain stem, including Parkinsonism, idiopathic Parkinson disease (paralysis agitans), progressive supranuclear palsy, corticobasal degenration, multiple system atrophy, including striatonigral degenration, Shy-Drager syndrome, and olivopontocerebellar atrophy, and Huntington disease; spinocerebellar degenerations, including spinocerebellar ataxias, including Friedreich ataxia, and ataxia-telanglectasia, degenerative diseases affecting motor neurons, including amyotrophic lateral sclerosis (motor neuron disease), bulbospinal atrophy (Kennedy syndrome), and spinal muscular atrophy; inborn errors of metabolism, such as leukodystrophies, including Krabbe disease, metachromatic leukodystrophy, adrenoleukodystrophy, Pelizaeus-Merzbacher disease, and Canavan disease, mitochondrial encephalomyopathies, including Leigh disease and other mitochondrial encephalomyopathies; toxic and acquired metabolic diseases, including vitamin deficiencies such as thiamine (vitamin $B_1$) deficiency and vitamin $B_{12}$ deficiency, neurologic sequelae of metabolic disturbances, including hypoglycemia, hyperglycemia, and hepatic encephatopathy, toxic disorders, including carbon monoxide, methanol, ethanol, and radiation, including combined methotrexate and radiation-induced injury; tumors, such as gliomas, including astrocytoma, including fibrillary (diffuse) astrocytoma and glioblastoma multiforme, pilocytic astrocytoma, pleomorphic xanthoastrocytoma, and brain stem glioma, oligodendroglioma, and ependymoma and related paraventricular mass lesions, neuronal tumors, poorly differentiated neoplasms, including medulloblastoma, other parenchymal tumors, including primary brain lymphoma, germ cell tumors, and pineal parenchymal tumors, meningiomas, metastatic tumors, paraneoplastic syndromes, peripheral nerve sheath tumors, including schwannoma, neurofibroma, and malignant peripheral nerve sheath tumor (malignant schwannoma), and neurocutaneous syndromes (phakomatoses), including neurofibromotosis, including Type 1 neurofibromatosis (NF1) and TYPE 2 neurofibromatosis (NF2), tuberous sclerosis, and Von Hippel-Lindau disease.

As used herein, skeletal muscle disorders include, but are not limited to, muscular dystrophy (e.g., Duchenne muscular dystrophy, Becker muscular dystrophy, Emery-Dreifuss muscular dystrophy, limb-girdle muscular dystrophy, facioscapulohumeral muscular dystrophy, myotonic dystrophy, oculopharyngeal muscular dystrophy, distal muscular dystrophy, and congenital muscular dystrophy), motor neuron diseases (e.g., amyotrophic lateral sclerosis, infantile progressive spinal muscular atrophy, intermediate spinal muscular atrophy, spinal bulbar muscular atrophy, and adult spinal muscular atrophy), myopathies (e.g., inflammatory myopathies (e.g., dermatomyositis and polymyositis), myotonia congenita, paramyotonia congenita, central core disease, nemaline myopathy, myotubular myopathy, and periodic paralysis), tumors such as rhabdomyosarcoma, and metabolic diseases of muscle (e.g., phosphorylase deficiency, acid maltase deficiency, phosphofructokinase deficiency, debrancher enzyme deficiency, mitochondrial myopathy, carnitine deficiency, carnitine palmityl transferase deficiency, phosphoglycerate kinase deficiency, phosphoglycerate mutase deficiency, lactate dehydrogenase deficiency, and myoadenylate deaminase deficiency).

As used herein, an “endothelial cell disorder” includes a disorder characterized by aberrant, unregulated, or unwanted endothelial cell activity, e.g., proliferation, migration, angiogenesis, or vascularization; or aberrant expression of cell surface adhesion molecules or genes associated with angiogenesis, e.g., TIE-2, FLT and FLK. Endothelial cell disorders include tumorigenesis, tumor metastasis, psoriasis, diabetic retinopathy, endometriosis, Grave’s disease, ischemic disease (e.g., atherosclerosis), and chronic inflammatory diseases (e.g., rheumatoid arthritis).

Disorders involving the liver (hepatic disorders) include, but are not limited to, hepatic injury; jaundice and cholestasis, such as bilirubin and bile formation; hepatic failure and cirrhosis, such as cirrhosis, portal hypertension, including ascites, portosystemic shunts, and splenomegaly; infectious disorders, such as viral hepatitis, including hepatitis A-E infection and infection by other hepatitis viruses, clinicopathologic syndromes, such as the carrier state, asymptomatic infection, acute viral hepatitis, chronic viral hepatitis, and fulminant hepatitis; autoimmune hepatitis; drug- and toxin-induced liver disease, such as alcoholic liver disease; inborn errors of metabolism and pediatric liver disease, such as hemochromatosis, Wilson disease, $a_1$-antitrypsin deficiency, and neonatal hepatitis; primary bile acid malabsorption; intrahepatic biliary tract disease, such as secondary biliary cirrhosis, primary biliary cirrhosis, primary sclerosing cholangitis, and anomalies of the biliary tree; circulatory disorders, such as impaired blood flow into the liver, including hepatic artery compromise and portal vein obstruction and thrombosis, impaired blood flow through the liver, including passive congestion and centrilobular necrosis and peliosis hepatis, hepatic vein outflow obstruction, including hepatic vein thrombosis (Budd-Chiari syndrome) and veno-occlusive disease; hepatic disease associated with pregnancy, such as preeclampsia and eclampsia, acute fatty liver of pregnancy, and intrehepatic cholestasis of pregnancy; hepatic complications of organ or bone marrow transplantation, such as drug toxicity after bone marrow transplantation, graft-versus-host disease and liver rejection, and nonimmunologic damage to liver allografts; tumors and tumorous conditions, such as nodular hyperplasias, adenomas, and malignant tumors, including primary carcinoma of the liver and metastatic tumors.

Disorders which can be treated or diagnosed by methods described herein include, but are not limited to, disorders associated with an accumulation in the liver of fibrous tissue, such as that resulting from an imbalance between production and degradation of the extracellular matrix accompanied by the collapse and condensation of preexisting fibers. The methods described herein can be used to diagnose or treat hepatocellular necrosis or injury induced by a wide variety of agents including processes which disturb homeostasis, such as an inflammatory process, tissue damage resulting from toxic injury or altered hepatic blood flow, and infections (e.g., bacterial, viral and parasitic). For example, the methods can be used for the early detection of hepatic injury, such as portal hypertension or hepatic fibrosis. In addition, the methods can be employed to detect liver fibrosis attributed to inborn errors of metabolism, for example, fibrosis resulting from a storage disorder such as Gaucher’s disease (lipid abnormalities) or a glycogen storage disease, A1-antitrypsin deficiency; a disorder mediating the accumulation (e.g., storage) of an exogenous substance, for example, hemochromatosis (iron-overload syndrome) and copper storage diseases (Wilson’s disease), disorders resulting in the accumulation of a toxic metabolite (e.g., tyrosinemia, fructosemia and galactosemia) and peroxisomal disorders (e.g., Zellweger syndrome). Additionally, the methods described herein can be used for the early detection and treatment of liver injury associated with the administration of various chemicals or drugs, such as for example, methotrexate, isonizaid, oxyphenisatin, methyldopa, chlorpromazine, tolbutamide or alcohol, or which represents a hepatic manifestation of a vascular disorder such as obstruction of either the intrahepatic or extrahepatic bile flow or an alteration in hepatic circulation resulting, for example, from chronic heart failure, veno-occlusive disease, portal vein thrombosis or Budd-Chiari syndrome.

Additionally, the molecules of the invention can play an important role in the etiology of certain viral diseases, including but not limited to Hepatitis B, Hepatitis C and Herpes Simplex Virus (HSV). Modulators of the activity of the molecules of the invention could be used to control viral diseases. The modulators can be used in the treatment and/or diagnosis of viral infected tissue or virus-associated tissue fibrosis, especially liver and liver fibrosis. Also, such modulators can be used in the treatment and/or diagnosis of virus-associated carcinoma, especially hepatocellular cancer.

Disorders related to reduced platelet number, thrombocytopenia, include idiopathic thrombocytopenic purpura, including acute idiopathic thrombocytopenic purpura, drug-induced thrombocytopenia, HIV-associated thrombocytopenia, and thrombotic microangiopathies: thrombotic thrombocytopenic purpura and hemolytic-uremic syndrome.

As used herein, neurological disorders include disorders of the central nervous system (CNS) and the peripheral nervous system, e.g., cognitive and neurodegenerative disorders, Examples of neurological disorders include, but are not limited to, autonomic function disorders such as hypertension and sleep disorders, and neuropsychiatric disorders, such as depression, schizophrenia, schizoaffective disorder, Korsakoff's psychosis, alcoholism, anxiety disorders, or phobic disorders; learning or memory disorders, e.g., amnesia or age-related memory loss, attention deficit disorder, dysthymic disorder, major depressive disorder, mania, obsessive-compulsive disorder, psychoactive substance use disorders, anxiety, phobias, panic disorder, as well as bipolar affective disorder, e.g., severe bipolar affective (mood) disorder (BP-1), and bipolar affective neurological disorders, e.g., migraine and obesity. Such neurological disorders include, for example, disorders involving neurons, and disorders involving glia, such as astrocytes, oligodendrocytes, ependymal cells, and microglia; cerebral edema, raised intracranial pressure and herniation, and hydrocephalus; malformations and developmental diseases, such as neural tube defects, forebrain anomalies, posterior fossa anomalies, and syringomyelia and hydromyelia; perinatal brain injury; cerebrovascular diseases, such as those related to hypoxia, ischemia, and infarction, including hypotension, hypoperfusion, and low-flow states—global cerebral ischemia and focal cerebral ischemia—infarction from obstruction of local blood supply, intracranial hemorrhage, including intracerebral (intraparenchymal) hemorrhage, subarachnoid hemorrhage and ruptured berry aneurysms, and vascular malformations, hypertensive cerebrovascular disease, including lacunar infarcts, slit hemorrhages, and hypertensive encephalopathy; infections, such as acute meningitis, including acute pyogenic (bacterial) meningitis and acute aseptic (viral) meningitis, acute focal suppurative infections, including brain abscess, subdural empyema, and extradural abscess, chronic bacterial meningoencephalitis, including tuberculosis and mycobacterioses, neurosyphilis, and neuroborreliosis (Lyme disease), viral meningoencephalitis, including arthropod-borne (Arbo) viral encephalitis, Herpes simplex virus Type 1, Herpes simplex virus Type 2, Varicella-zoster virus (*Herpes zoster*), cytomegalovirus, poliomyelitis, rabies, and human immunodeficiency virus 1, including HIV-1 meningoencephalitis (subacute encephalitis), vacuolar myelopathy, AIDS-associated myopathy, peripheral neuropathy, and AIDS in children, progressive multifocal leukoencephalopathy, subacute sclerosing panencephalitis, fungal meningoencephalitis, other infectious diseases of the nervous system; transmissible spongiform encephalopathies (prion diseases); demyelinating diseases, including multiple sclerosis, multiple sclerosis variants, acute disseminated encephalomyelitis and acute necrotizing hemorrhagic encephalomyelitis, and other diseases with demyelination; degenerative diseases, such as degenerative diseases affecting the cerebral cortex, including Alzheimer's disease and Pick's disease, degenerative diseases of basal ganglia and brain stem, including Parkinsonism, idiopathic Parkinson's disease (paralysis agitans) and other Lewy diffuse body diseases, progressive supranuclear palsy, corticobasal degenration, multiple system atrophy, including striatonigral degenration, Shy-Drager syndrome, and olivopontocerebellar atrophy, and Huntington's disease, senile dementia, Gilles de la Tourette's syndrome, epilepsy, and Jakob-Creutzfieldt disease; spinocerebellar degenerations, including spinocerebellar ataxias, including Friedreich ataxia, and ataxia-telanglectasia, degenerative diseases affecting motor neurons, including amyotrophic lateral sclerosis (motor neuron disease), bulbospinal atrophy (Kennedy syndrome), and spinal muscular atrophy; inborn errors of metabolism, such as leukodystrophies, including Krabbe disease, metachromatic leukodystrophy, adrenoleukodystrophy, Pelizaeus-Merzbacher disease, and Canavan disease, mitochondrial encephalomyopathies, including Leigh disease and other mitochondrial encephalomyopathies; toxic and acquired metabolic diseases, including vitamin deficiencies such as thiamine (vitamin $B_1$) deficiency and vitamin $B_{12}$ deficiency, neurologic sequelae of metabolic disturbances, including hypoglycemia, hyperglycemia, and hepatic encephatopathy, toxic disorders, including carbon monoxide, methanol, ethanol, and radiation, including combined methotrexate and radiation-induced injury; tumors, such as gliomas, including astrocytoma, including fibrillary (diffuse) astrocytoma and glioblastoma multiforme, pilocytic astrocytoma, pleomorphic xanthoastrocytoma, and brain stem glioma, oligodendroglioma, and ependymoma and related paraventricular mass lesions, neuronal tumors, poorly differentiated neoplasms, including medulloblastoma, other parenchymal tumors, including primary brain lymphoma, germ cell tumors, and pineal parenchymal tumors, meningiomas, metastatic tumors, paraneoplastic syndromes, peripheral nerve sheath tumors, including schwannoma, neurofibroma, and malignant peripheral nerve sheath tumor (malignant schwannoma), and neurocutaneous syndromes (phakomatoses), including neurofibromotosis, including Type 1 neurofibromatosis (NF1) and TYPE 2 neurofibromatosis (NF2), tuberous sclerosis, and Von Hippel-Lindau disease. Further CNS-related disorders include, for example, those listed in the American Psychiatric Association's Diagnostic and Statistical manual of Mental Disorders (DSM), the most current version of which is incorporated herein by reference in its entirety.

As used herein, diseases of the skin (dermal disorders), include but are not limited to, disorders of pigmentation and melanocytes, including but not limited to, vitiligo, freckle, melasma, lentigo, nevocellular nevus, dysplastic nevi, and malignant melanoma; benign epithelial tumors, including but not limited to, seborrheic keratoses, acanthosis nigricans, fibroepithelial polyp, epithelial cyst, keratoacanthoma, and adnexal (appendage) tumors; premalignant and malignant epidermal tumors, including but not limited to, actinic keratosis, squamous cell carcinoma, basal cell carcinoma, and merkel cell carcinoma; tumors of the dermis, including but not limited to, benign fibrous histiocytoma, dermatofibrosarcoma protuberans, xanthomas, and dermal vascular tumors; tumors of cellular immigrants to the skin, including but not limited to, histiocytosis X, mycosis fungoides (cutaneous T-cell lymphoma), and mastocytosis; disorders of epidermal maturation, including but not limited to, ichthyosis; acute inflammatory dermatoses, including but not limited to, urticaria, acute eczematous dermatitis, and erythema multiforme; chronic inflammatory dermatoses, including but not limited to, psoriasis, lichen planus, and lupus erythematosus; blistering (bullous) diseases, including but not limited to, pemphigus, bullous pemphigoid, dermatitis herpetiformis, and noninflammatory blistering diseases: epidermolysis bullosa and porphyria; disorders of epidermal appendages, including but not limited to, acne vulgaris; panniculitis, including but not limited to, erythema nodosum and erythema induratum; and infection and infestation, such as verrucae, molluscum contagiosum, impetigo, superficial fungal infections, and arthropod bites, stings, and infestations.

Additionally, molecules of the invention can play an important role in the regulation of metabolism or pain disorders. Diseases of metabolic imbalance include, but are not limited to, obesity, anorexia nervosa, cachexia, lipid disorders, and diabetes. Examples of pain disorders include, but are not limited to, pain response elicited during various forms of tissue injury, e.g., inflammation, infection, and ischemia, usually referred to as hyperalgesia (described in, for example, Fields (1987) *Pain*, New York: McGraw-Hill); pain associated with musculoskeletal disorders, e.g., joint pain; tooth pain; headaches; pain associated with surgery; pain related to irritable bowel syndrome; or chest pain.

As used herein, the term "erythroid associated disorders" include disorders involving aberrant (increased or deficient) erythroblast proliferation, e.g., an erythroleukemia, and aberrant (increased or deficient) erythroblast differentiation, e.g., an anemia. Erythrocyte-associated disorders include anemias such as, for example, drug- (chemotherapy-) induced anemias, hemolytic anemias due to hereditary cell membrane abnormalities, such as hereditary spherocytosis, hereditary elliptocytosis, and hereditary pyropoikilocytosis; hemolytic anemias due to acquired cell membrane defects, such as paroxysmal nocturnal hemoglobinuria and spur cell anemia; hemolytic anemias caused by antibody reactions, for example to the RBC antigens, or antigens of the ABO system, Lewis system, Ii system, Rh system, Kidd system, Duffy system, and Kell system; methemoglobinemia; a failure of erythropoiesis, for example, as a result of aplastic anemia, pure red cell aplasia, myelodysplastic syndromes, sideroblastic anemias, and congenital dyserythropoietic anemia; secondary anemia in non-hematolic disorders, for example, as a result of chemotherapy, alcoholism, or liver disease; anemia of chronic disease, such as chronic renal failure; and endocrine deficiency diseases. Another example of an erythroid-associated disorder is erythrocytosis. Erythrocytosis, a disorder of red blood cell overproduction caused by excessive and/or ectopic erythropoietin production, can be caused by cancers, e.g., a renal cell cancer, a hepatocarcinoma, and a central nervous system cancer. Diseases associated with erythrocytosis include polycythemias, e.g., polycythemia vera, secondary polycythemia, and relative polycythemia.

Compounds herein can be used to treat anemias, in particular, anemias associated with cancer chemotherapy, chronic renal failure, malignancies, adult and juvenile rheumatoid arthritis, disorders of haemoglobin synthesis, prematurity, and zidovudine treatment of HIV infection.

Various aspects of the invention are described in further detail below.

Isolated Nucleic Acid Molecules

In one aspect, the invention provides, an isolated or purified, nucleic acid molecule that encodes a 26199, 33530, 33949, 47148, 50226, 58764, 62113, 32144, 32235, 23565, 13305, 14911, 86216, 25206 or 8843 polypeptide described herein, e.g., a full length 26199, 33530, 33949, 47148, 50226, 58764, 62113, 32144, 32235, 23565, 13305, 14911, 86216, 25206 or 8843 protein or a fragment thereof, e.g., a biologically active portion of 26199, 33530, 33949, 47148, 50226, 58764, 62113, 32144, 32235, 23565, 13305, 14911, 86216, 25206 or 8843 protein. Also included is a nucleic acid fragment suitable for use as a hybridization probe, which can be used, e.g., to identify a nucleic acid molecule encoding a polypeptide of the invention, 26199, 33530, 33949, 47148, 50226, 58764, 62113, 32144, 32235, 23565, 13305, 14911, 86216, 25206 or 8843 mRNA, and fragments suitable for use as primers, e.g., PCR primers for the amplification or mutation of nucleic acid molecules.

In one embodiment, an isolated nucleic acid molecule of the invention includes the nucleotide sequence shown in SEQ ID NO:1, 3, 4, 6, 7, 9, 10, 12, 13, 15, 16, 18, 53, 55, 61, 63, 67, 69, 78, 80, 88, 90, 100, 102, 113, 115, 122, 124, 129 or 131, or a portion of any of this nucleotide sequence. In one embodiment, the nucleic acid molecule includes sequences encoding the human 26199, 33530, 33949, 47148, 50226, 58764, 62113, 32144, 32235, 23565, 13305, 14911, 86216, 25206 or 8843 protein (i.e., "the coding region" of SEQ ID NO:1, 4, 7, 10, 13, 16, 53, 61, 67, 78, 88, 100, 113, 122 or 129, as shown in SEQ ID NO:3, 6, 9, 12, 15, 18, 55, 63, 69, 80, 90, 102, 115, 124 or 131, respectively), as well as 5' untranslated sequences and 3' untranslated sequences. Alternatively, the nucleic acid molecule can include only the coding region of SEQ ID NO:1, 4, 7, 10, 13, 16, 53, 61, 67, 78, 88, 100, 113, 122 or 129 (e.g., SEQ ID NO:3, 6, 9, 12, 15, 18, 55, 63, 69, 80, 90, 102, 115, 124 or 131) and, e.g., no flanking sequences which normally accompany the subject sequence. In another embodiment, the nucleic acid molecule encodes a sequence corresponding to a fragment of the protein corresponding to domains within SEQ ID NO:2, 5, 8, 11, 14, 17, 54, 62, 68, 79, 89, 101, 114, 123 or 130.

In another embodiment, an isolated nucleic acid molecule of the invention includes a nucleic acid molecule which is a complement of the nucleotide sequence shown in SEQ ID NO:1, 3, 4, 6, 7, 9, 10, 12, 13, 15, 16, 18, 53, 55, 61, 63, 67, 69, 78, 80, 88, 90, 100, 102, 113, 115, 122, 124, 129 or 131, or a portion of any of these nucleotide sequences. In other embodiments, the nucleic acid molecule of the invention is sufficiently complementary to the nucleotide sequence shown in SEQ ID NO:1, 3, 4, 6, 7, 9, 10, 12, 13, 15, 16, 18, 53, 55, 61, 63, 67, 69, 78, 80, 88, 90, 100, 102, 113, 115, 122, 124, 129 or 131 such that it can hybridize to the nucleotide sequence shown in SEQ ID NO:1, 3, 4, 6, 7, 9, 10, 12, 13, 15, 16, 18, 53, 55, 61, 63, 67, 69, 78, 80, 88, 90, 100, 102, 113, 115, 122, 124, 129 or 131, thereby forming a stable duplex.

In one embodiment, an isolated nucleic acid molecule of the present invention includes a nucleotide sequence which is at least about: 60%, 65%, 70%, 75%, 80%, 85%, 90%, 91%, 92%, 93%, 94%, 95%, 96%, 97%, 98%, 99%, or more homologous to the entire length of the nucleotide sequence shown in SEQ ID NO:1, 3, 4, 6, 7, 9, 10, 12, 13, 15, 16, 18, 53, 55, 61, 63, 67, 69, 78, 80, 88, 90, 100, 102, 113, 115, 122, 124, 129 or 131, or a portion, preferably of the same length, of any of these nucleotide sequences.

26199, 33530, 33949, 47148, 50226, 58764, 62113, 32144, 32235, 23565, 13305, 14911, 86216, 25206 or 8843 Nucleic Acid Fragments A nucleic acid molecule of the invention can include only a portion of the nucleic acid sequence of SEQ ID NO:1, 3, 4, 6, 7, 9, 10, 12, 13, 15, 16, 18, 53, 55, 61, 63, 67, 69, 78, 80, 88, 90, 100, 102, 113, 115, 122, 124, 129 or 131. For example, such a nucleic acid molecule can include a fragment which can be used as a probe or primer or a fragment encoding a portion of a 26199, 33530, 33949, 47148, 50226, 58764, 62113, 32144, 32235, 23565, 13305, 14911, 86216, 25206 or 8843 protein, e.g., an immunogenic or biologically active portion of a 26199, 33530, 33949, 47148, 50226, 58764, 62113, 32144, 32235, 23565, 13305, 14911, 86216, 25206 or 8843 protein. A fragment can comprise those nucleotides of SEQ ID NO:1, 3, 4, 6, 7, 9, 10, 12, 13, 15, 16, 18, 53, 55, 61, 63, 67, 69, 78, 80, 88, 90, 100, 102, 113, 115, 122, 124, 129 or 131, which encode a domain of human 26199, 33530, 33949, 47148, 50226, 58764, 62113, 32144, 32235, 23565, 13305, 14911, 86216, 25206 or 8843. The nucleotide sequence determined from the cloning of the 26199, 33530, 33949, 47148, 50226, 58764, 62113, 32144, 32235, 23565, 13305, 14911, 86216, 25206 or 8843 gene allows for the generation of probes and primers designed for use in identifying and/or cloning other 26199, 33530, 33949, 47148, 50226, 58764, 62113, 32144, 32235, 23565, 13305, 14911, 86216, 25206 or 8843 family members, or fragments thereof, as well as 26199, 33530, 33949, 47148, 50226, 58764, 62113, 32144, 32235, 23565, 13305, 14911, 86216, 25206 or 8843 homologs, or fragments thereof, from other species.

In another embodiment, a nucleic acid includes a nucleotide sequence that includes part, or all, of the coding region and extends into either (or both) the 5' or 3' noncoding region. Other embodiments include a fragment which includes a nucleotide sequence encoding an amino acid fragment described herein. Nucleic acid fragments can encode a specific domain or site described herein or fragments thereof, particularly fragments thereof which are at least 100 amino acids in length. Fragments also include nucleic acid sequences corresponding to specific amino acid sequences described above or fragments thereof. Nucleic acid fragments should not to be construed as encompassing those fragments that may have been disclosed prior to the invention.

A nucleic acid fragment can include a sequence corresponding to a domain, region, or functional site described herein. A nucleic acid fragment can also include one or more domain, region, or functional site described herein. Thus, for example, a 26199, 33530, 33949, 47148, 50226, 58764, 62113, 32144, 32235, 23565, 13305, 14911, 86216, 25206 or 8843 nucleic acid fragment can include a sequence corresponding to a domain, as described herein.

26199, 33530, 33949, 47148, 50226, 58764, 62113, 32144, 32235, 23565, 13305, 14911, 86216, 25206 or 8843 probes and primers are provided. Typically a probe/primer is an isolated or purified oligonucleotide. The oligonucleotide typically includes a region of nucleotide sequence that hybridizes under stringent conditions to at least about 7, 12 or 15, preferably about 20 or 25, more preferably about 30, 35, 40, 45, 50, 55, 60, 65, or 75 consecutive nucleotides of a sense or antisense sequence of SEQ ID NO:1, 3, 4, 6, 7, 9, 10, 12, 13, 15, 16, 18, 53, 55, 61, 63, 67, 69, 78, 80, 88, 90, 100, 102, 113, 115, 122, 124, 129 or 131, or of a naturally occurring allelic variant or mutant of SEQ ID NO:1, 3, 4, 6, 7, 9, 10, 12, 13, 15, 16, 18, 53, 55, 61, 63, 67, 69, 78, 80, 88, 90, 100, 102, 113, 115, 122, 124, 129 or 131.

In a preferred embodiment the nucleic acid is a probe which is at least 5 or 10, and less than 200, more preferably less than 100, or less than 50, base pairs in length. It should be identical, or differ by 1, or less than in 5 or 10 bases, from a sequence disclosed herein. If alignment is needed for this comparison the sequences should be aligned for maximum homology. "Looped" out sequences from deletions or insertions, or mismatches, are considered differences.

A probe or primer can be derived from the sense or antisense strand of a nucleic acid which encodes a domain identified in the 26199, 33530, 33949, 47148, 50226, 58764, 62113, 32144, 32235, 23565, 13305, 14911, 86216, 25206 or 8843 sequences.

In another embodiment a set of primers is provided, e.g., primers suitable for use in a PCR, which can be used to amplify a selected region of a 26199, 33530, 33949, 47148, 50226, 58764, 62113, 32144, 32235, 23565, 13305, 14911, 86216, 25206 or 8843 sequence, e.g., a domain, region, site or other sequence described herein. The primers should be at least 5, 10, or 50 base pairs in length and less than 100, or less than 200, base pairs in length. The primers should be identical, or differ by one base from a sequence disclosed herein or from a naturally occurring variant.

A nucleic acid fragment can encode an epitope bearing region of a polypeptide described herein.

A nucleic acid fragment encoding a "biologically active portion of a 26199, 33530, 33949, 47148, 50226, 58764, 62113, 32144, 32235, 23565, 13305, 14911, 86216, 25206 or 8843 polypeptide" can be prepared by isolating a portion of the nucleotide sequence of SEQ ID NO:1, 3, 4, 6, 7, 9, 10, 12, 13, 15, 16, 18, 53, 55, 61, 63, 67, 69, 78, 80, 88, 90, 100, 102, 113, 115, 122, 124, 129 or 131, which encodes a polypeptide having a 26199, 33530, 33949, 47148, 50226, 58764, 62113, 32144, 32235, 23565, 13305, 14911, 86216, 25206 or 8843 biological activity (e.g., the biological activities of the 26199, 33530, 33949, 47148, 50226, 58764, 62113, 32144, 32235, 23565, 13305, 14911, 86216, 25206 or 8843 proteins are described herein), expressing the encoded portion of the 26199, 33530, 33949, 47148, 50226, 58764, 62113, 32144, 32235, 23565, 13305, 14911, 86216, 25206 or 8843 protein (e.g., by recombinant expression in vitro) and assessing the activity of the encoded portion of the 26199, 33530, 33949, 47148, 50226, 58764, 62113, 32144, 32235, 23565, 13305, 14911, 86216, 25206 or 8843 protein. A nucleic acid fragment encoding a biologically active portion of a 26199, 33530, 33949, 47148, 50226, 58764, 62113, 32144, 32235, 23565, 13305, 14911, 86216, 25206 or 8843 polypeptide, can comprise a nucleotide sequence which is greater than 300 or more nucleotides in length.

In preferred embodiments, a nucleic acid includes a nucleotide sequence which is about 300, 400, 500, 600, 700, 800, 900, 1000, 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900, 4000, 4100, 4200, 4300, 4400, 4500, 4600, 4700, 4800, 4900, 5000, 5100, 5200, 5300 or more nucleotides in length and hybridizes under stringent hybridization conditions to a nucleic acid molecule of SEQ ID NO:1, 3, 4, 6, 7, 9, 10, 12, 13, 15, 16, 18, 53, 55, 61, 63, 67, 69, 78, 80, 88, 90, 100, 102, 113, 115, 122, 124, 129 or 131.

26199, 33530, 33949, 47148, 50226, 58764, 62113, 32144, 32235, 23565, 13305, 14911, 86216, 25206 or 8843 Nucleic Acid Variants The invention further encompasses nucleic acid molecules that differ from the nucleotide sequence shown in SEQ ID NO:1, 3, 4, 6, 7, 9, 10, 12, 13, 15, 16, 18, 53, 55, 61, 63, 67, 69, 78, 80, 88, 90, 100, 102, 113, 115, 122, 124, 129 or 131. Such differences can be due to degeneracy of the genetic code (and result in a nucleic acid which encodes the same 26199, 33530, 33949, 47148, 50226, 58764, 62113, 32144, 32235, 23565, 13305, 14911, 86216, 25206 or 8843 proteins as those encoded by the nucleotide sequence disclosed herein. In another embodiment, an isolated nucleic acid molecule of the invention has a nucleotide sequence encoding a protein having an amino acid sequence which differs, by at least 1, but less than 5, 10, 20, 50, or 100 amino acid residues that shown in SEQ ID NO:2, 5, 8, 11, 14, 17, 54, 62, 68, 79, 89, 101, 114, 123 or 130. If alignment is needed for this comparison the sequences should be aligned for maximum homology. "Looped" out sequences from deletions or insertions, or mismatches, are considered differences.

Nucleic acids of the inventor can be chosen for having codons, which are preferred, or non-preferred, for a particular expression system. E.g., the nucleic acid can be one in which at least one codon, at preferably at least 10%, or 20% of the codons has been altered such that the sequence is optimized for expression in *E. coli*, yeast, human, insect, or CHO cells.

Nucleic acid variants can be naturally occurring, such as allelic variants (same locus), homologs (different locus), and orthologs (different organism) or can be non naturally occurring. Non-naturally occurring variants can be made by mutagenesis techniques, including those applied to polynucleotides, cells, or organisms. The variants can contain nucleotide substitutions, deletions, inversions and insertions. Variation can occur in either or both the coding and non-coding regions. The variations can produce both conservative and non-conservative amino acid substitutions (as compared in the encoded product).

In a preferred embodiment, the nucleic acid differs from that of SEQ ID NO:1, 3, 4, 6, 7, 9, 10, 12, 13, 15, 16, 18, 53, 55, 61, 63, 67, 69, 78, 80, 88, 90, 100, 102, 113, 115, 122, 124, 129 or 131, e.g., as follows: by at least one but less than, 10, 20, 30, or 40 nucleotides; at least one but less than 1%, 5%, 10% or 20% of the nucleotides in the subject nucleic acid. If necessary for this analysis the sequences should be aligned for maximum homology. "Looped" out sequences from deletions or insertions, or mismatches, are considered differences.

Orthologs, homologs, and allelic variants can be identified using methods known in the art. These variants comprise a nucleotide sequence encoding a polypeptide that is 50%, at least about 55%, typically at least about 70-75%, more typically at least about 80-85%, and most typically at least about 90-95% or more identical to the nucleotide sequence shown in SEQ ID NO:2, 5, 8, 11, 14, 17, 54, 62, 68, 79, 89, 101, 114, 123 or 130 or a fragment of this sequence. Such nucleic acid molecules can readily be identified as being able to hybridize under stringent conditions, to the nucleotide sequence shown in SEQ ID NO:2, 5, 8, 11, 14, 17, 54, 62, 68, 79, 89, 101, 114, 123 or 130 or a fragment of the sequence. Nucleic acid molecules corresponding to orthologs, homologs, and allelic variants of the 26199, 33530, 33949, 47148, 50226, 58764, 62113, 32144, 32235, 23565, 13305, 14911, 86216, 25206 or 8843 cDNAs of the invention can further be isolated by mapping to the same chromosome or locus as the 26199, 33530, 33949, 47148, 50226, 58764, 62113, 32144, 32235, 23565, 13305, 14911, 86216, 25206 or 8843 gene.

Preferred variants include those that are correlated with activities specific to the molecules of the invention, i.e. arginine methyltransferase activity, glycosyltransferase activity, gamma-glutamyltraspeptidase activity, phosphoribosylglycinamide transferase activity, acyltransferase activity, acyl-CoA dehydrogenase activity, fatty acid amide hydrolase activity, aminotransferase activity, zinc carboxypeptidase activity, protein kinase activity, DEAD helicase activity, short-chain dehydrogenase/reductase activity or phosphatase activity, or other.

Allelic variants of 26199, 33530, 33949, 47148, 50226, 58764, 62113, 32144, 32235, 23565, 13305, 14911, 86216, 25206 or 8843, e.g., human 26199, 33530, 33949, 47148, 50226, 58764, 62113, 32144, 32235, 23565, 13305, 14911, 86216, 25206 or 8843, include both functional and non-functional proteins. Functional allelic variants are naturally occurring amino acid sequence variants of the 26199, 33530, 33949, 47148, 50226, 58764, 62113, 32144, 32235, 23565, 13305, 14911, 86216, 25206 or 8843 protein within a population that maintain the ability to bind a 26199, 33530, 33949, 47148, 50226, 58764, 62113, 32144, 32235, 23565, 13305, 14911, 86216, 25206 or 8843 ligand or substrate and/or modulate cell proliferation and/or migration mechanisms. Functional allelic variants will typically contain only conservative substitution of one or more amino acids of SEQ ID NO:2, 5, 8, 11, 14, 17, 54, 62, 68, 79, 89, 101, 114, 123 or 130, or substitution, deletion or insertion of non-critical residues in non-critical regions of the protein. Non-functional allelic variants are naturally-occurring amino acid sequence variants of the 26199, 33530, 33949, 47148, 50226, 58764, 62113, 32144, 32235, 23565, 13305, 14911, 86216, 25206 or 8843, e.g., human 26199, 33530, 33949, 47148, 50226, 58764, 62113, 32144, 32235, 23565, 13305, 14911, 86216, 25206 or 8843, protein within a population that do not have the ability to bind a 26199, 33530, 33949, 47148, 50226, 58764, 62113, 32144, 32235, 23565, 13305, 14911, 86216, 25206 or 8843 ligand or substrate and/or modulate cell proliferation and/or migration mechanisms. Non-functional allelic variants will typically contain a non-conservative substitution, a deletion, or insertion, or premature truncation of the amino acid sequence of SEQ ID NO:2, 5, 8, 11, 14, 17, 54, 62, 68, 79, 89, 101, 114, 123 or 130, or a substitution, insertion, or deletion in critical residues or critical regions of the protein.

Moreover, nucleic acid molecules encoding other 26199, 33530, 33949, 47148, 50226, 58764, 62113, 32144, 32235, 23565, 13305, 14911, 86216, 25206 or 8843 family members and, thus, which have a nucleotide sequence which differs from the 26199, 33530, 33949, 47148, 50226, 58764, 62113, 32144, 32235, 23565, 13305, 14911, 86216, 25206 or 8843 sequences of SEQ ID NO:1, 3, 4, 6, 7, 9, 10, 12, 13, 15, 16, 18, 53, 55, 61, 63, 67, 69, 78, 80, 88, 90, 100, 102, 113, 115, 122, 124, 129 or 131 are intended to be within the scope of the invention.

Antisense Nucleic Acid Molecules, Ribozymes and Modified 26199, 33530, 33949, 47148, 50226, 58764, 62113, 32144, 32235, 23565, 13305, 14911, 86216, 25206 or 8843 Nucleic Acid Molecules In another aspect, the invention features, an isolated nucleic acid molecule which is antisense to 26199, 33530, 33949, 47148, 50226, 58764, 62113, 32144, 32235, 23565, 13305, 14911, 86216, 25206 or 8843. An "antisense" nucleic acid can include a nucleotide sequence which is complementary to a "sense" nucleic acid encoding a protein, e.g., complementary to the coding strand of a double-stranded cDNA molecule or complementary to an mRNA sequence. The antisense nucleic acid can be complementary to an entire 26199, 33530, 33949, 47148, 50226, 58764, 62113, 32144, 32235, 23565, 13305, 14911, 86216, 25206 or 8843 coding strand, or to only a portion thereof (e.g., the coding region of human 26199, 33530, 33949, 47148, 50226, 58764, 62113, 32144, 32235, 23565, 13305, 14911, 86216, 25206 or 8843 corresponding to SEQ ID NO:3, 6, 9, 12, 15, 18, 55, 63, 69, 80, 90, 102, 115, 124 or 131, respectively). In another embodiment, the antisense nucleic acid molecule is antisense to a "noncoding region" of the coding strand of a nucleotide sequence encoding 26199, 33530, 33949, 47148, 50226, 58764, 62113, 32144, 32235, 23565, 13305, 14911, 86216, 25206 or 8843 (e.g., the 5' and 3' untranslated regions).

An antisense nucleic acid can be designed such that it is complementary to the entire coding region of 26199, 33530, 33949, 47148, 50226, 58764, 62113, 32144, 32235, 23565, 13305, 14911, 86216, 25206 or 8843 mRNA, but more preferably is an oligonucleotide which is antisense to only a portion of the coding or noncoding region of 26199, 33530, 33949, 47148, 50226, 58764, 62113, 32144, 32235, 23565, 13305, 14911, 86216, 25206 or 8843 mRNA. For example, the antisense oligonucleotide can be complementary to the region surrounding the translation start site of 26199, 33530, 33949, 47148, 50226, 58764, 62113, 32144, 32235, 23565, 13305, 14911, 86216, 25206 or 8843 mRNA, e.g., between the −10 and +10 regions of the target gene nucleotide sequence of interest. An antisense oligonucleotide can be, for example, about 7, 10, 15, 20, 25, 30, 35, 40, 45, 50, 55, 60, 65, 70, 75, 80, or more nucleotides in length.

An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. The antisense nucleic acid also can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject (e.g., by direct injection at a tissue site), or generated in situ such that they hybridize with or bind to cellular mRNA and/or genomic DNA encoding a 26199, 33530, 33949, 47148, 50226, 58764, 62113, 32144, 32235, 23565, 13305, 14911, 86216, 25206 or 8843 protein to thereby inhibit expression of the protein, e.g., by inhibiting transcription and/or translation. Alternatively, antisense nucleic acid molecules can be modified to target selected cells and then administered systemically. For systemic administration, antisense molecules can be modified such that they specifically or selectively bind to receptors or antigens expressed on a selected cell surface, e.g., by linking the antisense nucleic acid molecules to peptides or antibodies which bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

In yet another embodiment, the antisense nucleic acid molecule of the invention is an α-anomeric nucleic acid molecule. An α-anomeric nucleic acid molecule forms specific double-stranded hybrids with complementary RNA in which, contrary to the usual β-units, the strands run parallel to each other (Gaultier et al. (1987) *Nucleic Acids. Res.* 15:6625-6641). The antisense nucleic acid molecule can also comprise a 2'-o-methylribonucleotide (Inoue et al. (1987) *Nucleic Acids Res.* 15:6131-6148) or a chimeric RNA-DNA analogue (Inoue et al. (1987) *FEBS Lett.* 215:327-330).

In still another embodiment, an antisense nucleic acid of the invention is a ribozyme. A ribozyme having specificity for a 26199, 33530, 33949, 47148, 50226, 58764, 62113, 32144, 32235, 23565, 13305, 14911, 86216, 25206 or 8843-encoding nucleic acid can include one or more sequences complementary to the nucleotide sequence of a 26199, 33530, 33949, 47148, 50226, 58764, 62113, 32144, 32235, 23565, 13305, 14911, 86216, 25206 or 8843 cDNA disclosed herein (i.e., SEQ ID NO:1, 3, 4, 6, 7, 9, 10, 12, 13, 15, 16, 18, 53, 55, 61, 63, 67, 69, 78, 80, 88, 90, 100, 102, 113, 115, 122, 124, 129 or 131), and a sequence having known catalytic sequence responsible for mRNA cleavage (see U.S. Pat. No. 5,093,246 or Haselhoff and Gerlach (1988) *Nature* 334:585-591). For example, a derivative of a Tetrahymena L-19 IVS RNA can be constructed in which the nucleotide sequence of the active site is complementary to the nucleotide sequence to be cleaved in a 26199, 33530, 33949, 47148, 50226, 58764, 62113, 32144, 32235, 23565, 13305, 14911, 86216, 25206 or 8843-encoding mRNA. See, e.g., Cech et al. U.S. Pat. No. 4,987,071; and Cech et al. U.S. Pat. No. 5,116,742. Alternatively, 26199, 33530, 33949, 47148, 50226, 58764, 62113, 32144, 32235, 23565, 13305, 14911, 86216, 25206 or 8843 mRNA can be used to select a catalytic RNA having a specific ribonuclease activity from a pool of RNA molecules. See, e.g., Bartel and Szostak (1993) *Science* 261:1411-1418.

26199, 33530, 33949, 47148, 50226, 58764, 62113, 32144, 32235, 23565, 13305, 14911, 86216, 25206 or 8843 gene expression can be inhibited by targeting nucleotide sequences complementary to the regulatory region of the 26199, 33530, 33949, 47148, 50226, 58764, 62113, 32144, 32235, 23565, 13305, 14911, 86216, 25206 or 8843 (e.g., the 26199, 33530, 33949, 47148, 50226, 58764, 62113, 32144, 32235, 23565, 13305, 14911, 86216, 25206 or 8843 promoter and/or enhancers) to form triple helical structures that prevent transcription of the 26199, 33530, 33949, 47148, 50226, 58764, 62113, 32144, 32235, 23565, 13305, 14911, 86216, 25206 or 8843 gene in target cells. See generally, Helene (1991) *Anticancer Drug Des.* 6:569-84; Helene (1992) *Ann. N.Y. Acad. Sci.* 660:27-36; and Maher (1992) *Bioassays* 14:807-15. The potential sequences that can be targeted for triple helix formation can be increased by creating a so-called "switchback" nucleic acid molecule. Switchback molecules are synthesized in an alternating 5'-3',3'-5' manner, such that they base pair with first one strand of a duplex and then the other, eliminating the necessity for a sizeable stretch of either purines or pyrimidines to be present on one strand of a duplex.

The invention also provides detectably labeled oligonucleotide primer and probe molecules. Typically, such labels are chemiluminescent, fluorescent, radioactive, or calorimetric.

A 26199, 33530, 33949, 47148, 50226, 58764, 62113, 32144, 32235, 23565, 13305, 14911, 86216, 25206 or 8843 nucleic acid molecule can be modified at the base moiety, sugar moiety or phosphate backbone to improve, e.g., the stability, hybridization, or solubility of the molecule. For example, the deoxyribose phosphate backbone of the nucleic acid molecules can be modified to generate peptide nucleic acids (see Hyrup et al. (1996) *Bioorganic & Medicinal Chemistry* 4: 5-23).

As used herein, the terms "peptide nucleic acid" or "PNA" refers to a nucleic acid mimic, e.g., a DNA mimic, in which the deoxyribose phosphate backbone is replaced by a pseudopeptide backbone and only the four natural nucleobases are retained. The neutral backbone of a PNA can allow for specific hybridization to DNA and RNA under conditions of low ionic strength. The synthesis of PNA oligomers can be performed using standard solid phase peptide synthesis protocols as described in Hyrup et al. (1996) supra; Perry-O'Keefe et al. (1996) *Proc. Natl. Acad. Sci.* 93: 14670-675.

PNAs of 26199, 33530, 33949, 47148, 50226, 58764, 62113, 32144, 32235, 23565, 13305, 14911, 86216, 25206 or 8843 nucleic acid molecules can be used in therapeutic and diagnostic applications. For example, PNAs can be used as antisense or antigene agents for sequence-specific modulation of gene expression by, for example, inducing transcription or translation arrest or inhibiting replication. PNAs of 26199, 33530, 33949, 47148, 50226, 58764, 62113, 32144, 32235, 23565, 13305, 14911, 86216, 25206 or 8843 nucleic acid molecules can also be used in the analysis of single base pair mutations in a gene, (e.g., by PNA-directed PCR clamping); as 'artificial restriction enzymes' when used in combination with other enzymes, (e.g., S1 nucleases (Hyrup et al. (1996) supra)); or as probes or primers for DNA sequencing or hybridization (Hyrup et al. (1996) supra; Perry-O'Keefe supra).

In other embodiments, the oligonucleotide can include other appended groups such as peptides (e.g., for targeting host cell receptors in vivo), or agents facilitating transport across the cell membrane (see, e.g., Letsinger et al. (1989) *Proc. Natl. Acad. Sci. USA* 86:6553-6556; Lemaitre et al. (1987) *Proc. Natl. Acad. Sci. USA* 84:648-652; PCT Publication No. WO88/09810) or the blood-brain barrier (see, e.g., PCT Publication No. WO89/10134). In addition, oligonucleotides can be modified with hybridization-triggered cleavage agents (see, e.g., Krol et al. (1988) *Bio-Techniques* 6:958-976) or intercalating agents. (see, e.g., Zon (1988) *Pharm. Res.* 5:539-549). To this end, the oligonucleotide can be conjugated to another molecule, (e.g., a peptide, hybridization triggered cross-linking agent, transport agent, or hybridization-triggered cleavage agent).

The invention also includes molecular beacon oligonucleotide primer and probe molecules having at least one region which is complementary to a 26199, 33530, 33949, 47148, 50226, 58764, 62113, 32144, 32235, 23565, 13305, 14911, 86216, 25206 or 8843 nucleic acid of the invention, two complementary regions one having a fluorophore and one a quencher such that the molecular beacon is useful for quantitating the presence of the 26199, 33530, 33949, 47148, 50226, 58764, 62113, 32144, 32235, 23565, 13305, 14911, 86216, 25206 or 8843 nucleic acid of the invention in a sample. Molecular beacon nucleic acids are described, for example, in Lizardi et al., U.S. Pat. No. 5,854,033; Nazarenko et al., U.S. Pat. No. 5,866,336, and Livak et al., U.S. Pat. No. 5,876,930.

Isolated 26199, 33530, 33949, 47148, 50226, 58764, 62113, 32144, 32235, 23565, 13305, 14911, 86216, 25206 or 8843 Polypeptides In another aspect, the invention features, an isolated 26199, 33530, 33949, 47148, 50226, 58764, 62113, 32144, 32235, 23565, 13305, 14911, 86216, 25206 or 8843 protein, or fragment, e.g., a biologically active portion, for use as immunogens or antigens to raise or test (or more generally to bind) anti-26199, 33530, 33949, 47148, 50226, 58764, 62113, 32144, 32235, 23565, 13305, 14911, 86216, 25206 or 8843 antibodies. 26199, 33530, 33949, 47148, 50226, 58764, 62113, 32144, 32235, 23565, 13305, 14911, 86216, 25206 or 8843 protein can be isolated from cells or tissue sources using standard protein purification techniques. 26199, 33530, 33949, 47148, 50226, 58764, 62113, 32144, 32235, 23565, 13305, 14911, 86216, 25206 or 8843 protein or fragments thereof can be produced by recombinant DNA techniques or synthesized chemically.

Polypeptides of the invention include those which arise as a result of the existence of multiple genes, alternative transcription events, alternative RNA splicing events, and alternative translational and post-translational events. The polypeptide can be expressed in systems, e.g., cultured cells, which result in substantially the same post-translational modifications present when the polypeptide is expressed in a native cell, or in systems which result in the alteration or omission of post-translational modifications, e.g., glycosylation or cleavage, present in a native cell.

In a preferred embodiment, a 26199, 33530, 33949, 47148, 50226, 58764, 62113, 32144, 32235, 23565, 13305, 14911, 86216, 25206 or 8843 polypeptide has one or more of the following characteristics: it has the ability: (i) to transfer an activated sugar residue to an acceptor molecule; (ii) to modulate the processing, folding, and secretion of proteins; (iii) to transport amino acids in the form of their gamma-glutamyl derivatives; (iv) to regulate the metabolism of glutathione; (v) to regulate the synthesis of purines; (vi) to modulate cell division and proliferation; (vii) to modulate cell death; (viii) to transfer an acyl chain to a lipid precursor; (ix) to regulate lipid biosynthesis; (x) to catalyze the transfer of hydrogen and electrons from one compound to another; (xi) to catalyze the I,ϑ-dehydrogenation of fatty acyl-CoA derivatives; (xii) to bind and catabolize fatty acid amides; (xiii) to modulate metabolism, e.g., amino acid metabolism; (xiv) to bind an amino acid, e.g., L-alanine; (xv) to bind an oxo acid, e.g., pyruvate; (xvi) to modulate the formation of a zinc ion complex with a carbonyl group of a substrate polypeptide and polarization of the carbon-oxygen bond; (xvii) to modulate formation of a tetrahedral intermediate due to attack of the carbonyl carbon by water in a reaction assisted by a carboxylate side chain of glutamate; (xviii) to modulate the production of a dianion intermediate by rapid ionization of the tetrahedral intermediate produced; (xix) to modulate ATP dependent nucleic acid unwinding; (xx) to modulate RNA metabolism (e.g., nuclear transcription, and mRNA splicing); (xxi) to modulate steroid biosynthesis or metabolism (breakdown); (xxii) to catalyze the removal of a phosphate group attached to a tyrosine residue in a protein; (xxiii) to catalyze the removal of a phosphate group attached to a serine or threonine residue in a protein; (xxiv) to modulate an intracellular signaling pathway, e.g., a MAP kinase or ERK kinase pathway; (xxv) to regulate the transmission of signals from cellular receptors, e.g., cardiac cell growth factor receptors; (xxvi) it has a molecular weight, e.g., a deduced molecular weight, preferably ignoring any contribution of post translational modifications, amino acid composition or other physical characteristic of a 26199, 33530, 33949, 47148, 50226, 58764, 62113, 32144, 32235, 23565, 13305, 14911, 86216, 25206 or 8843 polypeptide, e.g., a polypeptide of SEQ ID NO:2, 5, 8, 11, 14, 17, 54, 62, 68, 79, 89, 101, 114, 123 or 130; (xxvii) it has an overall sequence similarity of at least 60%, preferably at least 70%, more preferably at least 80, 90, or 95%, with a polypeptide of SEQ ID NO:2, 5, 8, 11, 14, 17, 54, 62, 68, 79, 89, 101, 114, 123 or 130; (xxviii) it is expressed in a multitude of human tissues and cell lines (refer to section for each molecule of the invention); and (xxix) it has specific domains which are preferably about 70%, 80%, 90% or 95% identical to the identified amino acid residues of SEQ ID NO:2, 5, 8, 11, 14, 17, 54, 62, 68, 79, 89, 101, 114, 123 or 130 (refer to section for each molecule of the invention for domain names and locations within amino acid sequence).

In a preferred embodiment the 26199, 33530, 33949, 47148, 50226, 58764, 62113, 32144, 32235, 23565, 13305, 14911, 86216, 25206 or 8843 protein, or fragment thereof, differs from the corresponding sequence in SEQ ID NO:2, 5, 8, 11, 14, 17, 54, 62, 68, 79, 89, 101, 114, 123 or 130. In one embodiment it differs by at least one but by less than 15, 10 or 5 amino acid residues. In another it differs from the corresponding sequence in SEQ ID NO:2, 5, 8, 11, 14, 17, 54, 62, 68, 79, 89, 101, 114, 123 or 130 by at least one residue but less than 20%, 15%, 10% or 5% of the residues in it differ from the corresponding sequence in SEQ ID NO:2, 5, 8, 11, 14, 17, 54, 62, 68, 79, 89, 101, 114, 123 or 130. (If this comparison requires alignment the sequences should be aligned for maximum homology. "Looped" out sequences from deletions or insertions, or mismatches, are considered differences.) The differences are, preferably, differences or changes at a nonessential residue or a conservative substitution. In a preferred embodiment the differences are not in the identified or conserved domain(s) within SEQ ID NO:2, 5, 8, 11, 14, 17, 54, 62, 68, 79, 89, 101, 114, 123 or 130. In another embodiment one or more differences are in the cidentified or conserved domain(s) within SEQ ID NO:2, 5, 8, 11, 14, 17, 54, 62, 68, 79, 89, 101, 114, 123 or 130.

Other embodiments include a protein that contains one or more changes in amino acid sequence, e.g., a change in an amino acid residue which is not essential for activity. Such 26199, 33530, 33949, 47148, 50226, 58764, 62113, 32144, 32235, 23565, 13305, 14911, 86216, 25206 or 8843 proteins differ in amino acid sequence from SEQ ID NO:2, 5, 8, 11, 14, 17, 54, 62, 68, 79, 89, 101, 114, 123 or 130, yet retain biological activity.

In one embodiment, the protein includes an amino acid sequence at least about 60%, 65%, 70%, 75%, 80%, 85%, 90%, 95%, 98% or more homologous to SEQ ID NO:2, 5, 8, 11, 14, 17, 54, 62, 68, 79, 89, 101, 114, 123 or 130.

A 26199, 33530, 33949, 47148, 50226, 58764, 62113, 32144, 32235, 23565, 13305, 14911, 86216, 25206 or 8843 protein or fragment is provided which varies from the sequence of SEQ ID NO:2, 5, 8, 11, 14, 17, 54, 62, 68, 79, 89, 101, 114, 123 or 130 in regions defined by amino acids that are not within identified or conserved domains or regions by at least one but by less than 15, 10 or 5 amino acid residues in the protein or fragment but which does not differ from SEQ ID NO:2, 5, 8, 11, 14, 17, 54, 62, 68, 79, 89, 101, 114, 123 or 130 in regions defined by amino acids that are within identified or conserved domains or regions. (If this comparison requires alignment the sequences should be aligned for maximum homology. "Looped" out sequences from deletions or insertions, or mismatches, are considered differences.) In some embodiments the difference is at a non-essential residue or is a conservative substitution, while in others the difference is at an essential residue or is a non-conservative substitution.

In one embodiment, a biologically active portion of a 26199, 33530, 33949, 47148, 50226, 58764, 62113, 32144, 32235, 23565, 13305, 14911, 86216, 25206 or 8843 protein includes an identified domain (refer to section for each molecule of the invention). Moreover, other biologically active portions, in which other regions of the protein are deleted, can be prepared by recombinant techniques and evaluated for one or more of the functional activities of a native 26199, 33530, 33949, 47148, 50226, 58764, 62113, 32144, 32235, 23565, 13305, 14911, 86216, 25206 or 8843 protein.

In a preferred embodiment, the 26199, 33530, 33949, 47148, 50226, 58764, 62113, 32144, 32235, 23565, 13305, 14911, 86216, 25206 or 8843 protein has an amino acid sequence shown in SEQ ID NO:2, 5, 8, 11, 14, 17, 54, 62, 68, 79, 89, 101, 114, 123 or 130. In other embodiments, the 26199, 33530, 33949, 47148, 50226, 58764, 62113, 32144, 32235, 23565, 13305, 14911, 86216, 25206 or 8843 protein is sufficiently or substantially identical to SEQ ID NO:2, 5, 8, 11, 14, 17, 54, 62, 68, 79, 89, 101, 114, 123 or 130. In yet another embodiment, the 26199, 33530, 33949, 47148, 50226, 58764, 62113, 32144, 32235, 23565, 13305, 14911, 86216, 25206 or 8843 protein is sufficiently or substantially identical to SEQ ID NO:2, 5, 8, 11, 14, 17, 54, 62, 68, 79, 89, 101, 114, 123 or 130 and retains the functional activity of the protein of SEQ ID NO:2, 5, 8, 11, 14, 17, 54, 62, 68, 79, 89, 101, 114, 123 or 130, as described in detail in the subsections above.

26199, 33530, 33949, 47148, 50226, 58764, 62113, 32144.32235, 23565, 13305, 14911, 86216, 25206 or 8843 Chimeric or Fusion Proteins In another aspect, the invention provides 26199, 33530, 33949, 47148, 50226, 58764, 62113, 32144, 32235, 23565, 13305, 14911, 86216, 25206 or 8843 chimeric or fusion proteins. As used herein, a 26199, 33530, 33949, 47148, 50226, 58764, 62113, 32144, 32235, 23565, 13305, 14911, 86216, 25206 or 8843 "chimeric protein" or "fusion protein" includes a 26199, 33530, 33949, 47148, 50226, 58764, 62113, 32144, 32235, 23565, 13305, 14911, 86216, 25206 or 8843 polypeptide linked to a non-26199, 33530, 33949, 47148, 50226, 58764, 62113, 32144, 32235, 23565, 13305, 14911, 86216, 25206 or 8843 polypeptide. A "non-26199, 33530, 33949, 47148, 50226, 58764, 62113, 32144, 32235, 23565, 13305, 14911, 86216, 25206 or 8843 polypeptide" refers to a polypeptide having an amino acid sequence corresponding to a protein which is not substantially homologous to the 26199, 33530, 33949, 47148, 50226, 58764, 62113, 32144, 32235, 23565, 13305, 14911, 86216, 25206 or 8843 protein, e.g., a protein which is different from the 26199, 33530, 33949, 47148, 50226, 58764, 62113, 32144, 32235, 23565, 13305, 14911, 86216, 25206 or 8843 protein and which is derived from the same or a different organism. The 26199, 33530, 33949, 47148, 50226, 58764, 62113, 32144, 32235, 23565, 13305, 14911, 86216, 25206 or 8843 polypeptide of the fusion protein can correspond to all or a portion e.g., a fragment described herein of a 26199, 33530, 33949, 47148, 50226, 58764, 62113, 32144, 32235, 23565, 13305, 14911, 86216, 25206 or 8843 amino acid sequence. In a preferred embodiment, a 26199, 33530, 33949, 47148, 50226, 58764, 62113, 32144, 32235, 23565, 13305, 14911, 86216, 25206 or 8843 fusion protein includes at least one (or two) biologically active portion of a 26199, 33530, 33949, 47148, 50226, 58764, 62113, 32144, 32235, 23565, 13305, 14911, 86216, 25206 or 8843 protein. The non-26199, 33530, 33949, 47148, 50226, 58764, 62113, 32144, 32235, 23565, 13305, 14911, 86216, 25206 or 8843 polypeptide can be fused to the N-terminus or C-terminus of the 26199, 33530, 33949, 47148, 50226, 58764, 62113, 32144, 32235, 23565, 13305, 14911, 86216, 25206 or 8843 polypeptide.

The fusion protein can include a moiety which has a high affinity for a ligand. For example, the fusion protein can be a GST-26199, 33530, 33949, 47148, 50226, 58764, 62113, 32144, 32235, 23565, 13305, 14911, 86216, 25206 or 8843 fusion protein in which the 26199, 33530, 33949, 47148, 50226, 58764, 62113, 32144, 32235, 23565, 13305, 14911, 86216, 25206 or 8843 sequences are fused to the C-terminus of the GST sequences. Such fusion proteins can facilitate the purification of recombinant 26199, 33530, 33949, 47148, 50226, 58764, 62113, 32144, 32235, 23565, 13305, 14911, 86216, 25206 or 8843. Alternatively, the fusion protein can be a 26199, 33530, 33949, 47148, 50226, 58764, 62113, 32144, 32235, 23565, 13305, 14911, 86216, 25206 or 8843 protein containing a heterologous signal sequence at its N-terminus. In certain host cells (e.g., mammalian host cells), expression and/or secretion of 26199, 33530, 33949, 47148, 50226, 58764, 62113, 32144, 32235, 23565, 13305, 14911, 86216, 25206 or 8843 can be increased through use of a heterologous signal sequence.

Fusion proteins can include all or a part of a serum protein, e.g., a portion of an immunoglobulin (e.g., IgG, IgA, or IgE), e.g., an Fc region and/or the hinge C1 and C2 sequences of an immunoglobulin or human serum albumin.

The 26199, 33530, 33949, 47148, 50226, 58764, 62113, 32144, 32235, 23565, 13305, 14911, 86216, 25206 or 8843 fusion proteins of the invention can be incorporated into pharmaceutical compositions and administered to a subject in vivo. The 26199, 33530, 33949, 47148, 50226, 58764, 62113, 32144, 32235, 23565, 13305, 14911, 86216, 25206 or 8843 fusion proteins can be used to affect the bioavailability of a 26199, 33530, 33949, 47148, 50226, 58764, 62113, 32144, 32235, 23565, 13305, 14911, 86216, 25206 or 8843 substrate. 26199, 33530, 33949, 47148, 50226, 58764, 62113, 32144, 32235, 23565, 13305, 14911, 86216, 25206 or 8843 fusion proteins can be useful therapeutically for the treatment of disorders caused by, for example, (i) aberrant modification or mutation of a gene encoding a 26199, 33530, 33949, 47148, 50226, 58764, 62113, 32144, 32235, 23565, 13305, 14911, 86216, 25206 or 8843 protein; (ii) mis-regulation of the 26199, 33530, 33949, 47148, 50226, 58764, 62113, 32144, 32235, 23565, 13305, 14911, 86216, 25206 or 8843 gene; and (iii) aberrant post-translational modification of a 26199, 33530, 33949, 47148, 50226, 58764, 62113, 32144, 32235, 23565, 13305, 14911, 86216, 25206 or 8843 protein.

Moreover, the 26199, 33530, 33949, 47148, 50226, 58764, 62113, 32144, 32235, 23565, 13305, 14911, 86216, 25206 or 8843-fusion proteins of the invention can be used as immunogens to produce anti-26199, 33530, 33949, 47148, 50226, 58764, 62113, 32144, 32235, 23565, 13305, 14911, 86216, 25206 or 8843 antibodies in a subject, to purify 26199, 33530, 33949, 47148, 50226, 58764, 62113, 32144, 32235, 23565, 13305, 14911, 86216, 25206 or 8843 ligands and in screening assays to identify molecules which inhibit the interaction of 26199, 33530, 33949, 47148, 50226, 58764, 62113, 32144, 32235, 23565, 13305, 14911, 86216, 25206 or 8843 with a 26199, 33530, 33949, 47148, 50226, 58764, 62113, 32144, 32235, 23565, 13305, 14911, 86216, 25206 or 8843 substrate.

Expression vectors are commercially available that already encode a fusion moiety (e.g., a GST polypeptide). A 26199, 33530, 33949, 47148, 50226, 58764, 62113, 32144, 32235, 23565, 13305, 14911, 86216, 25206 or 8843-encoding nucleic acid can be cloned into such an expression vector such that the fusion moiety is linked in-frame to the 26199, 33530, 33949, 47148, 50226, 58764, 62113, 32144, 32235, 23565, 13305, 14911, 86216, 25206 or 8843 protein.

Variants of 26199, 33530, 33949, 47148, 50226, 58764, 62113, 32144, 32235, 23565, 13305, 14911, 86216, 25206 or 8843 Proteins In another aspect, the invention also features a variant of a 26199, 33530, 33949, 47148, 50226, 58764, 62113, 32144, 32235, 23565, 13305, 14911, 86216, 25206 or 8843 polypeptide, e.g., which functions as an agonist (mimetics) or as an antagonist. Variants of the 26199, 33530, 33949, 47148, 50226, 58764, 62113, 32144, 32235, 23565, 13305, 14911, 86216, 25206 or 8843 proteins can be generated by mutagenesis, e.g., discrete point mutation, the insertion or deletion of sequences or the truncation of a 26199, 33530, 33949, 47148, 50226, 58764, 62113, 32144, 32235, 23565, 13305, 14911, 86216, 25206 or 8843 protein. An agonist of the 26199, 33530, 33949, 47148, 50226, 58764, 62113, 32144, 32235, 23565, 13305, 14911, 86216, 25206 or 8843 proteins can retain substantially the same, or a subset, of the biological activities of the naturally occurring form of a 26199, 33530, 33949, 47148, 50226, 58764, 62113, 32144, 32235, 23565, 13305, 14911, 86216, 25206 or 8843 protein. An antagonist of a 26199, 33530, 33949, 47148, 50226, 58764, 62113, 32144, 32235, 23565, 13305, 14911, 86216, 25206 or 8843 protein can inhibit one or more of the activities of the naturally occurring form of the 26199, 33530, 33949, 47148, 50226, 58764, 62113, 32144, 32235, 23565, 13305, 14911, 86216, 25206 or 8843 protein by, for example, competitively modulating a 26199, 33530, 33949, 47148, 50226, 58764, 62113, 32144, 32235, 23565, 13305, 14911, 86216, 25206 or 8843-mediated activity of a 26199, 33530, 33949, 47148, 50226, 58764, 62113, 32144, 32235, 23565, 13305, 14911, 86216, 25206 or 8843 protein. Thus, specific biological effects can be elicited by treatment with a variant of limited function. Preferably, treatment of a subject with a variant having a subset of the biological activities of the naturally occurring form of the protein has fewer side effects in a subject relative to treatment with the naturally occurring form of the 26199, 33530, 33949, 47148, 50226, 58764, 62113, 32144, 32235, 23565, 13305, 14911, 86216, 25206 or 8843 protein.

Variants of a 26199, 33530, 33949, 47148, 50226, 58764, 62113, 32144, 32235, 23565, 13305, 14911, 86216, 25206 or 8843 protein can be identified by screening combinatorial libraries of mutants, e.g., truncation mutants, of a 26199, 33530, 33949, 47148, 50226, 58764, 62113, 32144, 32235, 23565, 13305, 14911, 86216, 25206 or 8843 protein for agonist or antagonist activity.

Libraries of fragments e.g., N terminal, C terminal, or internal fragments, of a 26199, 33530, 33949, 47148, 50226, 58764, 62113, 32144, 32235, 23565, 13305, 14911, 86216, 25206 or 8843 protein coding sequence can be used to generate a variegated population of fragments for screening and subsequent selection of variants of a 26199, 33530, 33949, 47148, 50226, 58764, 62113, 32144, 32235, 23565, 13305, 14911, 86216, 25206 or 8843 protein.

Variants in which a cysteine residues is added or deleted or in which a residue which is glycosylated is added or deleted are particularly preferred.

Methods for screening gene products of combinatorial libraries made by point mutations or truncation, and for screening cDNA libraries for gene products having a selected property are known in the art. Recursive ensemble mutagenesis (REM), a new technique which enhances the frequency of functional mutants in the libraries, can be used in combination with the screening assays to identify 26199, 33530, 33949, 47148, 50226, 58764, 62113, 32144, 32235, 23565, 13305, 14911, 86216, 25206 or 8843 variants (Arkin and Yourvan (1992) *Proc. Natl. Acad. Sci. USA* 89:7811-7815; Delgrave et al. (1993) *Protein Engineering* 6:327-331).

Cell based assays can be exploited to analyze a variegated 26199, 33530, 33949, 47148, 50226, 58764, 62113, 32144, 32235, 23565, 13305, 14911, 86216, 25206 or 8843 library. For example, a library of expression vectors can be transfected into a cell line, e.g., a cell line, which ordinarily responds to 26199, 33530, 33949, 47148, 50226, 58764, 62113, 32144, 32235, 23565, 13305, 14911, 86216, 25206 or 8843 in a substrate-dependent manner. The transfected cells are then contacted with 26199, 33530, 33949, 47148, 50226, 58764, 62113, 32144, 32235, 23565, 13305, 14911, 86216, 25206 or 8843 and the effect of the expression of the mutant on signaling by the 26199, 33530, 33949, 47148, 50226, 58764, 62113, 32144, 32235, 23565, 13305, 14911, 86216, 25206 or 8843 substrate can be detected, e.g., by measuring either arginine methyltransferase activity, glycosyltransferase activity, gamma-glutamyltraspeptidase activity, phosphoribosylglycinamide transferase activity, acyltransferase activity, acyl-CoA dehydrogenase activity, fatty acid amide hydrolase activity, aminotransferase activity, zinc carboxypeptidase activity, protein kinase activity, DEAD helicase activity, short-chain dehydrogenase/reductase activity or phosphatase activity, or other activity. Plasmid DNA can then be recovered from the cells which score for inhibition, or alternatively, potentiation of signaling by the 26199, 33530, 33949, 47148, 50226, 58764, 62113, 32144, 32235, 23565, 13305, 14911, 86216, 25206 or 8843 substrate, and the individual clones further characterized.

In another aspect, the invention features a method of making a 26199, 33530, 33949, 47148, 50226, 58764, 62113, 32144, 32235, 23565, 13305, 14911, 86216, 25206 or 8843 polypeptide, e.g., a peptide having a non-wild type activity, e.g., an antagonist, agonist, or super agonist of a naturally occurring 26199, 33530, 33949, 47148, 50226, 58764, 62113, 32144, 32235, 23565, 13305, 14911, 86216, 25206 or 8843 polypeptide, e.g., a naturally occurring 26199, 33530, 33949, 47148, 50226, 58764, 62113, 32144, 32235, 23565, 13305, 14911, 86216, 25206 or 8843 polypeptide. The method includes altering the sequence of a 26199, 33530, 33949, 47148, 50226, 58764, 62113, 32144, 32235, 23565, 13305, 14911, 86216, 25206 or 8843 polypeptide, e.g., altering the sequence, e.g., by substitution or deletion of one or more residues of a non-conserved region, a domain or residue disclosed herein, and testing the altered polypeptide for the desired activity.

In another aspect, the invention features a method of making a fragment or analog of a 26199, 33530, 33949, 47148, 50226, 58764, 62113, 32144, 32235, 23565, 13305, 14911, 86216, 25206 or 8843 polypeptide a biological activity of a naturally occurring 26199, 33530, 33949, 47148, 50226, 58764, 62113, 32144, 32235, 23565, 13305, 14911, 86216, 25206 or 8843 polypeptide. The method includes altering the sequence, e.g., by substitution or deletion of one or more residues, of a 26199, 33530, 33949, 47148, 50226, 58764, 62113, 32144, 32235, 23565, 13305, 14911, 86216, 25206 or 8843 polypeptide, e.g., altering the sequence of a non-conserved region, or a domain or residue described herein, and testing the altered polypeptide for the desired activity.

Anti-26199, 33530, 33949, 47148.50226, 58764.62113.32144, 32235.23565.13305, 14911, 86216, 25206 or 8843 Antibodies In another aspect, the invention provides an anti-26199, 33530, 33949, 47148, 50226, 58764, 62113, 32144, 32235, 23565, 13305, 14911, 86216, 25206 or 8843 antibody. The term "antibody" as used herein refers to an immunoglobulin molecule or immunologically active portion thereof, i.e., an antigen-binding portion. Examples of immunologically active portions of immunoglobulin molecules include scFV and dcFV fragments, Fab and $F(ab)_2$ fragments which can be generated by treating the antibody with an enzyme such as papain or pepsin, respectively.

The antibody can be a polyclonal, monoclonal, recombinant, e.g., a chimeric or humanized, fully human, non-human, e.g., murine, or single chain antibody. In a preferred embodiment it has effector function and can fix complement. The antibody can be coupled to a toxin or imaging agent.

A full-length 26199, 33530, 33949, 47148, 50226, 58764, 62113, 32144, 32235, 23565, 13305, 14911, 86216, 25206 or 8843 protein or, antigenic peptide fragment of 26199, 33530, 33949, 47148, 50226, 58764, 62113, 32144, 32235, 23565, 13305, 14911, 86216, 25206 or 8843 can be used as an immunogen or can be used to identify anti-26199, 33530, 33949, 47148, 50226, 58764, 62113, 32144, 32235, 23565, 13305, 14911, 86216, 25206 or 8843 antibodies made with other immunogens, e.g., cells, membrane preparations, and the like. The antigenic peptide of 26199, 33530, 33949, 47148, 50226, 58764, 62113, 32144, 32235, 23565, 13305, 14911, 86216, 25206 or 8843 should include at least 8 amino acid residues of the amino acid sequence shown in SEQ ID NO:2, 5, 8, 11, 14, 17, 54, 62, 68, 79, 89, 101, 114, 123 or 130 and encompasses an epitope of 26199, 33530, 33949, 47148, 50226, 58764, 62113, 32144, 32235, 23565, 13305, 14911, 86216, 25206 or 8843. Preferably, the antigenic peptide includes at least 10 amino acid residues, more preferably at least 15 amino acid residues, even more preferably at least 20 amino acid residues, and most preferably at least 30 amino acid residues.

Fragments of 26199, 33530, 33949, 47148, 50226, 58764, 62113, 32144, 32235, 23565, 13305, 14911, 86216, 25206 or 8843 which include hydrophilic regions of SEQ ID NO:2, 5, 8, 11, 14, 17, 54, 62, 68, 79, 89, 101, 114, 123 or 130 can be used to make, e.g., used as immunogens or used to characterize the specificity of an antibody, antibodies against hydrophilic regions of the 26199, 33530, 33949, 47148, 50226, 58764, 62113, 32144, 32235, 23565, 13305, 14911, 86216, 25206 or 8843 protein. Similarly, fragments of 26199, 33530, 33949, 47148, 50226, 58764, 62113, 32144, 32235, 23565, 13305, 14911, 86216, 25206 or 8843 which include hydrophobic regions of SEQ ID NO:2, 5, 8, 11, 14, 17, 54, 62, 68, 79, 89, 101, 114, 123 or 130 can be used to make an antibody against a hydrophobic region of the 26199, 33530, 33949, 47148, 50226, 58764, 62113, 32144, 32235, 23565, 13305, 14911, 86216, 25206 or 8843 protein; fragments of 26199, 33530, 33949, 47148, 50226, 58764, 62113, 32144, 32235, 23565, 13305, 14911, 86216, 25206 or 8843 which include residues within extra cellular domain(s) of SEQ ID NO:2, 5, 8, 11, 14, 17, 54, 62, 68, 79, 89, 101, 114, 123 or 130 can be used to make an antibody against an extracellular or non-cytoplasmic region of the 26199, 33530, 33949, 47148, 50226, 58764, 62113, 32144, 32235, 23565, 13305, 14911, 86216, 25206 or 8843 protein; fragments of 26199, 33530, 33949, 47148, 50226, 58764, 62113, 32144, 32235, 23565, 13305, 14911, 86216, 25206 or 8843 which include residues within intracellular regions of SEQ ID NO:2, 5, 8, 11, 14, 17, 54, 62, 68, 79, 89, 101, 114, 123 or 130 can be used to make an antibody against an intracellular region of the 26199, 33530, 33949, 47148, 50226, 58764, 62113, 32144, 32235, 23565, 13305, 14911, 86216, 25206 or 8843 protein; a fragment of 26199, 33530, 33949, 47148, 50226, 58764, 62113, 32144, 32235, 23565, 13305, 14911, 86216, 25206 or 8843 which include residues within identified or conserved domains of SEQ ID NO:2, 5, 8, 11, 14, 17, 54, 62, 68, 79, 89, 101, 114, 123 or 130 can be used to make an antibody against the identified or conserved domain of the 26199, 33530, 33949, 47148, 50226, 58764, 62113, 32144, 32235, 23565, 13305, 14911, 86216, 25206 or 8843 protein.

Antibodies reactive with, or specific or selective for, any of these regions, or other regions or domains described herein are provided.

Preferred epitopes encompassed by the antigenic peptide are regions of 26199, 33530, 33949, 47148, 50226, 58764, 62113, 32144, 32235, 23565, 13305, 14911, 86216, 25206 or 8843 located on the surface of the protein, e.g., hydrophilic regions, as well as regions with high antigenicity. For example, an Emini surface probability analysis of the human 26199, 33530, 33949, 47148, 50226, 58764, 62113, 32144, 32235, 23565, 13305, 14911, 86216, 25206 or 8843 protein sequence can be used to indicate the regions that have a particularly high probability of being localized to the surface of the 26199, 33530, 33949, 47148, 50226, 58764, 62113, 32144, 32235, 23565, 13305, 14911, 86216, 25206 or 8843 protein and are thus likely to constitute surface residues useful for targeting antibody production.

In a preferred embodiment the antibody can bind to the extracellular portion of the 26199, 33530, 33949, 47148, 50226, 58764, 62113, 32144, 32235, 23565, 13305, 14911, 86216, 25206 or 8843 protein, e.g., it can bind to a whole cell which expresses the 26199, 33530, 33949, 47148, 50226, 58764, 62113, 32144, 32235, 23565, 13305, 14911, 86216, 25206 or 8843 protein. In another embodiment, the antibody binds an intracellular portion of the 26199, 33530, 33949, 47148, 50226, 58764, 62113, 32144, 32235, 23565, 13305, 14911, 86216, 25206 or 8843 protein.

In a preferred embodiment the antibody binds an epitope on any domain or region on 26199, 33530, 33949, 47148, 50226, 58764, 62113, 32144, 32235, 23565, 13305, 14911, 86216, 25206 or 8843 proteins described herein.

Additionally, chimeric, humanized, and completely human antibodies are also within the scope of the invention. Chimeric, humanized, but most preferably, completely human antibodies are desirable for applications which include repeated administration, e.g., therapeutic treatment of human patients, and some diagnostic applications.

Chimeric and humanized monoclonal antibodies, comprising both human and non-human portions, can be made using standard recombinant DNA techniques. Such chimeric and humanized monoclonal antibodies can be produced by recombinant DNA techniques known in the art, for example using methods described in Robinson et al. International Application No. PCT/US86/02269; Akira, et al. European Patent Application 184,187; Taniguchi, European Patent Application 171,496; Morrison et al. European Patent Application 173,494; Neuberger et al. PCT International Publication No. WO 86/01533; Cabilly et al. U.S. Pat. No. 4,816,567; Cabilly et al. European Patent Application 125,023; Better et al. (1988) *Science* 240:1041-1043; Liu et al. (1987) *Proc. Natl. Acad. Sci. USA* 84:3439-3443; Liu et al. (1987) *J. Immunol.* 139:3521-3526; Sun et al. (1987) *Proc. Natl. Acad. Sci. USA* 84:214-218; Nishimura et al. (1987) *Canc. Res.* 47:999-1005; Wood et al. (1985) *Nature* 314:446-449; and Shaw et al. (1988) *J. Natl. Cancer Inst.* 80:1553-1559).

A humanized or complementarity determining region (CDR)-grafted antibody will have at least one or two, but generally all three recipient CDR's (of heavy and or light immuoglobulin chains) replaced with a donor CDR. The antibody may be replaced with at least a portion of a non-human CDR or only some of the CDR's may be replaced with non-human CDR's. It is only necessary to replace the number of CDR's required for binding of the humanized antibody to a 26199, 33530, 33949, 47148, 50226, 58764, 62113, 32144, 32235, 23565, 13305, 14911, 86216, 25206 or 8843 or a fragment thereof. Preferably, the donor will be a rodent antibody, e.g., a rat or mouse antibody, and the recipient will be a human framework or a human consensus framework. Typically, the immunoglobulin providing the CDR's is called the "donor" and the immunoglobulin providing the framework is called the "acceptor." In one embodiment, the donor immunoglobulin is a non-human (e.g., rodent). The acceptor framework is a naturally-occurring (e.g., a human) framework or a consensus framework, or a sequence about 85% or higher, preferably 90%, 95%, 99% or higher identical thereto.

As used herein, the term "consensus sequence" refers to the sequence formed from the most frequently occurring amino acids (or nucleotides) in a family of related sequences (See e.g., Winnaker, (1987) *From Genes to Clones* (Verlagsgesellschaft, Weinheim, Germany). In a family of proteins, each position in the consensus sequence is occupied by the amino acid occurring most frequently at that position in the family. If two amino acids occur equally frequently, either can be included in the consensus sequence. A "consensus framework" refers to the framework region in the consensus immunoglobulin sequence.

An antibody can be humanized by methods known in the art. Humanized antibodies can be generated by replacing sequences of the Fv variable region which are not directly involved in antigen binding with equivalent sequences from human Fv variable regions. General methods for generating humanized antibodies are provided by Morrison (1985) *Science* 229:1202-1207, by Oi et al. (1986) *BioTechniques* 4:214, and by Queen et al. U.S. Pat. Nos. 5,585,089, 5,693,761 and 5,693,762, the contents of all of which are hereby incorporated by reference. Those methods include isolating, manipulating, and expressing the nucleic acid sequences that encode all or part of immunoglobulin Fv variable regions from at least one of a heavy or light chain. Sources of such nucleic acid are well known to those skilled in the art and, for example, may be obtained from a hybridoma producing an antibody against a 26199, 33530, 33949, 47148, 50226, 58764, 62113, 32144, 32235, 23565, 13305, 14911, 86216, 25206 or 8843 polypeptide or fragment thereof. The recombinant DNA encoding the humanized antibody, or fragment thereof, can then be cloned into an appropriate expression vector.

Humanized or CDR-grafted antibodies can be produced by CDR-grafting or CDR substitution, wherein one, two, or all CDR's of an immunoglobulin chain can be replaced. See e.g., U.S. Pat. No. 5,225,539; Jones et al. (1986) *Nature* 321:552-525; Verhoeyan et al. (1988) *Science* 239:1534; Beidler et al. (1988) *J. Immunol.* 141:4053-4060; Winter U.S. Pat. No. 5,225,539, the contents of all of which are hereby expressly incorporated by reference. Winter describes a CDR-grafting method which may be used to prepare the humanized antibodies of the present invention (UK Patent Application GB 2188638A, filed on Mar. 26, 1987; Winter U.S. Pat. No. 5,225,539), the contents of which is expressly incorporated by reference.

Also within the scope of the invention are humanized antibodies in which specific amino acids have been substituted, deleted or added. Preferred humanized antibodies have amino acid substitutions in the framework region, such as to improve binding to the antigen. For example, a humanized antibody will have framework residues identical to the donor framework residue or to another amino acid other than the recipient framework residue. To generate such antibodies, a selected, small number of acceptor framework residues of the humanized immunoglobulin chain can be replaced by the corresponding donor amino acids. Preferred locations of the substitutions include amino acid residues adjacent to the CDR, or which are capable of interacting with a CDR (see e.g., U.S. Pat. No. 5,585,089). Criteria for selecting amino acids from the donor are described in U.S. Pat. No. 5,585,089, e.g., columns 12-16 of U.S. Pat. No. 5,585,089, the e.g., columns 12-16 of U.S. Pat. No. 5,585,089, the contents of which are hereby incorporated by reference. Other techniques for humanizing antibodies are described in Padlan et al. EP 519596 A1, published on Dec. 23, 1992.

Completely human antibodies are particularly desirable for therapeutic treatment of human patients. Such antibodies can be produced using transgenic mice that are incapable of expressing endogenous immunoglobulin heavy and light chains genes, but which can express human heavy and light chain genes. See, for example, Lonberg and Huszar (1995) *Int. Rev. Immunol.* 13:65-93); and U.S. Pat. Nos. 5,625,126; 5,633,425; 5,569,825; 5,661,016; and 5,545,806. In addition, companies such as Abgenix, Inc. (Fremont, Calif.) and Medarex, Inc. (Princeton, N.J.), can be engaged to provide human antibodies directed against a selected antigen using technology similar to that described above.

Completely human antibodies that recognize a selected epitope can be generated using a technique referred to as "guided selection." In this approach a selected non-human monoclonal antibody, e.g., a murine antibody, is used to guide the selection of a completely human antibody recognizing the same epitope. This technology is described by Jespers et al. (1994) *Bio/Technology* 12:899-903).

The anti-26199, 33530, 33949, 47148, 50226, 58764, 62113, 32144, 32235, 23565, 13305, 14911, 86216, 25206 or 8843 antibody can be a single chain antibody. A single-chain antibody (scFV) can be engineered as described in, for example, Colcher et al. (1999) *Ann. NY Acad. Sci.* 880:263-80; and Reiter (1996) *Clin. Cancer Res.* 2:245-52. The single chain antibody can be dimerized or multimerized to generate multivalent antibodies having specificities for different epitopes of the same target 26199, 33530, 33949, 47148, 50226, 58764, 62113, 32144, 32235, 23565, 13305, 14911, 86216, 25206 or 8843 protein.

In a preferred embodiment, the antibody has reduced or no ability to bind an Fc receptor. For example, it is an isotype or subtype, fragment or other mutant, which does not support binding to an Fc receptor, e.g., it has a mutagenized or deleted Fc receptor binding region.

An antibody (or fragment thereof) may be conjugated to a therapeutic moiety such as a cytotoxin, a therapeutic agent or a radioactive ion. A cytotoxin or cytotoxic agent includes any agent that is detrimental to cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, puromycin, maytansinoids, e.g., maytansinol (see U.S. Pat. No. 5,208,020), CC-1065 (see U.S. Pat. Nos. 5,475,092, 5,585,499, 5,846,545) and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, CC-1065, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine, vinblastine, taxol and maytansinoids).

Radioactive ions include, but are not limited to, iodine, yttrium and praseodymium.

The conjugates of the invention can be used for modifying a given biological response, the therapeutic moiety is not to be construed as limited to classical chemical therapeutic agents. For example, the therapeutic moiety may be a protein or polypeptide possessing a desired biological activity. Such proteins may include, for example, a toxin such as abrin, ricin A, pseudomonas exotoxin, or diphtheria toxin; a protein such as tumor necrosis factor, α-interferon, β-interferon, nerve growth factor, platelet derived growth factor, tissue plasminogen activator; or, biological response modifiers such as, for example, lymphokines, interleukin-1 ("IL-1"), interleukin-2 ("IL-2"), interleukin-6 ("IL-6"), granulocyte macrophase colony stimulating factor ("G-CSF"), granulocyte colony stimulating factor ("G-CSF"), or other growth factors.

Alternatively, an antibody can be conjugated to a second antibody to form an antibody heteroconjugate as described by Segal in U.S. Pat. No. 4,676,980.

An anti-26199, 33530, 33949, 47148, 50226, 58764, 62113, 32144, 32235, 23565, 13305, 14911, 86216, 25206 or 8843 antibody (e.g., monoclonal antibody) can be used to isolate 26199, 33530, 33949, 47148, 50226, 58764, 62113, 32144, 32235, 23565, 13305, 14911, 86216, 25206 or 8843 by standard techniques, such as affinity chromatography or immunoprecipitation. Moreover, an anti-26199, 33530, 33949, 47148, 50226, 58764, 62113, 32144, 32235, 23565, 13305, 14911, 86216, 25206 or 8843 antibody can be used to detect 26199, 33530, 33949, 47148, 50226, 58764, 62113, 32144, 32235, 23565, 13305, 14911, 86216, 25206 or 8843 protein (e.g., in a cellular lysate or cell supernatant) in order to evaluate the abundance and pattern of expression of the protein. Anti-26199, 33530, 33949, 47148, 50226, 58764, 62113, 32144, 32235, 23565, 13305, 14911, 86216, 25206 or 8843 antibodies can be used diagnostically to monitor protein levels in tissue as part of a clinical testing procedure, e.g., to determine the efficacy of a given treatment regimen. Detection can be facilitated by coupling (i.e., physically linking) the antibody to a detectable substance (i.e., antibody labelling). Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^{3}H$.

In preferred embodiments, an antibody can be made by immunizing with a purified 26199, 33530, 33949, 47148, 50226, 58764, 62113, 32144, 32235, 23565, 13305, 14911, 86216, 25206 or 8843 antigen, or a fragment thereof, e.g., a fragment described herein, a membrane associated antigen, tissues, e.g., crude tissue preparations, whole cells, preferably living cells, lysed cells, or cell fractions, e.g., membrane fractions.

Antibodies which bind only a native 26199, 33530, 33949, 47148, 50226, 58764, 62113, 32144, 32235, 23565, 13305, 14911, 86216, 25206 or 8843 protein, only denatured or otherwise non-native 26199, 33530, 33949, 47148, 50226, 58764, 62113, 32144, 32235, 23565, 13305, 14911, 86216, 25206 or 8843 protein, or which bind both, are within the invention. Antibodies with linear or conformational epitopes are within the invention. Conformational epitopes sometimes can be identified by identifying antibodies which bind to native but not denatured 26199, 33530, 33949, 47148, 50226, 58764, 62113, 32144, 32235, 23565, 13305, 14911, 86216, 25206 or 8843 protein.

Recombinant Expression Vectors, Host Cells and Genetically Engineered Cells

In another aspect, the invention includes, vectors, preferably expression vectors, containing a nucleic acid encoding a polypeptide described herein. As used herein, the term "vector" refers to a nucleic acid molecule capable of transporting another nucleic acid to which it has been linked and can include a plasmid, cosmid or viral vector. The vector can be capable of autonomous replication or it can integrate into a host DNA. Viral vectors include, e.g., replication defective retroviruses, adenoviruses and adeno-associated viruses.

A vector can include a 26199, 33530, 33949, 47148, 50226, 58764, 62113, 32144, 32235, 23565, 13305, 14911, 86216, 25206 or 8843 nucleic acid in a form suitable for expression of the nucleic acid in a host cell.

Preferably the recombinant expression vector includes one or more regulatory sequences operatively linked to the nucleic acid sequence to be expressed. The term "regulatory sequence" includes promoters, enhancers and other expression control elements (e.g., polyadenylation signals). Regulatory sequences include those which direct constitutive expression of a nucleotide sequence, as well as tissue-specific regulatory and/or inducible sequences. The design of the expression vector can depend on such factors as the choice of the host cell to be transformed, the level of expression of protein desired, and the like. The expression vectors of the invention can be introduced into host cells to thereby produce proteins or polypeptides, including fusion proteins or polypeptides, encoded by nucleic acids as described herein (e.g., 26199, 33530, 33949, 47148, 50226, 58764, 62113, 32144, 32235, 23565, 13305, 14911, 86216, 25206 or 8843 proteins, mutant forms of 26199, 33530, 33949, 47148, 50226, 58764, 62113, 32144, 32235, 23565, 13305, 14911, 86216, 25206 or 8843 proteins, fusion proteins, and the like).

The recombinant expression vectors of the invention can be designed for expression of 26199, 33530, 33949, 47148, 50226, 58764, 62113, 32144, 32235, 23565, 13305, 14911, 86216, 25206 or 8843 proteins in prokaryotic or eukaryotic cells. For example, polypeptides of the invention can be expressed in *E. coli*, insect cells (e.g., using baculovirus expression vectors), yeast cells or mammalian cells. Suitable host cells are discussed further in Goeddel, (1990) *Gene Expression Technology: Methods in Enzymology* 185, Academic Press, San Diego, Calif. Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith and Johnson (1988) *Gene* 67:31-40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

Purified fusion proteins can be used in 26199, 33530, 33949, 47148, 50226, 58764, 62113, 32144, 32235, 23565, 13305, 14911, 86216, 25206 or 8843 activity assays, (e.g., direct assays or competitive assays described in detail below), or to generate antibodies specific or selective for 26199, 33530, 33949, 47148, 50226, 58764, 62113, 32144, 32235, 23565, 13305, 14911, 86216, 25206 or 8843 proteins. In a preferred embodiment, a fusion protein expressed in a retroviral expression vector of the present invention can be used to infect bone marrow cells which are subsequently transplanted into irradiated recipients. The pathology of the subject recipient is then examined after sufficient time has passed (e.g., six weeks).

To maximize recombinant protein expression in *E. coli* is to express the protein in a host bacteria with an impaired capacity to proteolytically cleave the recombinant protein (Gottesman (1990) *Gene Expression Technology: Methods in Enzymology* 185, Academic Press, San Diego, Calif. 119-128). Another strategy is to alter the nucleic acid sequence of the nucleic acid to be inserted into an expression vector so that the individual codons for each amino acid are those preferentially utilized in *E. coli* (Wada et al., (1992) *Nucleic Acids Res.* 20:2111-2118). Such alteration of nucleic acid sequences of the invention can be carried out by standard DNA synthesis techniques.

The 26199, 33530, 33949, 47148, 50226, 58764, 62113, 32144, 32235, 23565, 13305, 14911, 86216, 25206 or 8843 expression vector can be a yeast expression vector, a vector for expression in insect cells, e.g., a baculovirus expression vector or a vector suitable for expression in mammalian cells.

When used in mammalian cells, the expression vector's control functions are often provided by viral regulatory elements. For example, commonly used promoters are derived from polyoma, Adenovirus 2, cytomegalovirus and Simian Virus 40.

In another embodiment, the recombinant mammalian expression vector is capable of directing expression of the nucleic acid preferentially in a particular cell type (e.g., tissue-specific regulatory elements are used to express the nucleic acid). Non-limiting examples of suitable tissue-specific promoters include the albumin promoter (liver-specific; Pinkert et al. (1987) *Genes Dev.* 1:268-277), lymphoid-specific promoters (Calame and Eaton (1988) *Adv. Immunol.* 43:235-275), in particular promoters of T cell receptors (Winoto and Baltimore (1989) *EMBO J.* 8:729-733) and immunoglobulins (Banerji et al. (1983) *Cell* 33:729-740; Queen and Baltimore (1983) *Cell* 33:741-748), neuron-specific promoters (e.g., the neurofilament promoter; Byrne and Ruddle (1989) *Proc. Natl. Acad. Sci. USA* 86:5473-5477), pancreas-specific promoters (Edlund et al. (1985) *Science* 230:912-916), and mammary gland-specific promoters (e.g., milk whey promoter; U.S. Pat. No. 4,873,316 and European Application Publication No. 264,166). Developmentally-regulated promoters are also encompassed, for example, the murine hox promoters (Kessel and Gruss (1990) *Science* 249:374-379) and the α-fetoprotein promoter (Campes and Tilghman (1989) *Genes Dev.* 3:537-546).

The invention further provides a recombinant expression vector comprising a DNA molecule of the invention cloned into the expression vector in an antisense orientation. Regulatory sequences (e.g., viral promoters and/or enhancers) operatively linked to a nucleic acid cloned in the antisense orientation can be chosen which direct the constitutive, tissue specific or cell type specific expression of antisense RNA in a variety of cell types. The antisense expression vector can be in the form of a recombinant plasmid, phagemid or attenuated virus. For a discussion of the regulation of gene expression using antisense genes see Weintraub et al., (1986) *Reviews—Trends in Genetics* 1:1.

Another aspect the invention provides a host cell which includes a nucleic acid molecule described herein, e.g., a 26199, 33530, 33949, 47148, 50226, 58764, 62113, 32144, 32235, 23565, 13305, 14911, 86216, 25206 or 8843 nucleic acid molecule within a recombinant expression vector or a 26199, 33530, 33949, 47148, 50226, 58764, 62113, 32144, 32235, 23565, 13305, 14911, 86216, 25206 or 8843 nucleic acid molecule containing sequences which allow it to homologously recombine into a specific site of the host cell's genome. The terms "host cell" and "recombinant host cell" are used interchangeably herein. Such terms refer not only to the particular subject cell but to the progeny or potential progeny of such a cell. Because certain modifications can occur in succeeding generations due to either mutation or environmental influences, such progeny may not, in fact, be identical to the parent cell, but are still included within the scope of the term as used herein.

A host cell can be any prokaryotic or eukaryotic cell. For example, a 26199, 33530, 33949, 47148, 50226, 58764, 62113, 32144, 32235, 23565, 13305, 14911, 86216, 25206 or 8843 protein can be expressed in bacterial cells such as *E. coli*, insect cells, yeast or mammalian cells (such as Chinese hamster ovary (CHO) cells or CV-1 origin, SV-40 (COS) cells). Other suitable host cells are known to those skilled in the art.

Vector DNA can be introduced into host cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation.

A host cell of the invention can be used to produce (i.e., express) a 26199, 33530, 33949, 47148, 50226, 58764, 62113, 32144, 32235, 23565, 13305, 14911, 86216, 25206 or 8843 protein. Accordingly, the invention further provides methods for producing a 26199, 33530, 33949, 47148, 50226, 58764, 62113, 32144, 32235, 23565, 13305, 14911, 86216, 25206 or 8843 protein using the host cells of the invention. In one embodiment, the method includes culturing the host cell of the invention (into which a recombinant expression vector encoding a 26199, 33530, 33949, 47148, 50226, 58764, 62113, 32144, 32235, 23565, 13305, 14911, 86216, 25206 or 8843 protein has been introduced) in a suitable medium such that a 26199, 33530, 33949, 47148, 50226, 58764, 62113, 32144, 32235, 23565, 13305, 14911, 86216, 25206 or 8843 protein is produced. In another embodiment, the method further includes isolating a 26199, 33530, 33949, 47148, 50226, 58764, 62113, 32144, 32235, 23565, 13305, 14911, 86216, 25206 or 8843 protein from the medium or the host cell.

In another aspect, the invention features, a cell or purified preparation of cells which include a 26199, 33530, 33949, 47148, 50226, 58764, 62113, 32144, 32235, 23565, 13305, 14911, 86216, 25206 or 8843 transgene, or which otherwise misexpress 26199, 33530, 33949, 47148, 50226, 58764, 62113, 32144, 32235, 23565, 13305, 14911, 86216, 25206 or 8843. The cell preparation can consist of human or non-human cells, e.g., rodent cells, e.g., mouse or rat cells, rabbit cells, or pig cells. In preferred embodiments, the cell or cells include a 26199, 33530, 33949, 47148, 50226, 58764, 62113, 32144, 32235, 23565, 13305, 14911, 86216, 25206 or 8843 transgene, e.g., a heterologous form of a 26199, 33530, 33949, 47148, 50226, 58764, 62113, 32144, 32235, 23565, 13305, 14911, 86216, 25206 or 8843, e.g., a gene derived from humans (in the case of a non-human cell). The 26199, 33530, 33949, 47148, 50226, 58764, 62113, 32144, 32235, 23565, 13305, 14911, 86216, 25206 or 8843 transgene can be misexpressed, e.g., overexpressed or underexpressed. In other preferred embodiments, the cell or cells include a gene which misexpresses an endogenous 26199, 33530, 33949, 47148, 50226, 58764, 62113, 32144, 32235, 23565, 13305, 14911, 86216, 25206 or 8843, e.g., a gene the expression of which is disrupted, e.g., a knockout. Such cells can serve as a model for studying disorders which are related to mutated or misexpressed 26199, 33530, 33949, 47148, 50226, 58764, 62113, 32144, 32235, 23565, 13305, 14911, 86216, 25206 or 8843 alleles or for use in drug screening.

In another aspect, the invention features, a human cell, e.g., a hematopoietic stem cell, transformed with nucleic acid which encodes a subject 26199, 33530, 33949, 47148, 50226, 58764, 62113, 32144, 32235, 23565, 13305, 14911, 86216, 25206 or 8843 polypeptide.

Also provided are cells, preferably human cells, e.g., human hematopoietic or fibroblast cells, in which an endogenous 26199, 33530, 33949, 47148, 50226, 58764, 62113, 32144, 32235, 23565, 13305, 14911, 86216, 25206 or 8843 is under the control of a regulatory sequence that does not normally control the expression of the endogenous 26199, 33530, 33949, 47148, 50226, 58764, 62113, 32144, 32235, 23565, 13305, 14911, 86216, 25206 or 8843 gene. The expression characteristics of an endogenous gene within a cell, e.g., a cell line or microorganism, can be modified by inserting a heterologous DNA regulatory element into the genome of the cell such that the inserted regulatory element is operably linked to the endogenous 26199, 33530, 33949, 47148, 50226, 58764, 62113, 32144, 32235, 23565, 13305, 14911, 86216, 25206 or 8843 gene. For example, an endogenous 26199, 33530, 33949, 47148, 50226, 58764, 62113, 32144, 32235, 23565, 13305, 14911, 86216, 25206 or 8843 gene which is "transcriptionally silent," e.g., not normally expressed, or expressed only at very low levels, can be activated by inserting a regulatory element which is capable of promoting the expression of a normally expressed gene product in that cell. Techniques such as targeted homologous recombinations, can be used to insert the heterologous DNA as described in, e.g., Chappel, U.S. Pat. No. 5,272,071; WO 91/06667, published in May 16, 1991.

Transgenic Animals

The invention provides non-human transgenic animals. Such animals are useful for studying the function and/or activity of a 26199, 33530, 33949, 47148, 50226, 58764, 62113, 32144, 32235, 23565, 13305, 14911, 86216, 25206 or 8843 protein and for identifying and/or evaluating modulators of 26199, 33530, 33949, 47148, 50226, 58764, 62113, 32144, 32235, 23565, 13305, 14911, 86216, 25206 or 8843 activity. As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, and the like. A transgene is exogenous DNA or a rearrangement, e.g., a deletion of endogenous chromosomal DNA, which preferably is integrated into or occurs in the genome of the cells of a transgenic animal. A transgene can direct the expression of an encoded gene product in one or more cell types or tissues of the transgenic animal, other transgenes, e.g., a knockout, reduce expression. Thus, a transgenic animal can be one in which an endogenous 26199, 33530, 33949, 47148, 50226, 58764, 62113, 32144, 32235, 23565, 13305, 14911, 86216, 25206 or 8843 gene has been altered by, e.g., by homologous recombination between the endogenous gene and an exogenous DNA molecule introduced into a cell of the animal, e.g., an embryonic cell of the animal, prior to development of the animal.

Intronic sequences and polyadenylation signals can also be included in the transgene to increase the efficiency of expression of the transgene. A tissue-specific regulatory sequence(s) can be operably linked to a transgene of the invention to direct expression of a 26199, 33530, 33949, 47148, 50226, 58764, 62113, 32144, 32235, 23565, 13305, 14911, 86216, 25206 or 8843 protein to particular cells. A transgenic founder animal can be identified based upon the presence of a 26199, 33530, 33949, 47148, 50226, 58764, 62113, 32144, 32235, 23565, 13305, 14911, 86216, 25206 or 8843 transgene in its genome and/or expression of 26199, 33530, 33949, 47148, 50226, 58764, 62113, 32144, 32235, 23565, 13305, 14911, 86216, 25206 or 8843 mRNA in tissues or cells of the animals. A transgenic founder animal can then be used to breed additional animals carrying the transgene. Moreover, transgenic animals carrying a transgene encoding a 26199, 33530, 33949, 47148, 50226, 58764, 62113, 32144, 32235, 23565, 13305, 14911, 86216, 25206 or 8843 protein can further be bred to other transgenic animals carrying other transgenes.

26199, 33530, 33949, 47148, 50226, 58764, 62113, 32144, 32235, 23565, 13305, 14911, 86216, 25206 or 8843 proteins or polypeptides can be expressed in transgenic animals or plants, e.g., a nucleic acid encoding the protein or polypeptide can be introduced into the genome of an animal. In preferred embodiments the nucleic acid is placed under the control of a tissue specific promoter, e.g., a milk or egg specific promoter, and recovered from the milk or eggs produced by the animal. Suitable animals are mice, pigs, cows, goats, and sheep.

The invention also includes a population of cells from a transgenic animal, as discussed, e.g., below.

Uses

The nucleic acid molecules, proteins, protein homologs, and antibodies described herein can be used in one or more of the following methods: a) screening assays; b) predictive medicine (e.g., diagnostic assays, prognostic assays, monitoring clinical trials, and pharmacogenetics); and c) methods of treatment (e.g., therapeutic and prophylactic).

The isolated nucleic acid molecules of the invention can be used, for example, to express a 26199, 33530, 33949, 47148, 50226, 58764, 62113, 32144, 32235, 23565, 13305, 14911, 86216, 25206 or 8843 protein (e.g., via a recombinant expression vector in a host cell in gene therapy applications), to detect a 26199, 33530, 33949, 47148, 50226, 58764, 62113, 32144, 32235, 23565, 13305, 14911, 86216, 25206 or 8843 mRNA (e.g., in a biological sample) or a genetic alteration in a 26199, 33530, 33949, 47148, 50226, 58764, 62113, 32144, 32235, 23565, 13305, 14911, 86216, 25206 or 8843 gene, and to modulate 26199, 33530, 33949, 47148, 50226, 58764, 62113, 32144, 32235, 23565, 13305, 14911, 86216, 25206 or 8843 activity, as described further below. The 26199, 33530, 33949, 47148, 50226, 58764, 62113, 32144, 32235, 23565, 13305, 14911, 86216, 25206 or 8843 proteins can be used to treat disorders characterized by insufficient or excessive production of a 26199, 33530, 33949, 47148, 50226, 58764, 62113, 32144, 32235, 23565, 13305, 14911, 86216, 25206 or 8843 substrate or production of 26199, 33530, 33949, 47148, 50226, 58764, 62113, 32144, 32235, 23565, 13305, 14911, 86216, 25206 or 8843 inhibitors. In addition, the 26199, 33530, 33949, 47148, 50226, 58764, 62113, 32144, 32235, 23565, 13305, 14911, 86216, 25206 or 8843 proteins can be used to screen for naturally occurring 26199, 33530, 33949, 47148, 50226, 58764, 62113, 32144, 32235, 23565, 13305, 14911, 86216, 25206 or 8843 substrates, to screen for drugs or compounds which modulate 26199, 33530, 33949, 47148, 50226, 58764, 62113, 32144, 32235, 23565, 13305, 14911, 86216, 25206 or 8843 activity, as well as to treat disorders characterized by insufficient or excessive production of 26199, 33530, 33949, 47148, 50226, 58764, 62113, 32144, 32235, 23565, 13305, 14911, 86216, 25206 or 8843 protein or production of 26199, 33530, 33949, 47148, 50226, 58764, 62113, 32144, 32235, 23565, 13305, 14911, 86216, 25206 or 8843 protein forms which have decreased, aberrant or unwanted activity compared to 26199, 33530, 33949, 47148, 50226, 58764, 62113, 32144, 32235, 23565, 13305, 14911, 86216, 25206 or 8843 wild type protein (e.g., aberrant or deficient arginine methyltransferase activity, glycosyltransferase activity, gamma-glutamyltraspeptidase activity, phosphoribosylglycinamide transferase activity, acyltransferase activity, acyl-CoA dehydrogenase activity, fatty acid amide hydrolase activity, aminotransferase activity, zinc carboxypeptidase activity, protein kinase activity, DEAD helicase activity, short-chain dehydrogenase/reductase activity or phosphatase activity, or other activity). Moreover, the anti-26199, 33530, 33949, 47148, 50226, 58764, 62113, 32144, 32235, 23565, 13305, 14911, 86216, 25206 or 8843 antibodies of the invention can be used to detect and isolate 26199, 33530, 33949, 47148, 50226, 58764, 62113, 32144, 32235, 23565, 13305, 14911, 86216, 25206 or 8843 proteins, regulate the bioavailability of 26199, 33530, 33949, 47148, 50226, 58764, 62113, 32144, 32235, 23565, 13305, 14911, 86216, 25206 or 8843 proteins, and modulate 26199, 33530, 33949, 47148, 50226, 58764, 62113, 32144, 32235, 23565, 13305, 14911, 86216, 25206 or 8843 activity.

A method of evaluating a compound for the ability to interact with, e.g., bind, a subject 26199, 33530, 33949, 47148, 50226, 58764, 62113, 32144, 32235, 23565, 13305, 14911, 86216, 25206 or 8843 polypeptide is provided. The method includes: contacting the compound with the subject 26199, 33530, 33949, 47148, 50226, 58764, 62113, 32144, 32235, 23565, 13305, 14911, 86216, 25206 or 8843 polypeptide; and evaluating ability of the compound to interact with, e.g., to bind or form a complex with the subject 26199, 33530, 33949, 47148, 50226, 58764, 62113, 32144, 32235, 23565, 13305, 14911, 86216, 25206 or 8843 polypeptide. This method can be performed in vitro, e.g., in a cell free system, or in vivo, e.g., in a two-hybrid interaction trap assay. This method can be used to identify naturally occurring molecules which interact with subject 26199, 33530, 33949, 47148, 50226, 58764, 62113, 32144, 32235, 23565, 13305, 14911, 86216, 25206 or 8843 polypeptide. It can also be used to find natural or synthetic inhibitors of subject 26199, 33530, 33949, 47148, 50226, 58764, 62113, 32144, 32235, 23565, 13305, 14911, 86216, 25206 or 8843 polypeptide. Screening methods are discussed in more detail below.

Screening Assays

The invention provides methods (also referred to herein as "screening assays") for identifying modulators, i.e., candidate or test compounds or agents (e.g., proteins, peptides, peptidomimetics, peptoids, small molecules or other drugs) which bind to 26199, 33530, 33949, 47148, 50226, 58764, 62113, 32144, 32235, 23565, 13305, 14911, 86216, 25206 or 8843 proteins, have a stimulatory or inhibitory effect on, for example, 26199, 33530, 33949, 47148, 50226, 58764, 62113, 32144, 32235, 23565, 13305, 14911, 86216, 25206 or 8843 expression or 26199, 33530, 33949, 47148, 50226, 58764, 62113, 32144, 32235, 23565, 13305, 14911, 86216, 25206 or 8843 activity, or have a stimulatory or inhibitory effect on, for example, the expression or activity of a 26199, 33530, 33949, 47148, 50226, 58764, 62113, 32144, 32235, 23565, 13305, 14911, 86216, 25206 or 8843 substrate. Compounds thus identified can be used to modulate the activity of target gene products (e.g., 26199, 33530, 33949, 47148, 50226, 58764, 62113, 32144, 32235, 23565, 13305, 14911, 86216, 25206 or 8843 genes) in a therapeutic protocol, to elaborate the biological function of the target gene product, or to identify compounds that disrupt normal target gene interactions.

In one embodiment, the invention provides assays for screening candidate or test compounds which are substrates of a 26199, 33530, 33949, 47148, 50226, 58764, 62113, 32144, 32235, 23565, 13305, 14911, 86216, 25206 or 8843 protein or polypeptide or a biologically active portion thereof. In another embodiment, the invention provides assays for screening candidate or test compounds which bind to or modulate the activity of a 26199, 33530, 33949, 47148, 50226, 58764, 62113, 32144, 32235, 23565, 13305, 14911, 86216, 25206 or 8843 protein or polypeptide or a biologically active portion thereof.

The test compounds of the present invention can be obtained using any of the numerous approaches in combinatorial library methods known in the art, including: biological libraries; peptoid libraries (libraries of molecules having the functionalities of peptides, but with a novel, non-peptide backbone which are resistant to enzymatic degradation but which nevertheless remain bioactive; see, e.g., Zuckermann et al. (1994) *J. Med. Chem.* 37:2678-85); spatially addressable parallel solid phase or solution phase libraries; synthetic library methods requiring deconvolution; the 'one-bead one-compound' library method; and synthetic library methods using affinity chromatography selection. The biological library and peptoid library approaches are limited to peptide libraries, while the other four approaches are applicable to peptide, non-peptide oligomer or small molecule libraries of compounds (Lam (1997) *Anticancer Drug Des.* 12:145).

Examples of methods for the synthesis of molecular libraries can be found in the art, for example in: DeWit et al. (1993) *Proc. Natl. Acad. Sci. U.S.A.* 90:6909-13; Erb et al. (1994) *Proc. Natl. Acad. Sci. USA* 91:11422-426; Zuckermann et al. (1994). *J. Med. Chem.* 37:2678-85; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and in Gallop et al. (1994) *J. Med. Chem.* 37:1233-51.

Libraries of compounds can be presented in solution (e.g., Houghten (1992) *Biotechniques* 13:412-421), or on beads (Lam (1991) *Nature* 354:82-84), chips (Fodor (1993) *Nature* 364:555-556), bacteria (Ladner, U.S. Pat. No. 5,223,409), spores (Ladner U.S. Pat. No. '409), plasmids (Cull et al. (1992) *Proc Natl Acad Sci USA* 89:1865-1869) or on phage (Scott and Smith (1990) *Science* 249:386-390; Devlin (1990) *Science* 249:404-406; Cwirla et al. (1990) *Proc. Natl. Acad. Sci.* 87:6378-6382; Felici (1991) *J. Mol. Biol.* 222:301-310; Ladner supra.).

In one embodiment, an assay is a cell-based assay in which a cell which expresses a 26199, 33530, 33949, 47148, 50226, 58764, 62113, 32144, 32235, 23565, 13305, 14911, 86216, 25206 or 8843 protein or biologically active portion thereof is contacted with a test compound, and the ability of the test compound to modulate 26199, 33530, 33949, 47148, 50226, 58764, 62113, 32144, 32235, 23565, 13305, 14911, 86216, 25206 or 8843 activity is determined. Determining the ability of the test compound to modulate 26199, 33530, 33949, 47148, 50226, 58764, 62113, 32144, 32235, 23565, 13305, 14911, 86216, 25206 or 8843 activity can be accomplished by monitoring, for example, arginine methyltransferase activity, glycosyltransferase activity, gamma-glutamyltraspeptidase activity, phosphoribosylglycinamide transferase activity, acyltransferase activity, acyl-CoA dehydrogenase activity, fatty acid amide hydrolase activity, aminotransferase activity, zinc carboxypeptidase activity, protein kinase activity, DEAD helicase activity, short-chain dehydrogenase/reductase activity or phosphatase activity, or other activity. The cell, for example, can be of mammalian origin, e.g., human.

The ability of the test compound to modulate 26199, 33530, 33949, 47148, 50226, 58764, 62113, 32144, 32235, 23565, 13305, 14911, 86216, 25206 or 8843 binding to a compound, e.g., a 26199, 33530, 33949, 47148, 50226, 58764, 62113, 32144, 32235, 23565, 13305, 14911, 86216, 25206 or 8843 substrate, or to bind to 26199, 33530, 33949, 47148, 50226, 58764, 62113, 32144, 32235, 23565, 13305, 14911, 86216, 25206 or 8843 can also be evaluated. This can be accomplished, for example, by coupling the compound, e.g., the substrate, with a radioisotope or enzymatic label such that binding of the compound, e.g., the substrate, to 26199, 33530, 33949, 47148, 50226, 58764, 62113, 32144, 32235, 23565, 13305, 14911, 86216, 25206 or 8843 can be determined by detecting the labeled compound, e.g., substrate, in a complex. Alternatively, 26199, 33530, 33949, 47148, 50226, 58764, 62113, 32144, 32235, 23565, 13305, 14911, 86216, 25206 or 8843 could be coupled with a radioisotope or enzymatic label to monitor the ability of a test compound to modulate 26199, 33530, 33949, 47148, 50226, 58764, 62113, 32144, 32235, 23565, 13305, 14911, 86216, 25206 or 8843 binding to a 26199, 33530, 33949, 47148, 50226, 58764, 62113, 32144, 32235, 23565, 13305, 14911, 86216, 25206 or 8843 substrate in a complex. For example, compounds (e.g., 26199, 33530, 33949, 47148, 50226, 58764, 62113, 32144, 32235, 23565, 13305, 14911, 86216, 25206 or 8843 substrates) can be labeled with $^{125}I$, $^{14}C$, $^{35}S$ or $^{3}H$, either directly or indirectly, and the radioisotope detected by direct counting of radioemmission or by scintillation counting. Alternatively, compounds can be enzymatically labeled with, for example, horseradish peroxidase, alkaline phosphatase, or luciferase, and the enzymatic label detected by determination of conversion of an appropriate substrate to product.

The ability of a compound (e.g., a 26199, 33530, 33949, 47148, 50226, 58764, 62113, 32144, 32235, 23565, 13305, 14911, 86216, 25206 or 8843 substrate) to interact with 26199, 33530, 33949, 47148, 50226, 58764, 62113, 32144, 32235, 23565, 13305, 14911, 86216, 25206 or 8843 with or without the labeling of any of the interactants can be evaluated. For example, a microphysiometer can be used to detect the interaction of a compound with 26199, 33530, 33949, 47148, 50226, 58764, 62113, 32144, 32235, 23565, 13305, 14911, 86216, 25206 or 8843 without the labeling of either the compound or the 26199, 33530, 33949, 47148, 50226, 58764, 62113, 32144, 32235, 23565, 13305, 14911, 86216, 25206 or 8843. McConnell et al. (1992) *Science* 257:1906-1912. As used herein, a "microphysiometer" (e.g., Cytosensor) is an analytical instrument that measures the rate at which a cell acidifies its environment using a light-addressable potentiometric sensor (LAPS). Changes in this acidification rate can be used as an indicator of the interaction between a compound and 26199, 33530, 33949, 47148, 50226, 58764, 62113, 32144, 32235, 23565, 13305, 14911, 86216, 25206 or 8843.

In yet another embodiment, a cell-free assay is provided in which a 26199, 33530, 33949, 47148, 50226, 58764, 62113, 32144, 32235, 23565, 13305, 14911, 86216, 25206 or 8843 protein or biologically active portion thereof is contacted with a test compound and the ability of the test compound to bind to the 26199, 33530, 33949, 47148, 50226, 58764, 62113, 32144, 32235, 23565, 13305, 14911, 86216, 25206 or 8843 protein or biologically active portion thereof is evaluated. Preferred biologically active portions of the 26199, 33530, 33949, 47148, 50226, 58764, 62113, 32144, 32235, 23565, 13305, 14911, 86216, 25206 or 8843 proteins to be used in assays of the present invention include fragments which participate in interactions with non-26199, 33530, 33949, 47148, 50226, 58764, 62113, 32144, 32235, 23565, 13305, 14911, 86216, 25206 or 8843 molecules, e.g., fragments with high surface probability scores.

Soluble and/or membrane-bound forms of isolated proteins (e.g., 26199, 33530, 33949, 47148, 50226, 58764, 62113, 32144, 32235, 23565, 13305, 14911, 86216, 25206 or 8843 proteins or biologically active portions thereof) can be used in the cell-free assays of the invention. When membrane-bound forms of the protein are used, it may be desirable to utilize a solubilizing agent. Examples of such solubilizing agents include non-ionic detergents such as n-octylglucoside, n-dodecylglucoside, n-dodecylmaltoside, octanoyl-N-methylglucamide, decanoyl-N-methylglucamide, Triton® X-100, Triton® X-114, Thesit®, Isotridecypoly(ethylene glycol ether)$_n$, 3-[(3-cholamidopropyl)dimethylamminio]-1-propane sulfonate (CHAPS), 3-[(3-cholamidopropyl)dimethylamminio]-2-hydroxy-1-propane sulfonate (CHAPSO), or N-dodecyl=N,N-dimethyl-3-ammonio-1-propane sulfonate.

Cell-free assays involve preparing a reaction mixture of the target gene protein and the test compound under conditions and for a time sufficient to allow the two components to interact and bind, thus forming a complex that can be removed and/or detected.

The interaction between two molecules can also be detected, e.g., using fluorescence energy transfer (FET) (see, for example, Lakowicz et al., U.S. Pat. No. 5,631,169; Stavrianopoulos, et al., U.S. Pat. No. 4,868,103). A fluorophore label on the first, 'donor' molecule is selected such that its emitted fluorescent energy will be absorbed by a fluorescent label on a second, 'acceptor' molecule, which in turn is able to fluoresce due to the absorbed energy. Alternately, the 'donor' protein molecule can simply utilize the natural fluorescent energy of tryptophan residues. Labels are chosen that emit different wavelengths of light, such that the 'acceptor' molecule label can be differentiated from that of the 'donor'. Since the efficiency of energy transfer between the labels is related to the distance separating the molecules, the spatial relationship between the molecules can be assessed. In a situation in which binding occurs between the molecules, the fluorescent emission of the 'acceptor' molecule label in the assay should be maximal. An FET binding event can be conveniently measured through standard fluorometric detection means well known in the art (e.g., using a fluorimeter).

In another embodiment, determining the ability of the 26199, 33530, 33949, 47148, 50226, 58764, 62113, 32144, 32235, 23565, 13305, 14911, 86216, 25206 or 8843 protein to bind to a target molecule can be accomplished using real-time Biomolecular Interaction Analysis (BIA) (see, e.g., Sjolander and Urbaniczky (1991) *Anal. Chem.* 63:2338-2345 and Szabo et al. (1995) *Curr. Opin. Struct. Biol.* 5:699-705). "Surface plasmon resonance" or "BIA" detects biospecific interactions in real time, without labeling any of the interactants (e.g., BIAcore). Changes in the mass at the binding surface (indicative of a binding event) result in alterations of the refractive index of light near the surface (the optical phenomenon of surface plasmon resonance (SPR)), resulting in a detectable signal which can be used as an indication of real-time reactions between biological molecules.

In one embodiment, the target gene product or the test substance is anchored onto a solid phase. The target gene product/test compound complexes anchored on the solid phase can be detected at the end of the reaction. Preferably, the target gene product can be anchored onto a solid surface, and the test compound, (which is not anchored), can be labeled, either directly or indirectly, with detectable labels discussed herein.

It may be desirable to immobilize either 26199, 33530, 33949, 47148, 50226, 58764, 62113, 32144, 32235, 23565, 13305, 14911, 86216, 25206 or 8843, an anti-26199, 33530, 33949, 47148, 50226, 58764, 62113, 32144, 32235, 23565, 13305, 14911, 86216, 25206 or 8843 antibody or its target molecule to facilitate separation of complexed from uncomplexed forms of one or both of the proteins, as well as to accommodate automation of the assay. Binding of a test compound to a 26199, 33530, 33949, 47148, 50226, 58764, 62113, 32144, 32235, 23565, 13305, 14911, 86216, 25206 or 8843 protein, or interaction of a 26199, 33530, 33949, 47148, 50226, 58764, 62113, 32144, 32235, 23565, 13305, 14911, 86216, 25206 or 8843 protein with a target molecule in the presence and absence of a candidate compound, can be accomplished in any vessel suitable for containing the reactants. Examples of such vessels include microtiter plates, test tubes, and micro-centrifuge tubes. In one embodiment, a fusion protein can be provided which adds a domain that allows one or both of the proteins to be bound to a matrix. For example, glutathione-S-transferase/26199, 33530, 33949, 47148, 50226, 58764, 62113, 32144, 32235, 23565, 13305, 14911, 86216, 25206 or 8843 fusion proteins or glutathione-5-transferase/target fusion proteins can be adsorbed onto glutathione sepharose beads (Sigma Chemical, St. Louis, Mo.) or glutathione derivatized microtiter plates, which are then combined with the test compound or the test compound and either the non-adsorbed target protein or 26199, 33530, 33949, 47148, 50226, 58764, 62113, 32144, 32235, 23565, 13305, 14911, 86216, 25206 or 8843 protein, and the mixture incubated under conditions conducive to complex formation (e.g., at physiological conditions for salt and pH).

Following incubation, the beads or microtiter plate wells are washed to remove any unbound components, the matrix immobilized in the case of beads, complex determined either directly or indirectly, for example, as described above. Alternatively, the complexes can be dissociated from the matrix, and the level of 26199, 33530, 33949, 47148, 50226, 58764, 62113, 32144, 32235, 23565, 13305, 14911, 86216, 25206 or 8843 binding or activity determined using standard techniques.

Other techniques for immobilizing either a 26199, 33530, 33949, 47148, 50226, 58764, 62113, 32144, 32235, 23565, 13305, 14911, 86216, 25206 or 8843 protein or a target molecule on matrices include using conjugation of biotin and streptavidin. Biotinylated 26199, 33530, 33949, 47148, 50226, 58764, 62113, 32144, 32235, 23565, 13305, 14911, 86216, 25206 or 8843 protein or target molecules can be prepared from biotin-NHS(N-hydroxy-succinimide) using techniques known in the art (e.g., biotinylation kit, Pierce Chemicals, Rockford, Ill.), and immobilized in the wells of streptavidin-coated 96 well plates (Pierce Chemical).

In order to conduct the assay, the non-immobilized component is added to the coated surface containing the anchored component. After the reaction is complete, unreacted components are removed (e.g., by washing) under conditions such that any complexes formed will remain immobilized on the solid surface. The detection of complexes anchored on the solid surface can be accomplished in a number of ways. Where the previously non-immobilized component is pre-labeled, the detection of label immobilized on the surface indicates that complexes were formed. Where the previously non-immobilized component is not pre-labeled, an indirect label can be used to detect complexes anchored on the surface; e.g., using a labeled antibody specific or selective for the immobilized component (the antibody, in turn, can be directly labeled or indirectly labeled with, e.g., a labeled anti-Ig antibody).

In one embodiment, this assay is performed utilizing antibodies reactive with 26199, 33530, 33949, 47148, 50226, 58764, 62113, 32144, 32235, 23565, 13305, 14911, 86216, 25206 or 8843 protein or target molecules but which do not interfere with binding of the 26199, 33530, 33949, 47148, 50226, 58764, 62113, 32144, 32235, 23565, 13305, 14911, 86216, 25206 or 8843 protein to its target molecule. Such antibodies can be derivatized to the wells of the plate, and unbound target or 26199, 33530, 33949, 47148, 50226, 58764, 62113, 32144, 32235, 23565, 13305, 14911, 86216, 25206 or 8843 protein trapped in the wells by antibody conjugation. Methods for detecting such complexes, in addition to those described above for the GST-immobilized complexes, include immunodetection of complexes using antibodies reactive with the 26199, 33530, 33949, 47148, 50226, 58764, 62113, 32144, 32235, 23565, 13305, 14911, 86216, 25206 or 8843 protein or target molecule, as well as enzyme-linked assays which rely on detecting an enzymatic activity associated with the 26199, 33530, 33949, 47148, 50226, 58764, 62113, 32144, 32235, 23565, 13305, 14911, 86216, 25206 or 8843 protein or target molecule.

Alternatively, cell free assays can be conducted in a liquid phase. In such an assay, the reaction products are separated from unreacted components, by any of a number of standard techniques, including but not limited to: differential centrifugation (see, for example, Rivas and Minton (1993) *Trends Biochem Sci* 18:284-7); chromatography (gel filtration chromatography, ion-exchange chromatography); electrophoresis (see, e.g., Ausubel et al., eds. (1999) *Current Protocols in Molecular Biology*, J. Wiley, New York); and immunoprecipitation (see, for example, Ausubel et al., eds. (1999) *Current Protocols in Molecular Biology*, J. Wiley, New York). Such resins and chromatographic techniques are known to one skilled in the art (see, e.g., Heegaard (1998) *J Mol Recognit* 11:141-8; Hage and Tweed (1997) *J Chromatogr B Biomed Sci Appl.* 699:499-525). Further, fluorescence energy transfer can also be conveniently utilized, as described herein, to detect binding without further purification of the complex from solution.

In a preferred embodiment, the assay includes contacting the 26199, 33530, 33949, 47148, 50226, 58764, 62113, 32144, 32235, 23565, 13305, 14911, 86216, 25206 or 8843 protein or biologically active portion thereof with a known compound which binds 26199, 33530, 33949, 47148, 50226, 58764, 62113, 32144, 32235, 23565, 13305, 14911, 86216, 25206 or 8843 to form an assay mixture, contacting the assay mixture with a test compound, and determining the ability of the test compound to interact with a 26199, 33530, 33949, 47148, 50226, 58764, 62113, 32144, 32235, 23565, 13305, 14911, 86216, 25206 or 8843 protein, wherein determining the ability of the test compound to interact with a 26199, 33530, 33949, 47148, 50226, 58764, 62113, 32144, 32235, 23565, 13305, 14911, 86216, 25206 or 8843 protein includes determining the ability of the test compound to preferentially bind to 26199, 33530, 33949, 47148, 50226, 58764, 62113, 32144, 32235, 23565, 13305, 14911, 86216, 25206 or 8843 or biologically active portion thereof, or to modulate the activity of a target molecule, as compared to the known compound.

The target gene products of the invention can, in vivo, interact with one or more cellular or extracellular macromolecules, such as proteins. For the purposes of this discussion, such cellular and extracellular macromolecules are referred to herein as "binding partners." Compounds that disrupt such interactions can be useful in regulating the activity of the target gene product. Such compounds can include, but are not limited to molecules such as antibodies, peptides, and small molecules. The preferred target genes/products for use in this embodiment are the 26199, 33530, 33949, 47148, 50226, 58764, 62113, 32144, 32235, 23565, 13305, 14911, 86216, 25206 or 8843 genes herein identified. In an alternative embodiment, the invention provides methods for determining the ability of the test compound to modulate the activity of a 26199, 33530, 33949, 47148, 50226, 58764, 62113, 32144, 32235, 23565, 13305, 14911, 86216, 25206 or 8843 protein through modulation of the activity of a downstream effector of a 26199, 33530, 33949, 47148, 50226, 58764, 62113, 32144, 32235, 23565, 13305, 14911, 86216, 25206 or 8843 target molecule. For example, the activity of the effector molecule on an appropriate target can be determined, or the binding of the effector to an appropriate target can be determined, as previously described.

To identify compounds that interfere with the interaction between the target gene product and its cellular or extracellular binding partner(s), a reaction mixture containing the target gene product and the binding partner is prepared, under conditions and for a time sufficient, to allow the two products to form complex. In order to test an inhibitory agent, the reaction mixture is provided in the presence and absence of the test compound. The test compound can be initially included in the reaction mixture, or can be added at a time subsequent to the addition of the target gene and its cellular or extracellular binding partner. Control reaction mixtures are incubated without the test compound or with a placebo. The formation of any complexes between the target gene product and the cellular or extracellular binding partner is then detected. The formation of a complex in the control reaction, but not in the reaction mixture containing the test compound, indicates that the compound interferes with the interaction of the target gene product and the interactive binding partner.

Additionally, complex formation within reaction mixtures containing the test compound and normal target gene product can also be compared to complex formation within reaction mixtures containing the test compound and mutant target gene product. This comparison can be important in those cases wherein it is desirable to identify compounds that disrupt interactions of mutant but not normal target gene products.

These assays can be conducted in a heterogeneous or homogeneous format. Heterogeneous assays involve anchoring either the target gene product or the binding partner onto a solid phase, and detecting complexes anchored on the solid phase at the end of the reaction. In homogeneous assays, the entire reaction is carried out in a liquid phase. In either approach, the order of addition of reactants can be varied to obtain different information about the compounds being tested. For example, test compounds that interfere with the interaction between the target gene products and the binding partners, e.g., by competition, can be identified by conducting the reaction in the presence of the test substance. Alternatively, test compounds that disrupt preformed complexes, e.g., compounds with higher binding constants that displace one of the components from the complex, can be tested by adding the test compound to the reaction mixture after complexes have been formed. The various formats are briefly described below.

In a heterogeneous assay system, either the target gene product or the interactive cellular or extracellular binding partner, is anchored onto a solid surface (e.g., a microtiter plate), while the non-anchored species is labeled, either directly or indirectly. The anchored species can be immobilized by non-covalent or covalent attachments. Alternatively, an immobilized antibody specific or selective for the species to be anchored can be used to anchor the species to the solid surface.

In order to conduct the assay, the partner of the immobilized species is exposed to the coated surface with or without the test compound. After the reaction is complete, unreacted components are removed (e.g., by washing) and any complexes formed will remain immobilized on the solid surface. Where the non-immobilized species is pre-labeled, the detection of label immobilized on the surface indicates that complexes were formed. Where the non-immobilized species is not pre-labeled, an indirect label can be used to detect complexes anchored on the surface; e.g., using a labeled antibody specific or selective for the initially non-immobilized species (the antibody, in turn, can be directly labeled or indirectly labeled with, e.g., a labeled anti-Ig antibody). Depending upon the order of addition of reaction components, test compounds that inhibit complex formation or that disrupt preformed complexes can be detected.

Alternatively, the reaction can be conducted in a liquid phase in the presence or absence of the test compound, the reaction products separated from unreacted components, and complexes detected; e.g., using an immobilized antibody specific or selective for one of the binding components to anchor any complexes formed in solution, and a labeled antibody specific or selective for the other partner to detect anchored complexes. Again, depending upon the order of addition of reactants to the liquid phase, test compounds that inhibit complex or that disrupt preformed complexes can be identified.

In an alternate embodiment of the invention, a homogeneous assay can be used. For example, a preformed complex of the target gene product and the interactive cellular or extracellular binding partner product is prepared in that either the target gene products or their binding partners are labeled, but the signal generated by the label is quenched due to complex formation (see, e.g., U.S. Pat. No. 4,109,496 that utilizes this approach for immunoassays). The addition of a test substance that competes with and displaces one of the species from the preformed complex will result in the generation of a signal above background. In this way, test substances that disrupt target gene product-binding partner interaction can be identified.

In yet another aspect, the 26199, 33530, 33949, 47148, 50226, 58764, 62113, 32144, 32235, 23565, 13305, 14911, 86216, 25206 or 8843 proteins can be used as "bait proteins" in a two-hybrid assay or three-hybrid assay (see, e.g., U.S. Pat. No. 5,283,317; Zervos et al. (1993) *Cell* 72:223-232; Madura et al. (1993) *J. Biol. Chem.* 268:12046-12054; Bartel et al. (1993) *Biotechniques* 14:920-924; Iwabuchi et al. (1993) *Oncogene* 8:1693-1696; and Brent WO94/10300), to identify other proteins, which bind to or interact with 26199, 33530, 33949, 47148, 50226, 58764, 62113, 32144, 32235, 23565, 13305, 14911, 86216, 25206 or 8843 ("26199, 33530, 33949, 47148, 50226, 58764, 62113, 32144, 32235, 23565, 13305, 14911, 86216, 25206 or 8843-binding proteins" or "26199, 33530, 33949, 47148, 50226, 58764, 62113, 32144, 32235, 23565, 13305, 14911, 86216, 25206 or 8843-bp") and are involved in 26199, 33530, 33949, 47148, 50226, 58764, 62113, 32144, 32235, 23565, 13305, 14911, 86216, 25206 or 8843 activity. Such 26199, 33530, 33949, 47148, 50226, 58764, 62113, 32144, 32235, 23565, 13305, 14911, 86216, 25206 or 8843-bps can be activators or inhibitors of signals by the 26199, 33530, 33949, 47148, 50226, 58764, 62113, 32144, 32235, 23565, 13305, 14911, 86216, 25206 or 8843 proteins or 26199, 33530, 33949, 47148, 50226, 58764, 62113, 32144, 32235, 23565, 13305, 14911, 86216, 25206 or 8843 targets as, for example, downstream elements of a 26199, 33530, 33949, 47148, 50226, 58764, 62113, 32144, 32235, 23565, 13305, 14911, 86216, 25206 or 8843-mediated signaling pathway.

The two-hybrid system is based on the modular nature of most transcription factors, which consist of separable DNA-binding and activation domains. Briefly, the assay utilizes two different DNA constructs. In one construct, the gene that codes for a 26199, 33530, 33949, 47148, 50226, 58764, 62113, 32144, 32235, 23565, 13305, 14911, 86216, 25206 or 8843 protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. (Alternatively the: 26199, 33530, 33949, 47148, 50226, 58764, 62113, 32144, 32235, 23565, 13305, 14911, 86216, 25206 or 8843 protein can be the fused to the activator domain.) If the "bait" and the "prey" proteins are able to interact, in vivo, forming a 26199, 33530, 33949, 47148, 50226, 58764, 62113, 32144, 32235, 23565, 13305, 14911, 86216, 25206 or 8843-dependent complex, the DNA-binding and activation domains of the transcription factor are brought into close proximity. This proximity allows transcription of a reporter gene (e.g., lacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the 26199, 33530, 33949, 47148, 50226, 58764, 62113, 32144, 32235, 23565, 13305, 14911, 86216, 25206 or 8843 protein.

In another embodiment, modulators of 26199, 33530, 33949, 47148, 50226, 58764, 62113, 32144, 32235, 23565, 13305, 14911, 86216, 25206 or 8843 expression are identified. For example, a cell or cell free mixture is contacted with a candidate compound and the expression of 26199, 33530, 33949, 47148, 50226, 58764, 62113, 32144, 32235, 23565, 13305, 14911, 86216, 25206 or 8843 mRNA or protein evaluated relative to the level of expression of 26199, 33530, 33949, 47148, 50226, 58764, 62113, 32144, 32235, 23565, 13305, 14911, 86216, 25206 or 8843 mRNA or protein in the absence of the candidate compound. When expression of 26199, 33530, 33949, 47148, 50226, 58764, 62113, 32144, 32235, 23565, 13305, 14911, 86216, 25206 or 8843 mRNA or protein is greater in the presence of the candidate compound than in its absence, the candidate compound is identified as a stimulator of 26199, 33530, 33949, 47148, 50226, 58764, 62113, 32144, 32235, 23565, 13305, 14911, 86216, 25206 or 8843 mRNA or protein expression. Alternatively, when expression of 26199, 33530, 33949, 47148, 50226, 58764, 62113, 32144, 32235, 23565, 13305, 14911, 86216, 25206 or 8843 mRNA or protein is less (statistically significantly less) in the presence of the candidate compound than in its absence, the candidate compound is identified as an inhibitor of 26199, 33530, 33949, 47148, 50226, 58764, 62113, 32144, 32235, 23565, 13305, 14911, 86216, 25206 or 8843 mRNA or protein expression. The level of 26199, 33530, 33949, 47148, 50226, 58764, 62113, 32144, 32235, 23565, 13305, 14911, 86216, 25206 or 8843 mRNA or protein expression can be determined by methods described herein for detecting 26199, 33530, 33949, 47148, 50226, 58764, 62113, 32144, 32235, 23565, 13305, 14911, 86216, 25206 or 8843 mRNA or protein.

In another aspect, the invention pertains to a combination of two or more of the assays described herein. For example, a modulating agent can be identified using a cell-based or a cell free assay, and the ability of the agent to modulate the activity of a 26199, 33530, 33949, 47148, 50226, 58764, 62113, 32144, 32235, 23565, 13305, 14911, 86216, 25206 or 8843 protein can be confirmed in vivo, e.g., in an animal such as an animal model for aberrant or deficient arginine methyltransferase activity, glycosyltransferase activity, gamma-glutamyltraspeptidase activity, phosphoribosylglycinamide transferase activity, acyltransferase activity, acyl-CoA dehydrogenase activity, fatty acid amide hydrolase activity, aminotransferase activity, zinc carboxypeptidase activity, protein kinase activity, DEAD helicase activity, short-chain dehydrogenase/reductase activity or phosphatase activity.

This invention further pertains to novel agents identified by the above-described screening assays. Accordingly, it is within the scope of this invention to further use an agent identified as described herein (e.g., a 26199, 33530, 33949, 47148, 50226, 58764, 62113, 32144, 32235, 23565, 13305, 14911, 86216, 25206 or 8843 modulating agent, an antisense 26199, 33530, 33949, 47148, 50226, 58764, 62113, 32144, 32235, 23565, 13305, 14911, 86216, 25206 or 8843 nucleic acid molecule, a 26199, 33530, 33949, 47148, 50226, 58764, 62113, 32144, 32235, 23565, 13305, 14911, 86216, 25206 or 8843-specific antibody, or a 26199, 33530, 33949, 47148, 50226, 58764, 62113, 32144, 32235, 23565, 13305, 14911, 86216, 25206 or 8843-binding partner) in an appropriate animal model to determine the efficacy, toxicity, side effects, or mechanism of action, of treatment with such an agent. Furthermore, novel agents identified by the above-described screening assays can be used for treatments as described herein.

Detection Assays

Portions or fragments of the nucleic acid sequences identified herein can be used as polynucleotide reagents. For example, these sequences can be used to: (i) map their respective genes on a chromosome e.g., to locate gene regions associated with genetic disease or to associate 26199, 33530, 33949, 47148, 50226, 58764, 62113, 32144, 32235, 23565, 13305, 14911, 86216, 25206 or 8843 with a disease; (ii) identify an individual from a minute biological sample (tissue typing); and (iii) aid in forensic identification of a biological sample. These applications are described in the subsections below.

Chromosome Mapping

The 26199, 33530, 33949, 47148, 50226, 58764, 62113, 32144, 32235, 23565, 13305, 14911, 86216, 25206 or 8843 nucleotide sequences or portions thereof can be used to map the location of the 26199, 33530, 33949, 47148, 50226, 58764, 62113, 32144, 32235, 23565, 13305, 14911, 86216, 25206 or 8843 genes on a chromosome. This process is called chromosome mapping. Chromosome mapping is useful in correlating the 26199, 33530, 33949, 47148, 50226, 58764, 62113, 32144, 32235, 23565, 13305, 14911, 86216, 25206 or 8843 sequences with genes associated with disease.

Briefly, 26199, 33530, 33949, 47148, 50226, 58764, 62113, 32144, 32235, 23565, 13305, 14911, 86216, 25206 or 8843 genes can be mapped to chromosomes by preparing PCR primers (preferably 15-25 bp in length) from the 26199, 33530, 33949, 47148, 50226, 58764, 62113, 32144, 32235, 23565, 13305, 14911, 86216, 25206 or 8843 nucleotide sequences. These primers can then be used for PCR screening of somatic cell hybrids containing individual human chromosomes. Only those hybrids containing the human gene corresponding to the 26199, 33530, 33949, 47148, 50226, 58764, 62113, 32144, 32235, 23565, 13305, 14911, 86216, 25206 or 8843 sequences will yield an amplified fragment.

A panel of somatic cell hybrids in which each cell line contains either a single human chromosome or a small number of human chromosomes, and a full set of mouse chromosomes, can allow easy mapping of individual genes to specific human chromosomes. (D'Eustachio et al. (1983) *Science* 220:919-924).

Other mapping strategies e.g., in situ hybridization (described in Fan et al. (1990) *Proc. Natl. Acad. Sci. USA,* 87:6223-27), pre-screening with labeled flow-sorted chromosomes, and pre-selection by hybridization to chromosome specific cDNA libraries can be used to map 26199, 33530, 33949, 47148, 50226, 58764, 62113, 32144, 32235, 23565, 13305, 14911, 86216, 25206 or 8843 to a chromosomal location.

Fluorescence in situ hybridization (FISH) of a DNA sequence to a metaphase chromosomal spread can further be used to provide a precise chromosomal location in one step. The FISH technique can be used with a DNA sequence as short as 500 or 600 bases. However, clones larger than 1,000 bases have a higher likelihood of binding to a unique chromosomal location with sufficient signal intensity for simple detection. Preferably 1,000 bases, and more preferably 2,000 bases will suffice to get good results at a reasonable amount of time. For a review of this technique, see Verma et al. (1988) Human Chromosomes: A Manual of Basic Techniques, Pergamon Press, New York).

Reagents for chromosome mapping can be used individually to mark a single chromosome or a single site on that chromosome, or panels of reagents can be used for marking multiple sites and/or multiple chromosomes. Reagents corresponding to noncoding regions of the genes actually are preferred for mapping purposes. Coding sequences are more likely to be conserved within gene families, thus increasing the chance of cross hybridizations during chromosomal mapping.

Once a sequence has been mapped to a precise chromosomal location, the physical position of the sequence on the chromosome can be correlated with genetic map data. (Such data are found, for example, in McKusick, *Mendelian Inheritance in Man*, available on-line through Johns Hopkins University Welch Medical Library). The relationship between a gene and a disease, mapped to the same chromosomal region, can then be identified through linkage analysis (co-inheritance of physically adjacent genes), described in, for example, Egeland et al. (1987) *Nature,* 325:783-787.

Moreover, differences in the DNA sequences between individuals affected and unaffected with a disease associated with the 26199, 33530, 33949, 47148, 50226, 58764, 62113, 32144, 32235, 23565, 13305, 14911, 86216, 25206 or 8843 gene, can be determined. If a mutation is observed in some or all of the affected individuals but not in any unaffected individuals, then the mutation is likely to be the causative agent of the particular disease. Comparison of affected and unaffected individuals generally involves first looking for structural alterations in the chromosomes, such as deletions or translocations that are visible from chromosome spreads or detectable using PCR based on that DNA sequence. Ultimately, complete sequencing of genes from several individuals can be performed to confirm the presence of a mutation and to distinguish mutations from polymorphisms.

Tissue Typing 26199, 33530, 33949, 47148, 50226, 58764, 62113, 32144, 32235, 23565, 13305, 14911, 86216, 25206 or 8843 sequences can be used to identify individuals from biological samples using, e.g., restriction fragment length polymorphism (RFLP). In this technique, an individual's genomic DNA is digested with one or more restriction enzymes, the fragments separated, e.g., in a Southern blot, and probed to yield bands for identification. The sequences of the present invention are useful as additional DNA markers for RFLP (described in U.S. Pat. No. 5,272,057).

Furthermore, the sequences of the present invention can also be used to determine the actual base-by-base DNA sequence of selected portions of an individual's genome. Thus, the 26199, 33530, 33949, 47148, 50226, 58764, 62113, 32144, 32235, 23565, 13305, 14911, 86216, 25206 or 8843 nucleotide sequences described herein can be used to prepare two PCR primers from the 5' and 3' ends of the sequences. These primers can then be used to amplify an individual's DNA and subsequently sequence it. Panels of corresponding DNA sequences from individuals, prepared in this manner, can provide unique individual identifications, as each individual will have a unique set of such DNA sequences due to allelic differences.

Allelic variation occurs to some degree in the coding regions of these sequences, and to a greater degree in the noncoding regions. Each of the sequences described herein can, to some degree, be used as a standard against which DNA from an individual can be compared for identification purposes. Because greater numbers of polymorphisms occur in the noncoding regions, fewer sequences are necessary to differentiate individuals. The noncoding sequences of SEQ ID NO:1, 4, 7, 10, 13, 16, 53, 61, 67, 78, 88, 100, 113, 122 or 129 can provide positive individual identification with a panel of perhaps 10 to 1,000 primers which each yield a noncoding amplified sequence of 100 bases. If predicted coding sequences, such as those in SEQ ID NO:3, 6, 9, 12, 15, 18, 55, 63, 69, 80, 90, 102, 115, 124 or 131 are used, a more appropriate number of primers for positive individual identification would be 500-2,000.

If a panel of reagents from 26199, 33530, 33949, 47148, 50226, 58764, 62113, 32144, 32235, 23565, 13305, 14911, 86216, 25206 or 8843 nucleotide sequences described herein is used to generate a unique identification database for an individual, those same reagents can later be used to identify tissue from that individual. Using the unique identification database, positive identification of the individual, living or dead, can be made from extremely small tissue samples.

Use of Partial 26199, 33530, 33949, 47148, 50226, 58764, 62113, 32144, 32235, 23565, 13305, 14911, 86216, 25206 or 8843 Sequences in Forensic Biology DNA-based identification techniques can also be used in forensic biology. To make such an identification, PCR technology can be used to amplify DNA sequences taken from very small biological samples such as tissues, e.g., hair or skin, or body fluids, e.g., blood, saliva, or semen found at a crime scene. The amplified sequence can then be compared to a standard, thereby allowing identification of the origin of the biological sample.

The sequences of the present invention can be used to provide polynucleotide reagents, e.g., PCR primers, targeted to specific loci in the human genome, which can enhance the reliability of DNA-based forensic identifications by, for example, providing another "identification marker" (i.e. another DNA sequence that is unique to a particular individual). As mentioned above, actual base sequence information can be used for identification as an accurate alternative to patterns formed by restriction enzyme generated fragments. Sequences targeted to noncoding regions of SEQ ID NO:1, 4, 7, 10, 13, 16, 53, 61, 67, 78, 88, 100, 113, 122 or 129 (e.g., fragments derived from the noncoding regions of SEQ ID NO:1, 4, 7, 10, 13, 16, 53, 61, 67, 78, 88, 100, 113, 122 or 129 having a length of at least 20 bases, preferably at least 30 bases) are particularly appropriate for this use.

The 26199, 33530, 33949, 47148, 50226, 58764, 62113, 32144, 32235, 23565, 13305, 14911, 86216, 25206 or 8843 nucleotide sequences described herein can further be used to provide polynucleotide reagents, e.g., labeled or labelable probes which can be used in, for example, an in situ hybridization technique, to identify a specific tissue. This can be very useful in cases where a forensic pathologist is presented with a tissue of unknown origin. Panels of such 26199, 33530, 33949, 47148, 50226, 58764, 62113, 32144, 32235, 23565, 13305, 14911, 86216, 25206 or 8843 probes can be used to identify tissue by species and/or by organ type.

In a similar fashion, these reagents, e.g., 26199, 33530, 33949, 47148, 50226, 58764, 62113, 32144, 32235, 23565, 13305, 14911, 86216, 25206 or 8843 primers or probes can be used to screen tissue culture for contamination (i.e. screen for the presence of a mixture of different types of cells in a culture).

Predictive Medicine

The present invention also pertains to the field of predictive medicine in which diagnostic assays, prognostic assays, and monitoring clinical trials are used for prognostic (predictive) purposes to thereby treat an individual.

Generally, the invention provides, a method of determining if a subject is at risk for a disorder related to a lesion in or the misexpression of a gene which encodes 26199, 33530, 33949, 47148, 50226, 58764, 62113, 32144, 32235, 23565, 13305, 14911, 86216, 25206 or 8843.

Such disorders include, e.g., a disorder associated with the misexpression of 26199, 33530, 33949, 47148, 50226, 58764, 62113, 32144, 32235, 23565, 13305, 14911, 86216, 25206 or 8843 gene; cellular proliferative and/or differentiative disorder, a brain, platelet, breast, colon, kidney (renal), lung, ovarian, prostate, hematopoeitic, pancreatic, skeletal muscle, skin (dermal), bone metabolism, immune, e.g., inflammatory, cardiovascular, endothelial cell, liver, viral diseases, pain, metabolic, neurological or CNS, erythroid or anemic disorder.

The method includes one or more of the following: detecting, in a tissue of the subject, the presence or absence of a mutation which affects the expression of the 26199, 33530, 33949, 47148, 50226, 58764, 62113, 32144, 32235, 23565, 13305, 14911, 86216, 25206 or 8843 gene, or detecting the presence or absence of a mutation in a region which controls the expression of the gene, e.g., a mutation in the 5' control region; detecting, in a tissue of the subject, the presence or absence of a mutation which alters the structure of the 26199, 33530, 33949, 47148, 50226, 58764, 62113, 32144, 32235, 23565, 13305, 14911, 86216, 25206 or 8843 gene; detecting, in a tissue of the subject, the misexpression of the 26199, 33530, 33949, 47148, 50226, 58764, 62113, 32144, 32235, 23565, 13305, 14911, 86216, 25206 or 8843 gene, at the mRNA level, e.g., detecting a non-wild type level of an mRNA; or detecting, in a tissue of the subject, the misexpression of the gene, at the protein level, e.g., detecting a non-wild type level of a 26199, 33530, 33949, 47148, 50226, 58764, 62113, 32144, 32235, 23565, 13305, 14911, 86216, 25206 or 8843 polypeptide.

In preferred embodiments the method includes: ascertaining the existence of at least one of: a deletion of one or more nucleotides from the 26199, 33530, 33949, 47148, 50226, 58764, 62113, 32144, 32235, 23565, 13305, 14911, 86216, 25206 or 8843 gene; an insertion of one or more nucleotides into the gene, a point mutation, e.g., a substitution of one or more nucleotides of the gene, a gross chromosomal rearrangement of the gene, e.g., a translocation, inversion, or deletion.

For example, detecting the genetic lesion can include: (i) providing a probe/primer including an oligonucleotide containing a region of nucleotide sequence which hybridizes to a sense or antisense sequence from SEQ ID NO:1, 4, 7, 10, 13, 16, 53, 61, 67, 78, 88, 100, 113, 122 or 129, or naturally occurring mutants thereof or 5' or 3' flanking sequences naturally associated with the 26199, 33530, 33949, 47148, 50226, 58764, 62113, 32144, 32235, 23565, 13305, 14911, 86216, 25206 or 8843 gene; (ii) exposing the probe/primer to nucleic acid of the tissue; and detecting, by hybridization, e.g., in situ hybridization, of the probe/primer to the nucleic acid, the presence or absence of the genetic lesion.

In preferred embodiments detecting the misexpression includes ascertaining the existence of at least one of: an alteration in the level of a messenger RNA transcript of the 26199, 33530, 33949, 47148, 50226, 58764, 62113, 32144, 32235, 23565, 13305, 14911, 86216, 25206 or 8843 gene; the presence of a non-wild type splicing pattern of a messenger RNA transcript of the gene; or a non-wild type level of 26199, 33530, 33949, 47148, 50226, 58764, 62113, 32144, 32235, 23565, 13305, 14911, 86216, 25206 or 8843.

Methods of the invention can be used prenatally or to determine if a subject's offspring will be at risk for a disorder.

In preferred embodiments the method includes determining the structure of a 26199, 33530, 33949, 47148, 50226, 58764, 62113, 32144, 32235, 23565, 13305, 14911, 86216, 25206 or 8843 gene, an abnormal structure being indicative of risk for the disorder.

In preferred embodiments the method includes contacting a sample from the subject with an antibody to the 26199, 33530, 33949, 47148, 50226, 58764, 62113, 32144, 32235, 23565, 13305, 14911, 86216, 25206 or 8843 protein or a nucleic acid, which hybridizes specifically with the gene. These and other embodiments are discussed below.

Diagnostic and Prognostic Assays

The presence, level, or absence of 26199, 33530, 33949, 47148, 50226, 58764, 62113, 32144, 32235, 23565, 13305, 14911, 86216, 25206 or 8843 protein or nucleic acid in a biological sample can be evaluated by obtaining a biological sample from a test subject and contacting the biological sample with a compound or an agent capable of detecting 26199, 33530, 33949, 47148, 50226, 58764, 62113, 32144, 32235, 23565, 13305, 14911, 86216, 25206 or 8843 protein or nucleic acid (e.g., mRNA, genomic DNA) that encodes 26199, 33530, 33949, 47148, 50226, 58764, 62113, 32144, 32235, 23565, 13305, 14911, 86216, 25206 or 8843 protein such that the presence of 26199, 33530, 33949, 47148, 50226, 58764, 62113, 32144, 32235, 23565, 13305, 14911, 86216, 25206 or 8843 protein or nucleic acid is detected in the biological sample. The term "biological sample" includes tissues, cells and biological fluids isolated from a subject, as well as tissues, cells and fluids present within a subject. A preferred biological sample is serum. The level of expression of the 26199, 33530, 33949, 47148, 50226, 58764, 62113, 32144, 32235, 23565, 13305, 14911, 86216, 25206 or 8843 gene can be measured in a number of ways, including, but not limited to: measuring the mRNA encoded by the 26199, 33530, 33949, 47148, 50226, 58764, 62113, 32144, 32235, 23565, 13305, 14911, 86216, 25206 or 8843 genes; measuring the amount of protein encoded by the 26199, 33530, 33949, 47148, 50226, 58764, 62113, 32144, 32235, 23565, 13305, 14911, 86216, 25206 or 8843 genes; or measuring the activity of the protein encoded by the 26199, 33530, 33949, 47148, 50226, 58764, 62113, 32144, 32235, 23565, 13305, 14911, 86216, 25206 or 8843 genes.

The level of mRNA corresponding to the 26199, 33530, 33949, 47148, 50226, 58764, 62113, 32144, 32235, 23565, 13305, 14911, 86216, 25206 or 8843 gene in a cell can be determined both by in situ and by in vitro formats.

The isolated mRNA can be used in hybridization or amplification assays that include, but are not limited to, Southern or Northern analyses, polymerase chain reaction analyses and probe arrays. One preferred diagnostic method for the detection of mRNA levels involves contacting the isolated mRNA with a nucleic acid molecule (probe) that can hybridize to the mRNA encoded by the gene being detected. The nucleic acid probe can be, for example, a full-length 26199, 33530, 33949, 47148, 50226, 58764, 62113, 32144, 32235, 23565, 13305, 14911, 86216, 25206 or 8843 nucleic acid, such as the nucleic acid of SEQ ID NO:1, 4, 7, 10, 13, 16, 53, 61, 67, 78, 88, 100, 113, 122 or 129, or a portion thereof, such as an oligonucleotide of at least 7, 15, 30, 50, 100, 250 or 500 nucleotides in length and sufficient to specifically hybridize under stringent conditions to 26199, 33530, 33949, 47148, 50226, 58764, 62113, 32144, 32235, 23565, 13305, 14911, 86216, 25206 or 8843 mRNA or genomic DNA. Other suitable probes for use in the diagnostic assays are described herein.

In one format, mRNA (or cDNA) is immobilized on a surface and contacted with the probes, for example by running the isolated mRNA on an agarose gel and transferring the mRNA from the gel to a membrane, such as nitrocellulose. In an alternative format, the probes are immobilized on a surface and the mRNA (or cDNA) is contacted with the probes, for example, in a two-dimensional gene chip array. A skilled artisan can adapt known mRNA detection methods for use in detecting the level of mRNA encoded by the 26199, 33530, 33949, 47148, 50226, 58764, 62113, 32144, 32235, 23565, 13305, 14911, 86216, 25206 or 8843 genes.

The level of mRNA in a sample that is encoded by one of 26199, 33530, 33949, 47148, 50226, 58764, 62113, 32144, 32235, 23565, 13305, 14911, 86216, 25206 or 8843 can be evaluated with nucleic acid amplification, e.g., by rtPCR (Mullis (1987) U.S. Pat. No. 4,683,202), ligase chain reaction (Barany (1991) *Proc. Natl. Acad. Sci. USA* 88:189-193), self sustained sequence replication (Guatelli et al., (1990) *Proc. Natl. Acad. Sci. USA* 87:1874-1878), transcriptional amplification system (Kwoh et al., (1989), *Proc. Natl. Acad. Sci. USA* 86:1173-1177), Q-Beta Replicase (Lizardi et al., (1988) *Bio/Technology* 6:1197), rolling circle replication (Lizardi et al., U.S. Pat. No. 5,854,033) or any other nucleic acid amplification method, followed by the detection of the amplified molecules using techniques known in the art. As used herein, amplification primers are defined as being a pair of nucleic acid molecules that can anneal to 5' or 3' regions of a gene (plus and minus strands, respectively, or vice-versa) and contain a short region in between. In general, amplification primers are from about 10 to 30 nucleotides in length and flank a region from about 50 to 200 nucleotides in length. Under appropriate conditions and with appropriate reagents, such primers permit the amplification of a nucleic acid molecule comprising the nucleotide sequence flanked by the primers.

For in situ methods, a cell or tissue sample can be prepared/processed and immobilized on a support, typically a glass slide, and then contacted with a probe that can hybridize to mRNA that encodes the 26199, 33530, 33949, 47148, 50226, 58764, 62113, 32144, 32235, 23565, 13305, 14911, 86216, 25206 or 8843 gene being analyzed.

In another embodiment, the methods further contacting a control sample with a compound or agent capable of detecting 26199, 33530, 33949, 47148, 50226, 58764, 62113, 32144, 32235, 23565, 13305, 14911, 86216, 25206 or 8843 mRNA, or genomic DNA, and comparing the presence of 26199, 33530, 33949, 47148, 50226, 58764, 62113, 32144, 32235, 23565, 13305, 14911, 86216, 25206 or 8843 mRNA or genomic DNA in the control sample with the presence of 26199, 33530, 33949, 47148, 50226, 58764, 62113, 32144, 32235, 23565, 13305, 14911, 86216, 25206 or 8843 mRNA or genomic DNA in the test sample.

A variety of methods can be used to determine the level of protein encoded by 26199, 33530, 33949, 47148, 50226, 58764, 62113, 32144, 32235, 23565, 13305, 14911, 86216, 25206 or 8843. In general, these methods include contacting an agent that selectively binds to the protein, such as an antibody with a sample, to evaluate the level of protein in the sample. In a preferred embodiment, the antibody bears a detectable label. Antibodies can be polyclonal, or more preferably, monoclonal. An intact antibody, or a fragment thereof (e.g., Fab or $F(ab')_2$) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with a detectable substance. Examples of detectable substances are provided herein.

The detection methods can be used to detect 26199, 33530, 33949, 47148, 50226, 58764, 62113, 32144, 32235, 23565, 13305, 14911, 86216, 25206 or 8843 protein in a biological sample in vitro as well as in vivo. In vitro techniques for detection of 26199, 33530, 33949, 47148, 50226, 58764, 62113, 32144, 32235, 23565, 13305, 14911, 86216, 25206 or 8843 protein include enzyme linked immunosorbent assays (ELISAs), immunoprecipitations, immunofluorescence, enzyme immunoassay (EIA), radioimmunoassay (RIA), and Western blot analysis. In vivo techniques for detection of 26199, 33530, 33949, 47148, 50226, 58764, 62113, 32144, 32235, 23565, 13305, 14911, 86216, 25206 or 8843 protein include introducing into a subject a labeled anti-26199, 33530, 33949, 47148, 50226, 58764, 62113, 32144, 32235, 23565, 13305, 14911, 86216, 25206 or 8843 antibody. For example, the antibody can be labeled with a radioactive marker whose presence and location in a subject can be detected by standard imaging techniques.

In another embodiment, the methods further include contacting the control sample with a compound or agent capable of detecting 26199, 33530, 33949, 47148, 50226, 58764, 62113, 32144, 32235, 23565, 13305, 14911, 86216, 25206 or 8843 protein, and comparing the presence of 26199, 33530, 33949, 47148, 50226, 58764, 62113, 32144, 32235, 23565, 13305, 14911, 86216, 25206 or 8843 protein in the control sample with the presence of 26199, 33530, 33949, 47148, 50226, 58764, 62113, 32144, 32235, 23565, 13305, 14911, 86216, 25206 or 8843 protein in the test sample.

The invention also includes kits for detecting the presence of 26199, 33530, 33949, 47148, 50226, 58764, 62113, 32144, 32235, 23565, 13305, 14911, 86216, 25206 or 8843 in a biological sample. For example, the kit can include a compound or agent capable of detecting 26199, 33530, 33949, 47148, 50226, 58764, 62113, 32144, 32235, 23565, 13305, 14911, 86216, 25206 or 8843 protein or mRNA in a biological sample; and a standard. The compound or agent can be packaged in a suitable container. The kit can further comprise instructions for using the kit to detect 26199, 33530, 33949, 47148, 50226, 58764, 62113, 32144, 32235, 23565, 13305, 14911, 86216, 25206 or 8843 protein or nucleic acid.

For antibody-based kits, the kit can include: (1) a first antibody (e.g., attached to a solid support) which binds to a polypeptide corresponding to a marker of the invention; and, optionally, (2) a second, different antibody which binds to either the polypeptide or the first antibody and is conjugated to a detectable agent.

For oligonucleotide-based kits, the kit can include: (1) an oligonucleotide, e.g., a detectably labeled oligonucleotide, which hybridizes to a nucleic acid sequence encoding a polypeptide corresponding to a marker of the invention or (2) a pair of primers useful for amplifying a nucleic acid molecule corresponding to a marker of the invention. The kit can also includes a buffering agent, a preservative, or a protein stabilizing agent. The kit can also includes components necessary for detecting the detectable agent (e.g., an enzyme or a substrate). The kit can also contain a control sample or a series of control samples which can be assayed and compared to the test sample contained. Each component of the kit can be enclosed within an individual container and all of the various containers can be within a single package, along with instructions for interpreting the results of the assays performed using the kit.

The diagnostic methods described herein can identify subjects having, or at risk of developing, a disease or disorder associated with misexpressed or aberrant or unwanted 26199, 33530, 33949, 47148, 50226, 58764, 62113, 32144, 32235, 23565, 13305, 14911, 86216, 25206 or 8843 expression or activity. As used herein, the term "unwanted" includes an unwanted phenomenon involved in a biological response such as pain or deregulated cell proliferation.

In one embodiment, a disease or disorder associated with aberrant or unwanted 26199, 33530, 33949, 47148, 50226, 58764, 62113, 32144, 32235, 23565, 13305, 14911, 86216, 25206 or 8843 expression or activity is identified. A test sample is obtained from a subject and 26199, 33530, 33949, 47148, 50226, 58764, 62113, 32144, 32235, 23565, 13305, 14911, 86216, 25206 or 8843 protein or nucleic acid (e.g., mRNA or genomic DNA) is evaluated, wherein the level, e.g., the presence or absence, of 26199, 33530, 33949, 47148, 50226, 58764, 62113, 32144, 32235, 23565, 13305, 14911, 86216, 25206 or 8843 protein or nucleic acid is diagnostic for a subject having or at risk of developing a disease or disorder associated with aberrant or unwanted 26199, 33530, 33949, 47148, 50226, 58764, 62113, 32144, 32235, 23565, 13305, 14911, 86216, 25206 or 8843 expression or activity. As used herein, a "test sample" refers to a biological sample obtained from a subject of interest, including a biological fluid (e.g., serum), cell sample, or tissue.

The prognostic assays described herein can be used to determine whether a subject can be administered an agent (e.g., an agonist, antagonist, peptidomimetic, protein, peptide, nucleic acid, small molecule, or other drug candidate) to treat a disease or disorder associated with aberrant or unwanted 26199, 33530, 33949, 47148, 50226, 58764, 62113, 32144, 32235, 23565, 13305, 14911, 86216, 25206 or 8843 expression or activity. For example, such methods can be used to determine whether a subject can be effectively treated with an agent for a cellular proliferation or differentiation disorder, a brain, platelet, breast, colon, kidney (renal), lung, ovarian, prostate, hematopoeitic, pancreatic, skeletal muscle, skin (dermal), bone metabolism, immune, e.g., inflammatory, cardiovascular, endothelial cell, liver, viral diseases, pain, metabolic, neurological or CNS, erythroid or anemic disorder.

The methods of the invention can also be used to detect genetic alterations in a 26199, 33530, 33949, 47148, 50226, 58764, 62113, 32144, 32235, 23565, 13305, 14911, 86216, 25206 or 8843 gene, thereby determining if a subject with the altered gene is at risk for a disorder characterized by misregulation in 26199, 33530, 33949, 47148, 50226, 58764, 62113, 32144, 32235, 23565, 13305, 14911, 86216, 25206 or 8843 protein activity or nucleic acid expression, such as a cellular proliferation or differentiation disorder, a brain, platelet, breast, colon, kidney (renal), lung, ovarian, prostate, hematopoeitic, pancreatic, skeletal muscle, skin (dermal), bone metabolism, immune, e.g., inflammatory, cardiovascular, endothelial cell, liver, viral diseases, pain, metabolic, neurological or CNS, erythroid or anemic disorder. In preferred embodiments, the methods include detecting, in a sample from the subject, the presence or absence of a genetic alteration characterized by at least one of an alteration affecting the integrity of a gene encoding a 26199, 33530, 33949, 47148, 50226, 58764, 62113, 32144, 32235, 23565, 13305, 14911, 86216, 25206 or 8843-protein, or the mis-expression of the 26199, 33530, 33949, 47148, 50226, 58764, 62113, 32144, 32235, 23565, 13305, 14911, 86216, 25206 or 8843 gene. For example, such genetic alterations can be detected by ascertaining the existence of at least one of 1) a deletion of one or more nucleotides from a 26199, 33530, 33949, 47148, 50226, 58764, 62113, 32144, 32235, 23565, 13305, 14911, 86216, 25206 or 8843 gene; 2) an addition of one or more nucleotides to a 26199, 33530, 33949, 47148, 50226, 58764, 62113, 32144, 32235, 23565, 13305, 14911, 86216, 25206 or 8843 gene; 3) a substitution of one or more nucleotides of a 26199, 33530, 33949, 47148, 50226, 58764, 62113, 32144, 32235, 23565, 13305, 14911, 86216, 25206 or 8843 gene, 4) a chromosomal rearrangement of a 26199, 33530, 33949, 47148, 50226, 58764, 62113, 32144, 32235, 23565, 13305, 14911, 86216, 25206 or 8843 gene; 5) an alteration in the level of a messenger RNA transcript of a 26199, 33530, 33949, 47148, 50226, 58764, 62113, 32144, 32235, 23565, 13305, 14911, 86216, 25206 or 8843 gene, 6) aberrant modification of a 26199, 33530, 33949, 47148, 50226, 58764, 62113, 32144, 32235, 23565, 13305, 14911, 86216, 25206 or 8843 gene, such as of the methylation pattern of the genomic DNA, 7) the presence of a non-wild type splicing pattern of a messenger RNA transcript of a 26199, 33530, 33949, 47148, 50226, 58764, 62113, 32144, 32235, 23565, 13305, 14911, 86216, 25206 or 8843 gene, 8) a non-wild type level of a 26199, 33530, 33949, 47148, 50226, 58764, 62113, 32144, 32235, 23565, 13305, 14911, 86216, 25206 or 8843-protein, 9) allelic loss of a 26199, 33530, 33949, 47148, 50226, 58764, 62113, 32144, 32235, 23565, 13305, 14911, 86216, 25206 or 8843 gene, and 10) inappropriate post-translational modification of a 26199, 33530, 33949, 47148, 50226, 58764, 62113, 32144, 32235, 23565, 13305, 14911, 86216, 25206 or 8843-protein.

An alteration can be detected without a probe/primer in a polymerase chain reaction, such as anchor PCR or RACE PCR, or, alternatively, in a ligation chain reaction (LCR), the latter of which can be particularly useful for detecting point mutations in the 26199, 33530, 33949, 47148, 50226, 58764, 62113, 32144, 32235, 23565, 13305, 14911, 86216, 25206 or 8843-gene. This method can include the steps of collecting a sample of cells from a subject, isolating nucleic acid (e.g., genomic, mRNA or both) from the sample, contacting the nucleic acid sample with one or more primers which specifically hybridize to a 26199, 33530, 33949, 47148, 50226, 58764, 62113, 32144, 32235, 23565, 13305, 14911, 86216, 25206 or 8843 gene under conditions such that hybridization and amplification of the 26199, 33530, 33949, 47148, 50226, 58764, 62113, 32144, 32235, 23565, 13305, 14911, 86216, 25206 or 8843 gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein. Alternatively, other amplification methods described herein or known in the art can be used.

In another embodiment, mutations in a 26199, 33530, 33949, 47148, 50226, 58764, 62113, 32144, 32235, 23565, 13305, 14911, 86216, 25206 or 8843 gene from a sample cell can be identified by detecting alterations in restriction enzyme cleavage patterns. For example, sample and control DNA is isolated, amplified (optionally), digested with one or more restriction endonucleases, and fragment length sizes are determined, e.g., by gel electrophoresis and compared. Differences in fragment length sizes between sample and control DNA indicates mutations in the sample DNA. Moreover, the use of sequence specific ribozymes (see, for example, U.S. Pat. No. 5,498,531) can be used to score for the presence of specific mutations by development or loss of a ribozyme cleavage site.

In other embodiments, genetic mutations in 26199, 33530, 33949, 47148, 50226, 58764, 62113, 32144, 32235, 23565, 13305, 14911, 86216, 25206 or 8843 can be identified by hybridizing a sample and control nucleic acids, e.g., DNA or RNA, two dimensional arrays, e.g., chip based arrays. Such arrays include a plurality of addresses, each of which is positionally distinguishable from the other. A different probe is located at each address of the plurality. The arrays can have a high density of addresses, e.g., can contain hundreds or thousands of oligonucleotides probes (Cronin et al. (1996) *Human Mutation* 7: 244-255; Kozal et al. (1996) *Nature Medicine* 2: 753-759). For example, genetic mutations in 26199, 33530, 33949, 47148, 50226, 58764, 62113, 32144, 32235, 23565, 13305, 14911, 86216, 25206 or 8843 can be identified in two dimensional arrays containing light-generated DNA probes as described in Cronin, M. T. et al. supra. Briefly, a first hybridization array of probes can be used to scan through long stretches of DNA in a sample and control to identify base changes between the sequences by making linear arrays of sequential overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

In yet another embodiment, any of a variety of sequencing reactions known in the art can be used to directly sequence the 26199, 33530, 33949, 47148, 50226, 58764, 62113, 32144, 32235, 23565, 13305, 14911, 86216, 25206 or 8843 gene and detect mutations by comparing the sequence of the sample 26199, 33530, 33949, 47148, 50226, 58764, 62113, 32144, 32235, 23565, 13305, 14911, 86216, 25206 or 8843 with the corresponding wild-type (control) sequence. Automated sequencing procedures can be utilized when performing the diagnostic assays (Naeve et al. (1995) *Biotechniques* 19:448-53), including sequencing by mass spectrometry.

Other methods for detecting mutations in the 26199, 33530, 33949, 47148, 50226, 58764, 62113, 32144, 32235, 23565, 13305, 14911, 86216, 25206 or 8843 gene include methods in which protection from cleavage agents is used to detect mismatched bases in RNA/RNA or RNA/DNA heteroduplexes (Myers et al. (1985) *Science* 230:1242; Cotton et al. (1988) *Proc. Natl. Acad Sci USA* 85:4397; Saleeba et al. (1992) *Methods Enzymol.* 217:286-295).

In still another embodiment, the mismatch cleavage reaction employs one or more proteins that recognize mismatched base pairs in double-stranded DNA (so called "DNA mismatch repair" enzymes) in defined systems for detecting and mapping point mutations in 26199, 33530, 33949, 47148, 50226, 58764, 62113, 32144, 32235, 23565, 13305, 14911, 86216, 25206 or 8843 cDNAs obtained from samples of cells. For example, the mutY enzyme of *E. coli* cleaves A at G/A mismatches and the thymidine DNA glycosylase from HeLa cells cleaves T at G/T mismatches (Hsu et al. (1994) *Carcinogenesis* 15:1657-1662; U.S. Pat. No. 5,459,039).

In other embodiments, alterations in electrophoretic mobility will be used to identify mutations in 26199, 33530, 33949, 47148, 50226, 58764, 62113, 32144, 32235, 23565, 13305, 14911, 86216, 25206 or 8843 genes. For example, single strand conformation polymorphism (SSCP) can be used to detect differences in electrophoretic mobility between mutant and wild type nucleic acids (Orita et al. (1989) *Proc Natl. Acad. Sci USA:* 86:2766, see also Cotton (1993) *Mutat. Res.* 285:125-144; and Hayashi (1992) *Genet. Anal. Tech. Appl.* 9:73-79). Single-stranded DNA fragments of sample and control 26199, 33530, 33949, 47148, 50226, 58764, 62113, 32144, 32235, 23565, 13305, 14911, 86216, 25206 or 8843 nucleic acids will be denatured and allowed to renature. The secondary structure of single-stranded nucleic acids varies according to sequence, the resulting alteration in electrophoretic mobility enables the detection of even a single base change. The DNA fragments can be labeled or detected with labeled probes. The sensitivity of the assay can be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al. (1991) *Trends Genet* 7:5).

In yet another embodiment, the movement of mutant or wild-type fragments in polyacrylamide gels containing a gradient of denaturant is assayed using denaturing gradient gel electrophoresis (DGGE) (Myers et al. (1985) *Nature* 313: 495). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner (1987) *Biophys Chem* 265:12753).

Examples of other techniques for detecting point mutations include, but are not limited to, selective oligonucleotide hybridization, selective amplification, or selective primer extension (Saiki et al. (1986) *Nature* 324:163); Saiki et al. (1989) *Proc. Natl. Acad. Sci USA* 86:6230).

Alternatively, allele specific amplification technology which depends on selective PCR amplification can be used in conjunction with the instant invention. Oligonucleotides used as primers for specific amplification can carry the mutation of interest in the center of the molecule (so that amplification depends on differential hybridization) (Gibbs et al. (1989) *Nucleic Acids Res.* 17:2437-2448) or at the extreme 3' end of one primer where, under appropriate conditions, mismatch can prevent, or reduce polymerase extension (Prossner (1993) *Tibtech* 11:238). In addition it may be desirable to introduce a novel restriction site in the region of the mutation to create cleavage-based detection (Gasparini et al. (1992) *Mol. Cell. Probes* 6:1). It is anticipated that in certain embodiments amplification can also be performed using Taq ligase for amplification (Barany (1991) *Proc. Natl. Acad. Sci USA* 88:189-93). In such cases, ligation will occur only if there is a perfect match at the 3' end of the 5' sequence making it possible to detect the presence of a known mutation at a specific site by looking for the presence or absence of amplification.

The methods described herein can be performed, for example, by utilizing pre-packaged diagnostic kits comprising at least one probe nucleic acid or antibody reagent described herein, which can be conveniently used, e.g., in clinical settings to diagnose patients exhibiting symptoms or family history of a disease or illness involving a 26199, 33530, 33949, 47148, 50226, 58764, 62113, 32144, 32235, 23565, 13305, 14911, 86216, 25206 or 8843 gene.

Use of 26199, 33530, 33949, 47148, 50226, 58764, 62113, 32144, 32235, 23565, 13305, 14911, 86216, 25206 or 8843 Molecules as Surrogate Markers The 26199, 33530, 33949, 47148, 50226, 58764, 62113, 32144, 32235, 23565, 13305, 14911, 86216, 25206 or 8843 molecules of the invention are also useful as markers of disorders or disease states, as markers for precursors of disease states, as markers for predisposition of disease states, as markers of drug activity, or as markers of the pharmacogenomic profile of a subject. Using the methods described herein, the presence, absence and/or quantity of the 26199, 33530, 33949, 47148, 50226, 58764, 62113, 32144, 32235, 23565, 13305, 14911, 86216, 25206 or 8843 molecules of the invention can be detected, and can be correlated with one or more biological states in vivo. For example, the 26199, 33530, 33949, 47148, 50226, 58764, 62113, 32144, 32235, 23565, 13305, 14911, 86216, 25206 or 8843 molecules of the invention can serve as surrogate markers for one or more disorders or disease states or for conditions leading up to disease states. As used herein, a "surrogate marker" is an objective biochemical marker which correlates with the absence or presence of a disease or disorder, or with the progression of a disease or disorder (e.g., with the presence or absence of a tumor). The presence or quantity of such markers is independent of the disease. Therefore, these markers can serve to indicate whether a particular course of treatment is effective in lessening a disease state or disorder. Surrogate markers are of particular use when the presence or extent of a disease state or disorder is difficult to assess through standard methodologies (e.g., early stage tumors), or when an assessment of disease progression is desired before a potentially dangerous clinical endpoint is reached (e.g., an assessment of cardiovascular disease can be made using cholesterol levels as a surrogate marker, and an analysis of HIV infection can be made using HIV RNA levels as a surrogate marker, well in advance of the undesirable clinical outcomes of myocardial infarction or fully-developed AIDS). Examples of the use of surrogate markers in the art include: Koomen et al. (2000) *J. Mass. Spectrom.* 35: 258-264; and James (1994) *AIDS Treatment News Archive* 209.

The 26199, 33530, 33949, 47148, 50226, 58764, 62113, 32144, 32235, 23565, 13305, 14911, 86216, 25206 or 8843 molecules of the invention are also useful as pharmacodynamic markers. As used herein, a "pharmacodynamic marker" is an objective biochemical marker which correlates specifically with drug effects. The presence or quantity of a pharmacodynamic marker is not related to the disease state or disorder for which the drug is being administered; therefore, the presence or quantity of the marker is indicative of the presence or activity of the drug in a subject. For example, a pharmacodynamic marker can be indicative of the concentration of the drug in a biological tissue, in that the marker is either expressed or transcribed or not expressed or transcribed in that tissue in relationship to the level of the drug. In this fashion, the distribution or uptake of the drug can be monitored by the pharmacodynamic marker. Similarly, the presence or quantity of the pharmacodynamic marker can be related to the presence or quantity of the metabolic product of a drug, such that the presence or quantity of the marker is indicative of the relative breakdown rate of the drug in vivo. Pharmacodynamic markers are of particular use in increasing the sensitivity of detection of drug effects, particularly when the drug is administered in low doses. Since even a small amount of a drug can be sufficient to activate multiple rounds of marker (e.g., a 26199, 33530, 33949, 47148, 50226, 58764, 62113, 32144, 32235, 23565, 13305, 14911, 86216, 25206 or 8843 marker) transcription or expression, the amplified marker can be in a quantity which is more readily detectable than the drug itself. Also, the marker can be more easily detected due to the nature of the marker itself; for example, using the methods described herein, anti-26199, 33530, 33949, 47148, 50226, 58764, 62113, 32144, 32235, 23565, 13305, 14911, 86216, 25206 or 8843 antibodies can be employed in an immune-based detection system for a 26199, 33530, 33949, 47148, 50226, 58764, 62113, 32144, 32235, 23565, 13305, 14911, 86216, 25206 or 8843 protein marker, or 26199, 33530, 33949, 47148, 50226, 58764, 62113, 32144, 32235, 23565, 13305, 14911, 86216, 25206 or 8843-specific radiolabeled probes can be used to detect a 26199, 33530, 33949, 47148, 50226, 58764, 62113, 32144, 32235, 23565, 13305, 14911, 86216, 25206 or 8843 mRNA marker. Furthermore, the use of a pharmacodynamic marker can offer mechanism-based prediction of risk due to drug treatment beyond the range of possible direct observations. Examples of the use of pharmacodynamic markers in the art include: Matsuda et al. U.S. Pat. No. 6,033,862; Hattis et al. (1991) *Env. Health Perspect.* 90: 229-238; Schentag (1999) *Am. J. Health-Syst. Pharm.* 56 Suppl. 3: S21-S24; and Nicolau (1999) *Am. J. Health-Syst. Pharm.* 56 Suppl. 3: S16-S20.

The 26199, 33530, 33949, 47148, 50226, 58764, 62113, 32144, 32235, 23565, 13305, 14911, 86216, 25206 or 8843 molecules of the invention are also useful as pharmacogenomic markers. As used herein, a "pharmacogenomic marker" is an objective biochemical marker which correlates with a specific clinical drug response or susceptibility in a subject (see, e.g., Mcleod et al. (1999) *Eur. J. Cancer* 35:1650-1652). The presence or quantity of the pharmacogenomic marker is related to the predicted response of the subject to a specific drug or class of drugs prior to administration of the drug. By assessing the presence or quantity of one or more pharmacogenomic markers in a subject, a drug therapy which is most appropriate for the subject, or which is predicted to have a greater degree of success, can be selected. For example, based on the presence or quantity of RNA, or protein (e.g., 26199, 33530, 33949, 47148, 50226, 58764, 62113, 32144, 32235, 23565, 13305, 14911, 86216, 25206 or 8843 protein or RNA) for specific tumor markers in a subject, a drug or course of treatment can be selected that is optimized for the treatment of the specific tumor likely to be present in the subject. Similarly, the presence or absence of a specific sequence mutation in 26199, 33530, 33949, 47148, 50226, 58764, 62113, 32144, 32235, 23565, 13305, 14911, 86216, 25206 or 8843 DNA can correlate with a 26199, 33530, 33949, 47148, 50226, 58764, 62113, 32144, 32235, 23565, 13305, 14911, 86216, 25206 or 8843 drug response. The use of pharmacogenomic markers therefore permits the application of the most appropriate treatment for each subject without having to administer the therapy.

Pharmaceutical Compositions

The nucleic acid and polypeptides, fragments thereof, as well as anti-26199, 33530, 33949, 47148, 50226, 58764, 62113, 32144, 32235, 23565, 13305, 14911, 86216, 25206 or 8843 antibodies (also referred to herein as "active compounds") of the invention can be incorporated into pharmaceutical compositions. Such compositions typically include the nucleic acid molecule, protein, or antibody and a pharmaceutically acceptable carrier. As used herein the language "pharmaceutically acceptable carrier" includes solvents, dispersion media, coatings, antibacterial and antifungal agents, isotonic and absorption delaying agents, and the like, compatible with pharmaceutical administration. Supplementary active compounds can also be incorporated into the compositions.

A pharmaceutical composition is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier.

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit high therapeutic indices are preferred. While compounds that exhibit toxic side effects can be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage can vary within this range depending upon the dosage form employed and the route of administration utilized. For any compound used in the method of the invention, the therapeutically effective dose can be estimated initially from cell culture assays. A dose can be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma can be measured, for example, by high performance liquid chromatography.

As defined herein, a therapeutically effective amount of protein or polypeptide (i.e., an effective dosage) ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight. The protein or polypeptide can be administered one time per week for between about 1 to 10 weeks, preferably between 2 to 8 weeks, more preferably between about 3 to 7 weeks, and even more preferably for about 4, 5, or 6 weeks. The skilled artisan will appreciate that certain factors can influence the dosage and timing required to effectively treat a subject, including but not limited to the severity of the disease or disorder, previous treatments, the general health and/or age of the subject, and other diseases present. Moreover, treatment of a subject with a therapeutically effective amount of a protein, polypeptide, or antibody, unconjugated or conjugated as described herein, can include a single treatment or, preferably, can include a series of treatments.

For antibodies, the preferred dosage is 0.1 mg/kg of body weight (generally 10 mg/kg to 20 mg/kg). If the antibody is to act in the brain, a dosage of 50 mg/kg to 100 mg/kg is usually appropriate. Generally, partially human antibodies and fully human antibodies have a longer half-life within the human body than other antibodies. Accordingly, lower dosages and less frequent administration is often possible. Modifications such as lipidation can be used to stabilize antibodies and to enhance uptake and tissue penetration (e.g., into the brain). A method for lipidation of antibodies is described by Cruikshank et al. ((1997) *J. Acquired Immune Deficiency Syndromes and Human Retrovirology* 14:193).

The present invention encompasses agents which modulate expression or activity. An agent can, for example, be a small molecule. For example, such small molecules include, but are not limited to, peptides, peptidomimetics (e.g., peptoids), amino acids, amino acid analogs, polynucleotides, polynucleotide analogs, nucleotides, nucleotide analogs, organic or inorganic compounds (i.e., including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

Exemplary doses include milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram. It is furthermore understood that appropriate doses of a small molecule depend upon the potency of the small molecule with respect to the expression or activity to be modulated. When one or more of these small molecules is to be administered to an animal (e.g., a human) in order to modulate expression or activity of a polypeptide or nucleic acid of the invention, a physician, veterinarian, or researcher can, for example, prescribe a relatively low dose at first, subsequently increasing the dose until an appropriate response is obtained. In addition, it is understood that the specific dose level for any particular animal subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

The nucleic acid molecules of the invention can be inserted into vectors and used as gene therapy vectors. Gene therapy vectors can be delivered to a subject by, for example, intravenous injection, local administration (see U.S. Pat. No. 5,328,470) or by stereotactic injection (see e.g., Chen et al. (1994) *Proc. Natl. Acad. Sci. USA* 91:3054-3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

The pharmaceutical compositions can be included in a container, pack, or dispenser together with instructions for administration.

Methods of Treatment:

The present invention provides for both prophylactic and therapeutic methods of treating a subject at risk of (or susceptible to) a disorder or having a disorder associated with aberrant or unwanted 26199, 33530, 33949, 47148, 50226, 58764, 62113, 32144, 32235, 23565, 13305, 14911, 86216, 25206 or 8843 expression or activity. As used herein, the term "treatment" is defined as the application or administration of a therapeutic agent to a patient, or application or administration of a therapeutic agent to an isolated tissue or cell line from a patient, who has a disease, a symptom of disease or a predisposition toward a disease, with the purpose to cure, heal, alleviate, relieve, alter, remedy, ameliorate, improve or affect the disease, the symptoms of disease or the predisposition toward disease. A therapeutic agent includes, but is not limited to, small molecules, peptides, antibodies, ribozymes and antisense oligonucleotides.

With regards to both prophylactic and therapeutic methods of treatment, such treatments can be specifically tailored or modified, based on knowledge obtained from the field of pharmacogenomics. "Pharmacogenomics", as used herein, refers to the application of genomics technologies such as gene sequencing, statistical genetics, and gene expression analysis to drugs in clinical development and on the market. More specifically, the term refers the study of how a patient's genes determine his or her response to a drug (e.g., a patient's "drug response phenotype", or "drug response genotype".) Thus, another aspect of the invention provides methods for tailoring an individual's prophylactic or therapeutic treatment with either the 26199, 33530, 33949, 47148, 50226, 58764, 62113, 32144, 32235, 23565, 13305, 14911, 86216, 25206 or 8843 molecules of the present invention or 26199, 33530, 33949, 47148, 50226, 58764, 62113, 32144, 32235, 23565, 13305, 14911, 86216, 25206 or 8843 modulators according to that individual's drug response genotype. Pharmacogenomics allows a clinician or physician to target prophylactic or therapeutic treatments to patients who will most benefit from the treatment and to avoid treatment of patients who will experience toxic drug-related side effects.

In one aspect, the invention provides a method for preventing in a subject, a disease or condition associated with an aberrant or unwanted 26199, 33530, 33949, 47148, 50226, 58764, 62113, 32144, 32235, 23565, 13305, 14911, 86216, 25206 or 8843 expression or activity, by administering to the subject a 26199, 33530, 33949, 47148, 50226, 58764, 62113, 32144, 32235, 23565, 13305, 14911, 86216, 25206 or 8843 or an agent which modulates 26199, 33530, 33949, 47148, 50226, 58764, 62113, 32144, 32235, 23565, 13305, 14911, 86216, 25206 or 8843 expression or at least one 26199, 33530, 33949, 47148, 50226, 58764, 62113, 32144, 32235, 23565, 13305, 14911, 86216, 25206 or 8843 activity. Subjects at risk for a disease which is caused or contributed to by aberrant or unwanted 26199, 33530, 33949, 47148, 50226, 58764, 62113, 32144, 32235, 23565, 13305, 14911, 86216, 25206 or 8843 expression or activity can be identified by, for example, any or a combination of diagnostic or prognostic assays as described herein. Administration of a prophylactic agent can occur prior to the manifestation of symptoms characteristic of the 26199, 33530, 33949, 47148, 50226, 58764, 62113, 32144, 32235, 23565, 13305, 14911, 86216, 25206 or 8843 aberrance, such that a disease or disorder is prevented or, alternatively, delayed in its progression. Depending on the type of 26199, 33530, 33949, 47148, 50226, 58764, 62113, 32144, 32235, 23565, 13305, 14911, 86216, 25206 or 8843 aberrance, for example, a 26199, 33530, 33949, 47148, 50226, 58764, 62113, 32144, 32235, 23565, 13305, 14911, 86216, 25206 or 8843, 26199, 33530, 33949, 47148, 50226, 58764, 62113, 32144, 32235, 23565, 13305, 14911, 86216, 25206 or 8843 agonist or 26199, 33530, 33949, 47148, 50226, 58764, 62113, 32144, 32235, 23565, 13305, 14911, 86216, 25206 or 8843 antagonist agent can be used for treating the subject. The appropriate agent can be determined based on screening assays described herein.

It is possible that some 26199, 33530, 33949, 47148, 50226, 58764, 62113, 32144, 32235, 23565, 13305, 14911, 86216, 25206 or 8843 disorders can be caused, at least in part, by an abnormal level of gene product, or by the presence of a gene product exhibiting abnormal activity. As such, the reduction in the level and/or activity of such gene products would bring about the amelioration of disorder symptoms.

The 26199, 33530, 33949, 47148, 50226, 58764, 62113, 32144, 32235, 23565, 13305, 14911, 86216, 25206 or 8843 molecules can act as novel diagnostic targets and therapeutic agents for controlling one or more of a cellular proliferation and/or differentiation disorder, a brain, platelet, breast, colon, kidney (renal), lung, ovarian, prostate, hematopoeitic, pancreatic, skeletal muscle, skin (dermal), bone metabolism, immune, e.g., inflammatory, cardiovascular, endothelial cell, liver, viral diseases, pain, metabolic, neurological or CNS, erythroid or anemic disorder, all of which are described above.

As discussed, successful treatment of 26199, 33530, 33949, 47148, 50226, 58764, 62113, 32144, 32235, 23565, 13305, 14911, 86216, 25206 or 8843 disorders can be brought about by techniques that serve to inhibit the expression or activity of target gene products. For example, compounds, e.g., an agent identified using an assays described above, that proves to exhibit negative modulatory activity, can be used in accordance with the invention to prevent and/or ameliorate symptoms of 26199, 33530, 33949, 47148, 50226, 58764, 62113, 32144, 32235, 23565, 13305, 14911, 86216, 25206 or 8843 disorders. Such molecules can include, but are not limited to peptides, phosphopeptides, small organic or inorganic molecules, or antibodies (including, for example, polyclonal, monoclonal, humanized, human, anti-idiotypic, chimeric or single chain antibodies, and Fab, $F(ab)_2$ and Fab expression library fragments, scFV molecules, and epitope-binding fragments thereof).

Further, antisense and ribozyme molecules that inhibit expression of the target gene can also be used in accordance with the invention to reduce the level of target gene expression, thus effectively reducing the level of target gene activity. Still further, triple helix molecules can be utilized in reducing the level of target gene activity. Antisense, ribozyme and triple helix molecules are discussed above.

It is possible that the use of antisense, ribozyme, and/or triple helix molecules to reduce or inhibit mutant gene expression can also reduce or inhibit the transcription (triple helix) and/or translation (antisense, ribozyme) of mRNA produced by normal target gene alleles, such that the concentration of normal target gene product present can be lower than is necessary for a normal phenotype. In such cases, nucleic acid molecules that encode and express target gene polypeptides exhibiting normal target gene activity can be introduced into cells via gene therapy method. Alternatively, in instances in that the target gene encodes an extracellular protein, it can be preferable to co-administer normal target gene protein into the cell or tissue in order to maintain the requisite level of cellular or tissue target gene activity.

Another method by which nucleic acid molecules can be utilized in treating or preventing a disease characterized by 26199, 33530, 33949, 47148, 50226, 58764, 62113, 32144, 32235, 23565, 13305, 14911, 86216, 25206 or 8843 expression is through the use of aptamer molecules specific for 26199, 33530, 33949, 47148, 50226, 58764, 62113, 32144, 32235, 23565, 13305, 14911, 86216, 25206 or 8843 protein. Aptamers are nucleic acid molecules having a tertiary structure which permits them to specifically or selectively bind to protein ligands (see, e.g., Osborne et al. (1997) *Curr. Opin. Chem Biol.* 1: 5-9; and Patel (1997) *Curr Opin Chem Biol* 1:32-46). Since nucleic acid molecules can in many cases be more conveniently introduced into target cells than therapeutic protein molecules can be, aptamers offer a method by which 26199, 33530, 33949, 47148, 50226, 58764, 62113, 32144, 32235, 23565, 13305, 14911, 86216, 25206 or 8843 protein activity can be specifically decreased without the introduction of drugs or other molecules which can have pluripotent effects.

Antibodies can be generated that are both specific for target gene product and that reduce target gene product activity. Such antibodies can, therefore, by administered in instances whereby negative modulatory techniques are appropriate for the treatment of 26199, 33530, 33949, 47148, 50226, 58764, 62113, 32144, 32235, 23565, 13305, 14911, 86216, 25206 or 8843 disorders. For a description of antibodies, see the Antibody section above.

In circumstances wherein injection of an animal or a human subject with a 26199, 33530, 33949, 47148, 50226, 58764, 62113, 32144, 32235, 23565, 13305, 14911, 86216, 25206 or 8843 protein or epitope for stimulating antibody production is harmful to the subject, it is possible to generate an immune response against 26199, 33530, 33949, 47148, 50226, 58764, 62113, 32144, 32235, 23565, 13305, 14911, 86216, 25206 or 8843 through the use of anti-idiotypic antibodies (see, for example, Herlyn (1999) *Ann Med* 31:66-78; and Bhattacharya-Chatterjee and Foon (1998) *Cancer Treat Res.* 94:51-68). If an anti-idiotypic antibody is introduced into a mammal or human subject, it should stimulate the production of anti-anti-idiotypic antibodies, which should be specific to the 26199, 33530, 33949, 47148, 50226, 58764, 62113, 32144, 32235, 23565, 13305, 14911, 86216, 25206 or 8843 protein.

Vaccines directed to a disease characterized by 26199, 33530, 33949, 47148, 50226, 58764, 62113, 32144, 32235, 23565, 13305, 14911, 86216, 25206 or 8843 expression can also be generated in this fashion.

In instances where the target antigen is intracellular and whole antibodies are used, internalizing antibodies can be preferred. Lipofectin or liposomes can be used to deliver the antibody or a fragment of the Fab region that binds to the target antigen into cells. Where fragments of the antibody are used, the smallest inhibitory fragment that binds to the target antigen is preferred. For example, peptides having an amino acid sequence corresponding to the Fv region of the antibody can be used. Alternatively, single chain neutralizing antibodies that bind to intracellular target antigens can also be administered. Such single chain antibodies can be administered, for example, by expressing nucleotide sequences encoding single-chain antibodies within the target cell population (see e.g., Marasco et al. (1993) *Proc. Natl. Acad. Sci. USA* 90:7889-7893).

The identified compounds that inhibit target gene expression, synthesis and/or activity can be administered to a patient at therapeutically effective doses to prevent, treat or ameliorate 26199, 33530, 33949, 47148, 50226, 58764, 62113, 32144, 32235, 23565, 13305, 14911, 86216, 25206 or 8843 disorders. A therapeutically effective dose refers to that amount of the compound sufficient to result in amelioration of symptoms of the disorders. Toxicity and therapeutic efficacy of such compounds can be determined by standard pharmaceutical procedures as described above.

The data obtained from the cell culture assays and animal studies can be used in formulating a range of dosage for use in humans. The dosage of such compounds lies preferably within a range of circulating concentrations that include the $ED_{50}$ with little or no toxicity. The dosage can vary within this range depending upon the dosage form employed and the route of administration utilized. For any compound used in the method of the invention, the therapeutically effective dose can be estimated initially from cell culture assays. A dose can be formulated in animal models to achieve a circulating plasma concentration range that includes the $IC_{50}$ (i.e., the concentration of the test compound that achieves a half-maximal inhibition of symptoms) as determined in cell culture. Such information can be used to more accurately determine useful doses in humans. Levels in plasma can be measured, for example, by high performance liquid chromatography.

Another example of determination of effective dose for an individual is the ability to directly assay levels of "free" and "bound" compound in the serum of the test subject. Such assays can utilize antibody mimics and/or "biosensors" that have been created through molecular imprinting techniques. The compound which is able to modulate 26199, 33530, 33949, 47148, 50226, 58764, 62113, 32144, 32235, 23565, 13305, 14911, 86216, 25206 or 8843 activity is used as a template, or "imprinting molecule", to spatially organize polymerizable monomers prior to their polymerization with catalytic reagents. The subsequent removal of the imprinted molecule leaves a polymer matrix which contains a repeated "negative image" of the compound and is able to selectively rebind the molecule under biological assay conditions. A detailed review of this technique can be seen in Ansell et al (1996) *Current Opinion in Biotechnology* 7:89-94 and in Shea (1994) *Trends in Polymer Science* 2:166-173. Such "imprinted" affinity matrixes are amenable to ligand-binding assays, whereby the immobilized monoclonal antibody component is replaced by an appropriately imprinted matrix. An example of the use of such matrixes in this way can be seen in Vlatakis et al (1993) *Nature* 361:645-647. Through the use of isotope-labeling, the "free" concentration of compound which modulates the expression or activity of 26199, 33530, 33949, 47148, 50226, 58764, 62113, 32144, 32235, 23565, 13305, 14911, 86216, 25206 or 8843 can be readily monitored and used in calculations of $IC_{50}$.

Such "imprinted" affinity matrixes can also be designed to include fluorescent groups whose photon-emitting properties measurably change upon local and selective binding of target compound. These changes can be readily assayed in real time using appropriate fiberoptic devices, in turn allowing the dose in a test subject to be quickly optimized based on its individual $IC_{50}$. An rudimentary example of such a "biosensor" is discussed in Kriz et al (1995) *Analytical Chemistry* 67:2142-2144.

Another aspect of the invention pertains to methods of modulating 26199, 33530, 33949, 47148, 50226, 58764, 62113, 32144, 32235, 23565, 13305, 14911, 86216, 25206 or 8843 expression or activity for therapeutic purposes. Accordingly, in an exemplary embodiment, the modulatory method of the invention involves contacting a cell with a 26199, 33530, 33949, 47148, 50226, 58764, 62113, 32144, 32235, 23565, 13305, 14911, 86216, 25206 or 8843 or agent that modulates one or more of the activities of 26199, 33530, 33949, 47148, 50226, 58764, 62113, 32144, 32235, 23565, 13305, 14911, 86216, 25206 or 8843 protein activity associated with the cell. An agent that modulates 26199, 33530, 33949, 47148, 50226, 58764, 62113, 32144, 32235, 23565, 13305, 14911, 86216, 25206 or 8843 protein activity can be an agent as described herein, such as a nucleic acid or a protein, a naturally-occurring target molecule of a 26199, 33530, 33949, 47148, 50226, 58764, 62113, 32144, 32235, 23565, 13305, 14911, 86216, 25206 or 8843 protein (e.g., a 26199, 33530, 33949, 47148, 50226, 58764, 62113, 32144, 32235, 23565, 13305, 14911, 86216, 25206 or 8843 substrate or receptor), a 26199, 33530, 33949, 47148, 50226, 58764, 62113, 32144, 32235, 23565, 13305, 14911, 86216, 25206 or 8843 antibody, a 26199, 33530, 33949, 47148, 50226, 58764, 62113, 32144, 32235, 23565, 13305, 14911, 86216, 25206 or 8843 agonist or antagonist, a peptidomimetic of a 26199, 33530, 33949, 47148, 50226, 58764, 62113, 32144, 32235, 23565, 13305, 14911, 86216, 25206 or 8843 agonist or antagonist, or other small molecule.

In one embodiment, the agent stimulates one or 26199, 33530, 33949, 47148, 50226, 58764, 62113, 32144, 32235, 23565, 13305, 14911, 86216, 25206 or 8843 activities. Examples of such stimulatory agents include active 26199, 33530, 33949, 47148, 50226, 58764, 62113, 32144, 32235, 23565, 13305, 14911, 86216, 25206 or 8843 protein and a nucleic acid molecule encoding 26199, 33530, 33949, 47148, 50226, 58764, 62113, 32144, 32235, 23565, 13305, 14911, 86216, 25206 or 8843. In another embodiment, the agent inhibits one or more 26199, 33530, 33949, 47148, 50226, 58764, 62113, 32144, 32235, 23565, 13305, 14911, 86216, 25206 or 8843 activities. Examples of such inhibitory agents include antisense 26199, 33530, 33949, 47148, 50226, 58764, 62113, 32144, 32235, 23565, 13305, 14911, 86216, 25206 or 8843 nucleic acid molecules, anti-26199, 33530, 33949, 47148, 50226, 58764, 62113, 32144, 32235, 23565, 13305, 14911, 86216, 25206 or 8843 antibodies, and 26199, 33530, 33949, 47148, 50226, 58764, 62113, 32144, 32235, 23565, 13305, 14911, 86216, 25206 or 8843 inhibitors. These modulatory methods can be performed in vitro (e.g., by culturing the cell with the agent) or, alternatively, in vivo (e.g., by administering the agent to a subject). As such, the present invention provides methods of treating an individual afflicted with a disease or disorder characterized by aberrant or unwanted expression or activity of a 26199, 33530, 33949, 47148, 50226, 58764, 62113, 32144, 32235, 23565, 13305, 14911, 86216, 25206 or 8843 protein or nucleic acid molecule. In one embodiment, the method involves administering an agent (e.g., an agent identified by a screening assay described herein), or combination of agents that modulates (e.g., up regulates or down regulates) 26199, 33530, 33949, 47148, 50226, 58764, 62113, 32144, 32235, 23565, 13305, 14911, 86216, 25206 or 8843 expression or activity. In another embodiment, the method involves administering a 26199, 33530, 33949, 47148, 50226, 58764, 62113, 32144, 32235, 23565, 13305, 14911, 86216, 25206 or 8843 protein or nucleic acid molecule as therapy to compensate for reduced, aberrant, or unwanted 26199, 33530, 33949, 47148, 50226, 58764, 62113, 32144, 32235, 23565, 13305, 14911, 86216, 25206 or 8843 expression or activity.

Stimulation of 26199, 33530, 33949, 47148, 50226, 58764, 62113, 32144, 32235, 23565, 13305, 14911, 86216, 25206 or 8843 activity is desirable in situations in which 26199, 33530, 33949, 47148, 50226, 58764, 62113, 32144, 32235, 23565, 13305, 14911, 86216, 25206 or 8843 is abnormally downregulated and/or in which increased 26199, 33530, 33949, 47148, 50226, 58764, 62113, 32144, 32235, 23565, 13305, 14911, 86216, 25206 or 8843 activity is likely to have a beneficial effect. For example, stimulation of 26199, 33530, 33949, 47148, 50226, 58764, 62113, 32144, 32235, 23565, 13305, 14911, 86216, 25206 or 8843 activity is desirable in situations in which a 26199, 33530, 33949, 47148, 50226, 58764, 62113, 32144, 32235, 23565, 13305, 14911, 86216, 25206 or 8843 is downregulated and/or in which increased 26199, 33530, 33949, 47148, 50226, 58764, 62113, 32144, 32235, 23565, 13305, 14911, 86216, 25206 or 8843 activity is likely to have a beneficial effect. Likewise, inhibition of 26199, 33530, 33949, 47148, 50226, 58764, 62113, 32144, 32235, 23565, 13305, 14911, 86216, 25206 or 8843 activity is desirable in situations in which 26199, 33530, 33949, 47148, 50226, 58764, 62113, 32144, 32235, 23565, 13305, 14911, 86216, 25206 or 8843 is abnormally upregulated and/or in which decreased 26199, 33530, 33949, 47148, 50226, 58764, 62113, 32144, 32235, 23565, 13305, 14911, 86216, 25206 or 8843 activity is likely to have a beneficial effect.

Pharmacogenomics

The 26199, 33530, 33949, 47148, 50226, 58764, 62113, 32144, 32235, 23565, 13305, 14911, 86216, 25206 or 8843 molecules of the present invention, as well as agents, or modulators which have a stimulatory or inhibitory effect on 26199, 33530, 33949, 47148, 50226, 58764, 62113, 32144, 32235, 23565, 13305, 14911, 86216, 25206 or 8843 activity (e.g., 26199, 33530, 33949, 47148, 50226, 58764, 62113, 32144, 32235, 23565, 13305, 14911, 86216, 25206 or 8843 gene expression) as identified by a screening assay described herein can be administered to individuals to treat (prophylactically or therapeutically) 26199, 33530, 33949, 47148, 50226, 58764, 62113, 32144, 32235, 23565, 13305, 14911, 86216, 25206 or 8843-associated disorders (e.g., aberrant or deficient arginine methyltransferase activity, glycosyltransferase activity, gamma-glutamyltraspeptidase activity, phosphoribosylglycinamide transferase activity, acyltransferase activity, acyl-CoA dehydrogenase activity, fatty acid amide hydrolase activity, aminotransferase activity, zinc carboxypeptidase activity, protein kinase activity, DEAD helicase activity, short-chain dehydrogenase/reductase activity or phosphatase activity) associated with aberrant or unwanted 26199, 33530, 33949, 47148, 50226, 58764, 62113, 32144, 32235, 23565, 13305, 14911, 86216, 25206 or 8843 activity.

In conjunction with such treatment, pharmacogenomics (i.e., the study of the relationship between an individual's genotype and that individual's response to a foreign compound or drug) can be considered. Differences in metabolism of therapeutics can lead to severe toxicity or therapeutic failure by altering the relation between dose and blood concentration of the pharmacologically active drug. Thus, a physician or clinician can consider applying knowledge obtained in relevant pharmacogenomics studies in determining whether to administer a 26199, 33530, 33949, 47148, 50226, 58764, 62113, 32144, 32235, 23565, 13305, 14911, 86216, 25206 or 8843 molecule or 26199, 33530, 33949, 47148, 50226, 58764, 62113, 32144, 32235, 23565, 13305, 14911, 86216, 25206 or 8843 modulator as well as tailoring the dosage and/or therapeutic regimen of treatment with a 26199, 33530, 33949, 47148, 50226, 58764, 62113, 32144, 32235, 23565, 13305, 14911, 86216, 25206 or 8843 molecule or 26199, 33530, 33949, 47148, 50226, 58764, 62113, 32144, 32235, 23565, 13305, 14911, 86216, 25206 or 8843 modulator.

Pharmacogenomics deals with clinically significant hereditary variations in the response to drugs due to altered drug disposition and abnormal action in affected persons. See, for example, Eichelbaum et al. (1996) *Clin. Exp. Pharmacol. Physiol.* 23:983-985 and Linder et al. (1997) *Clin. Chem.* 43:254-266. In general, two types of pharmacogenetic conditions can be differentiated. Genetic conditions transmitted as a single factor altering the way drugs act on the body (altered drug action) or genetic conditions transmitted as single factors altering the way the body acts on drugs (altered drug metabolism). These pharmacogenetic conditions can occur either as rare genetic defects or as naturally-occurring polymorphisms. For example, glucose-6-phosphate dehydrogenase deficiency (G6PD) is a common inherited enzymopathy in which the main clinical complication is haemolysis after ingestion of oxidant drugs (anti-malarials, sulfonamides, analgesics, nitrofurans) and consumption of fava beans.

One pharmacogenomics approach to identifying genes that predict drug response, known as "a genome-wide association", relies primarily on a high-resolution map of the human genome consisting of already known gene-related markers (e.g., a "bi-allelic" gene marker map which consists of 60,000-100,000 polymorphic or variable sites on the human genome, each of which has two variants.) Such a high-resolution genetic map can be compared to a map of the genome of each of a statistically significant number of patients taking part in a Phase II/III drug trial to identify markers associated with a particular observed drug response or side effect. Alternatively, such a high resolution map can be generated from a combination of some ten-million known single nucleotide polymorphisms (SNPs) in the human genome. As used herein, a "SNP" is a common alteration that occurs in a single nucleotide base in a stretch of DNA. For example, a SNP can occur once per every 1000 bases of DNA. A SNP can be involved in a disease process, however, the vast majority can not be disease-associated. Given a genetic map based on the occurrence of such SNPs, individuals can be grouped into genetic categories depending on a particular pattern of SNPs in their individual genome. In such a manner, treatment regimens can be tailored to groups of genetically similar individuals, taking into account traits that can be common among such genetically similar individuals.

Alternatively, a method termed the "candidate gene approach", can be utilized to identify genes that predict drug response. According to this method, if a gene that encodes a drug's target is known (e.g., a 26199, 33530, 33949, 47148, 50226, 58764, 62113, 32144, 32235, 23565, 13305, 14911, 86216, 25206 or 8843 protein of the present invention), all common variants of that gene can be fairly easily identified in the population and it can be determined if having one version of the gene versus another is associated with a particular drug response.

Alternatively, a method termed the "gene expression profiling", can be utilized to identify genes that predict drug response. For example, the gene expression of an animal dosed with a drug (e.g., a 26199, 33530, 33949, 47148, 50226, 58764, 62113, 32144, 32235, 23565, 13305, 14911, 86216, 25206 or 8843 molecule or 26199, 33530, 33949, 47148, 50226, 58764, 62113, 32144, 32235, 23565, 13305, 14911, 86216, 25206 or 8843 modulator of the present invention) can give an indication whether gene pathways related to toxicity have been turned on.

Information generated from more than one of the above pharmacogenomics approaches can be used to determine appropriate dosage and treatment regimens for prophylactic or therapeutic treatment of an individual. This knowledge, when applied to dosing or drug selection, can avoid adverse reactions or therapeutic failure and thus enhance therapeutic or prophylactic efficiency when treating a subject with a 26199, 33530, 33949, 47148, 50226, 58764, 62113, 32144, 32235, 23565, 13305, 14911, 86216, 25206 or 8843 molecule or 26199, 33530, 33949, 47148, 50226, 58764, 62113, 32144, 32235, 23565, 13305, 14911, 86216, 25206 or 8843 modulator, such as a modulator identified by one of the exemplary screening assays described herein.

The present invention further provides methods for identifying new agents, or combinations, that are based on identifying agents that modulate the activity of one or more of the gene products encoded by one or more of the 26199, 33530, 33949, 47148, 50226, 58764, 62113, 32144, 32235, 23565, 13305, 14911, 86216, 25206 or 8843 genes of the present invention, wherein these products can be associated with resistance of the cells to a therapeutic agent. Specifically, the activity of the proteins encoded by the 26199, 33530, 33949, 47148, 50226, 58764, 62113, 32144, 32235, 23565, 13305, 14911, 86216, 25206 or 8843 genes of the present invention can be used as a basis for identifying agents for overcoming agent resistance. By blocking the activity of one or more of the resistance proteins, target cells, e.g., human cells, will become sensitive to treatment with an agent to which the unmodified target cells were resistant.

Monitoring the influence of agents (e.g., drugs) on the expression or activity of a 26199, 33530, 33949, 47148, 50226, 58764, 62113, 32144, 32235, 23565, 13305, 14911, 86216, 25206 or 8843 protein can be applied in clinical trials. For example, the effectiveness of an agent determined by a screening assay as described herein to increase 26199, 33530, 33949, 47148, 50226, 58764, 62113, 32144, 32235, 23565, 13305, 14911, 86216, 25206 or 8843 gene expression, protein levels, or upregulate 26199, 33530, 33949, 47148, 50226, 58764, 62113, 32144, 32235, 23565, 13305, 14911, 86216, 25206 or 8843 activity, can be monitored in clinical trials of subjects exhibiting decreased 26199, 33530, 33949, 47148, 50226, 58764, 62113, 32144, 32235, 23565, 13305, 14911, 86216, 25206 or 8843 gene expression, protein levels, or downregulated 26199, 33530, 33949, 47148, 50226, 58764, 62113, 32144, 32235, 23565, 13305, 14911, 86216, 25206 or 8843 activity. Alternatively, the effectiveness of an agent determined by a screening assay to decrease 26199, 33530, 33949, 47148, 50226, 58764, 62113, 32144, 32235, 23565, 13305, 14911, 86216, 25206 or 8843 gene expression, protein levels, or downregulate 26199, 33530, 33949, 47148, 50226, 58764, 62113, 32144, 32235, 23565, 13305, 14911, 86216, 25206 or 8843 activity, can be monitored in clinical trials of subjects exhibiting increased 26199, 33530, 33949, 47148, 50226, 58764, 62113, 32144, 32235, 23565, 13305, 14911, 86216, 25206 or 8843 gene expression, protein levels, or upregulated 26199, 33530, 33949, 47148, 50226, 58764, 62113, 32144, 32235, 23565, 13305, 14911, 86216, 25206 or 8843 activity. In such clinical trials, the expression or activity of a 26199, 33530, 33949, 47148, 50226, 58764, 62113, 32144, 32235, 23565, 13305, 14911, 86216, 25206 or 8843 gene, and preferably, other genes that have been implicated in, for example, a protein kinase-associated or another 26199, 33530, 33949, 47148, 50226, 58764, 62113, 32144, 32235, 23565, 13305, 14911, 86216, 25206 or 8843-associated disorder can be used as a "read out" or markers of the phenotype of a particular cell.

OTHER EMBODIMENTS

In another aspect, the invention features a method of analyzing a plurality of capture probes. The method is useful, e.g., to analyze gene expression. The method includes: providing a two dimensional array having a plurality of addresses, each address of the plurality being positionally distinguishable from each other address of the plurality, and each address of the plurality having a unique capture probe, e.g., a nucleic acid or peptide sequence, wherein the capture probes are from a cell or subject which expresses 26199, 33530, 33949, 47148, 50226, 58764, 62113, 32144, 32235, 23565, 13305, 14911, 86216, 25206 or 8843 or from a cell or subject in which a 26199, 33530, 33949, 47148, 50226, 58764, 62113, 32144, 32235, 23565, 13305, 14911, 86216, 25206 or 8843 mediated response has been elicited; contacting the array with a 26199, 33530, 33949, 47148, 50226, 58764, 62113, 32144, 32235, 23565, 13305, 14911, 86216, 25206 or 8843 nucleic acid (preferably purified), a 26199, 33530, 33949, 47148, 50226, 58764, 62113, 32144, 32235, 23565, 13305, 14911, 86216, 25206 or 8843 polypeptide (preferably purified), or an anti-26199, 33530, 33949, 47148, 50226, 58764, 62113, 32144, 32235, 23565, 13305, 14911, 86216, 25206 or 8843 antibody, and thereby evaluating the plurality of capture probes. Binding, e.g., in the case of a nucleic acid, hybridization with a capture probe at an address of the plurality, is detected, e.g., by a signal generated from a label attached to the 26199, 33530, 33949, 47148, 50226, 58764, 62113, 32144, 32235, 23565, 13305, 14911, 86216, 25206 or 8843 nucleic acid, polypeptide, or antibody.

The capture probes can be a set of nucleic acids from a selected sample, e.g., a sample of nucleic acids derived from a control or non-stimulated tissue or cell.

The method can include contacting the 26199, 33530, 33949, 47148, 50226, 58764, 62113, 32144, 32235, 23565, 13305, 14911, 86216, 25206 or 8843 nucleic acid, polypeptide, or antibody with a first array having a plurality of capture probes and a second array having a different plurality of capture probes. The results of each hybridization can be compared, e.g., to analyze differences in expression between a first and second sample. The first plurality of capture probes can be from a control sample, e.g., a wild type, normal, or non-diseased, non-stimulated, sample, e.g., a biological fluid, tissue, or cell sample. The second plurality of capture probes can be from an experimental sample, e.g., a mutant type, at risk, disease-state or disorder-state, or stimulated, sample, e.g., a biological fluid, tissue, or cell sample.

The plurality of capture probes can be a plurality of nucleic acid probes each of which specifically hybridizes, with an allele of 26199, 33530, 33949, 47148, 50226, 58764, 62113, 32144, 32235, 23565, 13305, 14911, 86216, 25206 or 8843. Such methods can be used to diagnose a subject, e.g., to evaluate risk for a disease or disorder, to evaluate suitability of a selected treatment for a subject, to evaluate whether a subject has a disease or disorder.

The method can be used to detect SNPs, as described above.

In another aspect, the invention features, a method of analyzing 26199, 33530, 33949, 47148, 50226, 58764, 62113, 32144, 32235, 23565, 13305, 14911, 86216, 25206 or 8843, e.g., analyzing structure, function, or relatedness to other nucleic acid or amino acid sequences. The method includes: providing a 26199, 33530, 33949, 47148, 50226, 58764, 62113, 32144, 32235, 23565, 13305, 14911, 86216, 25206 or 8843 nucleic acid or amino acid sequence; comparing the 26199, 33530, 33949, 47148, 50226, 58764, 62113, 32144, 32235, 23565, 13305, 14911, 86216, 25206 or 8843 sequence with one or more preferably a plurality of sequences from a collection of sequences, e.g., a nucleic acid or protein sequence database; to thereby analyze 26199, 33530, 33949, 47148, 50226, 58764, 62113, 32144, 32235, 23565, 13305, 14911, 86216, 25206 or 8843.

The method can include evaluating the sequence identity between a 26199, 33530, 33949, 47148, 50226, 58764, 62113, 32144, 32235, 23565, 13305, 14911, 86216, 25206 or 8843 sequence and a database sequence. The method can be performed by accessing the database at a second site, e.g., over the internet. Preferred databases include GenBank™ and SwissProt.

In another aspect, the invention features, a set of oligonucleotides, useful, e.g., for identifying SNP's, or identifying specific alleles of 26199, 33530, 33949, 47148, 50226, 58764, 62113, 32144, 32235, 23565, 13305, 14911, 86216, 25206 or 8843. The set includes a plurality of oligonucleotides, each of which has a different nucleotide at an interrogation position, e.g., an SNP or the site of a mutation. In a preferred embodiment, the oligonucleotides of the plurality identical in sequence with one another (except for differences in length). The oligonucleotides can be provided with differential labels, such that an oligonucleotide which hybridizes to one allele provides a signal that is distinguishable from an oligonucleotides which hybridizes to a second allele.

The sequences of 26199, 33530, 33949, 47148, 50226, 58764, 62113, 32144, 32235, 23565, 13305, 14911, 86216, 25206 or 8843 molecules are provided in a variety of mediums to facilitate use thereof. A sequence can be provided as a manufacture, other than an isolated nucleic acid or amino acid molecule, which contains a 26199, 33530, 33949, 47148, 50226, 58764, 62113, 32144, 32235, 23565, 13305, 14911, 86216, 25206 or 8843 molecule. Such a manufacture can provide a nucleotide or amino acid sequence, e.g., an open reading frame, in a form which allows examination of the manufacture using means not directly applicable to examining the nucleotide or amino acid sequences, or a subset thereof, as they exist in nature or in purified form.

A 26199, 33530, 33949, 47148, 50226, 58764, 62113, 32144, 32235, 23565, 13305, 14911, 86216, 25206 or 8843 nucleotide or amino acid sequence can be recorded on computer readable media. As used herein, "computer readable media" refers to any medium that can be read and accessed directly by a computer. Such media include, but are not limited to: magnetic storage media, such as floppy discs, hard disc storage medium, and magnetic tape; optical storage media such as compact disc and CD-ROM; electrical storage media such as RAM, ROM, EPROM, EEPROM, and the like; and general hard disks and hybrids of these categories such as magnetic/optical storage media. The medium is adapted or configured for having thereon 26199, 33530, 33949, 47148, 50226, 58764, 62113, 32144, 32235, 23565, 13305, 14911, 86216, 25206 or 8843 sequence information of the present invention.

As used herein, the term "electronic apparatus" is intended to include any suitable computing or processing apparatus of other device configured or adapted for storing data or information. Examples of electronic apparatus suitable for use with the present invention include stand-alone computing apparatus; networks, including a local area network (LAN), a wide area network (WAN) Internet, Intranet, and Extranet; electronic appliances such as personal digital assistants (PDAs), cellular phones, pagers, and the like; and local and distributed processing systems.

As used herein, "recorded" refers to a process for storing or encoding information on the electronic apparatus readable medium. Those skilled in the art can readily adopt any of the presently known methods for recording information on known media to generate manufactures comprising the 26199, 33530, 33949, 47148, 50226, 58764, 62113, 32144, 32235, 23565, 13305, 14911, 86216, 25206 or 8843 sequence information.

A variety of data storage structures are available to a skilled artisan for creating a computer readable medium having recorded thereon a 26199, 33530, 33949, 47148, 50226, 58764, 62113, 32144, 32235, 23565, 13305, 14911, 86216, 25206 or 8843 nucleotide or amino acid sequence of the present invention. The choice of the data storage structure will generally be based on the means chosen to access the stored information. In addition, a variety of data processor programs and formats can be used to store the nucleotide sequence information of the present invention on computer readable medium. The sequence information can be represented in a word processing text file, formatted in commercially-available software such as WordPerfect and Microsoft Word, or represented in the form of an ASCII file, stored in a database application, such as DB2, Sybase, Oracle, or the like. The skilled artisan can readily adapt any number of data processor structuring formats (e.g., text file or database) in order to obtain computer readable medium having recorded thereon the nucleotide sequence information of the present invention.

By providing the 26199, 33530, 33949, 47148, 50226, 58764, 62113, 32144, 32235, 23565, 13305, 14911, 86216, 25206 or 8843 nucleotide or amino acid sequences of the invention in computer readable form, the skilled artisan can routinely access the sequence information for a variety of purposes. For example, one skilled in the art can use the nucleotide or amino acid sequences of the invention in computer readable form to compare a target sequence or target structural motif with the sequence information stored within the data storage means. A search is used to identify fragments or regions of the sequences of the invention which match a particular target sequence or target motif.

The present invention therefore provides a medium for holding instructions for performing a method for determining whether a subject has a arginine methyltransferase, glycosyltransferase, gamma-glutamyltraspeptidase, phosphoribosylglycinamide transferase, acyltransferase, acyl-CoA dehydrogenase, fatty acid amide hydrolase, aminotransferase, zinc carboxypeptidase, protein kinase, DEAD helicase, short-chain dehydrogenase/reductase or phosphatase-associated or another 26199, 33530, 33949, 47148, 50226, 58764, 62113, 32144, 32235, 23565, 13305, 14911, 86216, 25206 or 8843-associated disease or disorder or a pre-disposition to a arginine methyltransferase, glycosyltransferase, gamma-glutamyltraspeptidase, phosphoribosylglycinamide transferase, acyltransferase, acyl-CoA dehydrogenase, fatty acid amide hydrolase, aminotransferase, zinc carboxypeptidase, protein kinase, DEAD helicase, short-chain dehydrogenase/reductase or phosphatase-associated or another 26199, 33530, 33949, 47148, 50226, 58764, 62113, 32144, 32235, 23565, 13305, 14911, 86216, 25206 or 8843-associated disease or disorder, wherein the method comprises the steps of determining 26199, 33530, 33949, 47148, 50226, 58764, 62113, 32144, 32235, 23565, 13305, 14911, 86216, 25206 or 8843 sequence information associated with the subject and based on the 26199, 33530, 33949, 47148, 50226, 58764, 62113, 32144, 32235, 23565, 13305, 14911, 86216, 25206 or 8843 sequence information, determining whether the subject has a arginine methyltransferase, glycosyltransferase, gamma-glutamyltraspeptidase, phosphoribosylglycinamide transferase, acyltransferase, acyl-CoA dehydrogenase, fatty acid amide hydrolase, aminotransferase, zinc carboxypeptidase, protein kinase, DEAD helicase, short-chain dehydrogenase/reductase or phosphatase-associated or another 26199, 33530, 33949, 47148, 50226, 58764, 62113, 32144, 32235, 23565, 13305, 14911, 86216, 25206 or 8843-associated disease or disorder and/or recommending a particular treatment for the disease, disorder, or pre-disease condition.

The present invention further provides in an electronic system and/or in a network, a method for determining whether a subject has a arginine methyltransferase, glycosyltransferase, gamma-glutamyltraspeptidase, phosphoribosylglycinamide transferase, acyltransferase, acyl-CoA dehydrogenase, fatty acid amide hydrolase, aminotransferase, zinc carboxypeptidase, protein kinase, DEAD helicase, short-chain dehydrogenase/reductase or phosphatase-associated or another 26199, 33530, 33949, 47148, 50226, 58764, 62113, 32144, 32235, 23565, 13305, 14911, 86216, 25206 or 8843-associated disease or disorder or a pre-disposition to a disease associated with 26199, 33530, 33949, 47148, 50226, 58764, 62113, 32144, 32235, 23565, 13305, 14911, 86216, 25206 or 8843, wherein the method comprises the steps of determining 26199, 33530, 33949, 47148, 50226, 58764, 62113, 32144, 32235, 23565, 13305, 14911, 86216, 25206 or 8843 sequence information associated with the subject, and based on the 26199, 33530, 33949, 47148, 50226, 58764, 62113, 32144, 32235, 23565, 13305, 14911, 86216, 25206 or 8843 sequence information, determining whether the subject has a arginine methyltransferase, glycosyltransferase, gamma-glutamyltraspeptidase, phosphoribosylglycinamide transferase, acyltransferase, acyl-CoA dehydrogenase, fatty acid amide hydrolase, aminotransferase, zinc carboxypeptidase, protein kinase, DEAD helicase, short-chain dehydrogenase/reductase or phosphatase-associated or another 26199, 33530, 33949, 47148, 50226, 58764, 62113, 32144, 32235, 23565, 13305, 14911, 86216, 25206 or 8843-associated disease or disorder or a pre-disposition to a arginine methyltransferase, glycosyltransferase, gamma-glutamyltraspeptidase, phosphoribosylglycinamide transferase, acyltransferase, acyl-CoA dehydrogenase, fatty acid amide hydrolase, aminotransferase, zinc carboxypeptidase, protein kinase, DEAD helicase, short-chain dehydrogenase/reductase or phosphatase-associated or another 26199, 33530, 33949, 47148, 50226, 58764, 62113, 32144, 32235, 23565, 13305, 14911, 86216, 25206 or 8843-associated disease or disorder, and/or recommending a particular treatment for the disease, disorder, or pre-disease condition. The method may further comprise the step of receiving phenotypic information associated with the subject and/or acquiring from a network phenotypic information associated with the subject.

The present invention also provides in a network, a method for determining whether a subject has a arginine methyltransferase, glycosyltransferase, gamma-glutamyltraspeptidase, phosphoribosylglycinamide transferase, acyltransferase, acyl-CoA dehydrogenase, fatty acid amide hydrolase, aminotransferase, zinc carboxypeptidase, protein kinase, DEAD helicase, short-chain dehydrogenase/reductase or phosphatase-associated or another 26199, 33530, 33949, 47148, 50226, 58764, 62113, 32144, 32235, 23565, 13305, 14911, 86216, 25206 or 8843-associated disease or disorder or a pre-disposition to a arginine methyltransferase, glycosyltransferase, gamma-glutamyltraspeptidase, phosphoribosylglycinamide transferase, acyltransferase, acyl-CoA dehydrogenase, fatty acid amide hydrolase, aminotransferase, zinc carboxypeptidase, protein kinase, DEAD helicase, short-chain dehydrogenase/reductase or phosphatase-associated or another 26199, 33530, 33949, 47148, 50226, 58764, 62113, 32144, 32235, 23565, 13305, 14911, 86216, 25206 or 8843-associated disease or disorder, said method comprising the steps of receiving 26199, 33530, 33949, 47148, 50226, 58764, 62113, 32144, 32235, 23565, 13305, 14911, 86216, 25206 or 8843 sequence information from the subject and/or information related thereto, receiving phenotypic information associated with the subject, acquiring information from the network corresponding to 26199, 33530, 33949, 47148, 50226, 58764, 62113, 32144, 32235, 23565, 13305, 14911, 86216, 25206 or 8843 and/or corresponding to a arginine methyltransferase, glycosyltransferase, gamma-glutamyltraspeptidase, phosphoribosylglycinamide transferase, acyltransferase, acyl-CoA dehydrogenase, fatty acid amide hydrolase, aminotransferase, zinc carboxypeptidase, protein kinase, DEAD helicase, short-chain dehydrogenase/reductase or phosphatase-associated or another 26199, 33530, 33949, 47148, 50226, 58764, 62113, 32144, 32235, 23565, 13305, 14911, 86216, 25206 or 8843-associated disease or disorder, and based on one or more of the phenotypic information, the 26199, 33530, 33949, 47148, 50226, 58764, 62113, 32144, 32235, 23565, 13305, 14911, 86216, 25206 or 8843 information (e.g., sequence information and/or information related thereto), and the acquired information, determining whether the subject has a arginine methyltransferase, glycosyltransferase, gamma-glutamyltraspeptidase, phosphoribosylglycinamide transferase, acyltransferase, acyl-CoA dehydrogenase, fatty acid amide hydrolase, aminotransferase, zinc carboxypeptidase, protein kinase, DEAD helicase, short-chain dehydrogenase/reductase or phosphatase-associated or another 26199, 33530, 33949, 47148, 50226, 58764, 62113, 32144, 32235, 23565, 13305, 14911, 86216, 25206 or 8843-associated disease or disorder or a pre-disposition to a arginine methyltransferase, glycosyltransferase, gamma-glutamyltraspeptidase, phosphoribosylglycinamide transferase, acyltransferase, acyl-CoA dehydrogenase, fatty acid amide hydrolase, aminotransferase, zinc carboxypeptidase, protein kinase, DEAD helicase, short-chain dehydrogenase/reductase or phosphatase-associated or another 26199, 33530, 33949, 47148, 50226, 58764, 62113, 32144, 32235, 23565, 13305, 14911, 86216, 25206 or 8843-associated disease or disorder. The method may further comprise the step of recommending a particular treatment for the disease, disorder, or pre-disease condition.

The present invention also provides a business method for determining whether a subject has a arginine methyltransferase, glycosyltransferase, gamma-glutamyltraspeptidase, phosphoribosylglycinamide transferase, acyltransferase, acyl-CoA dehydrogenase, fatty acid amide hydrolase, aminotransferase, zinc carboxypeptidase, protein kinase, DEAD helicase, short-chain dehydrogenase/reductase or phosphatase-associated or another 26199, 33530, 33949, 47148, 50226, 58764, 62113, 32144, 32235, 23565, 13305, 14911, 86216, 25206 or 8843-associated disease or disorder or a pre-disposition to a arginine methyltransferase, glycosyltransferase, gamma-glutamyltraspeptidase, phosphoribosylglycinamide transferase, acyltransferase, acyl-CoA dehydrogenase, fatty acid amide hydrolase, aminotransferase, zinc carboxypeptidase, protein kinase, DEAD helicase, short-chain dehydrogenase/reductase or phosphatase-associated or another 26199, 33530, 33949, 47148, 50226, 58764, 62113, 32144, 32235, 23565, 13305, 14911, 86216, 25206 or 8843-associated disease or disorder, said method comprising the steps of receiving information related to 26199, 33530, 33949, 47148, 50226, 58764, 62113, 32144, 32235, 23565, 13305, 1491.1, 86216, 25206 or 8843 (e.g., sequence information and/or information related thereto), receiving phenotypic information associated with the subject, acquiring information from the network related to 26199, 33530, 33949, 47148, 50226, 58764, 62113, 32144, 32235, 23565, 13305, 14911, 86216, 25206 or 8843 and/or related to a arginine methyltransferase, glycosyltransferase, gamma-glutamyltraspeptidase, phosphoribosylglycinamide transferase, acyltransferase, acyl-CoA dehydrogenase, fatty acid amide hydrolase, aminotransferase, zinc carboxypeptidase, protein kinase, DEAD helicase, short-chain dehydrogenase/reductase or phosphatase-associated or another 26199, 33530, 33949, 47148, 50226, 58764, 62113, 32144, 32235, 23565, 13305, 14911, 86216, 25206 or 8843-associated disease or disorder, and based on one or more of the phenotypic information, the 26199, 33530, 33949, 47148, 50226, 58764, 62113, 32144, 32235, 23565, 13305, 14911, 86216, 25206 or 8843 information, and the acquired information, determining whether the subject has a arginine methyltransferase, glycosyltransferase, gamma-glutamyltraspeptidase, phosphoribosylglycinamide transferase, acyltransferase, acyl-CoA dehydrogenase, fatty acid amide hydrolase, aminotransferase, zinc carboxypeptidase, protein kinase, DEAD helicase, short-chain dehydrogenase/reductase or phosphatase-associated or another 26199, 33530, 33949, 47148, 50226, 58764, 62113, 32144, 32235, 23565, 13305, 14911, 86216, 25206 or 8843-associated disease or disorder or a pre-disposition to a arginine methyltransferase, glycosyltransferase, gamma-glutamyltraspeptidase, phosphoribosylglycinamide transferase, acyltransferase, acyl-CoA dehydrogenase, fatty acid amide hydrolase, aminotransferase, zinc carboxypeptidase, protein kinase, DEAD helicase, short-chain dehydrogenase/reductase or phosphatase-associated or another 26199, 33530, 33949, 47148, 50226, 58764, 62113, 32144, 32235, 23565, 13305, 14911, 86216, 25206 or 8843-associated disease or disorder. The method may further comprise the step of recommending a particular treatment for the disease, disorder, or pre-disease condition.

The invention also includes an array comprising a 26199, 33530, 33949, 47148, 50226, 58764, 62113, 32144, 32235, 23565, 13305, 14911, 86216, 25206 or 8843 sequence of the present invention. The array can be used to assay expression of one or more genes in the array. In one embodiment, the array can be used to assay gene expression in a tissue to ascertain tissue specificity of genes in the array. In this manner, up to about 7600 genes can be simultaneously assayed for expression, one of which can be 26199, 33530, 33949, 47148, 50226, 58764, 62113, 32144, 32235, 23565, 13305, 14911, 86216, 25206 or 8843. This allows a profile to be developed showing a battery of genes specifically expressed in one or more tissues.

In addition to such qualitative information, the invention allows the quantitation of gene expression. Thus, not only tissue specificity, but also the level of expression of a battery of genes in the tissue if ascertainable. Thus, genes can be grouped on the basis of their tissue expression per se and level of expression in that tissue. This is useful, for example, in ascertaining the relationship of gene expression in that tissue. Thus, one tissue can be perturbed and the effect on gene expression in a second tissue can be determined. In this context, the effect of one cell type on another cell type in response to a biological stimulus can be determined. In this context, the effect of one cell type on another cell type in response to a biological stimulus can be determined. Such a determination is useful, for example, to know the effect of cell-cell interaction at the level of gene expression. If an agent is administered therapeutically to treat one cell type but has an undesirable effect on another cell type, the invention provides an assay to determine the molecular basis of the undesirable effect and thus provides the opportunity to co-administer a counteracting agent or otherwise treat the undesired effect. Similarly, even within a single cell type, undesirable biological effects can be determined at the molecular level. Thus, the effects of an agent on expression of other than the target gene can be ascertained and counteracted.

In another embodiment, the array can be used to monitor the time course of expression of one or more genes in the array. This can occur in various biological contexts, as disclosed herein, for example development of an arginine methyltransferase, glycosyltransferase, gamma-glutamyltraspeptidase, phosphoribosylglycinamide transferase, acyltransferase, acyl-CoA dehydrogenase, fatty acid amide hydrolase, aminotransferase, zinc carboxypeptidase, protein kinase, DEAD helicase, short-chain dehydrogenase/reductase or phosphatase-associated or another 26199, 33530, 33949, 47148, 50226, 58764, 62113, 32144, 32235, 23565, 13305, 14911, 86216, 25206 or 8843-associated disease or disorder, progression of an arginine methyltransferase, glycosyltransferase, gamma-glutamyltraspeptidase, phosphoribosylglycinamide transferase, acyltransferase, acyl-CoA dehydrogenase, fatty acid amide hydrolase, aminotransferase, zinc carboxypeptidase, protein kinase, DEAD helicase, short-chain dehydrogenase/reductase or phosphatase-associated or another 26199, 33530, 33949, 47148, 50226, 58764, 62113, 32144, 32235, 23565, 13305, 14911, 86216, 25206 or 8843-associated disease or disorder, and processes, such a cellular transformation associated with the arginine methyltransferase, glycosyltransferase, gamma-glutamyltraspeptidase, phosphoribosylglycinamide transferase, acyltransferase, acyl-CoA dehydrogenase, fatty acid amide hydrolase, aminotransferase, zinc carboxypeptidase, protein kinase, DEAD helicase, short-chain dehydrogenase/reductase or phosphatase-associated or another 26199, 33530, 33949, 47148, 50226, 58764, 62113, 32144, 32235, 23565, 13305, 14911, 86216, 25206 or 8843-associated disease or disorder.

The array is also useful for ascertaining the effect of the expression of a gene on the expression of other genes in the same cell or in different cells (e.g., acertaining the effect of 26199, 33530, 33949, 47148, 50226, 58764, 62113, 32144, 32235, 23565, 13305, 14911, 86216, 25206 or 8843 expression on the expression of other genes). This provides, for example, for a selection of alternate molecular targets for therapeutic intervention if the ultimate or downstream target cannot be regulated.

The array is also useful for ascertaining differential expression patterns of one or more genes in normal and abnormal cells. This provides a battery of genes (e.g., including 26199, 33530, 33949, 47148, 50226, 58764, 62113, 32144, 32235, 23565, 13305, 14911, 86216, 25206 or 8843) that could serve as a molecular target for diagnosis or therapeutic intervention.

As used herein, a "target sequence" can be any DNA or amino acid sequence of six or more nucleotides or two or more amino acids. A skilled artisan can readily recognize that the longer a target sequence is, the less likely a target sequence will be present as a random occurrence in the database. Typical sequence lengths of a target sequence are from about 10 to 100 amino acids or from about 30 to 300 nucleotide residues. However, it is well recognized that commercially important fragments, such as sequence fragments involved in gene expression and protein processing, may be of shorter length.

Computer software is publicly available which allows a skilled artisan to access sequence information provided in a computer readable medium for analysis and comparison to other sequences. A variety of known algorithms are disclosed publicly and a variety of commercially available software for conducting search means are and can be used in the computer-based systems of the present invention. Examples of such software include, but are not limited to, MacPattern (EMBL), BLASTN and BLASTX (NCBI).

Thus, the invention features a method of making a computer readable record of a sequence of a 26199, 33530, 33949, 47148, 50226, 58764, 62113, 32144, 32235, 23565, 13305, 14911, 86216, 25206 or 8843 sequence which includes recording the sequence on a computer readable matrix. In a preferred embodiment the record includes one or more of the following: identification of an ORF; identification of a domain, region, or site; identification of the start of transcription; identification of the transcription terminator; the full length amino acid sequence of the protein, or a mature form thereof; the 5' end of the translated region.

In another aspect, the invention features a method of analyzing a sequence. The method includes: providing a 26199, 33530, 33949, 47148, 50226, 58764, 62113, 32144, 32235, 23565, 13305, 14911, 86216, 25206 or 8843 sequence, or record, in computer readable form; comparing a second sequence to the 26199, 33530, 33949, 47148, 50226, 58764, 62113, 32144, 32235, 23565, 13305, 14911, 86216, 25206 or 8843 sequence; thereby analyzing a sequence. Comparison can include comparing to sequences for sequence identity or determining if one sequence is included within the other, e.g., determining if the 26199, 33530, 33949, 47148, 50226, 58764, 62113, 32144, 32235, 23565, 13305, 14911, 86216, 25206 or 8843 sequence includes a sequence being compared. In a preferred embodiment the 26199, 33530, 33949, 47148, 50226, 58764, 62113, 32144, 32235, 23565, 13305, 14911, 86216, 25206 or 8843 or second sequence is stored on a first computer, e.g., at a first site and the comparison is performed, read, or recorded on a second computer, e.g., at a second site. E.g., the 26199, 33530, 33949, 47148, 50226, 58764, 62113, 32144, 32235, 23565, 13305, 14911, 86216, 25206 or 8843 or second sequence can be stored in a public or proprietary database in one computer, and the results of the comparison performed, read, or recorded on a second computer. In a preferred embodiment the record includes one or more of the following: identification of an ORF; identification of a domain, region, or site; identification of the start of transcription; identification of the transcription terminator;

the full length amino acid sequence of the protein, or a mature form thereof; the 5' end of the translated region.

EXEMPLIFICATION

Example 1

Tissue Distribution of 26199, 33530, 33949, 47148, 50226, 58764, 62113, 32144, 32235, 23565, 13305, 14911, 86216, 25206 or 8843 mRNA Northern blot hybridizations with various RNA samples can be performed under standard conditions and washed under stringent conditions, i.e., 0.2×SSC at 65° C. A DNA probe corresponding to all or a portion of the 26199, 33530, 33949, 47148, 50226, 58764, 62113, 32144, 32235, 23565, 13305, 14911, 86216, 25206 or 8843 cDNA (SEQ ID NO:1, 3, 4, 6, 7, 9, 10, 12, 13, 15, 16, 18, 53, 55, 61, 63, 67, 69, 78, 80, 88, 90, 100, 102, 113, 115, 122, 124, 129 or 131) or 26199, 33530, 33949, 47148, 50226, 58764, 62113, 32144, 32235, 23565, 13305, 14911, 86216, 25206 or 8843 cDNA can be used. The DNA was radioactively labeled with $^{32}$P-dCTP using the Prime-It Kit (Stratagene, La Jolla, Calif.) according to the instructions of the supplier. Filters containing mRNA from mouse hematopoietic and endocrine tissues, and cancer cell lines (Clontech, Palo Alto, Calif.) can be probed in ExpressHyb hybridization solution (Clontech) and washed at high stringency according to manufacturer's recommendations.

Example 2

Recombinant Expression of 26199, 33530, 33949, 47148, 50226, 58764, 62113, 32144, 32235, 23565, 13305, 14911, 86216, 25206 or 8843 in Bacterial Cells In this example, 26199, 33530, 33949, 47148, 50226, 58764, 62113, 32144, 32235, 23565, 13305, 14911, 86216, 25206 or 8843 is expressed as a recombinant glutathione-5-transferase (GST) fusion polypeptide in *E. coli* and the fusion polypeptide is isolated and characterized. Specifically, 26199, 33530, 33949, 47148, 50226, 58764, 62113, 32144, 32235, 23565, 13305, 14911, 86216, 25206 or 8843 is fused to GST and this fusion polypeptide is expressed in *E. coli*, e.g., strain PEB199. Expression of the GST-26199, -33530, -33949, -47148, -50226, -58764, -62113, -32144, -32235, -23565, -13305, -14911, -86216, -25206 or -8843 fusion protein in PEB199 is induced with IPTG. The recombinant fusion polypeptide is purified from crude bacterial lysates of the induced PEB199 strain by affinity chromatography on glutathione beads. Using polyacrylamide gel electrophoretic analysis of the polypeptide purified from the bacterial lysates, the molecular weight of the resultant fusion polypeptide is determined.

Example 3

Expression of Recombinant 26199, 33530, 33949, 47148, 50226, 58764, 62113, 32144, 32235, 23565, 13305, 14911, 86216, 25206 or 8843 Protein in COS Cells To express the 26199, 33530, 33949, 47148, 50226, 58764, 62113, 32144, 32235, 23565, 13305, 14911, 86216, 25206 or 8843 gene in COS cells, the pcDNA/Amp vector by Invitrogen Corporation (San Diego, Calif.) is used. This vector contains an SV40 origin of replication, an ampicillin resistance gene, an *E. coli* replication origin, a CMV promoter followed by a polylinker region, and an SV40 intron and polyadenylation site. A DNA fragment encoding the entire 26199, 33530, 33949, 47148, 50226, 58764, 62113, 32144, 32235, 23565, 13305, 14911, 86216, 25206 or 8843 protein and an HA tag (Wilson et al. (1984) *Cell* 37:767) or a FLAG tag fused in-frame to its 3' end of the fragment is cloned into the polylinker region of the vector, thereby placing the expression of the recombinant protein under the control of the CMV promoter.

To construct the plasmid, the 26199, 33530, 33949, 47148, 50226, 58764, 62113, 32144, 32235, 23565, 13305, 14911, 86216, 25206 or 8843 DNA sequence is amplified by PCR using two primers. The 5' primer contains the restriction site of interest followed by approximately twenty nucleotides of the 26199, 33530, 33949, 47148, 50226, 58764, 62113, 32144, 32235, 23565, 13305, 14911, 86216, 25206 or 8843 coding sequence starting from the initiation codon; the 3' end sequence contains complementary sequences to the other restriction site of interest, a translation stop codon, the HA tag or FLAG tag and the last 20 nucleotides of the 26199, 33530, 33949, 47148, 50226, 58764, 62113, 32144, 32235, 23565, 13305, 14911, 86216, 25206 or 8843 coding sequence. The PCR amplified fragment and the pCDNA/Amp vector are digested with the appropriate restriction enzymes and the vector is dephosphorylated using the CIAP enzyme (New England Biolabs, Beverly, Mass.). Preferably the two restriction sites chosen are different so that the 26199, 33530, 33949, 47148, 50226, 58764, 62113, 32144, 32235, 23565, 13305, 14911, 86216, 25206 or 8843 gene is inserted in the correct orientation. The ligation mixture is transformed into *E. coli* cells (strains HB101, DH5α, SURE, available from Stratagene Cloning Systems, La Jolla, Calif., can be used), the transformed culture is plated on ampicillin media plates, and resistant colonies are selected. Plasmid DNA is isolated from transformants and examined by restriction analysis for the presence of the correct fragment.

COS cells are subsequently transfected with the 26199-, 33530-, 33949-, 47148-, 50226-, 58764-, 62113-, 32144-, 32235-, 23565-, 13305-, 14911-, 86216-, 25206- or 8843-pcDNA/Amp plasmid DNA using the calcium phosphate or calcium chloride co-precipitation methods, DEAE-dextran-mediated transfection, lipofection, or electroporation. Other suitable methods for transfecting host cells can be found in Sambrook, J., Fritsh, E. F., and Maniatis, T. *Molecular Cloning: A Laboratory Manual. 2nd, ed., Cold Spring Harbor Laboratory*, Cold Spring Harbor Laboratory Press, Cold Spring Harbor, N.Y., 1989. The expression of the 26199, 33530, 33949, 47148, 50226, 58764, 62113, 32144, 32235, 23565, 13305, 14911, 86216, 25206 or 8843 polypeptide is detected by radiolabelling ($^{35}$S-methionine or $^{35}$S-cysteine available from NEN, Boston, Mass., can be used) and immunoprecipitation (Harlow, E. and Lane, D. Antibodies: A Laboratory Manual, Cold Spring Harbor Laboratory Press, Cold Spring Harbor, N.Y., 1988) using an HA specific monoclonal antibody. Briefly, the cells are labeled for 8 hours with $^{35}$S-methionine (or $^{35}$S-cysteine). The culture media are then collected and the cells are lysed using detergents (RIPA buffer, 150 mM NaCl, 1% NP-40, 0.1% SDS, 0.5% DOC, 50 mM Tris, pH 7.5). Both the cell lysate and the culture media are precipitated with an HA specific monoclonal antibody. Precipitated polypeptides are then analyzed by SDS-PAGE.

Alternatively, DNA containing the 26199, 33530, 33949, 47148, 50226, 58764, 62113, 32144, 32235, 23565, 13305, 14911, 86216, 25206 or 8843 coding sequence is cloned directly into the polylinker of the pCDNA/Amp vector using the appropriate restriction sites. The resulting plasmid is transfected into COS cells in the manner described above, and the expression of the 26199, 33530, 33949, 47148, 50226, 58764, 62113, 32144, 32235, 23565, 13305, 14911, 86216, 25206 or 8843 polypeptide is detected by radiolabelling and immunoprecipitation using a 26199, 33530, 33949, 47148, 50226, 58764, 62113, 32144, 32235, 23565, 13305, 14911, 86216, 25206 or 8843 specific monoclonal antibody.

Exmaple 4

TaqMan Analysis of 26199, 33530, 33949, 47148, 50226, 58764, 62113, 32144, 32235, 23565, 13305, 14911, 86216, 25206 or 8843

Human 26199, 33530, 33949, 47148, 50226, 58764, 62113, 32144, 32235, 23565, 13305, 14911, 86216, 25206 or 8843 expression was measured by TaqMan® quantitative PCR (Perkin Elmer Applied Biosystems) in cDNA prepared from a variety of normal and diseased (e.g., cancerous) human tissues or cell lines.

Probes were designed by PrimerExpress software (PE Biosystems) based on the sequence of the human 26199, 33530, 33949, 47148, 50226, 58764, 62113, 32144, 32235, 23565, 13305, 14911, 86216, 25206 or 8843 gene. Each human 26199, 33530, 33949, 47148, 50226, 58764, 62113, 32144, 32235, 23565, 13305, 14911, 86216, 25206 or 8843 gene probe was labeled using FAM (6-carboxyfluorescein), and the β2-microglobulin reference probe was labeled with a different fluorescent dye, VIC. The differential labeling of the target gene and internal reference gene thus enabled measurement in same well. Forward and reverse primers and the probes for both β2-microglobulin and target gene were added to the TaqMan® Universal PCR Master Mix (PE Applied Biosystems). Although the final concentration of primer and probe could vary, each was internally consistent within a given experiment. A typical experiment contained 200 nM of forward and reverse primers plus 100 nM probe for β-2 microglobulin and 600 nM forward and reverse primers plus 200 nM probe for the target gene. TaqMan matrix experiments were carried out on an ABI PRISM 7700 Sequence Detection System (PE Applied Biosystems). The thermal cycler conditions were as follows: hold for 2 min at 50° C. and 10 min at 95° C., followed by two-step PCR for 40 cycles of 95° C. for 15 sec followed by 60° C. for 1 min.

The following method was used to quantitatively calculate human 26199, 33530, 33949, 47148, 50226, 58764, 62113, 32144, 32235, 23565, 13305, 14911, 86216, 25206 or 8843 gene expression in the various tissues relative to β-2 microglobulin expression in the same tissue. The threshold cycle (Ct) value is defined as the cycle at which a statistically significant increase in fluorescence is detected. A lower Ct value is indicative of a higher mRNA concentration. The Ct value of the human 26199, 33530, 33949, 47148, 50226, 58764, 62113, 32144, 32235, 23565, 13305, 14911, 86216, 25206 or 8843 gene is normalized by subtracting the Ct value of the β-2 microglobulin gene to obtain a $_{\Delta}Ct$ value using the following formula: $_{\Delta}Ct=Ct_{sample}-Ct_{\beta\text{-2 microglobulin}}$. Expression is then calibrated against a cDNA sample showing a comparatively low level of expression of the human 26199, 33530, 33949, 47148, 50226, 58764, 62113, 32144, 32235, 23565, 13305, 14911, 86216, 25206 or 8843 gene. The $_{\Delta}Ct$ value for the calibrator sample is then subtracted from $_{\Delta}Ct$ for each tissue sample according to the following formula: $_{\Delta\Delta}Ct={}_{\Delta}Ct-_{sample}-{}_{\Delta}Ct-_{calibrator}$. Relative expression is then calculated using the arithmetic formula given by $2^{-\Delta\Delta Ct}$.

Example 5

In Situ Hybridization of 26199, 33530, 33949, 47148, 50226, 58764, 62113, 32144, 32235, 23565, 13305, 14911, 86216, 25206 or 8843

The following describes the tissue distribution of 26199, 33530, 33949, 47148, 50226, 58764, 62113, 32144, 32235, 23565, 13305, 14911, 86216, 25206 or 8843 mRNA, as may be determined by in situ hybridization analysis using oligonucleotide probes based on the human G2RF sequence.

For in situ analysis, various tissues, e.g. tissues obtained from brain, are first frozen on dry ice. Ten-micrometer-thick sections of the tissues are postfixed with 4% formaldehyde in DEPC treated 1× phosphate-buffered saline at room temperature for 10 minutes before being rinsed twice in DEPC 1× phosphate-buffered saline and once in 0.1 M triethanolamine-HCl (pH 8.0). Following incubation in 0.25% acetic anhydride-0.1 M triethanolamine-HCl for 10 minutes, sections are rinsed in DEPC 2×SSC (1×SSC is 0.15M NaCl plus 0.015M sodium citrate). Tissue is then dehydrated through a series of ethanol washes, incubated in 100% chloroform for 5 minutes, and then rinsed in 100% ethanol for 1 minute and 95% ethanol for 1 minute and allowed to air dry.

Hybridizations are performed with $^{35}S$-radiolabeled ($5\times10^7$ cpm/ml) cRNA probes. Probes are incubated in the presence of a solution containing 600 mM NaCl, 10 mM Tris (pH 7.5), 1 mM EDTA, 0.01% sheared salmon sperm DNA, 0.01% yeast tRNA, 0.05% yeast total RNA type ×1, 1× Denhardt's solution, 50% formamide, 10% dextran sulfate, 100 mM dithiothreitol, 0.1% sodium dodecyl sulfate (SDS), and 0.1% sodium thiosulfate for 18 hours at 55° C.

After hybridization, slides are washed with 2×SSC. Sections are then sequentially incubated at 37° C. in TNE (a solution containing 10 mM Tris-HCl (pH 7.6), 500 mM NaCl, and 1 mM EDTA), for 10 minutes, in TNE with 10 μg of RNase A per ml for 30 minutes, and finally in TNE for 10 minutes. Slides are then rinsed with 2×SSC at room temperature, washed with 2×SSC at 50° C. for 1 hour, washed with 0.2×SSC at 55° C. for 1 hour, and 0.2×SSC at 60° C. for 1 hour. Sections are then dehydrated rapidly through serial ethanol-0.3 M sodium acetate concentrations before being air dried and exposed to Kodak Biomax MR scientific imaging film for 24 hours and subsequently dipped in NB-2 photoemulsion and exposed at 4° C. for 7 days before being developed and counter stained.

The contents of all references, patents and published patent applications cited throughout this application are incorporated herein by reference.

EQUIVALENTS

Those skilled in the art will recognize, or be able to ascertain using no more than routine experimentation, many equivalents to the specific embodiments of the invention described herein.

What is claimed is:

1. An isolated polypeptide selected from the group consisting of:

a) a polypeptide which is encoded by a nucleic acid comprising the nucleotide sequence of SEQ ID NO: 1 or 3; and b) a polypeptide comprising the amino acid sequence of SEQ ID NO: 2.

2. The polypeptide of claim 1, wherein the polypeptide is encoded by a nucleic acid comprising the nucleotide sequence of SEQ ID NO: 1 or 3.

3. The polypeptide of claim 1, wherein the polypeptide comprises the amino acid sequence of SEQ ID NO: 2.

4. The polypeptide of claim 1, wherein the polypeptide is encoded by a nucleic acid consisting of the nucleotide sequence of SEQ ID NO: 1 or 3.

5. The polypeptide of claim 1, wherein the polypeptide consists of the amino acid sequence of SEQ ID NO: 2.

6. A fusion protein comprising the polypeptide of claim 1.

7. A fusion protein comprising the polypeptide of claim 2.

8. A fusion protein comprising the polypeptide of claim 3.

9. A fusion protein comprising the polypeptide of claim 4.

10. A fusion protein comprising the polypeptide of claim 5.

* * * * *

UNITED STATES PATENT AND TRADEMARK OFFICE

CERTIFICATE OF CORRECTION

PATENT NO. : 7,485,308 B2
APPLICATION NO. : 11/493347
DATED : February 3, 2009
INVENTOR(S) : Rachel E. Meyers and Kyle J. MacBeth It is certified that error appears in the above-identified patent and that said Letters Patent is hereby corrected as shown below:

On the Title Page:

INVENTORS

In Item (75) of the cover page of the patent, please delete the following Inventors:

Rachael E. Meyers, Newton, MA (US);
Kyle J. MacBeth, Boston, MA (US);
"~~Rory A.J. Curtis, Ashland, MA (US);~~
~~Laura A. Rudolph-Owen, Medford, MA (US);~~
~~Nadine S. Weich, Brookline, MA (US);~~
~~Peter J. Olandt, Buffalo, NY (US);~~
~~Fong-Ying Tsai, Newton, MA (US);~~
~~Rosana Kapeller-Libermann, Chestnut Hill, MA (US)~~
~~Joseph M. Carroll, Cambridge, MA (US)~~"

Signed and Sealed this
Twenty-eighth Day of August, 2012

David J. Kappos
*Director of the United States Patent and Trademark Office*